United States Patent
Brabander et al.

(10) Patent No.: US 11,479,560 B2
(45) Date of Patent: *Oct. 25, 2022

(54) OX2R COMPOUNDS

(71) Applicant: Board of Regents, The University of Texas System, Austin, TX (US)

(72) Inventors: Jef De Brabander, Dallas, TX (US); Daniel Rosenbaum, Dallas, TX (US); Qiren Liang, Dallas, TX (US); Wentian Wang, Dallas, TX (US)

(73) Assignee: Board of Regents, The University of Texas System

( * ) Notice: Subject to any disclaimer, the term of this patent is extended or adjusted under 35 U.S.C. 154(b) by 5 days.

This patent is subject to a terminal disclaimer.

(21) Appl. No.: 17/100,810

(22) Filed: Nov. 20, 2020

(65) Prior Publication Data
US 2021/0163494 A1  Jun. 3, 2021

Related U.S. Application Data

(63) Continuation of application No. 17/033,879, filed on Sep. 27, 2020, which is a continuation of application No. PCT/US2019/024426, filed on Mar. 27, 2019.

(60) Provisional application No. 62/648,933, filed on Mar. 27, 2018.

(51) Int. Cl.
| | |
|---|---|
| *A61K 31/4184* | (2006.01) |
| *A61K 31/4439* | (2006.01) |
| *A61K 31/4355* | (2006.01) |
| *A61K 31/506* | (2006.01) |
| *A61K 31/501* | (2006.01) |
| *A61K 31/422* | (2006.01) |
| *A61K 31/423* | (2006.01) |
| *A61K 31/427* | (2006.01) |
| *A61K 31/428* | (2006.01) |
| *A61K 31/4192* | (2006.01) |
| *A61K 31/4709* | (2006.01) |
| *C07D 491/107* | (2006.01) |
| *C07D 235/30* | (2006.01) |
| *C07D 401/06* | (2006.01) |
| *C07D 401/12* | (2006.01) |
| *C07D 403/12* | (2006.01) |
| *C07D 405/12* | (2006.01) |
| *C07D 409/06* | (2006.01) |
| *C07D 413/06* | (2006.01) |
| *C07D 413/12* | (2006.01) |
| *C07D 417/12* | (2006.01) |
| *C07D 471/04* | (2006.01) |

(52) U.S. Cl.
CPC ...... *C07D 491/107* (2013.01); *A61K 31/4184* (2013.01); *A61K 31/4192* (2013.01); *A61K 31/422* (2013.01); *A61K 31/423* (2013.01); *A61K 31/427* (2013.01); *A61K 31/428* (2013.01); *A61K 31/4355* (2013.01); *A61K 31/4439* (2013.01); *A61K 31/4709* (2013.01); *A61K 31/501* (2013.01); *A61K 31/506* (2013.01); *C07D 235/30* (2013.01); *C07D 401/06* (2013.01); *C07D 401/12* (2013.01); *C07D 403/12* (2013.01); *C07D 405/12* (2013.01); *C07D 409/06* (2013.01); *C07D 413/06* (2013.01); *C07D 413/12* (2013.01); *C07D 417/12* (2013.01); *C07D 471/04* (2013.01)

(58) Field of Classification Search
CPC ............ A61K 31/4184; A61K 31/4439; A61K 31/4355; A61K 31/506; A61K 31/501; A61K 31/422; A61K 31/423; A61K 31/427; A61K 31/428; A61K 31/4192; A61K 31/4709; C07D 491/107; C07D 235/30; C07D 235/26; C07D 235/32; C07D 401/06; C07D 401/12; C07D 403/12; C07D 405/12; C07D 409/06; C07D 413/06; C07D 413/12; C07D 417/12; C07D 471/04; C07D 245/04; C07D 403/06; C07D 417/06; C07D 487/10; C07D 405/06; C07D 487/04
See application file for complete search history.

(56) References Cited

U.S. PATENT DOCUMENTS

2021/0107914 A1*  4/2021  Brabander .............. A61P 25/16

OTHER PUBLICATIONS

Canada Examination Report dated Nov. 5, 2021; copending Ser. 3,095,451.
Canada Examination Report dated May 27, 2022; copending Ser. 3,095,451.
Extended European Search Report dated Feb. 7, 2022, copending Ser. No. 19774927.8.

* cited by examiner

*Primary Examiner* — Laura L Stockton
(74) *Attorney, Agent, or Firm* — Richard Aron Osman

(57) ABSTRACT

Methods and compositions for agonizing a type-2 orexin receptor (OX2R) in a cell determined to be in need thereof, including the general method of (a) administering to a subject a cyclic guanidinyl OX2R agonist and (b) detecting a resultant enhanced wakefulness or increased resistance to diet-induced accumulation of body fat, or abbreviated recovery from general anesthesia or jet lag.

40 Claims, 58 Drawing Sheets

R = (4-HO, 5-EtO), 4-Me, (4-HO, 5-MeO), 6-Cl, 4-Cl, 4-HO,

R = Me, Et, iPr, -CH$_2$(tetrahydrofuran-2-yl), cPent, Pr, -(CH$_2$)$_2$SEt, -CH$_2$(4-MeOPh), cHex, secBu, Pr, Bn, cHept, -(CH$_2$)$_2$OPh, -(CH$_2$)$_2$Ph, iBu, -(CH$_2$)$_2$OMe, R = H, CO$_2$Me (S) = H, Me, Ph, 2-thienyl, 2-MeOPh, gem-Me$_2$

| R | EC50 | R | EC50 |
|---|---|---|---|
| 4-MePh | 2 | 4-BrPh | >3 |
| 4-MePh | 1.5 | 4-BrPh | >3 |
| Ph | 3 | 4-CNPh | NA |
| Ph | 2 | 4-CNPh | NA |
| 2-MePh | NA | 4-Me$_2$NPh | 0.8 |
| 2-MePh | NA | 4-Me$_2$NPh | 0.7 |
| 3-MePh | 2 | 4-CF$_3$Ph | NA |
| 3-MePh | 1.5 | 4-CF$_3$Ph | NA |
| 4-NO$_2$Ph | >3 | 4-tBuPh | 0.6 |
| 4-NO$_2$Ph | >3 | 4-BuPh | 0.8 |
| 4-FPh | 2.5 | 4-MeOPh | 1.5 |
| 4-FPh | 2 | 4-MeSPh | 1.5 |
| 3-FPh | 2.5 | 2-thienyl | 2 |
| 3-FPhPh | 2 | benzodioxolyl | 1.5 |
| 3-ClPh | >3 | Me | NA |
| 3-ClPh | 3 | MeSO$_2$Ph | NA |
| 4-ClPh | 3 | CH$_2$Ph | NA |
| 4-ClPh | 3 | (CH$_2$)$_2$Ph | NA |
|  |  | cHex | 2.5 |

| R | EC50 |
|---|---|
| Me | 2 |
| Cl | 3 |
| F | >3 |
| SMe | 1.8 |
| NMe$_2$ | 1.8 | hit #47; OX2R selective
CLogP ~ 4.6 / MW 479 hit #16; OX2R selective
CLogP ~ 1.7 / MW 429 hit #9; OX2R selective
CLogP ~ 5.3 / MW 485 hit #6; OX2R selective
CLogP ~ 3.5 hit #42; OX2R selective
CLogP ~ 6.2 / MW 444 hit #26; OX2R selective
CLogP ~ 6.5 / MW 475 hit #22; OX2R selective
CLogP ~ 5.5 / MW 474

OX2R COMPOUNDS

CROSS-REFERENCE TO RELATED APPLICATIONS

This application claims priority to U.S. Provisional Application No. 62/648,933, filed Mar. 27, 2018, the disclosures of which are hereby incorporated by reference in their entireties for all purposes.

This invention was made with government support under Grant Number NS068963 awarded by the National Institutes of Health. The government has certain rights in the invention.

INTRODUCTION

This invention describes several chemically distinct classes of non-peptidic, small-molecule agonists for the type-2 orexin receptors (OX2R). Orexins are hypothalamic neuropeptides that are importantly implicated in sleep/wake control and body weight homeostasis.

Structurally distinct OX2R agonists are disclosed in U.S. Pat. No. 8,871,794.

SUMMARY OF THE INVENTION

The invention provides OXR2 agonist compounds, and related compositions, methods of making and methods of use thereof. Aspects and embodiments of the invention are embodied in claims.

In one aspect, the present disclosure relates to a compound of formula (A):

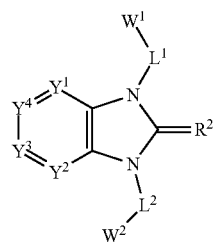

(A)

or a pharmaceutically acceptable salt thereof, wherein
$Y^1$, $Y^2$, $Y^3$, and $Y^4$, are each independently N or $CR^6$, wherein no more than two of Y, $Y^2$, $Y^3$, and $Y^4$ are N;
$W^1$ and $W^2$ are each independently selected from aryl, heterocyclyl, or heteroaryl, which are each optionally substituted with one or more $R^{10}$;
L is $C_1$-$C_6$ alkylene or $C_2$-$C_6$ alkenylene, optionally substituted with one or more $R^7$;
$L^2$ is $C_1$-$C_6$ alkylene or $C_2$-$C_6$ alkenylene, optionally substituted with one or more $R^8$;
$R^2$ is selected O, NH, $NR^{11}$;
$R^6$ is selected hydrogen, halogen, —CN, —$NO_2$, —$SC_1$-$C_6$ alkyl, —$COR^g$, —$C_1$-$C_6$ alkyl, —$C_3$-$C_6$ cycloalkyl, —$C_1$-$C_6$ haloalkyl, $C_1$-$C_6$ alkoxy, or —$C_1$-$C_6$ haloalkoxy,
$R^7$ is selected from halogen, —OH, —$NR^aR^b$, —CN, —$C_1$-$C_6$ alkyl, —$C_1$-$C_3$ alkylene-OH, —$C_1$-$C_3$ alkylene-CN, —$CH(OH)CH_2CN$, —$C_1$-$C_3$ alkylene-($C_1$-$C_6$ alkoxy), —$C_1$-$C_3$ alkylene-($C_1$-$C_6$ haloalkoxy), —$C_1$-$C_3$ alkylene-OCO(optionally substituted heterocyclyl), —$C_1$-$C_3$ alkylene-$OCOR^9$, —$C_1$-$C_3$ alkylene-$OCOOR^g$, —$C_1$-$C_3$ alkylene-$NR^aR^b$, —$C_1$-$C_3$ alkylene-$NR^aCOR^9$, —$C_1$-$C_3$ alkylene-$NR^aCO$(optionally substituted heterocyclyl), —$C_1$-$C_3$ alkylene-$NR^aCOOR^g$, —$C_1$-$C_3$ alkylene-$NR^aCONR^aR^b$, —$C_1$-$C_3$ alkylene-$CONR^aR^b$, —$C_1$-$C_3$ alkylene-$CONR^cR^d$, —$CONR^aR^b$, —$CONR^cR^d$, —($C_1$-$C_3$ alkylene)-O—($C_1$-$C_3$ alkylene)-OH, —($C_1$-$C_3$ alkylene)-O—($C_1$-$C_3$ alkylene)-CN, —($C_1$-$C_3$ alkylene)-O—($C_1$-$C_3$ alkylene)-O—($C_1$-$C_4$ alkyl), —($C_1$-$C_3$ alkylene)-O—($C_1$-$C_3$ alkylene)-O—($C_1$-$C_4$ haloalkyl), —($C_1$-$C_3$ alkylene)-O—($C_1$-$C_3$ alkylene)-S—($C_1$-$C_3$ alkyl), —$C_1$-$C_3$ alkylene-S($C_1$-$C_6$ alkyl), —$C_1$-$C_3$ alkylene-SO($C_1$-$C_6$ alkyl), —$C_1$-$C_3$ alkylene-$SO_2$($C_1$-$C_6$ alkyl), —$C_1$-$C_3$ alkylene-$SO_2R^{12}$, or hetercyclyl optionally substituted with $R^{10}$;
$R^8$ is selected from —OH, —CN, —$NO_2$, —$COR^g$, oxo, —$C_1$-$C_6$ alkyl, —$C_1$-$C_6$ alkylene-OH, —$C_1$-$C_6$ haloalkyl, —$C_3$-$C_6$ cycloalkyl,
$R^a$ and $R^b$ are each independently selected from H, —$C_1$-$C_6$ alkyl, —$C_1$-$C_6$ haloalkyl, —CHO, —COOH, —CO($C_1$-$C_3$ alkyl), —CO($C_1$-$C_3$ haloalkyl), —CO($C_3$-$C_8$ cycloalkyl), —CO($C_2$-$C_4$ alkenyl), —CO($C_1$-$C_6$ alkylene)-OH, —CO($C_1$-$C_6$ alkylene)-($C_1$-$C_6$ alkoxy), —$CONR^eR^f$, —CO($C_1$-$C_3$ alkylene)-$NR^eR^f$, —CO($C_1$-$C_3$ alkylene)-$NR^eSR^f$, —CO($C_1$-$C_3$ alkylene)-$NR^e$-$SOR^g$, —CO($C_1$-$C_3$ alkylene)-$NR^eSO_2R^f$, —CO($C_2$-$C_3$ alkenyl), —CO($C_1$-$C_3$ haloalkyl), —CO($CH_2$)(cycloalkyl), —CO($CH_2$)$_n$(optionally substituted aryl), —CO($CH_2$)$_n$(optionally substituted heterocyclyl), —CO($CH_2$)$_n$(optionally substituted heteroaryl);
$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;
$R^e$ and $R^f$ are each independently selected from H, —$C_1$-$C_6$ alkyl, —$C_1$-$C_6$ haloalkyl, or —$C_1$-$C_6$ alkylene-OH;
$R^g$ is H, —$C_1$-$C_6$ alkyl, —$C_3$-$C_6$ cycloalkyl, —$C_1$-$C_6$ haloalkyl, phenyl, or benzyl;
$R^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-$NR^aR^b$;
$R^{10}$ is halogen, —CN, oxo, —$C_1$-$C_6$ alkyl, —$C_1$-$C_6$ haloalkyl, —$C_1$-$C_6$ alkoxy, —$C_1$-$C_6$ haloalkoxy, —$SC_1$-$C_6$ alkyl, —S—S—($C_1$-$C_6$ alkyl), or optionally substituted phenyl;
$R^{11}$ is —$C_1$-$C_6$ alkyl, —$C_1$-$C_6$ haloalkyl, —$C_1$-$C_6$ alkoxy, —$C_1$-$C_3$ alkylene-OH, —$C_1$-$C_3$ alkylene-($C_1$-$C_3$ alkoxy), —COO($C_1$-$C_6$ alkyl);
alternatively, $R^{11}$ and $R^7$ together form a 5- to 7-membered ring, which is optionally substituted with $R^{10}$;
$R^{12}$ is —OH, —$C_1$-$C_6$ alkyl, —$C_3$-$C_6$ cycloalkyl, —$C_1$-$C_6$ haloalkyl, —$C_1$-$C_6$ alkoxy, phenyl, benzyl, —$NR^aR^b$, —$CONR^aR^b$, or —$NR^aCOR^g$;
n is 0, 1, or 2.

In one embodiment of the compounds of formula (A), $R^2$ is NH.

In one embodiment of the compounds of formula (A), $Y^3$ and $Y^4$, are each independently CH or $CR^6$.

In one embodiment of the compounds of formula (A), $Y^1$ and $Y^2$ is N and the other is CH or $CR^6$.

In one embodiment of the compounds of formula (A), Y, $Y^2$, $Y^3$ and $Y^4$, are each CH or $CR^6$.

In one embodiment of the compounds of formula (A), $R^6$ is halogen, methyl, —$CH_2F$, —$CHF_2$, or —$CF_3$.

In one embodiment of the compounds of formula (A), $R^{10}$ is halogen, methyl, —$CH_2F$, —$CHF_2$, or —$CF_3$.

In one embodiment of the compounds of formula (A), $L^2$ is $C_1$ alkeylene or $C_4$ alkenylene, optionally substituted with one $R^8$. In one embodiment, $L^2$ is $C_1$ alkeylene, optionally substituted with one $R^8$.

In one embodiment of the compounds of formula (A), $R^8$ is methyl, ethyl, isopropyl, cyclopropyl, cyclobutyl, —$CH_2F$, —$CHF_2$, or —$CF_3$.

In one embodiment of the compounds of formula (A), L is $C_2$ alkeylene optionally substituted with one $R^7$.

In one embodiment of the compounds of formula (A), -$L^1$-W is —$CHR^7CH_2$—$W^1$.

In one embodiment of the compounds of formula (A), $W^1$ is phenyl optionally substituted with $R^{10}$.

In one embodiment of the compounds of formula (A), $W^2$ is phenyl optionally substituted with $R^{10}$.

In one embodiment of the compounds of formula (A), $R^7$ is —$C_1$-$C_3$ alkylene-OH, —$C_1$-$C_3$ alkylene-CN, —$C_1$-$C_3$ alkylene-($C_1$-$C_6$ alkoxy), —$C_1$-$C_3$ alkylene-$NR^aR^b$, —$C_1$-$C_3$ alkylene-OCO(optionally substituted heterocyclyl), —$C_1$-$C_3$ alkylene-OCOR$^9$, —$C_1$-$C_3$ alkylene-$NR^aCOR^9$, —$C_1$-$C_3$ alkylene-$NR^a$CO(optionally substituted heterocyclyl), —$C_1$-$C_3$ alkylene-$NR^aCONR^aR^b$, —CONR$^c$R$^d$, —($C_1$-$C_3$ alkylene)-O—($C_1$-$C_3$ alkylene)-OH, —($C_1$-$C_3$ alkylene)-O—($C_1$-$C_3$ alkylene)-CN, —($C_1$-$C_3$ alkylene)-O—($C_1$-$C_3$ alkylene)-O—($C_1$-$C_3$ alkyl), —$C_1$-$C_3$ alkylene-S($C_1$-$C_6$ alkyl), —$C_1$-$C_3$ alkylene-SO($C_1$-$C_6$ alkyl), or —$C_1$-$C_3$ alkylene-$SO_2$($C_1$-$C_6$ alkyl). In one embodiment, $R^7$ is —$CH_2OH$, —$CH_2NH_2$, —$CH(CH_3)OH$, —$CH_2CN$, —$CH_2$($C_1$-$C_3$ alkoxy), —$CH_2$OCO(optionally substituted heterocyclyl), —$CH_2$OCOR$^g$, —$CH_2NR^aCOR^9$, —$CH_2NR^a$CO(optionally substituted heterocyclyl), —$CH_2NR^aCONR^aR^b$, —CONR$^c$R$^d$, —$CH_2$O—($C_1$-$C_3$ alkylene)-OH, —$CH_2$O—($C_1$-$C_3$ alkylene)-CN, —$CH_2$O—($C_1$-$C_3$ alkylene)-O—($C_1$-$C_3$ alkyl), —$CH_2$S($C_1$-$C_6$ alkyl), —$CH_2$SO($C_1$-$C_6$ alkyl), or —$CH_2SO_2$($C_1$-$C_6$ alkyl). In one embodiment, $R^7$ is —$CH_2OH$, —$CH_2NH_2$, —$CH(CH_3)OH$, —$CH_2CN$, —$CH_2OCH_3$, —$CH_2$OCO(optionally substituted azetidinyl), —$CH_2OCOCH_2OH$, —$CH_2NR^aCOCH_2OH$, —$CH_2NHCOCH_2NHCH_3$, —$CH_2NR^a$CO(azyridinyl), —$CH_2NR^aCONH_2$, —CONR$^c$R$^d$, —$CH_2$O—($C_1$-$C_3$ alkylene)-OH, —$CH_2$O—($C_1$-$C_3$ alkylene)-CN, —$CH_2$O—($C_1$-$C_3$ alkylene)-O—($C_1$-$C_3$ alkyl), —$CH_2$S($C_1$-$C_3$ alkyl), —$CH_2$SO($C_1$-$C_3$ alkyl), or —$CH_2SO_2$($C_1$-$C_3$ alkyl). In one embodiment, $R^7$ is —$CH_2OH$, —$CH_2NH_2$, —$CH(CH_3)OH$, —$CH_2CN$, —$CH_2OCH_3$, —$CH_2OCOCH_2OH$, —$CH_2NHCOCH_2OH$, —$CH_2N(CH_3)COCH_2OH$, —$CH_2NHCOCH_2NHCH_3$, —$CH_2NHCONH_2$, —$CH_2OCH_2OH$, —$CH_2OCH_2CH_2OH$, —$CH_2OCH_2CN$, —$CH_2OCH_2CH_2CN$, —$CH_2OH_2OCH_3$, —$CH_2OH_2CH_2OCH_3$, —$CH_2SCH_3$, —$CH_2SOCH_3$, or —$CH_2SO_2CH_3$. In one embodiment $R^7$ is —CONR$^c$R$^d$ selected from

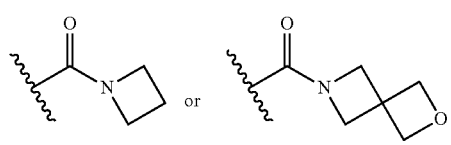 [SMILES: *C(=O)N1CCC1 ; *C(=O)N1CC2(COC2)C1]

each of which are optionally substituted with halogen, —CN, —$C_1$-$C_6$ alkyl, —$C_1$-$C_6$ haloalkyl, —$C_1$-$C_6$ alkylene-OH, or —$C_1$-$C_6$ alkylene-$NH_2$.

In one aspect, the present disclosure relates to a compound of formula (I):

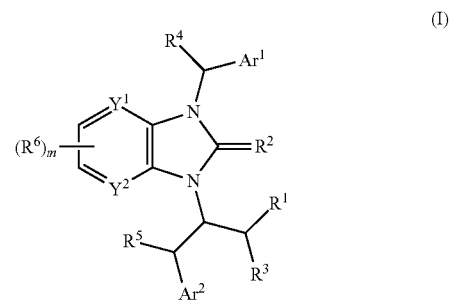

or a pharmaceutically acceptable salt thereof, wherein:
$Y^1$ and $Y^2$ are each independently N or CR$^6$;
Ar$^1$ and Ar$^2$ are each independently C5-C10 aryl or 5- to 10-membered heteroaryl comprising one, two, or three heteroatoms selected from N, O, or S, each of which are optionally substituted with one or more $R^{10}$;
$R^1$ is —OH, —$C_1$-$C_4$ alkoxy, —$C_1$-$C_4$ haloalkoxy, —$NR^aR^b$, —$NR^aCOR^9$, —$NR^a$CO(optionally substituted heterocyclyl), —CONR$^a$R$^b$, —CONR$^c$R$^d$, $SO_2R^{12}$, —O—($C_1$-$C_3$ alkylene)-O—($C_1$-$C_4$ alkyl) or —O—($C_1$-$C_3$ alkylene)-O—($C_1$-$C_4$ haloalkyl);
$R^2$ is selected O, NH, or NR$^{11}$,
$R^3$ is H or methyl;
$R^4$ is H, —CN, —$NO_2$, —COR$^g$, —$C_1$-$C_4$ alkyl, —$C_1$-$C_4$ haloalkyl, or —$C_3$-$C_4$ cycloalkyl;
$R^5$ is H or methyl;
$R^6$ is selected H, halogen, —CN, —$NO_2$, —$SCH_3$, —COR$^g$, —$C_1$-$C_4$ alkyl, —$C_1$-$C_4$ haloalkyl, —$C_3$-$C_4$ cycloalkyl, —$C_1$-$C_4$ alkoxy, or —$C_1$-$C_4$ haloalkoxy;
$R^a$ and $R^b$ are each independently selected from H, —$C_1$-$C_4$ alkyl, —$C_1$-$C_4$ haloalkyl, —CHO, —CO($C_1$-$C_3$ alkyl), —CO($C_1$-$C_6$ alkylene)-OH, —CONR$^e$R$^f$, —CO($C_1$-$C_3$ alkylene)-NR$^e$R$^f$, —CO($C_1$-$C_3$ alkylene)-NR$^e$SR$^f$, —CO($C_1$-$C_3$ alkylene)-NR$^e$SOR$^g$, —CO($C_1$-$C_3$ alkylene)-NR$^e$SO$_2$R$^f$, —CO($C_2$-$C_3$ alkenyl), —CO($C_1$-$C_3$ haloalkyl), —CO($CH_2$)$_n$(cycloalkyl), —CO($CH_2$)$_n$(optionally substituted aryl), —CO($CH_2$)$_n$(optionally substituted heterocyclyl), or —CO($CH_2$)$_n$(optionally substituted heteroaryl);
R$^c$ and R$^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;
R$^e$ and R$^f$ are each independently selected from H, —$C_1$-$C_6$ alkyl, —$C_1$-$C_6$ haloalkyl, or —$C_1$-$C_6$ alkylene-OH;
$R^9$ is H, —$C_1$-$C_6$ alkyl, —$C_3$-$C_6$ cycloalkyl, —$C_1$-$C_6$ haloalkyl, phenyl, benzyl,
$R^9$ is —$C_1$-$C_3$ alkylene-OH, —$C_1$-$C_3$ alkylene-CN, —$C_1$-$C_3$ alkylene-($C_1$ alkoxy), —$C_1$-$C_3$ alkylene-$NR^aR^b$,
$R^{10}$ is halogen, —CN, oxo, —$C_1$-$C_6$ alkyl, —$C_1$-$C_6$ haloalkyl, —$C_1$-$C_6$ alkoxy, —$C_1$-$C_6$ haloalkoxy, —S—S—($C_1$-$C_6$ alkyl), or optionally substituted phenyl;
$R^{11}$ is —$C_1$-$C_4$ alkyl, —$C_1$-$C_4$ fluoroalkyl, —$C_1$-$C_4$ alkoxy, or COO($C_1$-$C_4$ alkyl);
alternatively, $R^{11}$ and $R^7$ together form a 5- to 7-membered ring, which is optionally substituted with $R^{10}$;

$R^{11}$ is —OH, —$C_1$-$C_6$ alkyl, —$C_3$-$C_6$ cycloalkyl, —$C_1$-$C_6$ haloalkyl, —$C_1$-$C_6$ alkoxy, phenyl, benzyl, —$NR^aR^b$, —$CONR^aR^b$, or —$NR^aCOR^h$;

n is 0, 1, or 2; and m is 0, 1, or 2.

In one embodiment of the compounds of formula (A), $Ar^1$ is phenyl optionally substituted with one or more $R^{11}$.

In one embodiment of the compounds of formula (A), $R^{10}$ is halogen, —CN, —$C_1$-$C_4$ alkyl, or —$C_1$-$C_4$ fluoroalkyl.

In one embodiment of the compounds of formula (A), $Ar^1$ is 4-methylphenyl.

In one embodiment of the compounds of formula (A), $Ar^2$ is 4-methylphenyl.

In one embodiment of the compounds of formula (A),
$R^1$ is —OH, $C_1$-$C_4$ alkoxy, $C_1$-$C_4$ haloalkoxy, —$NR^aR^b$, —$NHCOR^9$, or —$CONR^aR^b$;
$R^a$ and $R^b$ are each independently H, —$C_1$-$C_4$ alkyl or —$C_1$-$C_4$ fluoroalkyl; and
$R^9$ is —$C_1$-$C_4$ alkyl or —$C_1$-$C_4$ fluoroalkyl.

In one embodiment of the compounds of formula (A),
$R^1$ is —OH, —$OCH_3$, $C_1$-$C_4$ haloalkoxy, —$NR^aR^b$, —$NHCOR^9$, or —$CONR^aR^b$, —$OCH_2O$—($C_1$-$C_4$ alkyl) or —$OCH_2O$—($C_1$-$C_4$ haloalkyl);
$R^a$ and $R^b$ are each independently H, —$C_1$-$C_4$ alkyl or —$C_1$-$C_4$ fluoroalkyl; and
$R^9$ is —$C_1$-$C_4$ alkyl or —$C_1$-$C_4$ fluoroalkyl.

In one embodiment of the compounds of formula (A),
$R^1$ is —OH, —$OCH_3$, —$NHCH_3$, —$N(CH_3)_2$, —$NHSO_2R^{12}$, or —$NHCOR^{12}$; and
$R^{12}$ is —$CH_3$, —$CH_2CH_3$, isopropyl, —$CF_3$, —OH, —$OCH_3$, —$OCH_2CH_3$, cyclopropyl, phenyl, benzyl, —$NR^aR^b$, —$CONR^aR^b$, or —$NR^aCOR^1$.

In one embodiment of the compounds of formula (A), $R^2$ is O, NH, or $NCH_3$.

In one embodiment of the compounds of formula (A), $R^3$ is H.

In one embodiment of the compounds of formula (A), $R^4$ is H or methyl.

In one embodiment of the compounds of formula (A), $R^6$ is H, halogen, —$CH_3$, —$CF_3$, —CN, —$SCH_3$, t-butyl, —$OCH_3$, or —$OCF_3$.

In one aspect, the present disclosure relates to compounds of formula (B):

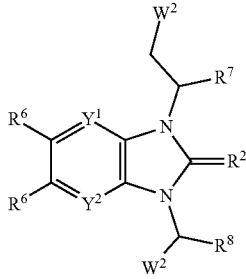

(B)

or a pharmaceutically acceptable salt thereof, wherein
$Y^1$ and $Y^2$ are each independently N or $CR^6$;
$W^1$ and $W^2$ are each independently selected from 5- to 10-membered aryl, heterocyclyl, or heteroaryl, which are each optionally substituted with one or more $R^{10}$;
$R^2$ is selected O or NH;
$R^6$ is selected hydrogen, halogen, —CN, —$C_1$-$C_3$ alkyl, —$C_3$-$C_6$ cycloalkyl, $C_1$-$C_3$ haloalkyl, $C_1$-$C_3$ alkoxy, or —$C_1$-$C_3$ haloalkoxy, $R^7$ is selected from halogen, —OH, —$NR^aR^b$, —CN, —$C_1$-$C_6$ alkyl, —$C_1$-$C_3$ alkylene-OH, —$C_1$-$C_3$ alkylene-CN, —$CH(OH)CH_2CN$, —$C_1$-$C_3$ alkylene-($C_1$-$C_6$ alkoxy), —$C_1$-$C_3$ alkylene-($C_1$-$C_6$ haloalkoxy), —$C_1$-$C_3$ alkylene-OCO(optionally substituted heterocyclyl), —$C_1$-$C_3$ alkylene-$OCOR^9$, —$C_1$-$C_3$ alkylene-$OCOOR^g$, —$C_1$-$C_3$ alkylene-$NR^aR^b$, —$C_1$-$C_3$ alkylene-$NR^aCOR^9$, —$C_1$-$C_3$ alkylene-$NR^aCO$(optionally substituted heterocyclyl), —$C_1$-$C_3$ alkylene-$NR^aCOOR^g$, —$C_1$-$C_3$ alkylene-$NR^aCONR^aR^b$, —$C_1$-$C_3$ alkylene-$CONR^aR^b$, —$C_1$-$C_3$ alkylene-$CONR^cR^d$, —$CONR^aR^b$, —$CONR^cR^d$, —($C_1$-$C_3$ alkylene)-O—($C_1$-$C_3$ alkylene)-OH, —($C_1$-$C_3$ alkylene)-O—($C_1$-$C_3$ alkylene)-CN, —($C_1$-$C_3$ alkylene)-O—($C_1$-$C_3$ alkylene)-O—($C_1$-$C_4$ alkyl), —($C_1$-$C_3$ alkylene)-O—($C_1$-$C_3$ alkylene)-O—($C_1$-$C_4$ haloalkyl), —($C_1$-$C_3$ alkylene)-O—($C_1$-$C_3$ alkylene)-S—($C_1$-$C_3$ alkyl), —$C_1$-$C_3$ alkylene-S($C_1$-$C_6$ alkyl), —$C_1$-$C_3$ alkylene-SO($C_1$-$C_6$ alkyl), or —$C_1$-$C_3$ alkylene-$SO_2$($C_1$-$C_6$ alkyl);

$R^8$ is selected from —OH, —CN, oxo, —$C_1$-$C_6$ alkyl, $C_1$-$C_6$ alkylene-OH, —$C_1$-$C_6$ haloalkyl, or —$C_3$-$C_6$ cycloalkyl, $R^a$ and $R^b$ are each independently selected from H, —$C_1$-$C_6$ alkyl, —$C_1$-$C_6$ haloalkyl, —CHO, —CO($C_1$-$C_3$ alkyl), —CO($C_1$-$C_6$ alkylene)-OH, —$CONR^eR^f$, —CO($C_1$-$C_3$ alkylene)-$NR^eR^f$, —CO($C_1$-$C_3$ alkylene)-$NR^eSR^f$, —CO($C_1$-$C_3$ alkylene)-$NR^eSOR^g$, —CO($C_1$-$C_3$ alkylene)-$NR^eSO_2R^f$, —CO($C_2$-$C_3$ alkenyl), —CO($C_1$-$C_3$ haloalkyl), —CO($CH_2$)(cycloalkyl), —CO($CH_2$)$_n$(optionally substituted aryl), —CO($CH_2$)$_n$(optionally substituted heterocyclyl), or —CO($CH_2$)$_n$(optionally substituted heteroaryl);

$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;

$R^e$ and $R^f$ are each independently selected from H, —$C_1$-$C_6$ alkyl, —$C_1$-$C_6$ haloalkyl, or —$C_1$-$C_6$ alkylene-OH;

$R^g$ is H, —$C_1$-$C_6$ alkyl, —$C_3$-$C_6$ cycloalkyl, —$C_1$-$C_6$ haloalkyl, phenyl, benzyl, $R^9$ is —$C_1$-$C_3$ alkylene-OH, —$C_1$-$C_3$ alkylene-CN, —$C_1$-$C_3$ alkylene-($C_1$-$C_3$ alkoxy), —$C_1$-$C_3$ alkylene-$NR^aR^b$, $R^{10}$ is halogen, —CN, oxo, —$C_1$-$C_6$ alkyl, —$C_1$-$C_6$ haloalkyl, —$C_1$-$C_6$ alkoxy, —$C_1$-$C_6$ haloalkoxy, —S—S—($C_1$-$C_6$ alkyl), or optionally substituted phenyl;

$R^{11}$ is —$C_1$-$C_6$ alkyl, —$C_1$-$C_6$ haloalkyl, —$C_1$-$C_6$ alkoxy, —$C_1$-$C_3$ alkylene-OH, —$C_1$-$C_3$ alkylene-($C_1$-$C_3$ alkoxy), or —COO($C_1$-$C_6$ alkyl);

alternatively, $R^{11}$ and $R^7$ together form a 5- to 7-membered ring, which is optionally substituted with $R^{10}$; and n is 0, 1, or 2.

In one aspect, the present disclosure relates to compounds of formula (C):

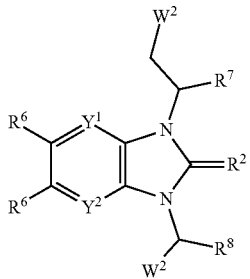

(C)

or a pharmaceutically acceptable salt thereof, wherein
$Y^1$ and $Y^2$ are each independently N or $CR^6$;
$W^1$ and $W^2$ are each independently selected from 5- to 10-membered aryl, heterocyclyl, or heteroaryl, which are each optionally substituted with one or more $R^{10}$;
$R^2$ is selected O or NH;
$R^6$ is selected hydrogen, halogen, —CN, —$C_1$-$C_3$ alkyl, —$C_3$-$C_6$ cycloalkyl, $C_1$-$C_3$ haloalkyl, $C_1$-$C_3$ alkoxy, or —$C_1$-$C_3$ haloalkoxy,
$R^7$ is selected from —$C_1$-$C_3$ alkylene-OH, —$C_1$-$C_3$ alkylene-CN, —$C_1$-$C_3$ alkylene-($C_1$-$C_6$ alkoxy), —$C_1$-$C_3$ alkylene-$NR^aR^b$, —$C_1$-$C_3$ alkylene-OCO(optionally substituted heterocyclyl), —$C_1$-$C_3$ alkylene-$OCOR^9$, —$C_1$-$C_3$ alkylene-$NR^aCOR^9$, —$C_1$-$C_3$ alkylene-$NR^a$CO(optionally substituted heterocyclyl), —$C_1$-$C_3$ alkylene-$NR^aCONR^aR^b$, —$CONR^cR^d$, —($C_1$-$C_3$ alkylene)-O—($C_1$-$C_3$ alkylene)-OH, —($C_1$-$C_3$ alkylene)-O—($C_1$-$C_3$ alkylene)-CN, —($C_1$-$C_3$ alkylene)-O—($C_1$-$C_3$ alkylene)-O—($C_1$-$C_3$ alkyl), —$C_1$-$C_3$ alkylene-S($C_1$-$C_6$ alkyl), —$C_1$-$C_3$ alkylene-SO($C_1$-$C_6$ alkyl), or —$C_1$-$C_3$ alkylene-$SO_2$($C_1$-$C_6$ alkyl);
$R^8$ is selected from —OH, —CN, oxo, —$C_1$-$C_6$ alkyl, $C_1$-$C_6$ alkylene-OH, —$C_1$-$C_6$ haloalkyl, —$C_3$-$C_6$ cycloalkyl,
$R^a$ and $R^b$ are each independently selected from H, —$C_1$-$C_6$ alkyl, —$C_1$-$C_6$ haloalkyl, —CHO, —CO($C_1$-$C_3$ alkyl), —CO($C_1$-$C_6$ alkylene)-OH, —$CONR^eR^f$, —CO($C_1$-$C_3$ alkylene)-$NR^eR^f$, —CO($C_1$-$C_3$ alkylene)-$NR^eSR^f$, —CO($C_1$-$C_3$ alkylene)-$NR^eSOR^g$, —CO($C_1$-$C_3$ alkylene)-$NR^eSO_2R^f$, —CO($C_2$-$C_3$ alkenyl), —CO($C_1$-$C_3$ haloalkyl), —CO($CH_2$)(cycloalkyl), —CO($CH_2$)$_n$(optionally substituted aryl), —CO($CH_2$)$_n$(optionally substituted heterocyclyl), —CO($CH_2$)$_n$(optionally substituted heteroaryl);
$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;
$R^e$ and $R^f$ are each independently selected from H, —$C_1$-$C_6$ alkyl, —$C_1$-$C_6$ haloalkyl, or —$C_1$-$C_6$ alkylene-OH;
$R^9$ is H, —$C_1$-$C_6$ alkyl, —$C_3$-$C_6$ cycloalkyl, —$C_1$-$C_6$ haloalkyl, phenyl, benzyl,
$R^9$ is —$C_1$-$C_3$ alkylene-OH, —$C_1$-$C_3$ alkylene-CN, —$C_1$-$C_3$ alkylene-($C_1$-$C_3$ alkoxy), —$C_1$-$C_3$ alkylene-$NR^aR^b$,
$R^{10}$ is halogen, —CN, oxo, —$C_1$-$C_6$ alkyl, —$C_1$-$C_6$ haloalkyl, —$C_1$-$C_6$ alkoxy, —$C_1$-$C_6$ haloalkoxy, —S—S—($C_1$-$C_6$ alkyl), or optionally substituted phenyl;

$R^{11}$ is —$C_1$-$C_6$ alkyl, —$C_1$-$C_6$ haloalkyl, —$C_1$-$C_6$ alkoxy, —$C_1$-$C_3$ alkylene-OH, —$C_1$-$C_3$ alkylene-($C_1$-$C_3$ alkoxy), —COO($C_1$-$C_6$ alkyl); and
n is 0, 1, or 2.

In one aspect, the present disclosure relates to compounds of formula (D):

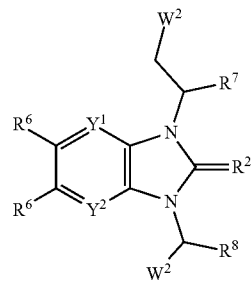

(D)

or a pharmaceutically acceptable salt thereof, wherein
$Y^1$ and $Y^2$ are each independently N or $CR^6$;
$W^1$ and $W^2$ are each phenyl, which are each optionally substituted with one or more $R^{10}$;
$R^2$ is selected O or NH;
$R^6$ is selected hydrogen, halogen, —CN, —$C_1$-$C_3$ alkyl, —$C_3$-$C_6$ cycloalkyl, $C_1$-$C_3$ haloalkyl, $C_1$-$C_3$ alkoxy, or —$C_1$-$C_3$ haloalkoxy,
$R^7$ is selected from —$CH_2$OH, —$CH_2NH_2$, —CH($CH_3$)OH, —$CH_2$CN, —$CH_2$($C_1$-$C_3$ alkoxy), —$CH_2$OCO(optionally substituted heterocyclyl), —$CH_2OCOR^9$, —$CH_2NR^aCOR^9$, —$CH_2NR^a$CO(optionally substituted heterocyclyl), —$CH_2NR^aCONR^aR^b$, —$CONR^cR^d$, —$CH_2$O—($C_1$-$C_3$ alkylene)-OH, —$CH_2$O—($C_1$-$C_3$ alkylene)-CN, —$CH_2$O—($C_1$-$C_3$ alkylene)-O—($C_1$-$C_3$ alkyl), —$CH_2$S($C_1$-$C_6$ alkyl), —$CH_2$SO($C_1$-$C_6$ alkyl), or —$CH_2SO_2$($C_1$-$C_6$ alkyl);
$R^8$ is selected from —OH, —CN, oxo, —$C_1$-$C_6$ alkyl, $C_1$-$C_6$ alkylene-OH, —$C_1$-$C_6$ haloalkyl, or —$C_3$-$C_6$ cycloalkyl,
$R^a$ and $R^b$ are each independently selected from H, —$C_1$-$C_6$ alkyl, —$C_1$-$C_6$ haloalkyl, —CHO, —CO($C_1$-$C_3$ alkyl), —CO($C_1$-$C_6$ alkylene)-OH, —$CONR^eR^f$, —CO($C_1$-$C_3$ alkylene)-$NR^eR^f$, —CO($C_1$-$C_3$ alkylene)-$NR^eSR^f$, —CO($C_1$-$C_3$ alkylene)-$NR^eSOR^g$, —CO($C_1$-$C_3$ alkylene)-$NR^eSO_2R^f$, —CO($C_2$-$C_3$ alkenyl), —CO($C_1$-$C_3$ haloalkyl), —CO($CH_2$)(cycloalkyl), —CO($CH_2$)$_n$(optionally substituted aryl), —CO($CH_2$)$_n$(optionally substituted heterocyclyl), —CO($CH_2$)$_n$(optionally substituted heteroaryl);
$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;
$R^e$ and $R^f$ are each independently selected from H, —$C_1$-$C_6$ alkyl, —$C_1$-$C_6$ haloalkyl, or —$C_1$-$C_6$ alkylene-OH;
$R^9$ is H, —$C_1$-$C_6$ alkyl, —$C_3$-$C_6$ cycloalkyl, —$C_1$-$C_6$ haloalkyl, phenyl, or benzyl;
$R^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-$NR^aR^b$,
$R^{10}$ is halogen, —CN, oxo, —$C_1$-$C_6$ alkyl, —$C_1$-$C_6$ haloalkyl, —$C_1$-$C_6$ alkoxy, —$C_1$-$C_6$ haloalkoxy, —S—S—($C_1$-$C_6$ alkyl), or optionally substituted phenyl;

R[11] is —$C_1$-$C_6$ alkyl, —$C_1$-$C_6$ haloalkyl, —$C_1$-$C_6$ alkoxy, —$C_1$-$C_3$ alkylene-OH, —$C_1$-$C_3$ alkylene-($C_1$-$C_3$ alkoxy), or —COO($C_1$-$C_6$ alkyl); and n is 0, 1, or 2.

In one embodiment of the compounds of formula (A) or (B)-(D), wherein $R^7$ is —$CH_2OH$, —$CH_2NH_2$, —$CH(CH_3)OH$, —$CH_2CN$, —$CH_2OCH_3$, —$CH_2OCO$(optionally substituted azetidinyl), —$CH_2OCOCH_2OH$, —$CH_2NR^aCOCH_2OH$, —$CH_2NHCOCH_2NHCH_3$, —$CH_2NR^aCO$(azyridinyl), —$CH_2NR^aCONH_2$, —$CONR^cR^d$, —$CH_2O$—($C_1$-$C_3$ alkylene)-OH, —$CH_2O$—($C_1$-$C_3$ alkylene)-CN, —$CH_2O$—($C_1$-$C_3$ alkylene)-O—($C_1$-$C_3$ alkyl), —$CH_2S(C_1$-$C_3$ alkyl), —$CH_2SO(C_1$-$C_3$ alkyl), or —$CH_2SO_2(C_1$-$C_3$ alkyl). In one embodiment, $R^7$ is —$CH_2OH$, —$CH_2NH_2$, —$CH(CH_3)OH$, —$CH_2CN$, —$CH_2OCH_3$, —$CH_2OCOCH_2OH$, —$CH_2NHCOCH_2OH$, —$CH_2N(CH_3)COCH_2OH$, —$CH_2NHCOCH_2NHCH_3$, —$CH_2NHCONH_2$, —$CH_2OCH_2OH$, —$CH_2OCH_2CH_2OH$, —$CH_2OCH_2CN$, —$CH_2OCH_2CH_2CN$, —$CH_2OH_2OCH_3$, —$CH_2OH_2CH_2OCH_3$, —$CH_2SCH_3$, —$CH_2SOCH_3$, or —$CH_2SO_2CH_3$. In one embodiment, $R^7$ is —$CONR^cR^d$ selected from

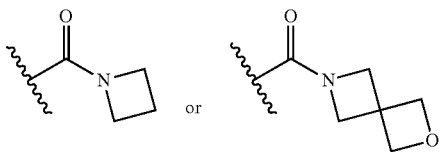 [SMILES: *C(=O)N1CCC1 ; *C(=O)N1CC2(COC2)C1]

each of which are optionally substituted with halogen, —CN, —$C_1$-$C_6$ alkyl, —$C_1$-$C_6$ haloalkyl, —$C_1$-$C_6$ alkylene-OH, or —$C_1$-$C_6$ alkylene-$NH_2$.

In one embodiment of the compounds of formula (A) or (B)-(D), $R^{10}$ is halogen, —CN, —$C_1$-$C_3$ alkyl, —$C_1$-$C_3$ haloalkyl, —$C_1$-$C_3$ alkoxy, —$C_1$-$C_3$ haloalkoxy, In one embodiment of the compounds of formula (A) or (B)-(D), $W^1$ is 4-methylphenyl.

In one embodiment of the compounds of formula (A) or (B)-(D), $W^2$ is 4-methylphenyl.

In one aspect, the present disclosure relates to compounds of formula (II):

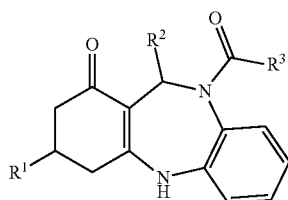

(II)

or a pharmaceutically acceptable salt thereof, wherein
$R^1$ is aryl or heteroaryl, optionally substituted with one or more $R^{1a}$;
$R^2$ is aryl or heteroaryl, optionally substituted with one or more $R^{2a}$;
$R^3$ is alkyl, cycloalkyl, aryl, -alkylaryl, heterocyclyl, or heteroaryl, optionally substituted with one or more $R^{3a}$; and
$R^{1a}$, $R^{2a}$, and $R^{3a}$ is each independently selected from halogen, —OH, —CN, —$NO_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, —$S(C_1$-$C_6$ alkyl), —$SO(C_1$-$C_6$ alkyl), —$SO_2(C_1$-$C_6$ alkyl), —$COR^g$, —$NR^aR^b$, —$OCOR^9$, —$OCOOR^g$, —$OCO$(optionally substituted heterocyclyl), —$NR^a$-$COR^9$, —$NR^aCO$(optionally substituted heterocyclyl), —$NR^aCOOR^g$, —$NR^aCONR^aR^b$, —$CONR^aR^b$, —$CONR^cR^d$, heterocyclyl, heteroaryl, or aryl;

$R^a$ and $R^b$ are each independently selected from H, —$C_1$-$C_6$ alkyl, —$C_1$-$C_6$ haloalkyl, —CHO, —$CO(C_1$-$C_3$ alkyl), —$CO(C_1$-$C_6$ alkylene)-OH, —$CONR^eR^f$, —$CO(C_1$-$C_3$ alkylene)-$NR^eR^f$, —$CO(C_1$-$C_3$ alkylene)-$NR^eSR^f$, —$CO(C_1$-$C_3$ alkylene)-$NR^eSOR^g$, —$CO(C_1$-$C_3$ alkylene)-$NR^eSO_2R^f$, —$CO(C_2$-$C_3$ alkenyl), —CO ($C_1$-$C_3$ haloalkyl), —$CO(CH_2)$(cycloalkyl), —CO ($CH_2)_n$(optionally substituted aryl), —$CO(CH_2)_n$ (optionally substituted heterocyclyl), —$CO(CH_2)_n$ (optionally substituted heteroaryl);

$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;

$R^e$ and $R^f$ are each independently selected from H, —$C_1$-$C_6$ alkyl, —$C_1$-$C_6$ haloalkyl, or —$C_1$-$C_6$ alkylene-OH;

$R^g$ is H, —$C_1$-$C_6$ alkyl, —$C_3$-$C_6$ cycloalkyl, —$C_1$-$C_6$ haloalkyl, phenyl, or benzyl; and $R^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-$NR^aR^b$.

In one embodiment of the compounds of formula (II), wherein $R^1$ is phenyl, optionally substituted with one or more $R^{1a}$.

In one embodiment of the compounds of formula (II), $R^2$ is phenyl, optionally substituted with one or more $R^{2a}$.

In one embodiment of the compounds of formula (II), $R^3$ is phenyl, optionally substituted with one or more $R^{3a}$.

In one embodiment of the compounds of formula (II), $R^{1a}$ is —$NO_2$.

In one embodiment of the compounds of formula (II), $R^{2a}$ is halogen, $C_1$-$C_3$ alkyl, —$S(C_1$-$C_3$ alkyl), —$NH_2$, —NH ($C_1$-$C_3$ alkyl), or —$N(C_1$-$C_3$ alkyl)$_2$.

In one embodiment of the compounds of formula (II), $R^{3a}$ is halogen, $C_1$-$C_4$ alkyl, $C_1$-$C_4$ haloalkyl, —$O(C_1$-$C_3$ alkyl), —$S(C_1$-$C_3$ alkyl), —$SO(C_1$-$C_3$ alkyl), —$SO_2(C_1$-$C_3$ alkyl), —CN, —$NO_2$, —$NH_2$, —NH($C_1$-$C_3$ alkyl), or —$N(C_1$-$C_3$ alkyl)$_2$.

In one aspect, the present disclosure relates to compounds of formula (III):

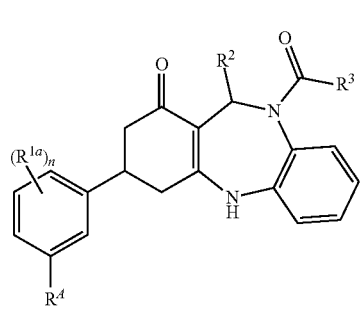

(III)

or a pharmaceutically acceptable salt thereof, wherein
$R^2$ is aryl or heteroaryl, optionally substituted with one or more $R^{2a}$;

R$^3$ is alkyl, cycloalkyl, aryl, -alkylaryl, heterocyclyl, or heteroaryl, optionally substituted with one or more R$^{3a}$; and R$^{1a}$, R$^{2a}$, and R$^{3a}$ is each independently selected from halogen, —OH, —CN, —NO$_2$, —C$_1$-C$_6$ alkyl, —C$_2$-C$_6$ alkenyl, —C$_2$-C$_6$ alkynyl, —C$_1$-C$_6$ haloalkyl, —C$_1$-C$_6$ alkoxy, —C$_1$-C$_6$ haloalkoxy, —C$_3$-C$_6$ cycloalkyl, —S(C$_1$-C$_6$ alkyl), —SO(C$_1$-C$_6$ alkyl), —SO$_2$(C$_1$-C$_6$ alkyl), —COR$^g$, —NR$^a$R$^b$, —OCOR$^9$, —OCOOR$^g$, —OCO(optionally substituted heterocyclyl), —NR$^a$COR$^9$, —NR$^a$CO(optionally substituted heterocyclyl), —NR$^a$COOR$^g$, —NR$^a$CONR$^a$R$^b$, —CONR$^a$R$^b$, —CONR$^c$R$^d$, heterocyclyl, heteroaryl, or aryl;

R$^A$ is selected from H, halogen, —OH, —CN, —NO$_2$, —C$_1$-C$_6$ alkyl, —C$_2$-C$_6$ alkenyl, —C$_2$-C$_6$ alkynyl, —C$_1$-C$_6$ haloalkyl, —C$_1$-C$_6$ alkoxy, —C$_1$-C$_6$ haloalkoxy, —C$_3$-C$_6$ cycloalkyl, —S(C$_1$-C$_6$ alkyl), —SO(C$_1$-C$_6$ alkyl), —SO$_2$(C$_1$-C$_6$ alkyl), —COR$^9$, —NR$^a$R$^b$, —OCOR$^9$, —OCOOR$^g$, —OCO(optionally substituted heterocyclyl), —NR$^a$COR$^9$, —NR$^a$CO(optionally substituted heterocyclyl), —NR$^a$COOR$^9$, —NR$^a$CONR$^a$R$^b$, —CONR$^a$R$^b$, —CONR$^c$R$^d$, heterocyclyl, heteroaryl, or aryl;

R$^a$ and R$^b$ are each independently selected from H, —C$_1$-C$_6$ alkyl, —C$_1$-C$_6$ haloalkyl, —CHO, —CO(C$_1$-C$_3$ alkyl), —CO(C$_1$-C$_6$ alkylene)-OH, —CONR$^e$R$^f$, —CO(C$_1$-C$_3$ alkylene)-NR$^e$R$^f$, —CO(C$_1$-C$_3$ alkylene)-NR$^e$SR$^f$, —CO(C$_1$-C$_3$ alkylene)-NR$^e$SOR$^g$, —CO(C$_1$-C$_3$ alkylene)-NR$^e$SO$_2$R$^f$, —CO(C$_2$-C$_3$ alkenyl), —CO(C$_1$-C$_3$ haloalkyl), —CO(CH$_2$)(cycloalkyl), —CO(CH$_2$)$_n$(optionally substituted aryl), —CO(CH$_2$)$_n$(optionally substituted heterocyclyl), —CO(CH$_2$)$_n$(optionally substituted heteroaryl);

R$^c$ and R$^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;

R$^e$ and R$^f$ are each independently selected from H, —C$_1$-C$_6$ alkyl, —C$_1$-C$_6$ haloalkyl, or —C$_1$-C$_6$ alkylene-OH;

R$^g$ is H, —C$_1$-C$_6$ alkyl, —C$_3$-C$_6$ cycloalkyl, —C$_1$-C$_6$ haloalkyl, phenyl, or benzyl;

R$^9$ is —C$_1$-C$_3$ alkylene-OH, —C$_1$-C$_3$ alkylene-CN, —C$_1$-C$_3$ alkylene-(C$_1$-C$_3$ alkoxy), or —C$_1$-C$_3$ alkylene-NR$^a$R$^b$; and n is 0, 1, 2, 3, or 4.

In one embodiment of the compounds of formula (III), R$^A$ is H or —NO$_2$.

In one embodiment of the compounds of formula (III), n is 0 or 1.

In one embodiment of the compounds of formula (III), R$^2$ is phenyl, optionally substituted with one or more R$^{2a}$.

In one embodiment of the compounds of formula (III), R$^3$ is phenyl, optionally substituted with one or more R$^{3a}$.

In one embodiment of the compounds of formula (III), R$^{2a}$ is halogen, C$_1$-C$_3$ alkyl, —S(C$_1$-C$_3$ alkyl), —NH$_2$, —NH(C$_1$-C$_3$ alkyl), or —N(C$_1$-C$_3$ alkyl)$_2$.

In one embodiment of the compounds of formula (III), R$^{3a}$ is halogen, C$_1$-C$_4$ alkyl, C$_1$-C$_4$ haloalkyl, —O(C$_1$-C$_3$ alkyl), —S(C$_1$-C$_3$ alkyl), —SO(C$_1$-C$_3$ alkyl), —SO$_2$(C$_1$-C$_3$ alkyl), —CN, —NO$_2$, —NH$_2$, —NH(C$_1$-C$_3$ alkyl), or —N(C$_1$-C$_3$ alkyl)$_2$.

In one aspect, the present disclosure relates to compounds of formula (IV):

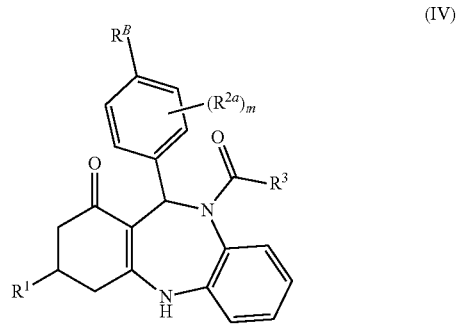

(IV)

or a pharmaceutically acceptable salt thereof, wherein

R$^1$ is aryl or heteroaryl, optionally substituted with one or more R$^{1a}$;

R$^3$ is alkyl, cycloalkyl, aryl, -alkylaryl, heterocyclyl, or heteroaryl, optionally substituted with one or more R$^{3a}$; and R$^{1a}$, R$^{2a}$, and R$^{3a}$ is each independently selected from halogen, —OH, —CN, —NO$_2$, —C$_1$-C$_6$ alkyl, —C$_2$-C$_6$ alkenyl, —C$_2$-C$_6$ alkynyl, —C$_1$-C$_6$ haloalkyl, —C$_1$-C$_6$ alkoxy, —C$_1$-C$_6$ haloalkoxy, —C$_3$-C$_6$ cycloalkyl, —S(C$_1$-C$_6$ alkyl), —SO(C$_1$-C$_6$ alkyl), —SO$_2$(C$_1$-C$_6$ alkyl), —COR$^g$, —NR$^a$R$^b$, —OCOR$^9$, —OCOOR$^g$, —OCO(optionally substituted heterocyclyl), —NR$^a$COR$^9$, —NR$^a$CO(optionally substituted heterocyclyl), —NR$^a$COOR$^g$, —NR$^a$CONR$^a$R$^b$, —CONR$^a$R$^b$, —CONR$^c$R$^d$, heterocyclyl, heteroaryl, or aryl;

R$^B$ is selected from H, halogen, —OH, —CN, —NO$_2$, —C$_1$-C$_6$ alkyl, —C$_2$-C$_6$ alkenyl, —C$_2$-C$_6$ alkynyl, —C$_1$-C$_6$ haloalkyl, —C$_1$-C$_6$ alkoxy, —C$_1$-C$_6$ haloalkoxy, —C$_3$-C$_6$ cycloalkyl, —S(C$_1$-C$_6$ alkyl), —SO(C$_1$-C$_6$ alkyl), —SO$_2$(C$_1$-C$_6$ alkyl), —COR$^9$, —NR$^a$R$^b$, —OCOR$^9$, —OCOOR$^g$, —OCO(optionally substituted heterocyclyl), —NR$^a$COR$^9$, —NR$^a$CO(optionally substituted heterocyclyl), —NR$^a$COOR$^g$, —NR$^a$CONR$^a$R$^b$, —CONR$^a$R$^b$, —CONR$^c$R$^d$, heterocyclyl, heteroaryl, or aryl;

R$^a$ and R$^b$ are each independently selected from H, —C$_1$-C$_6$ alkyl, —C$_1$-C$_6$ haloalkyl, —CHO, —CO(C$_1$-C$_3$ alkyl), —CO(C$_1$-C$_6$ alkylene)-OH, —CONR$^e$R$^f$, —CO(C$_1$-C$_3$ alkylene)-NR$^e$R$^f$, —CO(C$_1$-C$_3$ alkylene)-NR$^e$SR$^f$, —CO(C$_1$-C$_3$ alkylene)-NR$^e$SOR$^g$, —CO(C$_1$-C$_3$ alkylene)-NR$^e$SO$_2$R$^f$, —CO(C$_2$-C$_3$ alkenyl), —CO(C$_1$-C$_3$ haloalkyl), —CO(CH$_2$)(cycloalkyl), —CO(CH$_2$)$_n$(optionally substituted aryl), —CO(CH$_2$)$_n$(optionally substituted heterocyclyl), —CO(CH$_2$)$_n$(optionally substituted heteroaryl);

R$^c$ and R$^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;

R$^e$ and R$^f$ are each independently selected from H, —C$_1$-C$_6$ alkyl, —C$_1$-C$_6$ haloalkyl, or —C$_1$-C$_6$ alkylene-OH;

R$^g$ is H, —C$_1$-C$_6$ alkyl, —C$_3$-C$_6$ cycloalkyl, —C$_1$-C$_6$ haloalkyl, phenyl, or benzyl;

R$^9$ is —C$_1$-C$_3$ alkylene-OH, —C$_1$-C$_3$ alkylene-CN, —C$_1$-C$_3$ alkylene-(C$_1$-C$_3$ alkoxy), or —C$_1$-C$_3$ alkylene-NR$^a$R$^b$; and m is 0, 1, 2, 3, or 4.

In one embodiment of the compounds of formula (IV), $R^B$ is H, halogen, $C_1$-$C_3$ alkyl, —S($C_1$-$C_3$ alkyl), —NH$_2$, —NH($C_1$-$C_3$ alkyl), or —N($C_1$-$C_3$ alkyl)$_2$In one embodiment, $R^B$ is H, Me, Cl, F, —SCH$_3$, or —N(CH$_3$)$_2$.

In one embodiment of the compounds of formula (IV), m is 0 or 1.

In one embodiment of the compounds of formula (IV), $R^1$ is phenyl, optionally substituted with one or more $R^{1a}$.

In one embodiment of the compounds of formula (IV), $R^3$ is phenyl, optionally substituted with one or more $R^{3a}$.

In one embodiment of the compounds of formula (IV), $R^{1a}$ is —NO$_2$.

In one embodiment of the compounds of formula (IV), $R^{3a}$ is halogen, $C_1$-$C_4$ alkyl, $C_1$-$C_4$ haloalkyl, —O($C_1$-$C_3$ alkyl), —S($C_1$-$C_3$ alkyl), —SO($C_1$-$C_3$ alkyl), —SO$_2$($C_1$-$C_3$ alkyl), —CN, —NO$_2$, —NH$_2$, —NH($C_1$-$C_3$ alkyl), or —N($C_1$-$C_3$ alkyl)$_2$.

In one aspect, the present disclosure relates to compounds of formula (V):

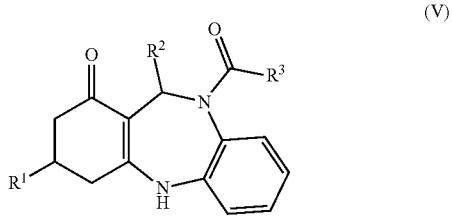

(V)

or a pharmaceutically acceptable salt thereof, wherein:
$R^1$ is aryl or heteroaryl, optionally substituted with one or more $R^{1a}$;
$R^2$ is aryl or heteroaryl, optionally substituted with one or more $R^{2a}$;
$R^3$ is $C_1$-$C_6$ alkyl, cyclohexyl, phenyl, benzyl, —CH$_2$CH$_2$-phenyl, benzodioxolyl, or thienyl, optionally substituted with one or more $R^{3a}$;
$R^{1a}$, $R^{2a}$, and $R^{3a}$ is each independently selected from halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, —S($C_1$-$C_6$ alkyl), —SO($C_1$-$C_6$ alkyl), —SO$_2$($C_1$-$C_6$ alkyl), —COR$^9$, —NR$^a$R$^b$, —OCOR$^9$, —OCOOR$^g$, —OCO(optionally substituted heterocyclyl), —NR$^a$COR$^9$, —NR$^a$CO(optionally substituted heterocyclyl), —NR$^a$COOR$^g$, —NR$^a$CONR$^a$R$^b$, —CONR$^a$R$^b$, —CONR$^c$R$^d$, heterocyclyl, heteroaryl, or aryl;
$R^a$ and $R^b$ are each independently selected from H, —$C_1$-$C_6$ alkyl, —$C_1$-$C_6$ haloalkyl, —CHO, —CO($C_1$-$C_3$ alkyl), —CO($C_1$-$C_6$ alkylene)-OH, —CONR$^e$R$^f$, —CO($C_1$-$C_3$ alkylene)-NR$^e$R$^f$, —CO($C_1$-$C_3$ alkylene)-NR$^e$SR$^f$, —CO($C_1$-$C_3$ alkylene)-NR$^e$SOR$^g$, —CO($C_1$-$C_3$ alkylene)-NR$^e$SO$_2$R$^f$, —CO($C_2$-$C_3$ alkenyl), —CO($C_1$-$C_3$ haloalkyl), —CO(CH$_2$)(cycloalkyl), —CO(CH$_2$)$_n$(optionally substituted aryl), —CO(CH$_2$)$_n$ (optionally substituted heterocyclyl), —CO(CH$_2$)$_n$ (optionally substituted heteroaryl);
$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;
$R^e$ and $R^f$ are each independently selected from H, —$C_1$-$C_6$ alkyl, —$C_1$-$C_6$ haloalkyl, or —$C_1$-$C_6$ alkylene-OH;

$R^g$ is H, —$C_1$-$C_6$ alkyl, —$C_3$-$C_6$ cycloalkyl, —$C_1$-$C_6$ haloalkyl, phenyl, or benzyl;
$R^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-NR$^a$R$^b$.

64. The compound of claim 63, wherein $R^3$ is methyl, cyclohexyl, phenyl, benzyl, —CH$_2$CH$_2$-phenyl, 2-methylphenyl, 3-methylphenyl, 4-methylphenyl, 3-fluorophenyl, 4-fluorophenyl, 4-nitrophenyl, 3-chlorophenyl, 4-chlorophenyl, 4-bromophenyl, 4-cyanophenyl, 4-dimethylaminophenyl, 4-trifluoromethylphenyl, 4-t-butylphenyl, 4-n-butylphenyl, 4-methoxylphenyl, 4-methoxylphenyl, 4-methylsulfonylphenyl, 4-methylthiophenyl, 2-thienyl, or benzodioxolyl.

In one embodiment of the compounds of formula (V), $R^3$ is 4-methylphenyl, 4-dimethylaminophenyl, 4-t-butylphenyl, or 4-n-butylphenyl.

In one embodiment of the compounds of formula (V), $R^1$ is phenyl, optionally substituted with one or more $R^{1a}$.

In one embodiment of the compounds of formula (V), $R^2$ is phenyl, optionally substituted with one or more $R^{2a}$.

In one embodiment of the compounds of formula (V), $R^3$ is phenyl, optionally substituted with one or more $R^{3a}$.

In one embodiment of the compounds of formula (V), $R^{1a}$ is —NO$_2$.

In one embodiment of the compounds of formula (V), $R^{2a}$ is halogen, $C_1$-$C_3$ alkyl, —S($C_1$-$C_3$ alkyl), —NH$_2$, —NH($C_1$-$C_3$ alkyl), or —N($C_1$-$C_3$ alkyl)$_2$.

In one embodiment of the compounds of formula (V), $R^{3a}$ is halogen, $C_1$-$C_4$ alkyl, $C_1$-$C_4$ haloalkyl, —O($C_1$-$C_3$ alkyl), —S($C_1$-$C_3$ alkyl), —SO($C_1$-$C_3$ alkyl), —SO$_2$($C_1$-$C_3$ alkyl), —CN, —NO$_2$, —NH$_2$, —NH($C_1$-$C_3$ alkyl), or —N($C_1$-$C_3$ alkyl)$_2$. In one embodiment, $R^{3a}$ is $C_1$-$C_4$ alkyl or —N($C_1$-$C_3$ alkyl)$_2$.

In one aspect, the present disclosure relates to compounds of formula (VI):

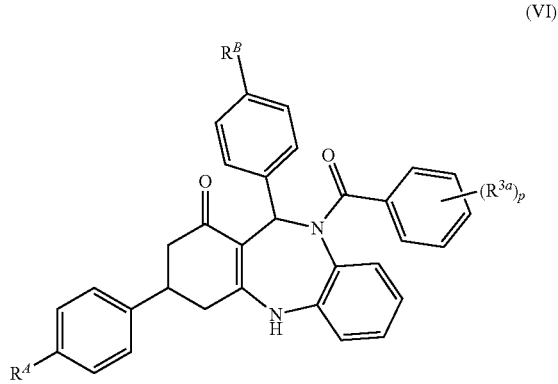

(VI)

or a pharmaceutically acceptable salt thereof, wherein
$R^{3a}$ is each independently selected from halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, —S($C_1$-$C_6$ alkyl), —SO($C_1$-$C_6$ alkyl), —SO$_2$($C_1$-$C_6$ alkyl), —COR$^9$, —NR$^a$R$^b$, —OCOR$^9$, —OCOOR$^9$, —OCO(optionally substituted heterocyclyl), —NR$^a$COR$^9$, —NR$^a$CO(optionally substituted heterocyclyl), —NR$^a$COOR$^g$, —NR$^a$CONR$^a$R$^b$, —CONR$^a$R$^b$, —CONR$^c$R$^d$, heterocyclyl, heteroaryl, or aryl;
$R^A$ and $R^B$ are each independently selected from H, halogen, —OH, —CN, —NO$_2$, —$C_1$-$C_6$ alkyl, —$C_2$-

$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, —S($C_1$-$C_6$ alkyl), —SO($C_1$-$C_6$ alkyl), —SO$_2$($C_1$-$C_6$ alkyl), —COR$^g$, —NR$^a$R$^b$, —OCOR$^9$, —OCOOR$^g$, —OCO(optionally substituted heterocyclyl), —NR$^a$COR$^9$, —NR$^a$CO(optionally substituted heterocyclyl), —NR$^a$COOR$^9$, —NR$^a$CONR$^a$R$^b$, —CONR$^a$R$^b$, —CONR$^e$R$^d$, heterocyclyl, heteroaryl, or aryl;

R$^a$ and R$^b$ are each independently selected from H, —$C_1$-$C_6$ alkyl, —$C_1$-$C_6$ haloalkyl, —CHO, —CO($C_1$-$C_3$ alkyl), —CO($C_1$-$C_6$ alkylene)-OH, —CONR$^e$R$^f$, —CO($C_1$-$C_3$ alkylene)-NR$^e$R$^f$, —CO($C_1$-$C_3$ alkylene)-NR$^e$SR$^f$, —CO($C_1$-$C_3$ alkylene)-NR$^e$SOR$^g$, —CO($C_1$-$C_3$ alkylene)-NR$^e$SO$_2$R$^f$, —CO($C_2$-$C_3$ alkenyl), —CO($C_1$-$C_3$ haloalkyl), —CO(CH$_2$)(cycloalkyl), —CO(CH$_2$)$_n$(optionally substituted aryl), —CO(CH$_2$)$_n$(optionally substituted heterocyclyl), —CO(CH$_2$)$_n$(optionally substituted heteroaryl);

R$^e$ and R$^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;

R$^e$ and R$^f$ are each independently selected from H, —$C_1$-$C_6$ alkyl, —$C_1$-$C_6$ haloalkyl, or —$C_1$-$C_6$ alkylene-OH;

R$^g$ is H, —$C_1$-$C_6$ alkyl, —$C_3$-$C_6$ cycloalkyl, —$C_1$-$C_6$ haloalkyl, phenyl, or benzyl;

R$^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-NR$^a$R$^b$; and p is 0, 1, 2, 3, or 4.

In one embodiment of the compounds of formula (VI), R$^A$ is H or —NO$_2$.

In one embodiment of the compounds of formula (VI), R$^B$ is H, halogen, $C_1$-$C_3$ alkyl, —S($C_1$-$C_3$ alkyl), —NH$_2$, —NH($C_1$-$C_3$ alkyl), or —N($C_1$-$C_3$ alkyl)$_2$. In one embodiment, R$^B$ is H, Me, Cl, F, —SCH$_3$, or —N(CH$_3$)$_2$.

In one embodiment of the compounds of formula (VI), R$^{3a}$ is halogen, $C_1$-$C_4$ alkyl, $C_1$-$C_4$ haloalkyl, —O($C_1$-$C_3$ alkyl), —S($C_1$-$C_3$ alkyl), —SO($C_1$-$C_3$ alkyl), —SO$_2$($C_1$-$C_3$ alkyl), —CN, —NO$_2$, —NH$_2$, —NH($C_1$-$C_3$ alkyl), or —N($C_1$-$C_3$ alkyl)$_2$. In one embodiment, R$^{3a}$ is $C_1$-$C_4$ alkyl or —N($C_1$-$C_3$ alkyl)$_2$.

In one aspect, the present disclosure relates to compounds of formula (VII):

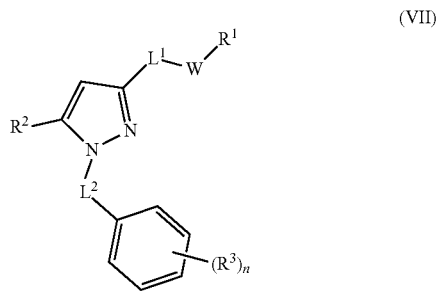

(VII)

or a pharmaceutically acceptable salt thereof, wherein
L$^1$ is —NR$^7$C(=O)—, —CONR$^7$—, —CH$_2$C(=O)—, —C(=O)CH$_2$—, —OC(=O)—, —C(=O)O—, —SC(=O)—, —C(=O)S—, —NRC(=O)—, —CH$_2$NR$^7$—, —CH$_2$CH$_2$—, —OCH$_2$—, —CH$_2$O—, —SCH$_2$—, —CH$_2$S—, —NR$^7$SO$_2$—, —SO$_2$NR$^7$—, —CH$_2$SO$_2$—, —SO$_2$CH$_2$—, —OSO$_2$—, —SO$_2$O—, —NR$^7$—, L$^2$ is —SO$_2$—, —C(=O)—, —CH$_2$—, —CH$_2$CH$_2$—, —CHR$^6$—, W is arylene or heteroarylene, each optionally substituted with one or more R$^4$;

R$^1$ is aryl or heteroaryl, each optionally substituted with one or more R$^4$;

R$^2$ is selected NH$_2$, or NHR$^{11}$;

R$^3$ is halogen, —CN, —NO$_2$, —SCH$_3$, —COR$^5$, —$C_1$-$C_6$ alkyl, —$C_3$-$C_6$ cycloalkyl, $C_1$-$C_6$ haloalkyl, $C_1$-$C_6$ alkoxy, or —$C_1$-$C_6$ haloalkoxy, R$^4$ is halogen, —CN, —NO$_2$, —SCH$_3$, —COR$^5$, —$C_1$-$C_6$ alkyl, —$C_3$-$C_6$ cycloalkyl, $C_1$-$C_6$ haloalkyl, $C_1$-$C_6$ alkoxy, or —$C_1$-$C_6$ haloalkoxy;

R$^5$ is H, —$C_1$-$C_6$ alkyl, —$C_3$-$C_6$ cycloalkyl, or —$C_1$-$C_6$ haloalkyl;

R$^6$ is selected halogen, —CN, —NO$_2$, —SCH$_3$, —COR$^5$, —$C_1$-$C_6$ alkyl, —$C_3$-$C_6$ cycloalkyl, $C_1$-$C_6$ haloalkyl, $C_1$-$C_6$ alkoxy, or —$C_1$-$C_6$ haloalkoxy, R$^7$ is —$C_1$-$C_6$ alkyl, —$C_1$-$C_6$ haloalkyl, —$C_1$-$C_6$ alkoxy, —$C_1$-$C_3$ alkylene-OH, —$C_1$-$C_3$ alkylene-($C_1$-$C_3$ alkoxy), —COO($C_1$-$C_6$ alkyl); and n is 0, 1, 2, 3, 4, or 5.

In one embodiment of the compounds of formula (VII), W is phenylene, optionally substituted with one or two R$^4$. In one embodiment, W is

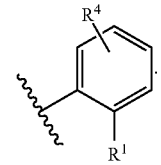

In one embodiment of the compounds of formula (VII), W is 5- or 6-membered heteroarylene, optionally substituted with one or two R$^4$. In one embodiment, W is divalent oxazole or isoxazole, optionally substituted with one or two R$^4$. In one embodiment, W is

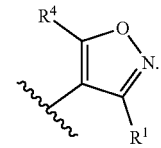

In one embodiment of the compounds of formula (VII), R$^1$ is phenyl, optionally substituted with one or two R$^4$.

In one embodiment of the compounds of formula (VII), —W—R$^1$ is

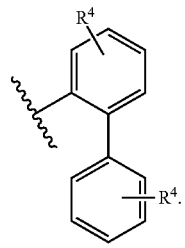

In one embodiment of the compounds of formula (VII), $R^4$ is selected from halogen, —$C_1$-$C_3$ alkyl, —$C_1$-$C_3$ haloalkyl, or $C_1$-$C_3$ alkoxy.

In one embodiment of the compounds of formula (VII), $L^1$ is —NHC(=O)—, —CONH—, —NCH$_3$C(=O)—, —CONCH$_3$—, —CH$_2$C(=O)—, —C(=O)CH$_2$—, —OC(=O)—, —C(=O)O—, —SC(=O)—, —C(=O)S—, —NHC(=O)—, —CH$_2$NH—, —NCH$_3$C(=O)—, —CH$_2$NCH$_3$—, —CH$_2$CH$_2$—, —OCH$_2$—, —CH$_2$O—, —SCH$_2$—, —CH$_2$S—, —NHSO$_2$—, —SO$_2$NH—, —NCH$_3$SO$_2$—, —SO$_2$NCH$_3$—, —CH$_2$SO$_2$—, —SO$_2$CH$_2$—, —OSO$_2$—, or —SO$_2$O—.

In one embodiment of the compounds of formula (VII), $R^2$ is —NH$_2$.

In one embodiment of the compounds of formula (VII), $R^3$ is selected from halogen, —$C_1$-$C_3$ alkyl, —$C_1$-$C_3$ haloalkyl, or $C_1$-$C_3$ alkoxy. In one embodiment, $R^3$ is selected from halogen, methyl, methoxy, or —CF$_3$.

In one embodiment of the compounds of formula (VII), n is 1 and $R^3$ is para to $L^2$.

In one aspect, the present disclosure relates to compounds of formula (VIII):

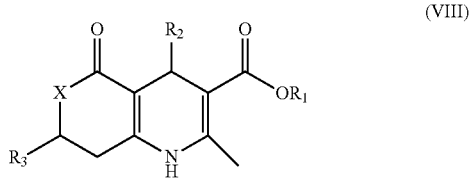

(VIII)

or a pharmaceutically acceptable salt thereof, wherein
$R^1$ is alkyl, cycloalkyl, aryl, -alkylaryl, heterocyclyl, or heteroaryl, optionally substituted with one or more $R^{1a}$;
$R^2$ is aryl or heteroaryl, optionally substituted with one or more $R^{2a}$;
$R^3$ is H, or —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, aryl or heteroaryl, optionally substituted with one or more $R^{3a}$
$R^{1a}$ is each independently selected from halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, —S($C_1$-$C_6$ alkyl), —SO($C_1$-$C_6$ alkyl), —SO$_2$($C_1$-$C_6$ alkyl), —COR$^g$, —NR$^a$R$^b$, —OCOR$^9$, —OCOOR$^g$, —OCO(optionally substituted heterocyclyl), heterocyclyl, heteroaryl, or aryl
$R^{2a}$ and $R^{3a}$ is each independently selected from halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, —$C_3$-$C_6$ cycloalkyl, —S($C_1$-$C_6$ alkyl), —SO($C_1$-$C_6$ alkyl), —SO$_2$($C_1$-$C_6$ alkyl), —COR$^g$, —NR$^a$R$^b$, —OCOR$^9$, —OCOOR$^g$, —OCO(optionally substituted heterocyclyl), —NR$^a$COOR$^g$, —NR$^a$CONR$^a$R$^b$, —CONR$^a$R$^b$, —CONR$^c$R$^d$, heterocyclyl, heteroaryl, or aryl;
$R^a$ and $R^b$ are each independently selected from H, —$C_1$-$C_6$ alkyl, —$C_1$-$C_6$ haloalkyl, —CHO, —CO($C_1$-$C_3$ alkyl), —CO($C_1$-$C_6$ alkylene)-OH, —CONR$^e$R$^f$, —CO($C_1$-$C_3$ alkylene)-NR$^e$R$^f$, —CO($C_1$-$C_3$ alkylene)-NR$^e$SR$^f$, —CO($C_1$-$C_3$ alkylene)-NR$^e$SOR$^g$, —CO($C_1$-$C_3$ alkylene)-NR$^e$SO$_2$R$^f$, —CO($C_2$-$C_3$ alkenyl), —CO($C_1$-$C_3$ haloalkyl), —CO(CH$_2$)$_n$(cycloalkyl), —CO(CH$_2$)$_n$(optionally substituted aryl), —CO(CH$_2$)$_n$(optionally substituted heterocyclyl), —CO(CH$_2$)$_n$(optionally substituted heteroaryl);
$R^c$ and $R^d$ together with the nitrogen atom to which it is attached to form an optionally substituted ring, which can be monocyclic, fused bicyclic, or spiral bicyclic, wherein the ring atom can contain up to 3 heteroatoms selected from N, O, or S;
$R^e$ and $R^f$ are each independently selected from H, —$C_1$-$C_6$ alkyl, —$C_1$-$C_6$ haloalkyl, or —$C_1$-$C_6$ alkylene-OH;
$R^g$ is H, —$C_1$-$C_6$ alkyl, —$C_3$-$C_6$ cycloalkyl, —$C_1$-$C_6$ haloalkyl, phenyl, or benzyl;
$R^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-NR$^a$R$^b$; and
X is, O or NH, or CH$_2$ optionally substituted with —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, —$C_1$-$C_6$ haloalkoxy, o-$C_3$-$C_6$ cycloalkyl, —COR$^g$, —NR$^a$R$^b$, or —OCOR$^9$.

In one embodiment of the compounds of formula (VIII), $R_2$ is phenyl optionally substituted with one or more with one or more $R^{2a}$.

In one embodiment of the compounds of formula (VIII), at least one $R^{2a}$ is halogen, —CN or —NO$_2$.

In one embodiment of the compounds of formula (VIII), at least one $R^{2a}$ is —NO$_2$.

In one embodiment of the compounds of formula (VIII), $R_1$ is —$C_1$-$C_6$ alkyl.

In one embodiment of the compounds of formula (VIII), $R_3$ is aryl or heteroaryl, optionally substituted with one or more halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, or —$C_1$-$C_6$ haloalkoxy. In one embodiment, $R_3$ is phenyl or thienyl optionally substituted with one or more halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, or —$C_1$-$C_6$ haloalkoxy. In one embodiment, $R_3$ is phenyl or thienyl optionally substituted with one or more halogen or —OCH$_3$. In one embodiment, $R_3$ is phenyl substituted with Cl.

In one embodiment of the compounds of formula (VIII), X is CH$_2$.

In one embodiment of the compounds of formula (VIII), $R_1$ is —$C_1$-$C_6$ alkyl;
$R_2$ is phenyl optionally substituted with one or more with one or more $R^{2a}$,
$R_3$ is aryl or heteroaryl, optionally substituted with one or more halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, or —$C_1$-$C_6$ haloalkoxy; and
X is CH$_2$.

In one embodiment of the compounds of formula (VIII), $R^{2a}$ is halogen, —CN or —NO$_2$.

In one embodiment of the compounds of formula (VIII), at least one $R^{2a}$ is —NO$_2$.

In one embodiment of the compounds of formula (VIII), $R_1$ is —$C_1$-$C_6$ alkyl;
$R_2$ is phenyl optionally substituted with one or more with one or more $R^{2a}$,
$R_3$ is phenyl or thienyl optionally substituted with one or more halogen, —OH, —CN, —NO$_2$, —$C_1$-$C_6$ alkyl, —$C_2$-$C_6$ alkenyl, —$C_2$-$C_6$ alkynyl, —$C_1$-$C_6$ haloalkyl, —$C_1$-$C_6$ alkoxy, or —$C_1$-$C_6$ haloalkoxy; and
X is CH$_2$.

In one embodiment of the compounds of formula (VIII), $R_1$ is —$C_1$-$C_6$ alkyl;

R₂ is phenyl optionally substituted with one or more with one or more R²ᵃ,

R₃ is phenyl or thienyl optionally substituted with one or more halogen or —OCH₃; and X is CH₂.

In one embodiment of the compounds of formula (VIII),

R₁ is —C₁-C₆ alkyl;

R₂ is phenyl optionally substituted with one or more with one or more R²ᵃ,

R₃ is phenyl substituted with Cl; and

X is CH₂.

In one embodiment of the compounds of formula (VIII),

R₁ is —C₁-C₆ alkyl;

R₂ is phenyl optionally substituted with one or more with one or more R²ᵃ,

R²ᵃ is halogen, —CN or —NO₂ and R₃ is phenyl or thienyl optionally substituted with one or more halogen or —OCH₃;

R₃ is aryl or heteroaryl, optionally substituted with one or more halogen, —OH, —CN, —NO₂, —C₁-C₆ alkyl, —C₂-C₆ alkenyl, —C₂-C₆ alkynyl, —C₁-C₆ haloalkyl, —C₁-C₆ alkoxy, or —C₁-C₆ haloalkoxy; and X is CH₂.

In one embodiment of the compounds of formula (VIII),

R₁ is isopropyl;

R₂ is phenyl optionally substituted with one or more with one or more R²ᵃ,

R₃ is aryl or heteroaryl, optionally substituted with one or more halogen, —OH, —CN, —NO₂, —C₁-C₆ alkyl, —C₂-C₆ alkenyl, —C₂-C₆ alkynyl, —C₁-C₆ haloalkyl, —C₁-C₆ alkoxy, or —C₁-C₆ haloalkoxy; and X is CH₂.

In one aspect, the present disclosure relates to pharmaceutical compositions comprising a compound of formula (A) or (I)-(VIII) or a pharmaceutically acceptable salt thereof, and a pharmaceutically acceptable carrier or excipient.

In one aspect, the present disclosure relates to methods of treating a subject suffering from or diagnosed with a disease, disorder, or medical condition mediated by orexin receptor activity, wherein the disease, disorder, or medical condition is a disorder of the sleep-wake cycle, insomnia, restless legs syndrome, jet-lag, disturbed sleep, a sleep disorder secondary to neurological disorders, mania, depression, manic depression, schizophrenia, a pain syndromes, fibromyalgia, neuropathic pain, catatonia, Parkinson's disease, Tourette's syndrome, anxiety, delirium, dementia, overweight, obesity or a condition related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, hypertension, tachycardia, arrhythmias, angina pectoris, acute heart failure, ulcers, irritable bowel syndrome, diarrhea, gastroesophageal reflux, post-traumatic stress disorder, panic disorders, attention deficit disorders, cognitive deficiencies, or substance abuse, comprising administering to the subject an effective amount of a compound of formula (A) or (I)-(VIII) or a pharmaceutically acceptable salt thereof.

In one aspect, the present disclosure relates to methods for the treatment of one or more sleep disorders, comprising administering to the subject an effective amount of a compound of formula (A) or (I)-(VIII) or a pharmaceutically acceptable salt thereof.

In one aspect, the present disclosure relates to methods of promoting or enhancing wakefulness, anti-obesity, or recovery from general anesthesia or jet lag in a subject in need thereof, comprising administering to the subject an effective amount of a compound of formula (A) or (I)-(VIII) or a pharmaceutically acceptable salt thereof.

In one aspect, the present disclosure relates to methods of increasing resistance to diet-induced accumulation of body fat, comprising administering to the subject an effective amount of a compound of formula (A) or (I)-(VIII) or a pharmaceutically acceptable salt thereof.

In one aspect, the present disclosure relates to methods of shortening recovery period from general anesthesia or jet lag, comprising administering to the subject an effective amount of a compound of formula (A) or (I)-(VIII) or a pharmaceutically acceptable salt thereof.

In one aspect, the present disclosure relates to methods of treating narcolepsy in a subject in need thereof, comprising administering to the subject an effective amount of a compound of formula (A) or (I)-(VIII) or a pharmaceutically acceptable salt thereof.

In one aspect, the present disclosure relates to methods for agonizing a type-2 orexin receptor (OX2R), comprising contacting the OX2R with a compound of formula (A) or (I)-(VIII) or a pharmaceutically acceptable salt thereof.

In one embodiment of the methods of agonizing OX2R, the contacting is in a cell.

In one embodiment of any of the methods as disclosed herein, the compound is administered to the subject regularly and/or chronically.

In one embodiment of any of the methods as disclosed herein, the compound is administered to the subject orally.

In particular embodiments, the invention includes the compounds, genera, and subgenera in Tables 1-14.

Other aspects and embodiments of the invention are embodied in the following additional numbered Embodiments:

1. A OX2R agonist compound of formula I:

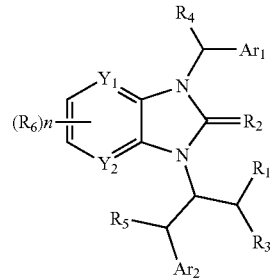

wherein:

Ar1 and Ar2 are independently optionally substituted C5-C10 aryl or heteroaryl (having from one to three heteroatoms selected from nitrogen, oxygen and sulfur);

Ar1 and Ar2 are independently optionally substituted phenyl;

Ar1 and Ar2 are independently phenyl, optionally substituted with halo, cyano, optionally fluorinated C1-C4 alkyl, or Ar1 and Ar2 are 4-methyl phenyl;

R1 is optionally substituted, optionally hetero-, optionally cyclic C1-C10 hydrocarbyl, or optionally substituted heteroatom;

R1 is amide, amine, hydroxyl, hydrocarbyloxy;

R1 is OR, NRR, NHCOR, CONRR, wherein each R is independently H, optionally fluorinated C1-C4 alkyl, etc.; or R1 is OH, OMe, OMeOR, NRR, CONRR, NHC(O)R, wherein each R is independently H, optionally fluorinated C1-C4 alkyl, etc.;

R2 together with its double bond is carbonyl or imine,

R2 is O or NR, wherein R is H, Me, tert-butyloxycarbonyl (Boc), optionally fluorinated C1-C4 alkyl, C1-C4 alkyloxy, C1-C4 alkyloxycarbonyl, etc.; or R2 is O or NH or NMe;

R3, R4 and R5 are independently H or optionally fluorinated C1-C4 alkyl (e.g. Me, Et, CF3, isopropyl, cyclopropyl, cyclobutyl), cyano, nitro, carboxyl, acetyl;

each R6 is independently optionally fluorinated C1-C4 alkyl (e.g. Me, Et, CF3, isopropyl, cyclopropyl, cyclobutyl), cyano, nitro, carboxyl, acetyl; or each R6 is independently halide, Me, CF3, CN, SMe, t-butyl, OCF3, OMe;

n is an integer 0-4; and

Y1 and Y2 are independently N or CR, where R is H or $R^6$; or a stereoisomer, hydrate or salt thereof.

2. The compound of Embodiment 1 wherein:

Ar1 and Ar2 are independently optionally substituted phenyl;

R1 is amide, amine, hydroxyl, hydrocarbyloxy; and

R2 together with its double bond is carbonyl or imine;

Y1 and Y2 are independently N or CH, or a stereoisomer, hydrate or salt thereof.

3. The compound of Embodiment 1 wherein:

Ar1 and Ar2 are independently phenyl, optionally substituted with halo, cyano, optionally fluorinated C1-C4 alkyl;

R1 is amide, amine, hydroxyl, hydrocarbyloxy; and

R2 together with its double bond is carbonyl or imine;

Y1 and Y2 are independently N or CH, or a stereoisomer, hydrate or salt thereof.

4. The compound of Embodiment 1 wherein:

Ar1 and Ar2 are 4-methyl phenyl;

R1 is OH, OMe, OMeOR, NRR, CONRR, NHC(O)R, wherein each R is independently H, optionally fluorinated C1-C4 alkyl;

R2 is O or NR, wherein R is H, Me, tert-butyloxycarbonyl (Boc), optionally fluorinated C1-C4 alkyl, C1-C4 alkyloxy, C1-C4 alkyloxycarbonyl;

R3, R4 and R5 are independently H or optionally fluorinated C1-C4 Me;

Y1 and Y2 are independently N or CH, or a stereoisomer, hydrate or salt thereof.

5. The compound of Embodiment 1 wherein:

Ar1 and Ar2 are 4-methyl phenyl;

R1 is OH, OMe, NHMe, NMe2, NHSO2R16 or NHCOR16, where R16 is Me, CF3, OH, OMe, OEt, ethyl, phenyl, cyclo propyl, isopropyl, benzyl, NH2, NRR, CONR2 (reverse amides) or NHC(O)R (amides), R2 is O or NH or NMe;

R3, R4 and R5 are independently H or optionally fluorinated C1-C4 Me;

n is 0;

Y1 and Y2 are independently N or CH, or a stereoisomer, hydrate or salt thereof.

6. The compound of Embodiment 1 wherein:

Ar1 and Ar2 are independently 4-methyl phenyl;

R1 is OH, OMe, NHMe, NMe2, NHSO2R16 or NHCOR16, where R16 is Me, CF3, OH, OMe, OEt, ethyl, phenyl, cyclo propyl, isopropyl, benzyl, NH2, NRR, CONR2 (reverse amides) or NHC(O)R (amides);

R2 is O or NH;

R3, R4 and R5 are independently H or optionally fluorinated C1-C4 Me;

n is 0;

Y1 and Y2 are N and CH, or a stereoisomer, hydrate or salt thereof.

7. The compound of Embodiment 1 wherein:

Ar1 and Ar2 are independently optionally substituted phenyl, and

R1 is OH, OMe, NHMe, $NMe_2$, $NHSO_2R16$ or NHCOR16, where R16 is Me, $CF_3$, OH, OMe, OEt, ethyl, phenyl, cyclo propyl, isopropyl, benzyl, NH2, NRR, CONR2 (reverse amides) or NHC(O)R (amides);

R1 is OH, OMe, OMeOR, NRR, CONRR, NHC(O)R, wherein each R is independently H, optionally fluorinated C1-C4 alkyl, etc.;

R2 is O, NH or NMe;

R3 is H;

R4 is H or Me; and

R5 is H or Me, n is 0;

Y1 and Y2 are N and CH, or a stereoisomer, hydrate or salt thereof.

8. The compound of Embodiment 1 wherein:

Ar1 and Ar2 are 4-methyl phenyl;

R1 is OMe;

R2 is O or NH;

R3 is H;

R4 is H or Me;

R5 is H or Me;

n is 0;

Y1 and Y2 are N and CH, or a stereoisomer, hydrate or salt thereof.

9. The compound of Embodiments 1, 2, 3, 4, 5, 6, 7 or 8 comprising all combinations wherein:

R is independently H, or optionally substituted, optionally hetero-, optionally cyclic C1-C10 hydrocarbyl, or optionally substituted heteroatom;

substituents are optionally substituted, optionally hetero-, optionally cyclic C1-C10 hydrocarbyl, or optionally substituted heteroatom, the hydrocarbyl is alkyl, akenyl, alkynyl, carbonyl, carbonothioyl, carbonothioyl, cyano, oxime or imine;

the carbonyl is ester, carboxyl, ketone, aldehyde, amide, acyl halide, acid anhydride or imide; and/or the optionally substituted heteroatom is halide, amine, nitro, nitroso, nitrile, cyanato, isocyanato, isocyano, oxo, hydroxyl, hydrocarbyloxy, nitrate, nitrosoxy, azo, azide, thiol, sulfide, sulfoxide, sulfonyl, sulfinic acids, sulfonic acid, thiocyanate, phosphate, phosphono or borono, or a stereoisomer, hydrate or salt thereof.

10. The compound of Embodiment 1 comprising a structure of Table 1, Table 2 or Table 3.

11. A pharmaceutical composition comprising the compound of any of Embodiments 1-10, a stereoisomer, hydrate or salt thereof, in effective unit dosage that promotes wakefulness, anti-obesity, or recovery from general anesthesia or jet lag.

12. A pharmaceutical composition of Embodiment 11 coformulated with a different compound which promotes wakefulness, anti-obesity, or recovery from general anesthesia or jet lag.

13. A pharmaceutical composition of Embodiment 11 formulated in unit dosages separately packaged in a multi-pack adapted for sequential use.

14. A method for agonizing a type-2 orexin receptor (OX2R) in a cell determined to be in need thereof, comprising the steps of:

contacting the receptor with the compound of any of Embodiments 1-10, or a stereoisomer, hydrate or salt thereof, or prodrug thereof; and optionally, detecting a resultant agonizing or activation of the receptor.

15. The method of Embodiment 14 wherein:

the cell is in situ in a subject, the compound or stereoisomer, hydrate or salt thereof, or prodrug thereof is orally administered to the subject, and the agonizing or activation is inferred from enhanced wakefulness or increased resistance to diet-induced accumulation of body fat, or abbreviated recovery from general anesthesia or jet lag;

the method comprises administering to the subject the compound or stereoisomer, hydrate or salt thereof, or prodrug thereof regularly and chronically;

the method comprises comprising administering to the subject the compound or stereoisomer, hydrate or salt thereof, or prodrug thereof in conjunction with an effective amount of a different compound which promotes wakefulness, anti-obesity, or recovery from general anesthesia or jet lag; or the method comprises comprising administering to the subject the compound or stereoisomer, hydrate or salt thereof, or prodrug thereof in unit dosage form, and comprising the antecedent step of removing a capsule or tablet comprising the unit dosage form from a multipack adapted for sequential use.

The disclosed orally active, blood-brain barrier permeable, small-molecule OX2R agonists provide effective physiological agonists and treatments for narcolepsy.

The disclosed OX2R agonists may also be used to promote or maintain proper wakefulness, and to treat medical conditions accompanying daytime sleepiness, such as nighttime insomnia, and depression with hypersomnia.

The disclosed OX2R agonists also provide treatments of obesity and associated metabolic syndrome, and may also be used to facilitate or expedite recovery from general anesthesia.

In particular embodiments, the method provides a therapy or prophylaxis, wherein the cell is in situ in a subject, the OX2R agonist is orally administered to the subject, and the agonizing or activation is inferred from a resultant physiological effect, such as enhanced wakefulness or increased resistance to diet-induced accumulation of body fat, or enhanced recovery from general anesthesia or jet lag. In more specific embodiments, this in situ protocol comprises (i) administering to the subject the OX2R agonist regularly and chronically; (ii) administering to the subject the OX2R agonist in conjunction with an effective amount of a different compound which promotes wakefulness, anti-obesity, or recovery from general anesthesia or jet lag; or (iii) administering to the subject the OX2R agonist in unit dosage form, and comprising the antecedent step of removing a capsule or tablet comprising the unit dosage form from a multipack adapted for sequential use.

The invention also provides pharmaceutical compositions comprising a subject OX2R agonist, particularly as coformulated with a different compound which promotes wakefulness, anti-obesity, or recovery from general anesthesia or jet lag, and/or formulated in unit dosages separately packaged in a multipack adapted for sequential use.

pharmaceutical composition comprising a subject OX2R agonist, including all embodiments described herein, coformulated with a different compound which promotes wakefulness, anti-obesity, or recovery from general anesthesia or jet lag A pharmaceutical composition comprising a subject OX2R agonist, including all embodiments described herein, formulated in unit dosages separately packaged in a multipack adapted for sequential use.

A method for agonizing a type-2 orexin receptor (OX2R) in a cell determined to be in need thereof, comprising the steps of:

contacting the receptor with a disclosed OX2R agonist, or a pharmaceutically acceptable salt thereof, or prodrug thereof; and optionally, detecting a resultant agonizing or activation of the receptor.

A method herein, wherein the cell is in situ in a subject, the OX2R agonist is orally administered to the subject, and the agonizing or activation is inferred from enhanced wakefulness or increased resistance to diet-induced accumulation of body fat, or abbreviated recovery from general anesthesia or jet lag.

A method herein comprising administering to the subject the OX2R agonist regularly and chronically.

A method herein comprising administering to the subject the OX2R agonist in conjunction with an effective amount of a different compound which promotes wakefulness, anti-obesity, or recovery from general anesthesia or jet lag.

A method herein comprising administering to the subject the OX2R agonist in unit dosage form, and comprising the antecedent step of removing a capsule or tablet comprising the unit dosage form from a multipack adapted for sequential use.

The invention includes all combinations of recited particular embodiments as if each combination had been laboriously recited.

DESCRIPTION OF PARTICULAR EMBODIMENTS OF THE INVENTION

Figures 1, 2:
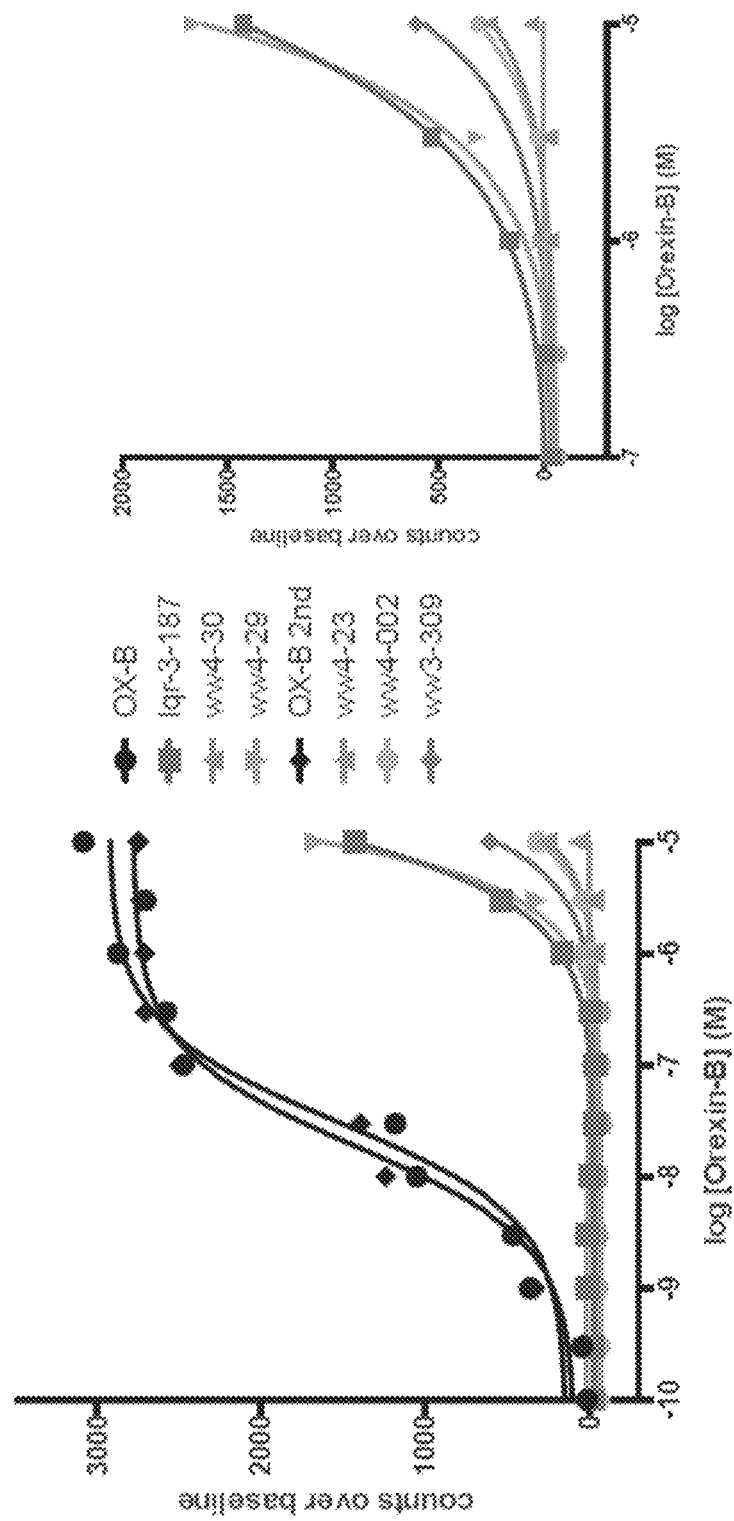
FIGS. 1-55 illustrate the IP accumulation assays for the compounds disclosed herein. Structures for these compounds can be found in Table 1.
Figure 3:
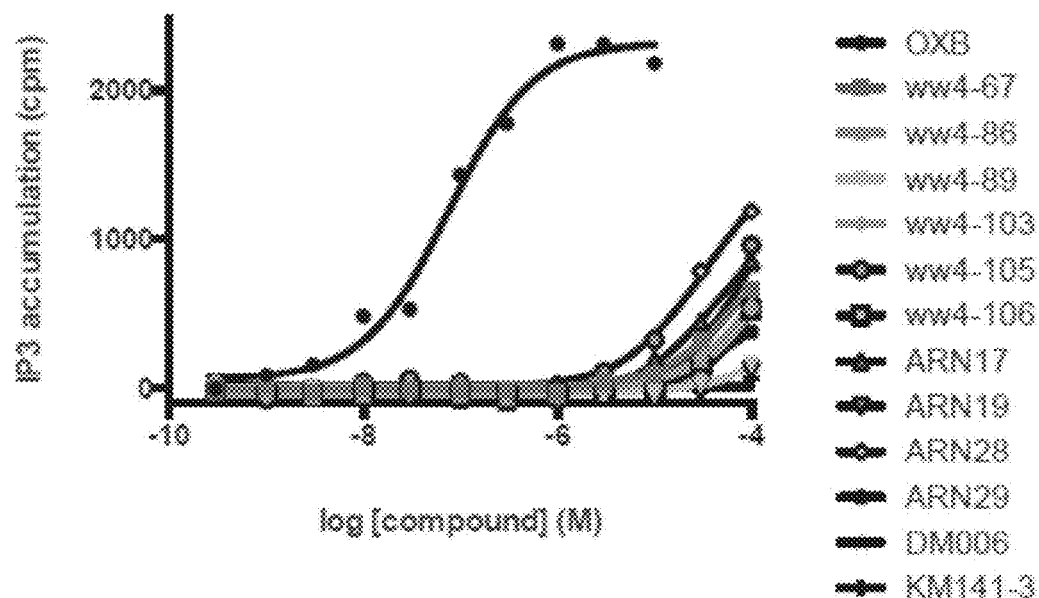
Figure 4:
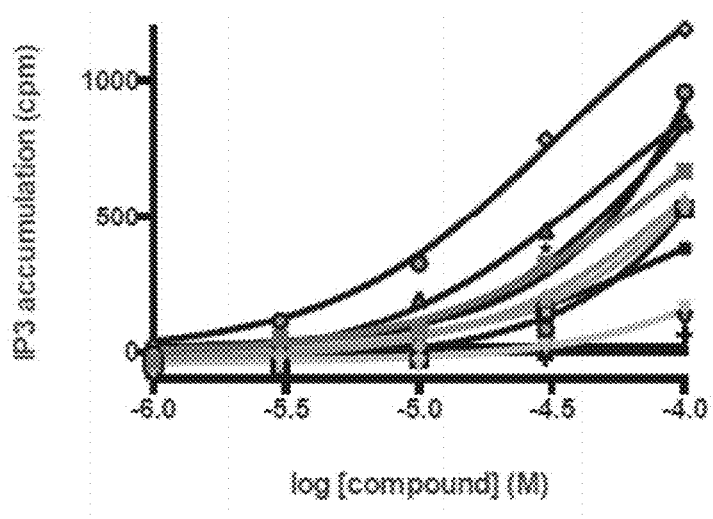
Figure 5:
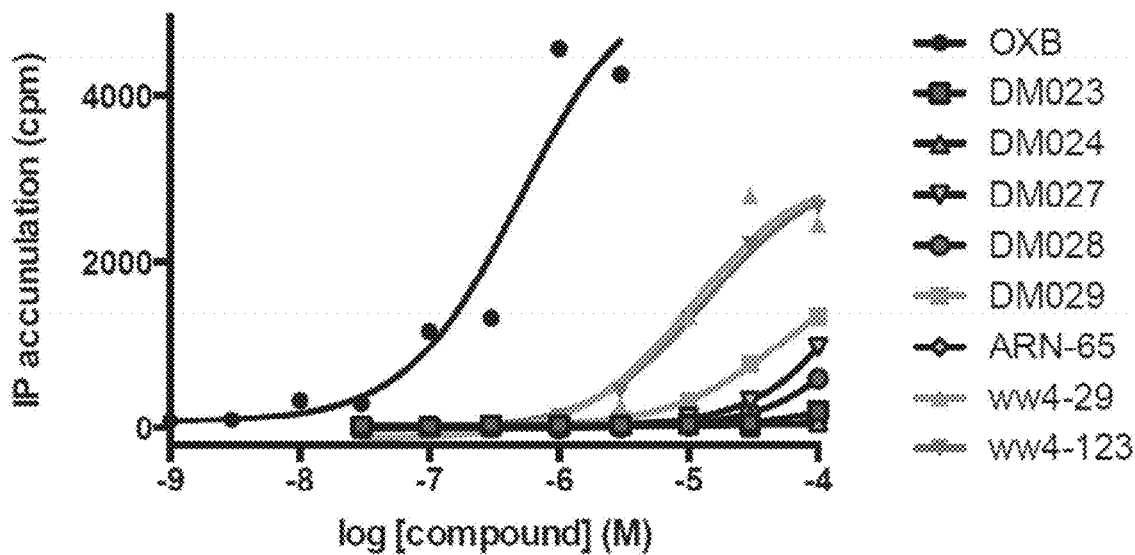
Figure 6:
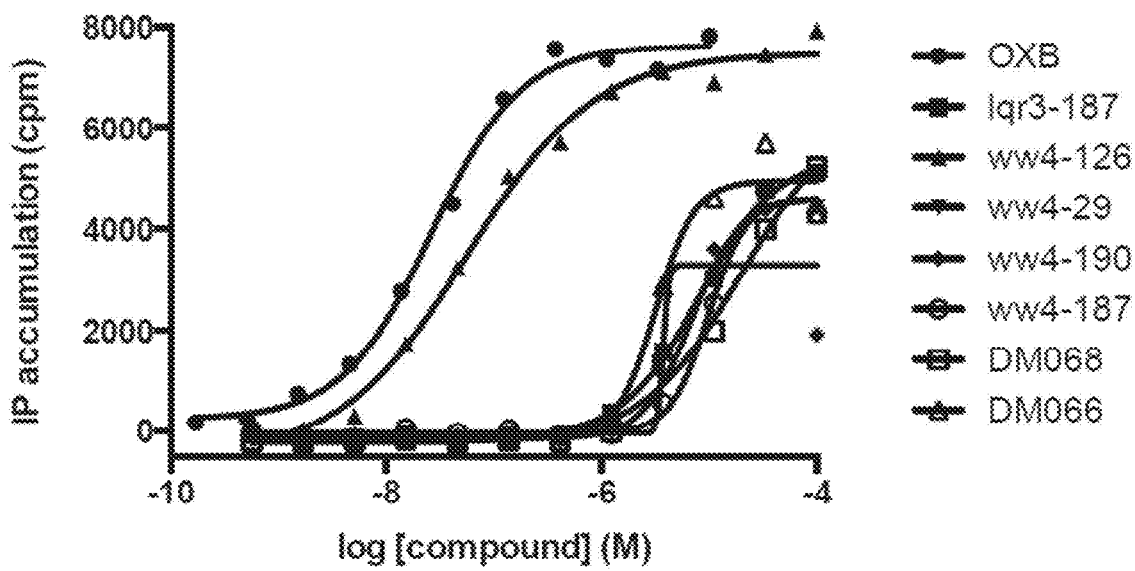
Figure 7:
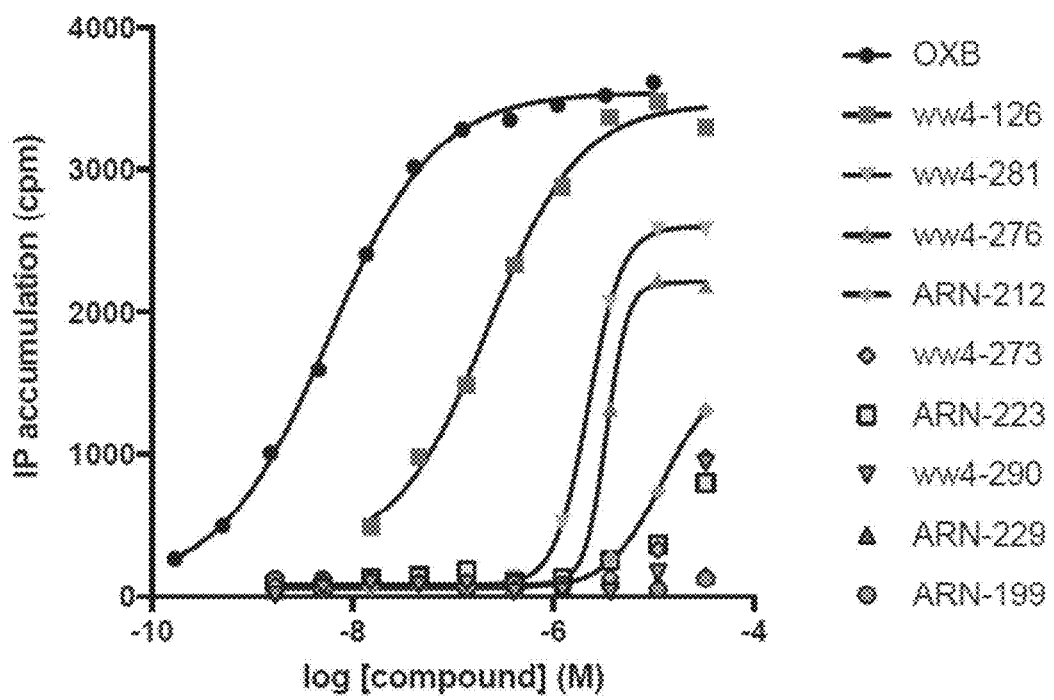
Figure 8:
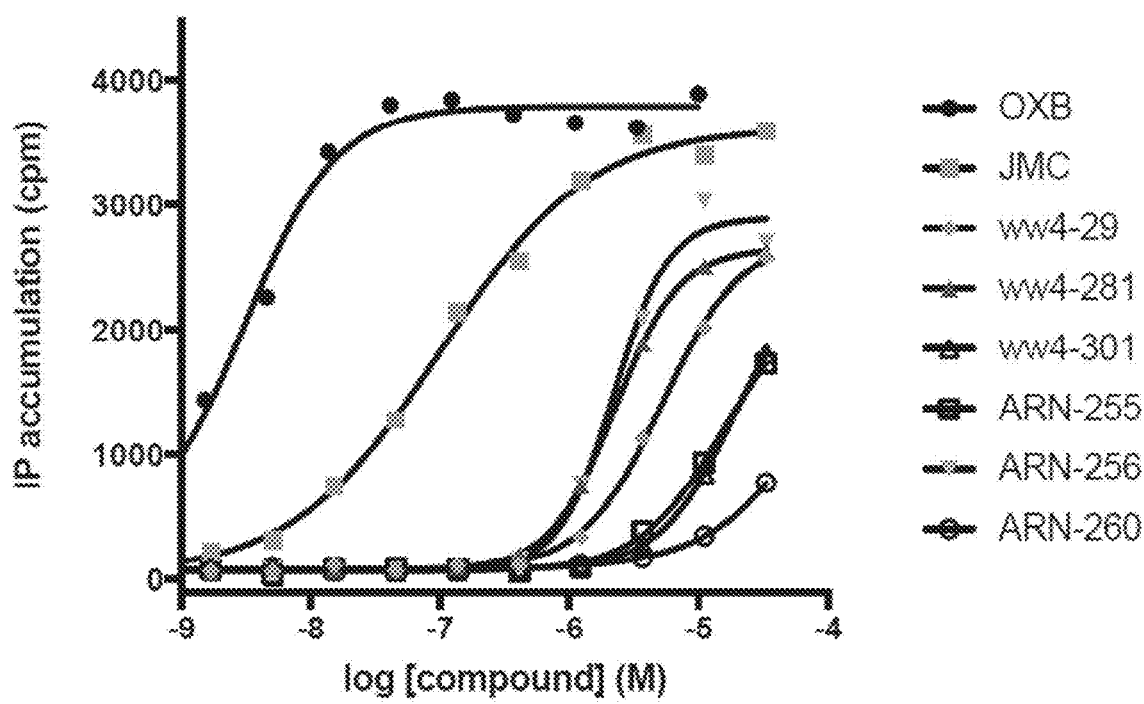
Figure 9:
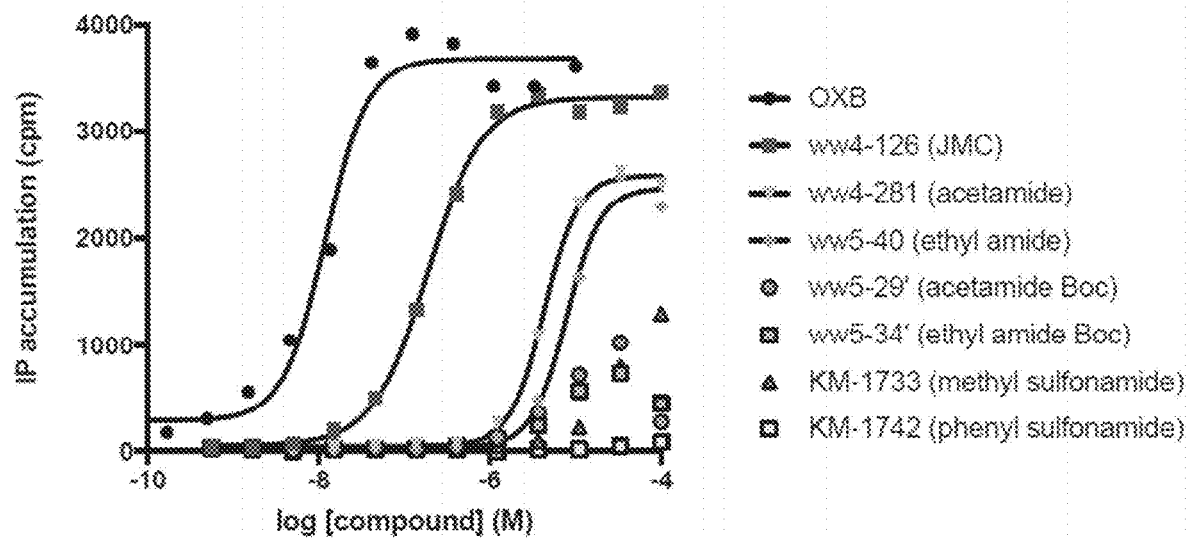
Figure 10:
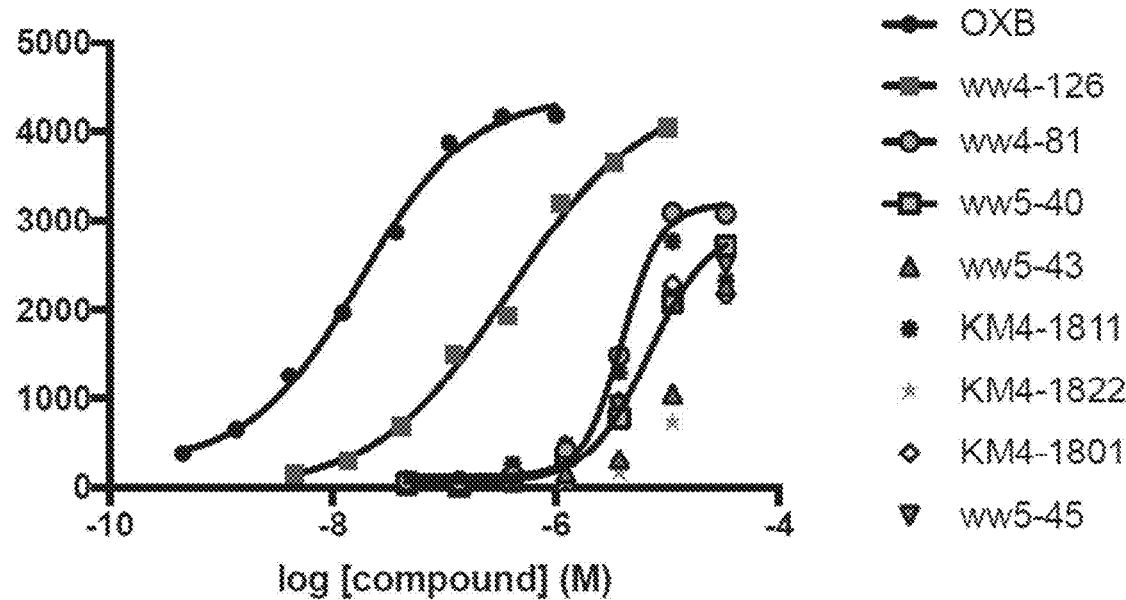
Figure 11:
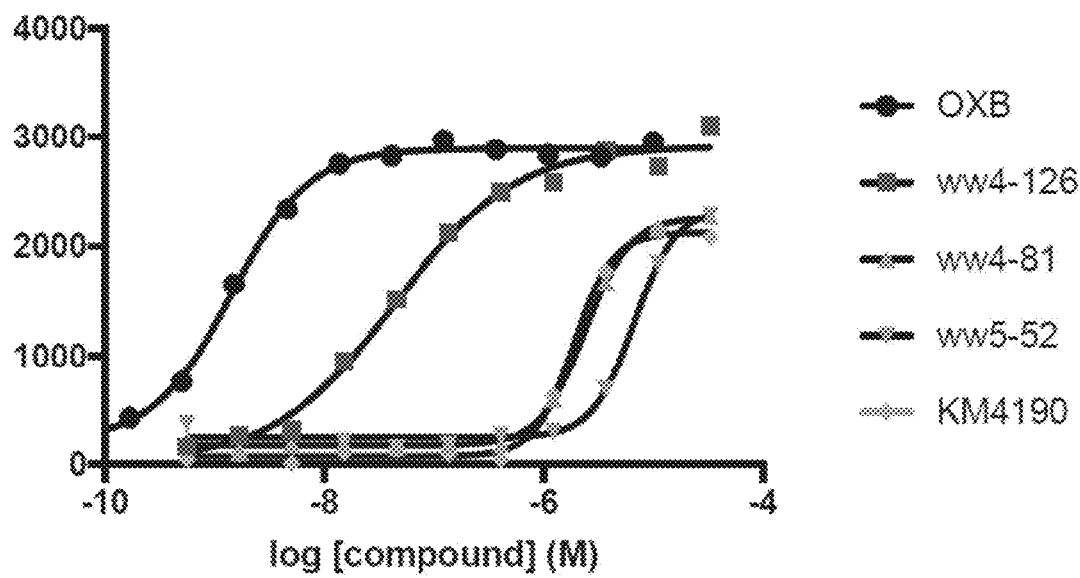
Figure 12:
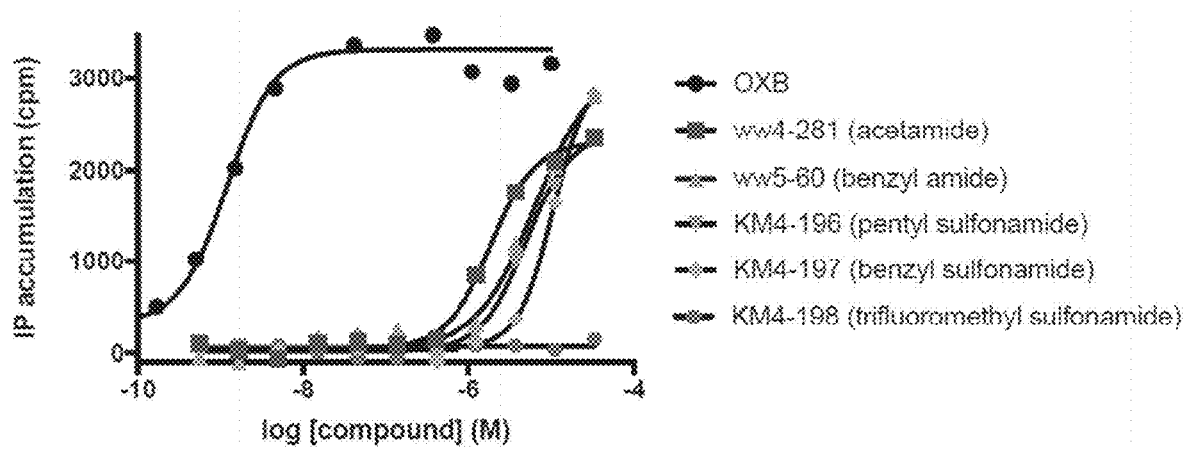
Figure 13:
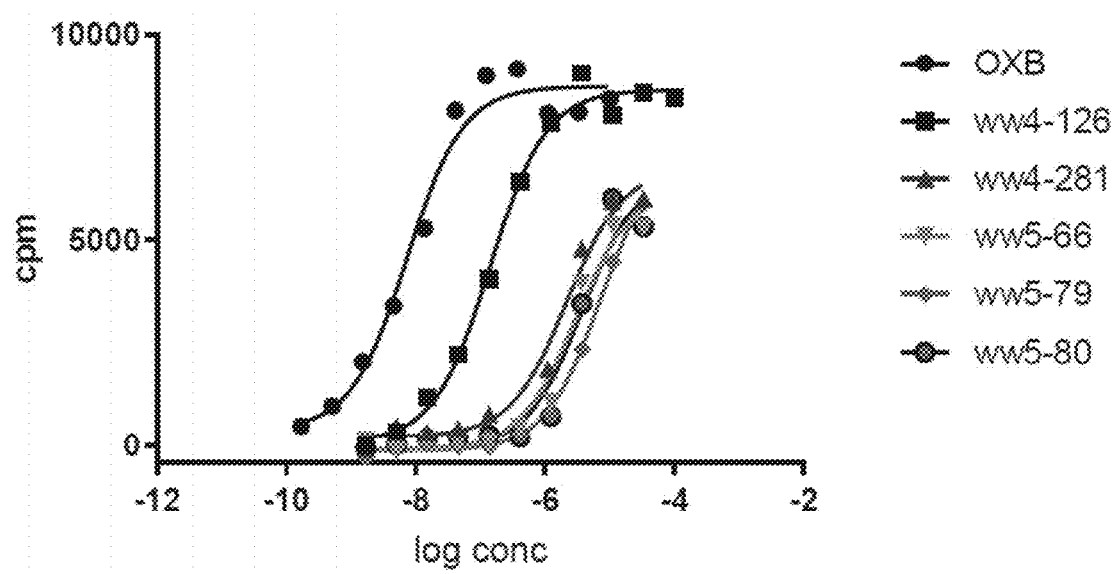
Figure 14:
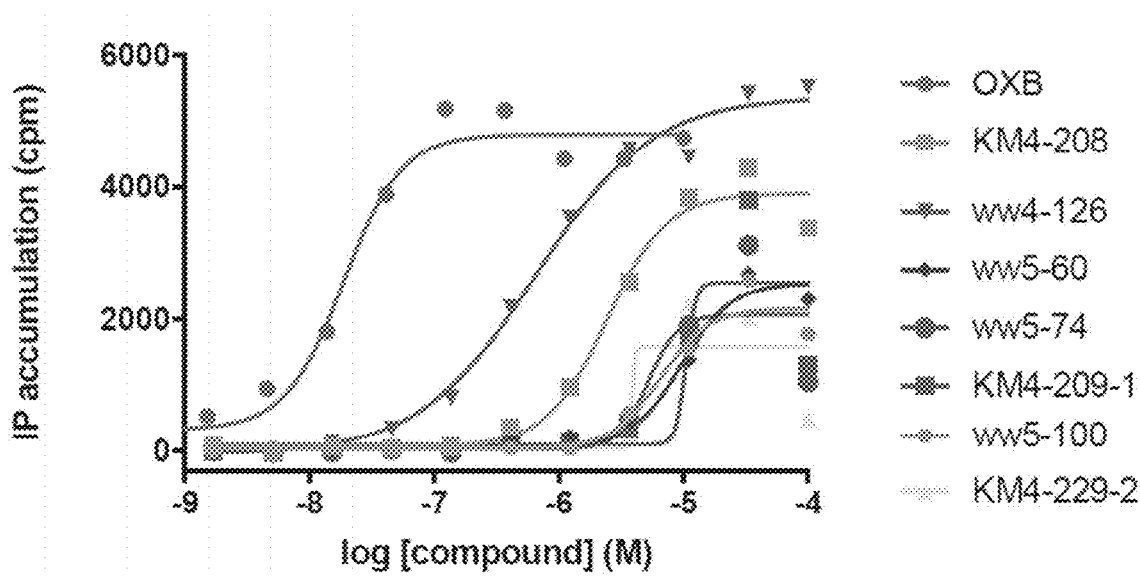
Figure 15:
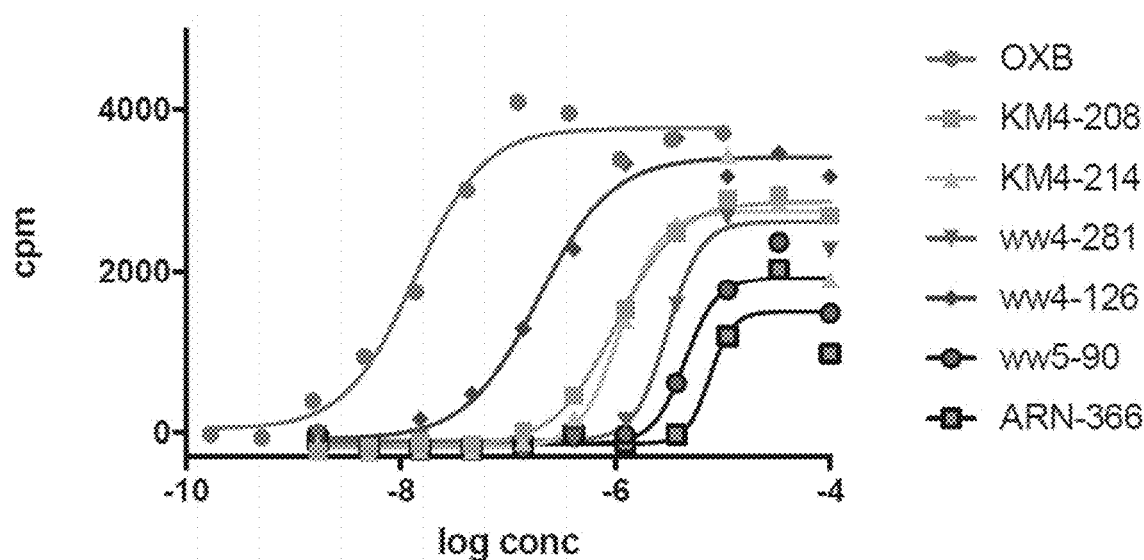
Figure 16:
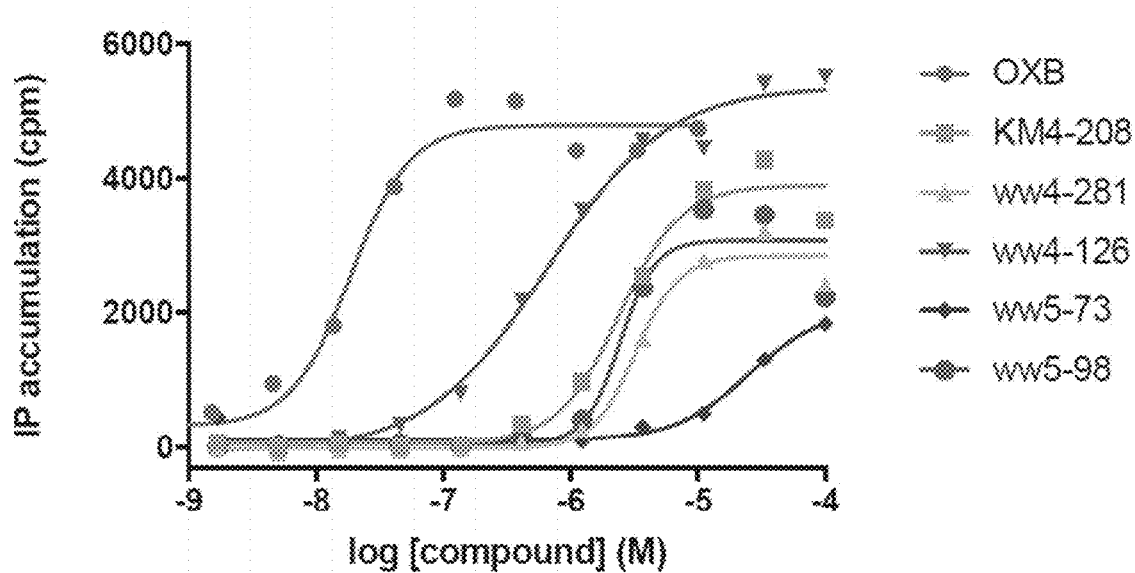
Figure 17:
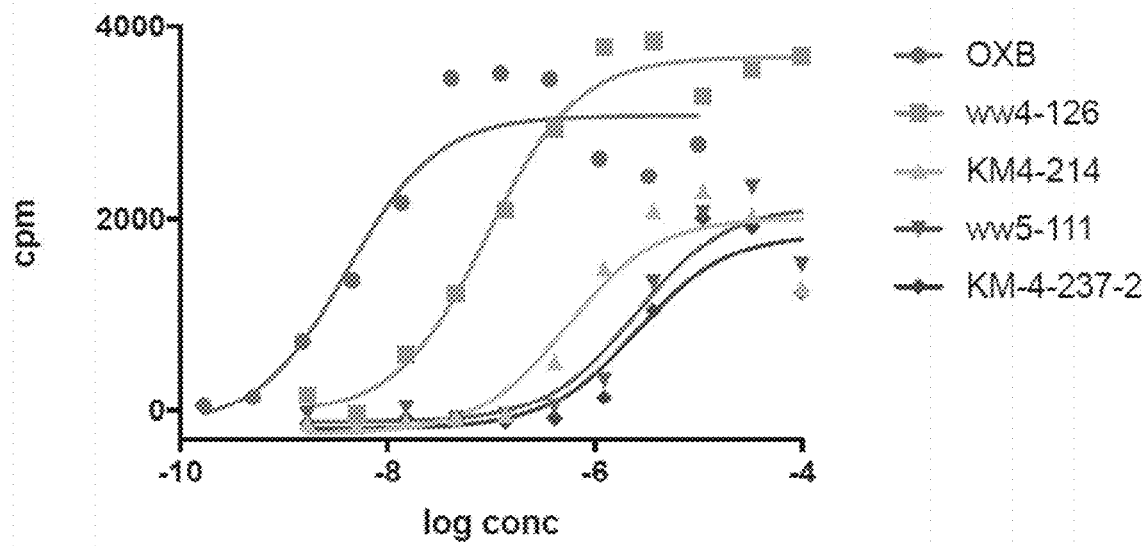
Figure 18:
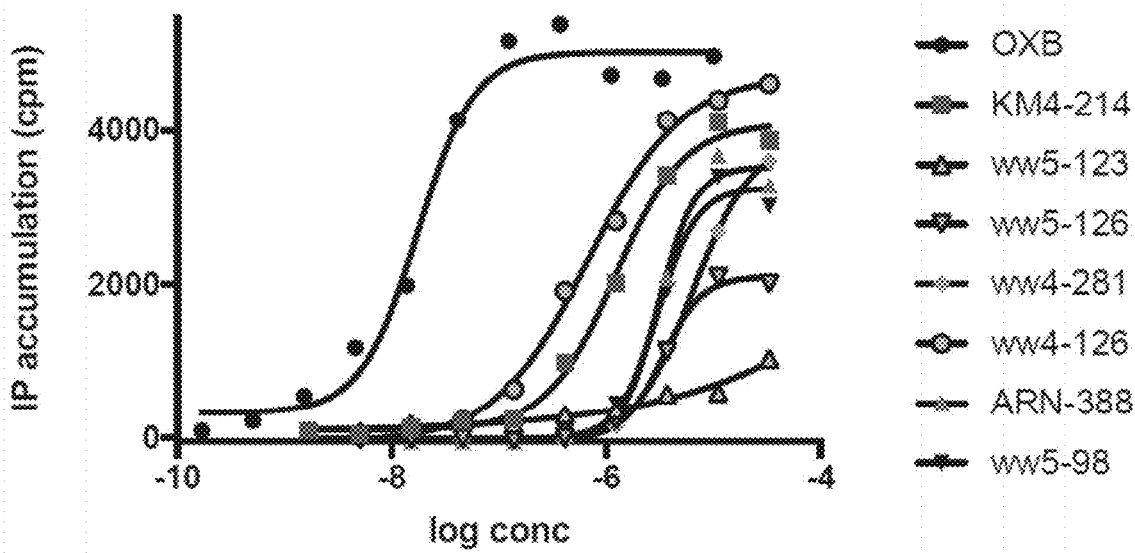
Figure 19:
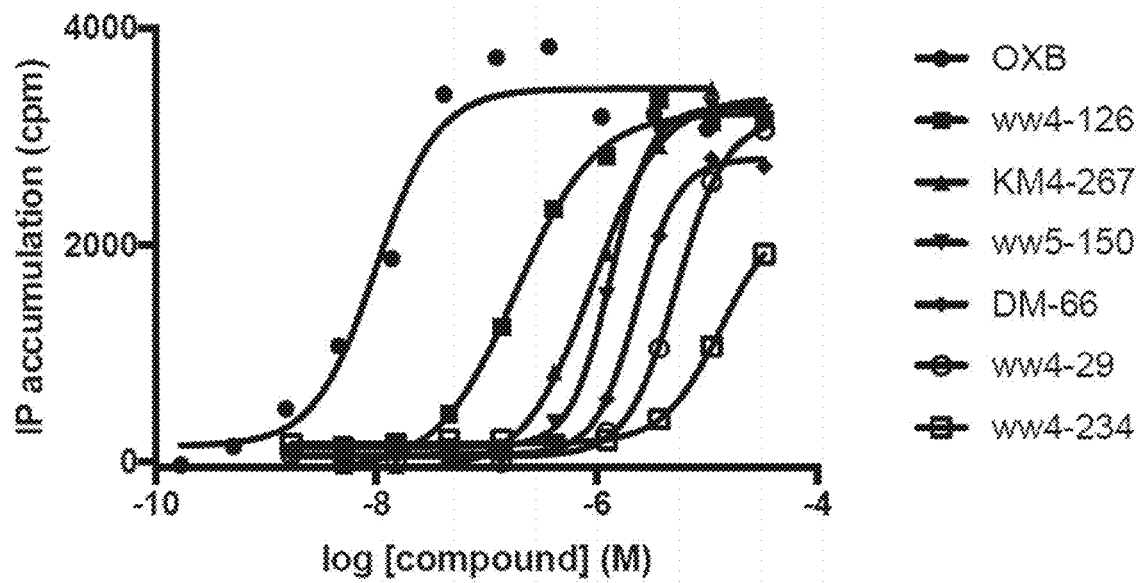
Figure 20:
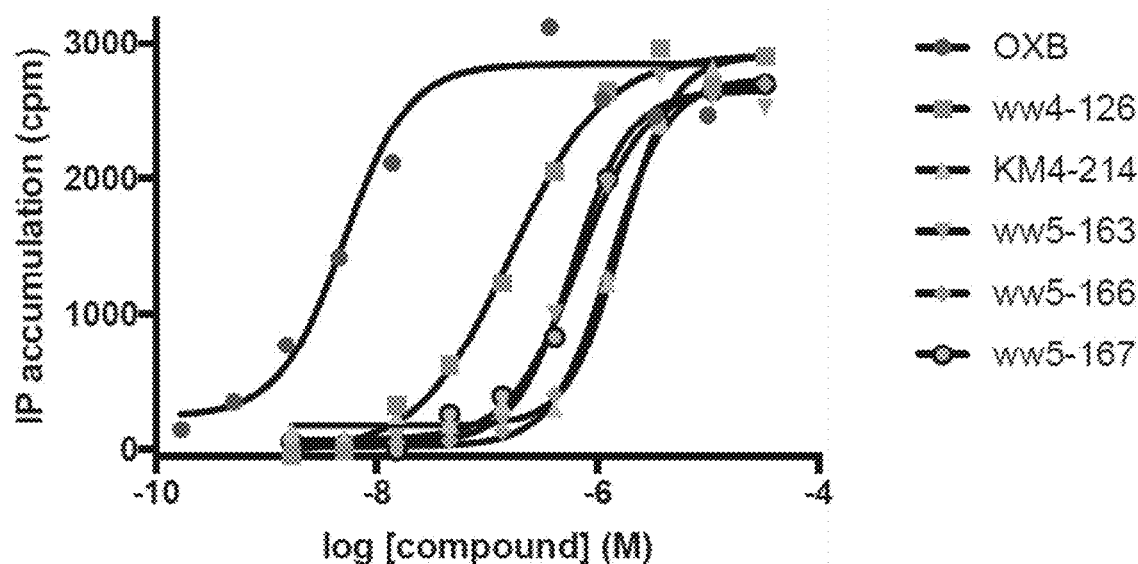
Figure 21:
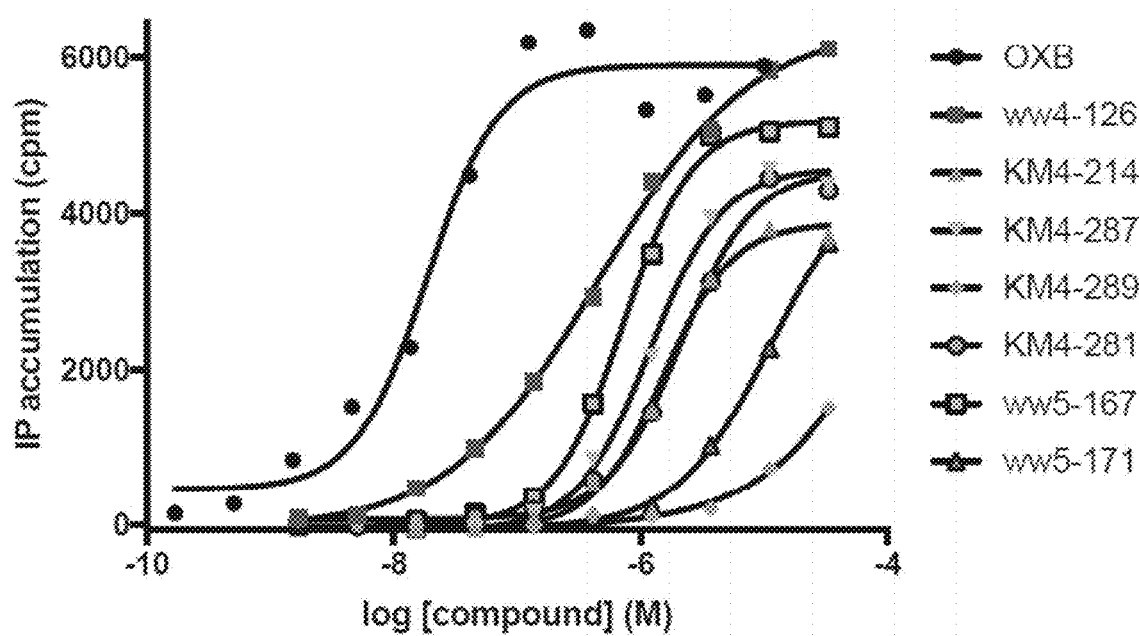
Figure 22:
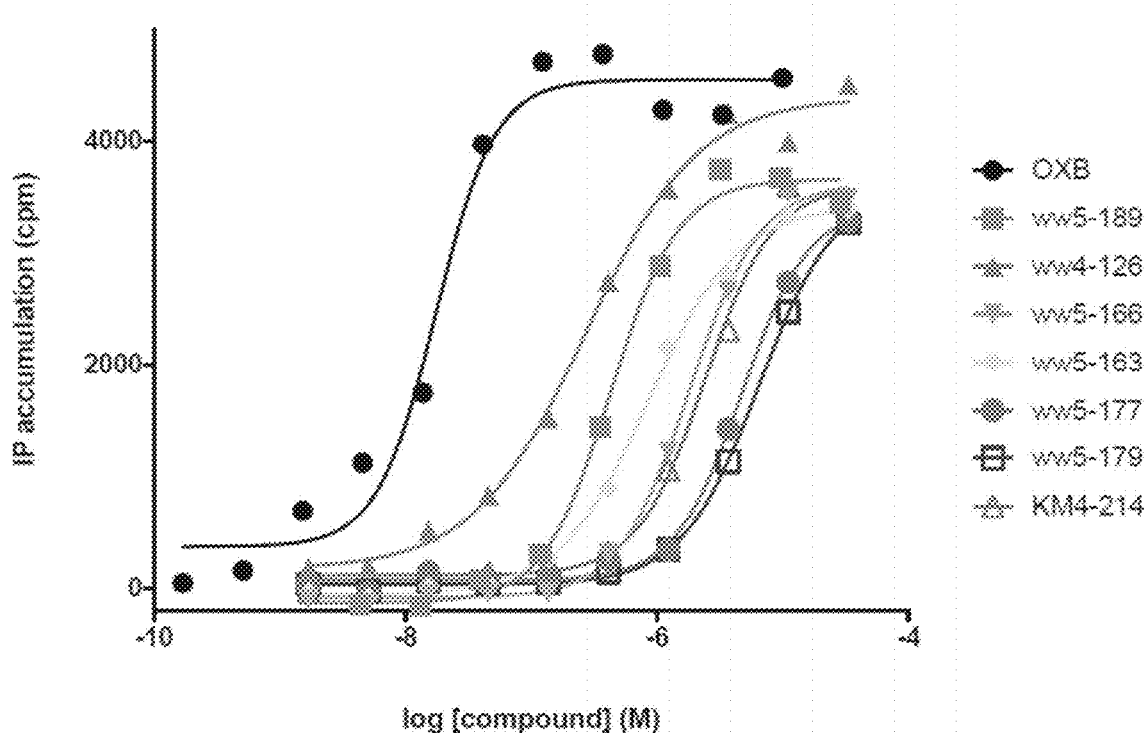
Figure 23:
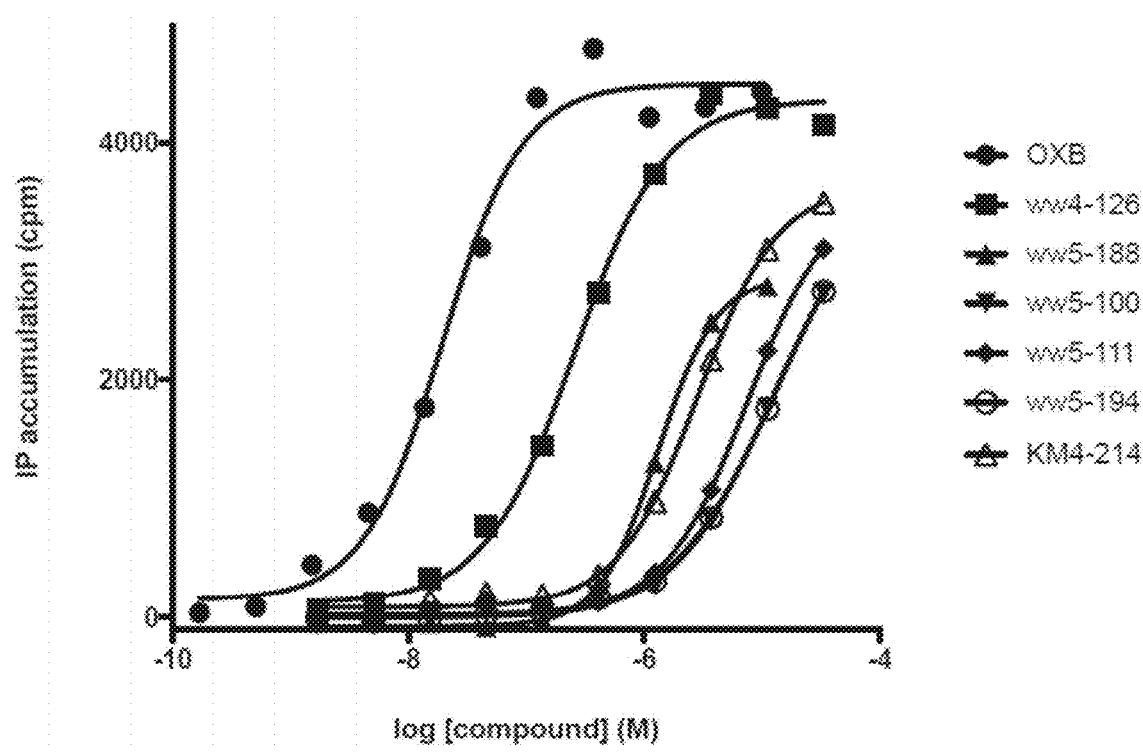
Figure 24:
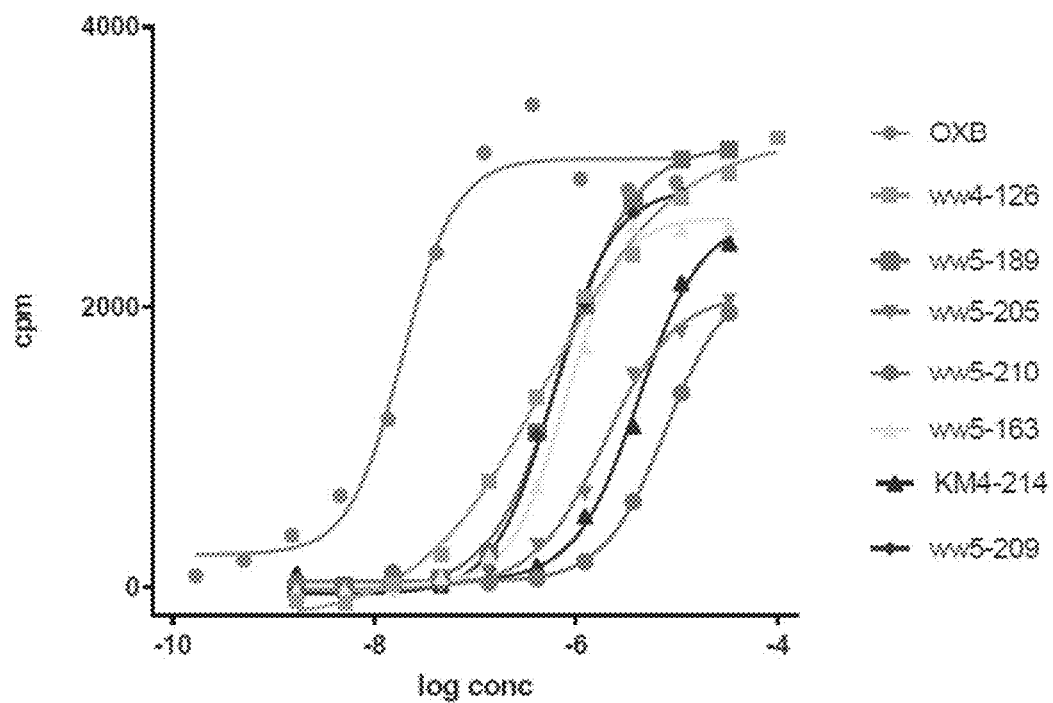
Figure 25:
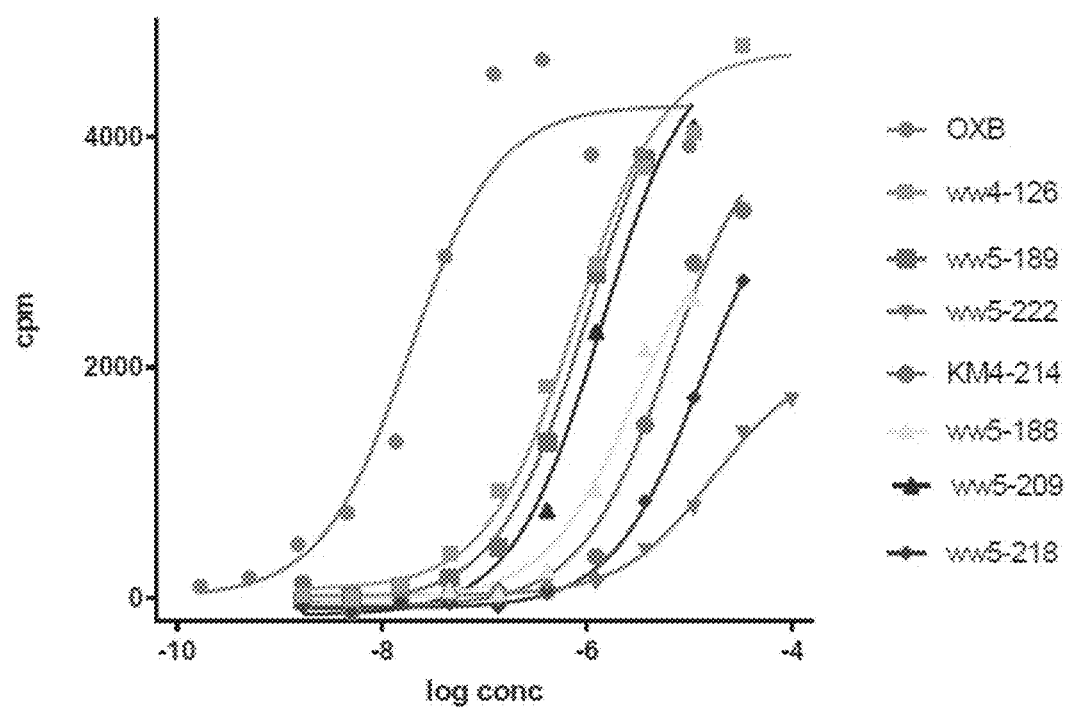
Figure 26:
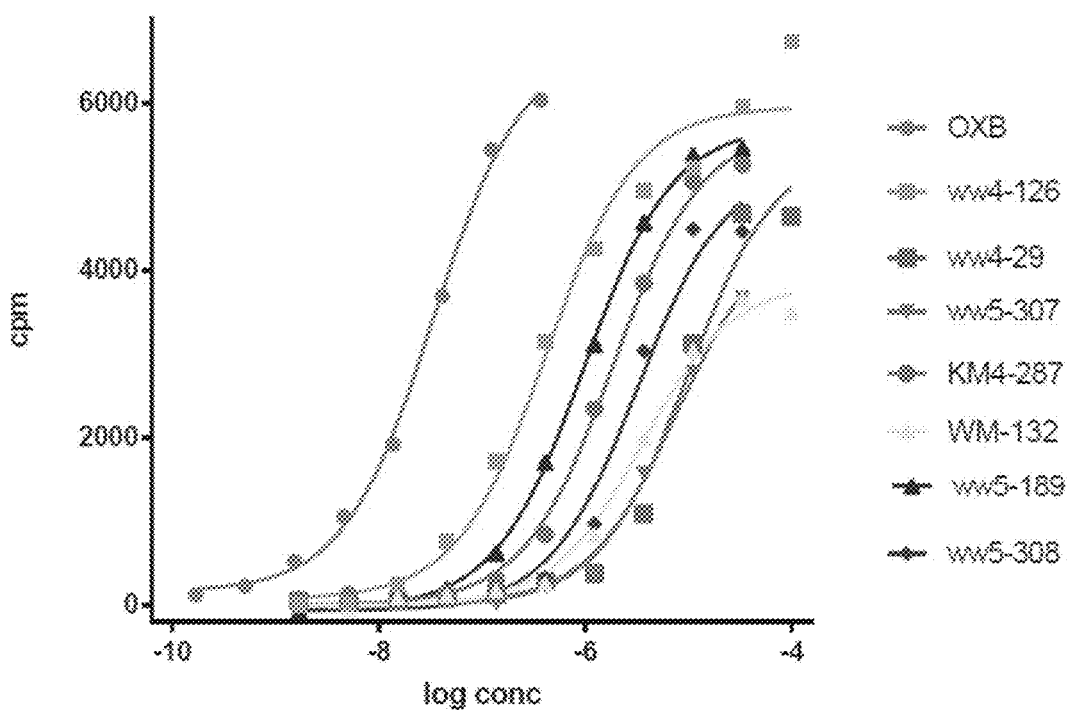
Figure 27:
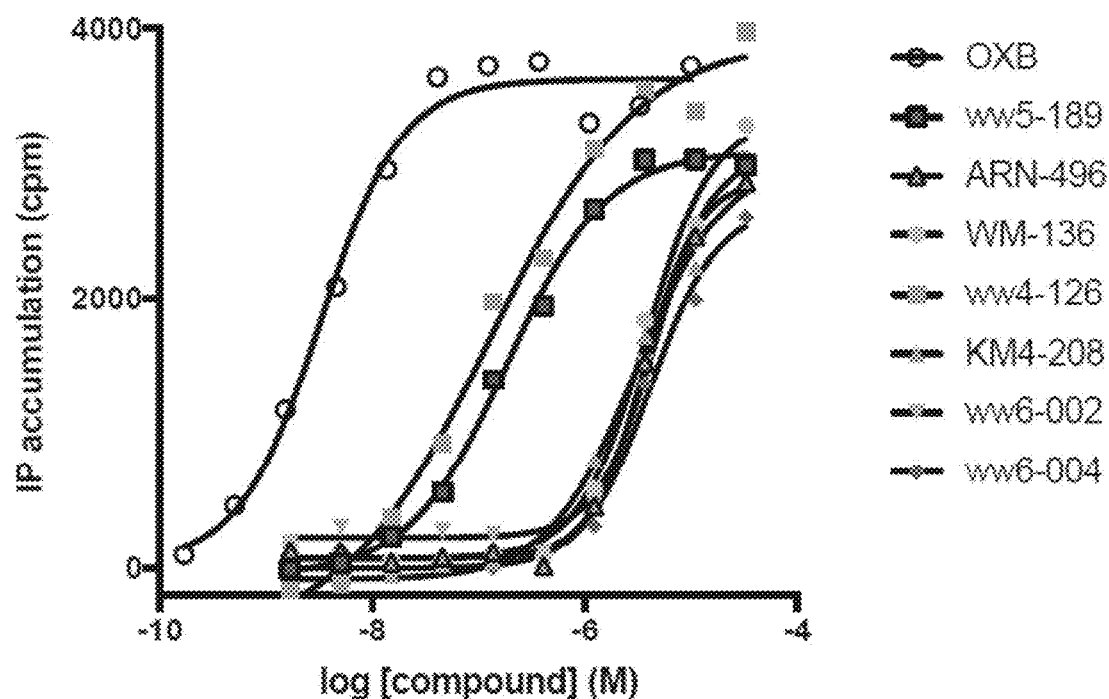
Figure 28:
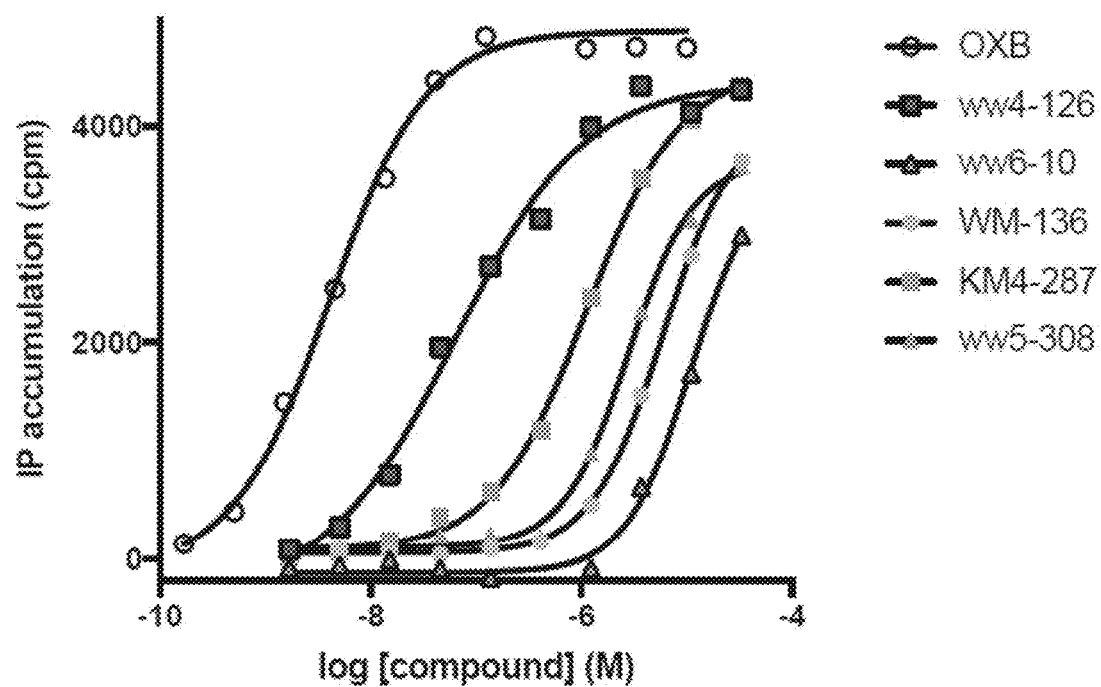
Figure 29:
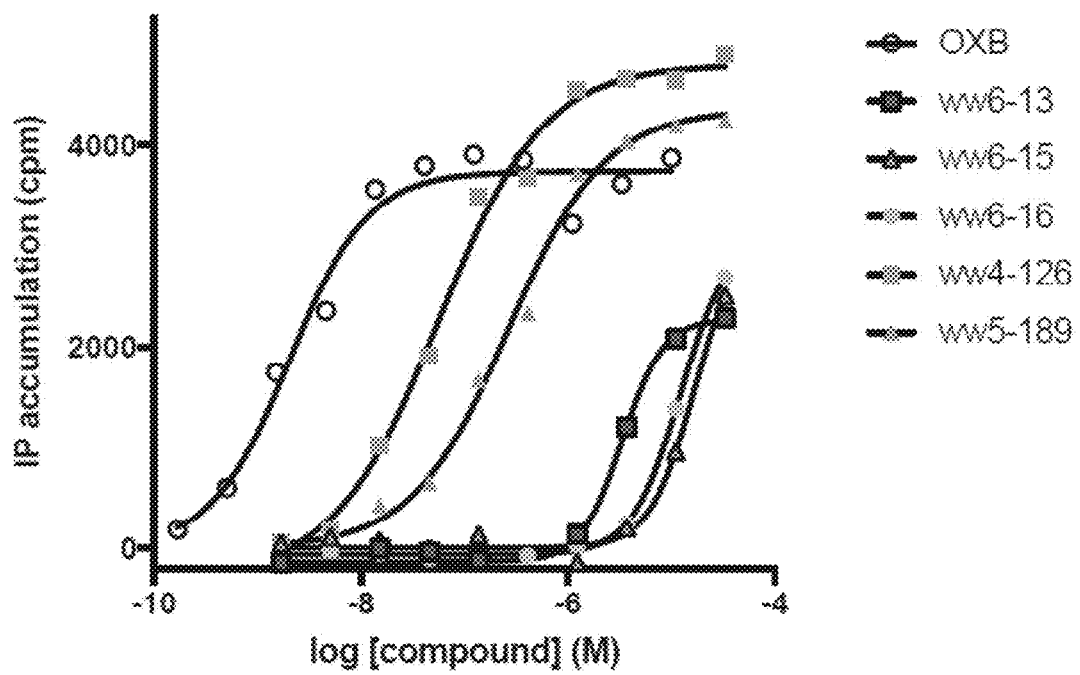
Figure 30:
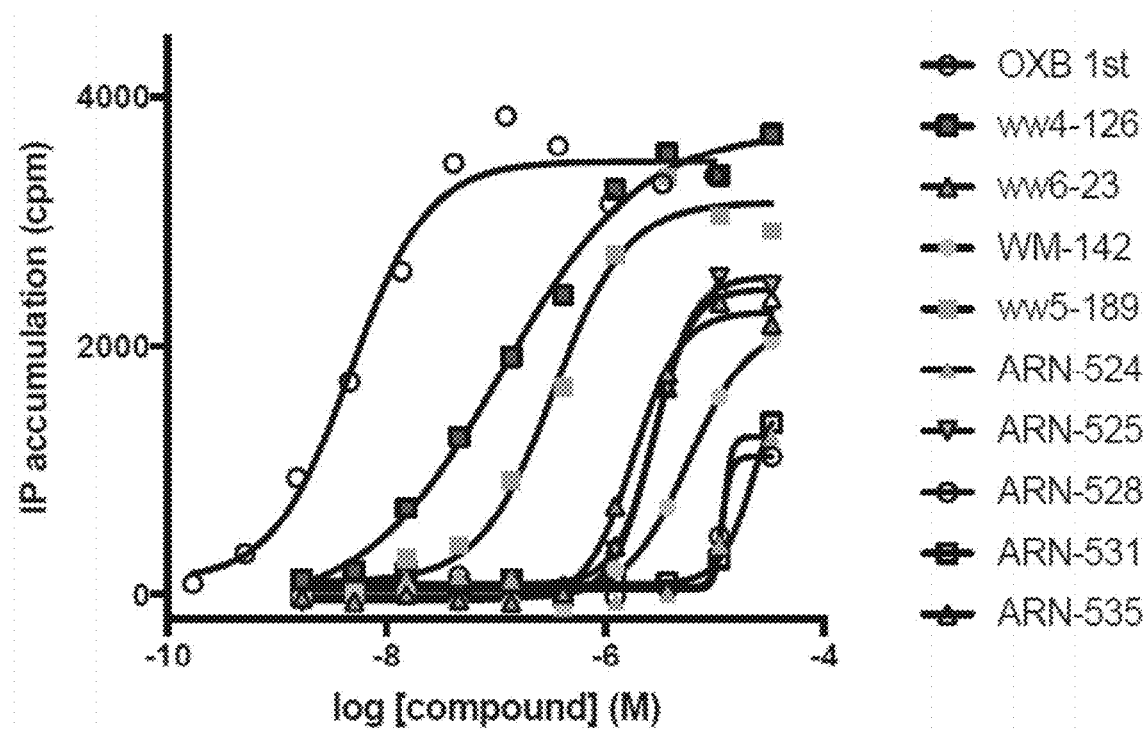
Figure 31:
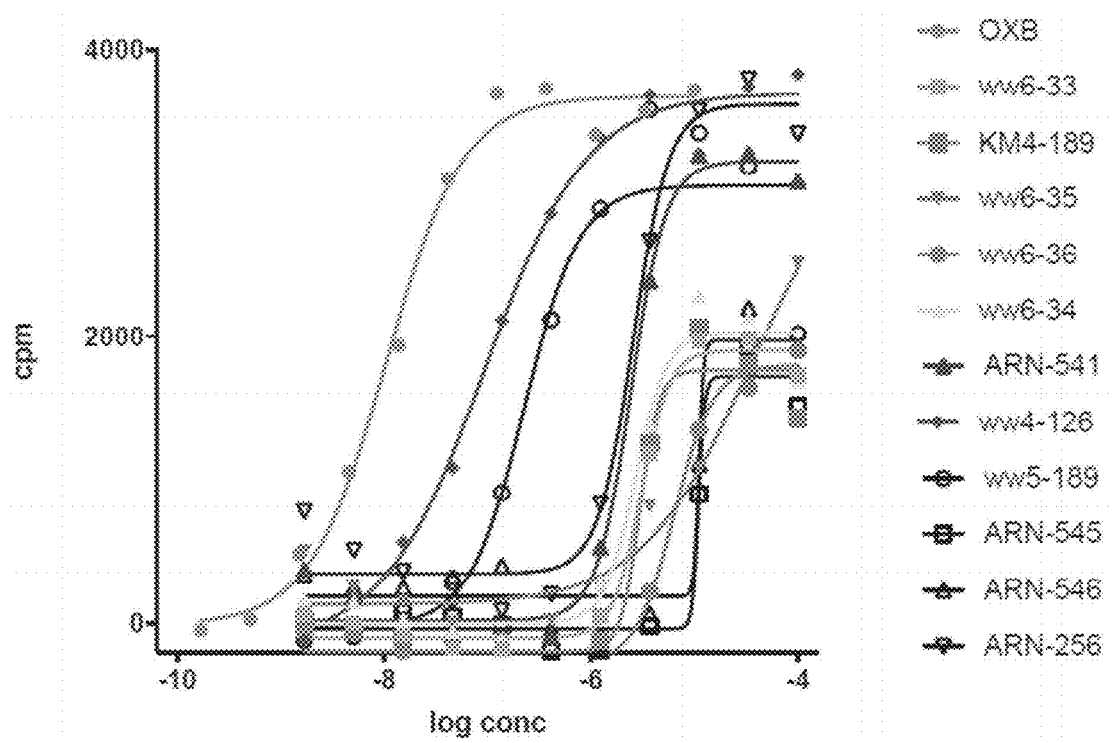
Figure 32:
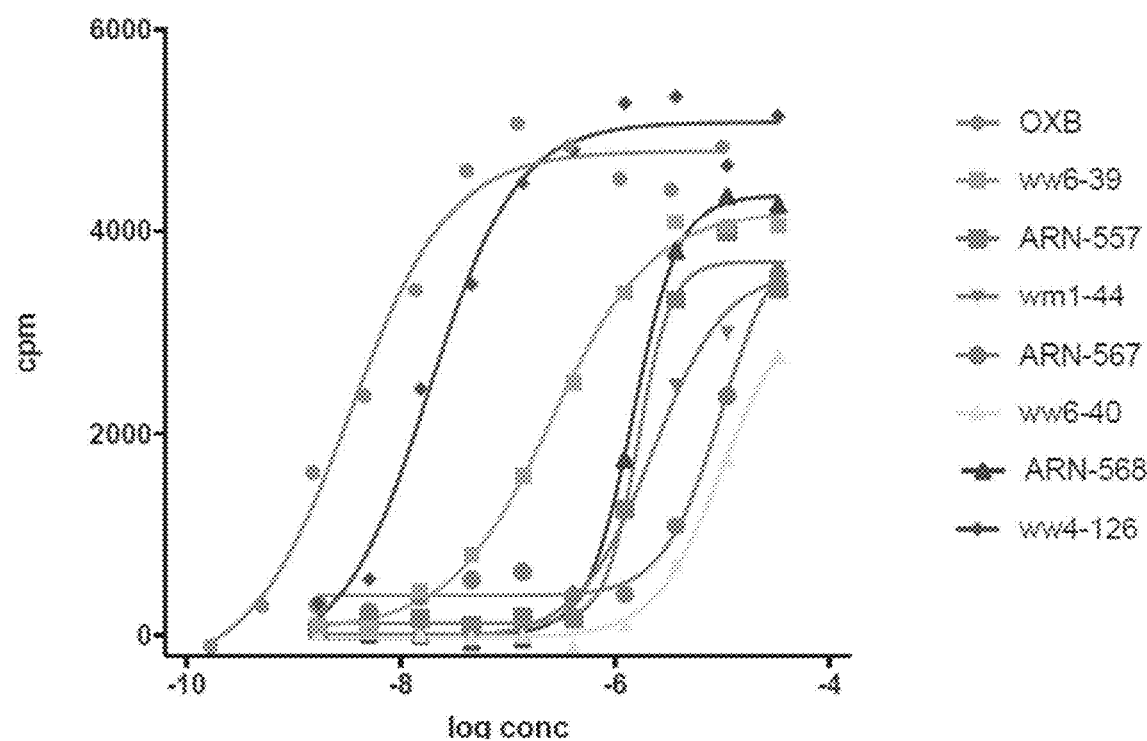
Figure 33:
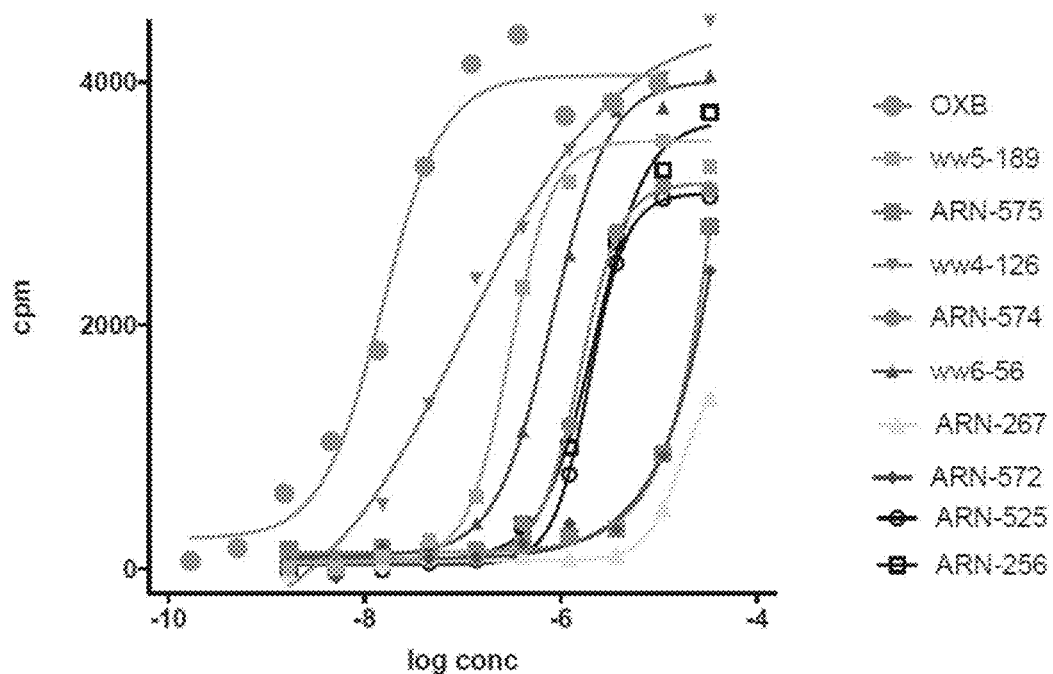
Figure 34:
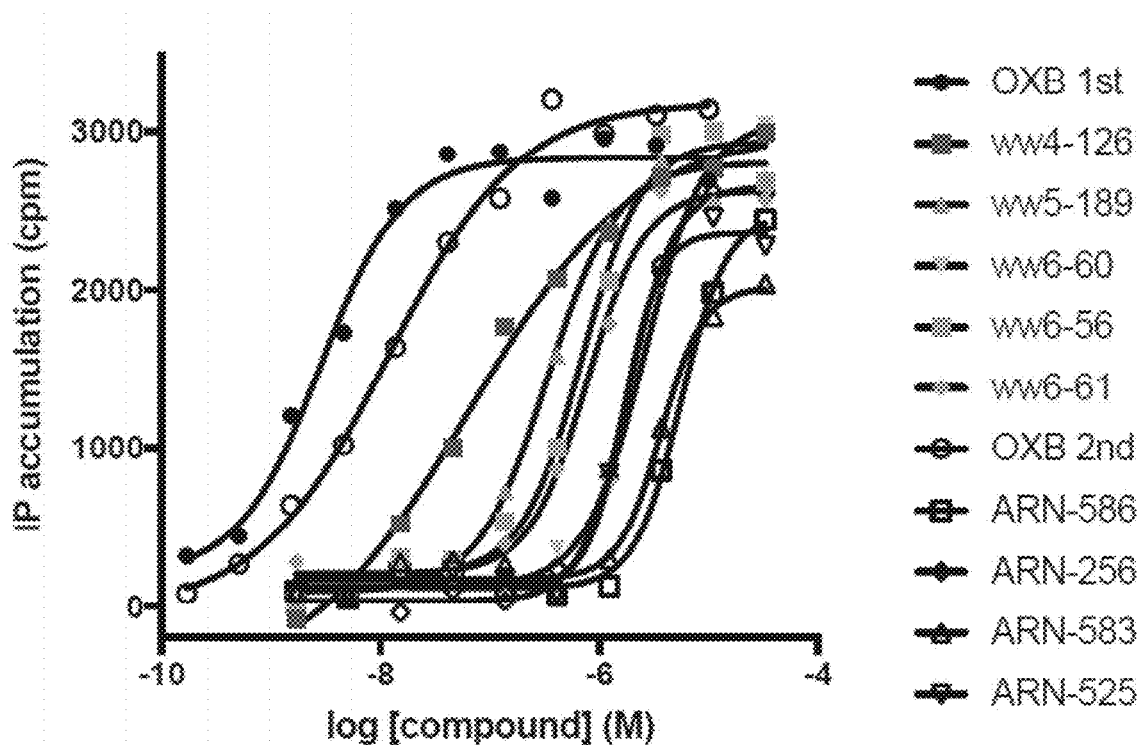
Figure 35:
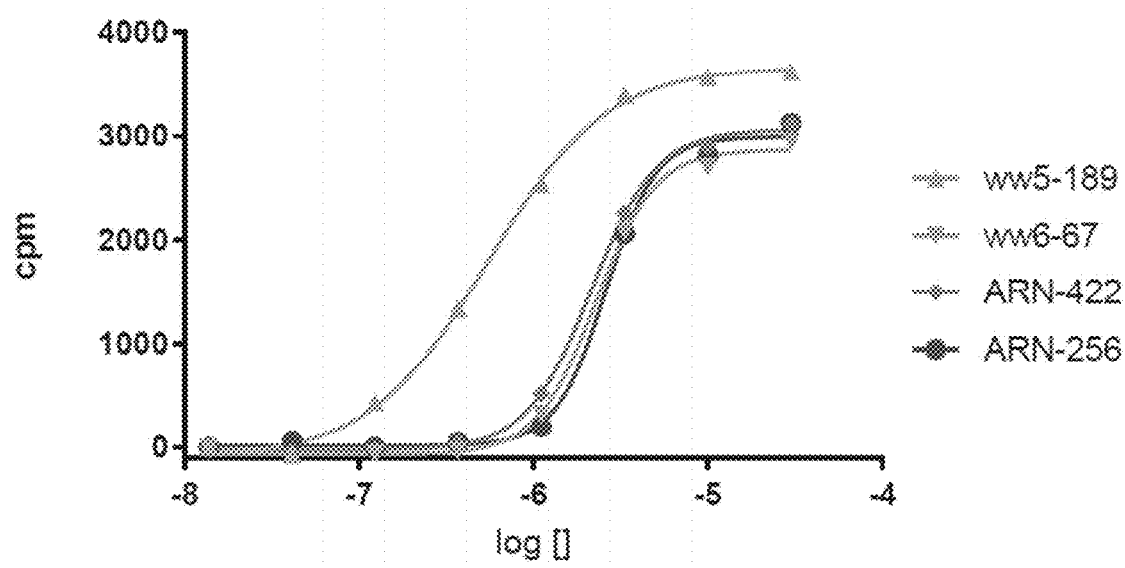
Figure 36:
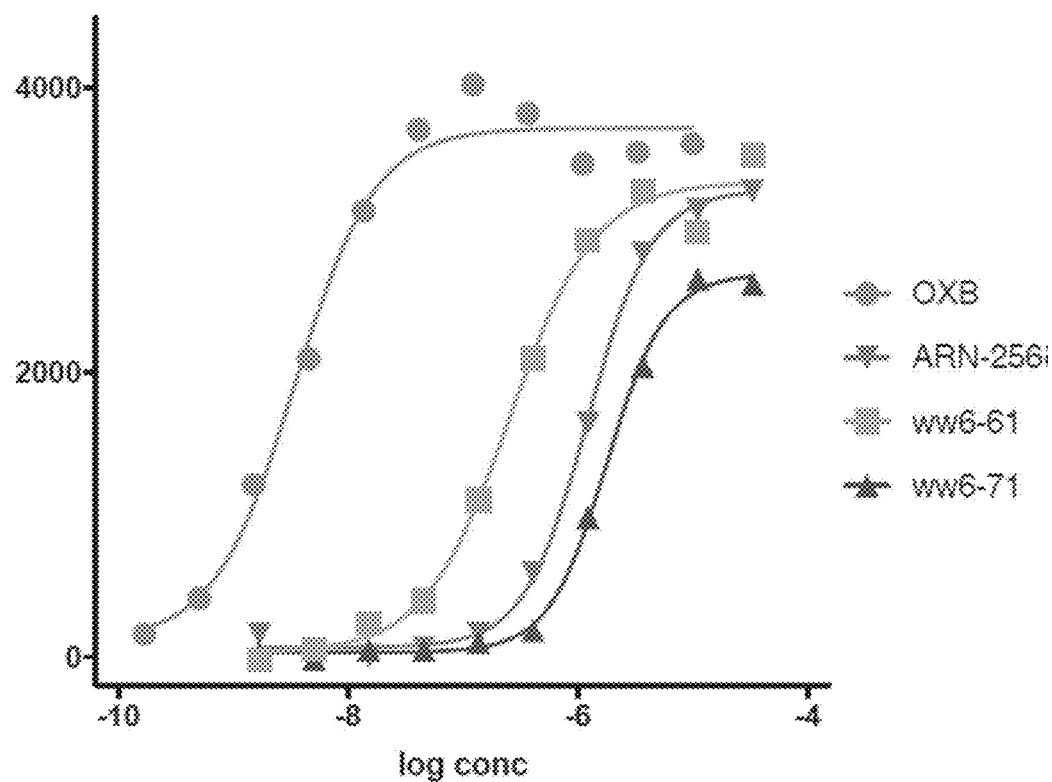
Figure 37:
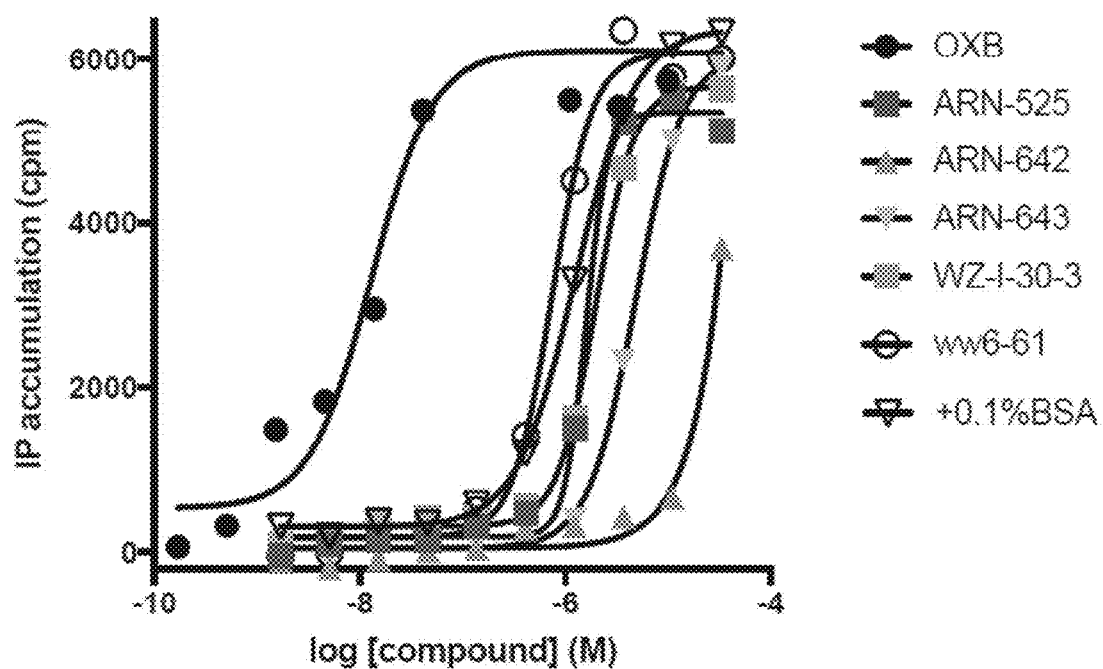
Figure 38:
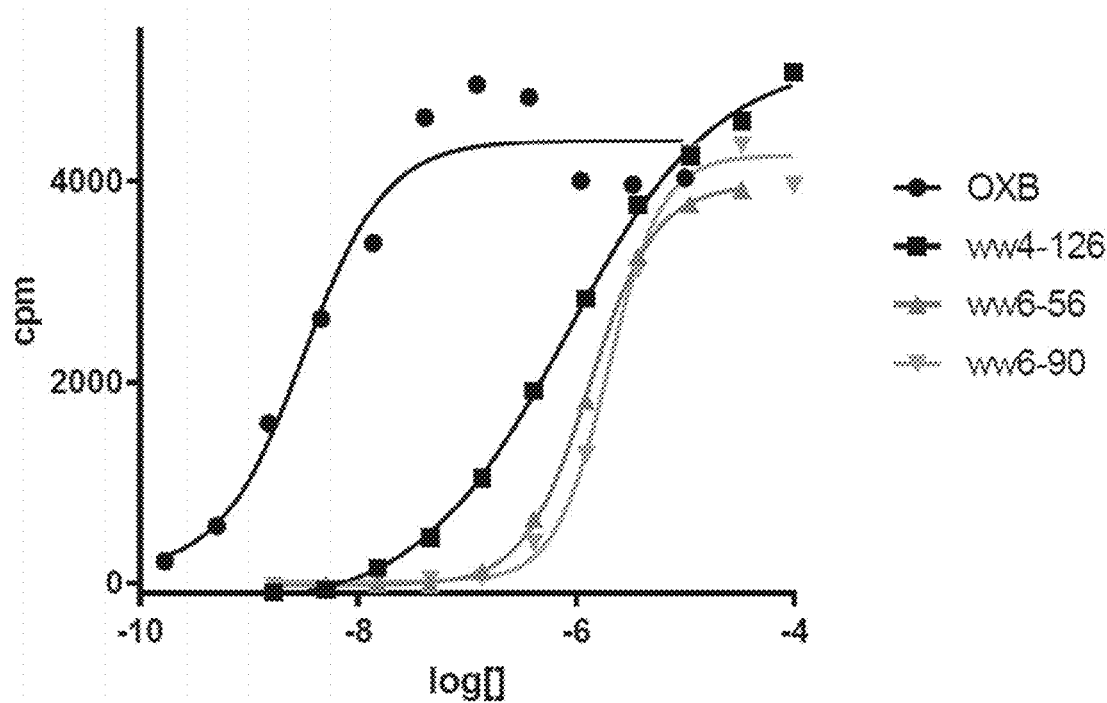
Figure 39:
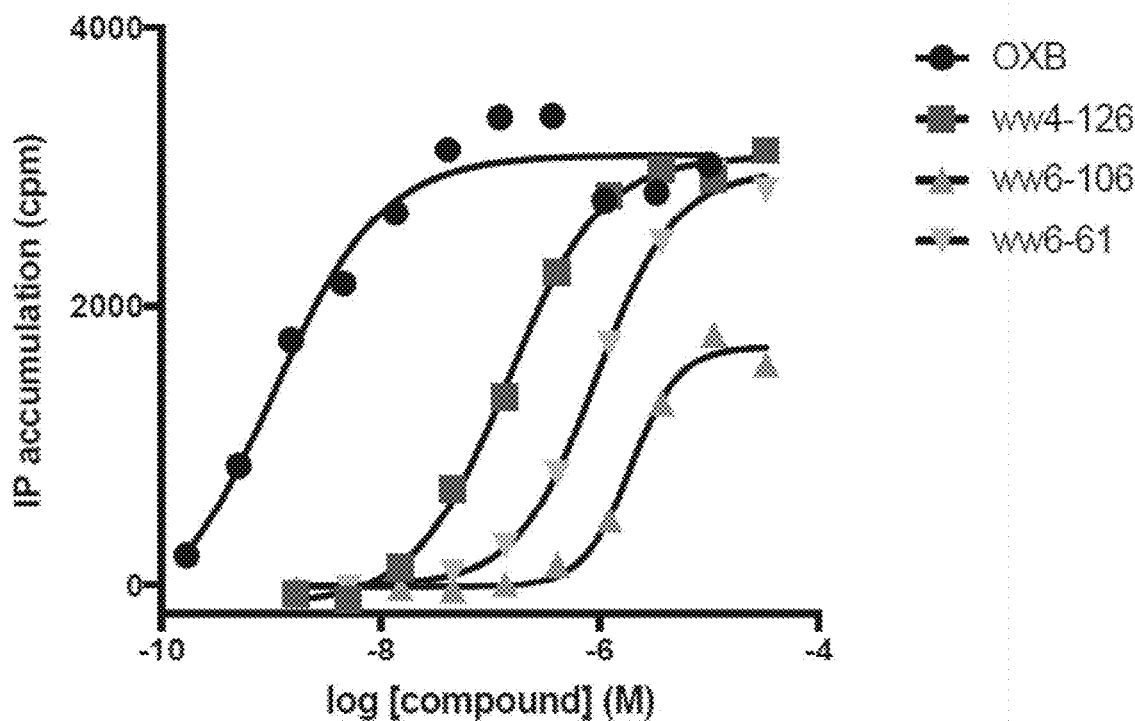
Figure 40:
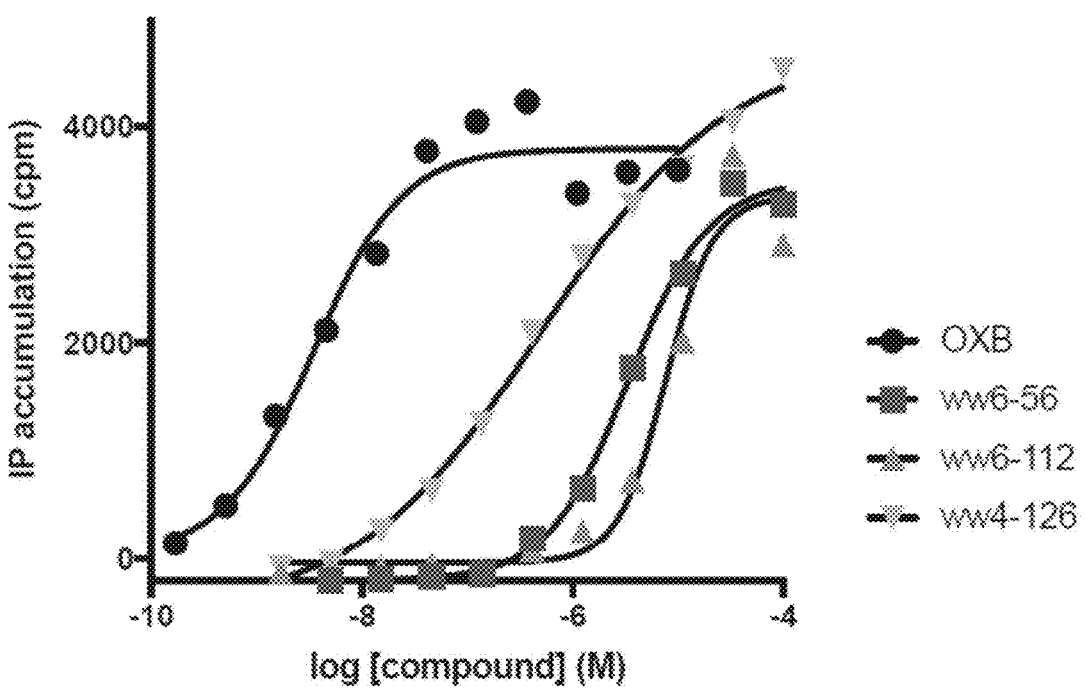
Figure 41:
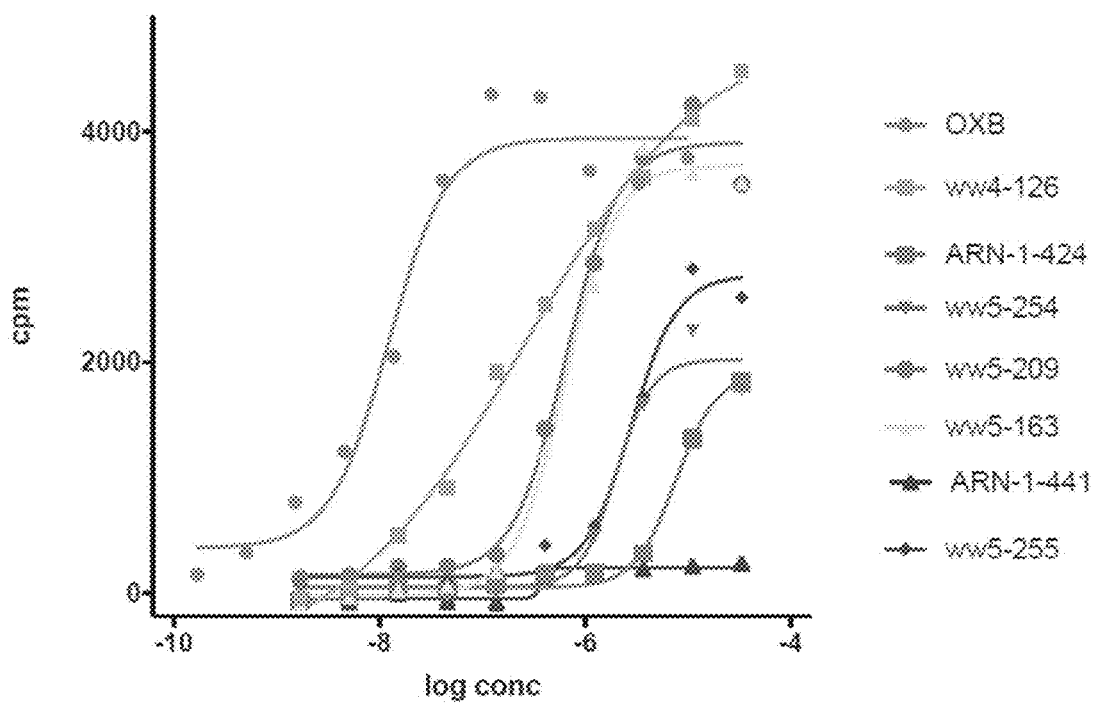
Figure 42:
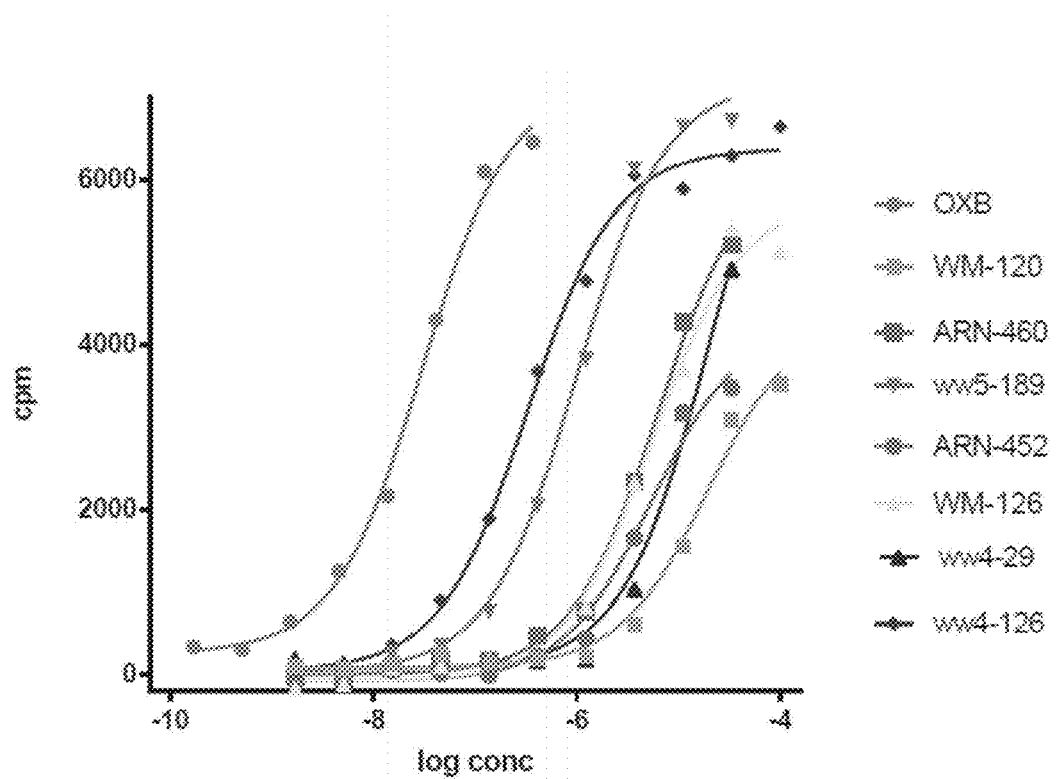
Figure 43:
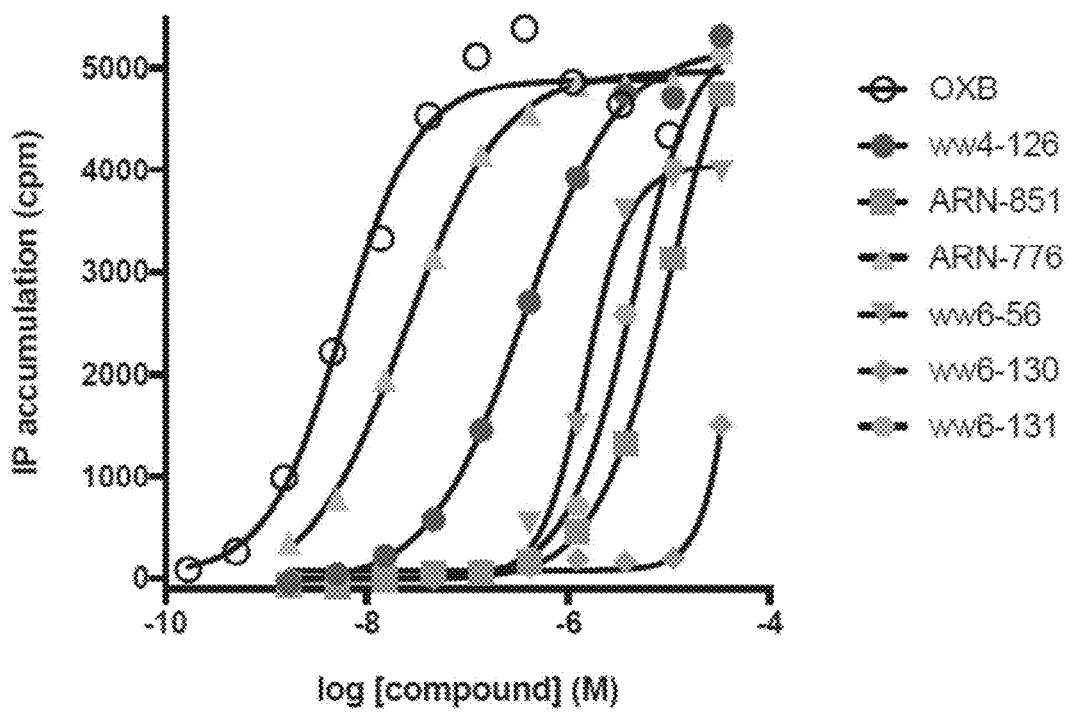
Figure 44:
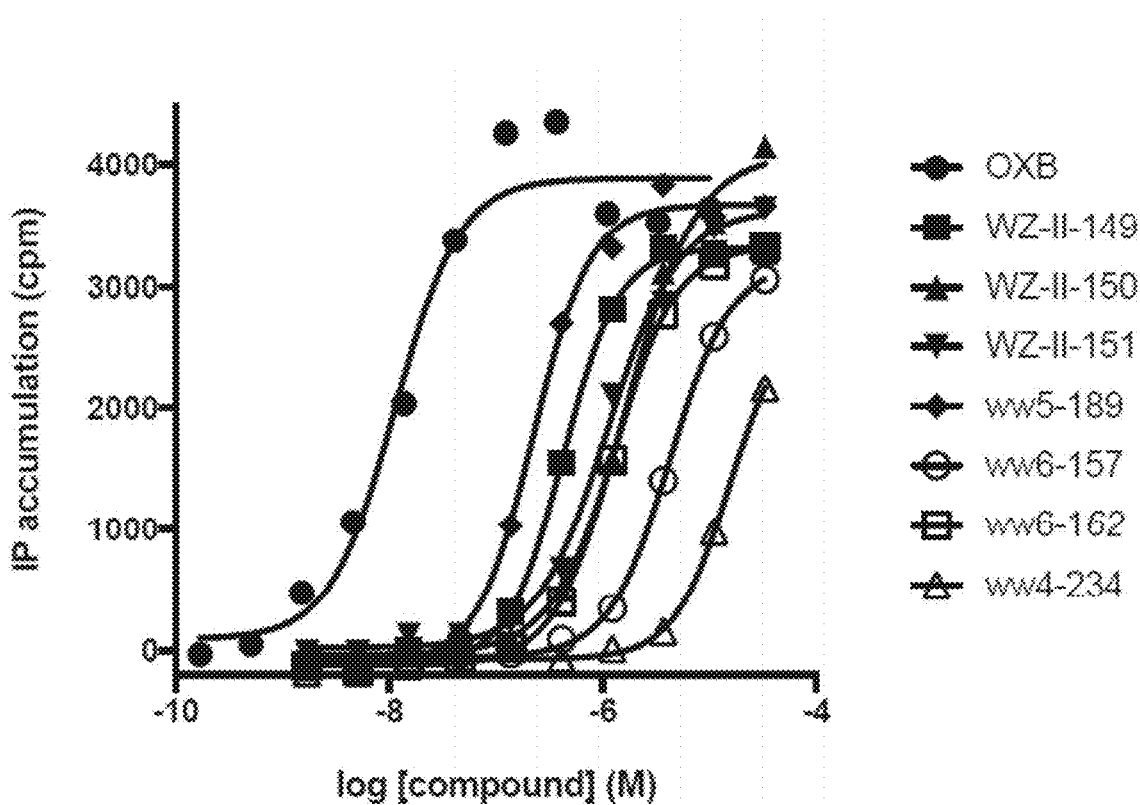
Figure 45:
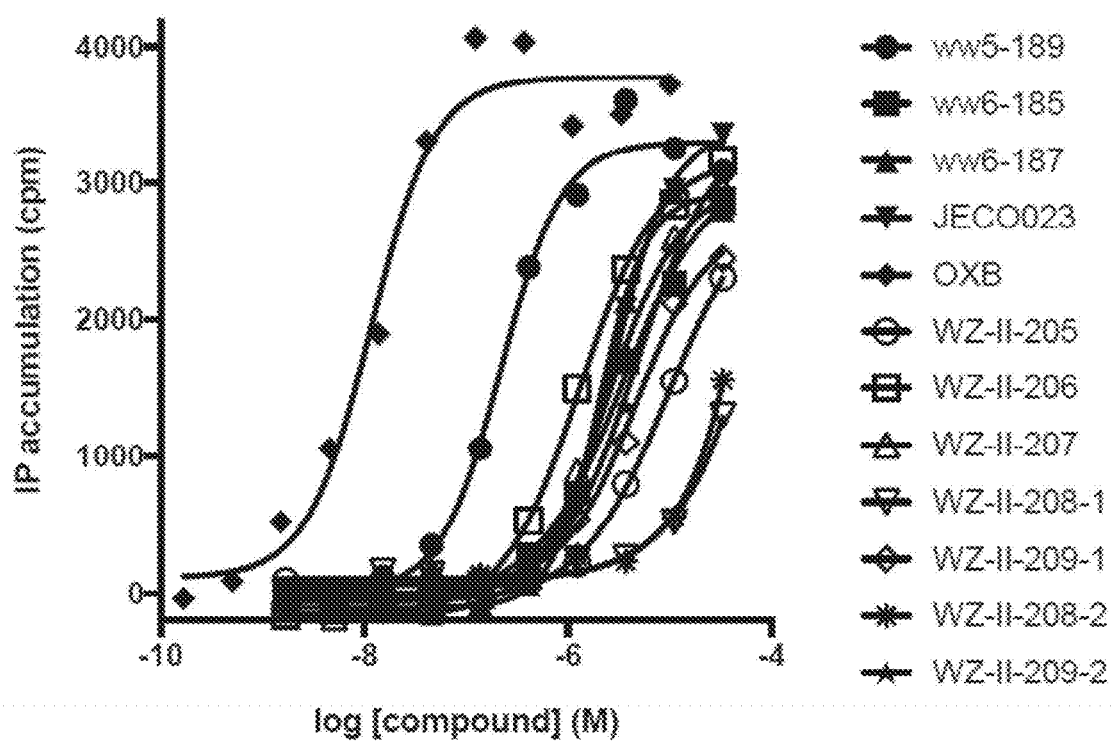
Figure 46:
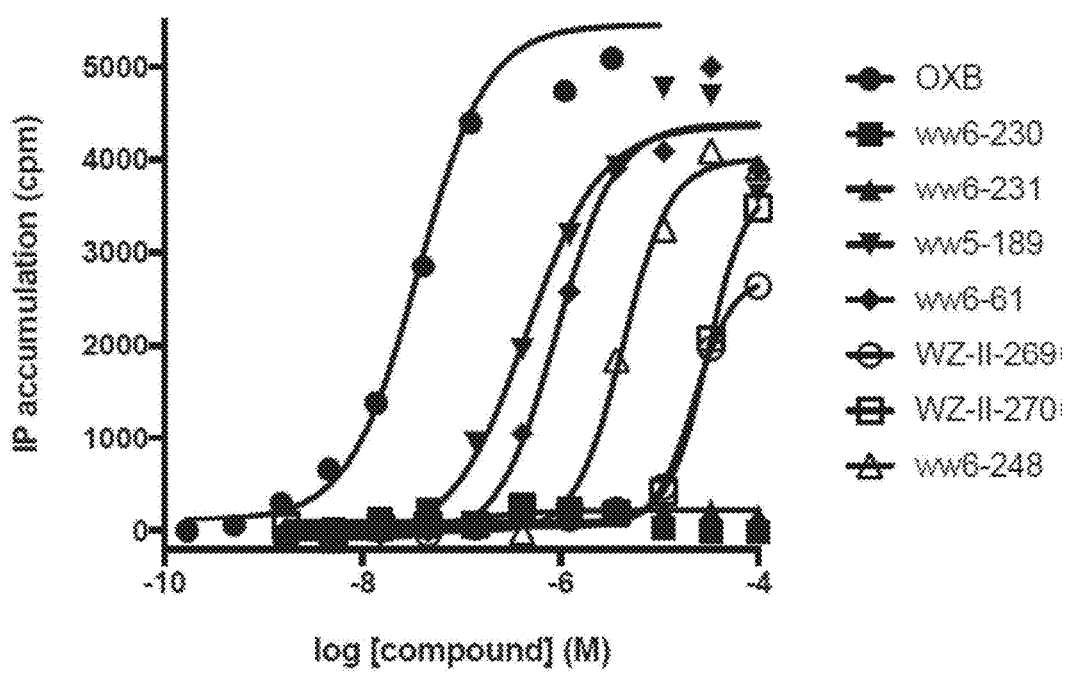
Figure 47:
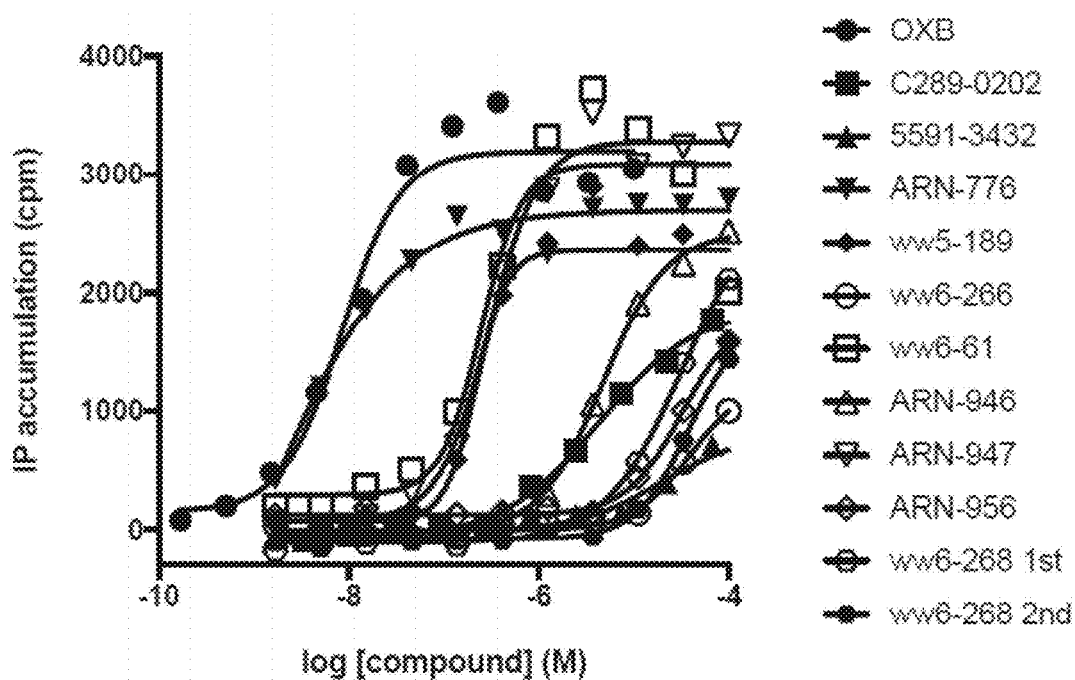
Figure 48:
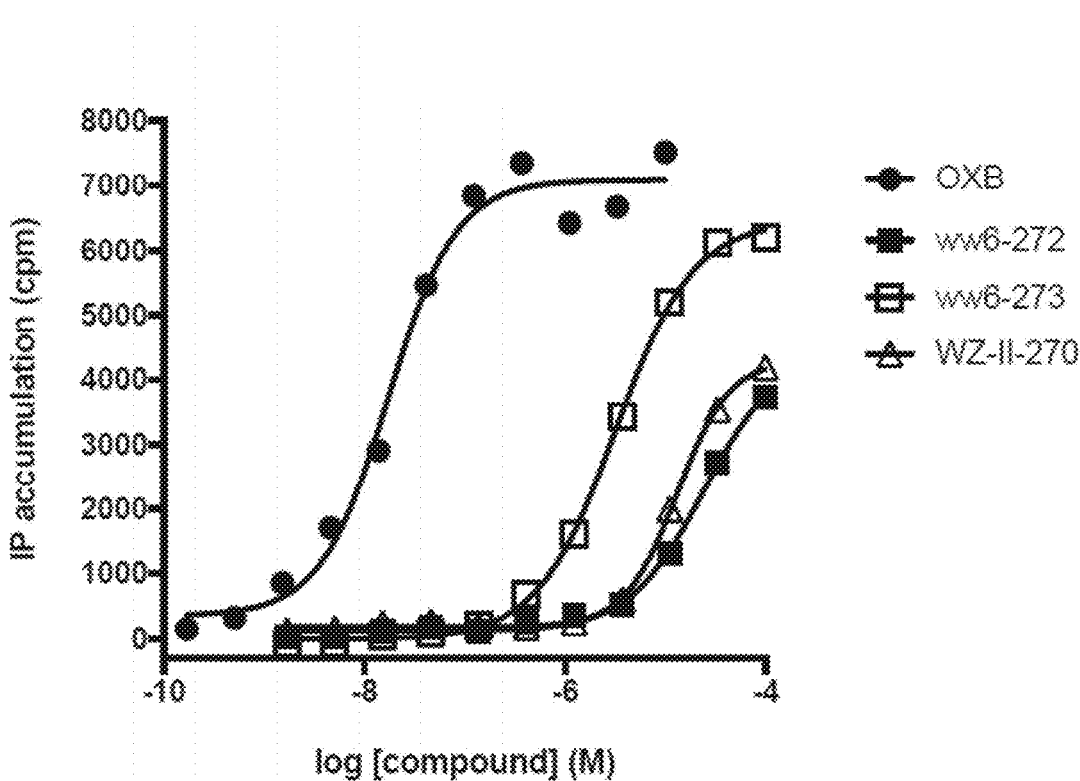
Figure 49:
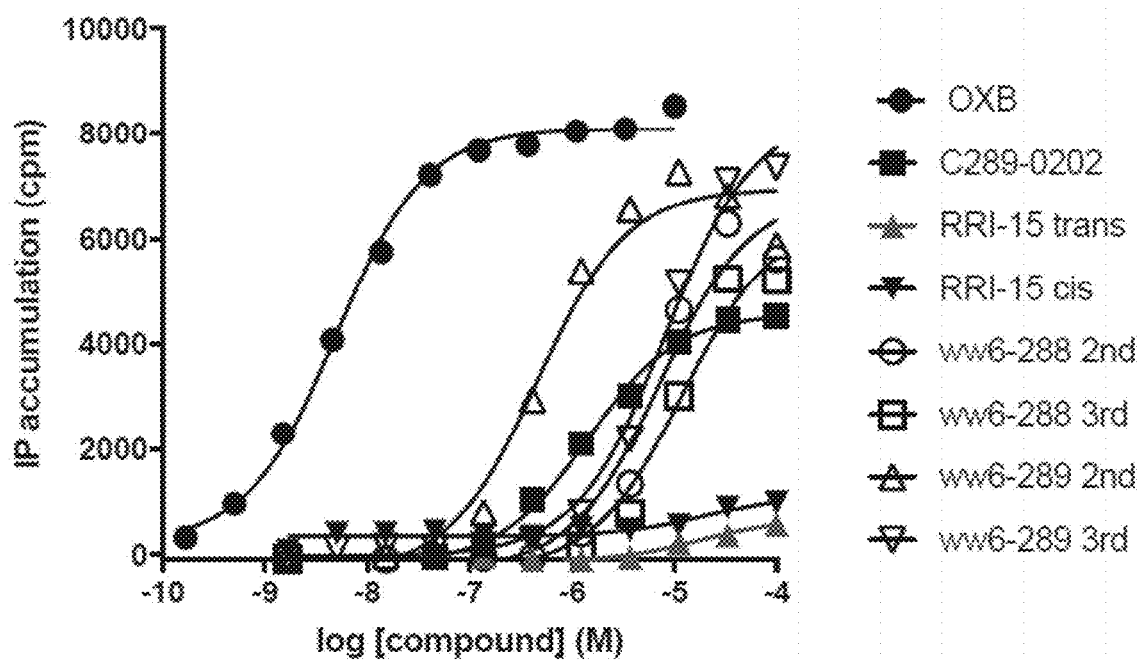
Figure 50:
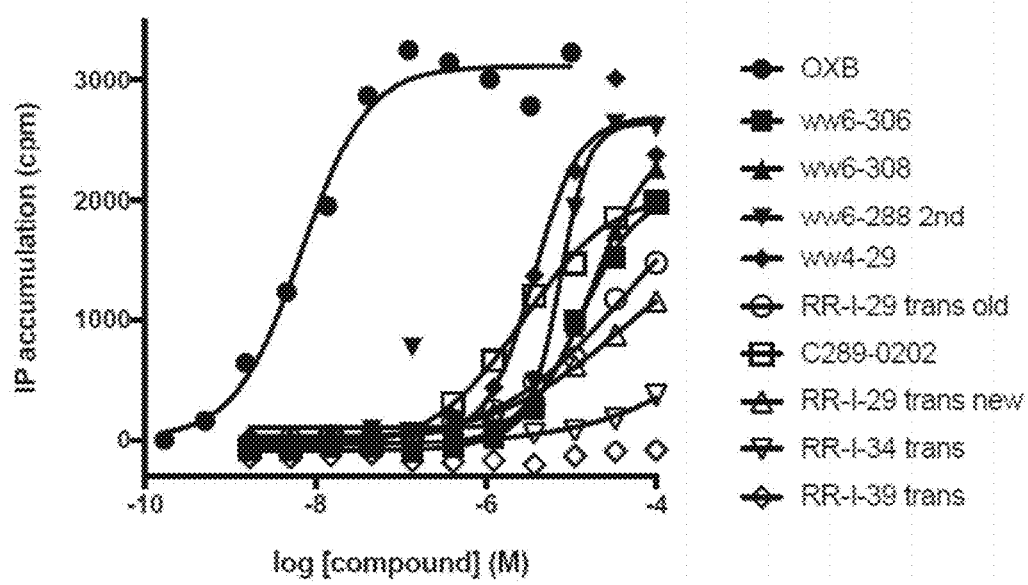
Figure 51:
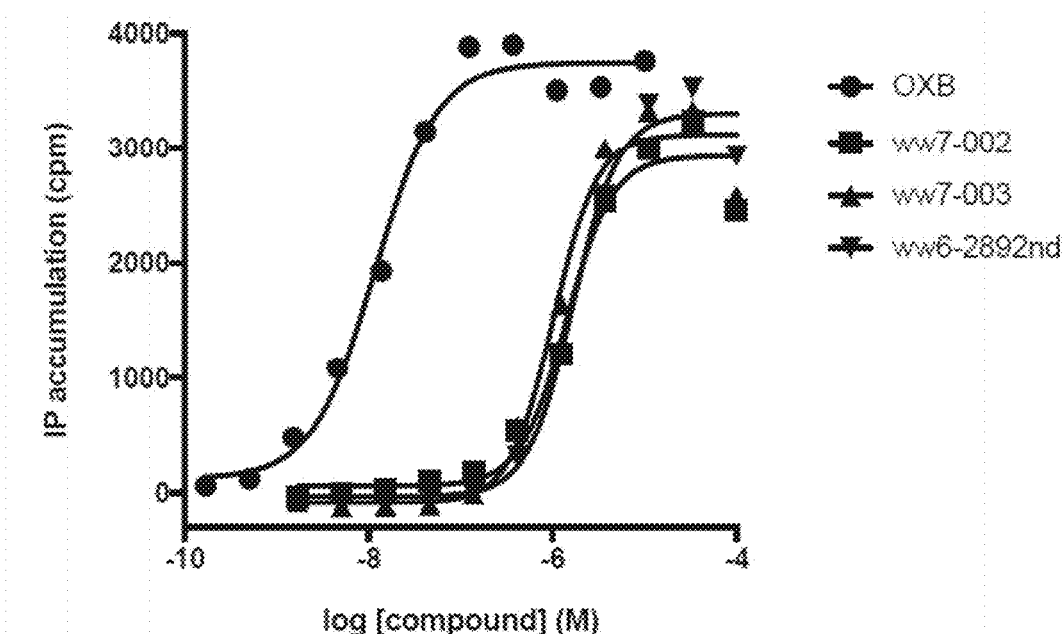
Figure 52:
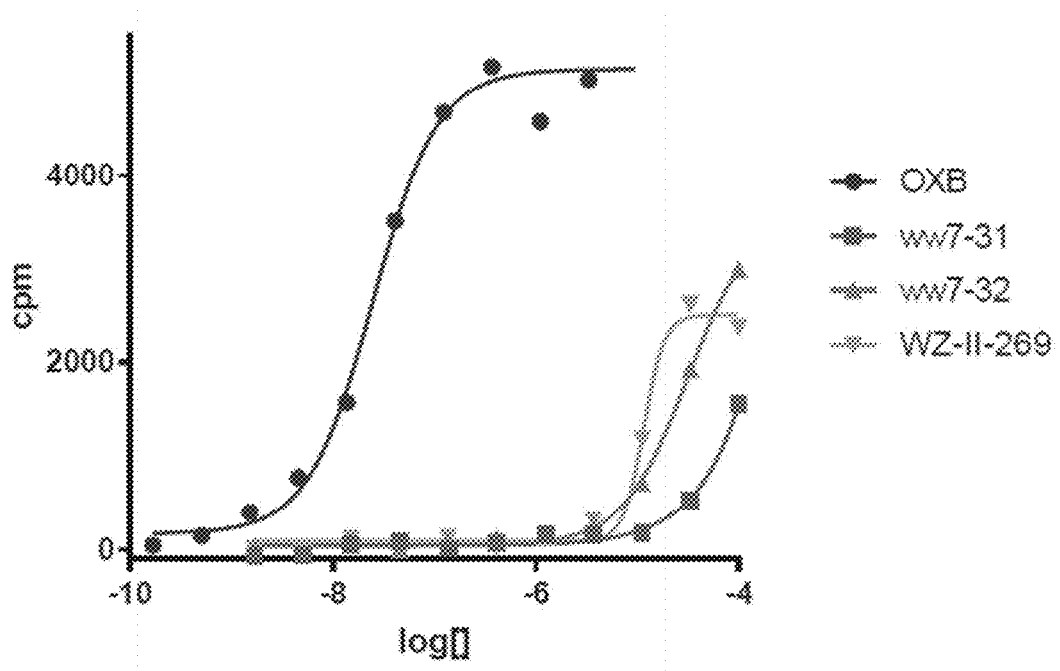
Figure 53:
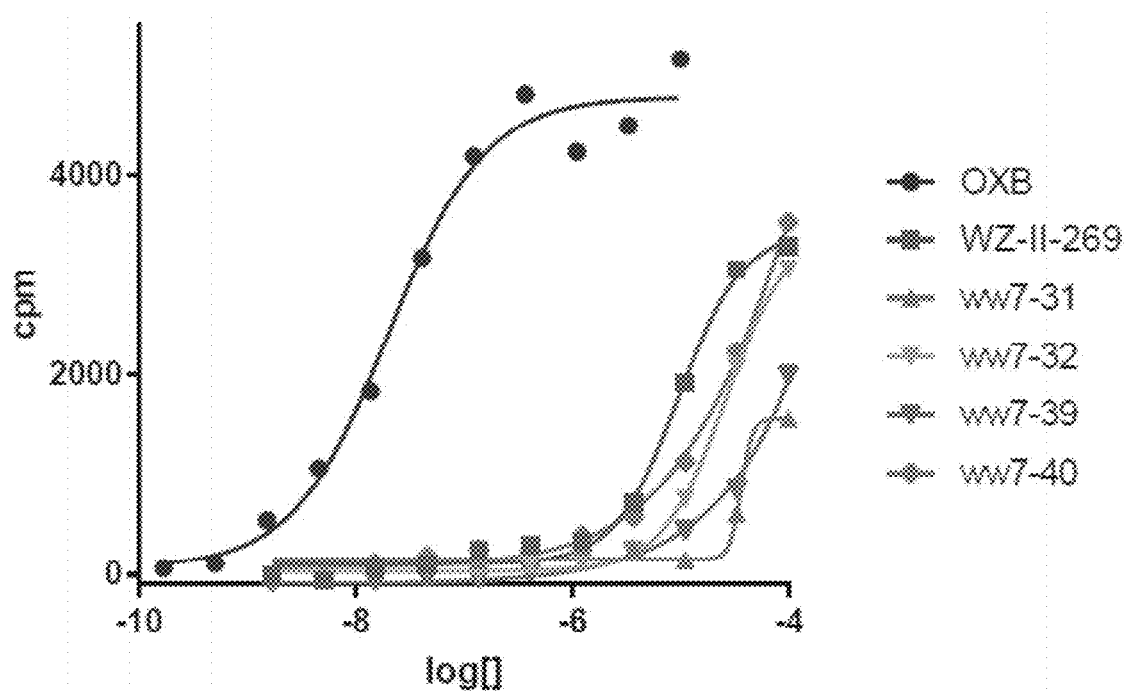
Figure 54:
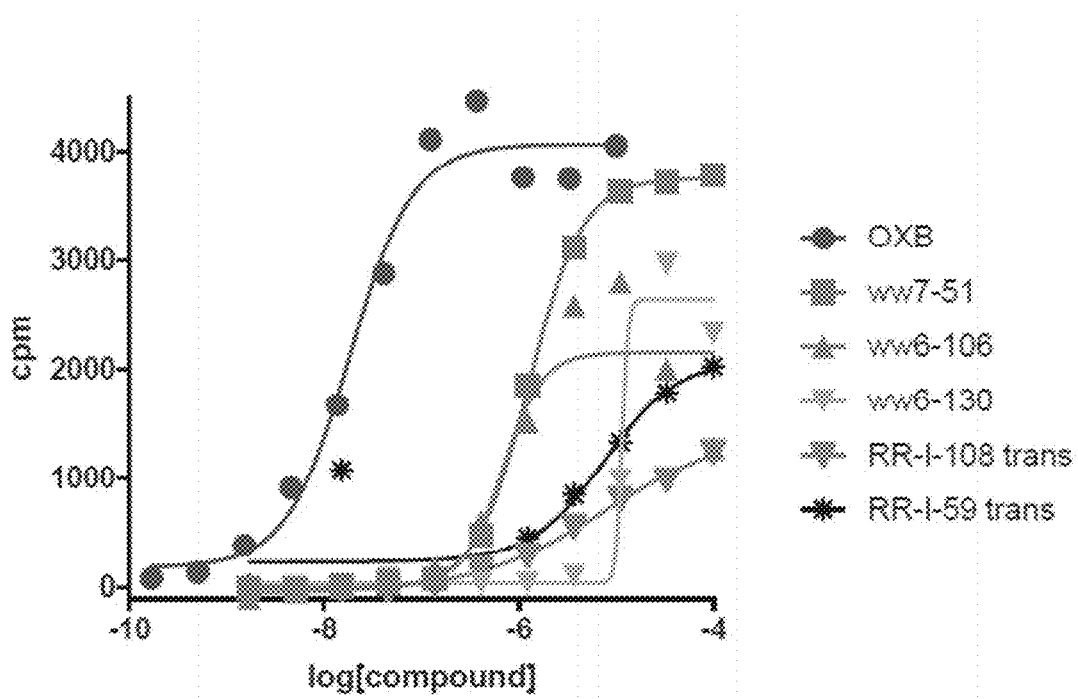
Figure 56:
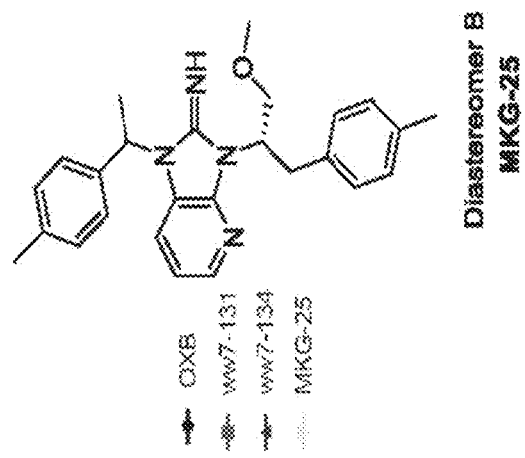
FIG. 56 illustrates the structure of MKG-25.
Figure 55:
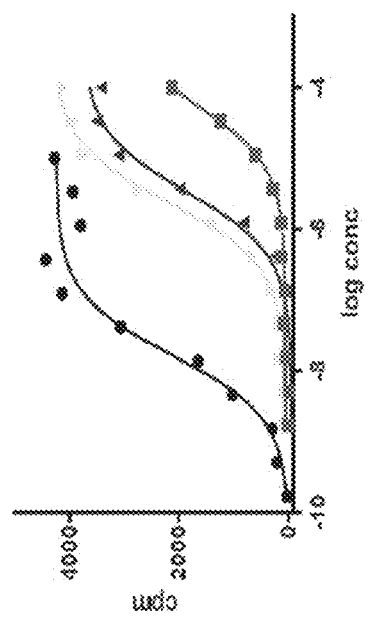
Figure 57:
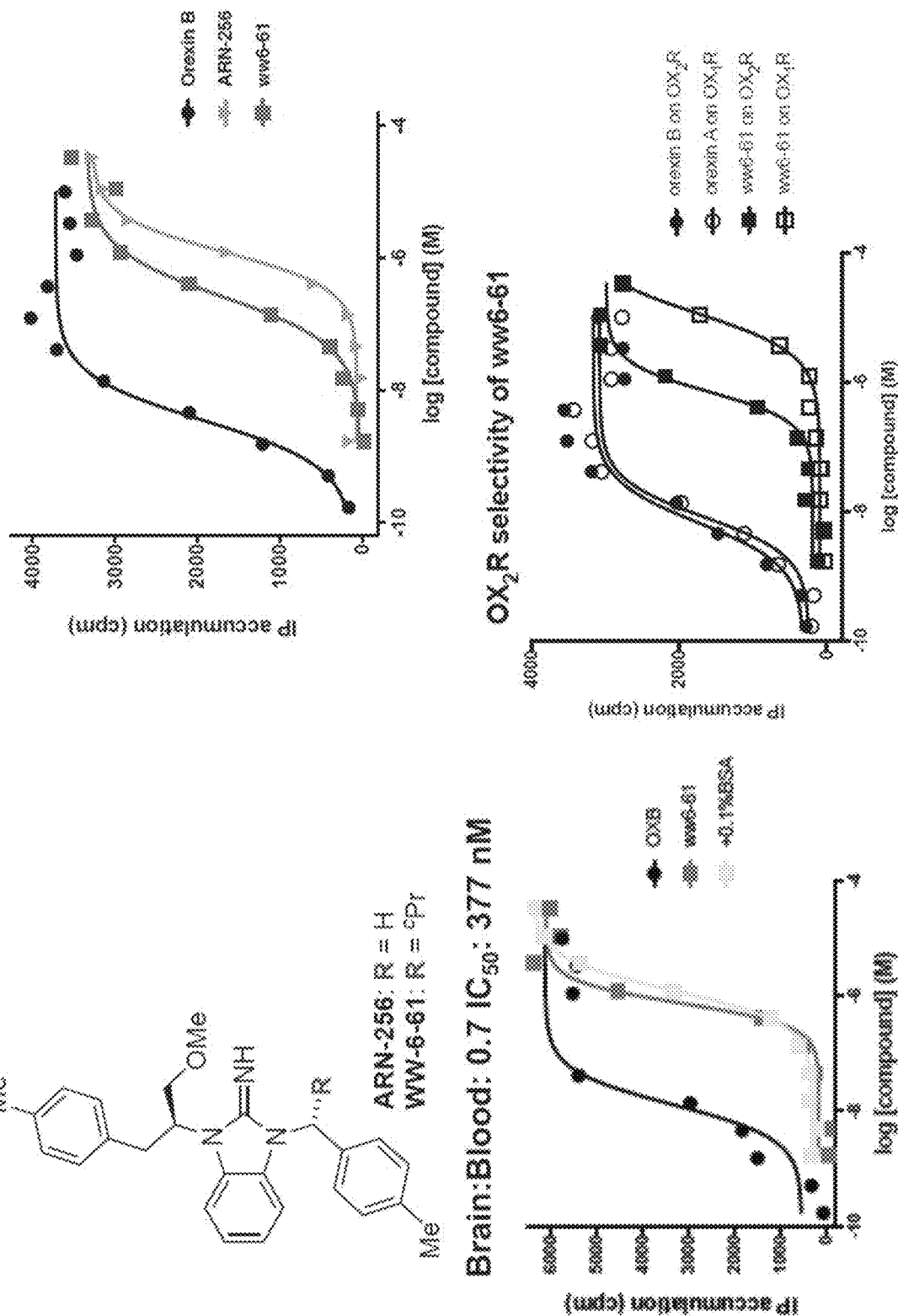
FIG. 57 illustrates the IP accumulation results of ARN-245 and WW-6-61, showing ether series: increased potency, better BBB.
Figure 58:
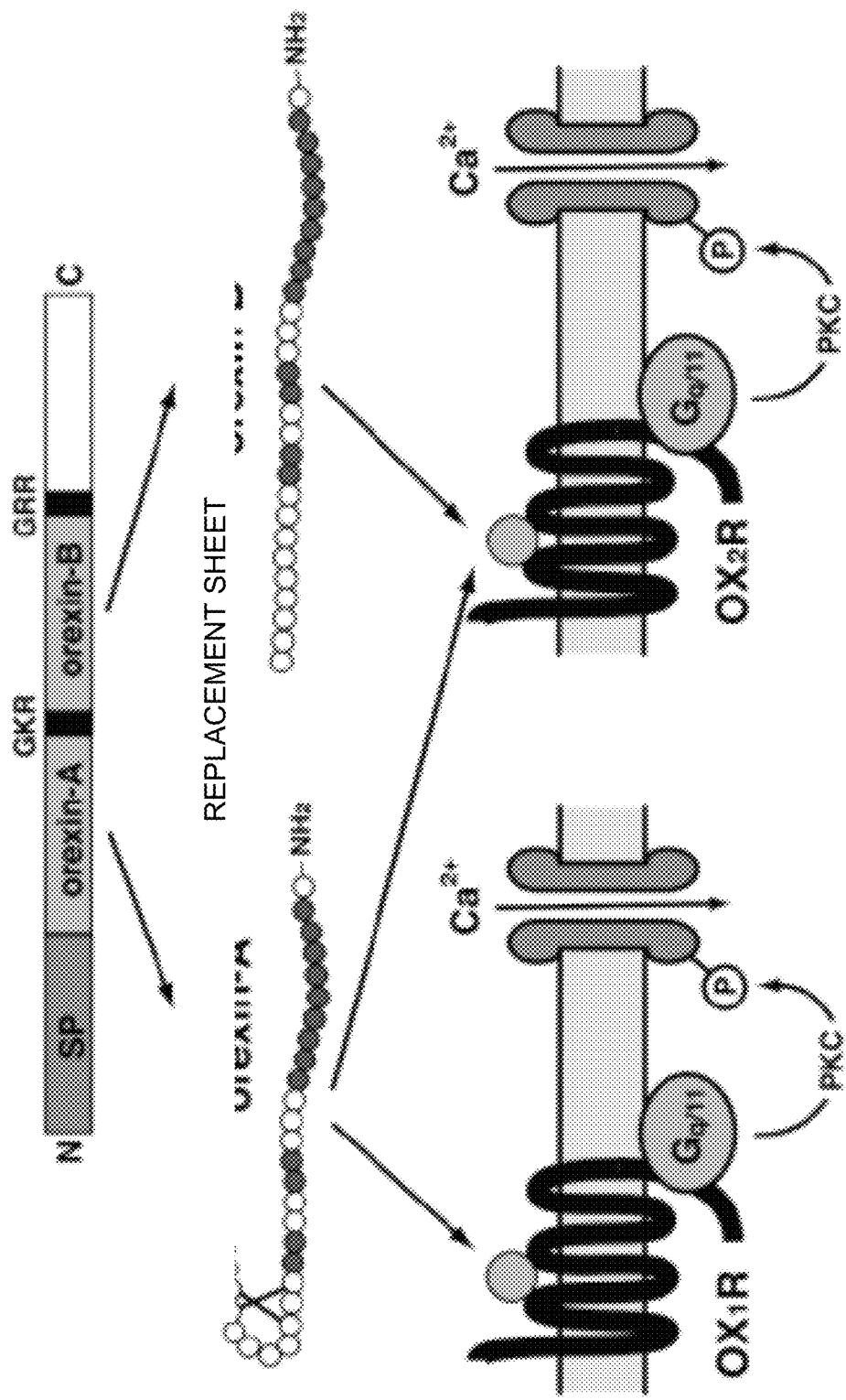
FIG. 58 illustrates the orexin neuropeptide system.
Figure 59:
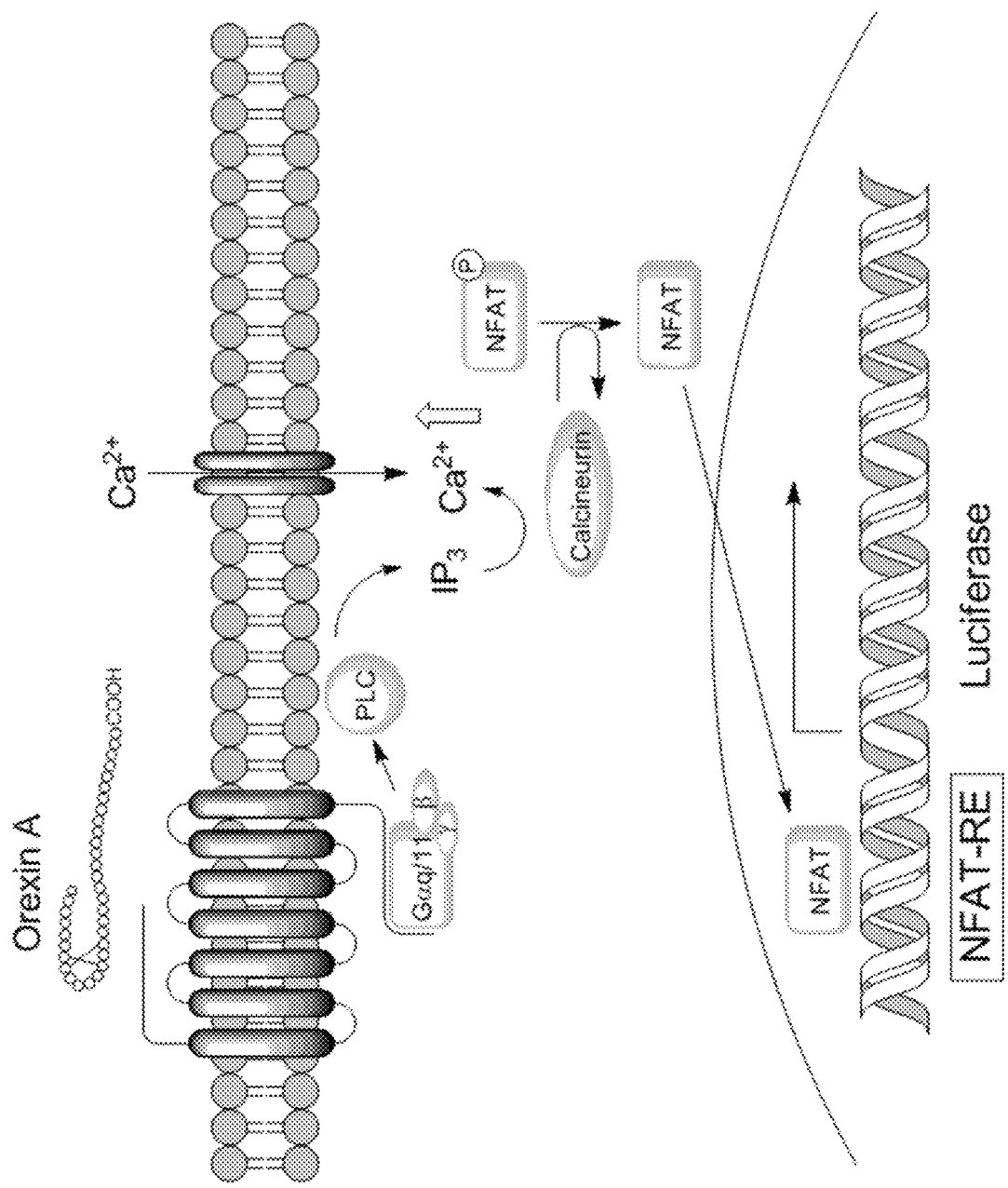
FIG. 59 illustrates a high-throughput screening assay.
Figure 61:
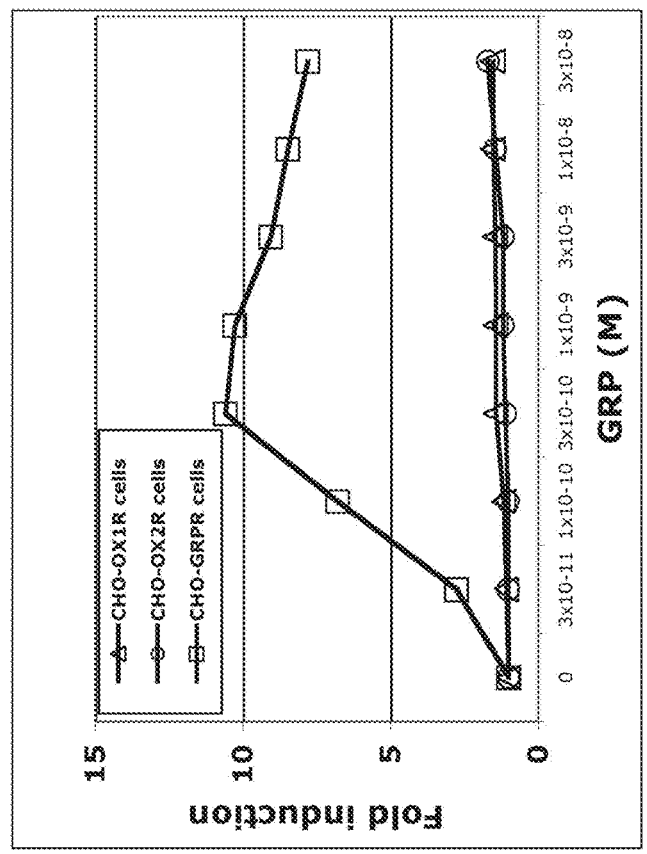
FIG. 61 illustrates the validation of the reporter cell lines using the high-throughput screening assay: CHO cells (NFAT-luciferase) co-transfected with OX1R, OX2R, or GRPR: GRM (M).
Figure 60:
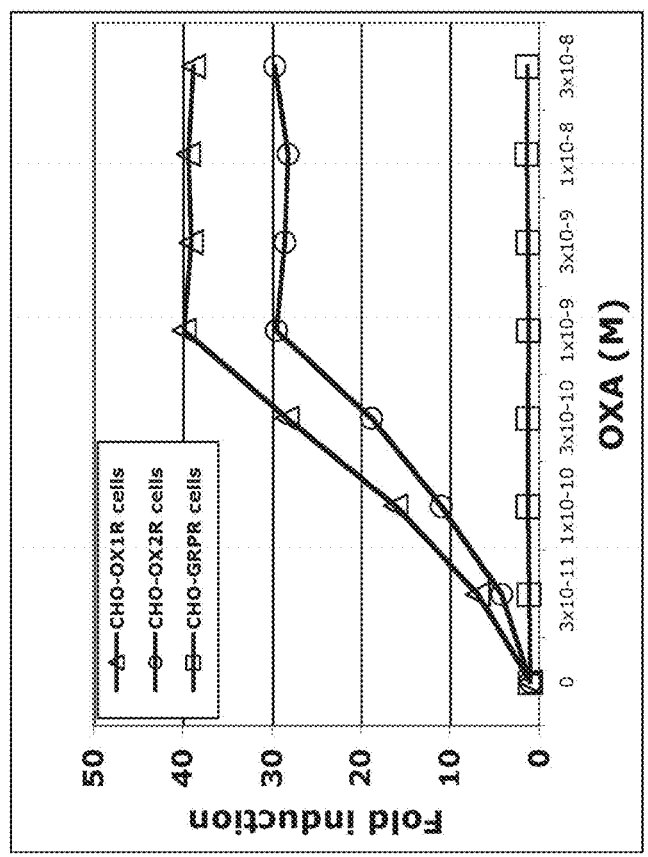
FIG. 60 illustrates the validation of the reporter cell lines using the high-throughput screening assay: CHO cells (NFAT-luciferase) co-transfected with OX1R, OX2R, or GRPR: OXA (M).
Figure 62:
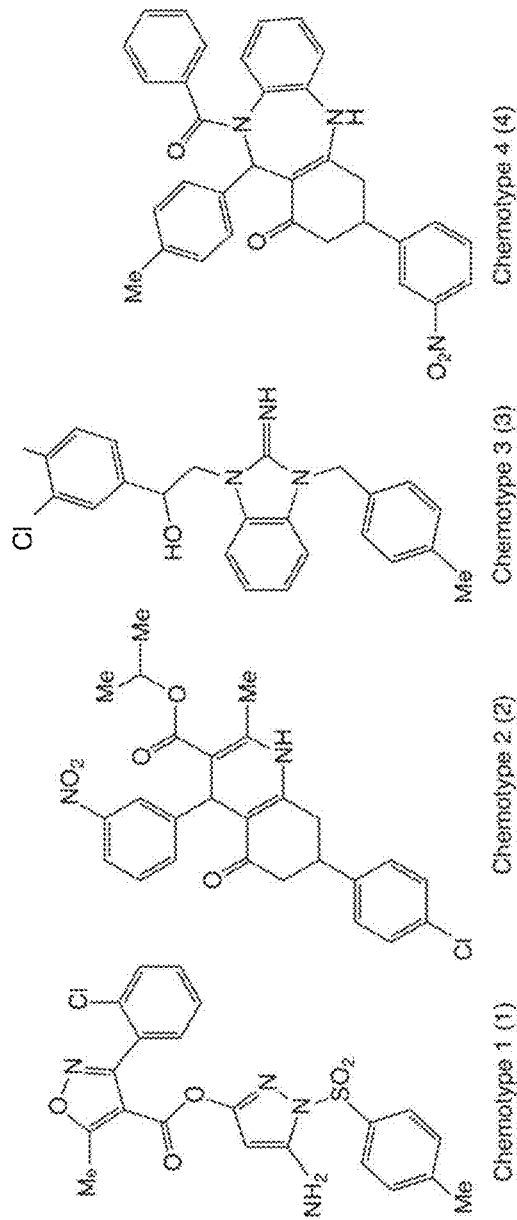
FIG. 62 illustrates four hit families identified through the high-throughput screening assay.
Figure 62:
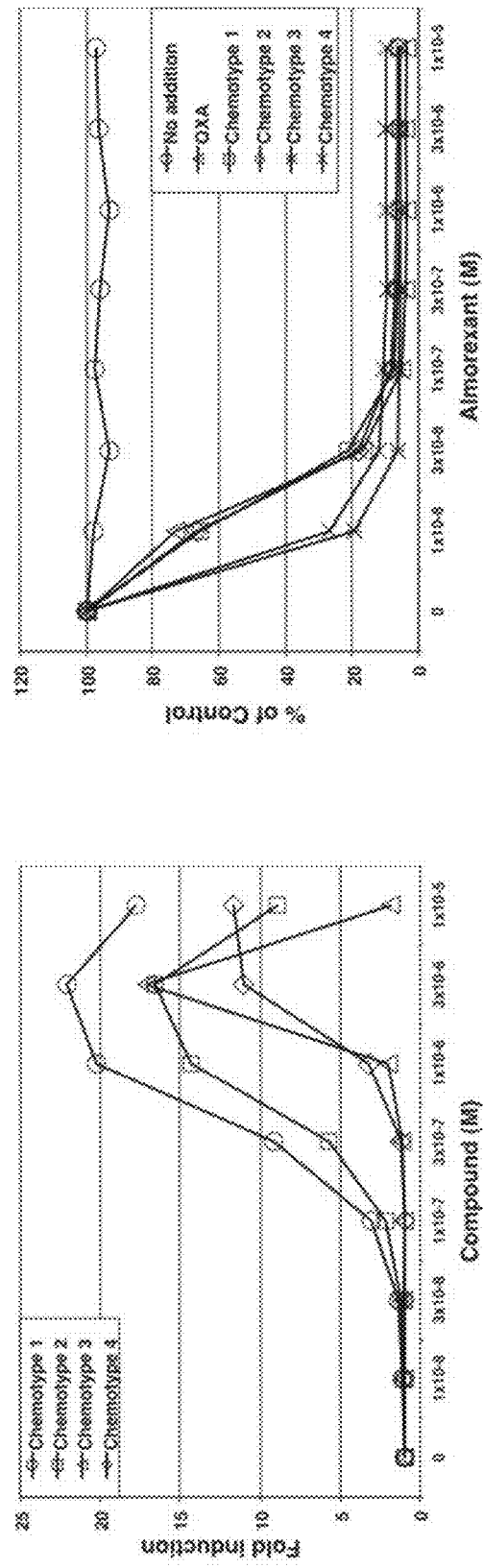
Figure 63:
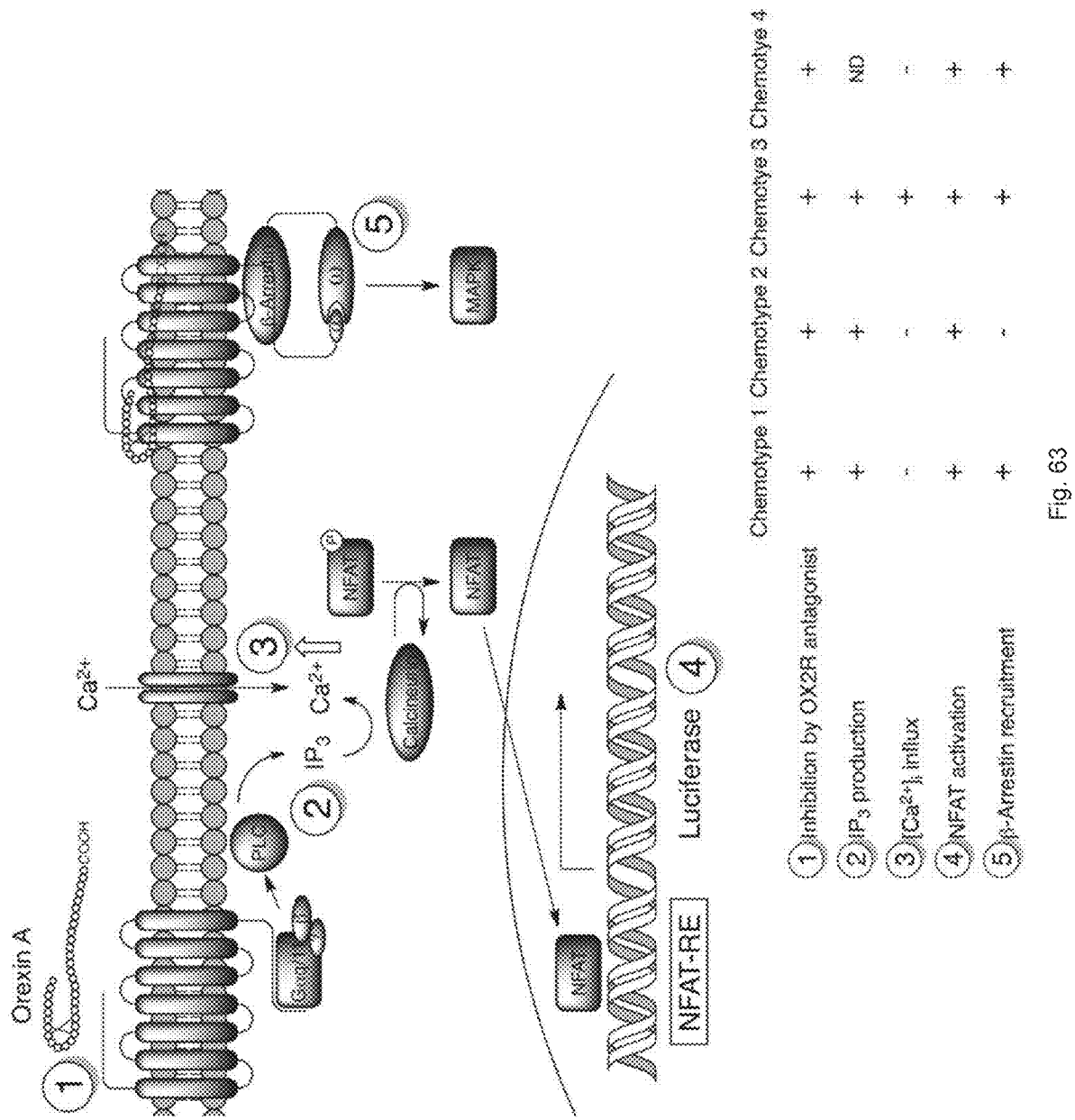
FIG. 63 illustrates the activity of the four hits in various assays.
Figure 64:
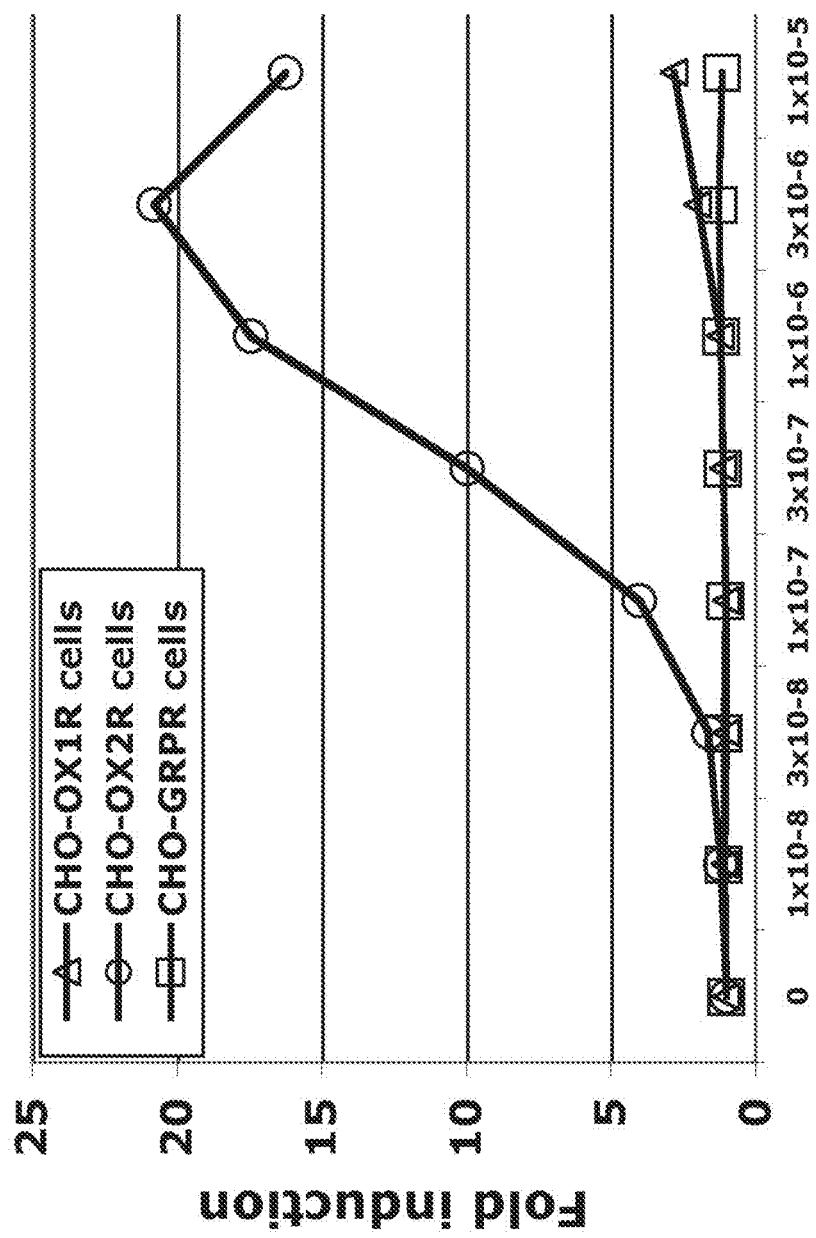
FIG. 64 illustrates an example of Chemotype 1 and its activity; 1A: X=Me; $EC_{50}$~300 nM.
Figure 64:
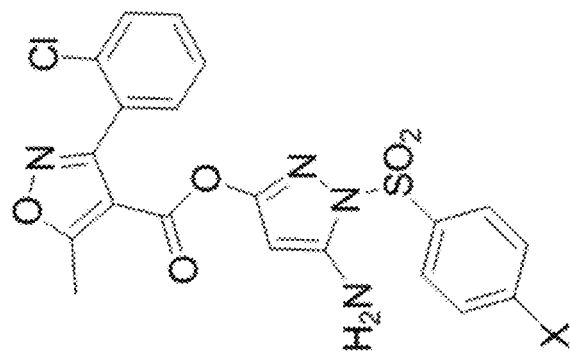
Figure 65:
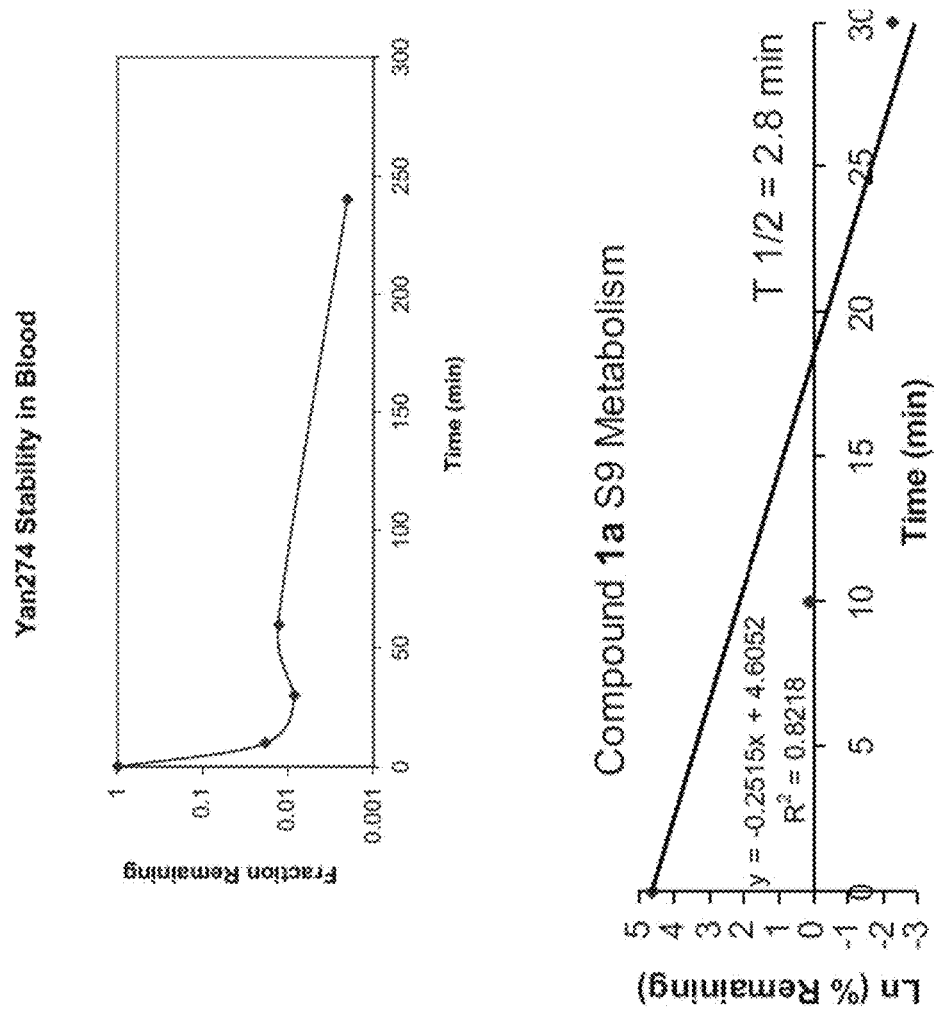
FIG. 65 illustrates the stability of a compound of Chemotype 1.
Figure 65:
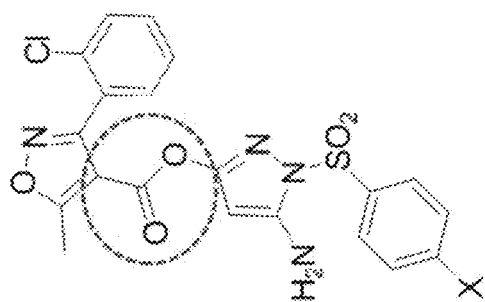
Figure 66:
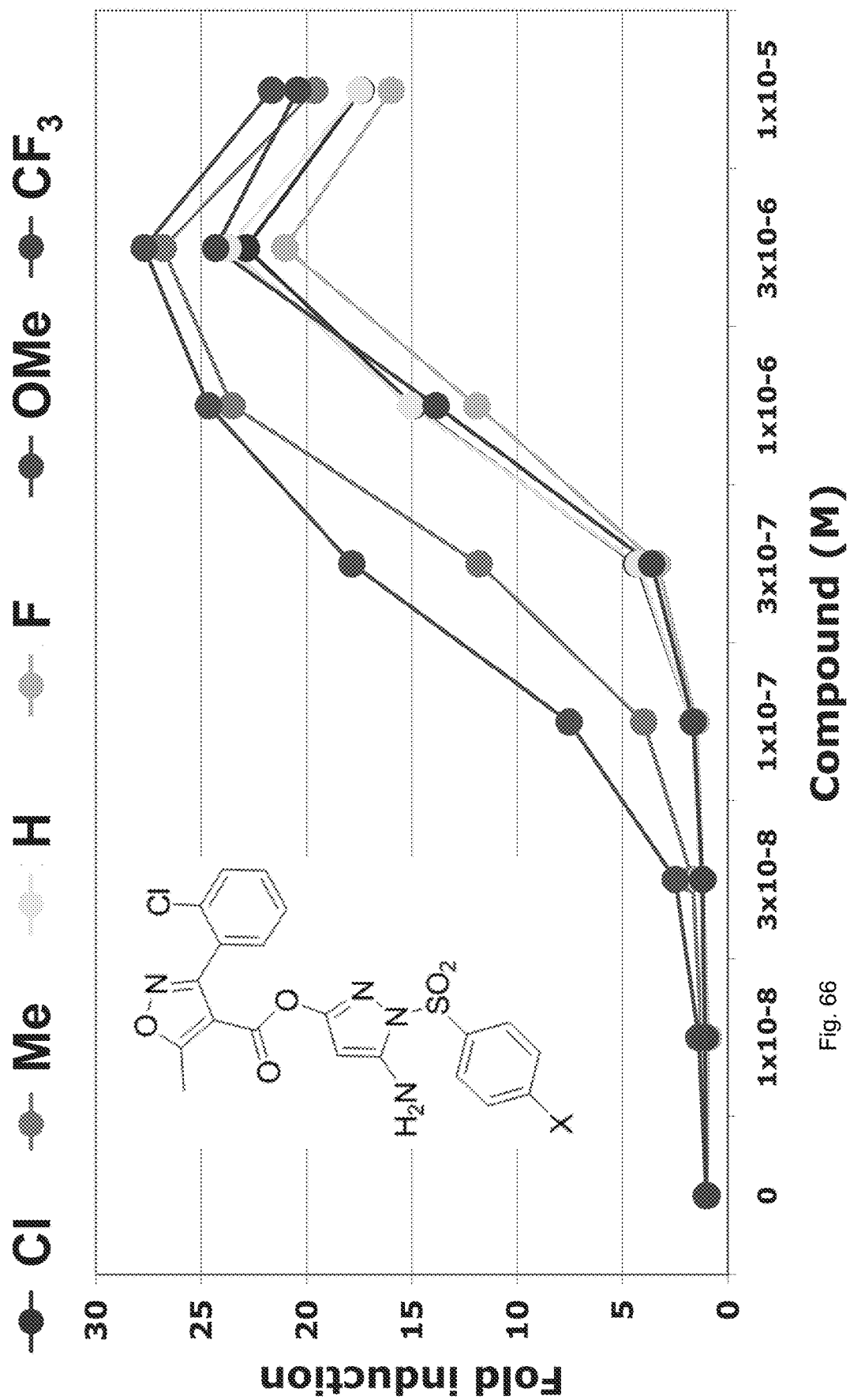
FIG. 66 illustrates the results of SAR analysis of certain compounds of Chemotype 1.
Figure 67:
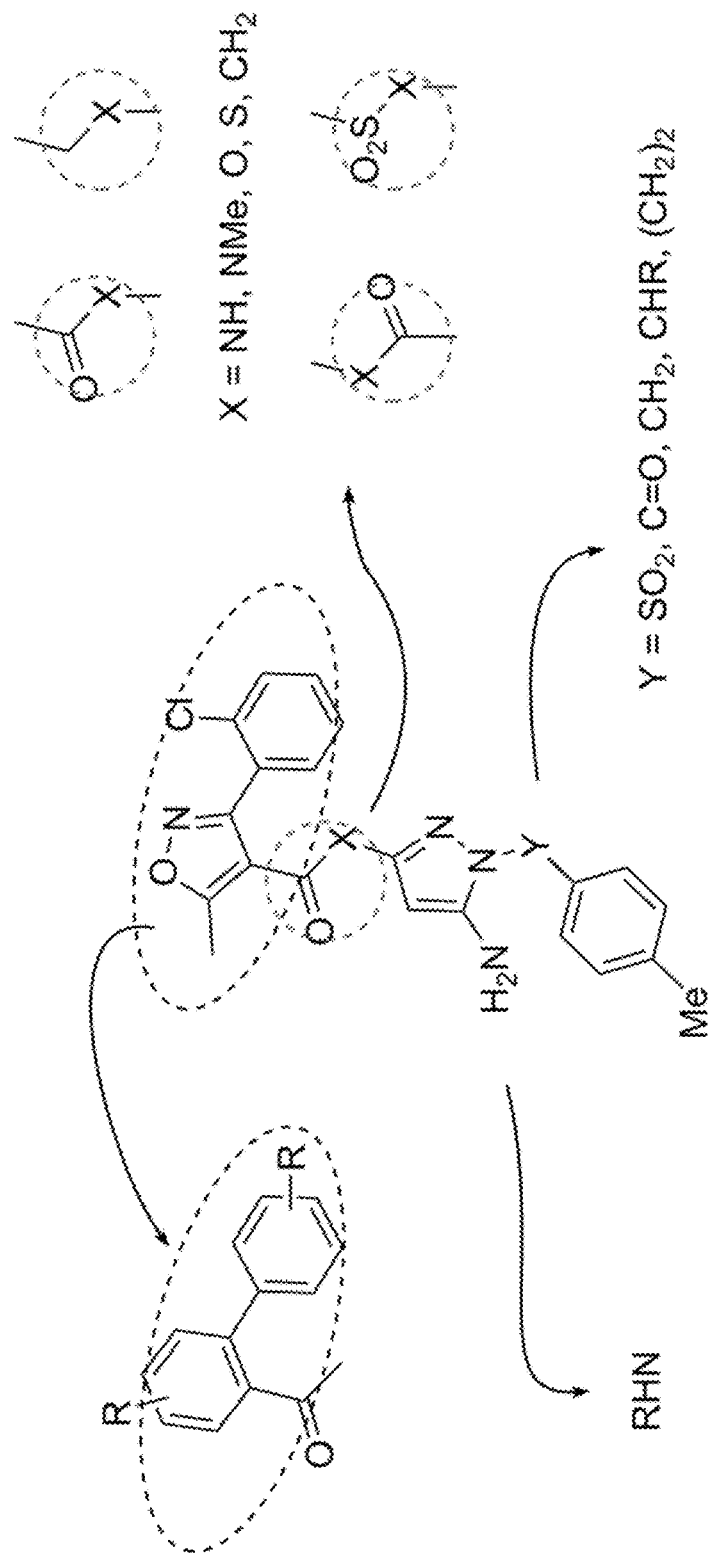
FIG. 67 summaries the tested activity of certain compounds of Chemotype 1.
Figure 68:
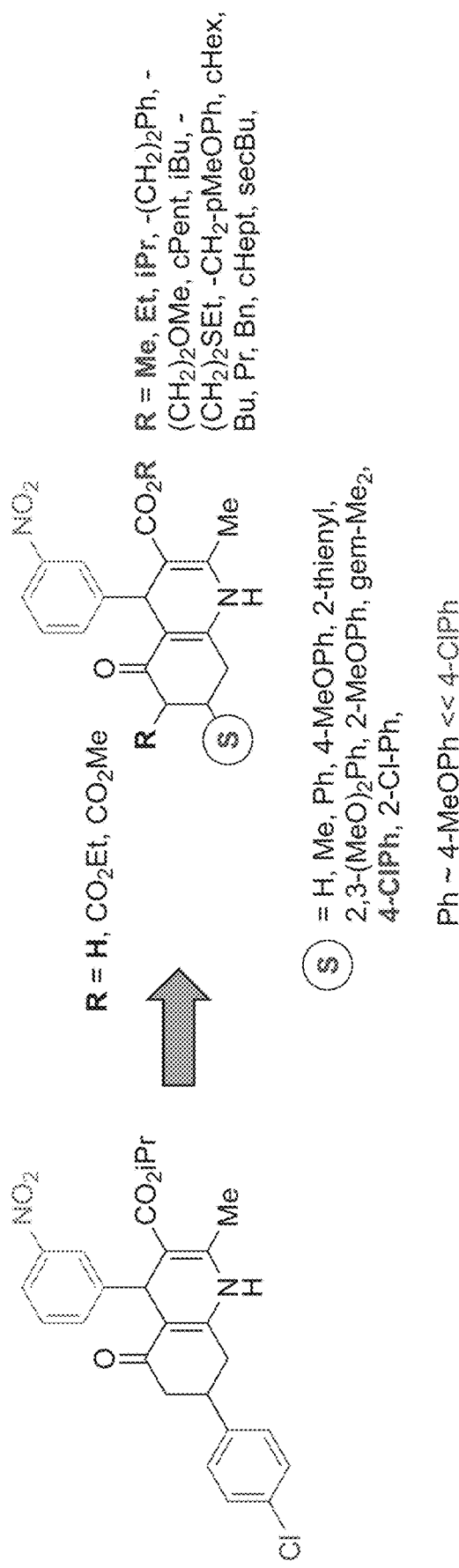
FIGS. 68-72 illustrate compounds of Chemotype 2.
Figure 69:
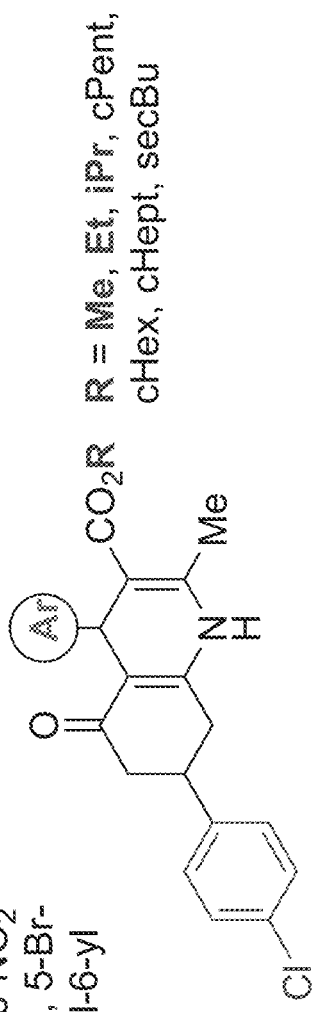
Figure 70:
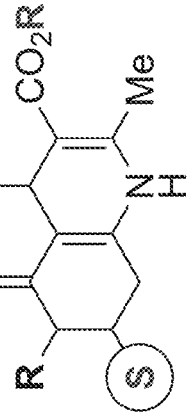
Figure 70:
Figure 70:
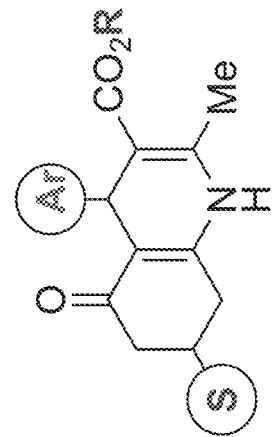
Figure 71:
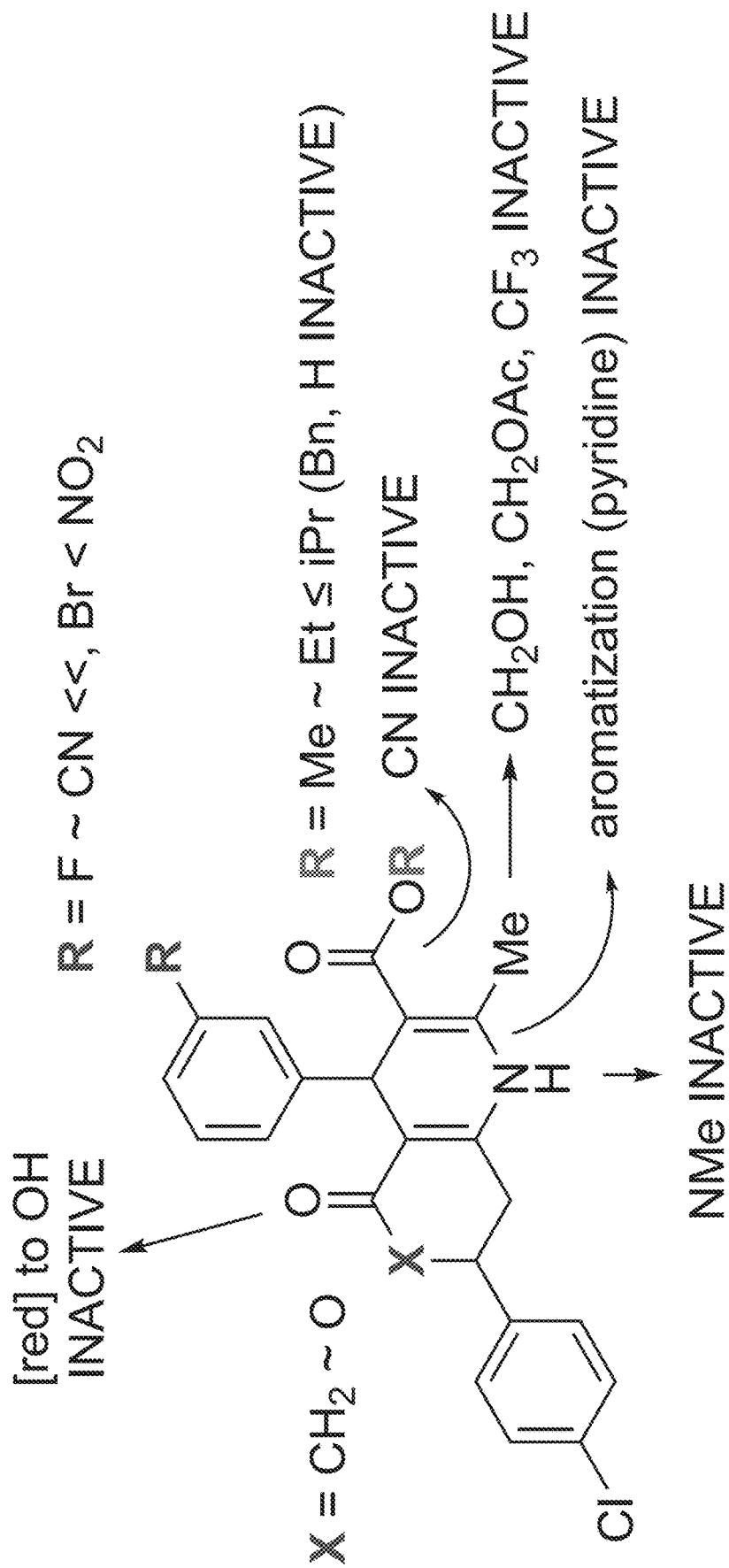
Figure 72:
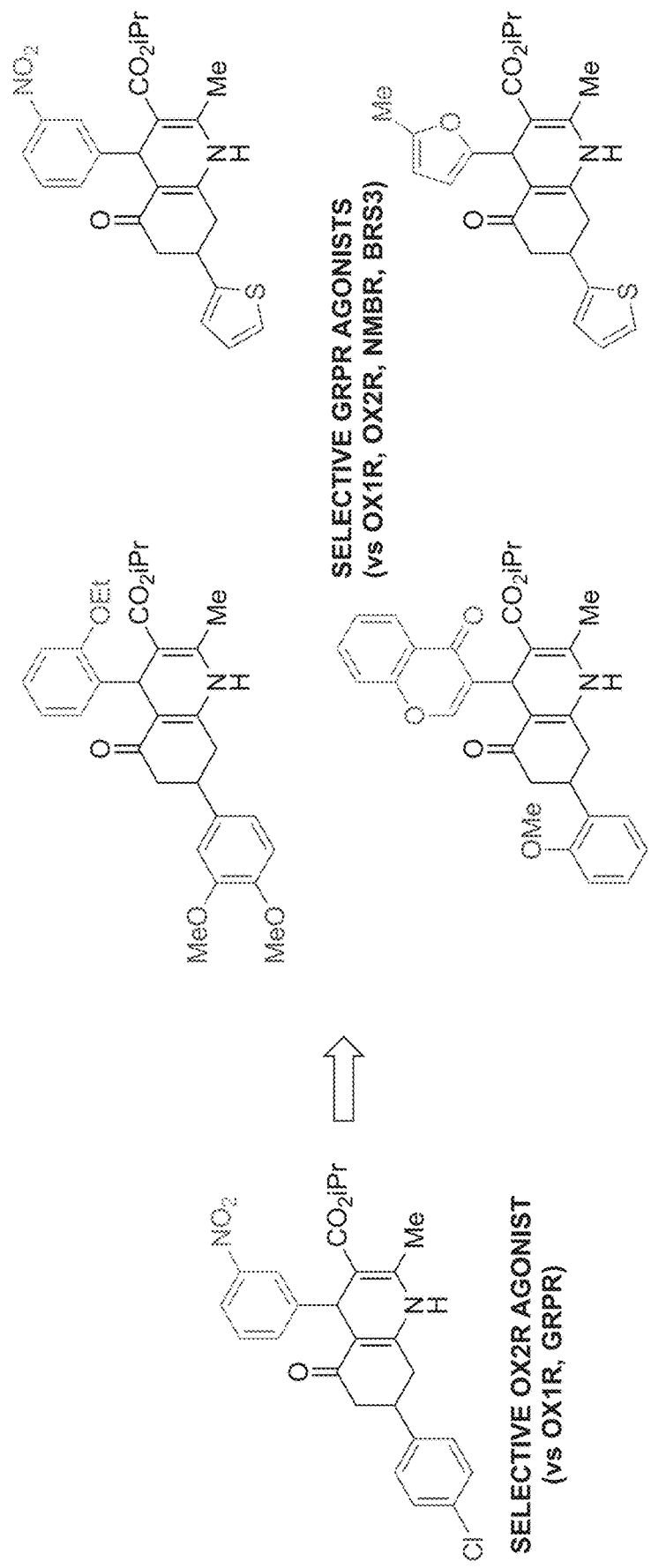
Figure 73:
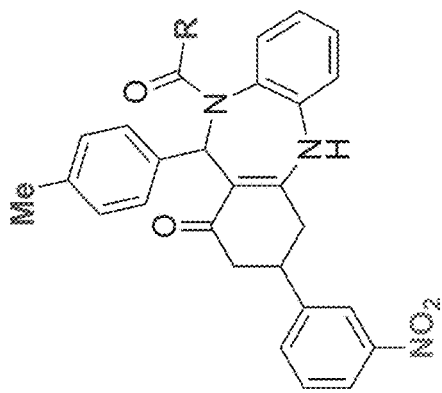
FIGS. 73 and 74 illustrate compounds of Chemotype 4.
Figure 73:
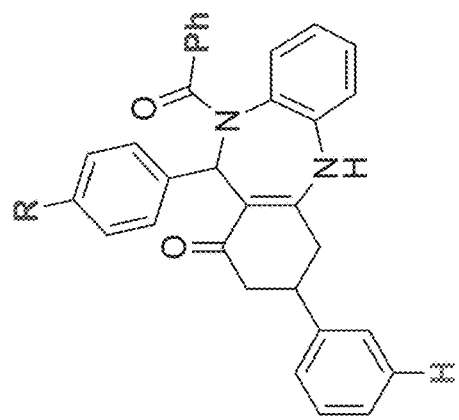
Figure 74:
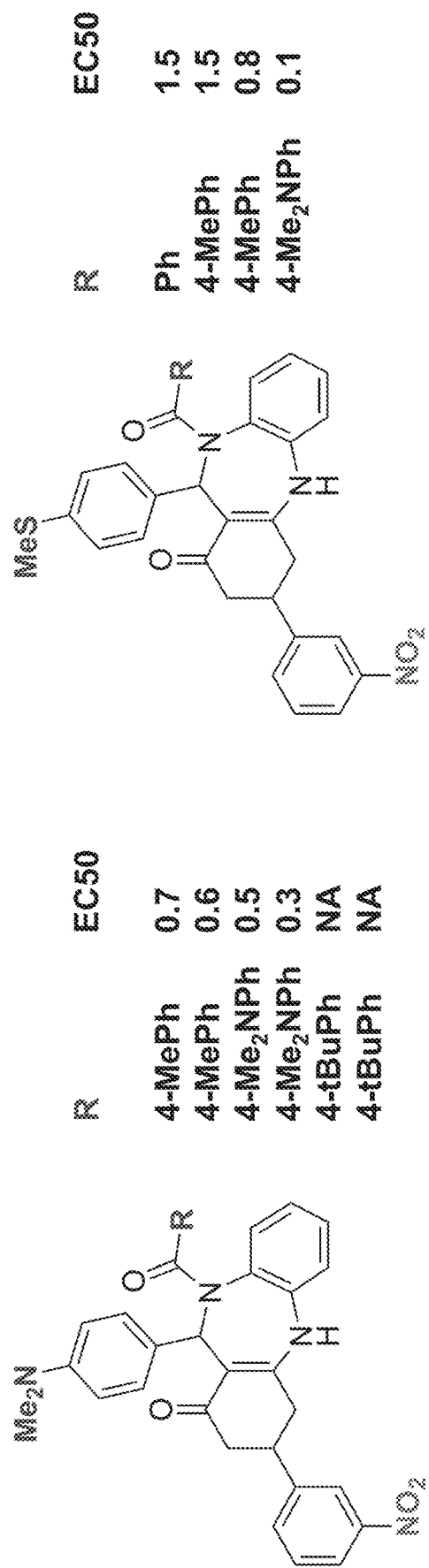
Figure 75:
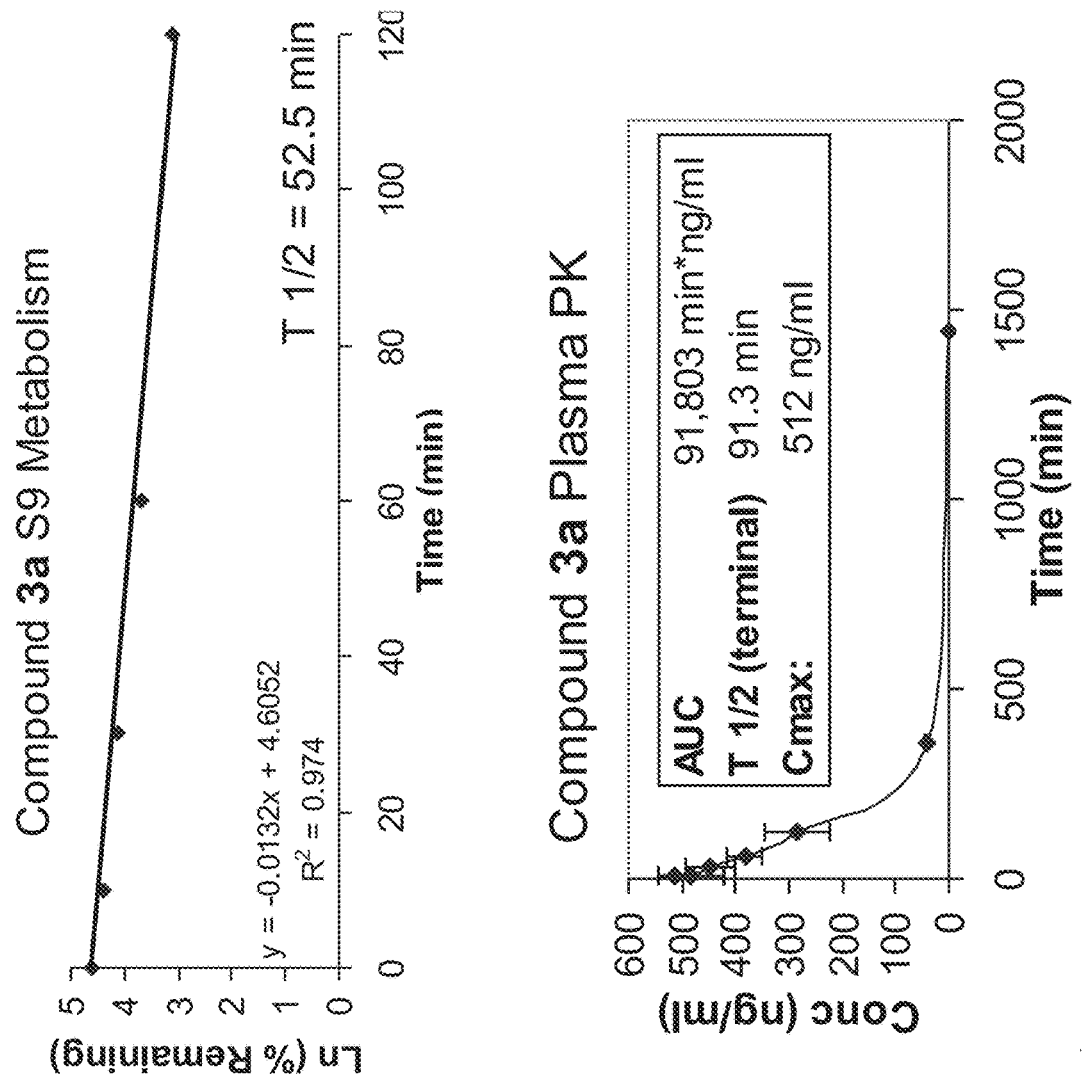
FIGS. 75-77 illustrate compounds of Chemotype 3.
Figure 75:
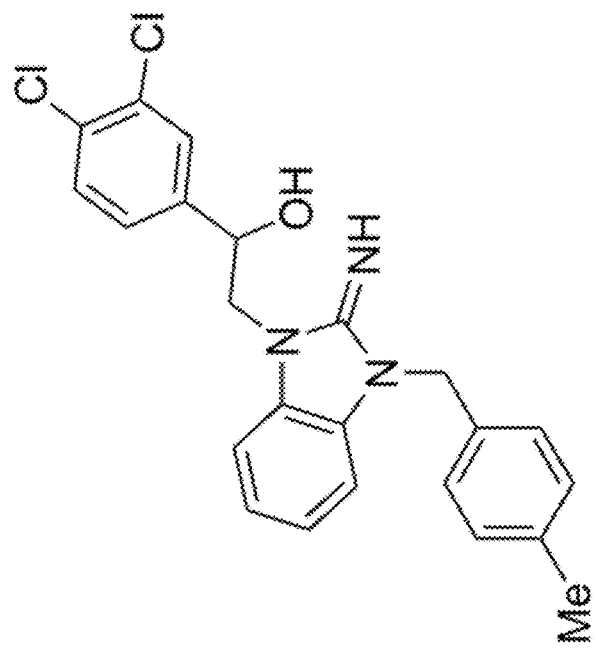
Figure 76:
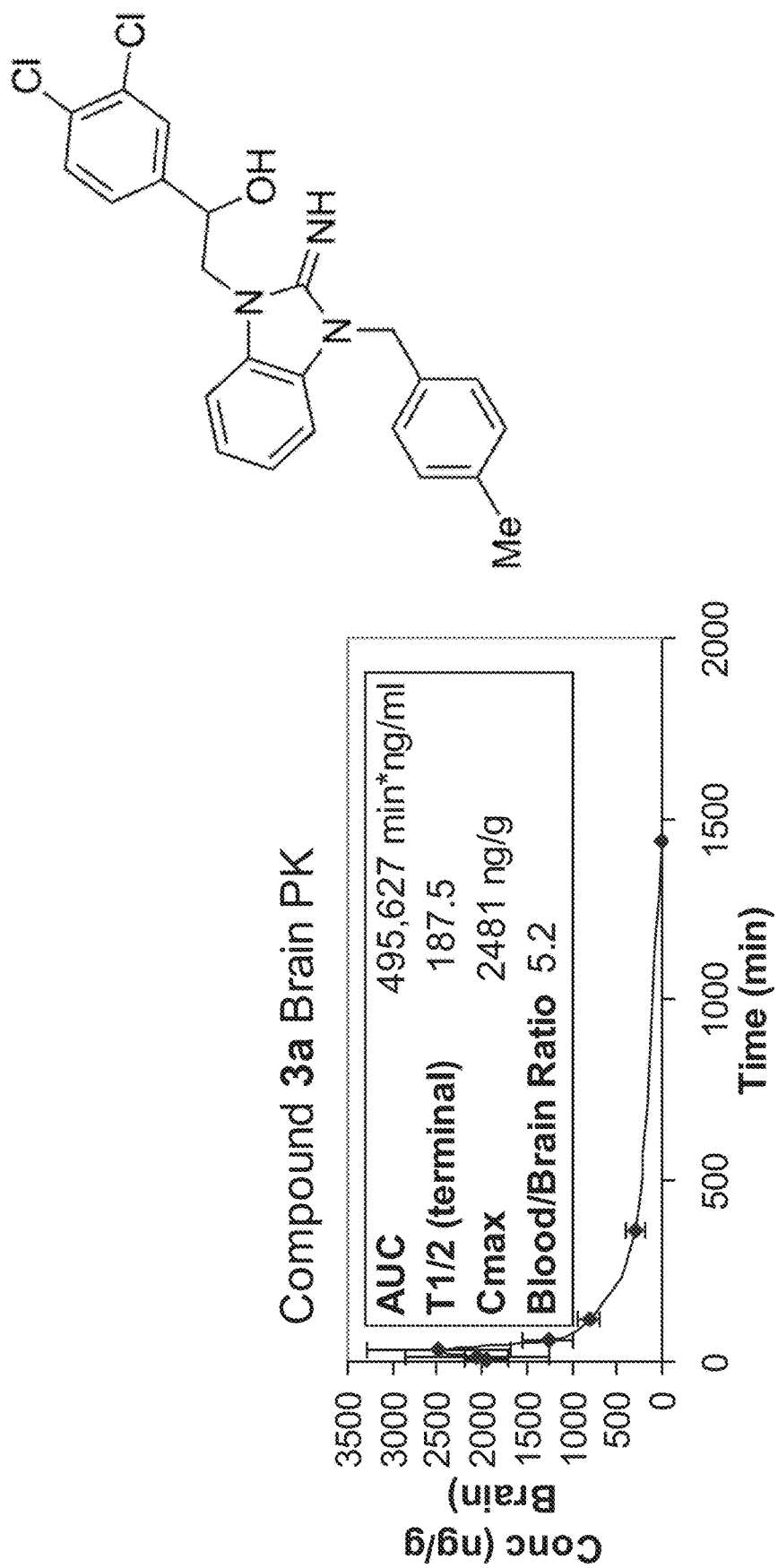
Figure 77:
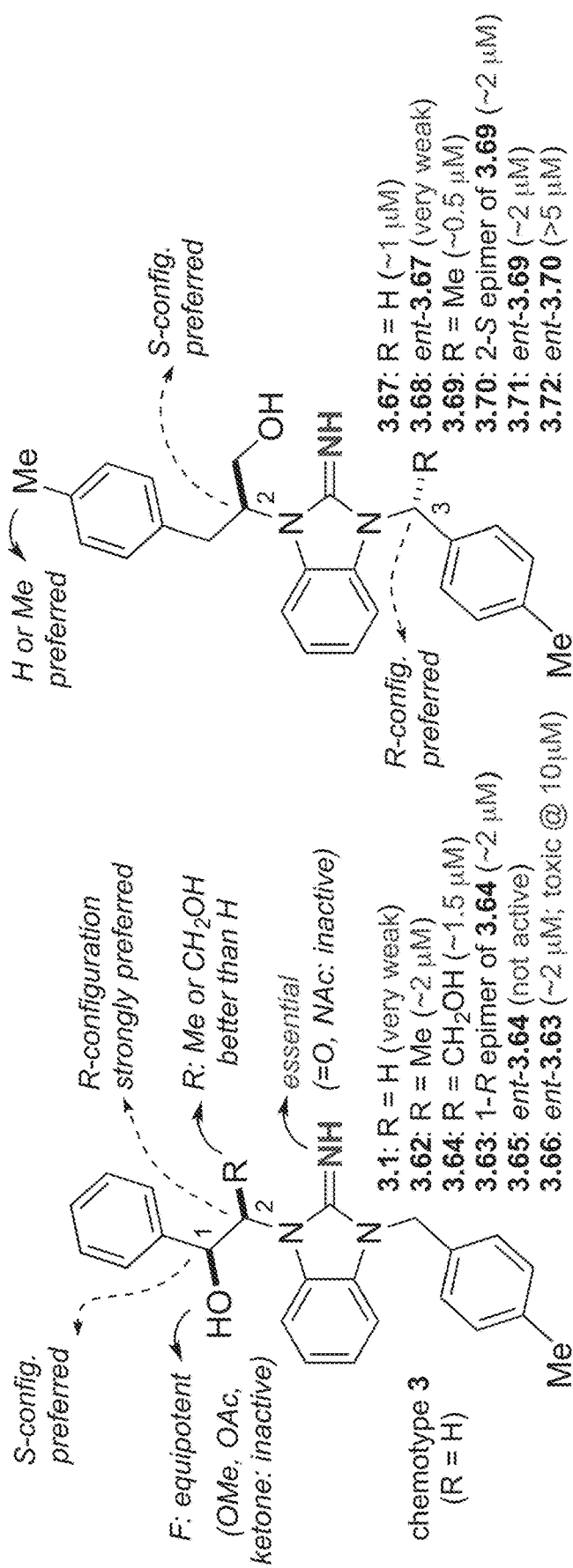
Figure 78:
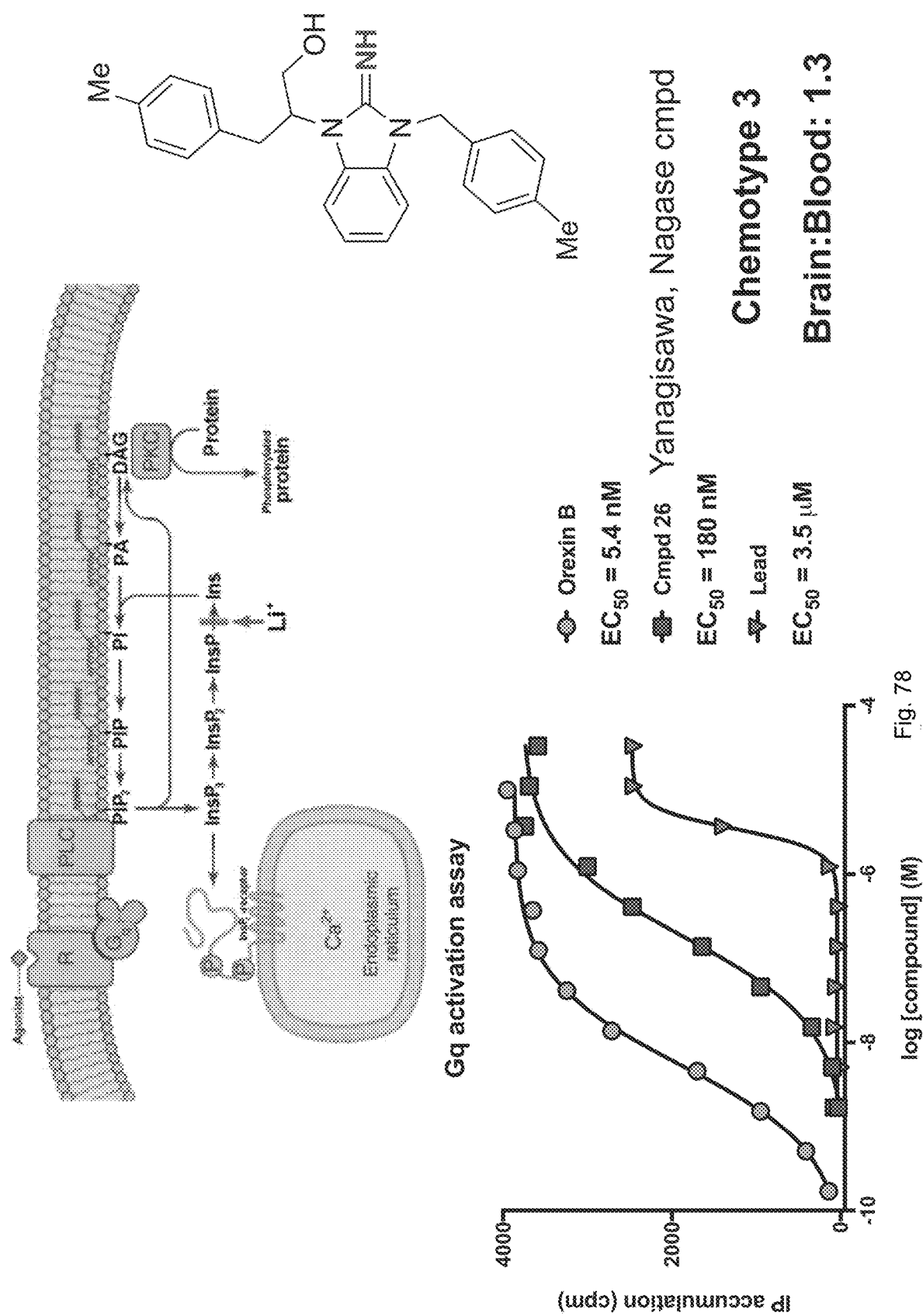
FIG. 78 illustrates the IP assay for $OX_2R$-expressing HEK cells.
Figure 79:
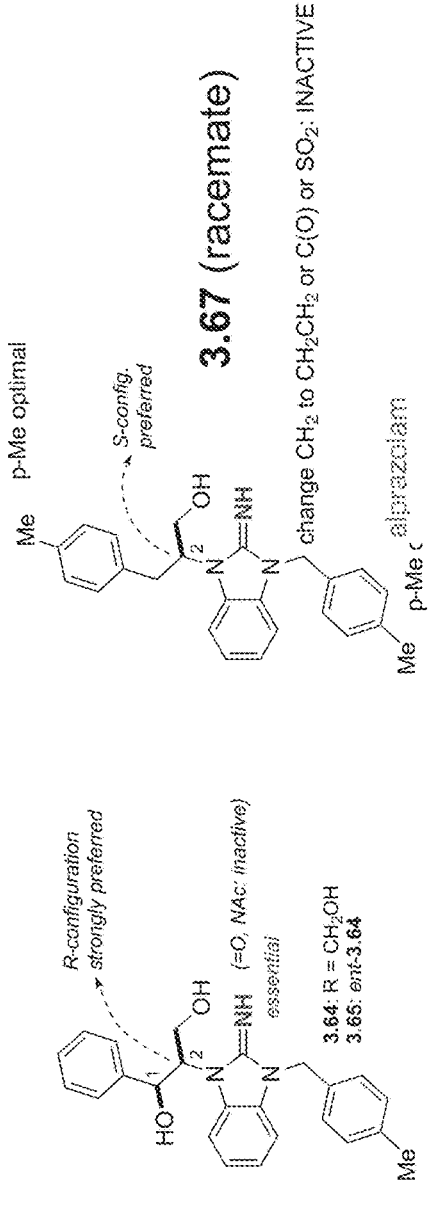
FIG. 79 shows results of the initial SAR studies.
Figure 79:
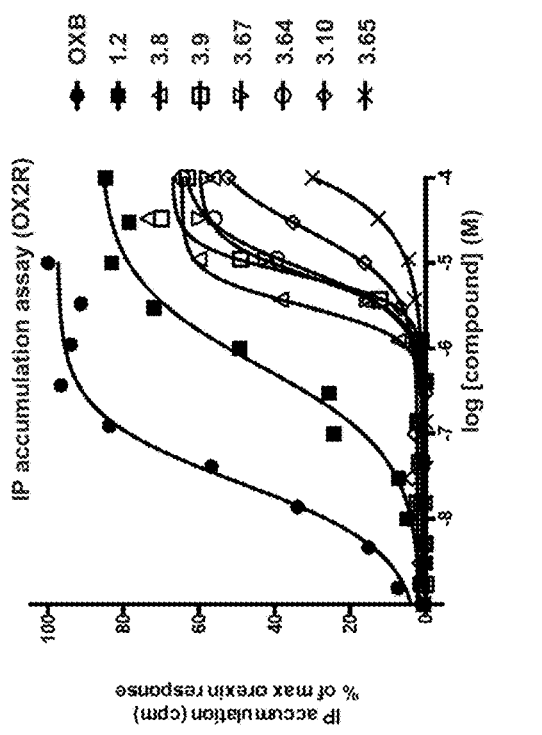
Figure 79:
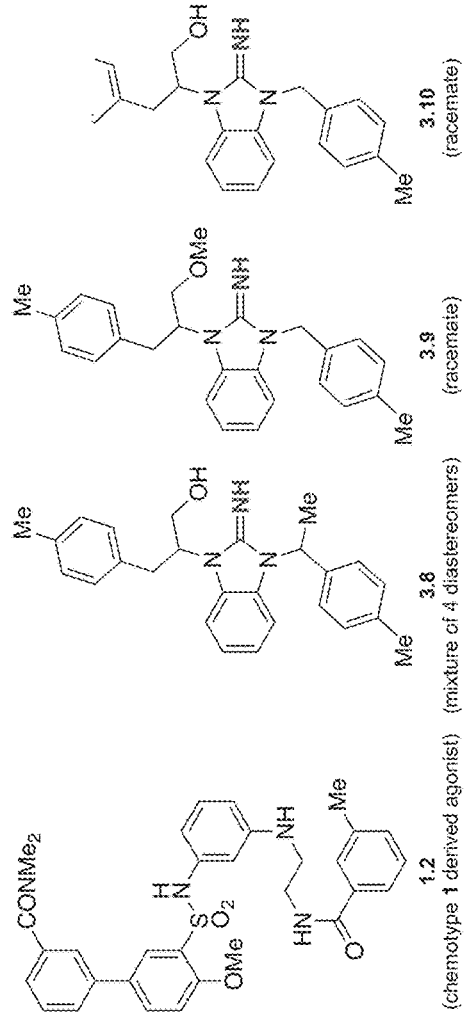
Figure 80:
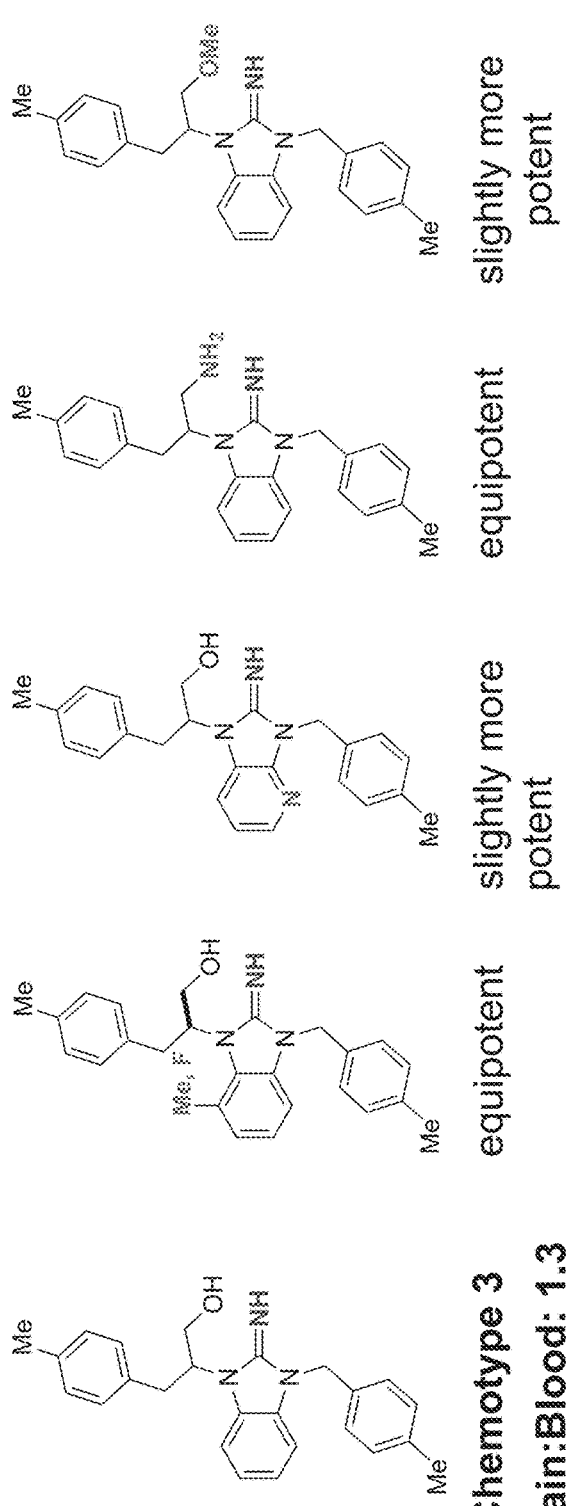
FIGS. 80-83 summarize SAR results for Chemotype 3.
Figure 80:
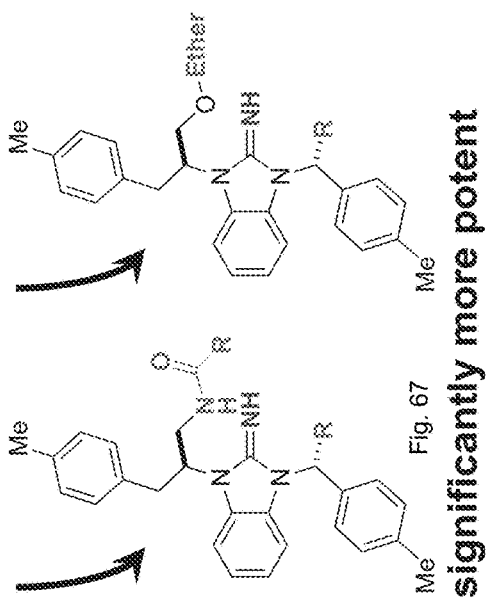
Figure 81:
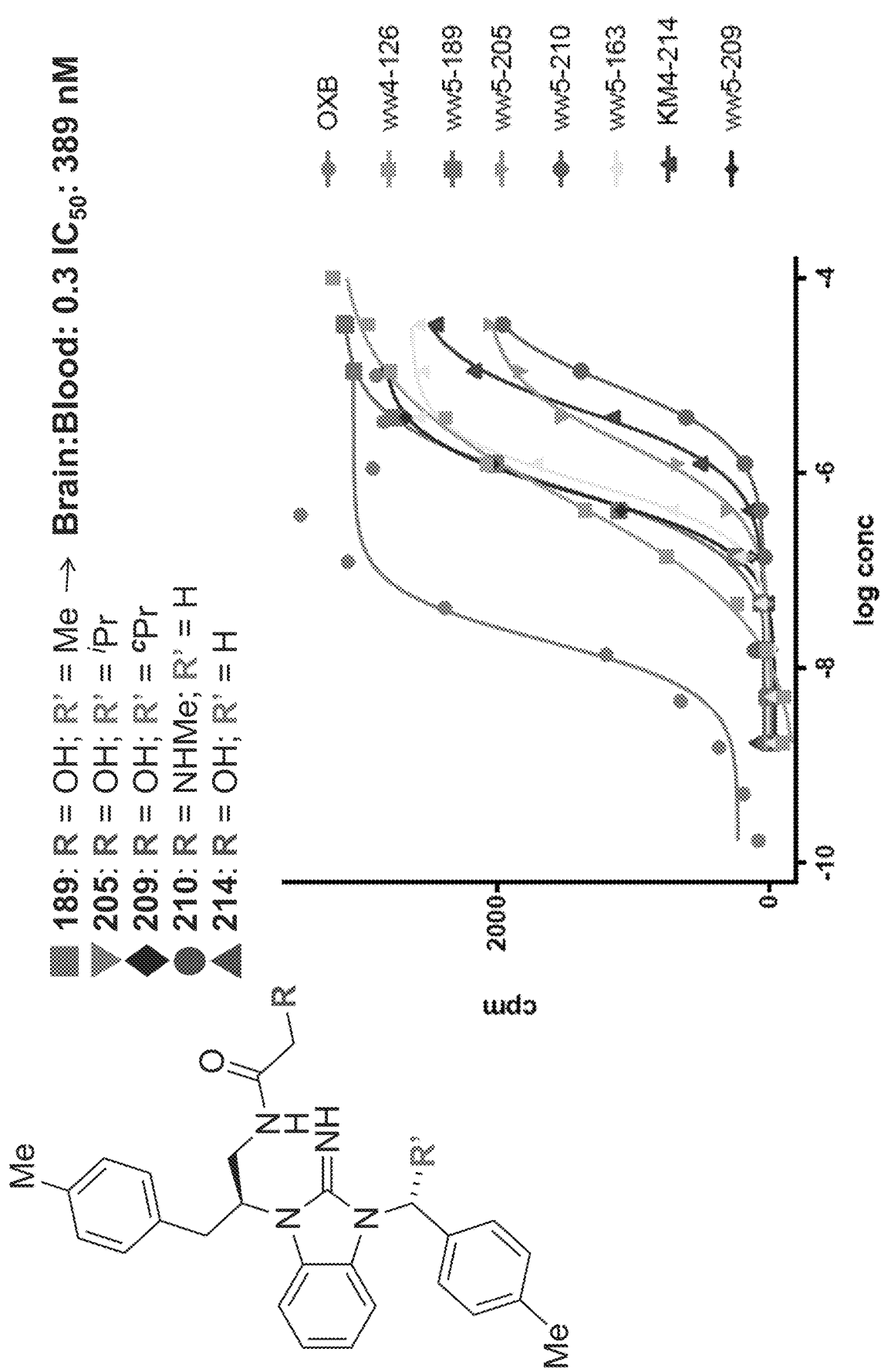
Figure 82:
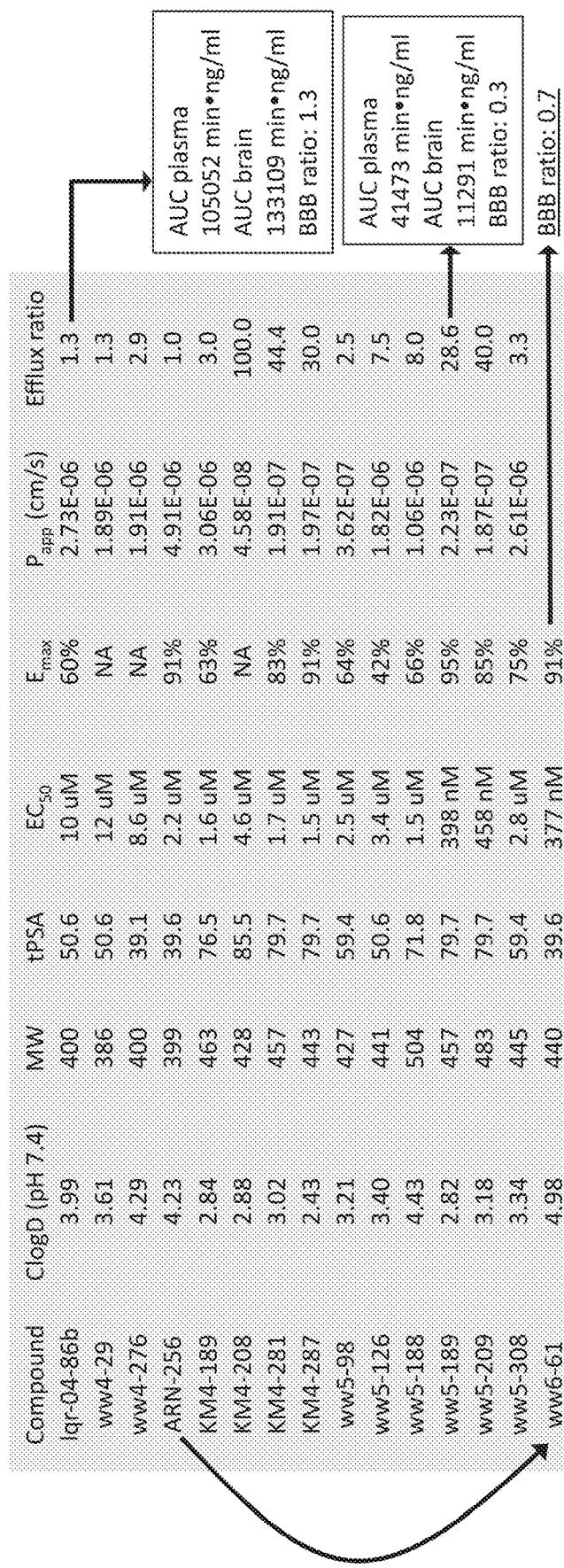
Figure 83:
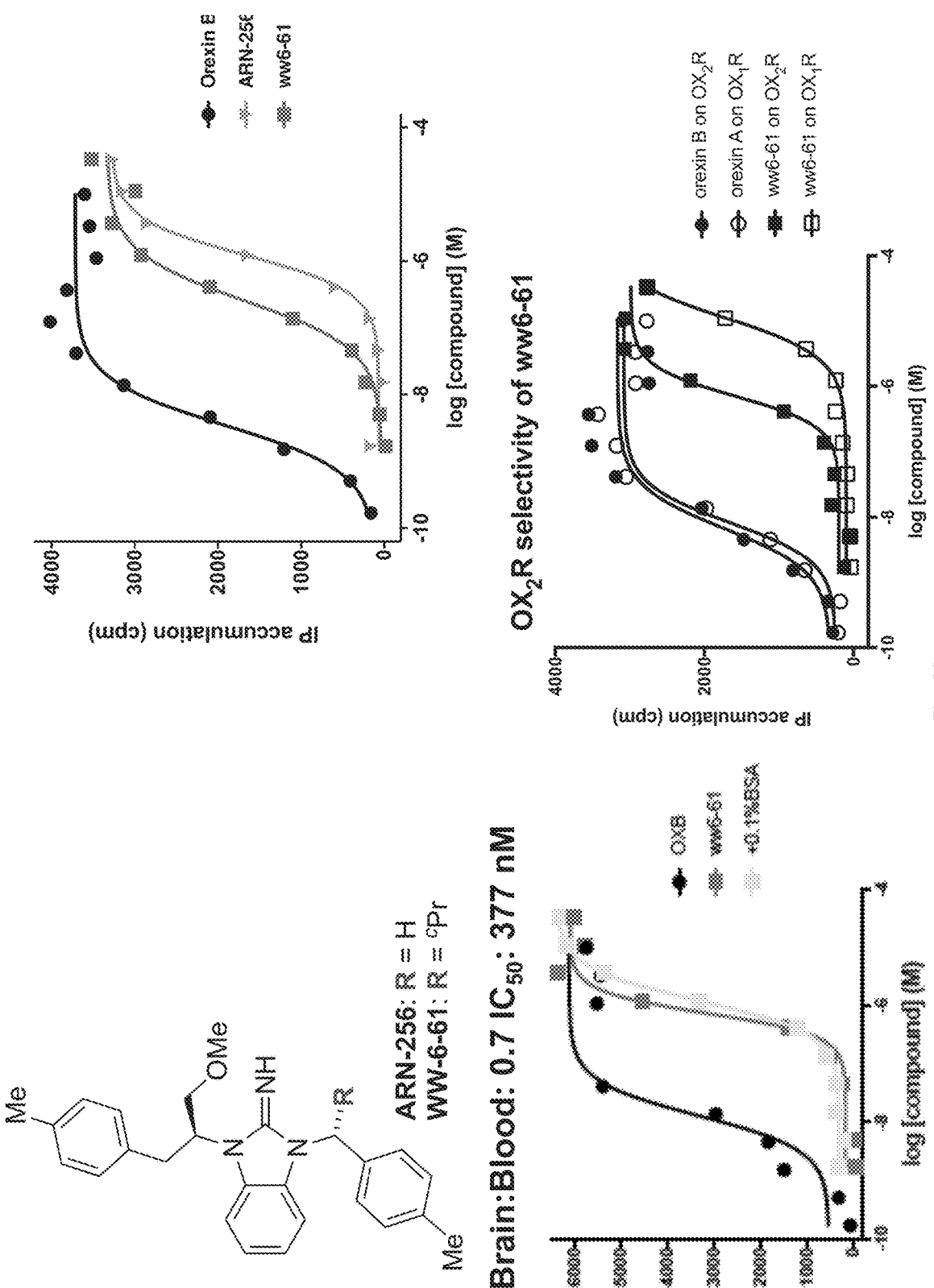
Figure 84:
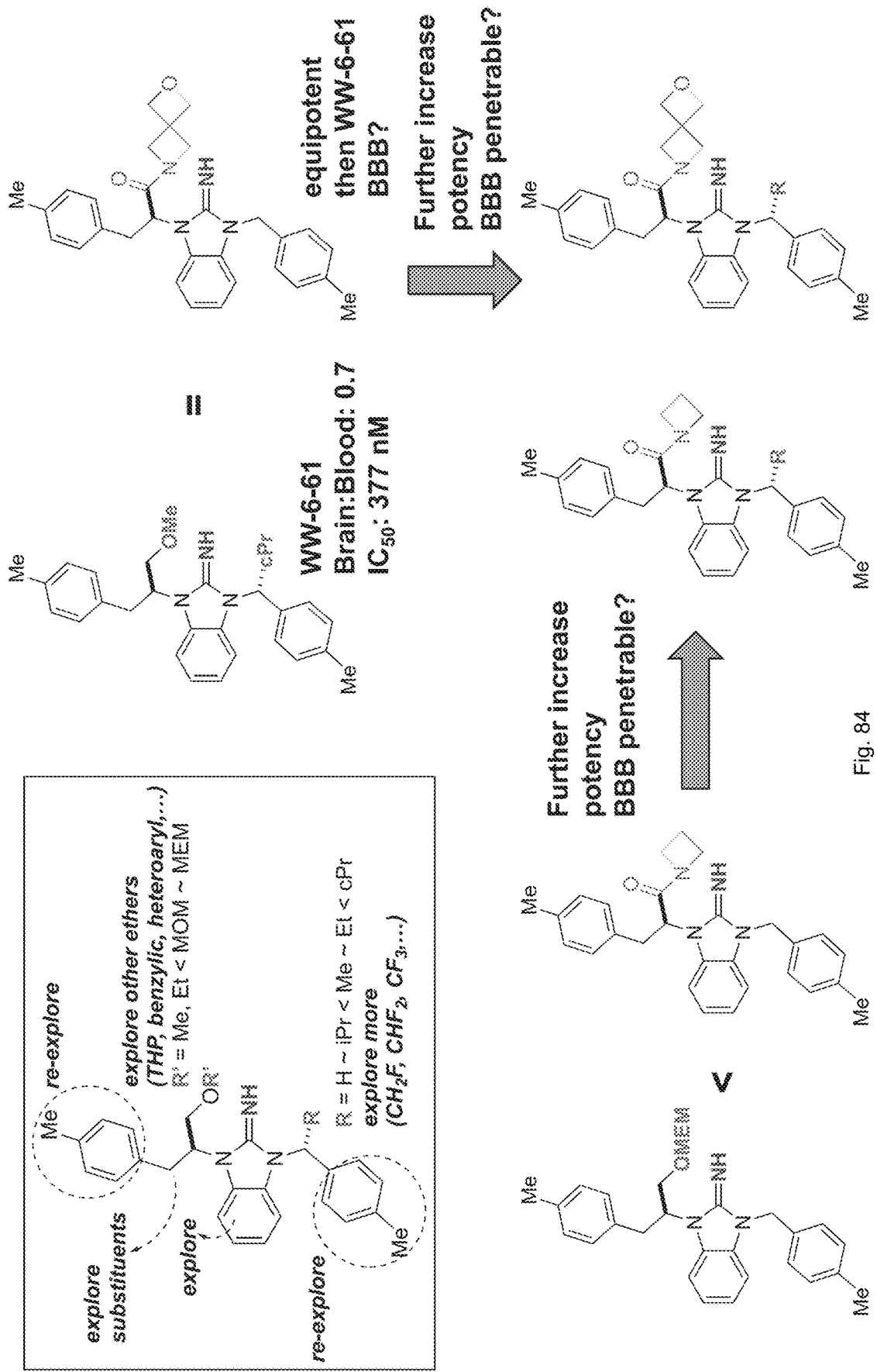
FIG. 84-85 illustrate additional compounds of Chemotype 3
Figure 85:
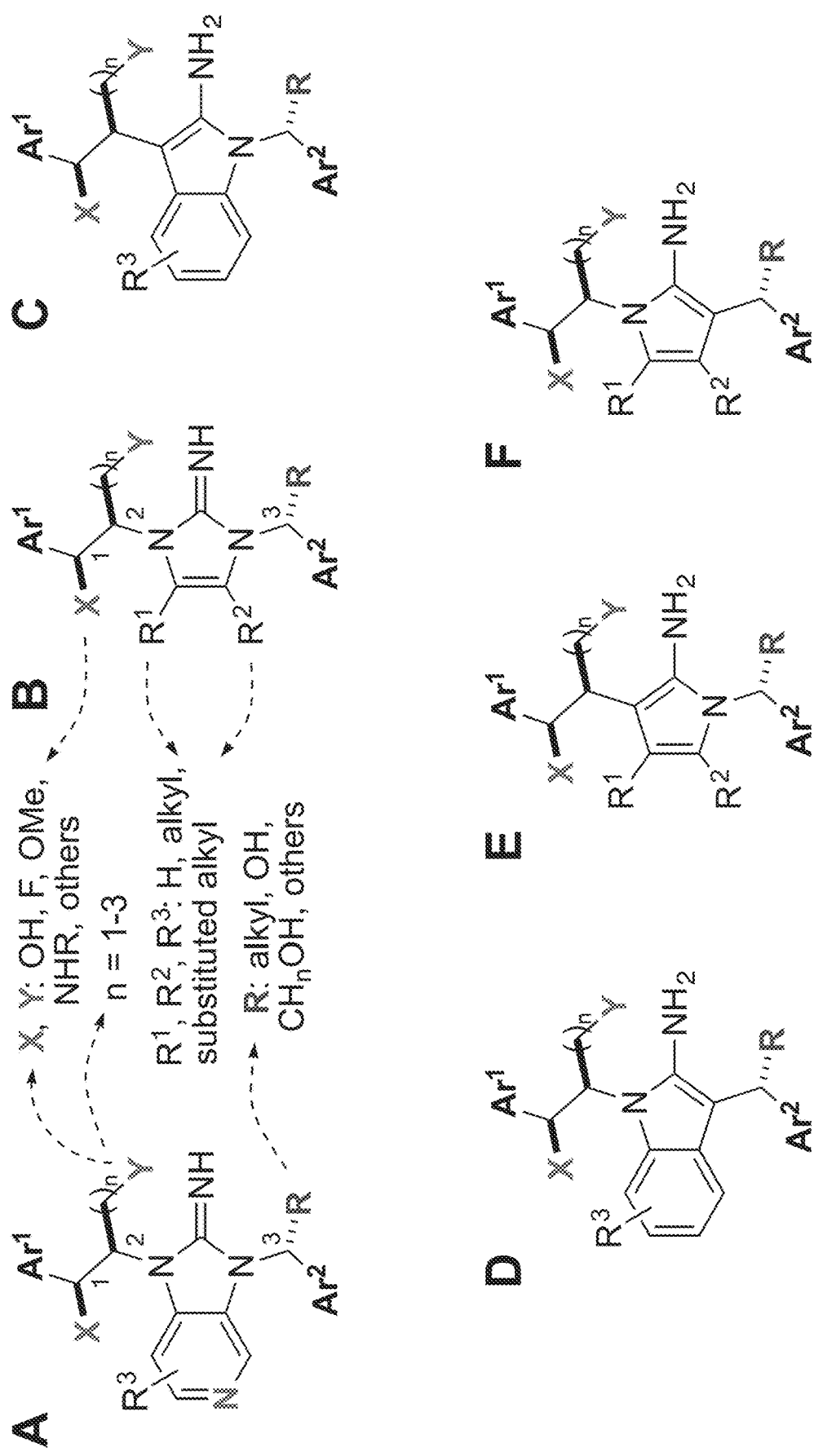
Figure 86:
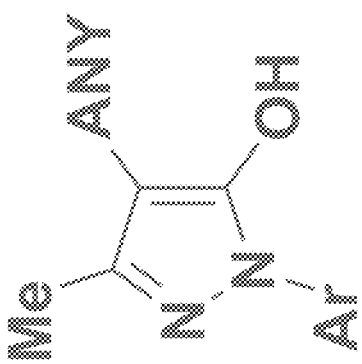
FIGS. 86 and 87 show additional chemotypes identified by the primary HTS.
Figure 86:
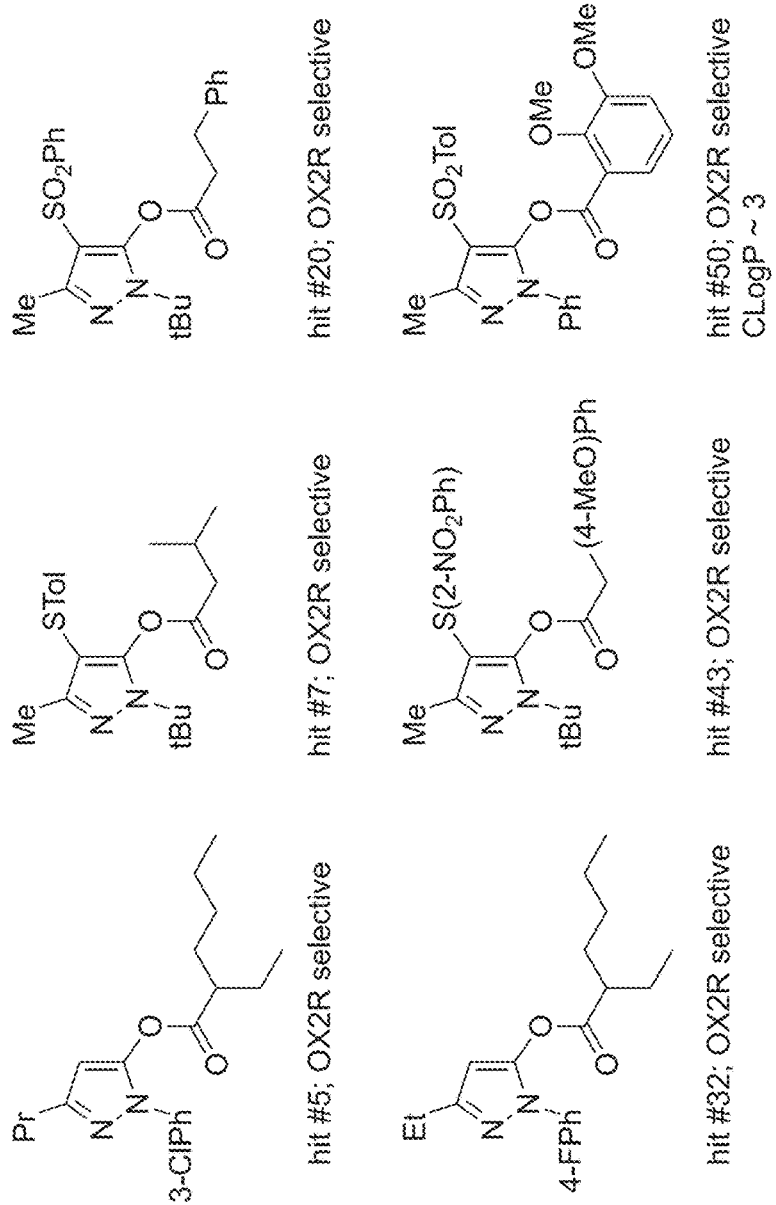
Figure 87:
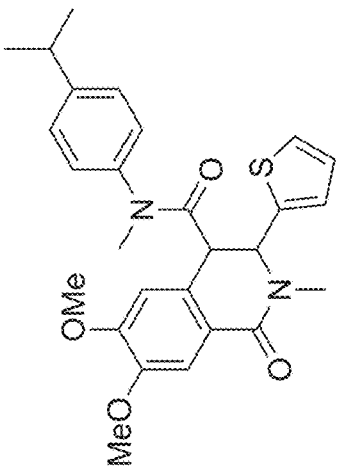
Figure 87:
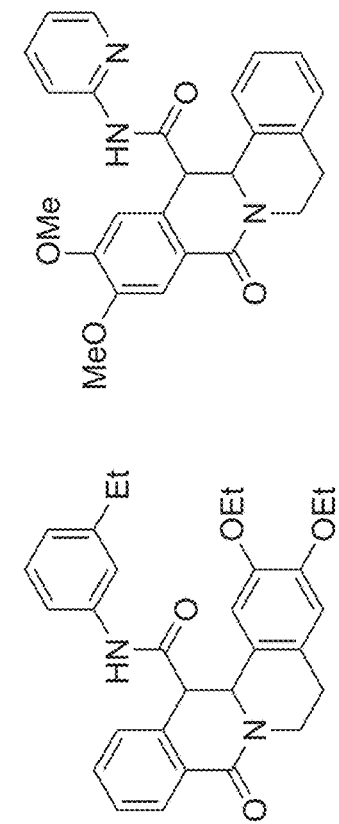
Figure 87:
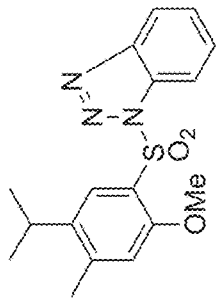
Figure 87:
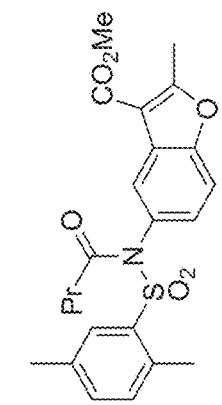
Figure 87:
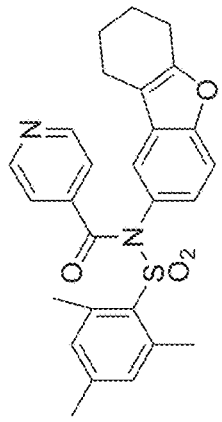
Figure 87:
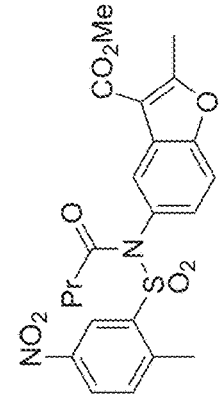

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "an orexin receptor agonist" refers to one or more orexin receptor anoists or at least one orexin receptor agonist. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

The term "alkyl" refers to a fully saturated, hydrocarbon group selected from linear and branched saturated hydrocarbon groups of 1-18 carbon atoms ($C_1$-$C_{18}$ alkyl), or 1-12 carbon atoms ($C_1$-$C_{12}$ alkyl), or 1-6 carbon atoms ($C_1$-$C_6$ alkyl), which is attached to the rest of the molecule by a single bond. Non-limiting examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other non-limiting examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. Unless stated otherwise specifically in the specification, an alkyl group can be optionally substituted.

The term "haloalkyl" refers to an alkyl group which is substituted with at least one halogen. Non-limiting examples of haloalkyl includes, $-CF_3$, $-CHF_2$, $-CH_2F$, $-CCF_2$, $-CFCl_2$, $-CCl_3$, $CHCl_2$, $-CH_2Cl$, $-CBr_3$, $CHBr_2$, $-CH_2Br$, $-Cl_3$, $CHI_2$, $-CH_2I$, $-CH_2CF_3$, $-CH_2CHF_2$, $-CH_2CH_2F$, $-CHFCF_3$, $-CF_2CF_3$, $-CH_2CCl_3$, $-CH_2CHCl_2$, $-CH_2CH_2Cl$, $-CHClCCl_3$, $-CCl_2CCl_3$, $-CH_2CH_2CF_3$, $-CH_2CH_2CHF_2$, $-CH_2CH_2CH_2F$, $-CF_2CF_2CF_3$.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

The term "alkenyl" refers to a hydrocarbon group selected from linear and branched hydrocarbon groups comprising at least one C=C double bond and of 2-18 carbon atoms ($C_2$-$C_{18}$ alkenyl), or 2-12 carbon atoms ($C_2$-$C_{12}$ alkenyl), or 2-6 carbon atoms ($C_2$-$C_6$ alkenyl). Non-limiting examples of the alkenyl group includes ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienylgroups. Other non-limiting examples of alkenyl groups include, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl Unless stated otherwise specifically in the specification, an alkenyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups. Unless stated otherwise specifically in the specification, an alkenyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

The term "lower alkyl" means alkyl groups of 1-8 carbon atoms ($C_1$-$C_8$ alkyl), 1-6 ($C_1$-$C_6$ alkyl), or 1-4 carbon atoms ($C_1$-$C_4$ alkyl). The term "lower alkenyl" or "lower alkynyl" means alkenyl or alkynyl groups of 2-8, 2-6 or 2-4 carbon atoms (e.g., $C_2$-$C_8$ alkenyl, $C_2$-$C_6$ alkenyl, $C_2$-$C_4$ alkenyl, $C_2$-$C_8$ alkynyl, $C_2$-$C_6$ alkynyl, $C_2$-$C_4$ alkynyl).

The term "cycloalkyl" refers to a monocyclic and polycyclic (e.g., bicyclic and tricyclic) hydrocarbon group which is saturated or partially unsaturated (non-aromatic). Cycloalkyl group can have from three to twenty carbon atoms, which can be fused or bridged. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein. Unless stated otherwise specifically in the specification, cycloalkyl group can be optionally substituted.

Partially unsaturated cycloalkyl group having at least one carbon-carbon double bond can be separately referred to as "cycloalkenyl". Partially unsaturated cycloalkyl group having at least one carbon-carbon triple bond can be separately referred to as "cycloalkynyl".

"Alkoxy" refers to a radical of the formula —OR$_a$ where R$_a$ is an alkyl, alkenyl or alknyl radical as defined above containing one to twelve carbon atoms. Unless stated otherwise specifically in the specification, an alkoxy group can be optionally substituted.

"Haloalkoxy" refers to a radical of the formula —OR$_a$ where R$_a$ is an haloalkyl, haloalkenyl or haloalknyl radical as defined above containing one to twelve carbon atoms. Unless stated otherwise specifically in the specification, an alkoxy group can be optionally substituted.

The term "Aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene. As used herein, a bicyclic or tricyclic aryl group comprises at least one aromatic group and includes fused and bridged rings. Unless stated otherwise specifically in the specification, an aryl group can be optionally substituted.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

"Arylene" refers to a divalent aryl group.

The term "halogen" or "halo" refers to F, Cl, Br or I.

The term "heteroalkyl" refers to alkyl comprising at least one heteroatom.

The term "heteroaryl" refers to a group selected from: 5- to 7-membered aromatic, monocyclic rings comprising 1, 2, 3 or 4 heteroatoms selected from N, O, and S, with the remaining ring atoms being carbon; 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring. As used herein, a bicyclic or tricyclic heteroaryl group comprises at least one aromatic group and includes fused and bridged rings. Unless stated otherwise specifically in the specification, a heteroaryl group can be optionally substituted.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heteroarylene" refers to a divalent heteroaryl group.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S, fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein. Unless stated otherwise specifically in the specification, a heterocyclic group can be optionally substituted.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

Unless otherwise specified in the specification, substituents are selected from: halogen, —R', —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR', —NR"CO$_2$R', —NH—C(NH$_2$)=NH, —NR'C(NH$_2$)$_2$=NH, —NH—C(NH$_2$)=NR', —S(O)R', —SO$_2$R', —SO$_2$NR'R", —NR"SO$_2$R, —CN and —NO$_2$, —N$_3$, —CH(Ph)$_2$, perfluoro(C$_1$-C$_4$)alkoxy and perfluoro(C$_1$-C$_4$)alkyl, in a number ranging from zero to three, with those groups having zero, one or two substituents being particularly preferred. R', R" and R' each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, perfluoro(C1-C4)alkoxy and perfluoro(C1-C4)alkyl, where R' and R" are as defined above.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicylclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)$n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof. The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient.

The subject compounds are incorporated into pharmaceutical compositions or formulations. The compositions will contain pharmaceutically acceptable diluents and/or carriers, i. e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound which also promotes wakefulness, anti-obesity, and/or recovery from general anesthesia or jet lag. Example of co-formulatable drugs include diet pills such as Orlistat (Xenical); narcolepsy drugs such as methylphenidate, racemic amphetamine, dextroamphetamine, and methamphetamine, or modafini; stimulants such as caffeine; etc. In one embodiment, a pharmaceutical composition comprises one or more compounds of Formula (I) to (VIII) or Formula (A) to (D) or a pharmaceutically acceptable salt or solvate thereof. In one embodiment, a pharmaceutical composition comprises one or more compounds of Table I or a pharmaceutically acceptable salt or solvate thereof.

Methods of the Invention

As with the field of modulation of sleep patterns, the molecular basis of the regulation of energy balance and feeding patterns is beginning to be better understood. The discovery of hypocretins (orexins) and the hypocretin receptors has facilitated the unraveling of the regulatory pathways involved in eating habits. Initially, the finding that preprohypocretin RNA molecules and hypocretin-immunoreactive cell bodies were discretely localized to a subregion of the dorsolateral hypothalamus and a hypothesized colocalization of hypocretins with melanin concentrating hormone (MCH), a potent orexigeneic peptide, suggested a possible role of this system in the control of feeding (De Lecea et al., 1998). Furthermore, centrally administered hypocretin-1 and -2 stimulate appetite in rodents, and preprohypocretin mRNA is upregulated by fasting (Sakurai et al., 1998). However, more recent experiments suggest a more complex picture. First, the suggested initial colocalization with MCH was not substantiated by further studies (Broberger et al. (1998) J. Comp. Neurol. 402, 460-474). Second, there is controversy regarding the magnitude of the effect of hypocretins on food consumption in rodents (Lubkin et al. (1998) Biochem. Biophys. Res. Commun. 253, 241-245; Edwards et al. (1999) J. Endocrinol. 160, R7-R12; Ida (1999) Brain Res. 821, 526-529; Moriguchi et al. (1999) Neurosci. Lett. 264, 101-104; Sweet (1999) Brain Res. 821, 535-538). For example, while hypocretins stimulate short-term food intake, these peptides do not alter 24 hour total food consumption (Ida et al (1999), supra). Some authors have also suggested that hypocretins exert a shift in the diurnal pattern of food intake. The effect on energy metabolism seems to be more pronounced than that on feeding behavior (Lubkin et al. (1998), supra) and differs with the circadian time of administration (Ida et al, (1999), supra). Recent studies suggest complex interactions between hypocretins, MCH-containing neurons, neuropeptide Y, agouti gene-related protein systems and leptins in the control of feeding and energy balance (Broberger et al. (1998), supra; Beck et al. (1999) Biochem. Biophys. Res. Commun. 258, 119-122; Horvath et al. (1999). J. Neurosci. 19, 1072-1087; Kalra et al. (1999) Endocrine Rev. 20, 68-100; Marsh et al. (1999) Nature Genet. 21, 119-122; Moriguchi et al., supra; Yamamoto et al. (1999) Mol. Brain Res. 65, 14-22).

This invention describes several chemically distinct classes of non-peptidic, small-molecule agonists for the type-2 orexin receptors (OX2R). Orexins are hypothalamic neuropeptides that are importantly implicated in sleep/wake control and body weight homeostasis. Orexin producing neurons are exclusively localized in the lateral hypothalamic area. The peptides act on two G protein-coupled receptors termed OX1R and OX2R. It has been demonstrated that deficiency in orexin/OX2R signaling causes the sleep disorder narcolepsy in humans, mice and dogs. Narcolepsy is a socially debilitating disorder characterized by an inability to properly maintain wakefulness (excessive daytime sleepiness, sleep attacks), and a pathological intrusion of signs of REM sleep into wakefulness (cataplexy, hipnagorgic hallucination, sleep paralysis, etc).

A transgenic mouse strain that has been engineered to mimic the neurochemical situation in human narcoleptics, i.e., with a postnatal loss of orexin neurons, exhibits all symptoms of narcolepsy/cataplexy. It has been further demonstrated that these mice can then be effectively treated for narcolepsy by providing exogenous orexin either genetically (via a transgene) or pharmacologically (via intracerebroventricular injections). Hence, orexin replacement therapy is expected to provide similarly effectively treat human narcolepsy patients.

Orexins themselves are peptides (thus orally inactive) and blood-brain barrier impermeable; they cannot be used as an orally active therapeutic agent. However, if we can develop an orally active, blood-brain barrier permeable, small-molecule OX2R agonist, such compound will be useful as a drug for the treatment of narcolepsy.

The practical uses for OX2R agonists go beyond the treatment of narcolepsy. Since orexin has been established as an endogenous neurotransmitter to maintain proper wakefulness, orexin receptor agonists effect a highly "natural" form of wakefulness. Therefore, such agonists may be used to treat medical conditions accompanying narcolepsy, daytime sleepiness, such as nighttime insomnia, and depression with hypersomnia.

It has also been shown that orexin/OX2R signaling acts as a net-negative regulator of body weight homeostasis. Thus, deficiencies in OX2R signaling can cause (besides narcolepsy) obesity in mice and humans, whereas transgenic OX2R over-activation renders mice resistant to high fat diet-induced obesity. Furthermore, intracerebroventricular infusion of a previously known peptidic OX2R-selective agonist similarly prevents high fat diet-induced obesity in mice. Therefore, orally active OX2R agonists also provide treatments of obesity and associated metabolic syndrome.

Orexin deficiency causes delayed recovery from gas anesthesia in mice, which effect can be antagonized by orexin and orexin agonists. See, Kelz et al. An essential role for orexins in emergence from general anesthesia. Proc. Natl. Acad. Sci. USA 105:1309-1314 (2008). Hence, the subject orexin agonists may also be used to facilitate or expedite recovery from general anesthesia.

The active OX2R agonists provided in this invention also provide lead compounds for the development of alternative and more potent forms with desirable pharmacokinetics, bioavailability, nontoxicity, and other properties. Such derivative compounds may be used, inter alia and after proper clinical trials, as therapeutic agents for treating (1) narcolepsy; (2) other neurologic conditions accompanying daytime sleepiness, such as night time insomnia and depression with hypersomnia, sleep apnea, jet lag, etc.; (3) obesity and metabolic syndrome; and (4) undesirable extension and lingering effects of general anesthesia.

The present disclosure thus relates to the use of one or more agents or one or more compounds of Formula (I) to (VIII) or Formula (A) to (D) or a pharmaceutically acceptable salt or solvate thereof as an agonist of a type-2 orexin receptor (OX2R). In another embodiment, the present disclosure relates to the use of one or more agents or one or more compounds of Table I or a pharmaceutically acceptable salt or solvate thereof as an agonist of a type-2 orexin receptor (OX2R). As agonists of OX2R, the compounds of the present invention may be administered to a subject with various diseases, disorders or medical conditions.

In a specific embodiment, the methods of the present invention may include treating a subject suffering from or diagnosed with a disease, disorder, or medical condition mediated by orexin receptor activity, wherein the disease, disorder, or medical condition is a disorder of the sleep-wake cycle, insomnia, restless legs syndrome, jet-lag, disturbed sleep, a sleep disorder secondary to neurological disorders, mania, depression, manic depression, schizophrenia, a pain syndromes, fibromyalgia, neuropathic pain, catatonia, Parkinson's disease, Tourette's syndrome, anxiety, delirium, dementia, overweight, obesity or a condition related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, hypertension, tachycardia, arrhythmias, angina pectoris, acute heart failure, ulcers, irritable bowel syndrome, diarrhea, gastroesophageal reflux, post-traumatic stress disorder, panic disorders, attention deficit disorders, cognitive deficiencies, or substance abuse, comprising administering to the subject an effective amount of any compound of Formula (I) to (VIII), Formula (A) to (D), Table I, or a pharmaceutically acceptable salt thereof.

In a specific embodiment, the methods may include the treatment of one or more sleep disorders, comprising administering to the subject an effective amount of any compound of Formula (I) to (VIII), Formula (A) to (D), Table I, or a pharmaceutically acceptable salt thereof.

In another embodiment, the methods may include promoting or enhancing wakefulness, anti-obesity, or recovery from general anesthesia or jet lag in a subject in need thereof, comprising administering to the subject an effective amount of a compound of any compound of Formula (I) to (VIII), Formula (A) to (D), or Table I, or a pharmaceutically acceptable salt thereof.

In another embodiment, the methods may include increasing resistance to diet-induced accumulation of body fat, comprising administering to the subject an effective amount of any compound of Formula (I) to (VIII), Formula (A) to (D), Table I, or a pharmaceutically acceptable salt thereof.

In another embodiment, the methods may include shortening recovery period from general anesthesia or jet lag, comprising administering to the subject an effective amount of any compound of Formula (I) to (VIII), Formula (A) to (D), Table I, or a pharmaceutically acceptable salt thereof.

In another embodiment, the methods may include treating narcolepsy in a subject in need thereof, comprising administering to the subject an effective amount of oany compound of Formula (I) to (VIII), Formula (A) to (D), Table I, or a pharmaceutically acceptable salt thereof.

In another embodiment, the methods may include agonizing a type-2 orexin receptor (OX2R), comprising contacting the OX2R with a compound of any compound of Formula (I) to (VIII), Formula (A) to (D), Table I, or a pharmaceutically acceptable salt thereof.

In a specific embodiment, the contacting is in a cell.

In another specific embodiment, the compound is administered to the subject regularly and/or chronically. In another embodiment, the compound is administered to the subject orally.

Examples

General Synthesis

The compound of the present disclosure can be prepared following protocols described in US 2014/0051700 and/or U.S. Pat. No. 8,871,794, the disclosures of which are hereby incorporated by reference in their entireties and common organic chemistry synthesis protocols known to one skilled in the art. Also see

[1] Allen, John Gordon et al. 6 substituted 2, 3,4,5 tetrahydro-1H-benzo[d]azepines as 5-HT2C receptor agonist. U.S. Ser. No. 10/598,302, Feb. 18, 2005.

[2] Ali, A. et al. Cholesteryl ester transfer protein inhibitors. U.S. Pat. No. 8,865,707, Oct. 21, 2014

[3] Clive, D. L. J. and Huang, X. *J. Org. Chem.* 2004, 69, 1872-1879

[4] Schnapperelle, I. et al. *Chem. Eur. J.* 2012, 18, 1073-1076

[5] Arp, F. O. and Fu, G. C. *J. Am. Chem. Soc.* 2005, 127, 10482-10483

[6] Qin, C. and Davies, H. M. *J. Am. Chem. Soc.* 2014, 136, 9792-9796

[7] Tino, J. A. Heterocyclic aromatic compounds useful as growth hormone secretagogues U.S. Pat. No. 6,525,203, 25 Feb. 2003

[8] Welch, J. T. and Seper, K. W. *J. Org. Chem.* 53(13), 1988, 2991-2999

[9] Dixon, D. L. et al. *Org. Lett.* 2013, 15, 2946-2949

[10] Ueda, H. et al. *Org. Lett.* 2014, 16, 4194-4197 each of which are hereby incorporated by reference in their entireties.

In general, the subject compounds may be prepared by a stepwise alkylation of 2-aminobenzimidazole (Scheme 1) or a ring-substituted 2-aminobenzimidazole where $R^6$ is other than hydrogen (Scheme 2).°

Scheme 1. Stepwise Alkylation

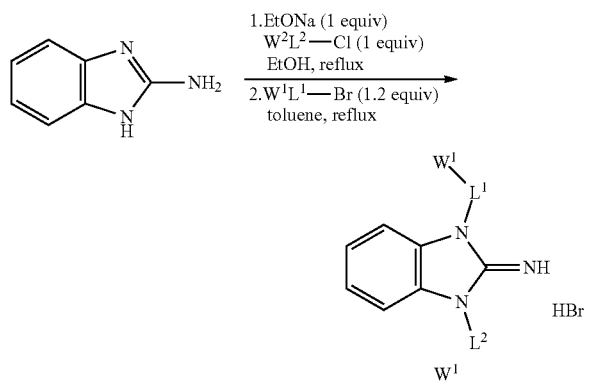

In the first alkylation, the sodium salt of 2-aminobenzimidazole reacts smoothly with alkyl and benzyl chlorides (Joseph, J Med Chem 28: 601 (1963); Ogura et al, J Med Chem 15: 923-926 (1972)). The second alkylation proceeds under conditions of high concentration in refluxing toluene, reacting exclusively at the 3-position of the imidazole moiety (Rehse, et al., Arch Pharm (Weinheirn) 328: 77-80, 1995). The precipitation of the product as the hydrobromide salt prohibits additional alkylation and simplifies the purification.

Alternatively, as described below with respect to the preparation of a combinatorial library, the compounds can be prepared by a process in which a resin-bound 4-fluoro-3-nitroarene is reacted with an amine having the formula $W^2L^2$-$NH_2$, reduced with tin (II) chloride (Bellamy, et al., Tetrahedron Lett 25: 839-842, 1984), cyclized with cyanogen bromide (U.S. Pat. No. 4,002,623), and reacted with a mono-substituted epoxide.

Scheme 2. Stepwise Alkylation where $R^6$ is not H

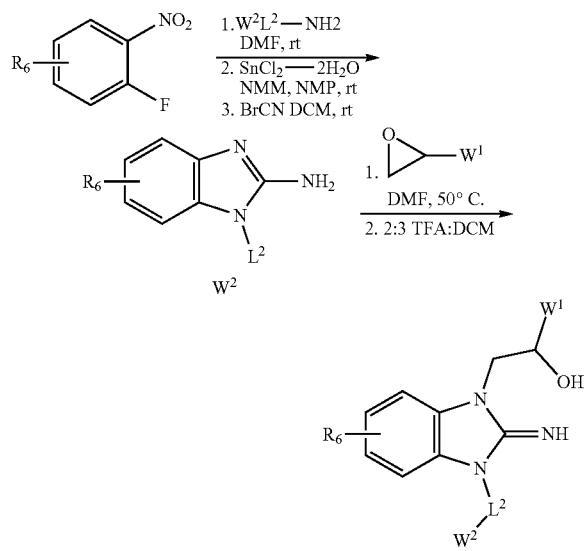

If $R^6$ is a group having the formula —CONR'R" that group is first introduced by amide coupling with the fluoronitrobenzoic acid.

General Procedure (A) to Convert Alcohols to Bromides Through Appel Reaction

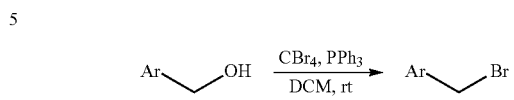

To a flame-dried flask were added an arylmethyl alcohol (1.0 eq.), anhydrous DCM (1.94 mL/mmol) and $CBr_4$ (1.1 eq.), followed by addition of $PPh_3$ (1.1 eq.) in portions under argon. The resulting reaction mixture was stirred at room temperature for 40 min and was then filtered through a short pad of celite. Upon the evaporation of the solvent, the residue was purified through flash chromatography on silica gel (9:1 or 2:1 hexane/EtOAc) to provide the desired product.

General Procedure (B) for the Synthesis of ethyl 2-amino-3-arylpropanoates

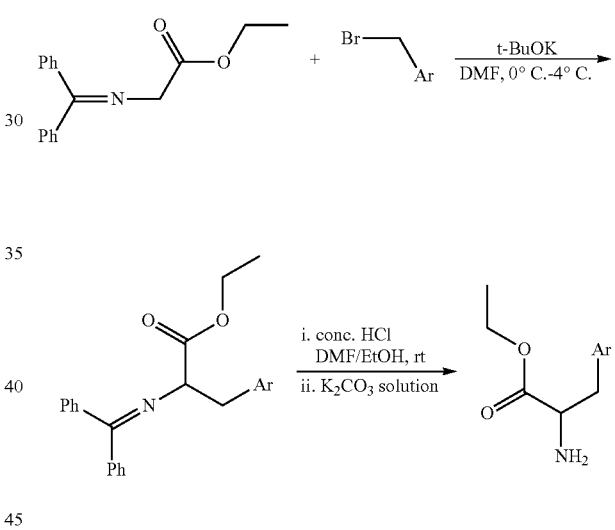

To a flame-dried flask containing t-BuOK (1.10 equiv.) and anhydrous DMF (2.5 mL/mmol) was added ethyl 2-((diphenylmethylene)amino)acetate (1.05 eq.) at 0° C. under argon. After 10 min, arylmethyl bromide (1.0 eq.) was added. The resulting reaction mixture was stirred at 0° C. for 10 min and was allowed to warm up to 4° C. and stirred at 4° C. overnight. The reaction mixture was then slowly poured into water, extracted with DCM. The combined organic layers were dried over $Na_2SO_4$, filtered and concentrated under reduced pressure to evaporate the DCM solvent. The residue was then treated with a mixture of EtOH/concentrated HCl (25:1 v/v). The resulting solution was stirred at room temperature for 2 h. Upon the evaporation of EtOH and most of the DMF, the residue was basified by 2 N $K_2CO_3$ solution to pH>10 and extracted with DCM. The combined organic layers were dried over $Na_2SO_4$, filtered and concentrated under reduced pressure. The residue was purified through flash chromatography on silica gel (1:19 $CH_3OH/CH_2Cl_2$) to afford the desired ethyl 2-amino-3-arylpropanoate product as a colorless gel.

General Procedure (C) for the Synthesis of ethyl 2-((2-nitrophenyl)amino)-3-arylpropanoates Through SNAr Reaction Between 1-fluoro-2-nitrobenzene and ethyl 2-amino-3-arylpropanoates

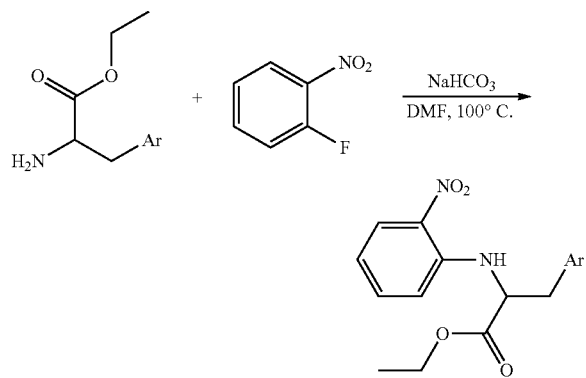

To a mixture of ethyl 2-amino-3-arylpropanoate (1.0 eq.) and DMF (3 mL/mmol) were added 1-fluoro-2-nitrobenzene (1.05 eq.) and NaHCO$_3$ (1.20 eq.). The resulting reaction suspension was then stirred rigorously at 100° C. overnight and cooled down to room temperature. The suspension was filtered through a pad of celite and the filter cake was washed by a small amount of DCM. Upon the evaporation of the solvents under reduced pressure, the residue was purified through flash chromatography on silica gel (EtOAc/hexane) to afford the ethyl 2-((2-nitrophenyl)amino)-3-arylpropanoate as a yellow gel.

General Procedure (D) for the Synthesis of 2-((2-aminophenyl)amino)-3-arylpropan-1-ols

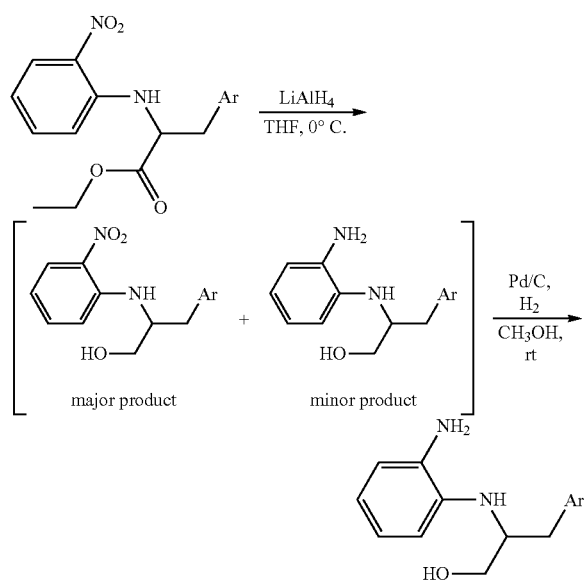

To a flame-dried flask were added lithium aluminum hydride (2.0 eq.) and anhydrous THF (7 mL/mmol) at 0° C., followed by addition of the ethyl 2-((2-nitrophenyl)amino)-3-arylpropanoate (1.0 eq.) under argon. The resulting reaction mixture was stirred at 0° C. for 1 h and 1 N KOH solution was added dropwise at 0° C. to quench the reaction. Upon the addition of KOH solution, the mixture was stirred for 15 more min at 0° C. and was condensed under reduced pressure to evaporate most of the THF. The residue was then mixed with water and extracted with EtOAc. The combined organic layers were dried over Na$_2$SO$_4$, filtered and concentrated under reduced pressure to afford a mixture of the 2-((2-aminophenyl)amino)-3-arylpropan-1-ol (major one) and the ethyl 2-((2-nitrophenyl)amino)-3-arylpropanoate (minor one).

To a flask were added the mixture above, methanol (8 mL/mmol) and Pd/C (10% on active carbon). The reaction flask was sealed by a septum and after the removal of air using vacuum, a hydrogen balloon was fitted on the top of the septum. The reaction suspension was then stirred at room temperature for 18 h and was filtered through a pad of celite. The filtrate was concentrated under reduced pressure and the residue was purified through flash chromatography on silica gel (1:19 CH$_3$OH/CH$_2$Cl$_2$) to provide the 2-((2-aminophenyl)amino)-3-arylpropan-1-ol as a brown gel.

General Procedure (E) for the Synthesis of 2-(2-imino-3-(4-methylbenzyl)-2,3-dihydro-1H-benzo[d]imidazol-1-yl)-3-arylpropan-1-ols through cyclization and alkylation

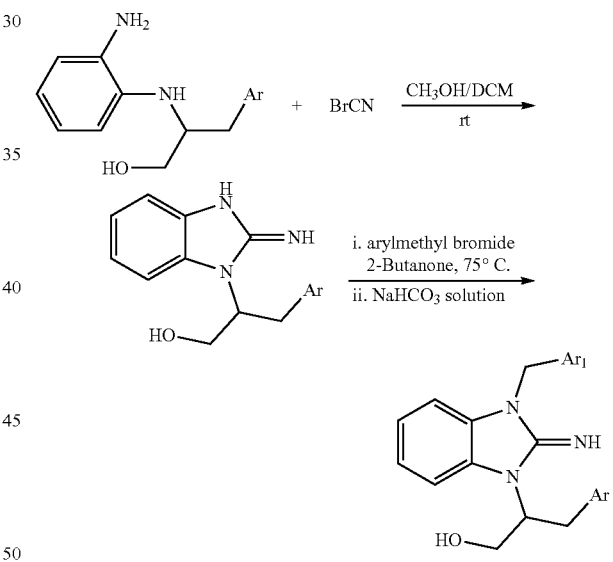

To a solution of 2-((2-aminophenyl)amino)-3-arylpropan-1-ol (1.0 eq.) in MeOH (4.5 mL/mmol) was added cyanogen bromide (3 M in DCM, 1.2 eq.). The resulting solution was stirred at room temperature with a reaction time ranging from 2 h to 12 h (until TLC indicated the complete consumption of the 2-((2-aminophenyl)amino)-3-arylpropan-1-ol) and after the evaporation of solvents, the residue was treated with saturated NaHCO$_3$ solution (after which the aqueous layer's pH is about 8~9) and then extracted with DCM. The combined organic layers were dried over Na$_2$SO$_4$, filtered and concentrated under reduced pressure to afford the 2-(2-imino-2,3-dihydro-1H-benzo[d]imidazol-1-yl)-3-arylpropan-1-ol as a dark brown gel.

To a flask equipped with a reflux condenser and stirring bar were added the 2-(2-imino-2,3-dihydro-1H-benzo[d]imidazol-1-yl)-3-arylpropan-1-ol (1.0 eq.), 2-butanone (12 mL/mmol) and arylmethyl bromide (1.2 eq.). The resulting mixture was stirred at 75° C. overnight and then cooled to room temperature. After the evaporation of most 2-butanone under reduced pressure, the residue was sonicated with Et$_2$O (40 mL/mmol) and then the supernatant was removed using pipette. This procedure was repeated three times and the remaining solid was treated with saturated NaHCO$_3$ solution, extracted with DCM. The combined organic layers were dried over Na$_2$SO$_4$, filtered and concentrated under reduced pressure to afford the 2-(2-imino-3-(4-methylbenzyl)-2,3-dihydro-1H-benzo[d]imidazol-1-yl)-3-arylpropan-1-ol as a brown gel.

General Procedure (F) of Synthesis of Pyridone Analogs from Demethylation of the Methoxypyridine Precursors

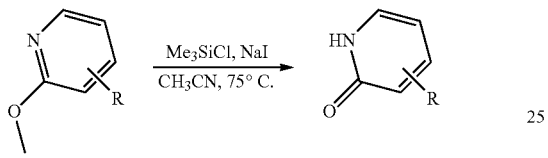

To a flame-dried flask equipped with a reflux condenser and stirring bar were added methoxypyridine analog (1.0 eq.), anhydrous CH$_3$CN (42 mL/mmol), NaI (4.0 eq.) and Me$_3$SiCl (10.5 eq.). The resulting mixture was stirred at 75° C. for 3.5 h and then cooled to room temperature. 20% NH$_4$H solution (50 mL/mmol) was then added to the reaction solution slowly and after the evaporation of CH$_3$CN, the remaining slurry solution was diluted with water (80 mL/mmol) and extracted with a mixture of DCM/Methanol (10:1, 3×160 mL/mmol). The combined organic layers were dried over Na$_2$SO$_4$, filtered and concentrated under reduced pressure to afford the entitled product as a brown foam.

General Procedure (G) for the Synthesis of Boc Protected Amide Analogs Through the Reaction Between tert-butyl-(1-(1-amino-3-(p-tolyl)propan-2-yl)-3-(4-methylbenzyl)-1,3-dihydro-2H-benzo[d]imidazol-2-ylidene)carbamate and acyl chlorides

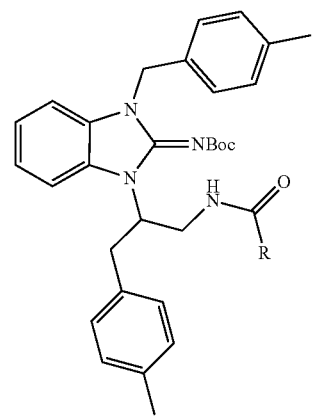

To a flask containing tert-butyl-(1-(1-amino-3-(p-tolyl)propan-2-yl)-3-(4-methylbenzyl)-1,3-dihydro-2H-benzo[d]imidazol-2-ylidene)carbamate (1.0 eq.) were added sequentially DCM (14 mL/mmol), Et$_3$N (1.5 eq.) and acyl chloride (1.2 eq.). The resulting solution was stirred at rt for 17 h and was diluted with DCM (70 mL/mmol), washed by saturated NaHCO$_3$ solution (70 mL/mmol). The organic layer was dried over Na$_2$SO$_4$, filtered and concentrated under reduced pressure. The residue was purified through flash chromatography on silica gel (1:19 methanol/DCM) to afford the Boc protected amide analogs.

General Procedure (H) for the Boc Deprotection of Boc Protected Amide Analogs Using TFA in Anhydrous DCM

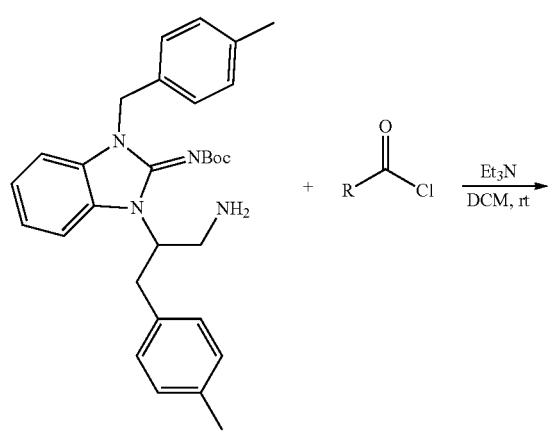
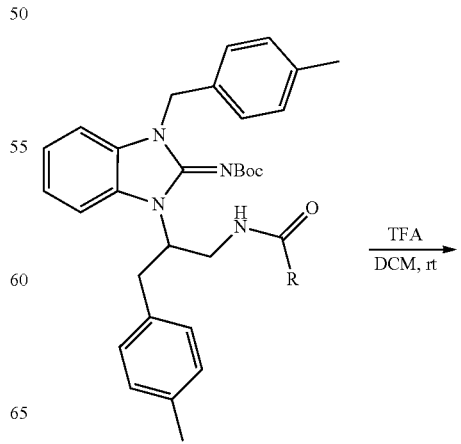

-continued

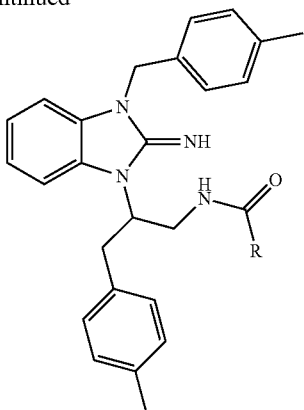

To a solution of Boc protected amide analog (1.0 eq.) in anhydrous DCM (40 mL/mmol) was added TFA (80 eq.). The resulting solution was stirred at rt for 3 h-6 h and was poured into 2N $K_2CO_3$ solution (600 mL/mmol), extracted with DCM (3×600 mL/mmol). The combined organic layers were dried over $Na_2SO_4$, filtered and concentrated under reduced pressure to afford the amide analogs.

General Procedure (I) of the Synthesis of Boc Protected Amide Analogs Through EDC Amide Coupling Reaction Between tert-butyl-(1-(1-amino-3-(p-tolyl)propan-2-yl)-3-(4-methylbenzyl)-1,3-dihydro-2H-benzo[d]imidazol-2-ylidene)carbamate and carboxylic acids

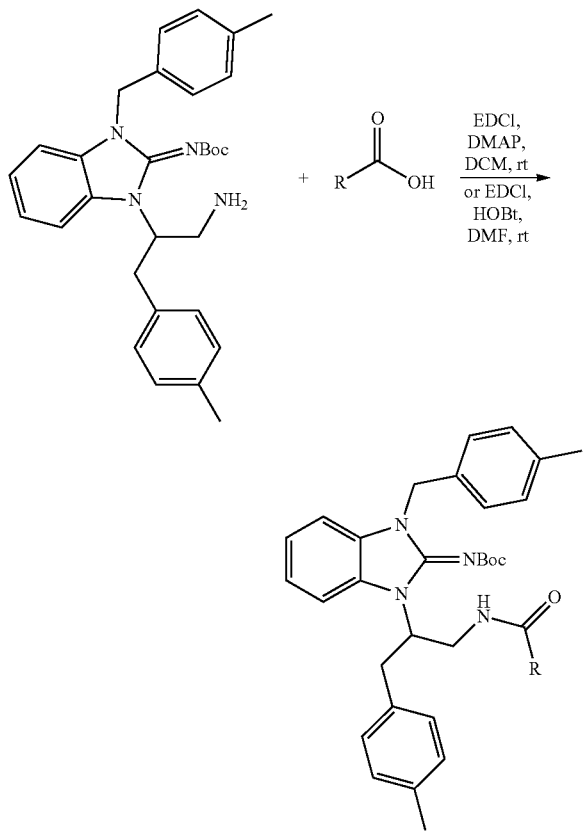

To a flask were added tert-butyl-(1-(1-amino-3-(p-tolyl)propan-2-yl)-3-(4-methylbenzyl)-1,3-dihydro-2H-benzo[d]imidazol-2-ylidene)carbamate (1.0 eq.), carboxylic acid (1.1 eq.), DMAP (0.3 eq.) (or HOBt (1.5 eq.)), EDC hydrochloride (1.2 eq.) and DCM (20 mL/mmol) [or DMF (2.5 mL/mmol) if HOBt was used]. The resulting solution was stirred for 24 h at rt and was diluted with DCM (140 mL/mmol), washed by brine (140 mL/mmol) and sat. $NaHCO_3$ solution (140 mL/mmol). The organic layer was dried over $Na_2SO_4$, filtered and concentrated under reduced pressure. The residue was purified through flash chromatography on silica gel (1:19 methanol/DCM) to afford the Boc protected amide analogs.

General Procedure (J) for Synthesis Boc Protected Sulfonamide Analogs Through the Reaction Between tert-butyl-(1-(1-amino-3-(p-tolyl)propan-2-yl)-3-(4-methylbenzyl)-1,3-dihydro-2H-benzo[d]imidazol-2-ylidene)carbamate and sulfonyl chlorides

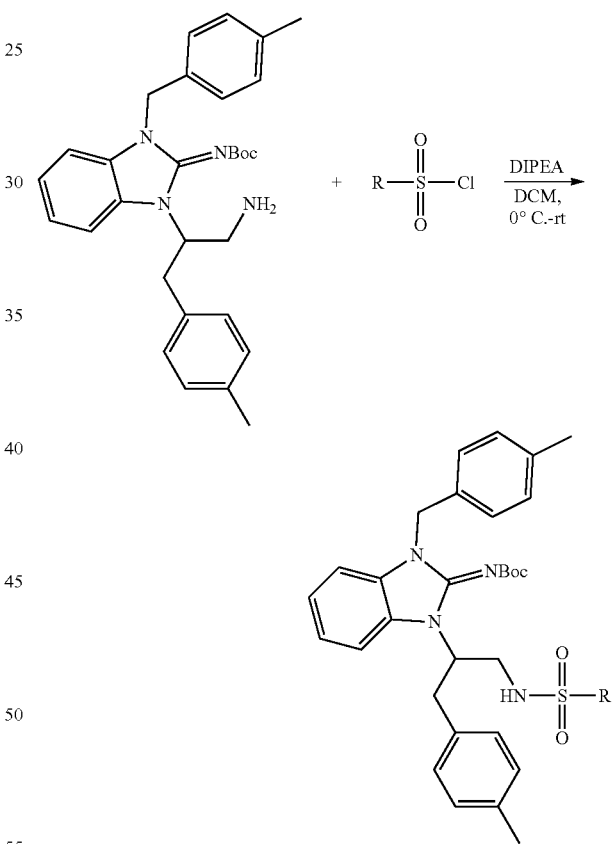

tert-Butyl-(1-(1-amino-3-(p-tolyl)propan-2-yl)-3-(4-methylbenzyl)-1,3-dihydro-2H-benzo[d]imidazol-2-ylidene)carbamate (1.0 eq.) was dissolved in DCM (5 mL/mmol), and DIPEA (3.0 eq.) was added. The solution was cooled to 0° C., and sulfonyl chloride (1.2 eq) was added. The solution was allowed to warm to ambient temperature overnight. Upon completion, the reaction was diluted with satd. aq. $NaHCO_3$, and the organic layer was loaded directly onto a silica column and purified ($SiO_2$, 0-30% or 50% EtOAc/DCM) to afford the Boc protected sulfonamides.

General Procedure (K) for the Boc Deprotection of Boc Protected Sulfonamide or Amide Analogs Using HCl in 1,4-dioxane

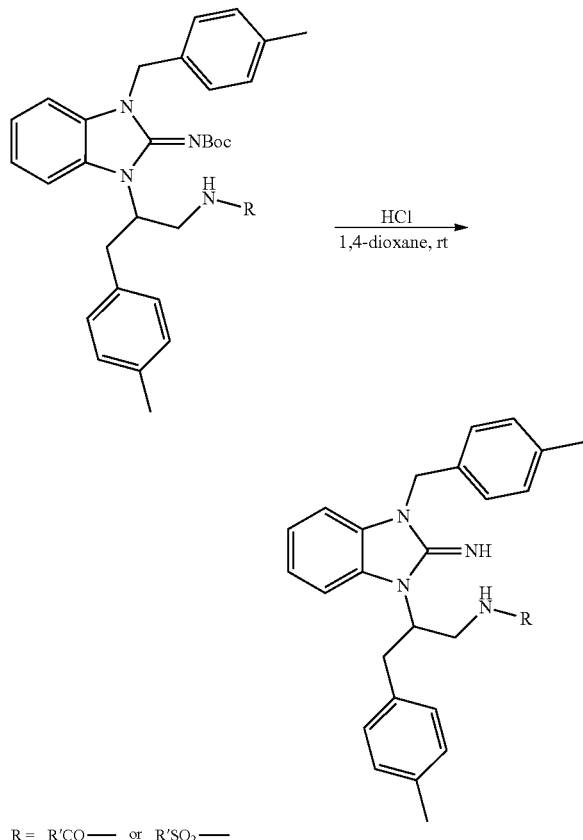

R = R'CO— or R'SO₂—

Boc protected sulfonamide analogs (1.0 eq.) was dissolved in 4 M HCl/1,4-dioxane (5.1 mL/mmol). The mixture was stirred at ambient temperature for 3.5 h, during which a white precipitate developed. Upon completion, the reaction was concentrated under a stream of air, dried under vacuum, and triturated 2× with Et₂O to remove any non-polar impurities. The resulting white solid was suspended in DCM, and satd. aq. NaHCO₃ was added to free-base the product. The bi-phasic mixture was stirred for 45 min, after which the layers were separated, and the aqueous layer was extracted twice more with DCM. The combined organic layers were passed through a plug of MgSO₄ and concentrated to afford the Boc deprotected sulfonamides.

General Procedure (L) for Nitro Compound Synthesis

At room temperature, fluoro-nitro-pyridine (fluoro-nitrobenzene) (1 eq.), amino alcohol (ether, ester) (1 eq.), such as (S)-2-amino-3-(p-tolyl)propan-1-ol, and potassium carbonate (excess) are mixed in dimethylformamide. The reaction was stirred at room temperature for overnight. After filtration and removing solvent, the residue was purified by flash chromatography using 20-30% hexanes in ethyl acetate as eluent. Giving diamine compounds, such as (S)-2-((3-nitropyridin-2-yl)amino)-3-(p-tolyl)propan-1-ol, as yellow solid or oil.

Alternatively, to a solution of amine (1 eq.). such as (S)-2-amino-N-methyl-3-(p-tolyl)propanamide, in DMF was added 1-fluoro-2-nitrobezene (1 eq.) and potassium carbonate (2 eq.). The mixture was stirred at 80° C. for overnight. After filtration the filtrate was concentrated at reduced pressure and the residue was purified using 50% ethyl acetate in hexanes as eluent, giving product, such as (S)—N-methyl-2-((2-nitrophenyl)amino)-3-(p-tolyl)propenamide, as yellow solid.

Alternatively, to a solution of amine (1 eq.) in DCM was added triethylamine (3 eq.) followed by addition of boc protected amino acid (1.3 eq.) and BOP reagent (1.3 eq.). The mixture was stirred at room temperature for overnight. Solvent was removed, and the residue was purified by flash chromatography using 40% ethyl acetate in hexanes as eluent. Giving product as yellow solid.

General Procedure (M) for Nitro Compound to Diamine Compound Synthesis

At room temperature, nitro compounds, such as (S)-2-((3-nitropyridin-2-yl)amino)-3-(p-tolyl)propan-1-ol, and palladium on charcoal (or Raney nickel) was mixed in methanol (or acetonitrile). The mixture was stirred at room temperature for 3-48 hours as the yellow color disappeared. After filtration to remove palladium on charcoal (or Raney nickel), solvent was removed, and the crude diamine product, such as (S)-2-((3-aminopyridin-2-yl)amino)-3-(p-tolyl)propan-1-ol was used in next step without purification.

General Procedure (N) for Diamine Compound Synthesis with 4-Methyl Benzyl Bromide At room temperature, substituted anilines (1 eq.), such as (S)-2-((3-aminopyridin-2-yl)amino)-3-(p-tolyl)propan-1-ol, 4-methyl benzyl bromide (1 eq.) and potassium carbonate (1 eq.) were mixed in dimethylformamide. The mixture was stirred at room temperature for overnight, followed by filtration to filter off the potassium carbonate. After removing solvent, the residue was purified by flash chromatography using 20-50% ethyl acetate in hexanes as eluent to provide diamine compound, such as (S)-2-((3-((4-methylbenzyl)amino)pyridin-2-yl)amino)-3-(p-tolyl)propan-1-ol.

General Procedure (O) for Diamine Compound Synthesis with Secondary Bromide

At room temperature, substituted anilines (1 eq.), such as (S)-2-((2-aminophenyl)amino)-1-(azetidin-1-yl)-3-(p-tolyl)propan-1-one, secondary bromide (1 eq.), such as 1-(1-bromoethyl)-4-methylbenzene, and potassium carbonate (1 eq.) were mixed in dimethylformamide. The mixture was stirred at 80° C. for overnight, followed by filtration to filter off the potassium carbonate. After removing solvent, the residue was purified by flash chromatography using 20-50% ethyl acetate in hexanes as eluent to provide the diamine compound, such as (2S)-1-(azetidin-1-yl)-3-(p-tolyl)-2-((2-((1-(p-tolyl)ethyl)amino)phenyl)amino)propan-1-one.

General Procedure (P) for Diamine Compound to Final Products

At room temperature, to the solution of diamine substrate, such as (S)—N1-(1-methoxy-3-phenylpropan-2-yl)-N2-(4-methyl benzyl)benzene-1,2-diamine, (1 eq.) in methanol (5 mL) was added cyanogen bromide (4 eq., 3M solution in dichloromethane). The mixture was stirred at room temperature for 4-48 hours. After completion of the reaction, the solvent was removed under reduced pressure. The remaining solid was mixed with saturated NaHCO$_3$ solution (25 m), extracted with CH$_2$Cl$_2$ (3×25 mL). The combined organic layers were dried over Na$_2$SO$_4$, filtered and concentrated under reduced pressure. The residue was purified by flash column chromatography on Biotage Isolera system using 5% methanol in dichloromethane as eluent to provide the target compound, such as (S)-1-(1-methoxy-3-phenylpropan-2-yl)-3-(4-methylbenzyl)-1H-benzo[d]imidazol-2(3H)-iminn.

Synthesis with General Procedure (A).

(6-methoxypyridin-2-yl)methanol. This compounds was prepared following the method described by Allen, J. G. et al. To a flask were added 2-Methoxy-6-pyridinecarboxaldehyde (1.4445 g, 10.54 mmol), THF (15 mL) and water (1.5 mL). The resulting solution was stirred at room temperature and NaBH$_4$ (0.4639 g, 12.21 mmol) was added in 7 min. The resulting reaction mixture was stirred at room temperature for 1.5 h and was poured into brine (60 mL), extracted with DCM (2×60 mL). The combined organic layers were dried over Na$_2$SO$_4$, filtered and concentrated under reduced pressure. The residue was purified through a short pad of silica gel, eluted with a mixture of 3:1 hexane/EtOAc to provide the desired product as a yellow liquid (1.4455 g, >95%). $^1$H NMR (400 MHz, CDCl$_3$) δ 7.55 (dd, J=8.2, 7.3 Hz, 1H), 6.79 (d, J=7.3 Hz, 1H), 6.62 (d, J=8.2 Hz, 0H), 4.66 (d, J=4.6 Hz, 2H), 3.94 (s, 3H), 3.56 (t, J=4.6 Hz, 1H). $^{13}$C NMR (100 MHz, CDCl$_3$) δ 163.6, 156.9, 139.2, 112.7, 109.0, 63.9, 53.3.

2-(bromomethyl)-6-methoxypyridine. Reaction of (6-methoxypyridin-2-yl)methanol (Procedure A) yielded the title product as a colorless liquid (73%). $^1$H NMR (400 MHz, CDCl$_3$) δ 7.53 (t, J=8.4 Hz, 1H), 6.98 (d, J=7.2 Hz, 1H), 6.65 (d, J=8.4 Hz, 1H), 4.45 (s, 2H), 3.93 (s, 3H). $^{13}$C NMR (100 MHz, CDCl$_3$) δ 163.8, 154.2, 139.2, 115.9, 110.4, 53.5, 34.1. LC-MS (ESI) calcd for: C$_7$H$_9$BrNO (MH$^+$): 202.0, found 202.0.

2-(bromomethyl)pyridine. Reaction of pyridin-2-yl-methanol (Procedure A) yielded the title product as a maroon gel (>95%). $^1$H NMR (400 MHz, CDCl$_3$) δ 8.56 (d, J=4.9 Hz, 1H), 7.67 (td, J=7.7, 1.8 Hz, 1H), 7.42 (d, J=7.8 Hz, 1H), 7.19 (ddd, J=7.6, 4.9, 1.2 Hz, 1H), 4.53 (s, 2H). $^{13}$C NMR (100 MHz, CDCl$_3$) δ 156.8, 149.6, 137.1, 123.4, 123.0, 33.8.

4-(bromomethyl)-2-methoxypyridine. Reaction of (2-methoxypyridin-4-yl)methanol (Procedure A) yielded the title product a colorless liquid (70%). $^1$H NMR (400 MHz, CDCl$_3$) δ 8.13 (d, J=5.3 Hz, 1H), 6.88 (d, J=5.4 Hz, 1H), 6.73 (s, 1H), 4.32 (s, 2H), 3.93 (s, 3H). $^{13}$C NMR (100 MHz, CDCl$_3$) δ 164.5, 148.7, 147.4, 116.9, 110.6, 53.6, 30.5.

Synthesis with General Procedure (B).

Ethyl 2-amino-3-(6-methoxypyridin-2-yl)propanoate. Reaction of 2-(bromomethyl)-6-methoxypyridine (Procedure B) yielded the title product (86%). $^1$H NMR (400 MHz, CDCl$_3$) δ 7.45 (dd, J=8.3, 7.2 Hz, 1H), 6.70 (d, J=7.2 Hz, 1H), 6.55 (d, J=8.3 Hz, 1H), 4.15 (q, J=7.1 Hz, 2H), 3.98-3.88 (m, 1H), 3.86 (s, 3H), 3.15 (dd, J=14.6, 4.7 Hz, 1H), 3.04 (dd, J=14.4, 7.2 Hz, 1H), 1.82 (s, 2H), 1.21 (t, J=7.2 Hz, 3H). $^{13}$C NMR (100 MHz, CDCl$_3$) δ 175.3, 163.6, 155.4, 138.8, 116.4, 108.5, 60.8, 53.9, 53.3, 41.6, 14.2. LC-MS (ESI) calcd for: C$_{11}$H$_{17}$N$_2$O$_3$ (MH$^+$): 225.1, found 225.1.

Ethyl 2-amino-3-(p-tolyl)propanoate. Reaction of 4-methylbenzylbromide (Procedure B) yielded the title product (95%). $^1$H NMR (400 MHz, CDCl$_3$) δ 7.13-7.02 (m, 4H), 4.15 (q, J=7.2 Hz, 2H), 3.66 (dd, J=7.9, 5.2 Hz, 1H), 3.03 (dd, J=13.5, 5.2 Hz, 1H), 2.80 (dd, J=13.5, 7.9 Hz, 1H), 2.30 (s, 3H), 1.47 (s, 2H), 1.23 (t, J=7.2 Hz, 3H). $^{13}$C NMR (100 MHz, CDCl$_3$) δ 175.1, 136.3, 134.1, 129.2, 129.2, 60.8, 55.9, 40.7, 21.0, 14.2; LC-MS (ESI) calcd for: C12H18NO2 (MH$^+$): 208.1, found 208.1.

Ethyl 2-amino-3-(pyridin-2-yl)propanoate. Reaction of 2-(bromomethyl)pyridine (Procedure B) yielded the title product (25%). $^1$H NMR (400 MHz, CDCl$_3$) δ 8.51 (d, J=4.2 Hz, 1H), 7.58 (t, J=7.6 Hz, 1H), 7.21-7.01 (m, 2H), 4.14 (q, J=7.1 Hz, 2H), 3.94 (dd, J=8.2, 4.7 Hz, 1H), 3.24 (dd, J=14.1, 4.7 Hz, 1H), 3.01 (dd, J=13.7, 8.2 Hz, 1H), 1.82 (s, 2H), 1.20 (t, J=7.1 Hz, 3H). $^{13}$C NMR (100 MHz, CDCl$_3$) δ 175.1, 158.0, 149.3, 136.3, 123.9, 121.6, 60.9, 54.4, 42.6, 14.1. LC-MS (ESI) calcd for: C$_{10}$H$_{14}$N$_2$O$_2$ (MH$^+$): 195.1, found 195.1.

Ethyl 2-amino-3-(2-methoxypyridin-4-yl)propanoate. Reaction of 4-(bromomethyl)-2-methoxypyridine (Procedure B) yielded the title product (61%). $^1$H NMR (400 MHz, CDCl$_3$) δ 8.03 (d, J=4.8 Hz, 1H), 6.69 (d, J=5.3 Hz, 1H), 6.55 (s, 1H), 4.13 (qd, J=7.2, 1.5 Hz, 2H), 3.87 (d, J=1.4 Hz, 3H), 3.75-3.58 (m, 1H), 2.97 (dd, J=13.6, 5.4 Hz, 1H), 2.75 (dd, J=13.6, 8.0 Hz, 1H), 1.51 (s, 2H), 1.21 (td, J=7.2, 1.5 Hz, 3H). $^{13}$C NMR (100 MHz, CDCl$_3$) δ 174.5, 164.4, 149.2, 146.8, 117.8, 111.3, 61.1, 55.0, 53.3, 40.2, 14.1.

Ethyl phenylalaninate. Reaction of benzylbromide (Procedure B) yielded the title product (>98%). $^1$H NMR (400 MHz, CDCl$_3$) δ 7.34-7.26 (m, 2H), 7.24-7.15 (m, 3H), 4.13 (q, J=7.1 Hz, 2H), 3.68 (dd, J=7.8, 5.4 Hz, 1H), 3.05 (dd, J=13.5, 5.4 Hz, 1H), 2.84 (dd, J=13.5, 7.9 Hz, 1H), 1.46 (s, 2H), 1.21 (t, J=7.1 Hz, 3H). $^{13}$C NMR (100 MHz, CDCl$_3$) δ 175.0, 137.3, 129.3, 128.5, 126.7, 60.9, 55.9, 41.2, 14.2.

Synthesis with General Procedure (C).

Ethyl 3-(6-methoxypyridin-2-yl)-2-((2-nitrophenyl)amino)propanoate. Reaction of ethyl 2-amino-3-(6-methoxypyridin-2-yl)propanoate (Procedure C) yielded the title product (32%). $^1$H NMR (400 MHz, CDCl$_3$) δ 8.57 (d, J=7.6 Hz, 1H), 8.15 (dd, J=8.6, 1.6 Hz, 1H), 7.47 (dd, J=8.3, 7.2 Hz, 1H), 7.43-7.37 (m, 1H), 6.83 (d, J=8.5 Hz, 1H), 6.74 (d, J=7.2 Hz, 1H), 6.67 (ddd, J=8.4, 7.0, 1.2 Hz, 1H), 6.60 (d, J=8.3 Hz, 1H), 4.72 (dd, J=13.5, 6.0 Hz, 1H), 4.19 (q, J=7.1 Hz, 2H), 3.94 (s, 3H), 3.33 (d, J=6.0 Hz, 2H), 1.20 (t, J=7.1 Hz, 3H). $^{13}$C NMR (100 MHz, CDCl$_3$) δ 171.6, 163.9, 153.7, 144.1, 139.0, 136.1, 132.6, 126.9, 116.3, 116.0, 113.8, 109.3, 61.5, 55.5, 53.5, 39.8, 14.1. LC-MS (ESI) calcd for: C17H20N3O5 (MH$^+$): 346.1, found 346.2.

Ethyl 3-(6-methoxypyridin-2-yl)-2-((2-nitrophenyl)amino)propanoate. Reaction of ethyl 2-amino-3-(p-tolyl)propanoate (Procedure C) yielded the title product (44%). $^1$H NMR (400 MHz, CDCl$_3$) δ 8.34 (d, J=7.3 Hz, 1H), 8.16 (dd, J=8.8, 1.6 Hz, 1H), 7.44-7.34 (m, 1H), 7.12 (s, 4H), 6.72-6.62 (m, 2H), 4.53-4.35 (m, 1H), 4.19 (qd, J=7.1, 1.0 Hz, 2H), 3.35-3.05 (m, 2H), 2.31 (s, 3H), 1.22 (t, J=7.1 Hz, 3H). $^{13}$C NMR (100 MHz, CDCl$_3$) δ 171.5, 143.9, 137.0, 136.1, 132.4, 129.5, 129.1, 127.0, 116.2, 113.8, 110.0, 61.6, 57.5, 38.2, 21.1, 14.1. LC-MS (ESI) calcd for: C$_{18}$H$_{21}$N$_2$O$_4$ (MH$^+$): 329.2, found 329.2.

Ethyl 2-((2-nitrophenyl)amino)-3-(pyridin-2-yl)propanoate. Reaction of ethyl 2-amino-3-(pyridin-2-yl)propanoate (Procedure C) yielded the title product (32%). $^1$H NMR (400 MHz, CDCl$_3$) δ 8.68 (d, J=7.6 Hz, 1H), 8.57 (d, J=4.9 Hz, 1H), 8.12 (dd, J=8.5, 1.7 Hz, 1H), 7.58 (td, J=7.7, 1.9 Hz, 1H), 7.36 (ddd, J=8.6, 6.9, 1.7 Hz, 1H), 7.20-7.10 (m, 2H), 6.76 (d, J=8.7 Hz, 1H), 6.64 (ddd, J=8.3, 6.9, 1.2 Hz, 1H), 4.75 (td, J=7.3, 5.7 Hz, 1H), 4.16 (q, J=7.2 Hz, 2H), 3.38 (qd, J=14.0, 6.3 Hz, 2H), 1.17 (t, J=7.1 Hz, 3H). $^{13}$C NMR (100 MHz, CDCl$_3$) δ 171.5, 156.2, 149.6, 144.0, 136.6, 136.1, 132.7, 126.9, 123.9, 122.2, 116.1, 113.9, 61.6, 55.8, 40.4, 14.1. LC-MS (ESI) calcd for: C16H18N3O4 (MH+): 316.1, found 316.1.

Ethyl 3-(2-methoxypyridin-4-yl)-2-((2-nitrophenyl)amino)propanoate. Reaction of ethyl 2-amino-3-(2-methoxypyridin-4-yl)propanoate (Procedure C) yielded the title product (10%). $^1$H NMR (400 MHz, CDCl$_3$) δ 8.33 (d, J=7.6 Hz, 1H), 8.22-8.14 (m, 1H), 8.08 (d, J=5.3 Hz, 1H), 7.50-7.34 (m, 1H), 6.81-6.65 (m, 3H), 6.60 (s, 1H), 4.47 (td, J=7.4, 5.6 Hz, 1H), 4.20 (q, J=7.1 Hz, 2H), 3.90 (s, 3H), 3.35-3.01 (m, 2H), 1.22 (t, J=7.1 Hz, 3H). $^{13}$C NMR (100 MHz, CDCl$_3$) δ 170.9, 164.6, 147.3, 147.2, 143.5, 136.2, 132.9, 127.1, 117.6, 116.6, 113.6, 111.3, 61.9, 56.5, 53.4, 37.7, 14.1. MS (ESI) calcd for: C17H20N3O5 (MH+): 346.1, found 346.1.

Ethyl (2-nitrophenyl)phenylalaninate. Reaction of ethyl phenylalaninate (Procedure C) yielded the title product (39%). $^1$H NMR (400 MHz, CDCl$_3$) δ 8.36 (d, J=7.3 Hz, 1H), 8.17 (dd, J=8.9, 1.6 Hz, 1H), 7.39 (t, J=8.6 Hz, 1H), 7.35-7.26 (m, 3H), 7.25-7.20 (m, 2H), 6.73-6.62 (m, 2H), 4.45 (td, J=7.4, 5.7 Hz, 1H), 4.18 (q, J=7.2 Hz, 2H), 3.36-3.11 (m, 2H), 1.21 (t, J=7.1 Hz, 3H). $^{13}$C NMR (100 MHz, CDCl$_3$) δ 171.5, 143.9, 136.1, 135.6, 129.2, 128.8, 127.4, 127.0, 116.3, 113.7, 61.7, 57.5, 38.7, 14.1. MS (APCI) calcd for: C17H19N2O4 (MH+): 315.1, found 315.1.

Synthesis with General Procedure (D).

2-((2-aminophenyl)amino)-3-(6-methoxypyridin-2-yl)propan-1-ol. Reaction of ethyl 3-(6-methoxypyridin-2-yl)-2-((2-nitrophenyl)amino)propanoate (Procedure D) yielded the title product (68% two steps). $^1$H NMR (400 MHz, Methanol-d4) δ 7.55 (t, J=7.8 Hz, 1H), 7.18-6.98 (m, 3H), 6.93-6.76 (m, 2H), 6.61 (d, J=8.3 Hz, 1H), 4.17-4.00 (s, 1H), 3.87 (s, 3H), 3.74-3.58 (br, 2H), 3.01 (d, J=6.9 Hz, 2H). $^{13}$C NMR (100 MHz, Methanol-d4) δ 163.9, 155.9, 139.4, 135.7, 126.0, 124.6, 121.7, 120.5, 116.5, 107.5, 61.7, 56.5, 52.7, 37.7. MS (ESI) calcd for: C15H20N3O2 (MH+): 274.2, found 274.2.

2-((2-aminophenyl)amino)-3-(p-tolyl)propan-1-ol. Reaction of ethyl 2-((2-nitrophenyl)amino)-3-(p-tolyl)propanoate (Procedure D) yielded the title product (35% two steps). $^1$H NMR (400 MHz, Methanol-d4) δ 7.10 (dd, J=23.4, 7.6 Hz, 4H), 6.81-6.64 (m, 3H), 6.63-6.51 (m, 1H), 3.72-3.42 (m, 3H), 2.83 (d, J=6.1 Hz, 2H), 2.27 (s, 3H). $^{13}$C NMR (100 MHz, Methanol-d4) δ 135.9, 135.8, 135.3, 135.1, 128.9, 128.6, 119.7, 118.5, 116.5, 113.3, 62.1, 56.4, 36.4, 19.7. MS (ESI) calcd for: C$_{16}$H$_{21}$N$_2$O (MH+): 257.2, found 257.2.

2-((2-aminophenyl)amino)-3-(pyridin-2-yl)propan-1-ol. Reaction of ethyl 2-((2-nitrophenyl)amino)-3-(pyridin-2-yl)propanoate (Procedure D) yielded the title product (53% two steps). $^1$H NMR (400 MHz, Methanol-d4) δ 8.43 (d, J=5.1 Hz, 1H), 7.68 (td, J=7.7, 1.7 Hz, 1H), 7.34 (d, J=7.8 Hz, 1H), 7.20 (ddd, J=7.7, 5.0, 1.2 Hz, 1H), 6.72-6.60 (m, 3H), 6.54 (ddd, J=7.6, 7.0, 1.9 Hz, 1H), 3.89-3.77 (m, 1H), 3.58 (d, J=4.7 Hz, 2H), 3.06 (qd, J=13.7, 6.8 Hz, 2H). $^{13}$C NMR (100 MHz, Methanol-d4) δ 159.3, 148.2, 137.1, 135.7, 134.9, 124.4, 121.6, 119.6, 118.4, 116.4, 113.0, 62.6, 55.4, 39.3.

2-((2-aminophenyl)amino)-3-(2-methoxypyridin-4-yl)propan-1-ol. Reaction of ethyl 3-(2-methoxypyridin-4-yl)-2-((2-nitrophenyl)amino)propanoate (Procedure D) yielded the title product (60% two steps). $^1$H NMR (400 MHz, Methanol-d4) δ 8.00 (d, J=5.3 Hz, 1H), 6.89 (d, J=5.5 Hz, 1H), 6.81-6.62 (m, 4H), 6.62-6.52 (m, 1H), 3.85 (s, 3H), 3.79-3.62 (m, 1H), 3.55 (d, J=4.8 Hz, 2H), 3.01-2.67 (m, 2H). $^{13}$C NMR (100 MHz, Methanol-d4) δ 164.51, 152.25, 145.87, 135.56, 134.98, 119.63, 118.51, 118.14, 116.47, 113.09, 110.63, 62.24, 55.37, 52.66, 36.33.

2-((2-aminophenyl)amino)-3-phenylpropan-1-ol. Reaction of ethyl (2-nitrophenyl)phenylalaninate (Procedure D) yielded the title product (78% two steps). $^1$H NMR (400 MHz, CDCl$_3$) δ 7.37-7.28 (m, 2H), 7.26-7.14 (m, 3H), 6.95-6.62 (m, 4H), 3.79-3.65 (m, 2H), 3.51 (dd, J=10.4, 4.6 Hz, 1H), 3.42-3.05 (br, 3H), 2.97 (dd, J=13.6, 5.6 Hz, 1H), 2.85 (dd, J=13.6, 7.5 Hz, 1H). $^{13}$C NMR (100 MHz, CDCl$_3$) δ 138.3, 136.1, 135.2, 129.3, 128.6, 126.5, 120.7, 119.6, 117.2, 114.2, 63.0, 56.1, 37.6. MS (APCI) calcd for: C15H19N2O (MH+): 243.2, found 243.4.

Synthesis with General Procedure (E).

2-(2-imino-3-(4-methylbenzyl)-2,3-dihydro-1H-benzo[d]imidazol-1-yl)-3-(2-methoxy pyridin-3-yl)propan-1-ol (ARN-17)

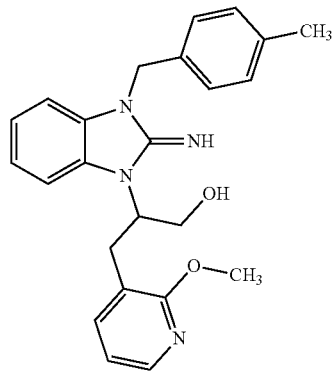 [SMILES: COc1ncccc1CC(CO)n1c(=N)n(Cc2ccc(C)cc2)c2ccccc21]

To a flask equipped with a reflux condenser and stirring bar were added 2-(2-imino-2,3-dihydro-1H-benzo[d]imidazol-1-yl)-3-(6-methoxypyridin-2-yl)propan-1-ol (0.1 g, 0.50 mmol), 2-butanone (10 mL) and 1-(bromomethyl)-4-methylbenzene (0.111 g, 0.60 mmol). The resulting mixture was stirred at 75° C. for 8 h and then cooled to room temperature. After the evaporation of most 2-butanone under reduced pressure, the residue was sonicated with Et$_2$O (20 mL) and then the supernatant was removed using pipette. This procedure was repeated three times and the remaining solid was mixed with saturated NaHCO$_3$ solution (25 m), extracted with CH$_2$Cl$_2$ (3×25 mL). The combined organic layers were dried over Na$_2$SO$_4$, filtered and concentrated under reduced pressure to afford the entitled free amine product as a brown gel (0.16 g, 79%); $^1$H NMR (400 MHz, CDCl$_3$) δ 7.94 (dd, J=4.9, 1.9 Hz, 1H), 7.41 (dd, J=7.2, 2.0 Hz, 1H), 7.21-7.02 (m, 4H), 6.98-6.60 (m, 5H), 4.96-4.77 (m, 2H), 4.56 (td, J=7.7, 4.2 Hz, 1H), 4.14-3.92 (m, 4H), 3.87 (dd, J=12.5, 4.6 Hz, 1H), 3.29 (d, J=6.2 Hz, 2H), 2.33 (s, 3H). $^{13}$C NMR (100 MHz, CDCl$_3$) δ 162.18, 154.69, 144.99, 139.95, 137.75, 132.17, 131.73, 131.47, 129.66, 126.63, 121.09, 120.65, 120.56, 116.82, 106.93, 106.65, 62.89, 55.78, 53.31, 44.96, 28.72, 21.12. HRMS (ESI-TOF) calcd for C24H26N4O2 [M+H]+ 403.2128, found: 403.2126.

2-(2-imino-3-(4-methylbenzyl)-2,3-dihydro-1H-benzo[d]imidazol-1-yl)-3-(6-methoxy pyridin-3-yl)propan-1-ol (ARN-28). To a flask equipped with a reflux condenser and stirring bar were added 2-(2-imino-2,3-dihydro-1H-benzo[d]imidazol-1-yl)-3-(6-methoxypyridin-2-yl)propan-1-ol (0.1 g, 0.50 mmol), 2-butanone (10 mL) and 1-(bromomethyl)-4-methylbenzene (0.111 g, 0.60 mmol). The resulting mixture was stirred at 75° C. for 8 h and then cooled to room temperature. After the evaporation of most 2-butanone under reduced pressure, the residue was sonicated with Et$_2$O (20 mL) and then the supernatant was removed using pipette. This procedure was repeated three times and the remaining solid was mixed with saturated NaHCO$_3$ solution (25 mL), extracted with CH$_2$Cl$_2$ (3×25 mL). The combined organic layers were dried over Na$_2$SO$_4$, filtered and concentrated under reduced pressure to afford the entitled free amine product as a brown gel (0.150 g, 75%); $^1$H NMR (400 MHz, CDCl$_3$) δ 7.99 (s, 1H), 7.43 (d, J=8.4 Hz, 1H), 7.16-7.03 (m, 4H), 6.93-6.83 (m, 2H), 6.80-6.68 (m, 2H), 6.54 (d, J=8.4 Hz, 1H), 4.94-4.77 (m, 2H), 4.26 (d, J=4.5 Hz, 1H), 4.08 (d, J=12.3 Hz, 1H), 3.94 (dd, J=12.4, 4.8 Hz, 1H), 3.84 (s, 3H), 3.34-3.14 (m, 2H), 2.31 (s, 3H). $^{13}$C NMR (100 MHz, CDCl$_3$) δ 162.94, 154.71, 146.99, 139.87, 137.72, 132.10, 131.54, 131.35, 129.68, 126.59, 126.42, 121.15, 120.74, 110.36, 106.91, 106.88, 62.72, 59.04, 53.29, 44.94, 29.97, 21.12. HRMS (ESI-TOF) calcd for C24H26N4O2 [M+H]$^+$ 403.2134, found: 403.2188.

3-(benzo[d]oxazol-2-yl)-2-(2-imino-3-(4-methylbenzyl)-2,3-dihydro-1H-benzo[d]imidazol-1-yl)propan-1-ol (ARN-37). To a flask equipped with a reflux condenser and stirring bar were added 3-(benzo[d]oxazol-2-yl)-2-(2-imino-2,3-dihydro-1H-benzo[d]imidazol-1-yl)propan-1-ol (0.08 g, 0.26 mmol), 2-butanone (6 mL) and 1-(bromomethyl)-4-methylbenzene (0.058 g, 0.31 mmol). The resulting mixture was stirred at 75° C. for 8 h and then cooled to room temperature. After the evaporation of most 2-butanone under reduced pressure, the residue was sonicated with Et$_2$O (20 mL) and then the supernatant was removed using pipette. This procedure was repeated three times and the remaining solid was mixed with saturated NaHCO$_3$ solution (25 mL), extracted with CH$_2$Cl$_2$ (3×25 mL). The combined organic layers were dried over Na$_2$SO$_4$, filtered and concentrated under reduced pressure to afford the entitled free amine product as a brown gel (65%); $^1$H NMR (400 MHz, DMSO-d$_6$) δ 7.47-7.35 (m, 3H), 7.31-7.07 (m, 6H), 6.91-6.68 (m, 3H), 5.12 (s, 2H), 4.75-4.66 (m, 1H), 3.73 (d, J=4.6 Hz, 1H), 3.58 (d, J=5.6 Hz, 1H), 3.10 (dd, J=15.6, 7.4 Hz, 1H), 2.90 (d, J=15.5 Hz, 1H), 2.07 (s, 3H). $^{13}$C NMR (100 MHz, DMSO) δ 151.14, 150.27, 137.51, 133.34, 130.51, 129.61, 128.42, 125.65, 122.98, 122.74, 119.05, 115.95, 110.32, 110.04, 62.78, 52.23, 44.81, 31.15, 21.12.

(1R,2R)-2-(2-imino-3-(4-methylbenzyl)-2,3-dihydro-1H-benzo[d]imidazol-1-yl)-1-phenylpropane-1,3-diol (ARN-85). To a flask equipped with a reflux condenser and stirring bar were added (1R,2R)-2-(2-imino-2,3-dihydro-1H-benzo[d]imidazol-1-yl)-1-phenylpro pane-1,3-diol (0.10 g, 0.35 mmol), 2-butanone (6 mL) and 1-(bromomethyl)-4-methyl benzene (0.085 g, 0.45 mmol). The resulting mixture was stirred at 75° C. for 8 h and then cooled to room temperature. After the evaporation of most 2-butanone under reduced pressure, the residue was sonicated with Et$_2$O (20 mL) and then the supernatant was removed using pipette. This procedure was repeated three times and the remaining solid was mixed with saturated NaHCO$_3$ solution (25 mL), extracted with CH$_2$Cl$_2$ (3×25 mL). The combined organic layers were dried over Na$_2$SO$_4$, filtered and concentrated under reduced pressure to afford the entitled free amine product as a brown gel (68%); $^1$H NMR (400 MHz, CDCl$_3$) δ 7.39 (d, J=7.5 Hz, 2H), 7.22-7.05 (m, 5H), 6.87 (ddt, J=22.7, 15.3, 7.6 Hz, 4H), 6.67 (d, J=7.6 Hz, 1H), 5.45 (d, J=4.8 Hz, 1H), 4.94-4.75 (m, 3H), 4.54 (d, J=5.3 Hz, 1H), 4.36 (dd, J=11.7, 6.0 Hz, 1H), 4.08 (dd, J=11.6, 6.3 Hz, 1H), 2.32 (s, 3H). $^{13}$C NMR (100 MHz, CDCl$_3$) δ 154.74, 141.90, 137.67, 131.56, 131.14, 129.63, 128.03, 127.01, 126.30, 125.61, 121.50, 120.94, 107.05, 72.43, 62.63, 60.45, 44.81, 21.10.

(1S,2S)-2-(3-((5-chlorobenzo[d]oxazol-2-yl)methyl)-2-imino-2,3-dihydro-1H-benzo [d]imidazol-1-yl)-1-phenylpropane-1,3-diol (ARN-99). To a flask equipped with a reflux condenser and stirring bar were added (1S,2S)-2-(2-imino-2,3-dihydro-1H-benzo[d]imidazol-1-yl)-1-phenylpropane-1,3-diol (0.20 g, 0.7 mmol), 2-butanone (10 mL) and 2-(bromomethyl)-5-chlorobenzo[d]oxazole (0.23 g, 0.9 mmol). The resulting mixture was stirred at 75° C. for 8 h and then cooled to room temperature. After the evaporation of most 2-butanone under reduced pressure, the residue was sonicated with Et$_2$O (20 mL) and then the supernatant was removed using pipette. This procedure was repeated three times and the remaining solid was mixed with saturated NaHCO$_3$ solution (25 m), extracted with CH$_2$Cl$_2$ (3×25 m). The combined organic layers were dried over Na$_2$SO$_4$, filtered and concentrated under reduced pressure to afford the entitled free amine product as a brown gel (53%); $^1$H NMR (400 MHz, CDCl$_3$) δ 7.64-7.21 (m, 5H), 7.18-6.65 (m, 7H), 5.50-5.32 (m, 2H), 5.22-4.95 (m, 2H), 4.45 (s, 1H), 4.33-3.99 (m, 2H). $^{13}$C NMR (100 MHz, CDCl$_3$) δ 160.91, 149.44, 141.40, 130.35, 130.25, 128.12, 127.26, 126.13, 125.69, 122.44, 121.49, 120.27, 111.66, 107.36, 72.03, 63.62, 62.63, 60.07.

(1R,2R)-2-(2-imino-3-(4-methylbenzyl)-2,3-dihydro-1H-benzo[d]imidazol-1-yl)-3-methoxy-1-phenylpropan-1-ol (ARN-199). To a flask equipped with a reflux condenser and stirring bar were added (1R,2R)-2-(2-imino-2,3-dihydro-1H-benzo[d]imidazol-1-yl)-3-methoxy-1-phenylpropan-1-ol (0.08 g, 0.27 mmol), 2-butanone (6 mL) and 1-(bromomethyl)-4-methylbenzene (0.086 g, 0.35 mmol). The resulting mixture was stirred at 75° C. for 8 h and then cooled to room temperature. After the evaporation of most 2-butanone under reduced pressure, the residue was sonicated with Et$_2$O (20 mL) and then the supernatant was removed using pipette. This procedure was repeated three times and the remaining solid was mixed with saturated NaHCO$_3$ solution (25 m), extracted with CH$_2$Cl$_2$ (3×25 m). The combined organic layers were dried over Na$_2$SO$_4$, filtered and concentrated under reduced pressure to afford the entitled free amine product as a brown gel (71%); $[α]_D^{20}$ −9.0 (c 5.0, CHCl$_3$); $^1$H NMR (400 MHz, CDCl$_3$) δ 7.99 (s, 1H), 7.43 (d, J=8.4 Hz, 1H), 7.16-7.03 (m, 4H), 6.93-6.83 (m, 2H), 6.80-6.68 (m, 2H), 6.54 (d, J=8.4 Hz, 1H), 4.94-4.77 (m, 2H), 4.26 (d, J=4.5 Hz, 1H), 4.08 (d, J=12.3 Hz, 1H), 3.94 (dd, J=12.4, 4.8 Hz, 1H), 3.84 (s, 3H), 3.34-3.14 (m, 2H), 2.31 (s, 3H). $^{13}$C NMR (100 MHz, CDCl$_3$) δ 162.94, 154.71, 146.99, 139.87, 137.72, 132.10, 131.54, 131.35, 129.68, 126.59, 126.42, 121.15, 120.74, 110.36, 106.91, 106.88, 62.72, 59.04, 53.29, 44.94, 29.97, 21.12. HRMS (ESI-TOF) calcd for C25H27N3O2 [M+H]$^+$ 402.2182, found: 402.2291.

2-(2-imino-3-(4-methylbenzyl)-2,3-dihydro-1H-benzo[d]imidazol-1-yl)-3-(6-methoxypyridin-2-yl)propan-1-ol.
Reaction of 2-((2-aminophenyl)amino)-3-(6-methoxypyridin-2-yl)propan-1-ol (Procedure E) yielded the title product. After the cyclization, the intermediate 2-(2-imino-2,3-dihydro-1H-benzo[d]imidazol-1-yl)-3-(6-methoxypyridin-2-yl)propan-1-ol was obtained as a dark brown gel (72%). $^1$H NMR (400 MHz, DMSO-d6) δ 7.41 (dd, J=8.2, 7.2 Hz, 1H), 7.28 (s, 1H), 7.03 (d, J=7.5 Hz, 1H), 6.92-6.74 (m, 2H), 6.63 (d, J=7.2 Hz, 1H), 6.48 (d, J=8.2 Hz, 1H), 6.30 (s, 2H), 4.86 (s, 1H), 3.94 (dd, J=11.2, 7.1 Hz, 1H), 3.90-3.77 (br, 1H), 3.86-3.81 (m, 1H), 3.73 (s, 3H), 3.40 (dd, J=14.4, 9.7 Hz, 1H), 3.23 (dd, J=14.4, 5.5 Hz, 1H). $^{13}$C NMR (100 MHz, DMSO-d6) δ 163.3, 156.1, 155.4, 142.5, 139.6, 120.5, 118.3, 116.5, 114.9, 108.5, 62.5, 56.7, 43.2, 36.6. After the alkylation of the intermediate above with 4-methylbenzyl bromide, the desired final product was obtained as a brown gel (71%). ¹H NMR (400 MHz, CDCl₃) δ 7.31 (dd, J=8.3, 7.2 Hz, 1H), 7.19-7.05 (m, 4H), 6.94-6.83 (m, 3H), 6.74 (dd, J=8.0, 1.5 Hz, 1H), 6.69 (d, J=7.2 Hz, 1H), 6.46 (d, J=8.2 Hz, 1H), 4.89 (d, J=3.7 Hz, 2H), 4.77 (q, J=7.4, 6.7 Hz, 1H), 4.12 (dd, J=12.3, 1.3 Hz, 1H), 3.96 (dd, J=12.4, 4.6 Hz, 1H), 3.91 (s, 3H), 3.40 (dd, J=7.5, 2.1 Hz, 2H), 2.33 (s, 3H). ¹³C NMR (100 MHz, CDCl₃) δ 163.6, 156.0, 154.8, 138.8, 137.7, 132.1, 131.6, 131.4, 129.6, 126.6, 121.0, 120.5, 116.7, 108.2, 107.2, 106.6, 63.5, 57.3, 53.2, 45.0, 35.6, 21.1. MS (ESI) calcd for: C24H27N4O2 (MH⁺): 403.2, found 403.2.

2-(2-imino-3-(4-methylbenzyl)-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by alkylation with 4-methylbenzyl bromide (Procedure E) yielded the title product (75% two steps). ¹H NMR (400 MHz, CDCl₃) δ 7.17-7.12 (m, 4H), 7.10 (d, J=8.2 Hz, 2H), 7.01 (d, J=7.8 Hz, 2H), 6.97-6.87 (m, 3H), 6.80-6.73 (m, 2H), 4.89 (d, J=4.9 Hz, 2H), 4.33-4.19 (m, 1H), 4.06 (d, J=12.4 Hz, 1H), 3.94 (dd, J=12.4, 4.6 Hz, 1H), 3.41 (dd, J=13.4, 8.1 Hz, 1H), 3.14 (dd, J=13.4, 7.3 Hz, 1H), 2.34 (s, 3H), 2.27 (s, 3H). ¹³C NMR (100 MHz, CDCl₃) δ 154.8, 137.7, 135.9, 135.3, 132.1, 131.6, 131.6, 129.7, 129.3, 129.0, 126.6, 121.1, 120.5, 106.9, 106.8, 62.6, 59.5, 45.0, 33.3, 21.1, 21.0. MS (ESI) calcd for: $C_{25}H_{28}N_3O$ (MH⁺): 386.2, found 386.3.

2-(2-imino-3-(4-methylbenzyl)-2,3-dihydro-1H-benzo[d]imidazol-1-yl)-3-(pyridin-2-yl)propan-1-ol. Cyclization of 2-((2-aminophenyl)amino)-3-(pyridin-2-yl)propan-1-ol, followed by alkylation with 4-methylbenzyl bromide (Procedure E) yielded the title product (69% two steps). ¹H NMR (400 MHz, CDCl₃) δ 8.48 (d, J=4.9 Hz, 1H), 7.38 (td, J=7.6, 1.8 Hz, 1H), 7.21-7.02 (m, 6H), 7.03-6.95 (m, 1H), 6.89-6.76 (m, 3H), 6.75-6.69 (m, 1H), 4.87 (d, J=4.1 Hz, 2H), 4.73 (td, J=7.6, 4.4 Hz, 1H), 4.11 (dd, J=12.5, 1.1 Hz, 1H), 3.94 (dd, J=12.4, 4.5 Hz, 1H), 3.60-3.41 (m, 2H), 2.33 (s, 3H). ¹³C NMR (100 MHz, CDCl₃) δ 158.6, 154.9, 149.3, 137.7, 136.2, 132.2, 131.5, 131.3, 129.6, 126.6, 124.3, 121.5, 121.0, 120.4, 107.2, 106.5, 63.7, 57.6, 44.9, 36.0, 21.1.

2-(2-imino-3-(4-methylbenzyl)-2,3-dihydro-1H-benzo[d]imidazol-1-yl)-3-(2-methoxypyridin-4-yl)propan-1-ol. Cyclization of 2-((2-aminophenyl)amino)-3-(2-methoxypyridin-4-yl)propan-1-ol, followed by alkylation with 4-methylbenzyl bromide (Procedure E) yielded the title product (60% two steps). ¹H NMR (400 MHz, CDCl₃) δ 7.94 (d, J=5.2 Hz, 1H), 7.20-7.03 (m, 6H), 6.94-6.87 (m, 2H), 6.80-6.74 (m, 2H), 6.73-6.68 (m, 1H), 6.60 (s, 1H), 4.88 (d, J=8.2 Hz, 2H), 4.37-4.22 (m, 1H), 4.08 (d, J=11.3 Hz, 1H), 3.93 (dd, J=12.5, 4.6 Hz, 1H), 3.84 (s, 3H), 3.28 (dd, J=7.7, 3.4 Hz, 2H), 2.33 (s, 3H). ¹³C NMR (100 MHz, CDCl₃) δ 164.4, 154.7, 150.3, 146.7, 137.8, 132.0, 131.5, 131.4, 129.7, 126.6, 121.1, 120.8, 118.2, 111.3, 106.8, 106.6, 63.2, 58.3, 53.3, 45.0, 33.0, 21.1.

2-(2-imino-3-(4-methylbenzyl)-2,3-dihydro-1H-benzo[d]imidazol-1-yl)-3-phenylpropan-1-ol. Cyclization of 2-((2-aminophenyl)amino)-3-phenylpropan-1-ol, followed by alkylation with 4-methylbenzyl bromide (Procedure E) yielded the title product (63% two steps). ¹H NMR (400 MHz, CDCl₃) δ 7.26-7.04 (m, 10H), 6.93-6.84 (m, 2H), 6.79-6.74 (m, 1H), 6.72-6.66 (m, 1H), 4.89 (d, J=5.6 Hz, 2H), 4.29 (td, J=7.9, 4.7 Hz, 1H), 4.08 (d, J=12.4 Hz, 1H), 3.95 (dd, J=12.3, 4.6 Hz, 1H), 3.41 (dd, J=13.4, 7.7 Hz, 1H), 3.25 (dd, J=13.4, 7.8 Hz, 1H), 2.34 (s, 3H). ¹³C NMR (100 MHz, CDCl₃) δ 154.8, 138.5, 137.8, 132.1, 131.6, 131.6, 129.7, 129.4, 128.3, 126.6, 126.4, 121.0, 120.5, 106.8, 106.7, 62.9, 59.5, 45.0, 33.8, 21.1.

2-(2-imino-3-((6-methoxypyridin-2-yl)methyl)-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by the alkylation with 2-(bromomethyl)-6-methoxypyridine (Procedure E) yielded the title product as a brown gel (91% two steps). ¹H NMR (400 MHz, CDCl₃) δ 7.50 (t, J=8.3 Hz, 1H), 7.12 (d, J=7.8 Hz, 2H), 7.03-6.88 (m, 5H), 6.86-6.77 (m, 1H), 6.68 (dd, J=14.6, 7.8 Hz, 2H), 4.94 (s, 2H), 4.35 (s, 1H), 4.07 (d, J=12.6 Hz, 1H), 4.00-3.90 (m, 1H), 3.88 (s, 3H), 3.54-3.33 (m, 1H), 3.12 (dd, J=13.5, 7.4 Hz, 1H), 2.25 (s, 3H). ¹³C NMR (100 MHz, CDCl₃) δ 164.02, 154.57, 152.34, 139.41, 135.88, 135.07, 131.49, 131.42, 129.18, 129.04, 121.34, 120.74, 113.78, 110.30, 107.32, 107.14, 62.49, 59.70, 53.55, 47.03, 33.36, 21.00. MS (ESI) calcd for: C24H27N4O2 (MH⁺): 403.2, found 403.2.

2-(3-benzyl-2-imino-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by the alkylation with benzylbromide (Procedure E) yielded the title product as a brown gel (84% two steps). ¹H NMR (400 MHz, CDCl₃) δ 7.39-7.28 (m, 3H), 7.21 (d, J=6.6 Hz, 2H), 7.15 (d, J=8.0 Hz, 2H), 7.01 (d, J=7.8 Hz, 2H), 6.99-6.87 (m, 3H), 6.79-6.72 (m, 2H), 4.93 (d, J=4.3 Hz, 2H), 4.35-4.20 (m, 1H), 4.06 (d, J=12.5 Hz, 1H), 3.94 (dd, J=12.4, 4.6 Hz, 1H), 3.42 (dd, J=13.4, 8.1 Hz, 1H), 3.15 (dd, J=13.4, 7.3 Hz, 1H), 2.27 (s, 3H). ¹³C NMR (100 MHz, CDCl₃) δ 154.9, 135.9, 135.3, 135.2, 131.6, 131.6, 129.3, 129.1, 129.0, 128.0, 126.6, 121.1, 120.5, 106.9, 106.7, 62.6, 59.5, 45.2, 33.3, 21.0. MS (ESI) calcd for: $C_{24}H_2N_3O$ (MH⁺): 372.2, found 372.2.

2-(2-imino-3-(4-methylbenzyl)-2,3-dihydro-1H-benzo[d]imidazol-1-yl)-4-(p-tolyl)butan-1-ol. Cyclization of 2-((2-aminophenyl)amino)-4-(p-tolyl)butan-1-ol, followed by the alkylation with 4-methylbenzyl bromide (Procedure E) yielded the title product as a brown gel (>95% two steps). ¹H NMR (400 MHz, CDCl₃) δ 7.19-7.06 (m, 8H), 6.98 (p, J=7.6, 7.1 Hz, 3H), 6.82 (d, J=7.3 Hz, 1H), 6.73 (d, J=6.4 Hz, 1H), 4.88 (s, 2H), 4.13 (s, 1H), 4.07 (s, 2H), 2.75 (ddd, J=14.3, 9.0, 5.9 Hz, 1H), 2.60 (dt, J=14.2, 7.7 Hz, 1H), 2.48 (td, J=13.7, 8.0 Hz, 1H), 2.34 (s, 3H), 2.33 (s, 3H), 2.31 (s, 1H). ¹³C NMR (100 MHz, CDCl₃) δ 154.9, 138.1, 137.7, 135.4, 132.2, 131.7, 131.7, 129.7, 129.1, 128.3, 126.7, 121.1, 120.6, 107.1, 106.9, 63.2, 56.5, 45.0, 31.8, 28.9, 21.1, 21.0.

2-(2-imino-5-methyl-3-(4-methylbenzyl)-2,3-dihydro-1H-benzo[d]imidazol-1-yl)-3-(p-tolyl)propan-1-ol. Cyclization of 2-((2-amino-4-methylphenyl)amino)-3-(p-tolyl)propan-1-ol, followed by alkylation with 4-methylbenzyl bromide (Procedure E) yielded the title product (77% two steps). ¹H NMR (400 MHz, CDCl₃) δ 7.16 (dd, J=8.2, 2.7 Hz, 4H), 7.10 (d, J=8.0 Hz, 2H), 7.04 (d, J=7.7 Hz, 2H), 6.76 (d, J=7.3 Hz, 1H), 6.67 (d, J=8.0 Hz, 1H), 6.61 (s, 1H), 4.87 (d, J=4.4 Hz, 2H), 4.23 (q, J=7.3, 6.8 Hz, 1H), 4.05 (d, J=13.2 Hz, 1H), 3.93 (dd, J=12.3, 4.6 Hz, 1H), 3.43 (dd, J=13.4, 8.3 Hz, 1H), 3.11 (dd, J=13.4, 7.1 Hz, 1H), 2.35 (s, 3H), 2.31 (s, 3H), 2.28 (s, 3H). ¹³C NMR (100 MHz, CDCl₃)

δ 155.0, 137.7, 135.8, 135.4, 132.3, 131.8, 130.4, 129.7, 129.5, 129.3, 129.1, 126.5, 121.5, 107.5, 106.7, 62.5, 59.5, 44.9, 33.4, 21.3, 21.1, 21.1.

Synthesis with General Procedure (E).

2-(3-(3,5-dimethylbenzyl)-2-imino-2,3-dihydro-1H-benzo[d]imidazol-1-yl)-3-(p-tolyl)propan-1-ol

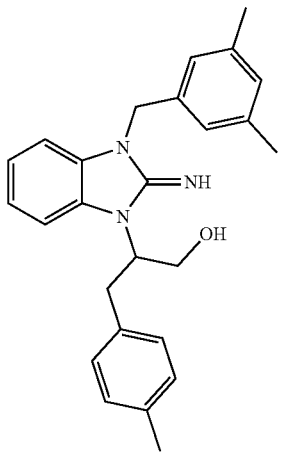 [SMILES: Cc1ccc(CC(CO)n2c(=N)n(Cc3cc(C)cc(C)c3)c3ccccc32)cc1]

Cyclization of 2-((2-aminophenyl)amino)-3-(p-tolyl)propan-1-ol, followed by alkylation with 3,5-dimethylbenzyl bromide (Procedure E) yielded the title product (94% two steps) as a brown gel. $^1$H NMR (400 MHz, CDCl$_3$) δ 7.15 (d, J=7.7 Hz, 2H), 7.01 (d, J=7.8 Hz, 2H), 6.96-6.87 (m, 3H), 6.83 (s, 2H), 6.83-6.76 (m, 1H), 6.76-6.69 (m, 1H), 4.85 (d, J=3.4 Hz, 2H), 4.25 (m, 1H), 4.06 (d, J=12.5 Hz, 1H), 3.93 (dd, J=12.4, 4.6 Hz, 1H) 3.41 (dd, J=13.4, 8.1 Hz, 1H), 3.14 (dd, J=13.4, 7.2 Hz, 1H), 2.30 (s, 6H), 2.26 (s, 3H). $^{13}$C NMR (100 MHz, CDCl$_3$) δ 154.86, 138.71, 135.86, 135.35, 135.13, 131.73, 131.62, 129.68, 129.23, 129.05, 124.37, 121.04, 120.52, 106.88, 106.74, 62.64, 59.58, 45.32, 33.36, 21.34, 21.01.

2-(2-imino-3-((2-methoxypyridin-4-yl)methyl)-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by alkylation with 4-(bromomethyl)-2-methoxypyridine (Procedure E) yielded the title product (93% two steps) as a brown gel. $^1$H NMR (400 MHz, CDCl$_3$) δ 8.12 (d, J=5.3 Hz, 1H), 7.13 (d, J=7.6 Hz, 2H), 7.07-6.87 (m, 5H), 6.78 (d, J=7.5 Hz, 1H), 6.70 (d, J=7.1 Hz, 1H), 6.50 (s, 1H), 4.88 (d, J=7.5 Hz, 2H), 4.38-4.23 (m, 1H), 4.11-4.04 (m, 1H), 3.96 (dd, J=12.4, 4.9 Hz, 1H), 3.92 (s, 3H), 3.39 (dd, J=13.5, 7.9 Hz, 1H), 3.17 (dd, J=13.5, 7.6 Hz, 1H), 2.26 (s, 3H). $^{13}$C NMR (100 MHz, CDCl$_3$) δ 164.80, 154.45, 147.66, 146.98, 135.98, 135.02, 129.41, 129.18, 129.11, 128.69, 121.55, 120.78, 114.65, 108.46, 107.31, 106.70, 62.68, 59.62, 53.52, 44.05, 33.30, 21.02.

2-(2-imino-3-(4-methylbenzyl)-2,3-dihydro-1H-benzo[d]imidazol-1-yl)-2-phenylethanol. Cyclization of 2-((2-aminophenyl)amino)-2-phenylethanol, followed by alkylation with 4-methylbenzyl bromide (Procedure E) yielded the title product (91% two steps) as a brown gel. $^1$H NMR (400 MHz, CDCl$_3$) δ 7.32 (d, J=5.7 Hz, 4H), 7.29-7.21 (m, 2H), 7.16 (s, 3H), 6.99-6.69 (m, 4H), 5.38-5.27 (m, 1H), 4.95 (s, 2H), 4.46-4.31 (m, 2H), 2.34 (s, 3H). $^{13}$C NMR (100 MHz, CDCl$_3$) δ 155.27, 137.79, 137.47, 132.11, 131.80, 131.72, 129.74, 128.59, 127.49, 127.03, 126.62, 121.24, 121.03, 107.93, 106.78, 63.68, 61.68, 45.14, 21.12.

2-(2-imino-3-(4-methylbenzyl)-2,3-dihydro-1H-benzo[d]imidazol-1-yl)-2-(p-tolyl)ethanol. Cyclization of 2-((2-aminophenyl)amino)-2-(p-tolyl)ethan-1-ol, followed by alkylation with 4-methylbenzyl bromide (Procedure E) yielded the title product (46% two steps) as a brown gel. $^1$H NMR (400 MHz, CDCl$_3$) δ 7.23-7.09 (m, 7H), 6.99-6.87 (m, 2H), 6.83 (d, J=7.0 Hz, 1H), 6.73 (d, J=7.3 Hz, 1H), 5.37-5.25 (m, 1H), 4.96 (s, 2H), 4.46-4.27 (m, 2H), 2.34 (s, 3H), 2.31 (s, 3H). $^{13}$C NMR (100 MHz, CDCl$_3$) δ 155.23, 137.77, 137.13, 134.35, 132.11, 131.79, 131.74, 129.73, 129.30, 126.91, 126.62, 121.25, 120.98, 107.97, 106.76, 63.74, 61.44, 45.14, 21.11, 21.10.

2-(2-imino-3-((2-methoxypyridin-4-yl)methyl)-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by alkylation with 4-(bromomethyl)-2-methoxypyridine (Procedure E) yielded the title product (79% two steps) as a brown foam. $^1$H NMR (400 MHz, CDCl$_3$) δ 8.12 (d, J=5.2 Hz, 1H), 7.20-6.32 (m, 11H), 5.06-4.78 (m, 2H), 4.41-4.27 (m, 1H), 4.13-3.83 (m, 5H), 3.38 (dd, J=13.5, 7.8 Hz, 1H), 3.18 (dd, J=13.5, 7.7 Hz, 1H), 2.26 (s, 3H). $^{13}$C NMR (100 MHz, CDCl$_3$) δ 164.75, 154.54, 147.56, 147.21, 135.95, 134.98, 131.10, 129.26, 129.14, 129.11, 121.44, 120.72, 114.72, 108.44, 107.44, 106.69, 62.59, 59.48, 53.51, 43.91, 33.37, 21.10, 21.03, 21.00.

2-(2-imino-3-((6-methoxypyridin-2-yl)methyl)-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by alkylation with 2-(bromomethyl)-6-methoxypyridine (Procedure E) yielded the title product (79% two steps) as a brown foam. $^1$H NMR (400 MHz, CDCl$_3$) δ 7.58-7.42 (m, 1H), 7.13 (d, J=7.8 Hz, 2H), 7.04-6.59 (m, 8H), 4.92 (s, 2H), 4.35-4.23 (m, 1H), 4.08-3.87 (m, 5H), 3.42 (dd, J=13.4, 8.2 Hz, 1H), 3.11 (dd, J=13.4, 7.2 Hz, 1H), 2.25 (s, 3H). $^{13}$C NMR (100 MHz, CDCl$_3$) δ 164.03, 154.72, 152.43, 139.40, 135.87, 135.16, 131.53, 129.31, 129.21, 129.04, 121.24, 120.61, 113.70, 110.26, 107.12, 106.97, 62.49, 59.61, 53.55, 46.98, 33.34, 21.00.

2-(3-(3,5-dimethylbenzyl)-2-imino-2,3-dihydro-1H-benzo[d]imidazol-1-yl)-2-(p-tolyl)ethanol. Cyclization of 2-((2-aminophenyl)amino)-2-(p-tolyl)ethan-1-ol, followed by alkylation with 1-(bromomethyl)-3,5-dimethylbenzene (Procedure E) yielded the title product (76% two steps) as a brown foam. $^1$H NMR (400 MHz, CDCl$_3$) δ 7.22 (d, J=7.8 Hz, 2H), 7.14 (d, J=7.9 Hz, 2H), 7.00-6.80 (m, 6H), 6.76 (d, J=7.4 Hz, 1H), 5.35-5.26 (m, 1H), 4.91 (s, 2H), 4.52-4.16 (m, 2H), 2.31 (s, 9H). $^{13}$C NMR (100 MHz, CDCl$_3$) δ 155.37, 138.73, 137.12, 135.14, 134.46, 131.92, 131.81, 129.66, 129.30, 126.94, 124.37, 121.20, 120.97, 107.89, 106.73, 63.74, 61.37, 45.27, 21.36, 21.11.

2-(2-imino-3-(thiophen-3-ylmethyl)-2,3-dihydro-1H-benzo[d]imidazol-1-yl)-3-(p-tolyl)propan-1-ol. Cyclization of 2-((2-aminophenyl)amino)-3-(p-tolyl)propan-1-ol, followed by alkylation with 3-(bromomethyl)thiophene (Procedure E) yielded the title product (81% two steps) as a brown foam. $^1$H NMR (400 MHz, CDCl$_3$) δ 7.38-7.29 (m, 1H), 7.13 (d, J=7.6 Hz, 2H), 7.09-6.69 (m, 8H), 4.92 (s, 2H), 4.31-4.20 (m, 1H), 4.06 (d, J=12.4 Hz, 1H), 3.94 (dd, J=12.4, 4.6 Hz, 1H), 3.41 (dd, J=13.4, 8.1 Hz, 1H), 3.14 (dd, J=13.4, 7.3 Hz, 1H), 2.26 (s, 3H). $^{13}$C NMR (100 MHz, CDCl$_3$) δ 154.61, 136.05, 135.88, 135.24, 131.58, 131.28, 129.24, 129.06, 127.18, 126.23, 122.26, 121.13, 120.53, 106.99, 106.64, 62.63, 59.48, 41.00, 33.33, 21.02.

2-(2-imino-3-((5-(trifluoromethyl)furan-2-yl)methyl)-2,3-dihydro-1H-benzo[d]imidazol-1-yl)-3-(p-toyl)propan-1-ol. Cyclization of 2-((2-aminophenyl)amino)-3-(p-tolyl)propan-1-ol, followed by alkylation with 2-(bromomethyl)-5-(trifluoromethyl)furan (Procedure E) yielded the title product (42% two steps) as a brown foam. $^1$H NMR (400 MHz, CDCl$_3$) δ 7.09 (d, J=7.6 Hz, 2H), 7.05-6.68 (m, 8H), 6.26 (d, J=4.0 Hz, 1H), 4.91 (s, 2H), 4.30-4.17 (m, 1H), 4.08-3.90 (m, 2H), 3.37 (dd, J=13.5, 7.9 Hz, 1H), 3.13 (dd, J=13.5, 7.5 Hz, 1H), 2.24 (s, 3H). $^{13}$C NMR (100 MHz, CDCl$_3$) δ 154.17, 151.51, 135.94, 135.05, 131.52, 130.77, 129.33, 129.14, 129.05, 121.55, 120.70, 119.20 (q), 112.58, 109.02, 107.26, 106.63, 62.49, 59.55, 38.44, 33.31, 20.97.

1-(1-methoxy-3-(p-tolyl)propan-2-yl)-3-(4-methylbenzyl)-1,3-dihydro-2H-benzo[d]imidazol-2-imine. Cyclization of $N^1$-(1-methoxy-3-(p-tolyl)propan-2-yl)benzene-1,2-diamine, followed by alkylation with 4-methylbenzyl bromide (Procedure E) yielded the title product (74% two steps) as a brown foam. $^1$H NMR (400 MHz, CDCl$_3$) δ 7.20-6.78 (m, 11H), 6.69 (d, J=7.5 Hz, 1H), 4.91 (m, 3H), 4.50 (br, 1H), 3.98 (m, J=8.3 Hz, 1H), 3.80 (dd, J=9.9, 4.9 Hz, 1H), 3.37 (s, 4H), 3.23 (dd, J=13.9, 6.5 Hz, 1H), 2.32 (s, 3H), 2.29 (s, 3H). $^{13}$C NMR (100 MHz, CDCl$_3$) δ 154.79, 137.08, 135.83, 134.75, 132.93, 131.67, 129.38, 129.07, 128.96, 126.66, 120.33, 120.17, 106.56, 72.37, 59.04, 55.86, 44.73, 34.27, 21.12, 21.10.

(R)-2-hydroxy-N-(2-(2-imino-3-(4-methylbenzyl)-2,3-dihydro-1H-benzo[d]imidazol-1-yl)-3-(p-tolyl)propyl)acetamide. Cyclization of (R)—N-(2-((2-aminophenyl)amino)-3-(p-tolyl)propyl)-2-hydroxyacetamide, followed by alkylation with 4-methylbenzyl bromide (Procedure E) yielded the title product (76% two steps). $[α]_D^{20}$ 85.58 (c 0.25, DCM). H NMR (400 MHz, CDCl$_3$) δ 7.35 (br s, 1H), 7.18-7.03 (m, 3H), 7.03-6.96 (m, 2H), 6.95 (s, 4H), 6.91-6.79 (m, 2H), 6.75 (d, J=7.6 Hz, 1H), 4.88 (d, J=16.8 Hz, 1H), 4.78 (d, J=17.0 Hz, 1H), 4.16-4.02 (m, 1H), 4.01-3.89 (m, 2H), 3.74 (br s, 1H), 3.56-3.32 (m, 1H), 3.14 (dd, J=14.2, 5.8 Hz, 1H), 2.96 (br s, 2H), 2.31 (s, 3H), 2.25 (s, 3H).

(S)-2-hydroxy-N-(2-(2-imino-3-(4-methylbenzyl)-2,3-dihydro-1H-benzo[d]imidazol-1-yl)-3-(p-tolyl)propyl)acetamide. Cyclization of (S)—N-(2-((2-aminophenyl)amino)-3-(p-tolyl)propyl)-2-hydroxyacetamide, followed by alkylation with 4-methylbenzyl bromide (Procedure E) yielded the title product (50% two steps). $[α]_D^{20}$ –39.19 (c 0.25, DCM). H NMR (400 MHz, CDCl$_3$) δ 7.30 (br s, 1H), 7.25-7.19 (m, 1H), 7.13-7.02 (m, 2H), 6.96 (d, J=7.7 Hz, 2H), 6.83 (d, J=7.7 Hz, 2H), 4.59 (s, 1H), 4.42 (br s, 1H), 3.95 (s, 1H), 3.83 (d, J=3.8 Hz, 2H), 3.80-3.60 (m, 1H), 3.30 (dd, J=11.8 Hz, 1H), 3.12 (dd, J=13.9, 5.2 Hz, 1H), 2.23 (s, 3H). $^{13}$C NMR (101 MHz, CDCl$_3$) δ 174.3, 155.0, 141.5, 136.7, 133.8, 129.5, 128.6, 122.0, 120.1, 116.3, 110.2, 61.3, 57.2, 40.9, 36.3, 21.1.

Synthesis with General Procedure (F).

6-(3-hydroxy-2-(2-imino-3-(4-methylbenzyl)-2,3-dihydro-1H-benzo[d]imidazol-1-yl)propyl)pyridin-2(1H)-one

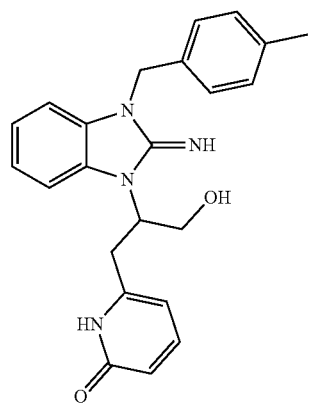 [SMILES: Cc1ccc(Cn2c(=N)n(C(CO)Cc3cccc(=O)[nH]3)c3ccccc32)cc1]

Reaction of 2-(2-imino-3-(4-methylbenzyl)-2,3-dihydro-1H-benzo[d]imidazol-1-yl)-3-(6-methoxypyridin-2-yl)propan-1-ol (Procedure F) yielded the title product as a brown foam (0.0451 g, >95%). $^1$H NMR (400 MHz, CDCl$_3$) δ 7.22 (dd, J=9.1, 6.8 Hz, 1H), 7.18-7.04 (m, 6H), 6.99-6.86 (m, 2H), 6.78 (d, J=7.3 Hz, 1H), 6.35 (d, J=9.5 Hz, 1H), 6.08 (d, J=6.8 Hz, 1H), 4.88 (d, J=9.0 Hz, 2H), 4.77 (s, 1H), 4.13 (d, J=12.9 Hz, 1H), 4.01 (dd, J=12.6, 4.6 Hz, 1H), 3.43-3.20 (m, 2H), 2.33 (s, 3H). $^{13}$C NMR (100 MHz, CDCl$_3$) δ 165.6, 154.6, 145.6, 141.6, 137.8, 132.0, 131.4, 129.7, 126.6, 121.3, 120.9, 117.8, 107.7, 107.6, 106.8, 63.2, 56.2, 45.0, 31.4, 21.1. MS (ESI) calcd for: $C_{23}H_{25}N_4O_2$ (MH$^+$): 389.2, found 389.2.

4-((3-(1-hydroxy-3-(p-tolyl)propan-2-yl)-2-imino-2,3-dihydro-1H-benzo[d]imidazol-1-yl)methyl)pyridin-2(1H)-one. Reaction of 2-(2-imino-3-((2-methoxypyridin-4-yl)methyl)-2,3-dihydro-1H-benzo[d]imi-dazol-1-yl)-3-(p-tolyl)propan-1-ol (Procedure F) yielded the title product as a red powder (77%). $^1$H NMR (400 MHz, CDCl$_3$) δ 7.24-6.88 (m, 9H), 6.82 (d, J=7.6 Hz, 1H), 6.69 (d, J=7.5 Hz, 1H), 6.26 (s, 1H), 6.02 (d, J=6.5 Hz, 1H), 4.74 (s, 2H), 4.44-4.23 (m, 1H), 4.09-3.88 (m, 2H), 3.36 (dd, J=13.5, 7.8 Hz, 1H), 3.21-3.05 (m, 1H), 2.22 (d, J=14.5 Hz, 4H). $^{13}$C NMR (100 MHz, CDCl$_3$) δ 164.79, 154.37, 150.40, 136.00, 135.23, 134.91, 130.95, 129.27, 129.14, 129.11, 128.72, 121.64, 120.91, 116.84, 106.82, 105.17, 62.24, 59.59, 44.13, 33.48, 21.02.

6-((3-(1-hydroxy-3-(p-tolyl)propan-2-yl)-2-imino-2,3-dihydro-1H-benzo[d]imidazol-1-yl)methyl)pyridin-2(1H)-one. Reaction of 2-(2-imino-3-((6-methoxypyridin-2-yl)methyl)-2,3-dihydro-1H-benzo[d]imi-dazol-1-yl)-3-(p-tolyl)propan-1-ol (Procedure F) yielded the title product as a pale brown powder (70%). $^1$H NMR (400 MHz, CDCl$_3$) δ 7.30 (t, J=8.0 Hz, 1H), 6.97 (m, 12H), 6.45 (d, J=9.1 Hz, 1H), 5.91 (d, J=6.9 Hz, 1H), 4.92 (s, 2H), 4.42 (s, 1H), 4.17-3.93 (m, 2H), 3.33 (dd, J=13.7, 7.3 Hz, 1H), 3.16 (dd, J=13.7, 8.0 Hz, 1H), 2.24 (s, 3H). $^{13}$C NMR (100 MHz, CDCl$_3$) δ 165.38, 154.33, 143.68, 141.35, 136.06, 134.65, 130.83, 129.10, 129.01, 121.71, 121.10, 118.87, 110.00, 108.04, 106.98, 104.66, 62.40, 59.68, 33.56, 21.02.

Synthesis with General Procedure (G).

tert-butyl-(1-(1-benzamido-3-(p-tolyl)propan-2-yl)-3-(4-methylbenzyl)-1,3-dihydro-2H-benzo[d]imidazol-2-ylidene)carbamate

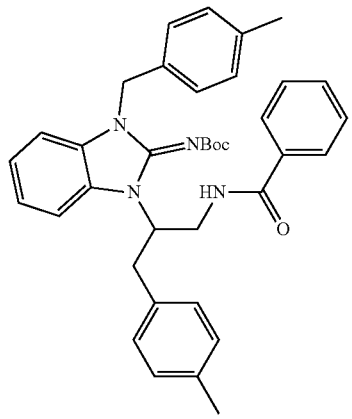

Reaction of tert-butyl-(1-(1-amino-3-(p-tolyl)propan-2-yl)-3-(4-methylbenzyl)-1,3-dihydro-2H-benzo[d]imidazol-2-ylidene)carbamate with benzoyl chloride (Procedure G) yielded the title product (88%) as a white foam. $^1$H NMR (400 MHz, CDCl$_3$, 50° C.) δ 7.83 (d, J=7.6 Hz, 2H), 7.39 (t, J=7.4 Hz, 1H), 7.30 (t, J=7.6 Hz, 2H), 7.20-7.11 (m, 1H), 7.07 (t, J=7.7 Hz, 1H), 7.03-6.82 (m, 10H), 5.17 (dd, J=27.4, 15.7 Hz, 2H), 5.08 (s, 1H), 4.60 (s, 1H), 3.79 (s, 1H), 3.36 (s, 1H), 3.22 (dd, J=14.0, 6.7 Hz, 1H), 2.27 (s, 3H), 2.26 (s, 3H), 1.53 (s, 9H). $^{13}$C NMR (100 MHz, CDCl3, 50° C.) δ 167.4, 159.3, 153.2, 137.4, 136.5, 134.1, 132.0, 130.9, 130.4, 129.3, 128.7, 128.1, 127.3, 127.0, 123.0, 110.4, 78.3, 57.3, 46.7, 41.9, 36.9, 28.6, 20.9, 20.9.

tert-butyl-(1-(1-(cyclopropanecarboxamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with cyclopropanecarbonyl chloride (Procedure G) yielded the title product (54%) as a white foam. $^1$H NMR (400 MHz, CDCl$_3$, 50° C.) δ 7.13 (t, J=7.9 Hz, 1H), 7.07 (d, J=6.9 Hz, 3H), 7.02 (d, J=8.1 Hz, 2H), 6.94 (q, J=8.1 Hz, 6H), 5.18 (s, 2H), 4.91 (s, 1H), 4.27 (d, J=15.0 Hz, 1H), 3.66 (d, J=15.2 Hz, 1H), 3.33 (s, 1H), 3.13 (dd, J=14.1, 6.4 Hz, 1H), 2.30 (s, 3H), 2.24 (s, 3H), 1.51 (s, 9H), 1.38-1.29 (m, 1H), 0.73 (s, 2H), 0.52 (s, 2H). $^{13}$C NMR (100 MHz, CDCl3, 50° C.) δ 174.0, 137.5, 136.3, 132.0, 130.3, 129.3, 129.2, 128.7, 127.2, 122.9, 122.8, 110.3, 78.2, 57.6, 46.9, 41.6, 28.6, 20.9, 20.9, 14.4, 6.7, 6.4.

tert-butyl-(1-(4-methylbenzyl)-3-(1-(2-phenylacetamido)-3-(p-tolyl)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-phenylacetyl chloride (Procedure G) yielded the title product (30%) as a white foam. $^1$H NMR (400 MHz, CDOD$_3$, 50° C.) δ 7.46-6.76 (m, 18H), 5.32-5.09 (m, 2H), 4.95 (s, 1H), 4.07 (s, 1H), 3.77 (s, 1H), 3.50-3.35 (m, 1H), 3.32 (s, 2H), 3.12 (s, 1H), 2.25 (s, 3H), 2.18 (s, 3H), 1.44 (s, 9H).

tert-butyl-(1-(1-(2-(4-methoxyphenyl)acetamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-(4-methoxyphenyl)acetyl chloride (Procedure G) yielded the title product (54%) as a white gel. $^1$H NMR (400 MHz, CDCl$_3$, 50° C.) δ 7.18-6.98 (m, 6H), 6.97-6.76 (m, 8H), 6.58 (d, J=8.2 Hz, 2H), 5.14 (q, J=16.0 Hz, 2H), 4.85 (s, 1H), 4.25 (s, 1H), 3.72 (s, 3H), 3.62 (s, 1H), 3.36 (s, 1H), 3.27 (s, 2H), 3.08 (dd, J=14.0, 6.3 Hz, 1H), 2.30 (s, 3H), 2.24 (s, 3H), 1.49 (s, 9H).

tert-butyl-1-(1-((E)-but-2-enamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with crotonoyl chloride (90% trans) (Procedure G) yielded the title product (71%) as a white gel with a small amount of cis product. $^1$H NMR (400 MHz, CDCl$_3$, 50° C.) δ 7.22-6.84 (m, 12H), 6.78-6.49 (m, 1H), 5.75 (dd, J=15.4, 1.8 Hz, 1H), 5.18 (s, 2H), 4.92 (d, J=9.3 Hz, 1H), 4.37 (s, 1H), 3.67 (d, J=14.6 Hz, 1H), 3.39-3.25 (m, 1H), 3.14 (dd, J=14.0, 6.6 Hz, 1H), 2.30 (s, 3H), 2.25 (s, 3H), 1.75 (dd, J=6.9, 1.8 Hz, 3H), 1.51 (s, 9H).

Synthesis with General Procedure (H).

N-(2-(2-imino-3-(4-methylbenzyl)-2,3-dihydro-1H-benzo[d]imidazol-1-yl)-3-(p-tolyl)propyl)propionamide

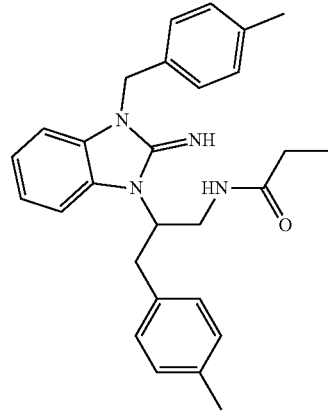 [SMILES: CCC(=O)NCC(Cc1ccc(C)cc1)n1c(=N)n(Cc2ccc(C)cc2)c2ccccc21]

Reaction of tert-butyl-(1-(4-methylbenzyl)-3-(1-propionamido-3-(p-tolyl)propan-2-yl)-1,3-dihydro-2H-benzo[d]imidazol-2-ylidene)carbamate (Procedure H) yielded the title product (63%) as a yellow gel. $^1$H NMR (400 MHz, CDCl$_3$) δ 7.25-6.61 (m, 12H), 5.46-4.80 (br, 1H), 4.88 (dd, J=24.7, 17.7 Hz, 2H), 4.55 (s, 2H), 4.05 (s, 1H), 3.69 (s, 1H), 3.44 (s, 1H), 3.14 (d, J=10.7 Hz, 1H), 2.31 (s, 3H), 2.22 (s, 3H), 2.12 (q, J=7.6 Hz, 2H), 1.04 (t, J=7.6 Hz, 3H). $^{13}$C NMR (100 MHz, CDCl$_3$) δ 174.4, 154.1, 137.7, 136.0, 134.2, 131.0, 129.6, 129.1, 128.7, 126.4, 121.7, 107.8, 56.6, 45.0, 41.6, 34.8, 29.6, 21.1, 21.0, 9.8.

N-(2-(2-imino-3-(4-methylbenzyl)-2,3-dihydro-1H-benzo[d]imidazol-1-yl)-3-(p-tolyl)propyl)benzamide. Reaction of tert-butyl-(1-(1-benzamido-3-(p-tolyl)propan-2-yl)-3-(4-methylbenzyl)-1,3-dihydro-2H-benzo[d]imidazol-2-ylidene)carbamate (Procedure H) yielded the title product (93%) as a yellow gel. $^1$H NMR (400 MHz, CDCl$_3$) δ 7.84

(s, 2H), 7.45 (t, J=7.3 Hz, 1H), 7.41-7.29 (m, 2H), 7.20-6.77 (m, 11H), 6.73 (d, J=7.5 Hz, 1H), 5.02-4.49 (br, 1H), 4.88 (dd, J=20.8, 17.2 Hz, 2H), 4.34 (s, 1H), 3.71 (s, 1H), 3.58 (s, 1H), 3.23 (dd, J=13.8, 6.2 Hz, 1H), 2.31 (s, 3H), 2.23 (s, 3H). $^{13}$C NMR (100 MHz, CDCl$_3$) δ 167.5, 155.3, 137.5, 136.0, 132.1, 131.4, 131.1, 129.6, 129.4, 129.1, 128.9, 128.3, 127.3, 126.4, 121.1, 120.6, 106.7, 55.9, 44.7, 43.3, 28.6, 21.1, 21.0.

N-(2-(2-imino-3-(4-methylbenzyl)-2,3-dihydro-1H-benzo[d]imidazol-1-yl)-3-(p-tolyl)propyl)cyclopropanecarboxamide. Reaction of tert-butyl-(1-(1-(cyclopropanecarboxamido)-3-(p-tolyl)propan-2-yl)-3-(4-methylbenzyl)-1,3-dihydro-2H-benzo[d]imidazol-2-ylidene)carbamate (Procedure H) yielded the title product (94%) as a yellow gel. $^1$H NMR (400 MHz, CDCl$_3$) δ 7.22-6.63 (m, 12H), 5.50-4.92 (br, 1H), 4.86 (s, 2H), 3.98 (s, 1H), 3.75 (s, 1H), 3.46 (s, 1H), 3.13 (dd, J=13.9, 5.7 Hz, 1H), 2.32 (s, 3H), 2.23 (s, 3H), 1.42-1.32 (m, 1H), 0.88 (s, 2H), 0.65 (d, J=5.2 Hz, 2H). $^{13}$C NMR (100 MHz, CDCl$_3$) δ 174.0, 154.5, 137.4, 135.8, 131.1, 129.5, 129.0, 128.7, 126.2, 121.3, 107.3, 56.2, 44.7, 41.8, 34.6, 21.0, 21.0, 14.6, 7.0, 6.8.

2,2,2-trifluoro-N-(2-(2-imino-3-(4-methylbenzyl)-2,3-dihydro-1H-benzo[d]imidazol-1-yl)-3-(p-tolyl)propyl)acetamide. Reaction of tert-butyl-(1-(4-methylbenzyl)-3-(1-(p-tolyl)-3-(2,2,2-trifluoroacetamido)propan-2-yl)-1,3-dihydro-2H-benzo[d]imidazol-2-ylidene)carbamate (Procedure H) yielded the title product (84%) as a yellow gel. $^1$H NMR (400 MHz, CDCl$_3$) δ 7.15 (d, J=7.8 Hz, 2H), 7.03 (d, J=7.7 Hz, 2H), 6.99-6.85 (m, 7H), 6.85-6.71 (m, 2H), 4.88 (d, J=4.8 Hz, 2H), 4.64 (s, 1H), 4.21 (dd, J=14.4, 6.0 Hz, 1H), 3.46 (dt, J=13.9, 10.1 Hz, 2H), 3.16 (dd, J=13.8, 6.6 Hz, 1H), 2.35 (s, 3H), 2.23 (s, 3H). $^{13}$C NMR (100 MHz, CDCl$_3$) δ 157.6 (q, J=36.5 Hz), 154.9, 137.9, 136.3, 134.0, 131.8, 131.3, 129.7, 129.2, 128.8, 126.4, 121.3, 121.0, 107.1, 55.7, 44.9, 43.0, 33.6, 21.1, 21.0.

N-(2-(2-imino-3-(4-methylbenzyl)-2,3-dihydro-1H-benzo[d]imidazol-1-yl)-3-(p-tolyl)propyl)-2-phenylacetamide. Reaction of tert-butyl-(1-(4-methylbenzyl)-3-(1-(2-phenylacetamido)-3-(p-tolyl)propan-2-yl)-1,3-dihydro-2H-benzo[d]imidazol-2-ylidene)carbamate (Procedure H) yielded the title product (20% over two steps combined with the synthesis of tert-butyl-(1-(4-methylbenzyl)-3-(1-(2-phenylacetamido)-3-(p-tolyl)propan-2-yl)-1,3-dihydro-2H-benzo[d]imidazol-2-ylidene)carbamate) as a yellow gel. $^1$H NMR (400 MHz, CDCl$_3$) δ 7.21-7.15 (m, 3H), 7.13-7.02 (m, 5H), 6.93 (s, 9H), 6.71 (d, J=7.2 Hz, 1H), 5.04-4.46 (m, 3H), 3.98 (s, 1H), 3.64 (d, J=13.5 Hz, 1H), 3.46 (s, 2H), 3.44-3.29 (m, 1H), 3.06 (dd, J=13.9, 6.0 Hz, 1H), 2.33 (s, 3H), 2.23 (s, 3H). $^{13}$C NMR (100 MHz, CDCl$_3$) δ 171.5, 154.4, 137.5, 135.9, 135.0, 132.2, 131.3, 129.6, 129.4, 129.1, 128.9, 128.8, 128.7, 128.6, 126.9, 126.5, 121.1, 120.6, 106.7, 55.7, 44.8, 43.8, 41.7, 28.6, 21.1, 21.0.

N-(2-(2-imino-3-(4-methylbenzyl)-2,3-dihydro-1H-benzo[d]imidazol-1-yl)-3-(p-tolyl)propyl)formamide. Reaction of tert-butyl-(1-(1-formamido-3-(p-tolyl)propan-2-yl)-3-(4-methylbenzyl)-1,3-dihydro-2H-benzo[d]imidazol-2-ylidene)carbamate (Procedure H) yielded the title product (>95%) as a yellow gel. $^1$H NMR (400 MHz, CDCl$_3$) δ 8.13 (s, 1H), 7.10 (d, J=7.7 Hz, 2H), 7.06-6.88 (m, 9H), 6.73 (d, J=7.5 Hz, 1H), 5.00-4.52 (m, 4H), 4.09 (s, 1H), 3.67 (d, J=14.2 Hz, 1H), 3.54-3.37 (m, 1H), 3.12 (dd, J=13.9, 5.8 Hz, 1H), 2.32 (s, 3H), 2.24 (s, 3H). $^{13}$C NMR (100 MHz, CDCl$_3$) δ 161.5, 154.8, 137.6, 136.1, 134.3, 132.1, 131.3, 129.6, 129.1, 128.8, 126.4, 121.1, 120.8, 106.9, 55.8, 44.8, 40.4, 34.5, 21.1, 21.1.

N-(2-(2-imino-3-(4-methylbenzyl)-2,3-dihydro-1H-benzo[d]imidazol-1-yl)-3-(p-tolyl)propyl)-2-(4-methoxyphenyl)acetamide. Reaction of tert-butyl-(1-(1-(2-(4-methoxyphenyl)acetamido)-3-(p-tolyl)propan-2-yl)-3-(4-methylbenzyl)-1,3-dihydro-2H-benzo[d]imidazol-2-ylidene)carbamate (Procedure H) yielded the title product (53% over two steps combined with the synthesis of tert-butyl-(1-(1-(2-(4-methoxyphenyl)acetamido)-3-(p-tolyl)propan-2-yl)-3-(4-methylbenzyl)-1,3-dihydro-2H-benzo[d]imidazol-2-ylidene)carbamate) as a yellow gel. $^1$H NMR (400 MHz, CDCl$_3$) δ 7.11 (d, J=7.8 Hz, 3H), 7.02-6.76 (m, 10H), 6.70 (d, J=8.7 Hz, 3H), 4.87-4.73 (m, 2H), 4.68 (s, 1H), 3.94 (s, 1H), 3.75 (s, 3H), 3.71-3.61 (m, 1H), 3.42 (s, 1H), 3.39 (s, 2H), 3.05 (dd, J=13.9, 6.1 Hz, 1H), 2.33 (s, 3H), 2.23 (s, 3H). $^{13}$C NMR (100 MHz, CDCl$_3$) δ 171.9, 158.5, 137.5, 135.9, 132.4, 131.4, 130.4, 129.6, 129.1, 128.8, 126.9, 126.5, 120.8, 120.4, 114.1, 106.5, 55.4, 55.2, 44.6, 42.9, 41.6, 34.7, 21.1, 21.0.

(E)-N-(2-(2-imino-3-(4-methylbenzyl)-2,3-dihydro-1H-benzo[d]imidazol-1-yl)-3-(p-tolyl)propyl)but-2-enamide. Reaction of tert-butyl-1-(1-((E)-but-2-enamido)-3-(p-tolyl)propan-2-yl)-3-(4-methylbenzyl)-1,3-dihydro-2H-benzo[d]imidazol-2-ylidene)carbamate (Procedure H) yielded the title product (57% over two steps combined with the synthesis of tert-butyl-1-(1-((E)-but-2-enamido)-3-(p-tolyl)propan-2-yl)-3-(4-methylbenzyl)-1,3-dihydro-2H-benzo[d]imidazol-2-ylidene)carbamate) as a yellow gel. $^1$H NMR (400 MHz, CDCl$_3$) δ 7.11 (dd, J=8.0, 5.0 Hz, 3H), 7.06-6.82 (m, 8H), 6.76 (dd, J=15.1, 7.0 Hz, 1H), 6.71 (d, J=7.4 Hz, 1H), 5.76 (d, J=14.6 Hz, 1H), 4.95-4.77 (m, 2H), 4.71 (s, 1H), 4.10 (s, 1H), 3.68 (s, 1H), 3.50 (s, 1H), 3.14 (dd, J=14.0, 6.2 Hz, 1H), 2.33 (s, 3H), 2.23 (s, 3H), 1.80 (d, J=6.8 Hz, 3H). $^{13}$C NMR (100 MHz, CDCl$_3$) δ 166.3, 155.2, 139.0, 137.5, 135.9, 134.6, 132.3, 131.4, 129.6, 129.1, 128.8, 126.4, 125.5, 120.9, 120.5, 106.6, 55.8, 44.7, 42.2, 34.4, 21.1, 21.0, 17.7.

N-(2-(2-imino-3-(4-methylbenzyl)-2,3-dihydro-1H-benzo[d]imidazol-1-yl)-3-(p-tolyl)propyl)-2-(pyridin-4-yl)acetamide. Reaction of tert-butyl-(1-(4-methylbenzyl)-3-(1-(2-(pyridin-4-yl)acetamido)-3-(p-tolyl)propan-2-yl)-1,3-dihydro-2H-benzo[d]imidazol-2-ylidene)carbamate (Procedure H) yielded the title product as a yellow gel (63% over two steps combined with the synthesis of tert-butyl-(1-(4-methylbenzyl)-3-(1-(2-(pyridin-4-yl)acetamido)-3-(p-tolyl)propan-2-yl)-1,3-dihydro-2H-benzo[d]imidazol-2-ylidene)carbamate). $^1$H NMR (400 MHz, CDCl$_3$) δ 8.42 (d, J=6.2 Hz, 2H), 7.12 (d, J=7.7 Hz, 2H), 7.06 (d, J=5.1 Hz, 2H), 6.99 (d, J=7.2 Hz, 2H), 6.94 (s, 4H), 6.91-6.83 (m, 2H), 6.75-6.67 (m, 1H), 4.79 (dd, J=22.5, 16.8 Hz, 2H), 4.64 (s, 1H), 4.06 (s, 1H), 3.55 (d, J=13.4 Hz, 1H), 3.45 (s, 3H), 3.06 (dd, J=13.8, 6.2 Hz, 1H), 2.33 (s, 3H), 2.23 (s, 3H). $^{13}$C NMR (100 MHz, CDCl$_3$) δ 169.5, 155.0, 149.9, 144.1, 137.6, 136.0, 134.4, 132.3, 131.3, 129.6, 129.1, 128.8, 126.5, 124.5, 120.9, 120.5, 107.4, 106.6, 55.4, 44.6, 43.0, 42.4, 34.3, 21.1, 21.0.

N-(2-(2-imino-3-(4-methylbenzyl)-2,3-dihydro-1H-benzo[d]imidazol-1-yl)-3-(p-tolyl)propyl)-2-(pyridin-3-yl)acetamide. Reaction of tert-butyl-(1-(4-methylbenzyl)-3-(1-(2-(pyridin-3-yl)acetamido)-3-(p-tolyl)propan-2-yl)-1,3-dihydro-2H-benzo[d]imidazol-2-ylidene)carbamate (Procedure H) yielded the title product as a yellow gel (61% over two steps combined with the synthesis of tert-butyl-(1-(4-methylbenzyl)-3-(1-(2-(pyridin-3-yl)acetamido)-3-(p-tolyl)propan-2-yl)-1,3-dihydro-2H-benzo[d]imidazol-2-ylidene)carbamate). $^1$H NMR (400 MHz, CDCl$_3$) δ 8.45 (d, J=4.8 Hz, 1H), 8.41 (s, 1H), 7.49 (d, J=7.8 Hz, 1H), 7.12 (dd, J=7.7, 4.7 Hz, 3H), 7.04-6.77 (m, 9H), 6.74-6.63 (m, 1H), 4.94-4.74 (m, 2H), 4.64 (s, 1H), 4.05 (s, 1H), 3.54 (d, J=14.2 Hz, 1H), 3.46 (s, 2H), 3.43-3.35 (m, 1H), 3.18-2.97 (m, 1H), 2.33 (s, 3H), 2.22 (s, 3H). $^{13}$C NMR (100 MHz, CDCl$_3$) δ 170.4, 155.1, 150.6, 148.4, 137.7, 137.0, 136.1, 132.4, 131.5, 131.1, 129.7, 129.2, 128.9, 126.6, 123.6, 121.1, 120.6, 106.8, 77.2, 55.7, 44.8, 42.7, 41.0, 28.7, 21.3, 21.2.

2-(4-aminophenyl)-N-(2-(2-imino-3-(4-methylbenzyl)-2,3-dihydro-1H-benzo[d]imidazol-1-yl)-3-(p-tolyl)propyl)acetamide. Reaction of tert-butyl-1-(1-(2-(4-((tert-butoxycarbonyl)amino)phenyl)acetamido)-3-(p-tolyl)propan-2-yl)-3-(4-methylbenzyl)-1,3-dihydro-2H-benzo[d]imidazol-2-ylidene)carbamate (Procedure H) yielded the title product as a yellow foam (90%). $^1$H NMR (400 MHz, CDCl$_3$) δ 7.11 (d, J=7.7 Hz, 2H), 7.03-6.84 (m, 8H), 6.78 (d, J=7.8 Hz, 2H), 6.70 (d, J=7.3 Hz, 1H), 6.46 (d, J=8.3 Hz, 2H), 4.80 (dd, J=22.0, 16.8 Hz, 2H), 3.92 (s, 1H), 3.82-3.51 (m, 3H), 3.41 (s, 1H), 3.32 (s, 2H), 3.06 (dd, J=13.9, 6.0 Hz, 1H), 2.33 (s, 3H), 2.23 (s, 3H). $^{13}$C NMR (100 MHz, CDCl$_3$) δ 172.3, 154.4, 145.3, 137.4, 135.9, 134.5, 132.4, 131.3, 130.3, 129.5, 129.1, 128.8, 126.5, 124.6, 120.9, 120.5, 115.3, 106.6, 55.5, 44.7, 42.9, 41.5, 34.6, 21.1, 21.0.

2-(2-aminophenyl)-N-(2-(2-imino-3-(4-methylbenzyl)-2,3-dihydro-1H-benzo[d]imidazol-1-yl)-3-(p-tolyl)propyl)acetamide. Reaction of tert-butyl-1-(1-(2-(2-((tert-butoxycarbonyl)amino)phenyl)acetamido)-3-(p-tolyl)propan-2-yl)-3-(4-methylbenzyl)-1,3-dihydro-2H-benzo[d]imidazol-2-ylidene)carbamate (Procedure H) yielded the title product as a yellow foam (80%). $^1$H NMR (400 MHz, CDCl$_3$) δ 7.12 (d, J=7.6 Hz, 2H), 7.02 (td, J=7.7, 1.6 Hz, 2H), 7.00-6.83 (m, 9H), 6.71 (d, J=6.6 Hz, 1H), 6.64 (t, J=7.4 Hz, 1H), 6.55 (d, J=7.8 Hz, 1H), 5.00-4.65 (br, 1H), 4.78 (dd, J=25.2, 17.0 Hz, 2H), 4.50-3.80 (br, 4H), 3.59 (d, J=13.8 Hz, 1H), 3.38 (s, 3H), 3.08 (dd, J=13.9, 6.2 Hz, 1H), 2.34 (s, 3H), 2.23 (s, 3H). $^{13}$C NMR (100 MHz, CDCl$_3$) δ 171.6, 154.7, 145.8, 137.6, 135.9, 134.4, 132.3, 131.3, 131.0, 129.6, 129.1, 128.8, 128.2, 126.5, 120.9, 120.4, 118.5, 116.1, 106.7, 55.6, 44.7, 41.9, 40.9, 34.5, 21.1, 21.1.

2-(3-aminophenyl)-N-(2-(2-imino-3-(4-methylbenzyl)-2,3-dihydro-1H-benzo[d]imidazol-1-yl)-3-(p-tolyl)propyl)acetamide. Reaction of tert-butyl-1-(1-(2-(3-((tert-butoxycarbonyl)amino)phenyl)acetamido)-3-(p-tolyl)propan-2-yl)-3-(4-methylbenzyl)-1,3-dihydro-2H-benzo[d]imidazol-2-ylidene)carbamate (Procedure H) yielded the title product as a yellow foam (95%). $^1$H NMR (400 MHz, CDCl$_3$) δ 7.10 (d, J=7.7 Hz, 3H), 7.02-6.82 (m, 9H), 6.70 (d, J=7.5 Hz, 1H), 6.48 (dd, J=8.0, 1.4 Hz, 1H), 6.41 (d, J=6.6 Hz, 1H), 6.29 (s, 1H), 4.90-4.55 (br, 1H), 4.82 (dd, J=30.3, 16.4 Hz, 2H), 3.95 (s, 1H), 3.67 (d, J=10.8 Hz, 1H), 3.42 (s, 1H), 3.34 (s, 2H), 3.06 (dd, J=13.9, 5.8 Hz, 1H), 2.33 (s, 3H), 2.23 (s, 3H). $^{13}$C NMR (100 MHz, CDCl$_3$) δ 171.6, 154.3, 146.8, 137.5, 135.9, 134.5, 132.4, 131.3, 129.6, 129.5, 129.1, 128.8, 126.5, 121.0, 120.4, 119.5, 115.9, 113.7, 106.7, 55.7, 44.7, 43.8, 41.4, 34.7, 21.1, 21.1.

N-(2-(2-imino-3-(4-methylbenzyl)-2,3-dihydro-1H-benzo[d]imidazol-1-yl)-3-(p-tolyl)propyl)-2-(pyridin-2-yl)acetamide. Reaction of tert-butyl-(1-(4-methylbenzyl)-3-(1-(2-(pyridin-2-yl)acetamido)-3-(p-tolyl)propan-2-yl)-1,3-dihydro-2H-benzo[d]imidazol-2-ylidene)carbamate (Procedure H) yielded the title product as a white gel (93%). $^1$H NMR (400 MHz, CDCl$_3$) δ 8.23 (d, J=4.6 Hz, 1H), 7.49 (t, J=7.5 Hz, 1H), 7.19-7.05 (m, 3H), 7.05-6.90 (m, 8H), 6.83 (s, 2H), 6.64 (d, J=5.2 Hz, 1H), 4.83 (dd, J=26.1, 17.0 Hz, 2H), 4.76 (s, 1H), 3.88 (d, J=54.4 Hz, 3H), 3.62 (dd, J=20.5, 15.4 Hz, 2H), 3.51-3.31 (m, 1H), 3.06 (dd, J=13.9, 5.8 Hz, 1H), 2.31 (s, 3H), 2.23 (s, 3H). $^{13}$C NMR (100 MHz, CDCl$_3$) δ 169.7, 155.4, 148.9, 137.3, 136.7, 135.8, 134.6, 132.6, 131.4, 129.5, 129.0, 128.8, 126.6, 123.8, 121.7, 120.6, 120.1, 106.4, 55.4, 45.4, 44.6, 41.1, 29.7, 21.1, 21.0.

2-amino-N-(2-(2-imino-3-(4-methylbenzyl)-2,3-dihydro-1H-benzo[d]imidazol-1-yl)-3-(p-tolyl)propyl)acetamide. Reaction of tert-butyl-(1-(1-(2-((tert-butoxycarbonyl)amino)acetamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (51%). $^1$H NMR (400 MHz, CD$_3$OD) δ 7.42 (s, 1H), 7.19-6.56 (m, 11H), 4.99 (d, J=15.9 Hz, 2H), 3.85 (s, 2H), 3.60 (s, 1H), 3.47-3.33 (m, 1H), 3.13 (s, 3H), 2.28 (s, 3H), 2.23 (s, 3H). $^{13}$C NMR (100 MHz, CD$_3$OD) δ 175.8, 156.9, 138.2, 137.1, 135.7, 134.4, 132.7, 130.2, 130.0, 130.0, 127.8, 122.2, 122.0, 110.9, 108.9, 57.1, 45.3, 45.1, 41.6, 35.9, 21.2, 21.1.

4-hydroxy-N-(2-(2-imino-3-(4-methylbenzyl)-2,3-dihydro-1H-benzo[d]imidazol-1-yl)-3-(p-tolyl)propyl)butanamide. Reaction of tert-butyl-(1-(1-(4-hydroxybutanamido)-3-(p-tolyl)propan-2-yl)-3-(4-methylbenzyl)-1,3-dihydro-2H-benzo[d]imidazol-2-ylidene)carbamate (Procedure H) yielded the title product as a yellow foam (>95%). $^1$H NMR (400 MHz, CDCl$_3$, 50° C.) δ 8.24-7.38 (m, 2H), 7.15 (t, J=7.7 Hz, 1H), 7.04 (d, J=7.8 Hz, 2H), 6.98 (d, J=7.8 Hz, 1H), 6.90 (d, J=7.9 Hz, 2H), 6.84 (d, J=7.9 Hz, 2H), 6.77 (d, J=7.4 Hz, 2H), 5.57 (s, 2H), 5.24-4.97 (m, 3H), 4.23 (dd, J=12.5, 5.6 Hz, 1H), 3.62 (dd, J=13.9, 4.5 Hz, 1H), 3.44 (t, J=5.7 Hz, 2H), 3.35 (dd, J=14.5, 10.5 Hz, 1H), 3.20 (dd, J=14.3, 5.3 Hz, 1H), 2.30 (s, 3H), 2.23 (s, 3H), 2.22-2.12 (m, 2H), 1.66 (h, J=6.7 Hz, 2H). $^{13}$C NMR (100 MHz, CDCl$_3$, 50° C.) δ 174.1, 161.8, 144.2, 138.1, 136.4, 130.4, 129.7, 129.2, 128.5, 126.3, 123.3, 61.7, 45.9, 40.8, 40.7, 35.2, 33.4, 28.1, 20.9, 20.9.

(S)-3,3,3-trifluoro-N-(2-(2-imino-3-(4-methylbenzyl)-2,3-dihydro-1H-benzo[d]imidazol-1-yl)-3-(p-tolyl)propyl)propenamide. Reaction of tert-butyl (S)-(1-(4-methylbenzyl)-3-(1-(p-tolyl)-3-(3,3,3-trifluoropropanamido)propan-2-yl)-1,3-dihydro-2H-benzo[d]imidazol-2-ylidene)carbamate (Procedure H) yielded the title product as a yellow gel (76%). $[□]_D^{20}$ −81.694 (c 1.028, CHCl$_3$). H NMR (400 MHz, CDCl$_3$) δ 7.14 (d, J=7.7 Hz, 2H), 7.08-6.79 (m, 9H), 6.74 (d, J=7.0 Hz, 1H), 4.85 (dd, J=25.8, 16.8 Hz, 2H), 4.65 (s, 1H), 4.12 (s, 1H), 3.66-3.32 (m, 2H), 3.13 (dd, J=13.9, 6.2 Hz, 1H), 2.99 (q, J=10.6 Hz, 2H), 2.34 (s, 3H), 2.24 (s, 3H). $^{13}$C NMR (100 MHz, CDCl$_3$) δ 162.9, 155.2, 137.7, 136.1, 134.4, 132.1, 131.4, 129.6, 129.1, 128.8, 126.5, 125.6, 122.8, 121.1, 120.7, 106.7, 55.6, 44.8, 42.8, 41.6 (q, J=28.3, 26.1 Hz), 34.0, 21.1, 21.0.

(S)-2-fluoro-N-(2-(2-imino-3-(4-methylbenzyl)-2,3-dihydro-1H-benzo[d]imidazol-1-yl)-3-(p-tolyl)propyl)acetamide. Reaction of tert-butyl (S)-(1-(1-(2-fluoroacetamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (84%). $[□]_D^{20}$ −64.341 (c 1.125, CHCl$_3$). $^1$H NMR (400 MHz, CDCl$_3$) δ 7.12 (d, J=7.8 Hz, 2H), 7.06-6.92 (m, 6H), 6.89 (d, J=7.5 Hz, 3H), 6.72 (d, J=7.1 Hz, 1H), 4.86 (d, J=2.9 Hz, 2H), 4.72 (d, J=47.4 Hz, 2H), 4.47 (s, 1H), 4.15 (s, 1H), 3.69 (d, J=7.6 Hz, 1H), 3.58-3.38 (m, 1H), 3.14 (dd, J=13.9, 6.1 Hz, 1H), 2.33 (s, 3H), 2.25 (s, 3H). $^{13}$C NMR (100 MHz, CDCl$_3$) δ 168.2, 168.0, 155.0, 137.5, 136.1, 134.4, 132.3, 131.5, 129.6, 129.1, 128.8, 126.5, 120.9, 120.5, 106.7, 80.2 (d, J=186.3 Hz), 55.4, 44.7, 41.4, 34.5, 21.1, 21.1.

(S)-3-(2-(2-imino-3-(4-methylbenzyl)-2,3-dihydro-1H-benzo[d]imidazol-1-yl)-3-(p-tolyl)propyl)-1,1-dimethylurea. Reaction of tert-butyl (S)-(1-(1-(3,3-dimethylureido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (60%). $[α]_D^{20}$ –88.897 (c 1.008, CHCl$_3$). H NMR (400 MHz, CDCl$_3$, 50° C.) δ 7.10 (d, J=7.8 Hz, 2H), 7.01 (d, J=7.9 Hz, 4H), 6.97-6.81 (m, 5H), 6.70 (d, J=7.4 Hz, 1H), 4.87 (dd, J=23.6, 16.8 Hz, 2H), 4.78 (s, 1H), 3.97 (dd, J=13.8, 8.1 Hz, 1H), 3.69 (d, J=15.1 Hz, 1H), 3.50 (dd, J=14.2, 9.2 Hz, 1H), 3.14 (dd, J=14.0, 6.0 Hz, 1H), 2.78 (s, 6H), 2.32 (s, 3H), 2.23 (s, 3H). $^{13}$C NMR (100 MHz, CDCl$_3$) δ 158.7, 155.2, 137.4, 135.8, 132.4, 131.4, 129.5, 129.0, 128.8, 126.5, 120.9, 120.4, 106.7, 56.4, 44.7, 43.6, 36.1, 28.6, 21.1, 21.0.

(S)—N-(2-(2-imino-3-(4-methylbenzyl)-2,3-dihydro-1H-benzo[d]imidazol-1-yl)-3-(p-tolyl)propyl)furan-2-carboxamide. Reaction of tert-butyl (S)-(1-(1-(furan-2-carboxamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (72%). $[α]_D^{20}$ –68.255 (c 0.9175, CHCl$_3$). H NMR (400 MHz, CDCl$_3$) δ 7.38 (s, 1H), 7.24-6.77 (m, 12H), 6.71 (d, J=7.4 Hz, 1H), 6.43 (dd, J=3.4, 1.7 Hz, 1H), 4.87 (s, 2H), 4.70-4.20 (br, 1H), 4.26 (s, 1H), 3.80 (s, 1H), 3.51 (t, J=11.9 Hz, 1H), 3.19 (dd, J=14.0, 6.0 Hz, 1H), 2.32 (s, 3H), 2.24 (s, 3H). $^{13}$C NMR (100 MHz, CDCl$_3$) δ 158.8, 155.1, 148.1, 144.0, 137.4, 136.0, 134.5, 132.3, 131.4, 129.6, 129.1, 128.9, 126.4, 121.0, 120.6, 113.8, 111.7, 106.7, 55.8, 44.7, 41.8, 34.6, 21.1, 21.1.

(S)—N-(2-(2-imino-3-(4-methylbenzyl)-2,3-dihydro-1H-benzo[d]imidazol-1-yl)-3-(p-tolyl)propyl)-6-methylpicolinamide. Reaction of tert-butyl (S)-(1-(4-methylbenzyl)-3-(1-(6-methylpicolinamido)-3-(p-tolyl)propan-2-yl)-1,3-dihydro-2H-benzo[d]imidazol-2-ylidene)carbamate (Procedure H) yielded the title product as a yellow gel (81%). $[α]_D^{20}$ –25.524 (c 1.23, CHCl$_3$). H NMR (400 MHz, CDCl$_3$) δ 8.70 (s, 1H), 7.94 (d, J=7.7 Hz, 1H), 7.67 (t, J=7.7 Hz, 1H), 7.21 (d, J=7.7 Hz, 1H), 7.12-6.74 (m, 10H), 6.66 (d, J=7.5 Hz, 1H), 4.87 (s, 2H), 4.51-3.88 (m, 3H), 3.71-3.37 (m, 1H), 3.22 (dd, J=14.0, 6.0 Hz, 1H), 2.44 (s, 3H), 2.29 (s, 3H), 2.25 (s, 3H). $^{13}$C NMR (100 MHz, CDCl$_3$) δ 165.1, 157.1, 154.9, 148.9, 137.3, 137.1, 135.9, 134.5, 132.6, 131.6, 129.4, 129.1, 128.9, 126.5, 125.7, 120.6, 120.3, 119.2, 106.6, 55.5, 44.6, 41.2, 35.1, 24.2, 21.1, 21.1.

(S)—N-(2-(2-imino-3-(4-methylbenzyl)-2,3-dihydro-1H-benzo[d]imidazol-1-yl)-3-(p-tolyl)propyl)-3-methylpicolinamide. Reaction of tert-butyl (S)-(1-(4-methylbenzyl)-3-(1-(3-methylpicolinamido)-3-(p-tolyl)propan-2-yl)-1,3-dihydro-2H-benzo[d]imidazol-2-ylidene)carbamate (Procedure H) yielded the title product as a yellow gel (73%). $[α]_D^{20}$ –17.973 (c 1.178, CHCl$_3$). H NMR (400 MHz, CDCl$_3$) δ 9.21-8.36 (br, 1H), 8.27 (dd, J=4.6, 1.6 Hz, 1H), 7.52 (d, J=7.9 Hz, 1H), 7.24 (dd, J=7.8, 4.6 Hz, 1H), 7.19-6.74 (m, 10H), 6.65 (d, J=7.6 Hz, 1H), 4.86 (s, 2H), 4.52-3.81 (m, 3H), 3.64-3.40 (br, 1H), 3.20 (dd, J=13.9, 5.7 Hz, 1H), 2.69 (s, 3H), 2.30 (s, 3H), 2.25 (s, 3H). $^{13}$C NMR (100 MHz, CDCl$_3$) δ 166.6, 155.0, 147.2, 145.5, 140.6, 137.1, 135.8, 135.2, 134.5, 132.8, 131.6, 129.4, 129.1, 128.9, 126.5, 125.4, 120.5, 120.2, 106.5, 55.5, 44.6, 40.9, 35.1, 21.1, 21.1, 20.4.

(S)—N-(2-(2-imino-3-(4-methylbenzyl)-2,3-dihydro-1H-benzo[d]imidazol-1-yl)-3-(p-tolyl)propyl)pyridazine-3-carboxamide. Reaction of tert-butyl (S)-(1-(4-methylbenzyl)-3-(1-(pyridazine-3-carboxamido)-3-(p-tolyl)propan-2-yl)-1,3-dihydro-2H-benzo[d]imidazol-2-ylidene)carbamate (Procedure H) yielded the title product as a yellow gel (82%). $[α]_D^{20}$ –31.599 (c 0.848, CHCl$_3$). $^1$H NMR (400 MHz, CDCl$_3$) δ 9.22 (dd, J=5.1, 1.8 Hz, 1H), 8.24 (dd, J=8.5, 1.7 Hz, 1H), 7.59 (dd, J=8.4, 5.0 Hz, 1H), 7.06 (dd, J=15.8, 7.7 Hz, 4H), 6.96 (d, J=7.8 Hz, 4H), 6.83 (d, J=7.9 Hz, 3H), 6.65 (d, J=7.3 Hz, 1H), 4.86 (dd, J=20.7, 17.1 Hz, 2H), 4.54-3.90 (m, 3H), 3.53 (s, 1H), 3.20 (dd, J=13.9, 6.0 Hz, 1H), 2.31 (s, 3H), 2.24 (s, 3H). $^{13}$C NMR (100 MHz, CDCl$_3$) δ 163.1, 154.8, 152.6, 152.5, 137.2, 135.9, 134.4, 132.6, 131.6, 129.5, 129.1, 128.9, 127.4, 126.5, 125.6, 120.5, 120.3, 106.6, 55.4, 44.6, 41.4, 34.9, 21.1, 21.1.

(S)—N-(2-(2-imino-3-(4-methylbenzyl)-2,3-dihydro-1H-benzo[d]imidazol-1-yl)-3-(p-tolyl)propyl)isoxazole-5-carboxamide. Reaction of tert-butyl (S)-(1-(1-(isoxazole-5-carboxamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (70%). $[α]_D^{20}$ –53.504 (c 1.11, CHCl$_3$). $^1$H NMR (400 MHz, CDCl$_3$) δ 8.27 (s, 1H), 7.09 (d, J=7.1 Hz, 2H), 7.04-6.87 (m, 8H), 6.85 (d, J=1.8 Hz, 1H), 6.74 (d, J=7.4 Hz, 1H), 6.72-6.49 (m, 1H), 4.90 (q, J=17.0 Hz, 3H), 4.36 (s, 1H), 3.70 (d, J=13.2 Hz, 1H), 3.51 (dd, J=13.9, 9.4 Hz, 1H), 3.22 (dd, J=14.1, 6.3 Hz, 1H), 2.32 (s, 3H), 2.23 (s, 3H). $^{13}$C NMR (100 MHz, CDCl$_3$) δ 163.5, 156.2, 154.8, 150.7, 137.6, 136.1, 131.9, 131.3, 129.6, 129.1, 128.8, 126.4, 126.1, 121.2, 120.9, 107.0, 105.9, 55.9, 44.9, 42.4, 34.2, 21.1, 21.0.

(S)—N-(2-(2-imino-3-(4-methylbenzyl)-2,3-dihydro-1H-benzo[d]imidazol-1-yl)-3-(p-tolyl)propyl)-5-methylisoxazole-4-carboxamide. Reaction of tert-butyl (S)-(1-(4-methylbenzyl)-3-(1-(5-methylisoxazole-4-carboxamido)-3-(p-tolyl)propan-2-yl)-1,3-dihydro-2H-benzo[d]imidazol-2-ylidene)carbamate (Procedure H) yielded the title product as a yellow gel (78%). $[α]_D^{20}$ –53.640 (c 1.178, CHCl$_3$). $^1$H NMR (400 MHz, CDCl$_3$) δ 8.53 (s, 1H), 7.16-6.50 (m, 12H), 5.17 (s, 1H), 4.86 (q, J=17.0 Hz, 2H), 4.27 (s, 1H), 3.59 (s, 2H), 3.21 (s, 1H), 2.66 (s, 3H), 2.32 (s, 3H), 2.22 (s, 3H). $^{13}$C NMR (100 MHz, CDCl$_3$) δ 172.1, 161.4, 155.1, 148.8, 137.8, 136.1, 134.4, 131.8, 131.2, 129.7, 129.1, 128.8, 126.3, 121.5, 112.1, 107.1, 56.3, 44.9, 42.7, 34.1, 21.1, 21.0, 12.3.

(S)-1,1-difluoro-N-(2-(2-imino-3-(4-methylbenzyl)-2,3-dihydro-1H-benzo[d]imidazol-1-yl)-3-(p-tolyl)propyl)methanesulfonamide. Reaction of tert-butyl (S)-(1-(1-(((difluoromethyl)sulfonamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (91%). $[α]_D^{20}$ –61.878 (c 0.740, CHCl$_3$). $^1$H NMR (400 MHz, CDCl$_3$) δ 7.18-6.60 (m, 13H), 6.04 (t, J=54.7 Hz, 1H), 5.10 (q, J=16.8 Hz, 2H), 4.61 (s, 1H), 3.87 (dd, J=13.5, 5.3 Hz, 1H), 3.70 (d, J=13.5 Hz, 1H), 3.48 (dd, J=14.2, 10.1 Hz, 1H), 3.13 (dd, J=14.1, 5.4 Hz, 1H), 2.29 (s, 3H), 2.17 (s, 3H). $^{13}$C NMR (100 MHz, CDCl$_3$) δ 153.2, 137.9, 136.1, 134.0, 131.2, 130.5, 129.6, 129.0, 128.8, 126.7, 126.6, 122.3, 122.0, 114.7 (t, J=278.5 Hz), 108.4, 59.3, 47.8, 45.5, 33.8, 21.1, 21.0.

(S)—N-(2-(2-imino-3-(4-methylbenzyl)-2,3-dihydro-1H-benzo[d]imidazol-1-yl)-3-(p-tolyl)propyl)-1,4-dimethyl-1H-imidazole-5-carboxamide. Reaction of tert-butyl (S)-(1-

(1-(1,4-dimethyl-1H-imidazole-5-carboxamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (67%). [□]$_D^{20}$ −80.382 (c 1.01, CHCl$_3$). H NMR (400 MHz, CDCl$_3$) δ 7.09 (d, J=7.7 Hz, 2H), 7.05-6.93 (m, 6H), 6.88 (s, 3H), 6.71 (d, J=7.0 Hz, 1H), 5.19-4.60 (m, 3H), 4.24 (s, 1H), 3.78 (d, J=12.9 Hz, 1H), 3.72 (s, 3H), 3.50 (t, J=11.0 Hz, 1H), 3.19 (dd, J=13.8, 6.3 Hz, 1H), 2.32 (s, 3H), 2.24 (s, 6H). $^{13}$C NMR (100 MHz, CDCl$_3$) δ 161.6, 154.9, 140.5, 139.1, 137.6, 136.0, 134.5, 132.3, 131.5, 129.6, 129.1, 128.9, 126.5, 120.8, 120.5, 106.6, 55.4, 44.7, 41.9, 34.8, 34.0, 21.1, 21.0, 15.1.

(S)—N-(2-(2-imino-3-(4-methylbenzyl)-2,3-dihydro-1H-benzo[d]imidazol-1-yl)-3-(p-tolyl)propyl)-2-(1H-pyrrol-1-yl)acetamide. Reaction of tert-butyl (S)-(1-(1-(2-(1H-pyrrol-1-yl)acetamido)-3-(p-tolyl)propan-2-yl)-3-(4-methylbenzyl)-1,3-dihydro-2H-benzo[d]imidazol-2-ylidene)carbamate (Procedure H) yielded the title product as a yellow gel (53%). [□]$_D^{20}$ −49.450 (c 0.833, CHCl$_3$). $^1$H NMR (400 MHz, CDCl$_3$) δ 7.14 (d, J=7.8 Hz, 2H), 6.99 (dt, J=13.8, 7.9 Hz, 8H), 6.71 (d, 2H), 6.32 (s, 2H), 6.05 (s, 2H), 4.89-4.74 (m, 2H), 4.65 (s, 1H), 4.52-4.32 (m, 2H), 3.95 (s, 1H), 3.66 (d, J=13.7 Hz, 1H), 3.42 (t, J=8.9, 5.7 Hz, 1H), 3.07 (dd, J=13.9, 6.3 Hz, 1H), 2.35 (s, 3H), 2.25 (s, 3H). $^{13}$C NMR (100 MHz, CDCl$_3$) δ 169.25, 154.47, 137.52, 135.99, 134.45, 132.46, 131.54, 129.56, 129.10, 128.79, 126.61, 121.60, 120.73, 120.37, 109.53, 106.54, 55.06, 52.95, 44.72, 41.32, 28.56, 21.14, 21.04.

(S)—N-(2-(2-imino-3-(4-methylbenzyl)-2,3-dihydro-1H-benzo[d]imidazol-1-yl)-3-(p-tolyl)propyl)nicotinamide. Reaction of tert-butyl (S)-(1-(4-methylbenzyl)-3-(1-(nicotinamido)-3-(p-tolyl)propan-2-yl)-1,3-dihydro-2H-benzo[d]imidazol-2-ylidene)carbamate (Procedure H) yielded the title product as a yellow gel (51%). [□]$_D^{20}$ −75.435 (c 1.134, CHCl$_3$). $^1$H NMR (400 MHz, CDCl$_3$) δ 9.12 (s, 1H), 8.65 (d, J=5.3 Hz, 1H), 8.19 (d, J=8.2 Hz, 1H), 7.32 (s, 1H), 7.07 (s, 3H), 7.02-6.89 (m, 8H), 6.77 (d, J=7.5 Hz, 1H), 4.90 (q, J=15.3 Hz, 2H), 4.39 (dd, J=14.4, 6.9 Hz, 2H), 3.63 (d, J=42.4 Hz, 2H), 3.22 (dd, J=13.8, 6.1 Hz, 1H), 2.31 (s, 3H), 2.23 (s, 3H). $^{13}$C NMR (100 MHz, CDCl$_3$) δ 165.57, 154.98, 151.78, 148.73, 137.73, 136.10, 135.24, 134.41, 131.73, 131.23, 130.08, 129.65, 129.14, 128.78, 126.34, 123.25, 121.22, 106.94, 56.29, 44.90, 43.37, 34.02, 21.11, 21.03.

Synthesis with General Procedure (I).

tert-butyl-1-(1-(2-(4-((tert-butoxycarbonyl)amino)phenyl)acetamido)-3-(p-tolyl)propan-2-yl)-3-(4-methylbenzyl)-1,3-dihydro-2H-benzo[d]imidazol-2-ylidene)carbamate

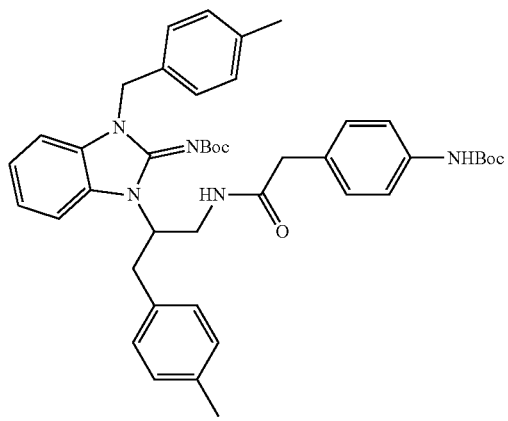

Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-(4-((tert-butoxycarbonyl)amino)phenyl)acetic acid (Procedure I) yielded the title product as a yellow foam (90%). $^1$H NMR (400 MHz, CDCl$_3$, 50° C.) δ 7.15-6.98 (m, 8H), 6.94 (d, J=5.0 Hz, 3H), 6.87 (s, 4H), 6.31 (s, 1H), 5.15 (dd, J=37.4, 16.1 Hz, 2H), 4.84 (s, 1H), 4.26 (s, 1H), 3.59 (s, 1H), 3.26 (s, 3H), 3.07 (dd, J=14.0, 6.3 Hz, 1H), 2.30 (s, 3H), 2.24 (s, 3H), 1.53 (s, 9H), 1.49 (s, 9H).

tert-butyl-1-(1-(2-(3-((tert-butoxycarbonyl)amino)phenyl)acetamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-(3-((tert-butoxycarbonyl)amino)phenyl)acetic acid (Procedure I) yielded the title product as a yellow foam (84%). $^1$H NMR (400 MHz, CDCl$_3$, 50° C.) δ 7.41 (d, J=7.9 Hz, 1H), 7.16-7.02 (m, 4H), 7.02-6.86 (m, 8H), 6.70 (dd, J=2.4, 1.3 Hz, 1H), 6.60 (d, J=7.6 Hz, 1H), 6.47 (s, 1H), 5.13 (q, J=15.8 Hz, 2H), 4.87 (s, 1H), 4.23 (s, 1H), 3.76-3.49 (m, 1H), 3.29 (s, 3H), 3.08 (dd, J=14.0, 6.3 Hz, 1H), 2.29 (s, 3H), 2.24 (s, 3H), 1.51 (s, 9H), 1.49 (s, 9H).

tert-butyl-1-(1-(2-(2-((tert-butoxycarbonyl)amino)phenyl)acetamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-(2-((tert-butoxycarbonyl)amino)phenyl)acetic acid (Procedure I) yielded the title product as a yellow foam (85%). $^1$H NMR (400 MHz, CDCl$_3$, 50° C.) δ 8.79 (s, 1H), 8.66 (s, 1H), 7.69 (d, J=8.2 Hz, 1H), 7.14-6.99 (m, 6H), 6.99-6.89 (m, 4H), 6.85 (d, J=7.7 Hz, 2H), 6.75 (t, J=7.5 Hz, 1H), 5.20 (d, J=15.6 Hz, 1H), 5.08 (d, J=15.9 Hz, 1H), 4.82 (s, 1H), 4.31 (s, 1H), 3.49 (s, 1H), 3.34 (s, 2H), 3.24 (s, 1H), 3.08 (dd, J=13.9, 6.7 Hz, 1H), 2.31 (s, 3H), 2.25 (s, 3H), 1.54 (s, 9H), 1.51 (s, 9H).

tert-butyl-(1-(1-(2-((tert-butoxycarbonyl)amino)acetamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with (tert-butoxycarbonyl)glycine (Procedure I) yielded the title product as a yellow foam (95%). $^1$H NMR (400 MHz, CDCl$_3$, 50° C.) δ 7.78 (s, 1H), 7.39 (s, 1H), 7.15 (d, J=7.9 Hz, 1H), 7.08 (d, J=8.1 Hz, 3H), 7.04-6.91 (m, 7H), 5.45-5.06 (m, 3H), 4.91 (s, 1H), 4.43-4.16 (m, 1H), 3.78-3.52 (m, 3H), 3.43-3.24 (m, 1H), 3.16 (dd, J=14.0, 7.0 Hz, 1H), 2.30 (s, 3H), 2.26 (s, 3H), 1.51 (s, 9H), 1.39 (s, 9H).

N-(2-(2-imino-3-(4-methylbenzyl)-2,3-dihydro-1H-benzo[d]imidazol-1-yl)-3-(p-tolyl)propyl)-2-(methylamino)acetamide. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with tert-butyl-(2-((2-(2-((tert-butoxycarbonyl)imino)-3-(4-methylbenzyl)-2,3-dihydro-1H-benzo[d]imidazol-1-yl)-3-(p-tolyl)propyl)amino)-2-oxoethyl)(methyl)carbamate (Procedure I) yielded the title product as a yellow gel (>95%). $^1$H NMR (400 MHz, CD$_3$OD, 50° C.) δ 7.39-6.81 (m, 11H), 6.77-6.70 (m, 1H), 4.89 (dt, J=34.9, 17.2 Hz, 3H), 3.92 (q, J=18.4, 15.6 Hz, 1H), 3.85-3.74 (m, 1H), 3.40 (d, J=13.3 Hz, 1H), 3.09 (dd, J=14.1, 5.2 Hz, 1H), 3.03 (s, 2H), 2.27 (s, 3H), 2.20 (s, 3H), 2.15 (s, 3H). $^{13}$C NMR (100 MHz, CD$_3$OD) δ 172.7, 136.7, 135.6, 134.3, 133.1, 128.8, 128.6, 126.4, 120.4, 118.3, 115.4, 109.3, 107.2, 55.3, 53.0, 52.9, 43.8, 40.3, 40.0, 34.6, 19.8, 19.7.

tert-butyl-(1-(4-methylbenzyl)-3-(1-(2-(pyrimidin-2-yl)acetamido)-3-(p-tolyl)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-(pyrimidin-2-yl)acetic acid (Procedure I) yielded the title product as a yellow foam (83%). $^1$H NMR (400 MHz, CDCl$_3$, 50° C.) δ 8.57-7.94 (m, 2H), 7.04 (s, 6H), 6.94 (s, 6H), 5.18 (s, 2H), 4.91 (s, 1H), 4.24 (s, 1H), 3.94-3.63 (m, 3H), 3.36 (s, 1H), 3.13 (dd, J=14.0, 6.3 Hz, 1H), 2.29 (s, 3H), 2.23 (s, 3H), 1.49 (s, 9H).

tert-butyl (S)-(1-(4-methylbenzyl)-3-(1-(p-tolyl)-3-(3,3,3-trifluoropropanamido)propan-2-yl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with 3,3,3-trifluoropropanoic acid (Procedure I) yielded the title product as a yellow foam (73%). $^1$H NMR (400 MHz, CDCl$_3$, 50° C.) δ 8.65 (s, 1H), 7.23-7.05 (m, 4H), 7.04-6.92 (m, 5H), 6.90 (d, J=7.7 Hz, 2H), 5.18 (s, 2H), 4.86 (s, 1H), 4.37 (s, 1H), 3.57 (d, J=14.0 Hz, 1H), 3.39-3.24 (m, 1H), 3.14 (dd, J=14.0, 6.6 Hz, 1H), 2.99-2.76 (m, 2H), 2.31 (s, 3H), 2.26 (s, 3H), 1.50 (s, 9H).

tert-butyl (S)-(1-(1-(2-fluoroacetamido)-3-(p-tolyl)propan-2-yl)-3-(4-methylbenzyl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with 2-fluoroacetic acid (Procedure I) yielded the title product as a yellow foam (80%). $^1$H NMR (400 MHz, CDCl$_3$, 50° C.) δ 7.13 (t, J=7.7 Hz, 1H), 7.07 (d, J=8.0 Hz, 3H), 6.97 (dt, J=14.8, 7.7 Hz, 8H), 5.18 (d, J=3.3 Hz, 2H), 4.97 (s, 1H), 4.59 (d, J=47.3 Hz, 2H), 4.43-4.23 (m, 1H), 3.74 (d, J=14.0 Hz, 1H), 3.35 (t, J=11.2 Hz, 1H), 3.15 (dd, J=14.0, 6.5 Hz, 1H), 2.30 (s, 3H), 2.26 (s, 3H), 1.51 (s, 9H).

tert-butyl (S)-(1-(1-(furan-2-carboxamido)-3-(p-tolyl)propan-2-yl)-3-(4-methylbenzyl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with furan-2-carboxylic acid (Procedure I) yielded the title product as a yellow gel (67%). $^1$H NMR (400 MHz, CDCl$_3$, 50° C.) δ 8.60-7.95 (br, 1H), 7.37 (s, 1H), 7.19-6.79 (m, 12H), 6.37 (dd, J=3.6, 1.7 Hz, 1H), 5.17 (s, 2H), 5.02 (s, 1H), 4.47 (s, 1H), 3.84 (d, J=13.3 Hz, 1H), 3.46-3.29 (m, 1H), 3.19 (dd, J=14.0, 6.5 Hz, 1H), 2.28 (s, 3H), 2.26 (s, 3H), 1.52 (s, 9H).

tert-butyl (S)-(1-(4-methylbenzyl)-3-(1-(6-methylpicolinamido)-3-(p-tolyl)propan-2-yl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with from 6-methylpicolinic acid (Procedure I) yielded the title product as a yellow foam (78%). $^1$H NMR (400 MHz, CDCl$_3$, 50° C.) δ 8.57 (s, 1H), 7.90 (d, J=7.7 Hz, 1H), 7.65 (t, J=7.7 Hz, 1H), 7.20 (d, J=7.7 Hz, 1H), 7.14-6.69 (m, 11H), 5.18 (s, 2H), 5.12 (s, 1H), 4.51-4.05 (m, 2H), 3.49 (s, 1H), 3.24 (dd, J=13.9, 5.9 Hz, 1H), 2.48 (s, 3H), 2.27 (s, 3H), 2.22 (s, 3H), 1.53 (s, 9H).

tert-butyl (S)-(1-(4-methylbenzyl)-3-(1-(3-methylpicolinamido)-3-(p-tolyl)propan-2-yl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with 3-methylpicolinic acid (Procedure I) yielded the title product as a yellow foam (85%). $^1$H NMR (400 MHz, CDCl$_3$, 50° C.) δ 8.50 (s, 1H), 8.35-8.17 (m, 1H), 7.48 (d, J=7.7 Hz, 1H), 7.21 (dd, J=7.8, 4.6 Hz, 1H), 7.12-6.89 (m, 10H), 6.86 (d, J=7.9 Hz, 1H), 5.16 (dd, J=23.1, 16.3 Hz, 2H), 5.10 (s, 1H), 4.33-4.08 (m, 2H), 3.51 (s, 1H), 3.23 (dd, J=14.1, 6.1 Hz, 1H), 2.61 (s, 3H), 2.28 (s, 3H), 2.22 (s, 3H), 1.50 (s, 9H).

tert-butyl (S)-(1-(4-methylbenzyl)-3-(1-(pyridazine-3-carboxamido)-3-(p-tolyl)propan-2-yl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with pyridazine-3-carboxylic acid (Procedure I) yielded the title product as a yellow foam (56%). $^1$H NMR (400 MHz, CDCl$_3$, 50° C.) δ 9.21 (dd, J=5.0, 1.8 Hz, 1H), 8.69 (s, 1H), 8.18 (dd, J=8.4, 1.8 Hz, 1H), 7.55 (dd, J=8.4, 5.0 Hz, 1H), 7.11-6.91 (m, 10H), 6.87 (d, J=7.8 Hz, 1H), 5.18 (q, J=15.9 Hz, 3H), 4.33 (s, 1H), 4.27-4.13 (m, 1H), 3.51 (s, 1H), 3.25 (dd, J=14.0, 6.5 Hz, 1H), 2.29 (s, 3H), 2.23 (s, 3H), 1.51 (s, 9H).

tert-butyl (S)-(1-(1-(isoxazole-5-carboxamido)-3-(p-tolyl)propan-2-yl)-3-(4-methylbenzyl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with isoxazole-5-carboxylic acid (Procedure I) yielded the title product as a yellow gel (85%). $^1$H NMR (400 MHz, CDCl$_3$, 50° C.) δ 9.07 (s, 1H), 8.19 (d, J=1.7 Hz, 1H), 7.39 (s, 1H), 7.22-6.87 (m, 11H), 6.81 (d, J=1.8 Hz, 1H), 5.17 (s, 2H), 5.02 (s, 1H), 4.54 (s, 1H), 3.78 (d, J=14.3 Hz, 1H), 3.38 (t, J=12.1 Hz, 1H), 3.20 (dd, J=14.0, 6.7 Hz, 1H), 2.29 (s, 3H), 2.27 (s, 3H), 1.53 (s, 9H).

tert-butyl (S)-(1-(4-methylbenzyl)-3-(1-(5-methylisoxazole-4-carboxamido)-3-(p-tolyl)propan-2-yl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with 5-methylisoxazole-4-carboxylic acid (Procedure I) yielded the title product as a yellow foam (79%). $^1$H NMR (400 MHz, CDCl$_3$, 50° C.) δ 8.90 (s, 1H), 8.60 (s, 1H), 7.47 (s, 1H), 7.20 (t, J=8.1 Hz, 1H), 7.13 (t, J=7.7 Hz, 1H), 7.06-6.90 (m, 9H), 5.25 (d, J=15.6 Hz, 1H), 5.10 (d, J=15.6 Hz, 1H), 4.97 (s, 1H), 4.52 (s, 1H), 3.62 (s, 1H), 3.31 (s, 1H), 3.20 (dd, J=13.9, 7.1 Hz, 1H), 2.56 (s, 3H), 2.28 (s, 6H), 1.52 (s, 9H).

tert-butyl (S)-(1-(1-(1,4-dimethyl-1H-imidazole-5-carboxamido)-3-(p-tolyl)propan-2-yl)-3-(4-methylbenzyl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with 1,4-dimethyl-1H-imidazole-5-carboxylic acid (Procedure I) yielded the title product as a white foam (80%). $^1$H NMR (400 MHz, CDCl$_3$, 50° C.) δ 7.35 (s, 1H), 7.17 (s, 1H), 7.15-6.66 (m, 11H), 5.33-4.94 (m, 3H), 4.50 (s, 1H), 3.77 (s, 1H), 3.47 (s, 3H), 3.36 (s, 1H), 3.17 (dd, J=13.9, 6.6 Hz, 1H), 2.29 (s, 3H), 2.26 (s, 3H), 2.07 (s, 3H), 1.49 (s, 9H).

tert-butyl (S)-(1-(1-(2-(1H-pyrrol-1-yl)acetamido)-3-(p-tolyl)propan-2-yl)-3-(4-methylbenzyl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with 2-(1H-pyrrol-1-yl)acetic acid (Procedure I) yielded the title product as a yellow gel (76%). $^1$H NMR (400 MHz, CDCl$_3$, 50° C.) δ 7.18-7.06 (m, 4H), 7.03 (d, J=7.8 Hz, 2H), 6.97 (t, J=7.3 Hz, 6H), 6.32 (s, 2H), 5.98 (s, 2H), 5.18 (q, J=15.6 Hz, 2H), 4.89 (s, 1H), 4.33 (s, 2H), 4.14 (s, 1H), 3.68 (s, 1H), 3.36 (s, 1H), 3.11 (dd, J=14.0, 6.6 Hz, 1H), 2.31 (s, 3H), 2.25 (s, 3H), 1.49 (s, 9H).

tert-butyl (S)-(1-(4-methylbenzyl)-3-(1-(nicotinamido)-3-(p-tolyl)propan-2-yl)-1,3-dihydro-2H-benzo[d]imidazol-2-ylidene)carbamate. Reaction of tert-butyl (S)-(1-(1-amino-3-(p-tolyl)propan-2-yl)-3-(4-methylbenzyl)-1,3-dihydro-2H-benzo[d]imidazol-2-ylidene)carbamate with nicotinic acid (Procedure I) yielded the title product as a yellow gel (53%). $^1$H NMR (400 MHz, CDCl$_3$, 50° C.) δ 9.07 (s, 1H), 8.63 (dd, J=4.8, 1.7 Hz, 1H), 8.12 (d, J=8.0 Hz, 1H), 7.52 (s, 1H), 7.24-7.15 (m, 2H), 7.10 (t, J=7.7 Hz, 1H), 7.05-6.88 (m, 9H), 5.17 (dd, J=27.8, 15.2 Hz, 2H), 5.06 (s, 1H), 4.63 (s, 1H), 3.74 (d, J=12.5 Hz, 1H), 3.34 (s, 1H), 3.22 (dd, J=13.9, 6.9 Hz, 1H), 2.28 (s, 3H), 2.27 (s, 3H), 1.52 (s, 9H).

Synthesis with General Procedure (J).

tert-butyl (1-(1-(ethylsulfonamido)-3-(p-tolyl)propan-2-yl)-3-(4-methylbenzyl)-1,3-dihydro-2H-benzo[d]imidazol-2-ylidene)carbamate

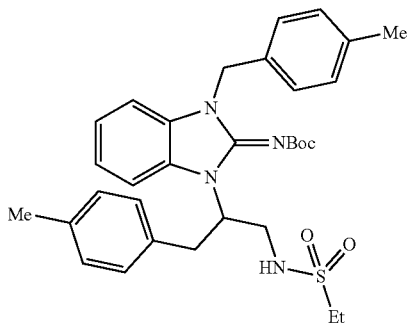

Reaction of tert-butyl-(1-(1-amino-3-(p-tolyl)propan-2-yl)-3-(4-methylbenzyl)-1,3-dihydro-2H-benzo[d]imidazol-2-ylidene)carbamate with ethanesulfonyl chloride (Procedure J) yielded the title product (71%) as a white solid (46%). $^1$H NMR (400 MHz, CDCl$_3$) δ 7.37 (br s, 1H), 7.18 (m, 1H), 7.12 (m, 1H), 7.08 (d, J=8.0 Hz, 2H), 7.00 (m, 5H), 6.91 (d, J=7.8 Hz, 2H), 5.20 (d, J=15.7 Hz, 1H), 5.15 (d, J=15.8 Hz, 1H), 4.84 (br s, 1H), 3.55 (ddd, J=13.2, 4.8, 3.2 Hz, 1H), 3.33-3.26 (m, 1H), 3.14 (dd, J=14.0, 6.6 Hz, 1H), 2.78 (br m, 2H), 2.30 (s, 3H), 2.27 (s, 3H), 1.49 (s, 9H), 1.16-1.01 (br t, J=7.2 Hz, 3H). MS (APCI) calcd for: C$_{32}$H$_{41}$N$_4$O$_4$S (MH$^+$): 577.3, found 577.1.

tert-butyl (1-(1-(cyclopropanesulfonamido)-3-(p-tolyl)propan-2-yl)-3-(4-methylbenzyl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with cyclopropanesulfonyl chloride (Procedure J) yielded the title product (46%) as a white solid. $^1$H NMR (400 MHz, CDCl$_3$) δ 7.38 (br s, 1H), 7.22-7.15 (m, 1H), 7.14-7.10 (m, 1H), 7.08 (d, J=7.5 Hz, 2H), 7.04-6.96 (m, 5H), 6.92 (d, J=7.7 Hz, 2H), 6.78 (br s, 1H), 5.20 (d, J=15.7 Hz, 1H), 5.15 (d, J=15.9 Hz, 1H), 4.87 (br s, 1H), 4.10-3.99 (m, 1H), 3.63 (dt, J=13.1, 4.1 Hz, 1H), 3.31 (dd, J=13.5, 9.5 Hz, 1H), 3.15 (dd, J=14.0, 6.8 Hz, 1H), 2.30 (s, 3H), 2.27 (s, 3H), 2.20-2.10 (m, 1H), 1.49 (s, 9H), 1.05-0.94 (m, 2H), 0.76-0.58 (m, 2H). MS (APCI) calcd for: C$_{33}$H$_{41}$N$_4$O$_4$S (MH$^+$): 589.3, found 589.3.

tert-butyl (1-(4-methylbenzyl)-3-(1-(phenylsulfonamido)-3-(p-tolyl)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with benzenesulfonyl chloride (Procedure J) yielded the title product (62%) as a yellow foam. $^1$H NMR (400 MHz, CDCl$_3$) δ 7.80-7.58 (m, 3H), 7.21-7.02 (m, 7H), 7.02-6.97 (m, 2H), 6.97-6.87 (m, 4H), 6.79 (br s, 2H), 5.15 (d, J=16.1 Hz, 1H), 5.08 (d, J=16.0 Hz, 1H), 4.75 (br s, 1H), 3.90 (td, J=12.1, 7.0 Hz, 1H), 3.39 (ddd, J=13.0, 4.4, 2.4 Hz, 1H), 3.26-3.10 (m, 1H), 3.03 (dd, J=14.0, 6.5 Hz, 1H), 2.31 (s, 3H), 2.25 (s, 3H), 1.48 (s, 9H). MS (APCI) calcd for: C$_{36}$H$_{41}$N$_4$O$_4$S (MH$^+$): 625.3, found 625.2.

tert-butyl (1-(4-methylbenzyl)-3-(1-(methylsulfonamido)-3-(p-tolyl)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with methanesulfonyl chloride (Procedure J) yielded the title product (34%). $^1$H NMR (400 MHz, CDCl$_3$) δ 7.36 (br s, 1H), 7.20 (br t, J=7.5 Hz, 1H), 7.12 (t, J=7.6 Hz, 1H), 7.08 (d, J=7.9 Hz, 2H), 7.00 (m, 5H), 6.91 (d, J=7.7 Hz, 2H), 6.82 (br s, 1H), 5.20 (d, J=15.7 Hz, 1H), 5.14 (d, J=15.8 Hz, 1H), 4.85 (br s, 1H), 4.06 (ddd, J=12.9, 10.7, 7.0 Hz, 1H), 3.57 (ddd, J=13.2, 4.7, 3.1 Hz, 1H), 3.30 (dd, J=13.9, 8.9 Hz, 1H), 3.15 (dd, J=13.9, 6.7 Hz, 1H), 2.66 (s, 3H), 2.30 (s, 3H), 2.27 (s, 3H), 1.49 (s, 9H). MS (APCI) calcd for: C$_{31}$H$_{39}$N$_4$O$_4$S (MH$^+$): 563.3, found 563.3.

tert-butyl (1-(4-methylbenzyl)-3-(1-((1-methylethyl)sulfonamido)-3-(p-tolyl)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with 2-propanesulfonyl chloride (Procedure J) yielded the title product (29%). H NMR (400 MHz, CDCl$_3$) δ 7.33 (br s, 1H), 7.16 (br t, J=8.3 Hz, 1H), 7.14-7.09 (m, 1H), 7.08 (d, J=7.8 Hz, 2H), 7.05-6.95 (m, 5H), 6.91 (d, J=7.7 Hz, 2H), 6.85-6.44 (br m, 1H), 5.22 (d, J=16.0 Hz, 1H), 5.17 (d, J=15.6 Hz, 1H), 4.84 (br s, 1H), 4.06 (ddd, J=13.1, 10.6, 7.1 Hz, 1H), 3.58 (ddd, J=13.3, 5.0, 3.5 Hz, 1H), 3.41-3.22 (m, 1H), 3.13 (dd, J=14.0, 6.5 Hz, 1H), 3.04-2.85 (m, 1H), 2.30 (s, 3H), 2.26 (s, 3H), 1.49 (s, 9H), 1.22 (d, J=6.8 Hz, 3H), 1.13 (br s, 3H). MS (APCI) calcd for: C$_{33}$H$_{43}$N$_4$O$_4$S (MH$^+$): 591.3, found 591.2.

tert-butyl (1-(4-methylbenzyl)-3-(1-((phenylmethyl)sulfonamido)-3-(p-tolyl)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with phenylmethanesulfonyl chloride (Procedure J) yielded the title product (64%). $^1$H NMR (400 MHz, CDCl$_3$) δ 7.81-7.60 (m, 1H), 7.43-7.22 (m, 4H), 7.22-7.09 (m, 2H), 7.09-7.04 (m, 3H), 7.03-6.90 (m, 6H), 6.85 (d, J=7.7 Hz, 2H), 5.20 (d, J=15.7 Hz, 1H), 5.12 (d, J=15.8 Hz, 1H), 4.74 (br s, 1H), 4.11 (d, J=13.5 Hz, 1H), 4.05 (d, J=13.9 Hz, 1H), 3.86 (ddd, J=13.2, 10.4, 6.4 Hz, 1H), 3.31-3.13 (m, 2H), 3.02 (dd, J=14.0, 6.5 Hz, 1H), 2.29 (s, 3H), 2.26 (s, 3H), 1.49 (s, 9H). MS (APCI) calcd for: C$_{37}$H$_{43}$N$_4$O$_4$S (MH$^+$): 639.3, found 639.2.

tert-butyl (1-(4-methylbenzyl)-3-(1-(p-tolyl)-3-((trifluoromethyl)sulfonamido)propan-2-yl)-1,3-dihydro-2H-benzo[d]imidazol-2-ylidene)carbamate. Reaction of tert-butyl-(1-(1-amino-3-(p-tolyl)propan-2-yl)-3-(4-methylbenzyl)-1,3-dihydro-2H-benzo[d]imidazol-2-ylidene)carbamate with trifluoromethanesulfonyl chloride (Procedure J) yielded the title product (29%). H NMR (400 MHz, CDCl$_3$) δ 7.73-7.30 (br s, 1H), 7.24-7.11 (m, 2H), 7.09 (d, J=7.7 Hz, 2H), 7.05-6.90 (m, 5H), 6.85 (d, J=7.6 Hz, 2H), 5.23 (d, J=15.1 Hz, 1H), 5.17 (d, J=15.8 Hz, 1H), 4.85 (br s, 1H), 4.16 (dd, J=12.2, 11.9 Hz, 1H), 3.69 (dd, J=12.7, 4.0 Hz, 1H), 3.43-3.23 (m, 1H), 3.13 (dd, J=14.0, 6.2 Hz, 1H), 2.31 (s, 3H), 2.27 (s, 3H), 1.48 (s, 9H). MS (APCI) calcd for: $C_{31}H_{36}F_3N_4O_4S$ (MH$^+$): 617.2, found 617.2.

Synthesis with General Procedure (K).

N-(2-(2-imino-3-(4-methylbenzyl)-2,3-dihydro-1H-benzo[d]imidazol-1-yl)-3-(p-tolyl)propyl)ethanesulfonamide

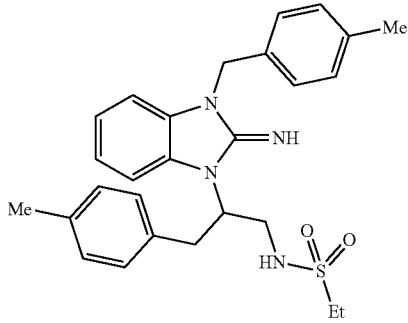 [SMILES: CCS(=O)(=O)NCC(Cc1ccc(C)cc1)n1c(=N)n(Cc2ccc(C)cc2)c2ccccc21]

Reaction of tert-butyl (1-(1-(ethylsulfonamido)-3-(p-tolyl)propan-2-yl)-3-(4-methylbenzyl)-1,3-dihydro-2H-benzo[d]imidazol-2-ylidene)carbamate (Procedure K) yielded the title product as an off-white solid (94%). $^1$H NMR (400 MHz, CDCl$_3$) δ 7.12 (d, J=7.8 Hz, 2H), 7.07-6.98 (m, 4H), 6.95 (d, J=7.8 Hz, 2H), 6.93-6.86 (m, 2H), 6.81 (br s, 1H), 6.76-6.66 (m, 1H), 4.88 (d, J=16.9 Hz, 1H), 4.82 (d, J=16.7 Hz, 1H), 4.65 (br s, 1H), 3.82 (dd, J=13.0, 7.4 Hz, 1H), 3.56-3.42 (m, 2H), 3.23 (dd, J=13.9, 6.5 Hz, 1H), 2.92 (q, J=7.4 Hz, 2H), 2.33 (s, 3H), 2.23 (s, 3H), 1.24 (t, J=7.4 Hz, 3H). $^{13}$C NMR (101 MHz, CDCl$_3$) δ 155.0, 137.8, 136.2, 134.5, 132.3, 131.6, 129.8, 129.2, 129.1, 126.7, 121.1, 120.8, 110.1, 107.5, 106.9, 56.5, 46.7, 45.7, 45.0, 34.3, 21.3, 21.2, 8.4.

N-(2-(2-imino-3-(4-methylbenzyl)-2,3-dihydro-1H-benzo[d]imidazol-1-yl)-3-(p-tolyl)propyl)cyclopropanesulfonamide. Reaction of tert-butyl (1-(1-(cyclopropanesulfonamido)-3-(p-tolyl)propan-2-yl)-3-(4-methylbenzyl)-1,3-dihydro-2H-benzo[d]imidazol-2-ylidene)carbamate (Procedure K) yielded the title product as an off-white solid (97%). $^1$H NMR (400 MHz, CDCl$_3$) δ 7.13 (d, J=7.9 Hz, 2H), 7.08-7.00 (m, 4H), 6.97 (d, J=7.8 Hz, 2H), 6.94-6.87 (m, 2H), 6.83 (br s, 1H), 6.77-6.68 (m, 1H), 4.88 (d, J=16.8 Hz, 1H), 4.82 (d, J=16.7 Hz, 1H), 4.67 (br s, 1H), 3.83 (dd, J=13.0, 7.5 Hz, 1H), 3.58 (dd, J=13.0, 3.2 Hz, 1H), 3.43 (dd, J=13.9, 8.6 Hz, 1H), 3.25 (dd, J=13.9, 6.7 Hz, 1H), 2.33 (s, 3H), 2.32-2.27 (m, 1H), 2.24 (s, 3H), 1.13-0.99 (m, 2H), 0.86-0.72 (m, 2H). $^{13}$C NMR (100 MHz, CDCl$_3$) δ 155.1, 137.8, 136.2, 134.5, 132.3, 131.7, 129.8, 129.3, 129.1, 126.7, 121.1, 120.8, 107.3, 106.9, 56.5, 45.6, 45.0, 34.4, 30.0, 21.3, 21.2, 5.3, 5.1.

N-(2-(2-imino-3-(4-methylbenzyl)-2,3-dihydro-1H-benzo[d]imidazol-1-yl)-3-(p-tolyl)propyl)benzenesulfonamide. Reaction of tert-butyl (1-(4-methylbenzyl)-3-(1-(phenylsulfonamido)-3-(p-tolyl)propan-2-yl)-1,3-dihydro-2H-benzo[d]imidazol-2-ylidene)carbamate (Procedure K) yielded the title product as a yellow solid (61%). $^1$H NMR (400 MHz, CDCl$_3$) δ 7.77 (d, J=7.3 Hz, 2H), 7.49-7.41 (m, 1H), 7.40-7.33 (m, 2H), 7.13 (d, J=7.8 Hz, 2H), 7.01 (d, J=7.8 Hz, 2H), 6.98 (d, J=8.1 Hz, 2H), 6.94 (d, J=8.0 Hz, 2H), 6.90-6.83 (m, 2H), 6.75-6.60 (m, 2H), 4.85 (d, J=16.8 Hz, 1H), 4.79 (d, J=16.8 Hz, 1H), 4.51 (br s, 1H), 3.65 (dd, J=12.8, 6.9 Hz, 1H), 3.35 (dd, J=13.8, 8.5 Hz, 1H), 3.25 (d, J=13.0, 2.8 Hz, 1H), 3.19 (dd, J=13.9, 6.9 Hz, 1H), 2.35 (s, 3H), 2.23 (s, 3H). $^{13}$C NMR (101 MHz, CDCl$_3$) δ 155.0, 140.4, 137.8, 136.2, 134.5, 132.2, 132.1, 131.5, 129.8, 129.2, 129.1, 128.9, 127.0, 126.7, 121.1, 120.8, 106.9, 56.3, 45.8, 45.0, 34.3, 21.3, 21.2

N-(2-(2-imino-3-(4-methylbenzyl)-2,3-dihydro-1H-benzo[d]imidazol-1-yl)-3-(p-tolyl)propyl)methanesulfonamide. Reaction of tert-butyl (1-(4-methylbenzyl)-3-(1-(methylsulfonamido)-3-(p-tolyl)propan-2-yl)-1,3-dihydro-2H-benzo[d]imidazol-2-ylidene)carbamate (Procedure K) yielded the title product (89%). $^1$H NMR (400 MHz, CDCl$_3$) δ 7.13 (d, J=7.8 Hz, 2H), 7.03 (d, J=8.0 Hz, 2H), 7.01 (d, J=7.6 Hz, 2H), 6.97 (d, J=7.9 Hz, 2H), 6.94-6.87 (m, 2H), 6.87-6.78 (br m, 1H), 6.77-6.72 (m, 1H), 4.87 (d, J=16.8 Hz, 1H), 4.81 (d, J=16.8 Hz, 1H), 4.65 (br s, 1H), 3.81 (dd, J=13.0, 7.4 Hz, 1H), 3.51 (dd, J=13.0, 3.1 Hz, 1H), 3.43 (dd, J=13.9, 8.7 Hz, 1H), 3.24 (dd, J=13.9, 6.7 Hz, 1H), 2.82 (s, 3H), 2.33 (s, 3H), 2.24 (s, 3H). $^{13}$C NMR (101 MHz, CDCl$_3$) δ 155.1, 137.9, 136.3, 134.4, 132.2, 131.6, 129.8, 129.3, 129.1, 126.7, 121.2, 120.9, 107.4, 107.0, 56.4, 45.7, 45.0, 40.1, 34.3, 21.3, 21.2.

Methyl (2-(2-imino-3-(4-methylbenzyl)-2,3-dihydro-1H-benzo[d]imidazol-1-yl)-3-(p-tolyl)propyl)carbamate. Reaction of tert-butyl (1-(1-((methoxycarbonyl)amino)-3-(p-tolyl)propan-2-yl)-3-(4-methylbenzyl)-1,3-dihydro-2H-benzo[d]imidazol-2-ylidene)carbamate (Procedure K) yielded the title product (81%). $^1$H NMR (400 MHz, CDCl$_3$) δ 7.10 (d, J=7.8 Hz, 2H), 6.98 (m, 5H), 6.88 (m, 3H), 6.69 (d, J=7.3 Hz, 1H), 4.89 (d, J=16.9 Hz, 1H), 4.83 (d, J=16.7 Hz, 1H), 4.75 (br s, 1H), 3.93 (br s, 1H), 3.75-3.63 (m, 1H), 3.61 (s, 3H), 3.52-3.32 (m, 1H), 3.12 (dd, J=13.9, 6.0 Hz, 1H), 2.32 (s, 3H), 2.24 (s, 3H). $^{13}$C NMR (101 MHz, CDCl$_3$) δ 157.4, 155.1, 137.5, 136.1, 132.6, 131.7, 129.7, 129.2, 129.0, 126.7, 120.9, 120.5, 111.6, 106.8, 56.2, 52.2, 44.9, 43.2, 29.9, 21.3, 21.2.

Ethyl (2-(2-imino-3-(4-methylbenzyl)-2,3-dihydro-1H-benzo[d]imidazol-1-yl)-3-(p-tolyl)propyl)carbamate. Reaction of tert-butyl (1-(1-((ethoxycarbonyl)amino)-3-(p-tolyl)propan-2-yl)-3-(4-methylbenzyl)-1,3-dihydro-2H-benzo[d]imidazol-2-ylidene)carbamate (Procedure K) yielded the title product (92%). $^1$H NMR (400 MHz, CDCl$_3$) δ 7.10 (d, J=7.8 Hz, 2H), 7.05-6.93 (m, 6H), 6.93-6.81 (m, 2H), 6.70 (d, J=7.4 Hz, 1H), 4.92 (d, J=17.0 Hz, 1H), 4.84 (d, J=16.7 Hz, 1H), 4.78 (br s, 1H), 4.05 (q, J=7.1 Hz, 2H), 3.92 (br s, 1H), 3.78-3.60 (m, 1H), 3.43 (br s, 1H), 3.12 (dd, J=13.9, 5.9 Hz, 1H), 2.32 (s, 3H), 2.24 (s, 3H), 1.17 (t, J=7.1 Hz, 3H). $^{13}$C NMR (101 MHz, CDCl$_3$) δ 156.7, 154.1, 138.7, 137.2, 135.7, 132.3, 131.3, 129.3, 128.9, 128.7, 126.4, 120.6, 120.2, 106.6, 60.6, 55.8, 44.6, 42.7, 29.5, 20.94, 20.88, 14.5.

N-(2-(2-imino-3-(4-methylbenzyl)-2,3-dihydro-1H-benzo[d]imidazol-1-yl)-3-(p-tolyl)propyl)propane-2-sulfonamide. Reaction of tert-butyl (1-(4-methylbenzyl)-3-(1-(((1-methylethyl)sulfonamido)-3-(p-tolyl)propan-2-yl)-1,3-dihydro-2H-benzo[d]imidazol-2-ylidene)carbamate (Procedure K) yielded the title product (88%). $^1$H NMR (400 MHz, CDCl$_3$) δ 7.13 (d, J=7.9 Hz, 2H), 7.07-6.98 (m, 4H), 6.95 (d, J=7.8 Hz, 2H), 6.92-6.83 (m, 2H), 6.77 (br s, 1H), 6.75-6.66 (m, 2H), 4.88 (d, J=16.8 Hz, 1H), 4.82 (d, J=16.8 Hz, 1H), 4.60 (br s, 1H), 3.85 (dd, J=13.1, 7.3 Hz, 1H), 3.52 (dd, J=13.0, 3.0 Hz, 1H), 3.48 (dd, J=13.6, 9.2 Hz, 1H), 3.20 (dd, J=13.9, 6.4 Hz, 1H), 3.06 (qq, J=6.9, 6.8 Hz, 1H), 2.34 (s, 3H), 2.23 (s, 3H), 1.30 (d, J=6.9 Hz, 3H), 1.27 (d, J=6.8 Hz, 3H). $^{13}$C NMR (101 MHz, CDCl$_3$) δ 155.1, 137.8, 136.2, 134.6, 132.3, 131.6, 129.8, 129.3, 129.2, 129.1, 126.7, 121.0, 120.7, 107.3, 106.8, 56.7, 53.1, 46.1, 44.9, 34.3, 21.3, 21.2, 16.7, 16.7.

N-(2-(2-imino-3-(4-methylbenzyl)-2,3-dihydro-1H-benzo[d]imidazol-1-yl)-3-(p-tolyl)propyl)-1-phenylmethanesulfonamide. Reaction of tert-butyl (1-(4-methylbenzyl)-3-(1-((phenylmethyl)sulfonamido)-3-(p-tolyl)propan-2-yl)-1,3-dihydro-2H-benzo[d]imidazol-2-ylidene)carbamate (Procedure K) yielded the title product (95%). ¹H NMR (400 MHz, CDCl₃) δ 7.36-7.29 (m, 2H), 7.30-7.19 (m, 5H), 7.13 (d, J=7.8 Hz, 2H), 7.01 (d, J=7.4 Hz, 2H), 6.97 (d, J=8.2 Hz, 2H), 6.93 (d, J=8.1 Hz, 2H), 6.91-6.85 (m, 2H), 6.77-6.67 (m, 2H), 4.84 (d, J=16.8 Hz, 1H), 4.78 (d, J=16.8 Hz, 1H), 4.49 (br s, 1H), 4.18 (s, 2H), 3.63 (dd, J=13.0, 7.1 Hz, 1H), 3.43 (dd, J=13.9, 9.1 Hz, 1H), 3.26 (dd, J=13.0, 3.1 Hz, 1H), 3.11 (dd, J=13.9, 6.2 Hz, 1H), 2.33 (s, 3H), 2.23 (s, 3H). ¹³C NMR (101 MHz, CDCl₃) δ 154.9, 137.8, 136.1, 134.5, 132.3, 131.6, 130.8, 129.8, 129.8, 129.2, 129.1, 128.7, 128.5, 126.7, 121.1, 120.7, 107.3, 106.8, 59.1, 56.6, 46.4, 44.9, 34.2, 21.3, 21.2.

1,1,1-trifluoro-N-(2-(2-imino-3-(4-methylbenzyl)-2,3-dihydro-1H-benzo[d]imidazol-1-yl)-3-(p-tolyl)propyl)methanesulfonamide. Reaction of tert-butyl (1-(4-methylbenzyl)-3-(1-(p-tolyl)-3-((trifluoromethyl)sulfonamido)propan-2-yl)-1,3-dihydro-2H-benzo[d]imidazol-2-ylidene)carbamate (Procedure K) yielded the title product (22%). ¹H NMR (400 MHz, d₆-acetone) δ 7.34 (br s, 1H), 7.33-7.27 (m, 1H), 7.23 (d, J=8.0 Hz, 2H), 7.17 (d, J=8.0 Hz, 2H), 7.15-7.08 (m, 2H), 7.01 (d, J=8.0 Hz, 2H), 6.82 (d, J=7.7 Hz, 2H), 5.46 (s, 2H), 5.15 (br s, 1H), 3.82 (br d, J=13.9 Hz, 1H), 3.68 (d, J=13.5 Hz, 1H), 3.59 (dd, J=11.1, 3.3 Hz, 1H), 3.12 (dd, J=14.2, 4.9 Hz, 1H), 2.33 (s, 3H), 2.10 (s, 3H). ¹³C NMR (101 MHz, d₆-acetone) δ 152.5, 138.8, 136.6, 135.1, 132.2, 130.7, 130.4, 129.8, 129.6, 127.9, 124.22, 124.16, 124.0, 111.3, 110.8, 61.6, 49.9, 46.5, 34.4, 21.1, 20.9.

1-(2-(2-imino-3-(4-methylbenzyl)-2,3-dihydro-1H-benzo[d]imidazol-1-yl)-3-(p-tolyl)propyl)urea. Reaction of tert-butyl (1-(4-methylbenzyl)-3-(1-(p-tolyl)-3-ureidopropan-2-yl)-1,3-dihydro-2H-benzo[d]imidazol-2-ylidene)carbamate (Procedure K) yielded the title product (73%). ¹H NMR (400 MHz, CDCl₃) δ 7.16-7.05 (m, 2H), 7.05-6.76 (m, 8H), 6.70 (d, J=7.4 Hz, 1H), 4.84 (d, J=16.8 Hz, 1H), 4.77 (d, J=16.7 Hz, 1H), 4.65 (br s, 1H), 4.37 (br s, 1H), 3.98 (br s, 1H), 3.70-3.54 (m, 1H), 3.53-3.33 (m, 1H), 3.12 (dd, J=13.9, 6.0 Hz, 1H), 2.32 (s, 3H), 2.24 (s, 3H). ¹³C NMR (101 MHz, CDCl₃) δ 159.2, 155.4, 137.4, 136.0, 134.5, 132.5, 131.4, 129.6, 129.4, 129.24, 129.18, 128.9, 127.3, 126.5, 121.1, 120.7, 107.0, 56.7, 44.5, 42.3, 34.8, 21.23, 21.19.

(2-(2-imino-3-(4-methylbenzyl)-2,3-dihydro-1H-benzo[d]imidazol-1-yl)-3-(p-tolyl)propyl)carbamic acid. Reaction of (2-(2-((tert-butoxycarbonyl)imino)-3-(4-methylbenzyl)-2,3-dihydro-1H-benzo[d]imidazol-1-yl)-3-(p-tolyl)propyl)carbamic acid (Procedure K) yielded the title product (93%) as a mixture of rotamers. ¹H NMR (400 MHz, CDCl₃) δ 7.88-7.55 (m, 4H), 7.31 (d, J=7.7 Hz, 0.5H), 7.22-6.88 (m, 8H), 6.82 (d, J=7.7 Hz, 1H), 6.73-6.34 (m, 2H), 5.28 (br s, 0.6H), 4.97-4.58 (m, 3H), 4.47-4.22 (m, 0.7H), 4.14 (d, J=5.3 Hz, 0.5H), 4.11 (d, J=6.3 Hz, 0.4H), 3.90 (s, 0.4H), 3.81-3.47 (br m, 1H), 3.46-3.34 (m, 1H), 3.24 (dd, J=14.1, 6.1 Hz, 1H), 2.47-2.06 (m, 6H). ¹³C NMR (101 MHz, CDCl₃) δ 168.3, 168.1, 155.0, 154.1, 137.4, 136.9, 136.2, 135.9, 135.0, 134.0, 133.8, 133.0, 132.7, 131.9, 131.6, 129.4, 129.6, 129.4, 129.3, 129.2, 128.8, 126.7, 123.5, 123.2, 120.7, 120.4, 119.8, 109.0, 107.0, 106.2, 105.7, 55.1, 53.5, 44.9, 44.5, 39.0, 38.9, 35.7, 34.6, 29.9, 21.24, 21.18.

N-(2-(2-imino-3-(4-methylbenzyl)-2,3-dihydro-1H-benzo[d]imidazol-1-yl)-3-(p-tolyl)propyl)-2-(p-tolyl)acetamide. Reaction of tert-butyl (1-(4-methylbenzyl)-3-(1-(p-tolyl)-3-(2-(p-tolyl)acetamido)propan-2-yl)-1,3-dihydro-2H-benzo[d]imidazol-2-ylidene)carbamate (Procedure K) yielded the title product (84%). ¹H NMR (400 MHz, CDCl₃) δ 7.12 (d, J=7.7 Hz, 2H), 7.05-6.73 (m, 13H), 6.70 (dd, J=6.5, 1.8 Hz, 1H), 4.82 (d, J=16.8 Hz, 1H), 4.77 (d, J=16.8 Hz, 1H), 4.67 (br s, 1H), 3.93 (br s, 1H), 3.66 (br d, J=13.1 Hz, 1H), 3.44 (br s, 1H), 3.41 (s, 2H), 3.06 (dd, J=13.8, 6.0 Hz, 1H), 2.34 (s, 3H), 2.28 (s, 3H), 2.24 (s, 3H). ¹³C NMR (101 MHz, CDCl₃) δ 171.8, 154.8, 137.6, 136.6, 136.0, 134.7, 132.6, 131.9, 131.6, 129.7, 129.5, 129.4, 129.2, 128.9, 126.6, 120.9, 120.4, 106.5, 55.4, 44.8, 43.5, 41.8, 34.7, 21.3, 21.22, 21.17.

2-hydroxy-N-(2-(2-imino-3-(4-methylbenzyl)-2,3-dihydro-1H-benzo[d]imidazol-1-yl)-3-(p-tolyl)propyl)acetamide. Reaction of tert-butyl (1-(1-(2-hydroxyacetamido)-3-(p-tolyl)propan-2-yl)-3-(4-methylbenzyl)-1,3-dihydro-2H-benzo[d]imidazol-2-ylidene)carbamate (Procedure K) yielded the title product (50%). ¹H NMR (400 MHz, CDCl₃) δ 7.66 (br s, 1H), 7.24-7.03 (m, 1H), 7.06 (d, J=7.5 Hz, 2H), 7.02-6.76 (m, 7H), 6.71 (d, J=7.6 Hz, 1H), 5.29-4.86 (br m, 1H), 4.83 (d, J=16.8 Hz, 1H), 4.75 (d, J=17.1 Hz, 1H), 4.42-4.02 (br m, 2H), 3.98 (d, J=15.8 Hz, 1H), 3.91 (d, J=16.1 Hz, 1H), 3.72 (br s, 1H), 3.51-3.29 (br m, 1H), 3.12 (dd, J=14.1, 5.9 Hz, 1H), 2.30 (s, 3H), 2.24 (s, 3H). ¹³C NMR (101 MHz, CDCl₃) δ 173.0, 155.5, 137.6, 136.1, 132.2, 131.5, 129.7, 129.2, 129.0, 128.9, 126.7, 126.5, 121.3, 120.7, 110.1, 107.3, 62.0, 56.0, 44.9, 41.0, 35.2, 21.24, 21.21.

Synthesis with General Procedure (L).

(S)-2-((3-nitropyridin-2-yl)amino)-3-(p-tolyl)propan-1-ol

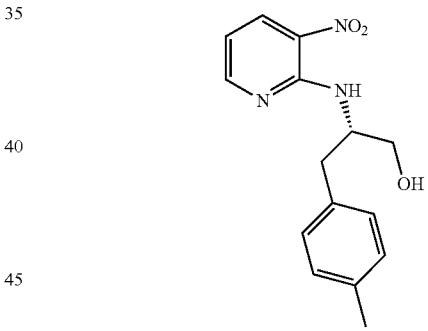

Reaction of 2-fluoro-3-nitro pyridine with (S)-2-amino-3-(p-tolyl)propan-1-ol yielded the product as yellow solid (50%). ¹H NMR (400 MHz, CDCl₃) δ 8.44-8.30 (m, 3H), 7.17 (d, J=8.0 Hz, 2H), 7.11 (d, J=7.9 Hz, 2H), 6.66 (dd, J=8.3, 4.5 Hz, 1H), 4.67-4.55 (m, 1H), 3.85 (d, J=10.9 Hz, 1H), 3.73 (dd, J=10.6, 6.0 Hz, 1H), 3.11 (s, 1H), 2.97 (dddd, J=13.8, 13.8, 13.8, 7.0 Hz, 2H), 2.31 (s, 3H). ¹³C NMR (101 MHz, CDCl₃) δ 155.27, 152.67, 136.33, 135.69, 134.26, 129.36, 129.13, 128.34, 112.11, 65.38, 54.96, 37.22, 21.04.

(S)—N-(1-methoxy-3-(p-tolyl)propan-2-yl)-3-nitropyridin-2-amine. Reaction of 2-fluoro-3-nitro pyridine with (S)-1-methoxy-3-(p-tolyl)propan-2-amine yielded the product as yellow solid (48%). ¹H NMR (400 MHz, CDCl₃) δ 8.47-8.34 (m, 3H), 7.17 (d, J=7.9 Hz, 2H), 7.10 (d, J=7.9 Hz, 2H), 6.61 (dd, J=8.1, 4.7 Hz, 1H), 4.83-4.59 (m, 1H), 3.48-3.40 (m, 2H), 3.39 (s, 3H), 3.05-2.88 (m, 2H), 2.31 (s, 3H). ¹³C NMR (101 MHz, CDCl₃) δ 155.71, 152.17, 135.96, 135.28, 134.89, 129.34, 129.14, 127.98, 111.64, 72.37, 59.15, 51.90, 37.05, 21.06.

(S)—N-(1-methoxy-3-(p-tolyl)propan-2-yl)-2-nitropyridin-3-amine. Reaction of 2-nitro-3-fluoro pyridine with (S)-1-methoxy-3-(p-tolyl)propan-2-amine yielded the product as yellow solid (37%). $^1$H NMR (400 MHz, CDCl$_3$) δ 8.01 (d, J=7.0 Hz, 1H), 7.84 (dd, J=3.6, 1.7 Hz, 1H), 7.34-7.32 (m, 1H), 7.10 (s, 4H), 3.99-3.86 (m, 1H), 3.47 (dd, J=4.7, 1.5 Hz, 2H), 3.40 (s, 3H), 3.00 (dd, J=13.8, 6.7 Hz, 1H), 2.89 (dd, J=14.0, 6.5 Hz, 1H), 2.31 (s, 3H). $^{13}$C NMR (101 MHz, CDCl$_3$) δ 140.77, 140.48, 136.48, 135.10, 133.86, 130.20, 129.40, 129.18, 123.72, 73.19, 59.27, 53.92, 37.38, 21.02.

(S)-3-(2-((3-nitropyridin-2-yl)amino)-3-(p-tolyl)propoxy)propanenitrile. Reaction of 2-fluoro-3-nitro pyridine with (S)-3-(2-amino-3-(p-tolyl)propoxy)propanenitrile yielded the product as yellow solid (81%). $^1$H NMR (400 MHz, CDCl$_3$) δ 8.44-8.34 (m, 2H), 7.15 (dd, J=32.4, 7.8 Hz, 4H), 6.66-6.58 (m, 1H), 4.84-4.69 (m, 1H), 3.69 (qt, J=9.5, 4.9 Hz, 2H), 3.55 (qd, J=9.4, 4.3 Hz, 2H), 3.05-2.93 (m, 2H), 2.65 (td, J=6.4, 1.3 Hz, 2H), 2.30 (s, 1H). $^{13}$C NMR (101 MHz, CDCl$_3$) δ 155.71, 152.02, 136.09, 135.32, 134.60, 129.32, 129.25, 128.05, 117.83, 111.91, 70.81, 65.84, 51.63, 36.91, 21.06, 18.85.

(S)—N-methyl-2-((2-nitrophenyl)amino)-3-(p-tolyl)propenamide. Reaction of 1-fluoro-2-nitrobezene with (S)-2-amino-N-methyl-3-(p-tolyl)propanamide yielded the product as yellow solid (36%). $^1$H NMR (400 MHz, CDCl$_3$) δ 8.15 (dd, J=8.6, 1.5 Hz, 1H), 7.47-7.39 (m, 1H), 7.21-7.08 (m, 4H), 6.79-6.73 (m, 1H), 6.68 (d, J=8.5 Hz, 1H), 4.18 (dq, J=7.4, 4.6 Hz, 1H), 3.79-3.71 (m, 1H), 3.28 (dd, J=14.0, 4.6 Hz, 1H), 3.22-3.15 (m, 1H), 3.10 (dd, J=14.3, 4.6 Hz, 1H), 2.79-2.74 (m, 3H), 2.31 (s, 3H). $^{13}$C NMR (101 MHz, CDCl$_3$) δ 171.87, 143.78, 137.15, 136.51, 132.52, 129.61, 129.34, 129.28, 129.16, 126.77, 117.29, 114.56, 60.04, 59.30, 38.56, 36.69, 26.17, 25.22, 21.07.

(S)-1-(azetidin-1-yl)-2-((2-nitrophenyl)amino)-3-(p-tolyl)propan-1-one. Reaction of 1-fluoro-2-nitrobezene with (S)-2-amino-1-(azetidin-1-yl)-3-(p-tolyl)propan-1-one yielded the product as yellow solid (59%). $^1$H NMR (400 MHz, CDCl$_3$) δ 8.37 (d, J=6.6 Hz, 1H), 8.17 (dd, J=8.5, 1.5 Hz, 1H), 7.49-7.41 (m, 1H), 7.20 (q, J=8.1 Hz, 3H), 6.71 (ddd, J=12.5, 6.9, 2.8 Hz, 2H), 4.26-4.19 (m, 1H), 4.11-3.89 (m, 2H), 3.74-3.63 (m, 1H), 3.46-3.32 (m, 1H), 3.17 (ddd, J=28.9, 13.6, 6.5 Hz, 2H), 2.35 (s, 3H), 2.15-1.91 (m, 2H). $^{13}$C NMR (101 MHz, CDCl$_3$) δ 170.03, 143.64, 137.18, 136.39, 132.85, 129.49, 129.24, 127.03, 116.22, 113.69, 56.64, 50.69, 48.39, 38.40, 21.12, 15.76.

(S)-2-((2-nitrophenyl)amino)-1-(pyrrolidin-1-yl)-3-(p-tolyl)propan-1-one. Reaction of 1-fluoro-2-nitrobezene with (S)-2-amino-1-(pyrrolidin-1-yl)-3-(p-tolyl)propan-1-one yielded the product as yellow solid (80%). $^1$H NMR (400 MHz, CDCl$_3$) δ 8.61 (d, J=7.3 Hz, 1H), 8.17 (dd, J=8.5, 1.5 Hz, 1H), 7.42-7.36 (m, 1H), 7.13 (q, J=8.0 Hz, 4H), 6.65 (ddd, J=12.2, 6.8, 2.6 Hz, 2H), 4.45 (q, J=7.1 Hz, 1H), 3.55-3.38 (m, 2H), 3.32 (tt, J=15.5, 7.6 Hz, 1H), 3.13 (d, J=7.0 Hz, 2H), 2.84-2.76 (m, 1H), 2.32 (s, 3H), 1.90-1.58 (m, 4H). $^{13}$C NMR (101 MHz, CDCl$_3$) δ 169.07, 143.74, 136.86, 136.08, 133.06, 129.32, 129.20, 127.15, 115.71, 113.56, 56.92, 46.24, 46.16, 38.96, 26.06, 23.86, 21.07.

(S)-2-((2-nitrophenyl)amino)-1-(piperidin-1-yl)-3-(p-tolyl)propan-1-one. Reaction of 1-fluoro-2-nitrobezene with (S)-2-amino-1-(piperidin-1-yl)-3-(p-tolyl)propan-1-one yielded the product as yellow solid (36%). $^1$H NMR (400 MHz, CDCl$_3$) δ 8.64 (d, J=7.2 Hz, 1H), 8.17 (dd, J=8.5, 1.4 Hz, 1H), 7.39-7.33 (m, 1H), 7.16-7.00 (m, 4H), 6.70-6.58 (m, 2H), 4.71 (q, J=7.0 Hz, 1H), 3.67-3.47 (m, 2H), 3.43-3.29 (m, 1H), 3.22-3.03 (m, 3H), 2.31 (s, 3H), 1.73-1.39 (m, 5H), 1.31-1.13 (m, 2H). $^{13}$C NMR (101 MHz, CDCl$_3$) δ 168.83, 143.80, 136.83, 135.95, 133.03, 129.38, 129.27, 127.18, 115.66, 113.57, 54.45, 46.49, 43.40, 38.99, 26.09, 25.43, 24.30, 21.09.

(S)-1-(3-methoxyazetidin-1-yl)-2-((2-nitrophenyl)amino)-3-(p-tolyl)propan-1-one. Reaction of 1-fluoro-2-nitrobezene with (S)-2-amino-1-(3-methoxyazetidin-1-yl)-3-(p-tolyl)propan-1-one yielded the product as yellow solid (46%). $^1$H NMR (400 MHz, CDCl$_3$) δ 8.36 (t, J=5.6 Hz, 1H), 8.19-8.08 (m, 1H), 7.41 (t, J=7.7 Hz, 1H), 7.22-7.12 (m, 4H), 6.68 (t, J=7.5 Hz, 2H), 4.27-3.99 (m, 2H), 3.99-3.71 (m, 3H), 3.58-3.40 (m, 1H), 3.26-3.05 (m, 5H), 2.33 (s, 3H). $^{13}$C NMR (101 MHz, CDCl$_3$) δ 170.48, 170.20, 143.53, 137.23, 137.17, 136.47, 136.45, 132.69, 132.39, 132.35, 129.62, 129.59, 129.20, 127.01, 116.36, 116.33, 113.69, 113.64, 69.04, 68.81, 57.49, 57.38, 56.95, 56.82, 56.01, 55.44, 38.45, 38.37, 21.10.

(S)-1-(3-(chloromethyl)-3-(hydroxymethyl)azetidin-1-yl)-2-((2-nitrophenyl)amino)-3-(p-tolyl)propan-1-one. Reaction of 1-fluoro-2-nitrobezene with (S)-2-amino-1-(3-(chloromethyl)-3-(hydroxymethyl)azetidin-1-yl)-3-(p-tolyl)propan-1-one yielded the product as yellow solid (40%).

methyl (S)-1-(2-((2-nitrophenyl)amino)-3-(p-tolyl)propanoyl)azetidine-3-carboxylate. Reaction of 1-fluoro-2-nitrobezene with methyl (S)-1-(2-amino-3-(p-tolyl)propanoyl)azetidine-3-carboxylate yielded the product as yellow solid (64%). $^1$H NMR (400 MHz, CDCl$_3$) δ 8.33 (dd, J=11.6, 6.6 Hz, 1H), 8.18-8.05 (m, 1H), 7.50-7.35 (m, 1H), 7.20-7.08 (m, 3H), 6.77-6.58 (m, 2H), 4.24-3.99 (m, 3H), 3.88-3.70 (m, 1H), 3.71-3.58 (m, 3H), 3.50-3.39 (m, 1H), 3.24-3.14 (m, 1H), 3.08 (ddd, J=15.1, 8.1, 4.9 Hz, 1H), 2.88 (d, J=31.0 Hz, 1H), 2.32 (s, 3H). $^{13}$C NMR (101 MHz, CDCl$_3$) δ 172.07, 171.86, 170.34, 170.13, 143.44, 137.28, 137.24, 136.51, 136.46, 132.60, 132.56, 132.41, 132.40, 129.62, 129.57, 129.19, 127.01, 116.44, 116.41, 113.68, 113.63, 56.74, 56.65, 52.91, 52.84, 52.38, 52.29, 50.71, 50.68, 38.39, 38.37, 32.26, 32.19, 21.12.

(S)-2-((3-nitropyridin-2-yl)amino)-1-(2-oxa-6-azaspiro[3.3]heptan-6-yl)-3-(p-tolyl)propan-1-one. Reaction of 2-fluoro-3-nitro pyridine with (S)-2-amino-1-(2-oxa-6-azaspiro[3.3]heptan-6-yl)-3-(p-tolyl)propan-1-one yielded the product as yellow solid (76%).

(S)-1-(2-((3-nitropyridin-2-yl)amino)-3-(p-tolyl)propanoyl)azetidine-3-carbonitrile Reaction of 2-fluoro-3-nitro pyridine with (S)-1-(2-amino-3-(p-tolyl)propanoyl)azetidine-3-carbonitrile yielded the product as yellow solid (73%). $^1$H NMR (400 MHz, CDCl$_3$) δ 8.56-8.34 (m, 3H), 7.24-7.09 (m, 4H), 6.73 (ddd, J=11.1, 8.3, 4.6 Hz, 1H), 4.83-4.63 (m, 1H), 4.49-4.38 (m, 0.5H), 4.33-3.98 (m, 3H), 3.66 (t, J=8.8 Hz, 0.5H), 3.35-2.98 (m, 4H), 2.41-2.33 (m, 3H). $^{13}$C NMR (101 MHz, CDCl$_3$) δ 171.96, 171.26, 155.30, 155.16, 151.08, 151.07, 137.70, 137.20, 135.38, 135.34, 132.93, 132.83, 129.65, 129.50, 129.16, 129.15, 119.12, 118.75, 112.99, 112.72, 53.64, 53.04, 52.89, 52.80, 51.25, 51.00, 38.67, 38.20, 21.15, 17.44, 17.11.

(S)-2-((2-nitrophenyl)amino)-1-(2-oxa-6-azaspiro[3.3]heptan-6-yl)-3-(p-tolyl)propan-1-one. Reaction of (S)-2-((2-nitrophenyl)amino)-3-(p-tolyl)propanoic acid with 2-Oxa-6-azaspiro[3.3]heptane hemioxalate yielded the product as yellow solid (83%). $^1$H NMR (400 MHz, CDCl$_3$) δ 8.40 (d, J=6.6 Hz, 1H), 8.19 (d, J=8.4 Hz, 1H), 7.44 (dd, J=7.7 Hz, 1H), 7.19 (ddd, J=8.0 Hz, 4H), 6.71 (dd, J=14.2, 8.1 Hz, 2H), 4.60 (d, J=6.9 Hz, 1H), 4.52 (d, J=7.0 Hz, 1H), 4.39 (d, J=6.9 Hz, 1H), 4.29 (d, J=7.0 Hz, 1H), 4.21 (dd, J=12.1, 6.5 Hz, 1H), 4.10 (d, J=10.9 Hz, 1H), 3.99 (d, J=10.9 Hz, 1H), 3.43 (d, J=9.5 Hz, 1H), 3.29 (dd, J=13.5, 4.8 Hz, 1H), 3.20 (d, J=9.4 Hz, 1H), 3.05 (dd, J=13.5, 7.0 Hz, 1H), 2.91 (d, J=29.9 Hz, 1H), 2.36 (s, 3H). $^{13}$C NMR (101 MHz, CDCl$_3$)

δ 170.12, 143.36, 137.47, 136.51, 132.79, 132.38, 129.54, 129.38, 127.12, 116.46, 113.51, 80.55, 80.32, 59.77, 57.82, 56.91, 38.54, 37.71, 21.11.

(S)-1-morpholino-2-((2-nitrophenyl)amino)-3-(p-tolyl)propan-1-one. Reaction of (S)-2-((2-nitrophenyl)amino)-3-(p-tolyl)propanoic acid with morpholine yielded the product as yellow solid (68%). $^1$H NMR (400 MHz, CDCl$_3$) δ 8.66 (d, J=7.3 Hz, 1H), 8.15 (dd, J=8.6, 1.4 Hz, 1H), 7.41 (ddd, J=8.2, 1.0 Hz, 1H), 7.16-7.07 (m, 4H), 6.73 (d, J=8.5 Hz, 1H), 6.66 (ddd, J=7.0, 1.0 Hz, 1H), 4.71 (dd, J=13.8, 7.7 Hz, 1H), 3.69-3.42 (m, 5H), 3.39-3.29 (m, 1H), 3.20-2.97 (m, 4H), 2.32 (s, 3H). $^{13}$C NMR (101 MHz, CDCl$_3$) δ 169.43, 143.48, 137.13, 136.18, 132.64, 129.50, 129.35, 127.20, 115.91, 113.47, 66.56, 65.93, 53.86, 45.90, 42.44, 39.16, 21.11.

(S)-1-(4-hydroxypiperidin-1-yl)-2-((2-nitrophenyl)amino)-3-(p-tolyl)propan-1-one. Reaction of (S)-2-((2-nitrophenyl)amino)-3-(p-tolyl)propanoic acid with 4-hydroxypiperidine hydrochloride yielded the product as yellow solid (86%). $^1$H NMR (400 MHz, CDCl$_3$) δ 8.17 (dd, J=8.5, 1.2 Hz, 1H), 7.42-7.33 (m, 1H), 7.15-7.05 (m, 4H), 6.70-6.62 (m, 2H), 4.73 (t, J=6.9 Hz, 1H), 4.05-3.94 (m, 1H), 3.87 (dtd, J=11.1, 7.5, 3.8 Hz, 1H), 3.58 (ddd, J=19.5, 14.6, 7.1 Hz, 1H), 3.35-3.19 (m, 2H), 2.98-2.85 (m, 1H), 2.31 (s, 3H), 1.89-1.66 (m, 2H), 1.55-1.38 (m, 2H), 1.11-0.95 (m, 1H). $^{13}$C NMR (101 MHz, CDCl$_3$) δ 169.20, 169.18, 143.63, 137.03, 136.99, 136.12, 136.10, 132.80, 132.77, 132.63, 129.50, 129.43, 129.27, 127.22, 115.90, 113.50, 66.46, 54.43, 54.34, 46.84, 42.67, 42.48, 39.60, 39.48, 39.05, 38.92, 33.89, 33.76, 33.53, 33.48, 21.08, 8.70.

tert-butyl (S)-6-(2-((2-nitrophenyl)amino)-3-(p-tolyl)propanoyl)-2,6-diazaspiro[3.3]heptane-2-carboxylate. Reaction of (S)-2-((2-nitrophenyl)amino)-3-(p-tolyl)propanoic acid with tert-butyl 2,6-diazaspiro[3.3]heptane-2-carboxylate oxalate yielded the product as yellow solid (73%). $^1$H NMR (400 MHz, CDCl$_3$) δ 8.36 (d, J=6.8 Hz, 1H), 8.11 (dd, J=14.6, 6.9 Hz, 1H), 7.38 (dd, J=15.5, 7.8 Hz, 1H), 7.19-7.10 (m, 4H), 6.65 (t, J=7.7 Hz, 2H), 4.16 (dd, J=12.1, 6.9 Hz, 1H), 4.01 (d, J=10.9 Hz, 1H), 3.90 (d, J=10.8 Hz, 1H), 3.83 (d, J=9.3 Hz, 1H), 3.73 (d, J=9.4 Hz, 1H), 3.64 (d, J=9.3 Hz, 1H), 3.49 (d, J=9.4 Hz, 1H), 3.45 (d, J=9.4 Hz, 1H), 3.23 (dd, J=13.4, 4.9 Hz, 1H), 3.10 (d, J=9.4 Hz, 1H), 2.99 (dd, J=13.4, 7.4 Hz, 1H), 2.32 (s, 3H), 1.35 (s, 9H). $^{13}$C NMR (101 MHz, CDCl$_3$) δ 169.91, 155.59, 143.31, 137.38, 136.50, 132.75, 132.28, 129.55, 129.34, 127.01, 116.37, 113.50, 79.80, 60.30, 58.29, 56.50, 38.57, 32.07, 28.24, 21.05, 14.17.

(S)-1-(3-(methoxymethyl)azetidin-1-yl)-2-((2-nitrophenyl)amino)-3-(p-tolyl)propan-1-one. Reaction of (S)-2-((2-nitrophenyl)amino)-3-(p-tolyl)propanoic acid with 3-(Methoxymethyl)azetidine hydrochloride yielded the product as yellow solid (39%). $^1$H NMR (400 MHz, CDCl$_3$) δ 8.37 (s, 1H), 8.16 (d, J=9.1 Hz, 1H), 7.77 (dd, J=8.6, 5.3 Hz, 1H), 7.46-7.38 (m, 2H), 7.22-7.14 (m, 4H), 6.78-6.62 (m, 2H), 4.29-4.18 (m, 1H), 4.01 (ddd, J=34.0, 9.5 Hz, 1H), 3.84-3.56 (m, 1H), 3.43 (dd, J=16.4, 7.5 Hz, 1H), 3.38-3.15 (m, 6H), 3.15-3.03 (m, 2H), 2.71-2.44 (m, 2H), 2.34 (d, J=2.4 Hz, 3H). $^{13}$C NMR (101 MHz, CDCl$_3$) δ 170.59, 170.49, 143.51, 143.48, 137.20, 137.16, 136.50, 136.37, 132.68, 132.62, 129.62, 129.57, 129.31, 129.27, 127.07, 127.04, 126.87, 126.56, 116.51, 116.41, 116.29, 113.62, 113.56, 111.57, 73.78, 73.60, 59.05, 58.95, 56.76, 56.14, 53.46, 53.39, 50.84, 50.78, 38.46, 38.34, 28.81, 28.50, 21.12.

(S)-1-(3-hydroxyazetidin-1-yl)-2-((2-nitrophenyl)amino)-3-(p-tolyl)propan-1-one. Reaction of (S)-2-((2-nitrophenyl)amino)-3-(p-tolyl)propanoic acid with 3-hydroxyazetidine, HCl yielded the product as yellow solid (40%).

(S)-1-(2-((2-nitrophenyl)amino)-3-(p-tolyl)propanoyl)azetidine-3-carbonitrile. Reaction of (S)-2-((2-nitrophenyl)amino)-3-(p-tolyl)propanoic acid with azetidine-3-carbonitrile, HCl yielded the product as yellow solid (45%). $^1$H NMR (400 MHz, CDCl$_3$) δ 8.32 (dd, J=15.5, 6.4 Hz, 1H), 8.18 (d, J=8.6 Hz, 1H), 7.47 (dd, J=14.1, 7.0 Hz, 1H), 7.31-7.19 (m, 4H), 6.75 (dd, J=8.3, 7.3 Hz, 1H), 6.72-6.67 (m, 1H), 4.31-4.04 (m, 3H), 3.71 (t, J=8.4 Hz, 0.5H), 3.50 (t, J=9.1 Hz, 0.5H), 3.37 (dd, J=13.8, 5.0 Hz, 0.5H), 3.31-3.01 (m, 4H), 2.38 (d, J=1.9 Hz, 3H). $^{13}$C NMR (101 MHz, CDCl$_3$) δ 170.91, 170.52, 143.14, 143.10, 138.23, 138.03, 136.73, 136.67, 132.54, 132.41, 132.33, 132.07, 130.18, 129.85, 129.16, 129.10, 127.22, 127.09, 118.55, 118.52, 116.97, 116.86, 113.56, 113.36, 57.73, 56.84, 53.77, 53.52, 51.60, 51.40, 38.53, 38.27, 21.16, 21.14, 17.52, 17.44.

(S)-1-(3-(hydroxymethyl)azetidin-1-yl)-2-((2-nitrophenyl)amino)-3-(p-tolyl)propan-1-one. At 0° C., to a solution of methyl (S)-1-(2-((2-nitrophenyl)amino)-3-(p-tolyl)propanoyl)azetidine-3-carboxylate (1 eq.) in THF was added lithium borohydride (1 eq.). The mixture was slowly warmed to room temperature and stirred for overnight. Saturated sodium bicarbonate aqueous solution was added to quench the reaction. After extraction with ethyl acetate for three times the combined organic phase was concentrated and purified by flash chromatography using 80% ethyl acetate in hexanes as eluent, yielding the product as yellow solid (57%). $^1$H NMR (400 MHz, CDCl$_3$) δ 8.38 (t, J=6.5 Hz, 1H), 8.20-8.12 (m, 1H), 7.47-7.37 (m, 1H), 7.24-7.13 (m, 4H), 6.74-6.64 (m, 2H), 4.22 (dddd, J=6.7, 6.7, 6.7, 2.2 Hz, 1H), 4.05-3.91 (m, 1H), 3.83-3.72 (m, 1H), 3.70-3.36 (m, 4H), 3.24-3.02 (m, 2H), 2.66-2.41 (m, 1H), 2.34 (s, 3H). $^{13}$C NMR (101 MHz, CDCl$_3$) δ 170.34, 170.26, 143.58, 143.56, 137.19, 136.45, 136.35, 132.85, 132.78, 132.44, 132.37, 129.57, 129.53, 129.33, 129.28, 127.10, 127.03, 116.28, 116.23, 113.69, 113.59, 63.80, 63.51, 56.50, 56.15, 52.68, 52.67, 50.34, 50.32, 38.47, 38.39, 30.68, 30.45, 21.12, 21.10.

(S)-1-(tert-butyl) 3-(2-((2-nitrophenyl)amino)-3-(p-tolyl)propyl) azetidine-1,3-dicarboxylate. At room temperature, alcohol (1 eq.), carboxylic acid (1 eq.), EDC HCl (1.1 eq.) and DMAP (1.1 eq.) was mixed in dry DCM and the mixture was stirred at room temperature for overnight. After removing solvent, the residue was purified by flash chromatography using 20% ethyl acetate in hexanes as eluent. Giving product as yellow solid (76%). $^1$H NMR (400 MHz, CDCl$_3$) δ 8.23-8.10 (m, 2H), 7.49-7.35 (m, 1H), 7.17-7.05 (m, 4H), 6.97 (dd, J=15.5, 8.4 Hz, 1H), 6.74-6.59 (m, 1H), 4.33-4.24 (m, 1H), 4.20-3.99 (m, 5H), 3.40-3.27 (m, 1H), 2.95 (d, J=6.3 Hz, 2H), 2.31 (s, 3H), 1.44 (s, 9H). $^{13}$C NMR (101 MHz, CDCl$_3$) δ 172.43, 155.95, 144.39, 136.75, 136.27, 133.07, 132.37, 129.52, 129.10, 127.10, 115.92, 113.92, 79.91, 65.28, 52.37, 37.57, 31.99, 28.33, 21.04.

(S)-2-(2-((3-nitropyridin-2-yl)amino)-3-(p-tolyl)propyl)isoindoline-1,3-dione. At 0° C., to a solution of alcohol (1 eq.), phthalimide (2 eq.) and triphenylphosphine (2 eq.) was added DIAD (2 eq.) dropwise. The mixture was warmed to room temperature and stirred for overnight. After removing solvent, the residue was purified using 20% ethyl acetate in hexanes as eluent. Giving product as yellow solid (84%). $^1$H NMR (400 MHz, CDCl$_3$) δ 8.27 (dd, J=8.3, 1.6 Hz, 1H), 8.22 (d, J=8.2 Hz, 1H), 8.06 (dd, J=4.4, 1.6 Hz, 1H), 7.86 (ddd, J=6.5, 3.3, 3.3 Hz, 1H), 7.77-7.72 (m, 2H), 7.68-7.63 (m, 2H), 7.17 (d, J=7.9 Hz, 2H), 7.10-7.04 (m, 2H), 6.43 (dd, J=8.3, 4.5 Hz, 1H), 5.13 (dddd, J=17.8, 17.8, 8.9, 8.9 Hz, 1H), 4.02-3.88 (m, 2H), 3.07-2.90 (m, 2H), 2.27 (s, 3H). $^{13}$C NMR (101 MHz, CDCl$_3$) δ 168.36, 155.08, 152.47, 136.29, 135.09, 134.30, 133.88, 133.77, 131.88, 129.30, 129.04, 123.58, 123.18, 111.83, 50.87, 41.63, 38.64, 21.03.

(S)—N2-(3-nitropyridin-2-yl)-3-(p-tolyl)propane-1,2-diamine. At 0° C., hydrazine (10 eq.) was added to a solution of starting material (1 eq.) in methanol dropwise. The mixture was warmed to room temperature and stirred for 3 hours. After removing solvent, the residue was purified using 50% ethyl acetate in hexanes as eluent. Giving product as yellow solid (60%). $^1$H NMR (400 MHz, CDCl$_3$) δ 8.40-8.31 (m, 3H), 7.10 (dd, J=19.7, 8.0 Hz, 4H), 6.60 (dd, J=8.0, 4.8 Hz, 1H), 4.71-4.54 (m, 1H), 2.99-2.78 (m, 4H), 2.29 (s, 3H).

(S)-2-hydroxy-N-(2-((3-nitropyridin-2-yl)amino)-3-(p-tolyl)propyl)acetamide. To a solution of acid (1 eq.) in dichloromethane was added HATU (1.1 eq.), followed by addition of amine (1 eq.) and DIPEA (1.2 eq.). The mixture was stirred at room temperature for overnight. After removing solvent, the residue was purified using 70% ethyl acetate in hexanes as eluent. Giving product as yellow solid (87%).

(S)-2-((3-nitropyridin-2-yl)amino)-3-(p-tolyl)propanal. At room temperature, to a solution of starting material in dichloromethane was added Dess-Martin periodinane (2 eq.). The solution was stirred at room temperature for 2 hours. After removing solvent, the residue was purified using 30% ethyl acetate in hexanes as eluent, giving product as yellow solid (69%). $^1$H NMR (400 MHz, CDCl$_3$) δ 9.66 (s, 1H), 8.42 (d, J=8.3 Hz, 1H), 8.35 (d, J=4.5 Hz, 1H), 7.14 (s, 4H), 6.73 (dd, J=8.3, 4.6 Hz, 1H), 4.90-4.73 (m, 1H), 3.32-3.03 (m, 2H), 2.32 (s, 3H). $^{13}$C NMR (101 MHz, CDCl$_3$) δ 199.91, 155.12, 151.55, 137.00, 135.32, 132.53, 129.70, 129.06, 113.10, 61.59, 34.98, 21.07.

(S)—N1-methyl-N2-(3-nitropyridin-2-yl)-3-(p-tolyl)propane-1,2-diamine. At room temperature, to a solution of aldehyde (1 eq.) was added methyl amine (1 eq., solution in ethanol) and sodium triacetoxyborohydride (2 eq.). The mixture was stirred at room temperature for 3 hours. After removing solvent, the residue was purified using 80% ethyl acetate in hexanes as eluent, giving product as yellow solid (40%). $^1$H NMR (400 MHz, CDCl$_3$) δ 8.41-8.35 (m, 2H), 8.30 (d, J=7.7 Hz, 1H), 7.11 (q, J=8.0 Hz, 4H), 6.67-6.59 (m, 1H), 4.86-4.74 (m, 1H), 3.05-2.74 (m, 4H), 2.46 (s, 3H), 2.30 (s, 3H). $^{13}$C NMR (101 MHz, CDCl$_3$) δ 155.64, 152.51, 136.14, 135.33, 134.43, 129.21, 129.18, 111.88, 54.13, 51.44, 38.68, 36.03, 21.04.

(S)-2-hydroxy-N-methyl-N-(2-((3-nitropyridin-2-yl)amino)-3-(p-tolyl)propyl)acetamide. To a solution of acid (1 eq.) in dichloromethane was added HATU (1.1 eq.), followed by addition of amine (1 eq.) and DIPEA (1.2 eq.). The mixture was stirred at room temperature for overnight. After removing solvent, the residue was purified using 70% ethyl acetate in hexanes as eluent. Giving product as yellow solid (61%). $^1$H NMR (400 MHz, CDCl$_3$) δ 8.38-8.32 (m, 2H), 7.16-7.04 (m, 4H), 6.68-6.56 (m, 1H), 5.02-4.84 (m, 1H), 3.97 (q, J=15.4 Hz, 1H), 3.77 (dt, J=13.8, 9.0 Hz, 1H), 3.01-2.83 (m, 4H), 2.80 (d, J=7.2 Hz, 3H), 2.28 (d, J=2.5 Hz, 3H). $^{13}$C NMR (101 MHz, CDCl$_3$) δ 172.57, 172.07, 155.61, 155.35, 152.38, 152.13, 135.40, 135.36, 129.53, 129.45, 129.30, 129.22, 129.04, 129.01, 128.91, 128.85, 128.11, 112.71, 112.55, 112.07, 111.81, 59.85, 51.85, 51.64, 50.64, 50.24, 38.71, 38.62, 33.79, 21.59, 21.04.

Synthesis with General Procedure (M).

(S)-2-((3-aminopyridin-2-yl)amino)-3-(p-tolyl)propan-1-ol

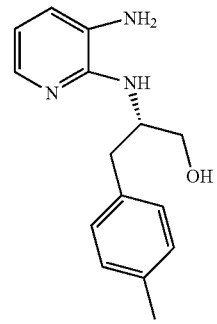 [SMILES: Cc1ccc(C[C@@H](CO)Nc2ncccc2N)cc1]

Reaction of (S)-2-((3-nitropyridin-2-yl)amino)-3-(p-tolyl)propan-1-ol with palladium on charcoal yielded the product as brown solid.

(S)—N2-(1-methoxy-3-(p-tolyl)propan-2-yl)pyridine-2,3-diamine. Reaction of (S)—N-(1-methoxy-3-(p-tolyl)propan-2-yl)-3-nitropyridin-2-amine with palladium on charcoal yielded the product as brown solid.

(S)—N3-(1-methoxy-3-(p-tolyl)propan-2-yl)pyridine-2,3-diamine. Reaction of (S)—N-(1-methoxy-3-(p-tolyl)propan-2-yl)-2-nitropyridin-3-amine with palladium on charcoal yielded the product as brown solid.

(S)-2-((2-aminophenyl)amino)-N-methyl-3-(p-tolyl)propenamide. Reaction of (S)—N-methyl-2-((2-nitrophenyl)amino)-3-(p-tolyl)propenamide with Raney nickel yielded the product as brown solid.

(S)-2-((2-aminophenyl)amino)-1-(azetidin-1-yl)-3-(p-tolyl)propan-1-one. Reaction of (S)-1-(azetidin-1-yl)-2-((2-nitrophenyl)amino)-3-(p-tolyl)propan-1-one with Raney nickel yielded the product as brown solid.

(S)-2-((2-aminophenyl)amino)-1-(pyrrolidin-1-yl)-3-(p-tolyl)propan-1-one. Reaction of (S)-2-((2-nitrophenyl)amino)-1-(pyrrolidin-1-yl)-3-(p-tolyl)propan-1-one with Raney nickel yielded the product as brown solid.

(S)-2-((2-aminophenyl)amino)-1-(piperidin-1-yl)-3-(p-tolyl)propan-1-one. Reaction of (S)-2-((2-nitrophenyl)amino)-1-(piperidin-1-yl)-3-(p-tolyl)propan-1-one with Raney nickel yielded the product as brown solid.

methyl (S)-1-(2-((2-aminophenyl)amino)-3-(p-tolyl)propanoyl)azetidine-3-carboxylate. Reaction of methyl (S)-1-(2-((2-nitrophenyl)amino)-3-(p-tolyl)propanoyl)azetidine-3-carboxylate with Raney nickel yielded the product as brown solid.

(S)-2-((2-aminophenyl)amino)-1-(3-methoxyazetidin-1-yl)-3-(p-tolyl)propan-1-one. Reaction of (S)-1-(3-methoxyazetidin-1-yl)-2-((2-nitrophenyl)amino)-3-(p-tolyl)propan-1-one with Raney nickel yielded the product as brown solid.

(S)-2-((2-aminophenyl)amino)-1-(3-(chloromethyl)-3-(hydroxymethyl)azetidin-1-yl)-3-(p-tolyl)propan-1-one. Reaction of (S)-1-(3-(chloromethyl)-3-(hydroxymethyl)azetidin-1-yl)-2-((2-nitrophenyl)amino)-3-(p-tolyl)propan-1-one with Raney nickel yielded the product as brown solid.

(S)-3-(2-((2-aminophenyl)amino)-3-(p-tolyl)propyl) 1-(tert-butyl) azetidine-1,3-dicarboxylate. Reaction of (S)-

1-(tert-butyl) 3-(2-((2-nitrophenyl)amino)-3-(p-tolyl)propyl) azetidine-1,3-dicarboxylate with Raney nickel yielded the product as brown solid.

(S)-2-((2-aminophenyl)amino)-1-(2-oxa-6-azaspiro[3.3]heptan-6-yl)-3-(p-tolyl)propan-1-one. Reaction of (S)-2-((2-nitrophenyl)amino)-1-(2-oxa-6-azaspiro[3.3]heptan-6-yl)-3-(p-tolyl)propan-1-one with Raney nickel yielded the product as brown solid.

(S)-2-((2-aminophenyl)amino)-1-morpholino-3-(p-tolyl)propan-1-one (WZ-II-109). Reaction of (S)-1-morpholino-2-((2-nitrophenyl)amino)-3-(p-tolyl)propan-1-one with Raney nickel yielded the product as brown solid.

(S)-2-((2-aminophenyl)amino)-1-(3-(hydroxymethyl)azetidin-1-yl)-3-(p-tolyl)propan-1-one (WZ-II-120). Reaction of (S)-1-(3-(hydroxymethyl)azetidin-1-yl)-2-((2-nitrophenyl)amino)-3-(p-tolyl)propan-1-one with Raney nickel yielded the product as brown solid.

(S)-2-((2-aminophenyl)amino)-1-(4-hydroxypiperidin-1-yl)-3-(p-tolyl)propan-1-one. Reaction of (S)-1-(4-hydroxypiperidin-1-yl)-2-((2-nitrophenyl)amino)-3-(p-tolyl)propan-1-one with Raney nickel yielded the product as brown solid.

tert-butyl (S)-6-(2-((2-aminophenyl)amino)-3-(p-tolyl)propanoyl)-2,6-diazaspiro[3.3]heptane-2-carboxylate. Reaction of tert-butyl (S)-6-(2-((2-nitrophenyl)amino)-3-(p-tolyl)propanoyl)-2,6-diazaspiro[3.3]heptane-2-carboxylate with Raney nickel yielded the product as brown solid.

(S)—N-(2-((3-aminopyridin-2-yl)amino)-3-(p-tolyl)propyl)-2-hydroxyacetamide. Reaction of (S)-2-hydroxy-N-(2-((3-nitropyridin-2-yl)amino)-3-(p-tolyl)propyl)acetamide with palladium on charcoal yielded the product as brown solid.

(S)—N-(2-((3-aminopyridin-2-yl)amino)-3-(p-tolyl)propyl)-2-hydroxy-N-methylacetamide. Reaction of (S)-2-hydroxy-N-methyl-N-(2-((3-nitropyridin-2-yl)amino)-3-(p-tolyl)propyl)acetamide with palladium on charcoal yielded the product as brown solid.

(S)-2-((2-aminophenyl)amino)-1-(3-(methoxymethyl)azetidin-1-yl)-3-(p-tolyl)propan-1-one. Reaction of (S)-1-(3-(methoxymethyl)azetidin-1-yl)-2-((2-nitrophenyl)amino)-3-(p-tolyl)propan-1-one with palladium on charcoal yielded the product as brown solid.

(S)-2-((3-aminopyridin-2-yl)amino)-1-(2-oxa-6-azaspiro[3.3]heptan-6-yl)-3-(p-tolyl)propan-1-on. Reaction of (S)-2-((3-nitropyridin-2-yl)amino)-1-(2-oxa-6-azaspiro[3.3]heptan-6-yl)-3-(p-tolyl)propan-1-one with palladium on charcoal yielded the product as brown solid.

(S)-2-((2-aminophenyl)amino)-1-(3-hydroxyazetidin-1-yl)-3-(p-tolyl)propan-1-one. Reaction of (S)-1-(3-hydroxyazetidin-1-yl)-2-((2-nitrophenyl)amino)-3-(p-tolyl)propan-1-one with palladium on charcoal yielded the product as brown solid.

(S)-1-(2-((2-aminophenyl)amino)-3-(p-tolyl)propanoyl)azetidine-3-carbonitrile. Reaction of (S)-1-(2-((2-nitrophenyl)amino)-3-(p-tolyl)propanoyl)azetidine-3-carbonitrile with palladium on charcoal yielded the product as brown solid.

(S)-1-(2-((3-aminopyridin-2-yl)amino)-3-(p-tolyl)propanoyl)azetidine-3-carbonitrile. Reaction of (S)-1-(2-((3-nitropyridin-2-yl)amino)-3-(p-tolyl)propanoyl)azetidine-3-carbonitrile with palladium on charcoal yielded the product as brown solid.

(S)-3-(2-((3-aminopyridin-2-yl)amino)-3-(p-tolyl)propoxy)propanenitrile. Reaction of (S)-3-(2-((3-nitropyridin-2-yl)amino)-3-(p-tolyl)propoxy)propanenitrile with palladium on charcoal yielded the product as brown solid.

Synthesis with General Procedure (N).

(S)-2-((3-((4-methylbenzyl)amino)pyridin-2-yl)amino)-3-(p-tolyl)propan-1-ol

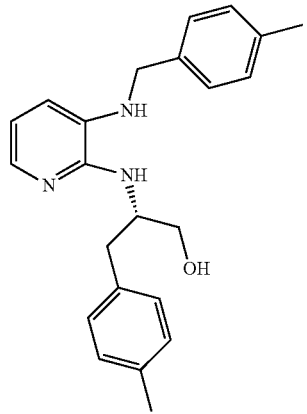 [SMILES: Cc1ccc(CNc2cccnc2N[C@H](CO)Cc2ccc(C)cc2)cc1]

Reaction of (S)-2-((3-aminopyridin-2-yl)amino)-3-(p-tolyl)propan-1-ol with 4-methyl benzyl bromide yielded the product as brown solid (50%). $^1$H NMR (400 MHz, CDCl$_3$) δ 7.58 (dd, J=5.1, 1.3 Hz, 1H), 7.20-7.13 (m, 4H), 7.06 (ddd, J=8.1, 8.1, 8.1 Hz, 4H), 6.75 (dd, J=7.6, 1.1 Hz, 1H), 6.58 (dd, J=7.6, 5.2 Hz, 1H), 4.39 (d, J=3.9 Hz, 1H), 4.16-4.04 (m, 3H), 3.86 (dd, J=10.9, 2.1 Hz, 1H), 3.66 (dd, J=10.9, 7.2 Hz, 1H), 3.05 (s, 1H), 3.00-2.93 (m, 1H), 2.81-2.73 (m, 1H), 2.38 (s, 3H), 2.30 (s, 3H). $^{13}$C NMR (101 MHz, CDCl$_3$) δ 149.89, 137.17, 136.18, 136.15, 135.37, 135.05, 131.53, 129.40, 129.28, 129.06, 127.74, 117.82, 114.15, 68.06, 56.58, 48.06, 37.56, 21.17, 21.05.

(S)—N2-(1-methoxy-3-(p-tolyl)propan-2-yl)-N3-(4-methylbenzyl)pyridine-2,3-diamine. Reaction of (S)—N2-(1-methoxy-3-(p-tolyl)propan-2-yl)pyridine-2,3-diamine with 4-methyl benzyl bromide yielded the product as brown solid (8%). $^1$H NMR (400 MHz, CDCl$_3$) δ 7.73 (d, J=4.2 Hz, 1H), 7.29-7.23 (m, 2H), 7.17 (dd, J=13.8, 7.9 Hz, 4H), 7.09 (d, J=7.8 Hz, 2H), 6.79-6.75 (m, 1H), 6.59 (dd, J=7.5, 5.1 Hz, 1H), 4.49 (q, J=11.9 Hz, 1H), 4.36 (s, 1H), 4.20 (s, 2H), 3.43 (ddd, J=22.2, 9.4, 4.4 Hz, 2H), 3.35 (s, 3H), 3.01 (dd, J=13.4, 5.6 Hz, 1H), 2.94-2.85 (m, 1H), 2.38 (s, 3H), 2.33 (s, 3H). $^{13}$C NMR (101 MHz, CDCl$_3$) δ 149.10, 137.32, 137.08, 135.68, 135.57, 131.48, 129.48, 129.31, 129.22, 128.98, 127.77, 127.10, 117.07, 113.67, 72.83, 58.92, 51.41, 48.12, 37.06, 21.15, 21.08.

(S)—N3-(1-methoxy-3-(p-tolyl)propan-2-yl)-N2-(4-methylbenzyl)pyridine-2,3-diamine. Reaction of (S)—N3-(1-methoxy-3-(p-tolyl)propan-2-yl)pyridine-2,3-diamine with 4-methyl benzyl bromide yielded the product as brown solid (12%). $^1$H NMR (400 MHz, CDCl$_3$) δ 7.76 (dd, J=5.0, 1.3 Hz, 1H), 7.25 (d, J=7.8 Hz, 2H), 7.18-7.12 (m, 2H), 7.08-7.02 (m, 4H), 6.90 (dd, J=7.5, 1.2 Hz, 1H), 6.59 (dd, J=7.5, 5.1 Hz, 1H), 4.51 (s, 2H), 3.55 (s, 1H), 3.39-3.33 (m, 1H), 3.33-3.24 (m, 4H), 2.82 (dddd, J=13.7, 13.7, 13.7, 6.6 Hz, 2H), 2.36 (s, 3H), 2.30 (s, 3H). $^{13}$C NMR (101 MHz, CDCl$_3$) δ 151.28, 138.63, 137.97, 137.34, 136.92, 136.64, 135.97, 135.08, 129.61, 129.23, 129.16, 129.13, 128.03, 127.10, 120.66, 113.34, 72.83, 65.23, 58.92, 54.58, 45.76, 37.14, 29.72, 21.14, 21.04.

(S)—N-methyl-2-((2-((4-methylbenzyl)amino)phenyl) amino)-3-(p-tolyl)propenamide Reaction of (S)-2-((2-aminophenyl)amino)-N-methyl-3-(p-tolyl)propenamide with 4-methyl benzyl bromide yielded the product as brown solid (17%). $^1$H NMR (400 MHz, CDCl$_3$) δ 7.23-7.06 (m, 4H), 7.02-6.92 (m, 4H), 6.88 (d, J=7.7 Hz, 2H), 6.72 (dt, J=14.9, 7.6 Hz, 1H), 6.26 (d, J=7.9 Hz, 1H), 5.64 (d, J=4.6 Hz, 1H), 3.83 (dt, J=29.6, 10.1 Hz, 3H), 3.23-3.07 (m, 1H), 3.01 (dd, J=14.3, 8.0 Hz, 1H), 2.57 (d, J=4.9 Hz, 2H), 2.39-2.24 (m, 6H). $^{13}$C NMR (101 MHz, CDCl$_3$) δ 173.65, 142.99, 137.06, 136.64, 136.53, 135.21, 133.64, 129.35, 129.20, 129.12, 128.67, 126.04, 123.67, 117.74, 110.69, 59.29, 58.67, 38.36, 25.93, 21.19, 21.13.

(S)-1-(azetidin-1-yl)-2-((2-((4-methylbenzyl)amino)phenyl)amino)-3-(p-tolyl)propan-1-one. Reaction of (S)-2-((2-aminophenyl)amino)-1-(azetidin-1-yl)-3-(p-tolyl)propan-1-one with 4-methyl benzyl bromide yielded the product as brown solid (41%). $^1$H NMR (400 MHz, CDCl$_3$) δ 7.22 (d, J=8.0 Hz, 2H), 7.16 (d, J=6.0 Hz, 4H), 7.10 (d, J=7.9 Hz, 2H), 6.83 (td, J=7.7, 1.7 Hz, 1H), 6.76-6.65 (m, 2H), 6.59 (t, J=9.1 Hz, 1H), 4.17 (s, 2H), 4.03-3.81 (m, 5H), 3.76 (td, J=8.8, 6.4 Hz, 1H), 3.38 (dt, J=15.0, 7.6 Hz, 1H), 3.06-2.90 (m, 2H), 2.37 (s, 3H), 2.33 (s, 3H), 2.12-1.90 (m, 2H). $^{13}$C NMR (101 MHz, CDCl$_3$) δ 172.62, 139.59, 136.62, 136.57, 136.36, 134.51, 129.32, 129.17, 129.09, 127.45, 121.83, 118.27, 116.90, 111.67, 56.49, 49.84, 48.03, 47.71, 39.20, 21.14, 21.10, 15.38.

(S)-2-((2-((4-methylbenzyl)amino)phenyl)amino)-1-(pyrrolidin-1-yl)-3-(p-tolyl)propan-1-one. Reaction of (S)-2-((2-aminophenyl)amino)-1-(pyrrolidin-1-yl)-3-(p-tolyl)propan-1-one with 4-methyl benzyl bromide yielded the product as brown solid (23%). $^1$H NMR (400 MHz, CDCl$_3$) δ 7.21 (d, J=8.0 Hz, 2H), 7.14 (dd, J=7.8, 4.1 Hz, 4H), 7.06 (d, J=7.8 Hz, 2H), 6.81 (td, J=7.7, 1.4 Hz, 1H), 6.73 (dd, J=7.7, 1.3 Hz, 1H), 6.63 (td, J=7.5, 1.2 Hz, 1H), 6.56 (dt, J=4.5, 2.3 Hz, 1H), 4.21-3.93 (m, 5H), 3.49-3.33 (m, 2H), 3.20-3.07 (m, 1H), 3.02-2.90 (m, 2H), 2.87-2.78 (m, 1H), 2.35 (s, 3H), 2.30 (s, 3H), 1.83-1.53 (m, 5H). $^{13}$C NMR (101 MHz, CDCl$_3$) δ 171.89, 140.17, 136.64, 136.52, 136.17, 134.70, 134.44, 129.35, 129.14, 128.96, 127.40, 122.09, 117.90, 111.38, 58.75, 47.93, 46.00, 45.70, 39.58, 25.85, 24.00, 21.13, 21.05.

(S)-2-((2-((4-methylbenzyl)amino)phenyl)amino)-1-(piperidin-1-yl)-3-(p-tolyl)propan-1-one. Reaction of (S)-2-((2-aminophenyl)amino)-1-(piperidin-1-yl)-3-(p-tolyl)propan-1-one with 4-methyl benzyl bromide yielded the product as brown solid (29%). $^1$H NMR (400 MHz, CDCl$_3$) δ 7.32-6.96 (m, 8H), 6.90-6.69 (m, 2H), 6.68-6.45 (m, 2H), 4.36 (s, 1H), 4.17-4.01 (m, 4H), 3.64-3.38 (m, 2H), 3.08 (ddd, J=48.2, 28.7, 6.4 Hz, 4H), 2.46-2.22 (m, 6H), 1.63-0.97 (m, 8H). $^{13}$C NMR (101 MHz, CDCl$_3$) δ 171.84, 140.32, 136.69, 136.50, 136.14, 134.76, 134.40, 129.40, 129.13, 129.02, 127.34, 122.28, 118.28, 117.77, 111.32, 55.92, 47.88, 46.33, 43.16, 39.79, 25.97, 25.54, 24.41, 21.13, 21.06.

methyl (S)-1-(2-((2-((4-methylbenzyl)amino)phenyl)amino)-3-(p-tolyl)propanoyl)azetidine-3-carboxylate. Reaction of methyl (S)-1-(2-((2-aminophenyl)amino)-3-(p-tolyl)propanoyl)azetidine-3-carboxylate with 4-methyl benzyl bromide yielded the product as brown solid (40%).

(S)-1-(3-methoxyazetidin-1-yl)-2-((2-((4-methylbenzyl)amino)phenyl)amino)-3-(p-tolyl)propan-1-one. Reaction of (S)-2-((2-aminophenyl)amino)-1-(3-methoxyazetidin-1-yl)-3-(p-tolyl)propan-1-one with 4-methyl benzyl bromide yielded the product as brown solid (38%).

(S)-1-(3-(chloromethyl)-3-(hydroxymethyl)azetidin-1-yl)-2-((2-((4-methylbenzyl)amino)phenyl)amino)-3-(p-tolyl)propan-1-one. Reaction of (S)-2-((2-aminophenyl)amino)-1-(3-(chloromethyl)-3-(hydroxymethyl)azetidin-1-yl)-3-(p-tolyl)propan-1-one with 4-methyl benzyl bromide yielded the product as brown solid (52%).

(S)-1-(tert-butyl) 3-(2-((2-((4-methylbenzyl)amino)phenyl)amino)-3-(p-tolyl)propyl) azetidine-1,3-dicarboxylate. Reaction of (S)-3-(2-((2-aminophenyl)amino)-3-(p-tolyl)propyl) 1-(tert-butyl) azetidine-1,3-dicarboxylate with 4-methyl benzyl bromide yielded the product as brown solid (47%). $^1$H NMR (400 MHz, CDCl$_3$) δ 7.27-7.22 (m, 2H), 7.20-7.15 (m, 2H), 7.12-7.05 (m, 4H), 6.85-6.74 (m, 3H), 6.71-6.64 (m, 1H), 4.24 (dd, J=11.2, 5.4 Hz, 1H), 4.19 (s, 1H), 4.14-4.08 (m, 1H), 4.06 (d, J=7.6 Hz, 3H), 3.83 (dt, J=11.5, 5.8 Hz, 1H), 3.30-3.21 (m, 1H), 2.94-2.79 (m, 2H), 2.38 (s, 3H), 2.32 (s, 3H), 1.45 (s, 9H). $^{13}$C NMR (101 MHz, CDCl$_3$) δ 172.54, 155.98, 138.60, 136.84, 136.42, 136.26, 134.86, 134.27, 129.30, 129.23, 129.17, 127.70, 120.61, 118.98, 114.63, 112.39, 79.84, 66.07, 53.39, 48.41, 37.62, 32.01, 28.36, 21.14, 21.04.

(S,E)-1-(3-(chloromethyl)-3-(hydroxymethyl)azetidin-1-yl)-3-(p-tolyl)-2-((2-((4-(p-tolyl)but-3-en-1-yl)amino)phenyl)amino)propan-1-one. Reaction of (S)-2-((2-aminophenyl)amino)-1-(3-(chloromethyl)-3-(hydroxymethyl)azetidin-1-yl)-3-(p-tolyl)propan-1-one with (E)-1-(4-bromobut-1-en-1-yl)-4-methylbenzene yielded the product as brown solid (4%).

(S,E)-1-(azetidin-1-yl)-3-(p-tolyl)-2-((2-((4-(p-tolyl)but-3-en-1-yl)amino)phenyl)amino)propan-1-one. Reaction of (S)-2-((2-aminophenyl)amino)-1-(azetidin-1-yl)-3-(p-tolyl)propan-1-one with (E)-1-(4-bromobut-1-en-1-yl)-4-methylbenzene yielded the product as brown solid (6%).

(S)-2-((2-((4-methylbenzyl)amino)phenyl)amino)-1-(2-oxa-6-azaspiro[3.3]heptan-6-yl)-3-(p-tolyl)propan-1-one. Reaction of (S)-2-((2-aminophenyl)amino)-1-(2-oxa-6-azaspiro[3.3]heptan-6-yl)-3-(p-tolyl)propan-1-one with 4-methyl benzyl bromide yielded the product as brown solid (44%). $^1$H NMR (400 MHz, CDCl$_3$) δ 7.27-7.22 (m, 2H), 7.19-7.06 (m, 6H), 6.88-6.80 (m, 1H), 6.68 (d, J=3.9 Hz, 2H), 6.64 (d, J=7.7 Hz, 1H), 4.60 (d, J=7.0 Hz, 1H), 4.53 (d, J=6.9 Hz, 1H), 4.45 (d, J=7.0 Hz, 1H), 4.26 (d, J=6.9 Hz, 1H), 4.02 (d, J=10.8 Hz, 1H), 3.95 (d, J=10.4 Hz, 1H), 3.86 (d, J=6.4 Hz, 1H), 3.66 (d, J=9.2 Hz, 1H), 3.13 (d, J=9.1 Hz, 1H), 3.05 (dd, J=13.0, 4.5 Hz, 1H), 2.89 (dd, J=12.9, 8.2 Hz, 1H), 2.37 (s, 3H), 2.33 (s, 3H). $^{13}$C NMR (101 MHz, CDCl$_3$) δ 172.71, 139.62, 136.79, 136.57, 136.44, 134.34, 134.27, 129.34, 129.23, 129.10, 127.55, 122.08, 118.33, 116.92, 111.87, 80.65, 80.46, 58.99, 57.02, 56.82, 48.12, 39.38, 37.36, 21.14, 21.07.

(2S)-2-((2-((cyclopropyl(p-tolyl)methyl)amino)phenyl)amino)-3-(p-tolyl)propan-1-ol. At room temperature, (S)-2-((2-aminophenyl)amino)-3-(p-tolyl)propan-1-ol (1.2 g, 4.69 mmol, 1 eq.), cyclopropyl(p-tolyl)methanol (0.91 g, 5.63 mmol, 1.2 eq.), pTSA (0.36 g, 1.88 mmol, 0.4 eq.) and magnesium sulfate (1.7 g, 14.07 mmol, 3 eq.) were mixed in toluene. The mixture was refluxed for 3 hours. After filtering off magnesium sulfate, solvent was removed under reduced pressure and the residue was purified by flash chromatography using 30% ethyl acetate in hexanes as eluent. Giving product as brown solid (13%).
Synthesis with General Procedure (O).

(2S)-1-(azetidin-1-yl)-3-(p-tolyl)-2-((2-((1-(p-tolyl)ethyl)amino)phenyl)amino)propan-1-one

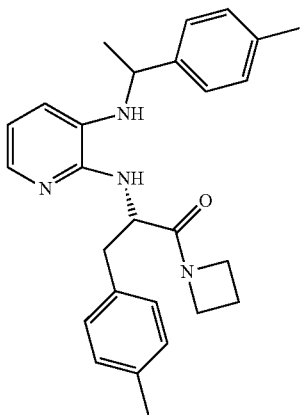

Reaction of (S)-2-((2-aminophenyl)amino)-1-(azetidin-1-yl)-3-(p-tolyl)propan-1-one with 1-(1-bromoethyl)-4-methylbenzene yielded the product as brown solid (18%).

(2S)-1-(3-(chloromethyl)-3-(hydroxymethyl)azetidin-1-yl)-3-(p-tolyl)-2-((2-((1-(p-tolyl)ethyl)amino)phenyl)amino)propan-1-one. Reaction of (S)-2-((2-aminophenyl)amino)-1-(3-(chloromethyl)-3-(hydroxymethyl)azetidin-1-yl)-3-(p-tolyl)propan-1-one with 1-(1-bromoethyl)-4-methylbenzene yielded the product as brown solid (11%).

(2S)-1-morpholino-3-(p-tolyl)-2-((2-((1-(p-tolyl)ethyl)amino)phenyl)amino)propan-1-one. Reaction of (S)-2-((2-aminophenyl)amino)-1-morpholino-3-(p-tolyl)propan-1-one with 1-(1-bromoethyl)-4-methylbenzene yielded the product as brown solid (26%). $^1$H NMR (400 MHz, CDCl$_3$) δ 7.24-7.06 (m, 8H), 6.77-6.66 (m, 2H), 6.60-6.53 (m, 1H), 6.38 (t, J=8.5 Hz, 1H), 4.45-4.24 (m, 2H), 3.74-3.33 (m, 5H), 3.24-2.75 (m, 7H), 2.37-2.25 (m, 6H), 1.43-1.23 (m, 3H). $^{13}$C NMR (101 MHz, CDCl$_3$) δ 172.47, 172.46, 142.68, 142.11, 140.00, 139.32, 136.51, 136.46, 136.37, 136.25, 134.79, 134.43, 133.78, 133.35, 129.41, 129.26, 129.21, 129.18, 125.71, 125.66, 123.29, 122.49, 119.90, 118.10, 117.67, 117.56, 112.83, 112.33, 66.69, 66.66, 66.05, 55.52, 55.38, 53.13, 52.85, 45.83, 45.77, 42.29, 42.26, 39.99, 39.67, 25.14, 24.88, 21.07, 21.06.

(2S)-1-(3-(hydroxymethyl)azetidin-1-yl)-3-(p-tolyl)-2-((2-((1-(p-tolyl)ethyl)amino)phenyl)amino)propan-1-one. Reaction of (S)-2-((2-aminophenyl)amino)-1-(3-(hydroxymethyl)azetidin-1-yl)-3-(p-tolyl)propan-1-one with 1-(1-bromoethyl)-4-methylbenzene with 1-(1-bromoethyl)-4-methylbenzene yielded the product as brown solid (29%).

N2-((S)-1-methoxy-3-(p-tolyl)propan-2-yl)-N3-(1-(p-tolyl)ethyl)pyridine-2,3-diamine. Reaction of (S)—N2-(1-methoxy-3-(p-tolyl)propan-2-yl)pyridine-2,3-diamine with 1-(1-bromoethyl)-4-methylbenzene with 1-(1-bromoethyl)-4-methylbenzene yielded the product as brown solid (10%). $^1$H NMR (400 MHz, CDCl$_3$) δ 7.65 (dd, J=5.0, 1.3 Hz, 1H), 7.20-7.09 (m, 8H), 6.54 (dd, J=7.6, 1.2 Hz, 1H), 6.45 (dd, J=7.6, 5.0 Hz, 1H), 4.42 (dt, J=12.8, 5.6 Hz, 3H), 3.49 (ddd, J=23.5, 9.4, 4.4 Hz, 2H), 3.40 (s, 3H), 3.05-2.93 (m, 2H), 2.35 (s, 3H), 2.34 (s, 3H), 1.50 (d, J=6.6 Hz, 3H). $^{13}$C NMR (101 MHz, CDCl$_3$) δ 149.21, 141.40, 137.11, 136.60, 135.66, 135.60, 130.38, 129.54, 129.33, 129.03, 125.75, 118.56, 113.71, 73.16, 58.97, 52.99, 51.53, 36.93, 25.17, 21.11.

(2S)-1-(2-oxa-6-azaspiro[3.3]heptan-6-yl)-3-(p-tolyl)-2-((2-((1-(p-tolyl)ethyl)amino)phenyl)amino)propan-1-one. Reaction of (S)-2-((2-aminophenyl)amino)-1-(2-oxa-6-azaspiro[3.3]heptan-6-yl)-3-(p-tolyl)propan-1-one with 1-(1-bromoethyl)-4-methylbenzene yielded the product as brown solid (18%). $^1$H NMR (400 MHz, CDCl$_3$) δ 7.22-7.00 (m, 8H), 6.78-6.55 (m, 3H), 6.48-6.35 (m, 1H), 4.65-4.49 (m, 2H), 4.47-4.22 (m, 3H), 4.07-3.93 (m, 2H), 3.91-3.73 (m, 1H), 3.69-3.46 (m, 1H), 3.28-3.02 (m, 2H), 2.98-2.85 (m, 1H), 2.33 (dd, J=9.6, 3.7 Hz, 6H), 1.40 (dd, J=34.0, 6.6 Hz, 3H). $^{13}$C NMR (101 MHz, CDCl$_3$) δ 173.08, 172.91, 142.53, 142.10, 139.44, 138.58, 136.64, 136.60, 136.41, 136.35, 134.64, 134.44, 134.12, 133.87, 129.43, 129.40, 129.25, 129.22, 129.19, 129.17, 125.77, 125.70, 122.69, 121.97, 118.47, 118.03, 117.75, 116.90, 113.22, 112.69, 80.65, 80.60, 80.55, 80.48, 59.00, 58.93, 57.28, 57.04, 57.01, 56.91, 53.12, 52.90, 39.51, 39.39, 37.36, 37.30, 25.09, 25.01, 21.08, 21.07.

(2S)-1-(4-hydroxypiperidin-1-yl)-3-(p-tolyl)-2-((2-((1-(p-tolyl)ethyl)amino)phenyl)amino)propan-1-one. Reaction of (S)-2-((2-aminophenyl)amino)-1-(4-hydroxypiperidin-1-yl)-3-(p-tolyl)propan-1-one with 1-(1-bromoethyl)-4-methylbenzene yielded the product as brown solid (26%). $^1$H NMR (400 MHz, CDCl$_3$) δ 7.28-7.01 (m, 8H), 6.80-6.67 (m, 2H), 6.63-6.49 (m, 1H), 6.41-6.26 (m, 1H), 4.40 (d, J=6.3 Hz, 1H), 4.29-4.18 (m, 1H), 4.01-3.89 (m, 1H), 3.81-3.62 (m, 1H), 3.55-3.22 (m, 2H), 3.11-2.73 (m, 3H), 2.38-2.23 (m, 6H), 1.66 (ddd, J=26.7, 22.1, 6.5 Hz, 2H), 1.43-1.20 (m, 4H), 1.16-0.49 (m, 2H). $^{13}$C NMR (101 MHz, CDCl$_3$) δ 172.58, 172.39, 172.36, 172.28, 142.83, 142.78, 142.23, 142.22, 140.22, 139.45, 136.38, 136.35, 136.30, 136.27, 136.19, 136.18, 135.03, 134.69, 134.68, 134.03, 134.00, 133.56, 129.48, 129.45, 129.41, 129.25, 129.19, 129.16, 125.73, 125.59, 123.30, 123.23, 122.40, 122.35, 120.27, 120.22, 118.24, 117.56, 117.49, 117.33, 117.27, 112.74, 112.70, 112.25, 112.12, 67.24, 66.92, 66.56, 66.17, 56.11, 56.01, 55.88, 55.78, 53.13, 52.87, 52.85, 42.94, 42.55, 42.40, 42.16, 39.97, 39.91, 39.77, 39.72, 39.41, 39.18, 38.92, 34.18, 34.06, 33.91, 33.79, 33.67, 33.65, 33.59, 25.21, 25.17, 25.01, 24.99, 21.08.

tert-butyl 6-((2S)-3-(p-tolyl)-2-((2-((1-(p-tolyl)ethyl)amino)phenyl)amino)propanoyl)-2,6-diazaspiro[3.3]heptane-2-carboxylate. Reaction of tert-butyl (S)-6-(2-((2-aminophenyl)amino)-3-(p-tolyl)propanoyl)-2,6-diazaspiro[3.3]heptane-2-carboxylate with 1-(1-bromoethyl)-4-methylbenzene yielded the product as brown solid (20%). $^1$H NMR (400 MHz, CDCl$_3$) δ 7.23-7.06 (m, 8H), 6.82-6.54 (m, 3H), 6.42 (dd, J=17.8, 7.7 Hz, 1H), 4.49-4.29 (m, 1H), 4.04-3.43 (m, 10H), 3.17 (ddd, J=24.5, 13.3, 5.9 Hz, 2H), 2.99-2.87 (m, 1H), 2.34 (dd, J=13.7, 7.3 Hz, 6H), 1.48-1.20 (m, 12H). $^{13}$C NMR (101 MHz, CDCl$_3$) δ 173.03, 172.85, 155.72, 155.71, 142.55, 142.13, 139.38, 138.53, 136.68, 136.62, 136.37, 136.32, 134.61, 134.40, 134.11, 133.88, 133.71, 132.51, 129.61, 129.43, 129.25, 125.79, 125.71, 123.87, 122.68, 121.96, 119.45, 118.33, 118.07, 117.81, 116.83, 115.44, 114.55, 113.22, 112.72, 79.89, 79.88, 60.41, 59.59, 59.51, 57.88, 57.68, 57.23, 56.83, 53.12, 52.91, 39.49, 39.37, 31.79, 31.74, 28.31, 25.07, 25.01, 21.07, 14.22.

2-hydroxy-N-((2S)-3-(p-tolyl)-2-((3-((1-(p-tolyl)ethyl)amino)pyridin-2-yl)amino)propyl)acetamide. Reaction of (S)—N-(2-((3-aminopyridin-2-yl)amino)-3-(p-tolyl)propyl)-2-hydroxyacetamide with 1-(1-bromoethyl)-4-methylbenzene yielded the product as brown solid (17%). ¹H NMR (400 MHz, CDCl₃) δ 7.48 (d, J=4.3 Hz, 1H), 7.13 (dd, J=22.4, 7.1 Hz, 8H), 6.57-6.32 (m, 2H), 4.74 (s, 1H), 4.29 (dd, J=14.4, 7.5 Hz, 2H), 4.00 (s, 2H), 3.56-3.34 (m, 3H), 2.30 (d, J=2.9 Hz, 6H), 1.44 (d, J=6.4 Hz, 3H). ¹³C NMR (101 MHz, CDCl₃) δ 172.89, 149.17, 141.20, 136.69, 136.15, 134.80, 129.35, 129.22, 125.73, 118.75, 113.78, 62.11, 53.22, 52.77, 44.41, 38.83, 29.70, 24.93, 21.04.

2-hydroxy-N-((2S)-3-(p-tolyl)-2-((3-((1-(p-tolyl)ethyl)amino)pyridin-2-yl)amino)propyl)acetamide. Reaction of (S)—N-(2-((3-aminopyridin-2-yl)amino)-3-(p-tolyl)propyl)-2-hydroxyacetamide with 1-(1-bromoethyl)-4-methylbenzene yielded the product as brown solid (17%). ¹H NMR (400 MHz, CDCl₃) δ 7.41 (d, J=4.1 Hz, 1H), 7.28-6.96 (m, 8H), 6.57-6.34 (m, 2H), 4.41-4.17 (m, 2H), 4.05 (s, 2H), 3.62-3.38 (m, 2H), 2.31 (s, 6H), 1.48 (d, J=6.1 Hz, 3H). ¹³C NMR (101 MHz, CDCl₃) δ 173.44, 148.74, 140.96, 136.65, 136.28, 134.43, 129.34, 129.24, 125.67, 118.78, 113.87, 62.04, 52.93, 44.41, 44.22, 38.47, 29.71, 25.07, 21.09.

2-hydroxy-N-methyl-N-((2S)-3-(p-tolyl)-2-((3-((1-(p-tolyl)ethyl)amino)pyridin-2-yl)amino)propyl)acetamide. Reaction of (S)—N-(2-((3-aminopyridin-2-yl)amino)-3-(p-tolyl)propyl)-2-hydroxy-N-methylacetamide with 1-(1-bromoethyl)-4-methylbenzene yielded the product as brown solid (8%). ¹H NMR (400 MHz, CDCl₃) δ 7.57 (M, 1H), 7.28-7.05 (m, 8H), 6.56-6.35 (m, 2H), 4.79-4.30 (m, 3H), 4.18-3.80 (m, 3H), 3.48-2.87 (m, 5H), 2.82-2.74 (m, 3H), 2.32 (d, J=9.0 Hz, 6H), 1.52 (dd, J=10.4, 6.7 Hz, 3H). ¹³C NMR (101 MHz, CDCl₃) δ 173.31, 148.91, 141.46, 136.68, 135.91, 135.10, 129.32, 129.24, 129.16, 125.77, 117.72, 113.31, 59.74, 52.96, 51.96, 50.57, 39.01, 33.65, 25.06, 21.08.

2-hydroxy-N-methyl-N-((2S)-3-(p-tolyl)-2-((3-((1-(p-tolyl)ethyl)amino)pyridin-2-yl)amino)propyl)acetamide. Reaction of (S)—N-(2-((3-aminopyridin-2-yl)amino)-3-(p-tolyl)propyl)-2-hydroxy-N-methylacetamide with 1-(1-bromoethyl)-4-methylbenzene yielded the product as brown solid (8%). ¹H NMR (400 MHz, CDCl₃) δ 7.64-7.43 (m, 1H), 7.26-7.03 (m, 8H), 6.50-6.32 (m, 2H), 4.62 (d, J=32.6 Hz, 1H), 4.41-4.26 (m, 1H), 4.21-3.88 (m, 3H), 3.35-2.72 (m, 7H), 2.35-2.24 (m, 6H), 1.48 (ddd, J=22.5, 15.4, 9.8 Hz, 3H). ¹³C NMR (101 MHz, CDCl₃) δ 173.42, 148.72, 141.45, 136.53, 135.97, 134.80, 129.30, 129.19, 129.15, 125.73, 117.75, 113.30, 59.80, 53.07, 52.01, 50.67, 38.56, 33.62, 29.71, 25.33, 21.10.

(2S)-1-(3-(methoxymethyl)azetidin-1-yl)-3-(p-tolyl)-2-((2-((1-(p-tolyl)ethyl)amino)phenyl)amino)propan-1-one. Reaction of (S)-2-((2-aminophenyl)amino)-1-(3-(methoxymethyl)azetidin-1-yl)-3-(p-tolyl)propan-1-one with 1-(1-bromoethyl)-4-methylbenzene yielded the product as brown solid (58%). ¹H NMR (400 MHz, CDCl₃) δ 7.32-7.02 (m, 8H), 6.86-6.54 (m, 3H), 6.39 (dd, J=16.0, 7.8 Hz, 1H), 4.36 (dd, J=36.9, 5.8 Hz, 1H), 4.15-3.78 (m, 4H), 3.74-3.38 (m, 2H), 3.34-2.83 (m, 7H), 2.64-2.42 (m, 1H), 2.32 (dt, J=33.8, 16.8 Hz, 6H), 1.48-1.15 (m, 3H). ¹³C NMR (101 MHz, CDCl₃) δ 173.20, 173.05, 172.94, 142.63, 142.61, 142.23, 142.21, 139.48, 139.34, 138.74, 138.68, 136.40, 136.39, 136.33, 136.32, 136.25, 136.22, 134.78, 134.57, 134.19, 134.16, 134.02, 133.91, 129.50, 129.47, 129.37, 129.34, 129.25, 129.24, 129.21, 129.20, 125.77, 125.71, 125.69, 122.57, 122.41, 121.92, 121.81, 118.55, 118.35, 117.95, 117.80, 117.76, 117.15, 116.98, 113.03, 112.99, 112.60, 112.50, 74.30, 74.20, 74.18, 74.16, 59.01, 58.96, 58.95, 56.82, 56.77, 56.40, 56.39, 53.15, 52.95, 52.91, 52.68, 52.61, 52.50, 50.09, 50.03, 49.98, 49.94, 39.46, 39.35, 39.22, 39.05, 28.42, 28.35, 28.09, 28.04, 25.19, 25.14, 25.07, 25.04, 21.12, 21.08.

(2S)-1-(2-oxa-6-azaspiro[3.3]heptan-6-yl)-3-(p-tolyl)-2-((3-((1-(p-tolyl)ethyl)amino)pyridin-2-yl)amino)propan-1-one. Reaction of (S)-2-((3-aminopyridin-2-yl)amino)-1-(2-oxa-6-azaspiro[3.3]heptan-6-yl)-3-(p-tolyl)propan-1-one with 1-(1-bromoethyl)-4-methylbenzene yielded the product as brown solid (13%). ¹H NMR (400 MHz, CDCl₃) δ 7.52 (d, J=3.4 Hz, 1H), 7.24-7.00 (m, 8H), 6.51-6.40 (m, 2H), 5.00 (d, J=8.4 Hz, 1H), 4.73 (ddd, J=9.6, 9.6, 5.3 Hz, 1H), 4.65 (dd, J=6.3 Hz, 1H), 4.62 (d, J=7.0 Hz, 1H), 4.56 (d, J=6.8 Hz, 1H), 4.34 (ddd, J=13.1, 13.1, 6.7 Hz, 3H), 4.07 (d, J=10.7 Hz, 1H), 3.93 (d, J=10.7 Hz, 1H), 3.19 (dd, J=11.4, 5.7 Hz, 2H), 3.02-2.93 (m, 1H), 2.35 (s, 3H), 2.29 (s, 3H), 1.51 (d, J=6.6 Hz, 3H). ¹³C NMR (101 MHz, CDCl₃) δ 173.27, 147.69, 141.27, 136.50, 136.42, 136.15, 134.48, 130.85, 129.44, 129.33, 128.96, 125.74, 117.88, 114.64, 80.95, 80.42, 59.36, 56.90, 53.47, 53.22, 52.47, 39.31, 37.44, 25.32, 21.10, 21.06.

(2S)-1-(2-oxa-6-azaspiro[3.3]heptan-6-yl)-3-(p-tolyl)-2-((3-((1-(p-tolyl)ethyl)amino)pyridin-2-yl)amino)propan-1-one. Reaction of (S)-2-((3-aminopyridin-2-yl)amino)-1-(2-oxa-6-azaspiro[3.3]heptan-6-yl)-3-(p-tolyl)propan-1-one with 1-(1-bromoethyl)-4-methylbenzene yielded the product as brown solid (13%). ¹H NMR (400 MHz, CDCl₃) δ 7.46 (d, J=4.4 Hz, 1H), 7.23-7.05 (m, 8H), 6.40 (dd, J=7.5, 5.1 Hz, 1H), 6.28 (d, J=7.3 Hz, 1H), 5.72 (d, J=6.5 Hz, 1H), 4.64 (s, 1H), 4.53 (d, J=6.9 Hz, 1H), 4.40 (d, J=9.3 Hz, 1H), 4.30 (d, J=6.9 Hz, 1H), 4.08-4.02 (m, 2H), 3.92 (d, J=10.8 Hz, 1H), 3.29 (dd, J=12.6, 4.9 Hz, 1H), 3.21 (d, J=9.2 Hz, 1H), 3.14-3.05 (m, 1H), 2.35 (s, 3H), 2.30 (s, 3H), 1.34 (d, J=6.5 Hz, 3H). ¹³C NMR (101 MHz, CDCl₃) δ 173.95, 147.40, 141.80, 136.44, 136.29, 135.34, 134.54, 130.49, 129.46, 129.24, 128.96, 125.63, 117.09, 114.23, 80.90, 80.40, 59.43, 57.00, 53.47, 53.11, 52.79, 38.76, 37.46, 25.10, 21.10, 21.08.

(2S)-1-(3-hydroxyazetidin-1-yl)-3-(p-tolyl)-2-((2-((1-(p-tolyl)ethyl)amino)phenyl)amino)propan-1-one. Reaction of (S)-2-((2-aminophenyl)amino)-1-(3-hydroxyazetidin-1-yl)-3-(p-tolyl)propan-1-one with 1-(1-bromoethyl)-4-methylbenzene yielded the product as brown solid (23%).

1-((2S)-3-(p-tolyl)-2-((2-((1-(p-tolyl)ethyl)amino)phenyl)amino)propanoyl)azetidine-3-carbonitrile. Reaction of (S)-1-(2-((2-aminophenyl)amino)-3-(p-tolyl)propanoyl)azetidine-3-carbonitrile with 1-(1-bromoethyl)-4-methylbenzene yielded the product as brown solid (27%). ¹H NMR (400 MHz, CDCl₃) δ 7.25-7.08 (m, 8H), 6.81-6.39 (m, 4H), 4.48-4.28 (m, 1H), 4.20-4.00 (m, 2H), 3.96-3.73 (m, 2H), 3.66-3.52 (m, 1H), 3.32 (dt, J=14.8, 8.6 Hz, 0.5H), 3.19-2.90 (m, 3H), 2.42-2.28 (m, 6H), 1.48-1.31 (m, 3H). ¹³C NMR (101 MHz, CDCl₃) δ 173.51, 173.38, 173.26, 173.01, 142.51, 142.30, 142.03, 141.96, 139.45, 138.61, 138.26, 137.39, 137.34, 137.25, 137.16, 137.03, 136.56, 136.50, 136.41, 134.61, 134.14, 134.13, 134.04, 133.97, 133.85, 133.82, 133.60, 129.61, 129.58, 129.56, 129.49, 129.29, 129.26, 129.25, 129.24, 129.16, 125.83, 125.78, 125.70, 125.68, 123.07, 122.36, 122.26, 121.54, 119.09, 118.84, 118.78, 118.77, 118.68, 118.67, 118.61, 118.16, 117.85, 116.99, 116.64, 115.21, 114.18, 113.44, 112.79, 60.43, 57.80, 57.51, 57.36, 57.06, 53.15, 53.13, 53.04, 52.94, 52.65, 52.58, 51.10, 51.04, 50.88, 50.83, 39.48, 39.31, 39.12, 39.02, 24.99, 24.82, 21.14, 21.12, 21.09, 17.33, 17.28, 16.96, 16.92.

1-((2S)-3-(p-tolyl)-2-((3-((1-(p-tolyl)ethyl)amino)pyridin-2-yl)amino)propanoyl)azetidine-3-carbonitrile. Reaction of (S)-1-(2-((3-aminopyridin-2-yl)amino)-3-(p-tolyl)propanoyl)azetidine-3-carbonitrile with 1-(1-bromoethyl)-4-methylbenzene yielded the product as brown solid (7%). ¹H NMR (400 MHz, CDCl₃) δ 7.67-7.45 (m, 1H), 7.24-7.00

(m, 8H), 6.52-6.40 (m, 2H), 4.89 (dt, J=41.6, 13.5 Hz, 1H), 4.73-4.49 (m, 1.5H), 4.36 (q, J=6.3 Hz, 0.5H), 4.26-4.05 (m, 1H), 4.00-3.93 (m, 1H), 3.62 (dd, J=21.3, 12.5 Hz, 2H), 3.31-2.91 (m, 4H), 2.43-2.22 (m, 6H), 1.52 (d, J=6.6 Hz, 3H).

1-((2S)-3-(p-tolyl)-2-((3-((1-(p-tolyl)ethyl)amino)pyridin-2-yl)amino)propanoyl)azetidine-3-carbonitrile. Reaction of (S)-1-(2-((3-aminopyridin-2-yl)amino)-3-(p-tolyl)propanoyl)azetidine-3-carbonitrile with 1-(1-bromoethyl)-4-methylbenzene yielded the product as brown solid (7%). $^{1}$H NMR (400 MHz, CDCl$_{3}$) δ 7.67-7.40 (m, 1H), 7.21-7.04 (m, 8H), 6.52-6.33 (m, 1H), 5.28 (t, J=7.6 Hz, 1H), 4.74-4.45 (m, 1H), 4.24-4.06 (m, 2H), 3.97 (d, J=3.5 Hz, 1H), 3.61 (dd, J=21.2, 12.5 Hz, 2H), 3.23 (ddd, J=22.3, 15.1, 12.2 Hz, 1H), 3.11-2.94 (m, 1H), 2.84 (dd, J=23.1, 11.9 Hz, 1H), 2.40-2.27 (m, 6H), 1.42 (t, J=7.5 Hz, 3H). $^{13}$C NMR (101 MHz, CDCl$_{3}$) δ 174.76, 174.20, 171.38, 171.27, 171.16, 155.05, 147.46, 147.38, 141.53, 141.47, 137.64, 137.30, 136.61, 136.47, 136.44, 135.97, 135.69, 134.07, 133.76, 133.17, 132.80, 130.60, 130.56, 129.60, 129.43, 129.29, 129.23, 129.16, 129.12, 129.09, 125.64, 119.19, 119.07, 118.63, 117.69, 117.60, 114.88, 114.67, 80.12, 80.06, 60.40, 53.67, 53.20, 53.10, 53.02, 52.80, 52.77, 52.75, 52.65, 52.01, 51.80, 51.03, 50.89, 50.79, 39.35, 39.30, 38.74, 38.44, 28.33, 25.11, 21.15, 21.11, 21.07, 17.28, 17.15, 17.07, 16.77, 14.21.

(2S)-3-(p-tolyl)-2-((3-((1-(p-tolyl)ethyl)amino)pyridin-2-yl)amino)propan-1-ol. Reaction of (S)-2-((3-aminopyridin-2-yl)amino)-3-(p-tolyl)propan-1-ol with 1-(1-bromoethyl)-4-methylbenzene yielded the product as brown solid (11%). $^{1}$H NMR (400 MHz, CDCl$_{3}$) δ 7.51 (dd, J=5.1, 1.4 Hz, 1H), 7.20-7.07 (m, 8H), 6.53-6.49 (m, 1H), 6.44 (dd, J=7.6, 5.1 Hz, 1H), 4.47-4.32 (m, 1H), 4.22 (q, J=6.6 Hz, 1H), 4.08 (s, 1H), 3.91 (dd, J=11.0, 1.9 Hz, 1H), 3.70 (dd, J=10.9, 7.4 Hz, 1H), 3.03 (dd, J=13.9, 5.4 Hz, 1H), 2.81 (dd, J=13.8, 9.7 Hz, 1H), 2.38-2.30 (m, 6H), 1.35 (d, J=6.6 Hz, 3H). $^{13}$C NMR (101 MHz, CDCl$_{3}$) δ 149.84, 141.06, 136.79, 136.24, 135.89, 135.28, 130.59, 129.49, 129.37, 129.12, 125.70, 119.49, 114.13, 68.35, 56.87, 53.15, 37.53, 24.87, 21.09, 21.07.

(2S)-3-(p-tolyl)-2-((3-((1-(p-tolyl)ethyl)amino)pyridin-2-yl)amino)propan-1-ol. Reaction of (S)-2-((3-aminopyridin-2-yl)amino)-3-(p-tolyl)propan-1-ol with 1-(1-bromoethyl)-4-methylbenzene yielded the product as brown solid (9%). $^{1}$H NMR (400 MHz, CDCl$_{3}$) δ 7.49 (dd, J=5.1, 1.5 Hz, 1H), 7.19-7.10 (m, 4H), 7.05 (d, J=7.9 Hz, 2H), 6.93 (d, J=8.0 Hz, 2H), 6.50 (d, J=7.7 Hz, 1H), 6.42 (dd, J=7.6, 5.1 Hz, 1H), 4.53 (s, 1H), 4.32 (q, J=6.5 Hz, 1H), 4.06 (s, 1H), 3.91 (dd, J=10.9, 2.0 Hz, 1H), 3.71 (dd, J=10.8, 7.6 Hz, 1H), 3.06 (dd, J=13.8, 5.0 Hz, 1H), 2.77 (dd, J=13.8, 10.0 Hz, 1H), 2.31 (d, J=6.2 Hz, 6H), 1.42 (d, J=6.6 Hz, 3H). $^{13}$C NMR (101 MHz, CDCl$_{3}$) δ 150.23, 140.95, 136.65, 136.42, 135.82, 135.04, 130.31, 129.55, 129.29, 129.18, 125.65, 119.30, 114.17, 68.55, 56.94, 52.68, 37.60, 25.17, 21.10, 21.08.

3-((2S)-3-(p-tolyl)-2-((3-((1-(p-tolyl)ethyl)amino)pyridin-2-yl)amino)propoxy)propanenitrile. Reaction of (S)-3-(2-((3-aminopyridin-2-yl)amino)-3-(p-tolyl)propoxy)propanenitrile with 1-(1-bromoethyl)-4-methylbenzene yielded the product as brown solid (8%). $^{1}$H NMR (400 MHz, CDCl$_{3}$) δ 7.65 (dd, J=5.0, 1.5 Hz, 1H), 7.24-7.20 (m, 4H), 7.17-7.10 (m, 4H), 6.57 (dd, J=6.1, 1.6 Hz, 1H), 6.48-6.43 (m, 1H), 4.52 (s, 2H), 4.37 (q, J=6.6 Hz, 1H), 3.85 (s, 1H), 3.71-3.62 (m, 2H), 3.60-3.52 (m, 2H), 3.12-3.03 (m, 1H), 3.01-2.91 (m, 1H), 2.63-2.56 (m, 2H), 2.37-2.24 (m, 6H), 1.52 (d, J=6.6 Hz, 3H). $^{13}$C NMR (101 MHz, CDCl$_{3}$) δ 149.02, 141.54, 137.01, 136.61, 135.76, 135.63, 130.52, 129.44, 129.35, 129.12, 125.82, 118.77, 113.76, 71.12, 65.55, 53.33, 51.53, 37.23, 25.08, 21.10, 18.90.

3-((2S)-3-(p-tolyl)-2-((3-((1-(p-tolyl)ethyl)amino)pyridin-2-yl)amino)propoxy)propanenitrile. Reaction of (S)-3-(2-((3-aminopyridin-2-yl)amino)-3-(p-tolyl)propoxy)propanenitrile with 1-(1-bromoethyl)-4-methylbenzene yielded the product as brown solid (8%). $^{1}$H NMR (400 MHz, CDCl$_{3}$) δ 7.66 (ddd, J=25.8, 5.0, 1.3 Hz, 1H), 7.17 (ddd, J=21.8, 7.5, 3.1 Hz, 8H), 6.79-6.59 (m, 1H), 6.49 (ddd, J=12.2, 8.6, 2.9 Hz, 1H), 4.56-4.34 (m, 3H), 3.75-3.52 (m, 5H), 3.13-2.97 (m, 3H), 2.61 (dt, J=9.3, 6.2 Hz, 2H), 2.34 (d, J=5.5 Hz, 6H), 1.51 (d, J=6.6 Hz, 3H). $^{13}$C NMR (101 MHz, CDCl$_{3}$) δ 149.01, 148.68, 141.46, 136.94, 136.71, 136.58, 135.79, 135.71, 135.60, 135.43, 131.86, 130.35, 129.48, 129.40, 129.34, 129.13, 129.09, 125.78, 118.69, 118.18, 116.53, 113.82, 113.74, 71.43, 71.10, 65.58, 65.53, 53.10, 51.49, 51.42, 38.59, 37.11, 36.98, 25.15, 21.11, 21.08, 18.94, 18.91, 14.74.

Synthesis with General Procedure (P).

(S)-2-(2-imino-1-(4-methylbenzyl)-1,2-dihydro-3H-imidazo[4,5-b]pyridin-3-yl)-3-(p-tolyl)propan-1-ol
(WZ-I-30-3)

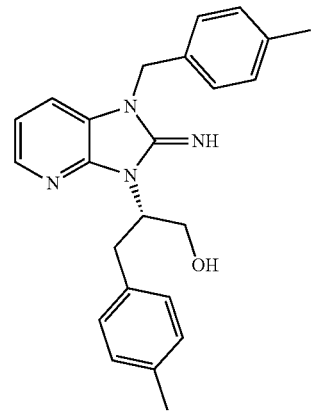 [SMILES: Cc1ccc(C[C@@H](CO)n2c(=N)n(Cc3ccc(C)cc3)c3cccnc32)cc1]

Reaction of (S)-2-((3-((4-methylbenzyl)amino)pyridin-2-yl)amino)-3-(p-tolyl)propan-1-ol with cyanogen bromide yielded product as off white solid (50%). $^{1}$H NMR (400 MHz, CDCl$_{3}$) δ 7.87 (dd, J=5.2, 1.0 Hz, 1H), 7.10 (t, J=7.3 Hz, 4H), 6.99 (dd, J=13.0, 7.9 Hz, 4H), 6.89 (dd, J=7.6, 1.0 Hz, 1H), 6.82 (dd, J=7.7, 5.3 Hz, 1H), 5.90 (s, 2H), 5.07-4.81 (m, 3H), 4.04 (s, 2H), 3.29 (d, J=8.0 Hz, 2H), 2.31 (s, 3H), 2.25 (s, 3H). $^{13}$C NMR (101 MHz, CDCl$_{3}$) δ 153.52, 144.90, 139.53, 137.87, 135.78, 134.65, 131.51, 129.66, 129.22, 128.96, 126.82, 125.44, 116.46, 112.87, 62.83, 57.97, 45.24, 33.43, 21.14, 21.08. HRMS (ESI-TOF) calculated for C24H26N4O [M+H]$^{+}$ 387.2185, found: 387.2200. [α]$_{D}^{20}$-120 (c 0.980, CHCl$_{3}$).

(S)-3-(1-methoxy-3-(p-tolyl)propan-2-yl)-1-(4-methylbenzyl)-1,3-dihydro-2H-imidazo[4,5-b]pyridin-2-imine (WZ-I-81). Reaction of (S)—N2-(1-methoxy-3-(p-tolyl)propan-2-yl)-N3-(4-methylbenzyl)pyridine-2,3-diamine with cyanogen bromide yielded product as brown solid (45%). $^{1}$H NMR (400 MHz, CDCl$_{3}$) δ 8.15 (dd, J=5.0, 1.1 Hz, 1H), 7.31-7.24 (m, 1H), 7.12-7.04 (m, 7H), 6.92 (d, J=7.9 Hz, 2H), 5.77 (d, J=16.3 Hz, 1H), 5.70-5.54 (m, 2H), 4.20-4.07 (m, 1H), 3.84 (dd, J=10.7, 3.0 Hz, 1H), 3.47 (s, 3H), 3.41-3.33 (m, 1H), 3.28 (dd, J=13.9, 7.3 Hz, 1H), 2.30 (s, 3H), 2.22 (s, 3H). $^{13}$C NMR (101 MHz, CDCl$_{3}$) δ 151.23, 143.44, 142.79, 138.20, 136.46, 132.59, 130.25, 129.62, 129.19, 128.96, 127.68, 123.60, 118.89, 117.39, 71.71, 59.45, 56.59, 47.77, 33.41, 21.15, 21.03. HRMS (ESI-TOF) calculated for C25H28N4O [M+H]+ 401.2341, found: 401.2344.

(S)-1-(1-methoxy-3-(p-tolyl)propan-2-yl)-3-(4-methylbenzyl)-1,3-dihydro-2H-imidazo[4,5-b]pyridin-2-imine (WZ-I-89). Reaction of (S)—N2-(1-methoxy-3-(p-tolyl)propan-2-yl)-N3-(4-methylbenzyl)pyridine-2,3-diamine with cyanogen bromide yielded product (40%). $^1$H NMR (400 MHz, CDCl$_3$) δ 8.21 (d, J=4.3 Hz, 1H), 7.95 (br, 1H), 7.20-7.11 (m, 3H), 7.02 (d, J=7.9 Hz, 2H), 6.93 (d, J=8.0 Hz, 2H), 6.84 (d, J=7.9 Hz, 2H), 5.74 (d, J=16.0 Hz, 1H), 5.60 (d, J=16.0 Hz, 1H), 4.01 (dd, J=10.9, 4.3 Hz, 1H), 3.92 (dd, J=10.9, 2.6 Hz, 1H), 3.41 (s, 3H), 3.38-3.33 (m, 1H), 3.23 (dd, J=14.4, 5.5 Hz, 1H), 2.28 (s, 3H), 2.19 (s, 3H). $^{13}$C NMR (101 MHz, CDCl$_3$) δ 150.86, 143.23, 143.12, 137.60, 136.38, 132.51, 130.87, 129.31, 129.25, 128.66, 127.82, 118.66, 73.48, 59.25, 58.67, 44.70, 34.20, 21.16, 21.04. HRMS (ESI-TOF) calculated for C25H28N4O [M+H]+ 401.2341, found: 401.2341.

(S)-2-(2-imino-3-(4-methylbenzyl)-2,3-dihydro-1H-benzo[d]imidazol-1-yl)-N-methyl-3-(p-tolyl)propenamide (WZ-I-236). Reaction of (S)—N-methyl-2-((2-((4-methylbenzyl)amino)phenyl)amino)-3-(p-tolyl)propenamide with cyanogen bromide yielded product as brown solid (25%). $^1$H NMR (400 MHz, CDCl$_3$) δ 9.01 (d, J=4.3 Hz, 1H), 8.34-8.20 (m, 1H), 7.78 (dd, J=8.8, 1.5 Hz, 1H), 7.64 (d, J=8.8 Hz, 1H), 7.57 (d, J=1.3 Hz, 1H), 7.41 (d, J=7.9 Hz, 1H), 7.18 (d, J=7.9 Hz, 2H), 6.99-6.89 (m, 3H), 6.78 (d, J=7.9 Hz, 2H), 6.37 (d, J=7.9 Hz, 2H), 5.63 (dd, J=7.9, 1.5 Hz, 1H), 5.39 (d, J=16.8 Hz, 1H), 5.08 (dd, J=22.4, 10.0 Hz, 2H), 3.89-3.75 (m, 2H), 3.66 (d, J=13.0 Hz, 1H), 3.39-3.26 (m, 1H), 2.86 (d, J=4.5 Hz, 2H), 2.41 (s, 3H), 2.39 (s, 3H), 2.32 (s, 3H). $^{13}$C NMR (101 MHz, CDCl$_3$) δ 165.62, 154.52, 144.38, 138.79, 137.30, 133.69, 132.66, 131.64, 130.90, 130.72, 130.02, 129.93, 129.61, 129.30, 129.25, 129.05, 128.73, 125.98, 121.16, 117.57, 116.61, 115.92, 63.61, 50.70, 35.14, 29.69, 26.78, 21.73, 21.18, 21.11.

(S)-2-(2-imino-3-(4-methylbenzyl)-2,3-dihydro-1H-benzo[d]imidazol-1-yl)-1-(pyrrolidin-1-yl)-3-(p-tolyl)propan-1-one (WZ-I-243). Reaction of (S)-2-((2-((4-methylbenzyl)amino)phenyl)amino)-1-(pyrrolidin-1-yl)-3-(p-tolyl)propan-1-one with cyanogen bromide yielded the product as off white solid (68%). $^1$H NMR (400 MHz, CDCl$_3$) δ 7.67 (d, J=7.7 Hz, 1H), 7.31-7.17 (m, 2H), 7.14-6.97 (m, 5H), 6.87 (dd, J=14.2, 7.9 Hz, 3H), 6.35 (s, 1H), 5.87 (d, J=16.7 Hz, 1H), 5.21 (d, J=16.7 Hz, 1H), 4.19 (s, 1H), 3.63-3.38 (m, 4H), 3.07 (dd, J=16.7, 7.1 Hz, 1H), 2.30 (s, 3H), 2.23 (s, 3H), 2.04-1.78 (m, 3H), 1.68 (dt, J=21.9, 7.2 Hz, 1H). $^{13}$C NMR (101 MHz, CDCl$_3$) δ 164.86, 150.12, 137.90, 136.53, 131.64, 130.11, 129.88, 129.71, 129.51, 129.12, 128.77, 127.10, 124.14, 110.46, 58.76, 47.21, 47.08, 46.80, 34.57, 26.26, 23.75, 21.20, 21.15. HRMS (ESI-TOF) calculated for C$_{29}$H$_{32}$N$_4$O [M+H]+ 453.2654, found: 453.2650. [α]$_D$$^{20}$–212 (c 1.165, CHCl$_3$).

(S)-1-(azetidin-1-yl)-2-(2-imino-3-(4-methylbenzyl)-2,3-dihydro-1H-benzo[d]imidazol-1-yl)-3-(p-tolyl)propan-1-one (WZ-I-244). Reaction of (S)-1-(azetidin-1-yl)-2-((2-((4-methylbenzyl)amino)phenyl)amino)-3-(p-tolyl)propan-1-one with cyanogen bromide yielded the product as off white solid (63%). $^1$H NMR (400 MHz, CDCl$_3$) δ 7.63 (d, J=7.8 Hz, 1H), 7.33-7.19 (m, 2H), 7.08 (d, J=7.5 Hz, 1H), 7.01 (dd, J=11.6, 8.0 Hz, 4H), 6.83 (dt, J=14.4, 7.0 Hz, 4H), 6.34 (dd, J=10.0, 6.3 Hz, 1H), 5.85 (t, J=17.2 Hz, 1H), 5.18 (d, J=16.7 Hz, 1H), 4.98-4.79 (m, 1H), 4.12 (td, J=9.7, 6.5 Hz, 1H), 4.00-3.85 (m, 2H), 3.56-3.31 (m, 2H), 2.28 (s, 3H), 2.22 (s, 3H), 2.18-2.05 (m, 2H). $^{13}$C NMR (101 MHz, CDCl$_3$) δ 166.07, 149.94, 137.85, 136.53, 131.44, 130.10, 129.86, 129.58, 129.50, 129.12, 128.53, 126.99, 124.21, 112.93, 110.54, 56.77, 51.29, 48.80, 47.21, 33.91, 21.21, 21.15, 15.60. HRMS (ESI-TOF) calculated for C28H30N4O [M+H]+ 439.2492, found: 439.2503. [α]$_D$$^{20}$–213 (c 1.095, CHCl$_3$).

(S)-2-(2-imino-3-(4-methylbenzyl)-2,3-dihydro-1H-benzo[d]imidazol-1-yl)-1-(piperidin-1-yl)-3-(p-tolyl)propan-1-one (WZ-I-249). Reaction of (S)-2-((2-((4-methylbenzyl)amino)phenyl)amino)-1-(piperidin-1-yl)-3-(p-tolyl)propan-1-one with cyanogen bromide yielded the product as off white solid (69%). $^1$H NMR (400 MHz, CDCl$_3$) δ 7.66 (d, J=7.8 Hz, 1H), 7.30-7.13 (m, 2H), 7.10-6.98 (m, 5H), 6.88 (dd, J=12.9, 7.9 Hz, 4H), 6.51 (d, J=4.5 Hz, 1H), 5.77 (d, J=16.7 Hz, 1H), 5.22 (d, J=16.7 Hz, 1H), 3.70-3.37 (m, 6H), 2.29 (s, 3H), 2.23 (s, 3H), 1.65-1.19 (m, 7H), 1.01-0.89 (m, 1H). $^{13}$C NMR (101 MHz, CDCl$_3$) δ 164.84, 149.94, 137.83, 136.50, 131.88, 130.32, 129.92, 129.71, 129.47, 129.10, 128.89, 127.08, 123.89, 112.83, 110.21, 57.09, 47.36, 47.06, 44.08, 35.14, 26.41, 25.66, 24.28, 21.21, 21.15. HRMS (ESI-TOF) calculated for C30H34N4O [M+H]+ 467.2811, found: 467.2864. [α]$_D$$^{20}$–184 (c 1.025, CHCl$_3$).

methyl (S)-1-(2-(2-imino-3-(4-methylbenzyl)-2,3-dihydro-1H-benzo[d]imidazol-1-yl)-3-(p-tolyl)propanoyl)azetidine-3-carboxylate (WZ-I-283). Reaction of methyl (S)-1-(2-((2-((4-methylbenzyl)amino)phenyl)amino)-3-(p-tolyl)propanoyl)azetidine-3-carboxylate with cyanogen bromide yielded the product as off white solid (59%). $^1$H NMR (400 MHz, CDCl$_3$) δ 7.57 (t, J=7.4 Hz, 1H), 7.31-7.15 (m, 2H), 7.05 (dt, J=14.0, 6.9 Hz, 3H), 6.97 (d, J=7.7 Hz, 2H), 6.85 (q, J=9.8 Hz, 4H), 6.42 (dd, J=29.4, 21.5 Hz, 1H), 5.81 (d, J=16.7 Hz, 1H), 5.17 (dt, J=16.9, 7.2 Hz, 2H), 4.76 (dt, J=18.3, 8.8 Hz, 1H), 4.39-4.16 (m, 1H), 3.99 (ddd, J=15.1, 9.5, 6.4 Hz, 1H), 3.72-3.55 (m, 3H), 3.53-3.35 (m, 3H), 2.29 (s, 3H), 2.23 (s, 3H). $^{13}$C NMR (101 MHz, CDCl$_3$) δ 172.28, 172.27, 166.77, 166.20, 150.19, 149.96, 137.88, 137.80, 136.71, 136.60, 131.32, 131.24, 130.17, 130.05, 130.01, 129.90, 129.54, 129.51, 129.29, 129.25, 129.16, 128.77, 128.29, 127.00, 126.93, 124.32, 124.26, 124.00, 123.80, 113.35, 112.55, 110.60, 110.37, 57.47, 56.74, 53.85, 53.37, 52.38, 52.27, 51.37, 47.19, 47.06, 33.98, 33.84, 32.33, 32.26, 21.19, 21.15. HRMS (ESI-TOF) calculated for C30H32N4O3 [M+H]+ 497.2547, found: 497.2550. [α]$_D$$^{20}$–161 (c 1.080, CHCl$_3$).

(S)-2-(2-imino-3-(4-methylbenzyl)-2,3-dihydro-1H-benzo[d]imidazol-1-yl)-1-(3-methoxyazetidin-1-yl)-3-(p-tolyl)propan-1-one (WZ-I-298). Reaction of (S)-1-(3-methoxyazetidin-1-yl)-2-((2-((4-methylbenzyl)amino)phenyl)amino)-3-(p-tolyl)propan-1-one with cyanogen bromide yielded the product as off white solid (65%). $^1$H NMR (400 MHz, CDCl$_3$) δ 7.61-7.54 (m, 1H), 7.31-7.16 (m, 3H), 7.12-6.96 (m, 5H), 6.86 (dt, J=10.8, 9.7 Hz, 3H), 6.34 (d, J=38.9 Hz, 1H), 5.86-5.64 (m, 1H), 5.15 (t, J=13.5 Hz, 2H), 4.56 (dd, J=24.7, 6.5 Hz, 1H), 4.31 (dd, J=10.7, 6.7 Hz, 1H), 4.24-4.10 (m, 1H), 3.97 (d, J=7.2 Hz, 1H), 3.81 (dd, J=10.7, 4.0 Hz, 1H), 3.61 (dd, J=9.4, 4.2 Hz, 1H), 3.45 (dd, J=8.1, 3.2 Hz, 2H), 3.23 (dd, J=29.9, 15.0 Hz, 3H), 2.30 (s, 3H), 2.23 (s, 3H). $^{13}$C NMR (101 MHz, CDCl$_3$) δ 166.73, 166.16, 150.28, 150.04, 137.98, 137.88, 136.67, 136.56, 131.47, 131.42, 129.99, 129.97, 129.59, 129.55, 129.34, 129.23, 129.13, 128.90, 128.41, 126.97, 126.90, 124.25, 124.22, 123.92, 123.76, 112.52, 110.43, 110.18, 69.01, 58.45, 58.22, 56.91, 56.41, 56.11, 55.95, 47.14, 47.02, 34.11, 33.95, 29.69, 21.19, 21.14.

(S)-1-(3-(chloromethyl)-3-(hydroxymethyl)azetidin-1-yl)-2-(2-imino-3-(4-methylbenzyl)-2,3-dihydro-1H-benzo[d]imidazol-1-yl)-3-(p-tolyl)propan-1-one (WZ-I-300). Reaction of (S)-1-(3-(chloromethyl)-3-(hydroxymethyl)azetidin-1-yl)-2-((2-((4-methylbenzyl)amino)phenyl)amino)-3-(p-tolyl)propan-1-one yielded the product as off white solid (73%). $^1$H NMR (400 MHz, CDCl$_3$) δ 7.60 (d, J=7.7 Hz, 1H), 7.54-7.45 (m, 1H), 7.36-7.28 (m, 1H), 7.22-7.17 (m, 1H), 7.14-7.02 (m, 3H), 6.96-6.87 (m, 3H), 6.84-6.75 (m, 3H), 6.26 (t, J=12.1 Hz, 1H), 5.63 (dd, J=41.4, 16.9 Hz, 1H), 5.42-5.08 (m, 1H), 4.74 (t, J=10.0 Hz, 1H), 4.58 (d, J=9.1 Hz, 1H), 4.41 (d, J=9.0 Hz, 1H), 3.93-3.26 (m, 10H), 2.31 (s, 3H), 2.27-2.18 (m, 3H). $^{13}$C NMR (101 MHz, CDCl$_3$) δ 166.58, 166.42, 149.74, 138.32, 138.10, 136.87, 131.69, 131.36, 129.90, 129.87, 129.76, 129.68, 129.37, 129.26, 129.24, 129.19, 128.46, 127.92, 126.93, 126.64, 124.67, 124.58, 124.38, 124.20, 113.55, 112.33, 110.73, 110.58, 63.38, 63.14, 58.06, 57.60, 56.77, 55.73, 53.47, 47.09, 46.83, 46.73, 41.66, 41.61, 33.99, 33.79, 21.18, 21.10. HRMS (ESI-TOF) calculated for C30H33ClN4O2 [M+H]+ 517.2365, found: 517.2364.

(S)-1-(tert-butyl) 3-(2-(2-imino-3-(4-methylbenzyl)-2,3-dihydro-1H-benzo[d]imidazol-1-yl)-3-(p-tolyl)propyl) azetidine-1,3-dicarboxylate (WZ-I-310). Reaction of (S)-1-(tert-butyl) 3-(2-((2-((4-methylbenzyl)amino)phenyl)amino)-3-(p-tolyl)propyl) azetidine-1,3-dicarboxylate with cyanogen bromide yielded the product as off white solid (67%). $^1$H NMR (400 MHz, CDCl$_3$) δ 7.57 (d, J=7.3 Hz, 1H), 7.33-7.13 (m, 3H), 7.04 (dd, J=23.3, 7.7 Hz, 4H), 6.90 (dd, J=19.3, 7.9 Hz, 2H), 6.80 (d, J=6.0 Hz, 2H), 6.20 (s, 1H), 5.90 (d, J=15.2 Hz, 1H), 4.74 (s, 2H), 4.21-3.87 (m, 5H), 3.45-3.21 (m, 3H), 2.27 (s, 3H), 2.23 (s, 3H), 1.46-1.27 (m, 9H). $^{13}$C NMR (101 MHz, CDCl$_3$) δ 172.05, 155.88, 137.77, 136.61, 131.57, 130.18, 129.51, 129.36, 128.94, 126.79, 124.00, 123.59, 112.42, 110.92, 79.68, 64.29, 57.24, 47.16, 31.85, 28.27, 21.12. HRMS (ESI-TOF) calculated for C34H40N4O4 [M+H]+ 569.3121, found: 569.3122. $[α]_D^{20}$ –85 (c 1.385, CHCl$_3$).

(2S)-1-(azetidin-1-yl)-2-(2-imino-3-(1-(p-tolyl)ethyl)-2,3-dihydro-1H-benzo[d]imidazol-1-yl)-3-(p-tolyl)propan-1-one (WZ-II-92). Reaction of (2S)-1-(azetidin-1-yl)-3-(p-tolyl)-2-((2-((1-(p-tolyl)ethyl)amino)phenyl)amino)propan-1-one and cyanogen bromide yielded the product as off white solid (42%). $^1$H NMR (400 MHz, CDCl$_3$) δ 7.59 (dd, J=16.1, 8.1 Hz, 1H), 7.20 (t, J=7.5 Hz, 1H), 7.15-6.89 (m, 9H), 6.80-6.63 (m, 2H), 6.47-6.16 (m, 2H), 4.99 (d, J=6.4 Hz, 1H), 4.23-4.11 (m, 1H), 3.98 (dd, J=24.5, 17.2 Hz, 2H), 3.59-3.38 (m, 2H), 2.27 (dd, J=35.8, 15.5 Hz, 9H), 1.85 (d, J=6.6 Hz, 1.5H), 1.58 (d, J=6.6 Hz, 1.5H). HRMS (ESI-TOF) calculated for C29H32N4O [M+H]+ 453.2649, found: 453.2649.

(2S)-1-(3-(chloromethyl)-3-(hydroxymethyl)azetidin-1-yl)-2-(2-imino-3-(1-(p-tolyl)ethyl)-2,3-dihydro-1H-benzo[d]imidazol-1-yl)-3-(p-tolyl)propan-1-one (WZ-II-93). Reaction of (2S)-1-(3-(chloromethyl)-3-(hydroxymethyl)azetidin-1-yl)-3-(p-tolyl)-2-((2-((1-(p-tolyl)ethyl)amino)phenyl)amino)propan-1-one and cyanogen bromide yielded the product as off white solid (43%). $^1$H NMR (400 MHz, CDCl$_3$) δ 7.51 (dd, J=20.5, 12.0 Hz, 1H), 7.28-6.65 (m, 11H), 6.16 (d, J=110.1 Hz, 2H), 5.05-4.79 (m, 1H), 4.35 (dd, J=28.0, 8.8 Hz, 1H), 4.08-3.22 (m, 9H), 2.31 (dd, J=20.2, 11.4 Hz, 6H), 1.75 (dt, J=15.5, 8.0 Hz, 3H). HRMS (ESI-TOF) calculated for C31H35ClN4O2 [M+H]+ 531.2521, found: 531.2514.

(S,E)-1-(3-(chloromethyl)-3-(hydroxymethyl)azetidin-1-yl)-2-(2-imino-3-(4-(p-tolyl)but-3-en-1-yl)-2,3-dihydro-1H-benzo[d]imidazol-1-yl)-3-(p-tolyl)propan-1-one (WZ-II-98). Reaction of (S,E)-1-(azetidin-1-yl)-3-(p-tolyl)-2-((2-((4-(p-tolyl)but-3-en-1-yl)amino)phenyl)amino)propan-1-one with cyanogen bromide yielded the product as off white solid (55%). HRMS (ESI-TOF) calculated for C33H37ClN4O2 [M+H]+ 557.2678, found: 557.2674.

(S,E)-1-(azetidin-1-yl)-2-(2-imino-3-(4-(p-tolyl)but-3-en-1-yl)-2,3-dihydro-1H-benzo[d]imidazol-1-yl)-3-(p-tolyl)propan-1-one (WZ-II-104). Reaction of (S,E)-1-(azetidin-1-yl)-3-(p-tolyl)-2-((2-((4-(p-tolyl)but-3-en-1-yl)amino)phenyl)amino)propan-1-one with cyanogen bromide yielded the product as brown solid (47%). HRMS (ESI-TOF) calculated for C31H34N4O [M+H]+ 479.2805, found: 479.2806.

(2S)-2-(2-imino-3-(1-(p-tolyl)ethyl)-2,3-dihydro-1H-benzo[d]imidazol-1-yl)-1-morpholino-3-(p-tolyl)propan-1-one (WZ-II-124). Reaction of (2S)-1-morpholino-3-(p-tolyl)-2-((2-((1-(p-tolyl)ethyl)amino)phenyl)amino)propan-1-one with cyanogen bromide yielded the product as off white solid (43%). $^1$H NMR (400 MHz, CDCl$_3$) δ 7.58 (dd, J=26.2, 14.9 Hz, 1H), 7.22-6.87 (m, 7H), 6.82 (d, J=7.9 Hz, 1H), 6.69 (dd, J=16.6, 8.1 Hz, 1H), 6.49 (d, J=21.7 Hz, 1H), 6.04 (s, 1H), 3.93-3.32 (m, 9H), 2.30 (dd, J=15.5, 8.1 Hz, 6H), 1.71 (dd, J=78.7, 6.9 Hz, 3H). $^{13}$C NMR (101 MHz, CDCl$_3$) δ 165.79, 165.71, 150.11, 149.72, 138.16, 137.99, 136.85, 136.78, 133.65, 133.54, 131.78, 129.71, 129.68, 129.56, 129.46, 129.24, 129.16, 129.13, 129.11, 128.75, 128.48, 126.47, 126.41, 123.31, 112.69, 112.49, 111.83, 111.64, 67.01, 66.97, 66.69, 56.77, 56.72, 53.57, 53.48, 46.34, 43.07, 43.05, 34.73, 34.70, 21.23, 21.15, 21.11, 21.08, 17.00, 16.33. HRMS (ESI-TOF) calculated for C30H34N4O2 [M+H]+ 483.2754, found: 483.2754.

(2S)-1-(3-(hydroxymethyl)azetidin-1-yl)-2-(2-imino-3-(1-(p-tolyl)ethyl)-2,3-dihydro-1H-benzo[d]imidazol-1-yl)-3-(p-tolyl)propan-1-one (WZ-II-129). Reaction of (2S)-1-(3-(hydroxymethyl)azetidin-1-yl)-3-(p-tolyl)-2-((2-((1-(p-tolyl)ethyl)amino)phenyl)amino)propan-1-one with cyanogen bromide yielded the product as off white solid (71%). $^1$H NMR (400 MHz, CDCl$_3$) δ 7.57-7.40 (m, 1H), 7.28-6.60 (m, 13H), 6.42-6.03 (m, 2H), 4.87-4.49 (m, 1H), 4.14-3.31 (m, 9H), 2.71 (d, J=68.1 Hz, 1H), 2.33-2.18 (m, 6H), 1.73 (dt, J=112.1, 7.4 Hz, 3H), 1.32-1.12 (m, 2H). $^{13}$C NMR (101 MHz, CDCl$_3$) δ 166.66, 166.64, 166.55, 149.78, 149.60, 149.54, 149.35, 138.30, 138.21, 138.04, 137.87, 136.98, 136.93, 136.86, 136.78, 133.64, 133.44, 133.15, 131.67, 131.54, 131.38, 131.20, 129.71, 129.66, 129.45, 129.40, 129.26, 129.25, 129.15, 129.12, 129.00, 128.64, 128.46, 128.35, 128.22, 128.07, 127.95, 126.68, 126.46, 126.38, 123.96, 123.92, 123.70, 123.64, 123.60, 123.50, 112.83, 112.62, 112.59, 112.29, 62.64, 62.59, 62.52, 57.88, 57.72, 57.16, 56.94, 54.29, 54.12, 53.98, 53.95, 53.61, 53.59, 50.78, 50.73, 50.68, 33.89, 33.86, 33.59, 33.53, 31.59, 31.46, 31.36, 22.72, 22.64, 22.57, 21.24, 21.12, 21.10, 21.09, 17.32, 17.27, 16.46, 16.44. HRMS (ESI-TOF) calculated for C30H34N4O2 [M+H]+ 483.2754, found: 483.2761.

3-((S)-1-methoxy-3-(p-tolyl)propan-2-yl)-1-(1-(p-tolyl)ethyl)-1,3-dihydro-2H-imidazo[4,5-b]pyridin-2-imine (WZ-II-149). Reaction of N2-((S)-1-methoxy-3-(p-tolyl)propan-2-yl)-N3-(1-(p-tolyl)ethyl)pyridine-2,3-diamine with cyanogen bromide yielded the product as brown solid (75%). $^1$H NMR (400 MHz, CDCl$_3$) δ 8.07 (d, J=4.3 Hz, 1H), 7.10-6.98 (m, 6H), 6.94 (d, J=7.8 Hz, 2H), 6.86 (dd, J=8.0, 5.0 Hz, 1H), 6.79-6.75 (m, 1H), 6.64 (br, 1H), 5.62 (br, 1H), 4.18 (br, 2H), 3.89 (d, J=10.7, 3.0 Hz, 1H), 3.52 (s, 3H), 3.37 (dd, J=19.3, 9.1 Hz, 1H), 3.27 (dd, J=13.7, 6.9 Hz, 1H), 2.30 (s, 3H), 2.23 (s, 3H), 1.87 (d, J=6.9 Hz, 3H). $^{13}$C NMR (101 MHz, CDCl$_3$) δ 150.92, 143.66, 142.37, 138.13, 136.48, 133.61, 132.60, 129.48, 129.13, 129.05, 126.83, 121.95, 119.10, 118.43, 71.71, 59.52, 54.42, 33.36, 21.10, 21.04, 17.29. HRMS (ESI-TOF) calculated for C26H30N4O [M+H]+ 415.2498, found: 415.2503. [α]$_D^{20}$ −194 (c 1.502, CHCl$_3$).

(S)-2-(2-imino-3-(4-methylbenzyl)-2,3-dihydro-1H-benzo[d]imidazol-1-yl)-1-(2-oxa-6-azaspiro[3.3]heptan-6-yl)-3-(p-tolyl)propan-1-one (WZ-II-150). Reaction of (S)-2-((2-((4-methylbenzyl)amino)phenyl)amino)-1-(2-oxa-6-azaspiro[3.3]heptan-6-yl)-3-(p-tolyl)propan-1-one with cyanogen bromide yielded the product as off white solid (88%). $^1$H NMR (400 MHz, CDCl$_3$) δ 7.56 (d, J=7.6 Hz, 1H), 7.31-7.18 (m, 2H), 7.07 (dd, J=17.8, 7.7 Hz, 3H), 6.96 (d, J=7.9 Hz, 2H), 6.86 (dd, J=7.5, 5.7 Hz, 4H), 6.32 (t, J=8.1 Hz, 1H), 5.79 (d, J=16.7 Hz, 1H), 5.19 (d, J=16.7 Hz, 1H), 5.07 (d, J=9.5 Hz, 1H), 4.82 (d, J=7.0 Hz, 1H), 4.72 (d, J=7.1 Hz, 1H), 4.69 (d, J=7.1 Hz, 1H), 4.62 (d, J=7.0 Hz, 1H), 4.25 (d, J=10.9 Hz, 1H), 4.21 (d, J=9.6 Hz, 1H), 4.11 (d, J=10.9 Hz, 1H), 3.42 (d, J=8.2 Hz, 2H), 2.29 (s, 3H), 2.23 (s, 3H). $^{13}$C NMR (101 MHz, CDCl$_3$) δ 166.53, 150.09, 137.97, 136.75, 131.33, 130.11, 129.95, 129.56, 129.44, 129.23, 128.50, 126.98, 124.19, 124.07, 112.92, 110.49, 80.76, 80.10, 60.31, 58.53, 57.12, 47.09, 38.24, 33.96, 21.21, 21.16. HRMS (ESI-TOF) calculated for C30H32N4O2 [M+H]+ 481.2604, found: 481.2609. [α]$_D^{20}$ −169 (c 1.260, CHCl$_3$).

(2S)-2-(2-imino-3-(1-(p-tolyl)ethyl)-2,3-dihydro-1H-benzo[d]imidazol-1-yl)-1-(2-oxa-6-azaspiro[3.3]heptan-6-yl)-3-(p-tolyl)propan-1-one (WZ-II-151). Reaction of (2S)-1-(2-oxa-6-azaspiro[3.3]heptan-6-yl)-3-(p-tolyl)-2-((2-((1-(p-tolyl)ethyl)amino)phenyl)amino)propan-1-one with cyanogen bromide yielded the product as off white solid (78%). $^1$H NMR (400 MHz, CDCl$_3$) δ 7.53 (dd, J=11.5, 8.3 Hz, 1H), 7.19 (t, J=7.8 Hz, 1H), 7.15-6.97 (m, 6H), 6.92 (dd, J=17.9, 8.0 Hz, 2H), 6.75 (d, J=8.0 Hz, 1H), 6.68 (d, J=8.2 Hz, 1H), 6.47-6.30 (m, 1H), 6.24 (dd, J=12.1, 6.6 Hz, 1H), 5.17 (d, J=7.8 Hz, 1H), 4.88 (dd, J=6.9, 4.0 Hz, 1H), 4.80-4.60 (m, 3H), 4.34-4.12 (m, 3H), 3.55-3.32 (m, 2H), 2.36-2.24 (m, 6H), 1.89-1.46 (m, 3H). $^{13}$C NMR (101 MHz, CDCl$_3$) δ 166.81, 166.75, 150.12, 149.77, 138.26, 137.94, 136.97, 136.88, 133.49, 133.42, 131.35, 131.26, 129.66, 129.58, 129.45, 129.42, 129.25, 129.18, 129.04, 128.87, 128.59, 128.28, 126.62, 126.42, 123.61, 123.58, 123.54, 123.51, 112.89, 112.84, 112.45, 112.19, 80.83, 80.80, 80.28, 80.20, 60.35, 58.62, 58.57, 57.16, 56.96, 54.02, 53.91, 38.37, 38.36, 33.80, 33.76, 21.27, 21.15, 21.12, 21.09, 17.23, 16.41. HRMS (ESI-TOF) calculated for C31H34N4O2 [M+H]+ 495.2760, found: 495.2750.

(2S)-1-(4-hydroxypiperidin-1-yl)-2-(2-imino-3-(1-(p-tolyl)ethyl)-2,3-dihydro-1H-benzo[d]imidazol-1-yl)-3-(p-tolyl)propan-1-one (WZ-II-174). Reaction of (2S)-1-(4-hydroxypiperidin-1-yl)-3-(p-tolyl)-2-((2-((1-(p-tolyl)ethyl)amino)phenyl)amino)propan-1-one with cyanogen bromide yielded the product as off white solid (94%). $^1$H NMR (400 MHz, CDCl$_3$) δ 7.61 (ddd, J=11.9, 7.7, 3.8 Hz, 1H), 7.17 (t, J=7.8 Hz, 1H), 7.13-6.94 (m, 5H), 6.91 (d, J=2.8 Hz, 2H), 6.76 (d, J=6.1 Hz, 1H), 6.70-6.48 (m, 2H), 6.15 (dd, J=24.0, 17.4 Hz, 1H), 3.97-3.69 (m, 3H), 3.63-3.27 (m, 4H), 2.27 (t, J=18.2 Hz, 6H), 2.00-1.51 (m, 5H), 1.41-0.77 (m, 3H). $^{13}$C NMR (101 MHz, CDCl$_3$) δ 165.12, 165.06, 164.89, 149.59, 149.18, 138.16, 138.11, 137.92, 136.87, 136.71, 133.54, 133.39, 131.74, 131.70, 131.59, 131.57, 129.82, 129.64, 129.60, 129.40, 129.17, 129.13, 128.92, 128.89, 128.29, 128.01, 127.92, 126.64, 126.55, 126.42, 123.69, 112.80, 112.56, 112.37, 66.21, 65.74, 65.41, 57.17, 57.12, 57.04, 56.98, 54.07, 53.88, 43.16, 43.08, 42.97, 42.69, 40.02, 39.87, 34.78, 34.45, 34.36, 34.18, 33.80, 33.40, 33.35, 33.22, 29.69, 21.25, 21.13, 21.12, 21.08, 17.49, 17.38, 16.46, 16.32. HRMS (ESI-TOF) calculated for C31H36N4O2 [M+H]+ 497.2917, found: 497.2924.

2-hydroxy-N-((2S)-2-(2-imino-1-(1-(p-tolyl)ethyl)-1,2-dihydro-3H-imidazo[4,5-b]pyridin-3-yl)-3-(p-tolyl)propyl)acetamide (WZ-II-186). Reaction of 2-hydroxy-N-((2S)-3-(p-tolyl)-2-((3-((1-(p-tolyl)ethyl)amino)pyridin-2-yl)amino)propyl)acetamide with cyanogen bromide yielded the product as brown solid (18%). $^1$H NMR (400 MHz, CDCl$_3$) δ 8.24 (s, 1H), 7.21-6.60 (m, 9H), 5.51 (d, J=6.7 Hz, 1H), 4.92 (s, 1H), 4.54 (s, 1H), 4.11-3.97 (m, 2H), 3.80 (d, J=14.4 Hz, 1H), 3.65 (d, J=11.5 Hz, 1H), 3.27 (dd, J=13.9, 4.8 Hz, 1H), 2.30 (s, 6H), 2.23 (s, 3H), 1.55 (d, J=6.4 Hz, 3H). $^{13}$C NMR (101 MHz, CDCl$_3$) δ 173.70, 150.70, 138.85, 136.62, 132.98, 129.91, 129.27, 128.50, 126.61, 122.44, 118.73, 61.90, 40.75, 34.95, 29.70, 21.07, 20.98, 16.35, 1.02. HRMS (ESI-TOF) calculated for C27H31N5O2 [M+H]+ 458.2566, found: 458.2562.

2-hydroxy-N-((2S)-2-(2-imino-1-(1-(p-tolyl)ethyl)-1,2-dihydro-3H-imidazo[4,5-b]pyridin-3-yl)-3-(p-tolyl)propyl)acetamide (WZ-II-187). Reaction of 2-hydroxy-N-((2S)-3-(p-tolyl)-2-((3-((1-(p-tolyl)ethyl)amino)pyridin-2-yl)amino)propyl)acetamide with cyanogen bromide yielded the product as brown solid (18%). $^1$H NMR (400 MHz, CDCl$_3$) δ 8.26 (d, J=4.1 Hz, 1H), 7.41 (s, 1H), 7.22-6.89 (m, 6H), 6.74 (dd, J=43.0, 7.6 Hz, 3H), 5.46 (d, J=6.6 Hz, 1H), 5.02 (s, 1H), 4.53 (s, 1H), 4.14-3.87 (m, 3H), 3.72 (dd, J=25.2, 12.7 Hz, 2H), 3.61-3.43 (m, 1H), 3.26 (dd, J=13.8, 4.3 Hz, 2H), 2.37-2.18 (m, 6H), 1.86 (d, J=6.8 Hz, 3H). $^{13}$C NMR (101 MHz, CDCl$_3$) δ 174.06, 150.20, 143.26, 143.00, 138.45, 136.64, 133.17, 132.89, 129.66, 129.37, 126.22, 121.90, 120.14, 119.14, 61.64, 60.05, 54.28, 40.51, 35.15, 29.71, 24.78, 21.11, 21.09, 16.99. HRMS (ESI-TOF) calculated for C27H31N5O2 [M+H]+ 458.2566, found: 458.2561.

2-hydroxy-N-((2S)-2-(2-imino-1-(1-(p-tolyl)ethyl)-1,2-dihydro-3H-imidazo[4,5-b]pyridin-3-yl)-3-(p-tolyl)propyl)-N-methylacetamide (WZ-II-205). Reaction of 2-hydroxy-N-methyl-N-((2S)-3-(p-tolyl)-2-((3-((1-(p-tolyl)ethyl)amino)pyridin-2-yl)amino)propyl)acetamide with cyanogen bromide yielded the product as brown oil (10%). HRMS (ESI-TOF) calculated for C28H33N5O2 [M+H]+ 472.2713, found: 472.2711.

2-hydroxy-N-((2S)-2-(2-imino-1-(1-(p-tolyl)ethyl)-1,2-dihydro-3H-imidazo[4,5-b]pyridin-3-yl)-3-(p-tolyl)propyl)-N-methylacetamide (WZ-II-206). Reaction of 2-hydroxy-N-methyl-N-((2S)-3-(p-tolyl)-2-((3-((1-(p-tolyl)ethyl)amino)pyridin-2-yl)amino)propyl)acetamide with cyanogen bromide yielded the product as brown oil (10%). HRMS (ESI-TOF) calculated for C28H33N5O2 [M+H]+ 472.2713, found: 472.2707.

(2S)-2-(2-imino-3-(1-(p-tolyl)ethyl)-2,3-dihydro-1H-benzo[d]imidazol-1-yl)-1-(3-(methoxymethyl)azetidin-1-yl)-3-(p-tolyl)propan-1-one (WZ-II-207). Reaction of (2S)-1-(3-(methoxymethyl)azetidin-1-yl)-3-(p-tolyl)-2-((2-((1-(p-tolyl)ethyl)amino)phenyl)amino)propan-1-one with cyanogen bromide yielded the product as off white solid (59%). $^1$H NMR (400 MHz, CDCl$_3$) δ 7.32-7.02 (m, 8H), 6.86-6.54 (m, 3H), 6.39 (dd, J=16.0, 7.8 Hz, 1H), 4.36 (dd, J=36.9, 5.8 Hz, 1H), 4.15-3.78 (m, 4H), 3.74-3.38 (m, 2H), 3.34-2.83 (m, 7H), 2.64-2.42 (m, 1H), 2.32 (dt, J=33.8, 16.8 Hz, 6H), 1.48-1.15 (m, 3H). $^{13}$C NMR (101 MHz, CDCl$_3$) δ 173.20, 173.05, 172.94, 142.63, 142.61, 142.23, 142.21, 139.48, 139.34, 138.74, 138.68, 136.40, 136.39, 136.33, 136.32, 136.25, 136.22, 134.78, 134.57, 134.19, 134.16, 134.02, 133.91, 129.50, 129.47, 129.37, 129.34, 129.25, 129.24, 129.21, 129.20, 125.77, 125.71, 125.69, 122.57, 122.41, 121.92, 121.81, 118.55, 118.35, 117.95, 117.80, 117.76, 117.15, 116.98, 113.03, 112.99, 112.60, 112.50, 74.30, 74.20, 74.18, 74.16, 59.01, 58.96, 58.95, 56.82, 56.77, 56.40, 56.39, 53.15, 52.95, 52.91, 52.68, 52.61, 52.50, 50.09, 50.03, 49.98, 49.94, 39.46, 39.35, 39.22, 39.05, 28.42, 28.35, 28.09, 28.04, 25.19, 25.14, 25.07, 25.04, 21.12, 21.08. HRMS (ESI-TOF) calculated for C31H36N4O2 [M+H]+ 497.2917, found: 497.2910.

(2S)-2-(2-imino-1-(1-(p-tolyl)ethyl)-1,2-dihydro-3H-imidazo[4,5-b]pyridin-3-yl)-1-(2-oxa-6-azaspiro[3.3]heptan-6-yl)-3-(p-tolyl)propan-1-one (WZ-II-208-1). Reaction of (2S)-1-(2-oxa-6-azaspiro[3.3]heptan-6-yl)-3-(p-tolyl)-2-((3-((1-(p-tolyl)ethyl)amino)pyridin-2-yl)amino)propan-1-one with cyanogen bromide yielded the product as off white solid (24%). $^1$H NMR (400 MHz, CDCl$_3$) δ 7.98 (d, J=4.8 Hz, 1H), 7.15 (q, J=8.3 Hz, 4H), 7.05 (d, J=7.9 Hz, 2H), 6.97 (d, J=7.8 Hz, 2H), 6.82 (dd, J=7.9, 5.1 Hz, 1H), 6.71 (d, J=7.7 Hz, 1H), 6.59 (s, 1H), 5.77 (dd, J=8.1 Hz, 1H), 4.70 (dd, J=7.0, 3.6 Hz, 2H), 4.64 (d, J=7.1 Hz, 1H), 4.60 (d, J=7.0 Hz, 1H), 4.34 (d, J=9.3 Hz, 1H), 4.17 (ddd, J=20.5, 10.3, 10.3 Hz, 3H), 3.51 (dd, J=13.7, 7.8 Hz, 1H), 3.37 (dd, J=13.6, 9.1 Hz, 1H), 2.34 (s, 3H), 2.24 (s, 3H), 1.80 (d, J=6.9 Hz, 3H). $^{13}$C NMR (101 MHz, CDCl$_3$) δ 167.59, 151.19, 143.45, 141.52, 138.09, 136.98, 134.02, 131.65, 129.53, 129.20, 126.89, 122.48, 118.22, 80.54, 80.21, 60.40, 57.86, 53.56, 37.65, 33.91, 21.12, 21.05, 16.83. HRMS (ESI-TOF) calculated for C30H33N5O2 [M+H]+ 496.2713, found: 496.2707.

(2S)-2-(2-imino-1-(1-(p-tolyl)ethyl)-1,2-dihydro-3H-imidazo[4,5-b]pyridin-3-yl)-1-(2-oxa-6-azaspiro[3.3]heptan-6-yl)-3-(p-tolyl)propan-1-one (WZ-II-209-1). Reaction of (2S)-1-(2-oxa-6-azaspiro[3.3]heptan-6-yl)-3-(p-tolyl)-2-((3-((1-(p-tolyl)ethyl)amino)pyridin-2-yl)amino)propan-1-one with cyanogen bromide yielded the product as off white solid (26%). $^1$H NMR (400 MHz, CDCl$_3$) δ 7.91 (s, 1H), 7.17 (d, J=8.0 Hz, 2H), 7.12 (d, J=8.1 Hz, 2H), 7.05 (d, J=7.9 Hz, 2H), 6.99 (d, J=7.6 Hz, 2H), 6.75 (d, J=22.9 Hz, 2H), 5.64 (s, 1H), 4.70 (dd, J=10.3, 7.2 Hz, 2H), 4.63 (d, J=7.1 Hz, 1H), 4.55 (d, J=6.9 Hz, 1H), 4.22-4.09 (m, 3H), 3.99 (d, J=9.1 Hz, 1H), 3.54 (dd, J=13.6, 8.1 Hz, 1H), 3.31 (dd, J=20.6, 12.2 Hz, 1H), 2.32 (s, 3H), 2.25 (s, 3H), 1.86 (d, J=6.9 Hz, 3H). HRMS (ESI-TOF) calculated for C30H33N5O2 [M+H]+ 496.2713, found: 496.2705.

(2S)-1-(3-(bromomethyl)-3-(hydroxymethyl)azetidin-1-yl)-2-(2-imino-1-(1-(p-tolyl)ethyl)-1,2-dihydro-3H-imidazo[4,5-b]pyridin-3-yl)-3-(p-tolyl)propan-1-one (WZ-II-208-2). Reaction of (2S)-1-(2-oxa-6-azaspiro[3.3]heptan-6-yl)-3-(p-tolyl)-2-((3-((1-(p-tolyl)ethyl)amino)pyridin-2-yl)amino)propan-1-one with cyanogen bromide yielded the product as off white solid (9%). $^1$H NMR (400 MHz, CDCl$_3$) δ 8.23-7.94 (m, 1H), 7.23-6.63 (m, 9H), 6.51 (s, 1H), 6.03-5.76 (m, 1H), 4.35-3.23 (m, 10H), 2.37-2.14 (m, 6H), 1.91-1.73 (m, 3H). HRMS (ESI-TOF) calculated for C30H34BrN5O2 [M+H]+ 576.1974, found: 576.1974.

(2S)-1-(3-(bromomethyl)-3-(hydroxymethyl)azetidin-1-yl)-2-(2-imino-1-(1-(p-tolyl)ethyl)-1,2-dihydro-3H-imidazo[4,5-b]pyridin-3-yl)-3-(p-tolyl)propan-1-one (WZ-II-209-2). Reaction of (2S)-1-(2-oxa-6-azaspiro[3.3]heptan-6-yl)-3-(p-tolyl)-2-((3-((1-(p-tolyl)ethyl)amino)pyridin-2-yl)amino)propan-1-one with cyanogen bromide yielded the product as off white solid (8%). $^1$H NMR (400 MHz, CDCl$_3$) δ 8.04 (dd, J=36.0, 4.5 Hz, 1H), 7.19-6.62 (m, 9H), 6.53-6.22 (m, 1H), 5.94 (dd, J=30.9, 22.9 Hz, 1H), 4.35 (d, J=21.0 Hz, 1H), 4.23-4.08 (m, 1H), 3.99 (dd, J=22.4, 10.5 Hz, 1H), 3.84-3.63 (m, 4H), 3.57-3.30 (m, 4H), 2.38-2.17 (m, 6H), 1.94-1.76 (m, 3H). $^{13}$C NMR (101 MHz, CDCl$_3$) δ 167.92, 167.42, 151.03, 150.90, 143.28, 142.36, 138.21, 138.16, 137.19, 136.78, 133.89, 133.61, 131.92, 131.74, 129.57, 129.38, 129.22, 129.17, 126.78, 122.10, 118.53, 63.86, 63.46, 56.46, 56.42, 54.26, 54.17, 53.87, 40.46, 40.25, 36.48, 36.37, 34.09, 33.73, 21.11, 21.10, 21.04, 17.24, 17.09. HRMS (ESI-TOF) calculated for C30H34BrN5O2 [M+H]+ 576.1974, found: 576.1976.

(2S)-1-(3-hydroxyazetidin-1-yl)-2-(2-imino-3-(1-(p-tolyl)ethyl)-2,3-dihydro-1H-benzo[d]imidazol-1-yl)-3-(p-tolyl)propan-1-one (WZ-II-229). Reaction of (2S)-1-(3-hydroxyazetidin-1-yl)-3-(p-tolyl)-2-((2-((1-(p-tolyl)ethyl)amino)phenyl)amino)propan-1-one with cyanogen bromide yielded the product as off white solid (74%). $^1$H NMR (400 MHz, CDCl$_3$) δ 7.55-7.38 (m, 3H), 7.22-6.60 (m, 11H), 6.26-5.90 (m, 2H), 5.02-4.83 (m, 1H), 4.71-4.58 (m, 1H), 4.50 (dd, J=10.8, 4.3 Hz, 1H), 4.34-3.83 (m, 4H), 3.49-3.31 (m, 2H), 2.34-2.17 (m, 6H), 1.95-1.51 (m, 3H). $^{13}$C NMR (101 MHz, CDCl$_3$) δ 166.92, 166.84, 166.50, 166.38, 149.61, 149.36, 138.37, 138.30, 138.08, 138.03, 136.94, 136.80, 133.45, 133.40, 133.08, 133.04, 131.45, 131.40, 131.30, 131.24, 129.75, 129.48, 129.39, 129.26, 129.24, 128.16, 127.94, 127.91, 126.70, 126.65, 126.44, 126.42, 123.96, 123.94, 123.90, 123.89, 112.81, 112.74, 112.50, 112.44, 61.24, 60.94, 60.85, 60.79, 60.70, 58.85, 58.78, 58.48, 58.41, 57.21, 57.08, 54.14, 54.00, 53.96, 33.63, 33.55, 33.49, 21.18, 21.11, 21.07, 17.35, 17.28, 16.55, 16.44. HRMS (ESI-TOF) calculated for C29H32N4O2 [M+H]+ 469.2604, found: 469.2602.

1-((2S)-2-(2-imino-3-(1-(p-tolyl)ethyl)-2,3-dihydro-1H-benzo[d]imidazol-1-yl)-3-(p-tolyl)propanoyl)azetidine-3-carbonitrile (WZ-J-230). Reaction of 1-((2S)-3-(p-tolyl)-2-((2-((1-(p-tolyl)ethyl)amino)phenyl)amino)propanoyl)azetidine-3-carbonitrile with cyanogen bromide yielded the product as off white solid (64%). $^1$H NMR (400 MHz, CDCl$_3$) δ 7.48 (dd, J=13.2, 7.6 Hz, 1H), 7.25-6.61 (m, 11H), 6.55-6.27 (m, 1H), 6.24-6.09 (m, 0.5H), 5.44 (dd, J=14.5, 8.8 Hz, 1H), 5.05-4.71 (m, 0.5H), 4.47 (t, J=9.7 Hz, 1H), 4.36-4.28 (m, 0.5H), 4.23-4.12 (m, 0.5H), 3.97 (t, J=7.5 Hz, 1H), 3.64-3.36 (m, 3H), 2.36-2.25 (m, 6H), 1.91-1.52 (m, 3H). $^{13}$C NMR (101 MHz, CDCl$_3$) δ 167.30, 167.18, 166.86, 166.79, 150.19, 150.01, 149.86, 149.61, 138.45, 138.27, 138.14, 137.92, 137.20, 137.09, 136.96, 133.55, 133.31, 133.27, 133.12, 131.13, 131.04, 131.00, 130.90, 129.83, 129.79, 129.68, 129.56, 129.50, 129.41, 129.34, 129.29, 129.26, 129.22, 129.11, 128.90, 128.85, 128.66, 128.56, 128.39, 128.29, 126.70, 126.52, 126.49, 126.38, 124.12, 124.11, 124.00, 123.97, 123.63, 123.44, 118.96, 118.94, 113.24, 113.18, 112.72, 112.60, 112.51, 112.30, 112.22, 112.15, 57.84, 57.62, 57.14, 56.80, 54.69, 54.67, 54.35, 54.21, 54.17, 54.08, 53.99, 53.98, 52.18, 52.11, 33.84, 33.77, 33.54, 33.51, 21.26, 21.17, 21.10, 17.70, 17.63, 17.28, 17.18, 16.48, 16.34. HRMS (ESI-TOF) calculated for C30H31N5O [M+H]+ 478.2607, found: 478.2651.

3-((S)-1-methoxy-3-(p-tolyl)propan-2-yl)-1-(1-(p-tolyl)ethyl)-1,3-dihydro-2H-imidazo[4,5-b]pyridin-2-imine (WZ-II-231). Reaction of N2-((S)-1-methoxy-3-(p-tolyl)propan-2-yl)-N3-(1-(p-tolyl)ethyl)pyridine-2,3-diamine with cyanogen bromide yielded the product as brown solid (76%). $^1$H NMR (400 MHz, CDCl$_3$) δ 8.07 (d, J=4.3 Hz, 1H), 7.10-6.98 (m, 6H), 6.94 (d, J=7.8 Hz, 2H), 6.86 (dd, J=8.0, 5.0 Hz, 1H), 6.79-6.75 (m, 1H), 6.64 (br, 1H), 5.62 (br, 1H), 4.18 (br, 1H), 3.89 (dd, J=10.7, 3.0 Hz, 1H), 3.52 (s, 3H), 3.37 (dd, J=19.3, 9.1 Hz, 1H), 3.27 (dd, J=13.7, 6.9 Hz, 1H), 2.30 (s, 3H), 2.23 (s, 3H), 1.87 (d, J=6.9 Hz, 3H). $^{13}$C NMR (101 MHz, CDCl$_3$) δ 150.92, 143.66, 142.37, 138.13, 136.48, 133.61, 132.60, 129.48, 129.13, 129.05, 126.83, 121.95, 119.10, 118.43, 71.71, 59.52, 54.42, 33.36, 21.10, 21.04, 17.29. HRMS (ESI-TOF) calculated for C26H30N4O [M+H]+ 415.2498, found: 415.2525.

1-((2S)-2-(2-imino-1-(1-(p-tolyl)ethyl)-1,2-dihydro-3H-imidazo[4,5-b]pyridin-3-yl)-3-(p-tolyl)propanoyl)azetidine-3-carbonitrile (WZ-II-252). Reaction of 1-((2S)-3-(p-tolyl)-2-((3-((1-(p-tolyl)ethyl)amino)pyridin-2-yl)amino)propanoyl)azetidine-3-carbonitrile with cyanogen bromide yielded the product as brown solid (58%). $^1$H NMR (400 MHz, CDCl$_3$) δ 8.19-7.90 (m, 1H), 7.21-6.61 (m, 10H), 6.47-6.21 (m, 1H), 5.85 (s, 1H), 5.61 (dd, J=14.3, 7.1 Hz, 0.5H), 4.93 (dd, J=5.2, 2.6 Hz, 0.5H), 4.71-4.56 (m, 1H), 4.51-4.06 (m, 3H), 3.92 (dt, J=16.4, 8.0 Hz, 1H), 3.56 (dqd, J=21.1, 14.2, 6.2 Hz, 3H), 2.28 (dd, J=31.0, 6.8 Hz, 6H), 1.78 (dd, J=39.9, 6.9 Hz, 3H). $^{13}$C NMR (101 MHz, CDCl$_3$) δ 188.04, 167.76, 151.13, 142.46, 138.09, 138.04, 137.00, 136.38, 134.35, 134.22, 130.83, 129.54, 129.51, 129.42, 129.25, 129.14, 129.04, 128.86, 126.65, 126.60, 126.43, 118.83, 118.18, 118.16, 117.13, 63.91, 54.46, 54.10, 53.70, 53.45, 52.25, 50.58, 34.82, 33.53, 21.14, 21.10, 21.06, 17.51, 17.44, 17.35, 17.09. HRMS (ESI-TOF) calculated for C29H30N6O [M+H]+ 479.2554, found: 479.2625. $[α]_D^{20}$+40 (c 1.070, CHCl$_3$).

1-((2S)-2-(2-imino-1-(1-(p-tolyl)ethyl)-1,2-dihydro-3H-imidazo[4,5-b]pyridin-3-yl)-3-(p-tolyl)propanoyl)azetidine-3-carbonitrile (WZ-II-253). Reaction of 1-((2S)-3-(p-tolyl)-2-((3-((1-(p-tolyl)ethyl)amino)pyridin-2-yl)amino)propanoyl)azetidine-3-carbonitrile with cyanogen bromide yielded the product as brown solid (64%). $^1$H NMR (400 MHz, CDCl$_3$) δ 8.20-8.00 (m, 1H), 7.17-6.73 (m, 10H), 6.57 (ddd, J=31.8, 20.5, 11.4 Hz, 2H), 6.34-5.96 (m, 2H), 4.92 (ddd, J=29.6, 17.0, 8.4 Hz, 1H), 4.74-4.56 (m, 1H), 4.45 (t, J=12.4 Hz, 1H), 4.31-4.14 (m, 1H), 3.89-3.38 (m, 4H), 2.34-2.19 (m, 6H), 1.81 (dd, J=28.6, 6.6 Hz, 3H). $^{13}$C NMR (101 MHz, CDCl$_3$) δ 167.49, 167.46, 150.64, 150.48, 143.18, 142.95, 142.80, 138.03, 137.14, 136.94, 133.07, 132.88, 131.47, 131.28, 129.58, 129.39, 129.30, 129.13, 128.96, 126.96, 126.79, 126.74, 126.68, 121.61, 119.73, 119.23, 119.07, 118.97, 118.78, 55.25, 54.73, 54.57, 54.23, 52.60, 52.19, 33.63, 33.52, 21.11, 21.06, 17.50, 17.43. HRMS (ESI-TOF) calculated for C29H30N6O [M+H]+ 479.2554, found: 479.2579. $[α]_D^{20}$−84 (c 0.917, CHCl$_3$).

(2S)-2-(2-imino-1-(1-(p-tolyl)ethyl)-1,2-dihydro-3H-imidazo[4,5-b]pyridin-3-yl)-3-(p-tolyl)propan-1-ol (WZ-II-269). Reaction of cyanogen bromide with (2S)-3-(p-tolyl)-2-((3-((1-(p-tolyl)ethyl)amino)pyridin-2-yl)amino)propan-1-ol yielded the product as brown oil (55%). $^1$H NMR (400 MHz, CDCl$_3$) δ 7.35-7.25 (m, 3H), 7.15 (dd, J=11.1, 7.9 Hz, 4H), 7.05 (d, J=7.8 Hz, 2H), 6.68 (d, J=6.3 Hz, 1H), 6.35 (t, J=7.1 Hz, 1H), 6.23 (d, J=8.0 Hz, 1H), 4.78-4.68 (m, 1H), 4.46-4.33 (m, 2H), 4.21 (dd, J=11.8, 7.0 Hz, 1H), 3.28 (dd, J=13.9, 3.5 Hz, 1H), 3.02 (dd, J=14.1, 8.2 Hz, 1H), 2.32 (s, 3H), 2.25 (s, 3H), 1.75 (d, J=6.8 Hz, 3H). $^{13}$C NMR (101 MHz, CDCl$_3$) δ 147.78, 140.19, 136.95, 136.89, 131.69, 131.27, 129.52, 129.48, 129.40, 125.93, 118.93, 114.74, 56.37, 55.23, 54.35, 39.71, 24.61, 21.12, 21.01. HRMS (ESI-TOF) calculated for C25H28N4O [M+H]+ 401.2336, found: 401.2332. $[α]_D^{20}$−14 (c 1.025, CHCl$_3$).

(2S)-2-(2-imino-1-(1-(p-tolyl)ethyl)-1,2-dihydro-3H-imidazo[4,5-b]pyridin-3-yl)-3-(p-tolyl)propan-1-ol (WZ-II-270). Reaction of cyanogen bromide with (2S)-3-(p-tolyl)-2-((3-((1-(p-tolyl)ethyl)amino)pyridin-2-yl)amino)propan-1-ol yielded the product as brown oil (48%). $^1$H NMR (400 MHz, CDCl$_3$) δ 7.28 (dd, J=10.5, 7.0 Hz, 3H), 7.12 (dd, J=19.1, 7.9 Hz, 8H), 6.74 (d, J=6.3 Hz, 1H), 6.42-6.36 (m, 1H), 6.27 (d, J=7.9 Hz, 1H), 4.70 (td, J=10.8, 4.0 Hz, 1H), 4.43-4.32 (m, 2H), 4.22 (dd, J=11.9, 7.4 Hz, 1H), 3.37 (dd, J=14.0, 3.8 Hz, 1H), 2.95 (dd, J=13.9, 9.0 Hz, 1H), 2.30 (d, J=8.7 Hz, 6H), 1.75 (d, J=6.8 Hz, 3H). $^{13}$C NMR (101 MHz, CDCl$_3$) δ 147.76, 140.14, 137.02, 136.88, 131.80, 131.52, 129.61, 129.50, 129.34, 125.88, 119.10, 114.93, 114.87, 56.65, 55.35, 54.43, 39.81, 24.64, 21.09, 21.04. HRMS (ESI-TOF) calculated for C25H28N4O [M+H]+ 401.2336, found: 401.2328. $[α]_D^{20}$+112 (c 1.155, CHCl$_3$).

3-((2S)-2-(2-imino-1-(1-(p-tolyl)ethyl)-1,2-dihydro-3H-imidazo[4,5-b]pyridin-3-yl)-3-(p-tolyl)propoxy)propanenitrile (WZ-III-10). Reaction of cyanogen bromide with 3-((2S)-3-(p-tolyl)-2-((3-((1-(p-tolyl)ethyl)amino)pyridin-2-yl)amino)propoxy)propanenitrile yielded the product as brown oil. $^1$H NMR (400 MHz, CDCl$_3$) δ 8.12 (d, J=4.8 Hz, 1H), 7.20-7.04 (m, 6H), 6.95 (d, J=7.8 Hz, 2H), 6.88 (dd, J=8.0, 5.1 Hz, 1H), 6.73 (d, J=7.9 Hz, 1H), 6.43-6.35 (m, 1H), 5.79 (s, 1H), 4.60 (s, 1H), 4.11-4.00 (m, 1H), 3.96 (dd, J=10.7, 4.2 Hz, 1H), 3.73 (dt, J=9.5, 6.4 Hz, 1H), 3.53 (dd, J=13.8, 10.5 Hz, 1H), 3.33 (dd, J=13.8, 6.1 Hz, 1H), 2.70-2.47 (m, 2H), 2.30 (s, 3H), 2.23 (s, 3H), 1.67 (d, J=5.8 Hz, 3H). $^{13}$C NMR (101 MHz, CDCl$_3$) δ 151.23, 143.86, 142.30, 138.24, 136.42, 133.48, 132.73, 129.63, 129.36, 129.13, 126.77, 122.22, 118.82, 118.27, 117.86, 69.69, 65.93, 54.12, 33.65, 29.69, 21.08, 21.03, 18.94, 16.88. HRMS (ESI-TOF) calculated for C28H31N5O [M+H]+ 454.2601, found: 454.2605. $[α]_D^{20}$+23 (c 0.918, CHCl$_3$).

3-((2S)-2-(2-imino-1-(1-(p-tolyl)ethyl)-1,2-dihydro-3H-imidazo[4,5-b]pyridin-3-yl)-3-(p-tolyl)propoxy)propanenitrile (WZ-III-11). Reaction of cyanogen bromide with 3-((2S)-3-(p-tolyl)-2-((3-((1-(p-tolyl)ethyl)amino)pyridin-2-yl)amino)propoxy)propanenitrile yielded the product as brown oil. $^1$H NMR (400 MHz, CDCl$_3$) δ 8.17 (dd, J=4.9, 1.0 Hz, 1H), 7.07 (dd, J=14.4, 8.0 Hz, 4H), 6.99-6.90 (m, 3H), 6.82 (dd, J=8.1, 1.0 Hz, 3H), 6.43 (d, J=6.5 Hz, 1H), 6.03-5.92 (m, 1H), 4.69 (dd, J=10.0 Hz, 1H), 4.13 (ddd, J=10.3, 8.4, 5.2 Hz, 1H), 4.00 (dd, J=10.9, 4.5 Hz, 1H), 3.78 (ddd, J=9.5, 7.1, 5.9 Hz, 1H), 3.56 (dd, J=13.5, 11.2 Hz, 1H), 3.32 (dd, J=13.8, 5.5 Hz, 1H), 2.70-2.55 (m, 2H), 2.31 (s, 3H), 2.29 (s, 3H), 1.87 (d, J=6.9 Hz, 3H). $^{13}$C NMR (101 MHz, CDCl$_3$) δ 150.92, 143.52, 142.69, 138.04, 136.33, 133.49, 132.73, 129.46, 129.27, 129.16, 126.56, 121.94, 119.59, 118.53, 117.85, 69.45, 65.97, 54.49, 33.62, 29.69, 21.17, 21.10, 19.00, 17.26. HRMS (ESI-TOF) calculated for C28H31N5O [M+H]+ 454.2601, found: 454.2610. $[α]_D^{20}$−145 (c 1.590, CHCl$_3$).

(S)-2-(2-imino-3-(4-methylbenzyl)-2,3-dihydro-H-benzo[d]imidazol-1-yl)-3-(p-tolyl)propyl azetidine-3-carboxylate (WZ-II-2). At room temperature, a solution of HCl in dioxanes (4M) was added to (S)-1-(tert-butyl) 3-(2-(2-imino-3-(4-methylbenzyl)-2,3-dihydro-1H-benzo[d]imidazol-1-yl)-3-(p-tolyl)propyl) azetidine-1,3-dicarboxylate. The mixture was stirred for 1 hour. After removing solvent, the residue was purified by flash chromatography using 5%-20% MeOH in dichloromethane as eluent. Giving product as off white solid (87%). HRMS (ESI-TOF) calculated for C29H32N4O2 [M+H]+ 469.2598, found: 469.2641. $[α]_D^{20}$−161 (c 1.170, CHCl$_3$).

(2S)-1-(3-(aminomethyl)-3-(bromomethyl)azetidin-1-yl)-2-(2-imino-3-(1-(p-tolyl)ethyl)-2,3-dihydro-1H-benzo[d]imidazol-1-yl)-3-(p-tolyl)propan-1-one (WZ-II-184-1). At room temperature, a solution of HCl in dioxanes (4M) was added to tert-butyl 6-((2S)-2-(2-imino-3-(1-(p-tolyl)ethyl)-2,3-dihydro-1H-benzo[d]imidazol-1-yl)-3-(p-tolyl)propanoyl)-2,6-diazaspiro[3.3]heptane-2-carboxylate. The mixture was stirred for 1 hour. After removing solvent, the residue was purified by flash chromatography using 5%-20% MeOH in dichloromethane as eluent. Giving product as off white solid (10%). $^1$H NMR (400 MHz, CDCl$_3$) δ 7.61-6.58 (m, 11H), 6.05-5.55 (m, 2H), 4.84-3.07 (m, 11H), 2.41-2.07 (m, 6H), 1.92-1.50 (m, 3H). HRMS (ESI-TOF) calculated for C31H36BrN5O [M+H]+ 574.2181, found: 574.2184.

(2S)-2-(2-imino-3-(1-(p-tolyl)ethyl)-2,3-dihydro-1H-benzo[d]imidazol-1-yl)-1-(2,6-diazaspiro[3.3]heptan-2-yl)-3-(p-tolyl)propan-1-one (WZ-II-184-2). At room temperature, a solution of HCl in dioxanes (4M) was added to tert-butyl 6-((2S)-2-imino-3-(1-(p-tolyl)ethyl)-2,3-dihydro-1H-benzo[d]imidazol-1-yl)-3-(p-tolyl)propanoyl)-2,6-diazaspiro[3.3]heptane-2-carboxylate. The mixture was stirred for 1 hour. After removing solvent, the residue was purified by flash chromatography using 5%-20% MeOH in dichloromethane as eluent. Giving product as off white solid (65%). $^1$H NMR (400 MHz, CDCl$_3$) δ 9.57-8.81 (m, 2H), 8.62 (s, 1H), 7.47-6.56 (m, 8H), 5.82 (d, J=31.4 Hz, 1H), 4.82 (s, 1H), 4.45-3.22 (m, 11H), 2.35-2.07 (m, 6H), 1.84-1.48 (m, 3H). $^{13}$C NMR (101 MHz, CDCl$_3$) δ 166.70, 166.64, 149.70, 149.41, 138.37, 138.06, 137.14, 136.97, 133.36, 133.15, 131.34, 131.18, 129.74, 129.42, 129.29, 129.27, 129.03, 128.88, 127.94, 127.81, 126.61, 126.49, 123.97, 112.82, 112.59, 60.77, 60.60, 58.37, 58.27, 56.97, 56.80, 55.41, 55.31, 54.40, 53.64, 35.61, 33.41, 29.70, 21.09, 21.02, 20.99, 20.86, 16.50, 16.11. HRMS (ESI-TOF) calculated for C31H35N5O [M+H]+ 494.2920, found: 494.2919.

1-((S)-1-methoxy-3-(p-tolyl)propan-2-yl)-3-(1-(p-tolyl)ethyl)-1,3-dihydro-2H-benzo[d]imidazol-2-one (WZ-II-264). At room temperature, to a solution of N2-((S)-1-methoxy-3-(p-tolyl)propan-2-yl)-N3-(1-(p-tolyl)ethyl)pyridine-2,3-diamine (78 mg, 0.2 mmol, 1 eq.) was added triethylamine (0.069 ml, 0.5 mmol, 2.5 eq.), followed by the addition of triphosgene (24 mg, 0.08 mmol, 0.4 eq.). The reaction was stirred at room temperature for 1 hour. Saturated sodium bicarbonate aqueous solution was added to quench the reaction and the aqueous phase was extracted with ethyl acetate for three times. The combined organic phase was concentrated and purified by column using 20% ethyl acetate in hexanes as eluent. Giving product as light yellow oil (86%). $^1$H NMR (400 MHz, CDCl$_3$) δ 7.92 (d, J=5.0 Hz, 1H), 7.11 (s, 4H), 6.98 (dd, J=20.5, 7.8 Hz, 4H), 6.73-6.62 (m, 2H), 5.74 (q, J=7.1 Hz, 1H), 5.15-5.05 (m, 1H), 4.26 (t, J=9.4 Hz, 1H), 3.81 (dd, J=9.9, 5.5 Hz, 1H), 3.48 (dd, J=13.8, 10.3 Hz, 1H), 3.36 (s, 3H), 3.20 (dd, J=13.8, 6.1 Hz, 1H), 2.32 (s, 3H), 2.25 (s, 3H), 1.70 (d, J=7.2 Hz, 3H). $^{13}$C NMR (101 MHz, CDCl$_3$) δ 153.46, 143.92, 139.81, 137.25, 136.21, 135.70, 134.59, 129.28, 128.92, 128.87, 126.58, 121.86, 116.12, 115.06, 71.96, 58.82, 53.91, 49.90, 34.43, 21.06, 21.03, 17.12. HRMS (ESI-TOF) calculated for C27H30N2O2 [M+H]+ 416.2333, found: 416.2344.

(S)-1-(1-methoxy-3-phenylpropan-2-yl)-3-(4-methylbenzyl)-1H-benzo[d]imidazol-2(3H)-iminn (ARN-163). Reaction of (S)—N1-(1-methoxy-3-phenylpropan-2-yl)-N2-(4-methyl benzyl)benzene-1,2-diamine with cyanogen bromide yielded product as Viscous oil (78%); $^1$H NMR (400 MHz, CDCl$_3$) δ 7.18-7.05 (m, 7H), 7.00-6.90 (m, 4H), 6.73 (d, J=7.3 Hz, 1H), 5.72 (s, 1H), 5.14-4.84 (m, 2H), 4.11-3.93 (m, 1H), 3.85 (dd, J=10.1, 4.6 Hz, 1H), 3.39 (s, 4H), 3.27 (dd, J=14.0, 6.2 Hz, 1H), 2.31 (s, 3H). $^{13}$C NMR (100 MHz, CDCl$_3$) δ 138.18, 136.11, 129.88, 129.50, 129.17, 128.91, 128.70, 128.53, 126.84, 126.27, 125.03, 124.46, 124.35, 73.29, 59.99, 59.41, 47.84, 34.62, 21.11.

(1S,2S)-2-(2-imino-3-(4-methylbenzyl)-2,3-dihydro-1H-benzo[d]imidazol-1-yl)-3-methoxy-1-phenylpropan-1-ol (ARN-212): (1S,2S)-3-methoxy-2-(2-(4-methylbenzylamino) phenylamino)-1-phenylpropan-1-ol with cyanogen bromide yielded product as Viscous oil (80%). [α]$_D^{20}$+53.8 (c 3.80, CHCl$_3$); $^1$H NMR (400 MHz, CDCl$_3$) δ 7.41-7.33 (m, 2H), 7.20-7.04 (m, 6H), 6.93-6.74 (m, 5H), 6.65 (dd, J=7.6, 1.2 Hz, 1H), 5.33 (d, J=4.0 Hz, 1H), 4.97-4.83 (m, 2H), 4.65 (td, J=11.1, 9.9, 5.6 Hz, 1H), 4.26 (dd, J=10.2, 8.1 Hz, 1H), 4.15 (dd, J=10.2, 5.0 Hz, 1H), 3.34 (s, 3H), 2.33 (s, 3H). $^{13}$C NMR (100 MHz, CDCl$_3$) δ 154.44, 142.23, 137.59, 131.61, 131.01, 129.58, 127.94, 126.84, 126.32, 125.38, 121.50, 120.89, 107.11, 73.46, 70.08, 61.48, 59.25, 44.78, 21.12. HRMS (ESI-TOF) calcd for C25H28N3O2 [M+H]$^+$ 402.2182, found: 402.2205.

(S)-1-(1-methoxy-3-p-tolylpropan-2-yl)-3-((6-methylpyridin-2-yl)methyl)-1H-benzo[d]imidazol-2(3H)-imine (ARN-223): (S)—N1-(1-methoxy-3-p-tolylpropan-2-yl)-N2-((6-methylpyridin-2-yl)methyl)benzene-1,2-diamine with cyanogen bromide yielded product as Viscous oil (80%) yield; [α]$_D^{20}$–213 (c 1.095, CHCl$_3$); $^1$H NMR (400 MHz, CDCl$_3$) δ 7.38 (t, J=7.7 Hz, 1H), 7.19-6.80 (m, 8H), 6.71 (dd, J=7.7, 1.3 Hz, 1H), 6.58-6.35 (m, 1H), 5.10-4.94 (m, 2H), 4.84 (s, 1H), 3.97 (q, J=7.4, 6.4 Hz, 2H), 3.78 (dd, J=9.9, 4.9 Hz, 1H), 3.36 (s, 4H), 3.22 (dd, J=13.9, 6.5 Hz, 1H), 2.55 (s, 3H), 2.26 (s, 3H). $^{13}$C NMR (100 MHz, CDCl$_3$) δ (158.20, 155.29, 137.14, 135.81, 134.69, 131.46, 129.03, 128.97, 122.01, 120.54, 120.24, 117.36, 106.58, 72.32, 59.04, 46.90, 34.26, 24.38, 21.09. HRMS (ESI-TOF) calcd for C25H29N4O [M+H]$^+$ 401.2341, found: 401.2364.

(S)-1-(benzo[d]thiazol-2-ylmethyl)-3-(1-methoxy-3-p-tolylpropan-2-yl)-1H-benzo[d]imidazol-2(3H)-imine (ARN-237): (S)—N1-(benzo[d]thiazol-2-ylmethyl)-N2-(1-methoxy-3-p-tolylpropan-2-yl)benzene-1,2-diamine (0.26 g, 0.64 mmole) with cyanogen bromide yielded product as Viscous oil (65%); [α]$_D^{20}$–0.3 (c 7.20, CHCl$_3$); $^1$H NMR (400 MHz, CDCl$_3$) δ 8.01 (dt, J=8.3, 0.9 Hz, 1H), 7.80-7.74 (m, 1H), 7.46 (ddd, J=8.3, 7.2, 1.2 Hz, 1H), 7.35 (ddd, J=8.2, 7.2, 1.2 Hz, 1H), 7.11-6.84 (m, 8H), 5.48-5.27 (m, 2H), 4.60 (d, J=47.6 Hz, 1H), 3.94 (dd, J=10.0, 6.7 Hz, 1H), 3.79 (dd, J=10.0, 4.7 Hz, 1H), 3.37 (s, 3H), 3.27 (qd, J=13.9, 7.7 Hz, 2H), 2.26 (s, 3H). $^{13}$C NMR (100 MHz, CDCl$_3$) δ 167.52, 152.98, 136.00, 135.46, 134.53, 130.89, 129.23, 128.90, 126.11, 125.25, 123.06, 121.66, 121.00, 120.56, 106.77, 72.18, 59.09, 56.38, 43.95, 34.28, 21.10. HRMS (ESI-TOF) calcd for C26H27N4OS [M+H]$^+$ 443.1900, found: 443.1896.

(S)-1-(3,4-dimethylbenzyl)-3-(1-methoxy-3-p-tolylpropan-2-yl)-1H-benzo[d]imidazol-2(3H)-imine (ARN-238): (S)—N1-(3,4-dimethylbenzyl)-N2-(1-methoxy-3-p-tolylpropan-2-yl)benzene-1,2-diamine (0.24 g, 0.64 mmole) with cyanogen bromide yielded product as Viscous oil (71%) yield; [α]$_D^{20}$–72.0 (c 4.35, CHCl$_3$); $^1$H NMR (400 MHz, CDCl$_3$) δ 7.15-6.99 (m, 5H), 7.02-6.86 (m, 4H), 6.82 (s, 2H), 6.78-6.68 (m, 1H), 4.95-4.80 (m, 3H), 3.99 (s, 1H), 3.80 (dd, J=9.9, 4.9 Hz, 1H), 3.37 (s, 4H), 3.26 (dd, J=13.8, 6.8 Hz, 1H), 2.28 (d, J=3.4 Hz, 9H). $^{13}$C NMR (100 MHz, CDCl$_3$) δ 138.34, 136.05, 135.85, 134.93, 131.89, 129.23, 129.12, 128.93, 124.48, 120.28, 120.09, 106.52, 77.34, 72.22, 59.02, 45.12, 34.34, 21.35, 21.07. HRMS (ESI-TOF) calcd for C27H32N3O [M+H]$^+$ 414.2545, found: 414.2561.

(S)-1-(1-methoxy-3-p-tolylpropan-2-yl)-3-((2-methylpyrimidin-5-yl)methyl)-1H-benzo[d]imidazol-2(3H)-imine (ARN-243): (S)—N1-(1-methoxy-3-p-tolylpropan-2-yl)-N2-((2-methylpyrimidin-5-yl)methyl)benzene-1,2-diamine (0.15 g, 0.48 mmole) with cyanogen bromide yielded product as Viscous oil (60%) yield; [α]$_D^{20}$=–90.6 (c 2.6, CHCl$_3$); $^1$H NMR (400 MHz, CDCl$_3$) δ 8.45 (s, 2H), 7.19-6.79 (m, 7H), 6.79-6.54 (m, 1H), 5.10-4.84 (m, 2H), 4.55 (s, 1H), 3.89 (dd, J=10.0, 6.8 Hz, 1H), 3.75 (dd, J=9.9, 4.6 Hz, 1H), 3.34 (s, 3H), 3.21 (dd, J=7.9, 3.2 Hz, 2H), 2.69 (s, 3H), 2.26 (s, 3H). $^{13}$C NMR (100 MHz, CDCl$_3$) δ 167.44, 156.04, 136.35, 134.24, 130.88, 129.40, 129.21, 128.81, 128.72, 126.60, 120.72, 120.54, 106.22, 72.17, 59.06, 56.42, 40.28, 34.27, 25.71, 21.03. HRMS (ESI-TOF) calcd for C24H28N5O [M+H]+ 402.2294, found: 402.2314.

(S)-1-(1-methoxy-3-p-tolylpropan-2-yl)-3-(thiophen-3-ylmethyl)-1H-benzo[d]imidazol-2(3H)-imine (ARN-255): (S)—N1-(1-methoxy-3-p-tolylpropan-2-yl)-N2-(thiophen-3-ylmethyl)benzene-1,2-diamine (0.08 g, 0.22 mmole) with cyanogen bromide yielded product as Viscous oil (50%); $[\alpha]_D^{20}$=−103.6 (c 1.08, CHCl$_3$); $^1$H NMR (400 MHz, CDCl$_3$) δ 7.34-7.19 (m, 1H), 6.95 (dq, J=32.9, 7.3, 6.4 Hz, 8H), 6.85-6.68 (m, 2H), 5.02-4.88 (m, 2H), 4.07 (s, 1H), 3.95 (d, J=8.1 Hz, 1H), 3.79 (dd, J=10.1, 4.9 Hz, 1H), 3.37 (s, 4H), 3.21 (dd, J=13.9, 6.3 Hz, 1H), 2.27 (s, 3H). $^{13}$C NMR (100 MHz, CDCl$_3$) δ 136.72, 135.92, 134.60, 131.37, 129.09, 128.93, 126.43, 121.82, 120.39, 120.23, 106.47, 72.41, 59.05, 55.80, 40.83, 34.23, 21.09. HRMS (ESI-TOF) calcd for C23H26N3OS [M+H]$^+$ 392.1791, found: 392.1804.

(S)-1-(1-methoxy-3-p-tolylpropan-2-yl)-3-(4-methylbenzyl)-1H-benzo[d]imidazol-2(3H)-imine (ARN-256,568, 574): (S)—N1-(1-methoxy-3-p-tolylpropan-2-yl)-N2-(4-methyl benzyl)benzene-1,2-diamine (0.15 g, 0.40 mmole) with cyanogen bromide yielded product as Viscous oil (80%); $[\alpha]_D^{20}$=−108.1 (c 4.25, CHCl$_3$); $^1$H NMR (400 MHz, CDCl$_3$) δ 7.19-6.99 (m, 8H), 6.92 (dt, J=23.9, 7.6 Hz, 3H), 6.70 (dd, J=7.7, 1.2 Hz, 1H), 4.91 (q, J=16.6 Hz, 3H), 4.69-4.51 (m, 1H), 4.07-3.93 (m, 1H), 3.82 (dd, J=9.9, 5.0 Hz, 1H), 3.39 (s, 4H), 3.26 (dd, J=13.8, 6.5 Hz, 1H), 2.33 (s, 3H), 2.33 (s, 3H). NMR(100 MHz, CDCl$_3$) δ 137.06, 135.82, 134.84, 133.05, 131.74, 129.41, 129.10, 129.00, 126.68, 120.28, 120.10, 106.49, 72.39, 59.05, 56.17, 44.67, 34.31, 21.16, 21.15. HRMS (ESI-TOF) calcd for C26H30N3O [M+H]$^+$ 400.2384, found: 400.2394.

(S)-1-(1-methoxy-3-p-tolylpropan-2-yl)-3-(quinolin-8-ylmethyl)-1H-benzo[d]imidazol-2(3H)-imine (ARN-260): (S)—N1-(1-methoxy-3-p-tolylpropan-2-yl)-N2-(quinolin-8-ylmethyl)benzene-1,2-diamine (0.11 g, 0.27 mmole) with cyanogen bromide yielded product as Viscous oil (80%); $[\alpha]_D^{20}$=−108.7 (c 3.1, CHCl$_3$); $^1$H NMR (400 MHz, CDCl$_3$) δ 8.98 (dd, J=4.3, 1.8 Hz, 1H), 8.19-8.09 (m, 1H), 7.72 (d, J=8.1 Hz, 1H), 7.47-7.44 (m, 1H), 7.35 (t, J=7.7 Hz, 1H), 7.14-6.73 (m, 9H), 5.73-5.58 (m, 2H), 4.90 (s, 1H), 4.03 (s, 1H), 3.83 (dd, J=10.0, 5.0 Hz, 1H), 3.39 (s, 4H), 3.26 (dd, J=13.9, 6.5 Hz, 1H), 2.28 (s, 3H). $^{13}$C NMR (100 MHz, CDCl$_3$) δ 149.60, 146.08, 136.34, 135.72, 134.88, 133.56, 131.92, 129.06, 129.03, 128.25, 127.33, 126.81, 126.36, 121.33, 120.37, 120.11, 106.54, 77.40, 72.48, 59.05, 41.15, 34.31, 21.15. HRMS (ESI-TOF) calcd for C$_{28}$H$_{29}$N$_4$O [M+H]$^+$ 437.2341, found: 437.2359.

(S)-1-((6-chloropyridin-3-yl)methyl)-3-(1-methoxy-3-p-tolylpropan-2-yl)-1H-benzo[d]imidazol-2(3H)-imine (ARN-265): (S)—N1-((6-chloropyridin-3-yl)methyl)-N2-(1-methoxy-3-p-tolylpropan-2-yl)benzene-1,2-diamine (0.11 g, 0.28 mmole) with cyanogen bromide yielded product as Viscous oil (78%); $[\alpha]_D^{20}$=−100.9 (c 1.2, CHCl$_3$); $^1$H NMR (400 MHz, CDCl$_3$) δ 8.26 (d, J=2.7 Hz, 1H), 7.29 (d, J=8.1 Hz, 1H), 7.18 (d, J=8.2 Hz, 2H), 6.87-6.95 (m, 7H), 6.73-6.58 (m, 1H), 5.06-4.82 (m, 2H), 4.62 (s, 1H), 3.98-3.88 (m, 2H), 3.77 (dd, J=9.9, 4.8 Hz, 1H), 3.36 (s, 3H), 3.23 (qd, J=13.9, 7.9 Hz, 2H), 2.27 (s, 3H). $^{13}$C NMR (100 MHz, CDCl$_3$) δ 150.61, 148.41, 137.66, 136.15, 134.36, 131.16, 130.95, 129.15, 128.81, 124.29, 120.71, 120.50, 106.30, 72.72, 59.09, 56.24, 41.77, 34.25, 21.08. HRMS (ESI-TOF) calcd for C$_{24}$H$_{26}$ClN4O [M+H]$^+$ 421.1789, found: 421.1793.

(S)-1-((5-chlorobenzo[d]thiazol-2-yl)methyl)-3-(1-methoxy-3-p-tolylpropan-2-yl)-1H-benzo[d]imidazol-2(3H)-imine (ARN-269): (S)—N1-((5-chlorobenzo[d]thiazol-2-yl)methyl)-N2-(1-methoxy-3-p-tolylpropan-2-yl)benzene-1,2-diamine (0.10 g, 0.22 mmole) with cyanogen bromide yielded product as Viscous oil (75%); $[\alpha]_D^{20}$=−95.7 (c 1.15, CHCl$_3$); $^1$H NMR (400 MHz, CDCl$_3$) δ 7.99 (d, J=2.0 Hz, 1H), 7.68 (d, J=8.5 Hz, 1H), 7.34 (dd, J=8.5, 2.0 Hz, 1H), 7.15-6.79 (m, 8H), 5.46-5.24 (m, 2H), 4.60 (s, 1H), 3.92 (dd, J=9.9, 6.7 Hz, 1H), 3.78 (dd, J=10.0, 4.7 Hz, 1H), 3.37 (s, 3H), 3.25 (dd, J=7.9, 3.5 Hz, 2H), 2.26 (s, 3H). $^{13}$C NMR (100 MHz, CDCl$_3$) δ 169.70, 153.84, 136.04, 134.47, 133.72, 132.15, 130.79, 129.22, 128.86, 125.76, 122.93, 122.34, 121.02, 120.58, 106.67, 72.14, 59.09, 56.41, 43.88, 34.28, 21.08. HRMS (ESI-TOF) calcd for C26H26ClN4OS [M+H]$^+$ 477.1510, found: 477.1507.

(S)-1-((5-bromobenzo[d]thiazol-2-yl)methyl)-3-(1-methoxy-3-p-tolylpropan-2-yl)-1H-benzo[d]imidazol-2(3H)-imine (ARN-279): (S)—N1-((5-bromobenzo[d]thiazol-2-yl)methyl)-N2-(1-methoxy-3-p-tolylpropan-2-yl)benzene-1,2-diamine (0.30 g, 0.62 mmole) with cyanogen bromide yielded product as Viscous oil (78%); $[\alpha]_D^{20}$=−88.2 (c 1.15, CHCl$_3$); $^1$H NMR (400 MHz, CDCl$_3$) δ 8.15 (d, J=1.8 Hz, 1H), 7.61 (d, J=8.5 Hz, 1H), 7.45 (dd, J=8.5, 1.9 Hz, 1H), 7.11-6.71 (m, 8H), 5.55-5.27 (m, 2H), 4.61 (s, 1H), 4.31 (s, 1H), 3.92 (dd, J=10.0, 6.8 Hz, 1H), 3.78 (dd, J=10.0, 4.6 Hz, 1H), 3.36 (s, 3H), 3.26 (dd, J=7.8, 4.5 Hz, 2H), 2.26 (s, 3H). $^{13}$C NMR (100 MHz, CDCl$_3$) δ 169.48, 154.16, 136.04, 134.47, 134.28, 130.79, 129.23, 128.87, 128.37, 125.98, 122.68, 121.05, 120.61, 119.70, 106.70, 72.15, 59.10, 56.42, 43.85, 34.28, 21.10. HRMS (ESI-TOF) calcd for C26H26BrN4OS [M+H]$^+$ 521.1011, found: 521.1022.

(S)-1-((5-fluorobenzo[d]thiazol-2-yl)methyl)-3-(1-methoxy-3-p-tolylpropan-2-yl)-1H-benzo[d]imidazol-2(3H)-iminee (ARN-284): (S)—N1-((5-fluorobenzo[d]thiazol-2-yl)methyl)-N2-(1-methoxy-3-p-tolylpropan-2-yl)benzene-1,2-diamine (0.22 g, 0.51 mmole) with cyanogen bromide yielded product as Viscous oil (83%); $[\alpha]_D^{20}$=−85.6 (c 3.2, CHCl$_3$); $^1$H NMR (400 MHz, CDCl$_3$) δ 7.80-7.62 (m, 2H), 7.21-6.78 (m, 9H), 5.48-5.28 (m, 2H), 4.61 (s, 1H), 3.93 (dd, J=10.0, 6.7 Hz, 2H), 3.78 (dd, J=10.0, 4.7 Hz, 2H), 3.37 (s, 3H), 3.26 (dd, J=7.9, 4.5 Hz, 2H), 2.26 (s, 3H). $^{13}$C NMR (100 MHz, CDCl$_3$) δ 170.22, 162.92, 160.49, 153.84, 136.04, 134.47, 130.82, 129.22, 128.87, 122.37, 122.27, 121.04, 120.59, 114.13, 113.88, 109.39, 109.15, 106.71, 72.14, 59.08, 56.41, 43.93, 34.28, 21.08. HRMS (ESI-TOF) calcd for C26H26FN4OS [M+H]$^+$ 461.1806, found: 461.1804.

(S)-1-((3-(2-chlorophenyl)isoxazol-5-yl)methyl)-3-(1-methoxy-3-p-tolylpropan-2-yl)-1H-benzo[d]imidazol-2(3H)-imine (ARN-288): (S)—N1-((3-(2-chlorophenyl)isoxazol-5-yl) methyl)-N2-(1-methoxy-3-p-tolylpropan-2-yl)benzene-1,2-diamine (0.20 g, 0.43 mmole) with cyanogen bromide yielded product as Viscous oil (75%); $[\alpha]_D^{20}$=−59.0 (c 3.0, CHCl$_3$); $^1$H NMR (400 MHz, CDCl$_3$) δ 7.70-7.62 (m, 1H), 7.50-7.43 (m, 1H), 7.38-7.30 (m, 2H), 7.12-6.83 (m, 8H), 6.43 (s, 1H), 5.14 (d, J=6.3 Hz, 2H), 4.59 (s, 1H), 3.91 (dd, J=9.9, 6.8 Hz, 1H), 3.76 (dd, J=10.0, 4.7 Hz, 1H), 3.35 (s, 3H), 3.94-3.74 (m, 2H), 2.12 (s, 3H). $^{13}$C NMR (100 MHz, CDCl$_3$) δ 167.01, 161.22, 136.11, 134.44, 132.88, 131.00, 130.91, 130.83, 130.33, 129.15, 128.79, 128.11, 127.05, 120.89, 120.60, 106.62, 103.97, 72.16, 59.05, 56.36, 37.43, 34.23, 20.84. HRMS (ESI-TOF) calcd for C28H28ClN4O2 [M+H]$^+$ 487.1895, found: 487.1895.

(S)-1-(4-chlorobenzyl)-3-(1-methoxy-3-p-tolylpropan-2-yl)-1H-benzo[d]imidazol-2(3H)-imine (ARN-303): (S)—

N1-(4-chlorobenzyl)-N2-(1-methoxy-3-p-tolylpropan-2-yl)benzene-1,2-diamine (0.13 g, 0.34 mmole) with cyanogen bromide yielded product as Viscous oil (80%); $[\alpha]_D^{20}=-98.2$ (c 3.45, CHCl$_3$); $^1$H NMR (400 MHz, CDCl$_3$) δ 7.32-7.19 (m, 2H), 7.17-6.81 (m, 9H), 6.64 (dd, J=7.7, 1.2 Hz, 1H), 5.01-4.82 (m, 2H), 4.65-4.46 (m, 1H), 4.04-3.90 (m, 1H), 3.80 (dd, J=9.9, 4.9 Hz, 1H), 3.37 (s, 4H), 3.22 (dd, J=13.9, 6.3 Hz, 1H), 2.29 (s, 3H). $^{13}$C NMR (100 MHz, CDCl$_3$) δ 135.93, 134.72, 134.62, 133.16, 131.41, 129.10, 128.93, 128.84, 128.12, 120.47, 120.24, 106.41, 72.36, 59.06, 55.93, 44.21, 34.26, 21.12. HRMS (ESI-TOF) calcd for C25H27ClN3O [M+H]$^+$ 420.1837, found: 420.1839.

(S)-1-(1-methoxy-3-p-tolylpropan-2-yl)-3-(3,4,5-trifluorobenzyl)-1H-benzo[d]imidazol-2(3H)-imine (ARN-306): (S)—N1-(1-methoxy-3-p-tolylpropan-2-yl)-N2-(3,4,5-trifluorobenzyl)benzene-1,2-diamine (0.11 g, 0.28 mmole) with cyanogen bromide yielded product as Viscous oil (76%); $[\alpha]_D^{20}=-103.4$ (c 3.1, CHCl$_3$); $^1$H NMR (400 MHz, CDCl$_3$) δ 7.17-6.86 (m, 7H), 6.74 (p, J=6.3, 5.1 Hz, 2H), 6.67-6.57 (m, 1H), 5.03-4.76 (m, 2H), 4.64 (s, 1H), 3.96 (dd, J=10.0, 6.9 Hz, 1H), 3.80 (dd, J=9.9, 4.9 Hz, 1H), 3.38 (s, 4H), 3.20 (dd, J=13.9, 6.0 Hz, 1H), 2.26 (s, 3H). $^{13}$C NMR (100 MHz, CDCl$_3$) δ 154.42, 152.68, 150.05, 140.20, 137.70, 136.31, 134.34, 131.04, 129.22, 128.73, 120.74, 120.45, 110.85, 110.79, 110.70, 110.64, 106.27, 72.31, 59.07, 56.27, 43.80, 34.21, 20.93. HRMS (ESI-TOF) calcd for C25H25F3N3O [M+H]$^+$ 440.1950, found: 440.1964.

(S)-1-(3,4-difluorobenzyl)-3-(1-methoxy-3-p-tolylpropan-2-yl)-1H-benzo[d]imidazol-2(3H)-imine (ARN-307): (S)—N1-(3,4-difluorobenzyl)-N2-(1-methoxy-3-p-tolylpropan-2-yl)benzene-1,2-diamine (0.17 g, 0.45 mmole) with cyanogen bromide yielded product as Viscous oil (71%); $[\alpha]_D^{20}=-100.5$ (c 4.9, CHCl$_3$); $^1$H NMR (400 MHz, CDCl$_3$) δ 7.18-6.98 (m, 6H), 6.99-6.80 (m, 4H), 6.72-6.58 (m, 1H), 5.02-4.80 (m, 2H), 4.71 (s, 1H), 4.02-3.89 (m, 1H), 3.80 (dd, J=9.9, 4.9 Hz, 1H), 3.38 (s, 4H), 3.21 (dd, J=13.9, 6.2 Hz, 1H), 2.27 (s, 3H). $^{13}$C NMR (100 MHz, CDCl$_3$) δ 151.80, 150.81, 149.33, 148.35, 136.12, 134.49, 133.36, 131.25, 129.16, 129.10, 128.82, 122.74, 122.71, 122.68, 122.64, 120.58, 120.33, 117.52, 117.34, 115.83, 115.65, 106.34, 72.33, 59.06, 56.10, 43.90, 34.23, 21.01. HRMS (ESI-TOF) calcd for C25H26F2N3O [M+H]$^+$ 422.2044, found: 422.2048.

(S)-1-(1-methoxy-3-p-tolylpropan-2-yl)-3-(4-(trifluoromethyl)benzyl)-1H-benzo[d]imidazol-2(3H)-imine (ARN-311): (S)—N1-(1-methoxy-3-p-tolylpropan-2-yl)-N2-(4-(trifluoro methyl)benzyl)benzene-1,2-diamine (0.18 g, 0.42 mmole) with cyanogen bromide yielded product as Viscous oil (89%); $[\alpha]_D^{20}=-100.5$ (c 4.9, CHCl$_3$); $^1$H NMR (400 MHz, CDCl$_3$) δ 7.52 (d, J=8.0 Hz, 2H), 7.29-6.78 (m, 9H), 6.75-6.52 (m, 1H), 5.14-4.89 (m, 2H), 4.76 (s, 1H), 3.97 (dd, J=10.1, 6.5 Hz, 1H), 3.81 (dd, J=9.9, 4.9 Hz, 1H), 3.38 (s, 4H), 3.23 (dd, J=13.9, 6.3 Hz, 1H), 2.29 (s, 3H). $^{13}$C NMR (100 MHz, CDCl$_3$) δ 140.31, 135.99, 134.51, 131.33, 129.12, 128.91, 126.92, 125.70, 125.66, 125.62, 125.59, 120.58, 120.33, 106.35, 72.39, 59.07, 55.98, 44.35, 34.25, 21.04. HRMS (ESI-TOF) calcd for C26H27F3N3O [M+H]$^+$ 454.2106, found: 454.2110.

(S)-1-(4-chloro-3-fluorobenzyl)-3-(1-methoxy-3-p-tolylpropan-2-yl)-1H-benzo[d]imidazol-2(3H)-imine (ARN-312): (S)—N1-(4-chloro-3-fluorobenzyl)-N2-(1-methoxy-3-p-tolylpropan-2-yl)benzene-1,2-diamine (0.19 g, 0.46 mmole) with cyanogen bromide yielded product as Viscous oil (87%); $[\alpha]_D^{20}=-103.1$ (c 6.9, CHCl$_3$); $^1$H NMR (400 MHz, CDCl$_3$) δ 7.29 (t, J=7.8 Hz, 1H), 7.20-6.78 (m, 9H), 6.63 (dd, J=7.8, 1.3 Hz, 1H), 5.04-4.79 (m, 2H), 4.71 (s, 1H), 4.09-3.87 (m, 1H), 3.80 (dd, J=9.9, 4.9 Hz, 1H), 3.38 (s, 4H), 3.21 (dd, J=13.9, 6.1 Hz, 1H), 2.28 (s, 3H). $^{13}$C NMR (100 MHz, CDCl$_3$) δ 159.48, 157.00, 137.41, 134.48, 131.22, 130.80, 129.18, 128.83, 123.15, 120.63, 120.37, 115.08, 114.87, 106.35, 72.34, 59.07, 56.12, 43.95, 34.23, 21.04. HRMS (ESI-TOF) calcd for C25H26ClFN3O [M+H]$^+$ 438.1748, found: 438.1750.

(S)-1-(3,4-dichlorobenzyl)-3-(1-methoxy-3-p-tolylpropan-2-yl)-1H-benzo[d]imidazol-2(3H)-imine (ARN-313): (S)—N1-(3,4-dichlorobenzyl)-N2-(1-methoxy-3-p-tolylpropan-2-yl)benzene-1,2-diamine (0.08 g, 0.18 mmole) with cyanogen bromide yielded product as Viscous oil (74%); $[\alpha]_D^{20}=-100.5$ (c 1.55, CHCl$_3$); $^1$H NMR (400 MHz, CDCl$_3$) δ 7.41-7.21 (m, 2H), 7.18-6.80 (m, 8H), 6.74-6.53 (m, 1H), 5.05-4.81 (m, 2H), 4.69 (s, 1H), 4.39 (s, 1H), 4.03-3.87 (m, 1H), 3.79 (dd, J=9.9, 4.7 Hz, 1H), 3.37 (s, 4H), 3.21 (dd, J=13.9, 6.3 Hz, 1H), 2.27 (s, 3H). $^{13}$C NMR (100 MHz, CDCl$_3$) δ 136.63, 136.08, 134.47, 132.80, 131.51, 131.20, 130.68, 129.18, 128.82, 128.73, 126.17, 120.71, 120.46, 106.45, 72.26, 59.08, 56.21, 43.98, 34.24, 21.08. HRMS (ESI-TOF) calcd for C25H26Cl2N3O [M+H]$^+$ 454.1453, found: 454.1450.

(S)-4-((2-imino-3-(1-methoxy-3-p-tolylpropan-2-yl)-2,3-dihydro-1H-benzo[d]imidazol-1-yl)methyl)benzonitrile (ARN-316): (S)-4-((2-(1-methoxy-3-p-tolylpropan-2-yl amino)phenylamino)methyl)benzonitrile (0.15 g, 0.39 mmole) with cyanogen bromide yielded product as Viscous oil (80%); $[\alpha]_D^{20}=-118.3$ (c 2.05, CHCl$_3$); $^1$H NMR (400 MHz, CDCl$_3$) δ 7.54 (d, J=7.9 Hz, 2H), 7.25-6.77 (m, 9H), 6.60 (d, J=7.5 Hz, 1H), 5.17-4.89 (m, 2H), 4.69 (s, 2H), 3.95 (dd, J=9.9, 7.0 Hz, 1H), 3.79 (dd, J=9.9, 4.7 Hz, 1H), 3.37 (s, 4H), 3.22 (dd, J=14.0, 6.4 Hz, 1H), 2.28 (s, 3H). $^{13}$C NMR (100 MHz, CDCl$_3$) δ 154.51, 141.89, 136.04, 134.45, 132.49, 131.16, 129.12, 128.89, 127.38, 120.72, 120.43, 118.68, 111.29, 106.32, 72.32, 59.09, 56.11, 44.47, 34.24, 21.13. HRMS (ESI-TOF) calcd for C26H27N4O [M+H]$^+$ 411.2185, found: 411.2184.

(S)-1-(4-bromo-3-fluorobenzyl)-3-(1-methoxy-3-p-tolylpropan-2-yl)-1H-benzo[d]imidazol-2(3H)-imine (ARN-317): (S)—N1-(4-bromo-3-fluorobenzyl)-N2-(1-methoxy-3-p-tolylpropan-2-yl)benzene-1,2-diamine (0.11 g, 0.24 mmole) with cyanogen bromide yielded product as Viscous oil (82%); $[\alpha]_D^{20}=-101.6$ (c 2.00, CHCl$_3$); $^1$H NMR (400 MHz, CDCl$_3$) δ 7.44 (dd, J=8.2, 7.0 Hz, 1H), 7.21-6.71 (m, 9H), 6.69-6.56 (m, 1H), 5.05-4.79 (m, 2H), 4.69 (s, 1H), 4.54 (s, 1H), 4.06-3.88 (m, 1H), 3.79 (dd, J=9.9, 4.9 Hz, 1H), 3.37 (s, 4H), 3.21 (dd, J=13.9, 6.1 Hz, 1H), 2.28 (s, 3H). $^{13}$C NMR (100 MHz, CDCl$_3$) δ 160.47, 158.00, 138.32, 136.15, 134.45, 133.70, 131.21, 129.17, 128.81, 123.59, 120.63, 120.37, 114.98, 114.75, 107.68, 106.35, 72.33, 59.08, 56.14, 43.99, 34.23, 21.04. HRMS (ESI-TOF) calcd for C25H26BrFN3O [M+H]$^+$ 482.1243, found: 482.1276.

(S)-2-bromo-4-((2-imino-3-(1-methoxy-3-p-tolylpropan-2-yl)-2,3-dihydro-1H-benzo[d]imidazol-1-yl)methyl)benzonitrile (ARN-320): (S)-2-bromo-4-((2-(1-methoxy-3-p-tolyl propan-2-ylamino)phenylamino)methyl)benzonitrile (0.20 g, 0.43 mmole) with cyanogen bromide yielded product as Viscous oil (70%); $[\alpha]_D^{20}=-121.3$ (c 2.55, CHCl$_3$); $^1$H NMR (400 MHz, CDCl$_3$) δ 7.52 (dd, J=8.0, 6.3 Hz, 1H), 7.22-6.83 (m, 9H), 6.59 (d, J=7.6 Hz, 1H), 5.18-4.85 (m, 2H), 4.74-4.49 (m, 1H), 3.95 (dd, J=10.0, 7.1 Hz, 1H), 3.79 (dd, J=9.9, 4.8 Hz, 1H), 3.37 (s, 4H), 3.20 (dd, J=13.9, 6.2 Hz, 1H), 2.27 (s, 3H). $^{13}$C NMR (100 MHz, CDCl$_3$) δ 164.71, 162.13, 145.42, 136.28, 134.29, 133.71, 130.95, 129.20, 128.76, 123.07, 123.04, 120.87, 120.54, 114.73, 114.53, 113.82, 106.22, 72.29, 59.10, 56.31, 44.22, 34.21, 21.03.

(S)-1-(3-bromo-4-fluorobenzyl)-3-(1-methoxy-3-p-tolyl-propan-2-yl)-1H-benzo[d]imidazol-2(3H)-imine (ARN-321): (S)—N1-(3-bromo-4-fluorobenzyl)-N2-(1-methoxy-3-p-tolylpropan-2-yl)benzene-1,2-diamine (0.11 g, 0.24) with cyanogen bromide yielded product as Viscous oil (83%); [α]$_D^{20}$=−84.2 (c 2.95, CHCl$_3$); $^1$H NMR (400 MHz, CDCl$_3$) δ 7.42 (dd, J=6.5, 2.0 Hz, 1H), 7.22-6.77 (m, 9H), 6.72-6.59 (m, 1H), 4.91 (q, J=16.6 Hz, 2H), 4.68 (s, 1H), 4.37 (s, 1H), 4.06-3.88 (m, 1H), 3.78 (dd, J=9.9, 4.8 Hz, 1H), 3.37 (s, 4H), 3.22 (dd, J=13.9, 6.5 Hz, 1H), 2.27 (s, 3H). $^{13}$C NMR (100 MHz, CDCl$_3$) δ 159.60, 157.14, 136.03, 134.58, 131.80, 131.28, 129.17, 128.84, 127.41, 127.33, 120.59, 120.34, 116.74, 116.52, 109.44, 109.23, 106.37, 72.24, 59.07, 56.13, 43.81, 34.28, 21.10. HRMS (ESI-TOF) calcd for C25H26BrFN3O [M+H]$^+$ 482.1237, found: 482.1218.

(S)-1-(1-methoxy-3-p-tolylpropan-2-yl)-3-(4-(methylthio)benzyl)-1H-benzo[d]imidazol-2(3H)-imine (ARN-328): (S)—N1-(1-methoxy-3-p-tolylpropan-2-yl)-N2-(4-(methylthio)benzyl)benzene-1,2-diamine (0.13 g, 0.32 mmole) with cyanogen bromide yielded product as Viscous oil (70%); $^1$H NMR (400 MHz, CDCl$_3$) δ 7.24-7.15 (m, 2H), 7.15-6.80 (m, 9H), 6.66 (dd, J=7.5, 1.4 Hz, 1H), 4.89 (q, J=16.7 Hz, 2H), 4.40 (s, 1H), 3.96 (s, 1H), 3.79 (dd, J=9.9, 4.9 Hz, 1H), 3.37 (s, 4H), 3.22 (dd, J=13.9, 6.5 Hz, 1H), 2.45 (s, 3H), 2.29 (s, 3H). $^{13}$C NMR (100 MHz, CDCl$_3$) δ 137.53, 135.84, 134.72, 133.01, 131.56, 129.08, 128.98, 128.94, 127.26, 126.96, 120.34, 120.14, 106.46, 72.35, 59.05, 55.84, 44.45, 34.27, 21.13, 15.94.

(S)-1-(4-tert-butylbenzyl)-3-(1-methoxy-3-p-tolylpropan-2-yl)-1H-benzo[d]imidazol-2(3H)-imine (ARN-333): (S)—N1-(4-tert-butylbenzyl)-N2-(1-methoxy-3-p-tolylpropan-2-yl) benzene-1,2-diamine (0.23 g, 0.55 mmole) with cyanogen bromide yielded product as Viscous oil (72%); [α]$_D^{20}$=−83.8 (c 4.7, CHCl$_3$); $^1$H NMR (400 MHz, CDCl$_3$) δ 7.42-7.30 (m, 2H), 7.23-6.81 (m, 9H), 6.81-6.65 (m, 1H), 5.07-4.81 (m, 2H), 4.70 (s, 1H), 4.01 (s, 1H), 3.83 (dd, J=9.9, 5.0 Hz, 1H), 3.40 (s, 4H), 3.26 (dd, J=13.9, 6.5 Hz, 1H), 2.32 (s, 3H), 1.34 (s, 9H). $^{13}$C NMR (100 MHz, CDCl$_3$) δ 154.98, 150.29, 135.77, 134.85, 132.98, 131.79, 129.10, 129.01, 126.35, 125.64, 120.28, 120.07, 106.46, 72.43, 59.06, 55.72, 44.51, 34.50, 34.31, 31.39, 21.18. HRMS (ESI-TOF) calcd for C$_{29}$H$_{36}$N$_3$O [M+H]$^+$ 442.2852, found: 442.2850.

(S)-1-(1-methoxy-3-p-tolylpropan-2-yl)-3-(4-(trifluoromethoxy)benzyl)-1H-benzo[d]imidazol-2(3H)-imine (ARN-337): (S)—N1-(1-methoxy-3-p-tolylpropan-2-yl)-N2-(4-(trifluoro methoxy)benzyl)benzene-1,2-diamine (0.17 g, 0.45 mmole) with cyanogen bromide yielded product as Viscous oil (71%); [α]$_D^{20}$=−91.4 (c 3.55, CHCl$_3$); $^1$H NMR (400 MHz, CDCl$_3$) δ 7.23-6.83 (m, 11H), 6.71-6.61 (m, 1H), 5.06-4.86 (m, 2H), 4.77 (s, 1H), 4.39 (s, 1H), 4.04-3.91 (m, 1H), 3.80 (dd, J=9.9, 4.9 Hz, 1H), 3.38 (s, 4H), 3.23 (dd, J=13.9, 6.3 Hz, 1H), 2.28 (s, 3H). $^{13}$C NMR (100 MHz, CDCl$_3$) δ 148.44, 148.42, 135.95, 134.89, 134.57, 131.39, 129.09, 128.92, 128.04, 121.19, 120.51, 120.28, 106.38, 72.38, 59.05, 55.95, 44.08, 34.25, 21.02. HRMS (ESI-TOF) calcd for C26H27F3N3O2 [M+H]$^+$ 470.2050, found: 470.2047.

(S)-3-((2-imino-3-(1-methoxy-3-p-tolylpropan-2-yl)-2,3-dihydro-1H-benzo[d]imidazol-1-yl)methyl)benzonitrile (ARN-338): (S)-3-((2-(1-methoxy-3-p-tolylpropan-2-ylamino) phenylamino)methyl)benzonitrile (0.13 g, 0.34) with cyanogen bromide yielded product as Viscous oil (85%); [α]$_D^{20}$=−105.3 (c 4.0, CHCl$_3$); $^1$H NMR (400 MHz, CDCl$_3$) δ 7.57-7.29 (m, 4H), 7.19-6.84 (m, 7H), 6.72-6.55 (m, 1H), 5.12-4.93 (m, 2H), 4.66 (s, 1H), 4.02-3.89 (m, 1H), 3.79 (dd, J=9.9, 4.7 Hz, 1H), 3.37 (s, 4H), 3.22 (dd, J=13.9, 6.4 Hz, 1H), 2.27 (s, 3H). $^{13}$C NMR (100 MHz, CDCl$_3$) δ 154.45, 138.12, 136.16, 134.50, 131.26, 131.22, 131.18, 130.20, 129.53, 129.19, 128.83, 120.72, 120.44, 118.65, 112.85, 106.31, 72.22, 59.09, 56.26, 44.18, 34.29, 21.08. HRMS (ESI-TOF) calcd for C26H27N4O [M+H]$^+$ 411.2185, found: 411.2204.

(S)-1-(1-methoxy-3-p-tolylpropan-2-yl)-3-(3-(trifluoromethyl)benzyl)-1H-benzo[d]imidazol-2(3H)-imine (ARN-344): (S)—N1-(1-methoxy-3-p-tolylpropan-2-yl)-N2-(3-(trifluoro methyl)benzyl)benzene-1,2-diamine tolylpropan (0.29 g, 0.68 mmole) with cyanogen bromide yielded product as Viscous oil (71%); [α]$_D^{20}$=−85.1 (c 7.65, CHCl$_3$); $^1$H NMR (400 MHz, CDCl$_3$) δ 7.53 (d, J=7.4 Hz, 2H), 7.39 (d, J=7.8 Hz, 1H), 7.29-7.14 (m, 1H), 7.16-6.81 (m, 7H), 6.66 (dd, J=7.6, 1.2 Hz, 1H), 5.08-4.95 (q, J=16.8 Hz, 2H), 4.73 (s, 1H), 3.99 (t, J=8.3 Hz, 1H), 3.81 (dd, J=9.9, 4.8 Hz, 1H), 3.38 (s, 4H), 3.25 (dd, J=13.9, 6.4 Hz, 1H), 2.28 (s, 3H). $^{13}$C NMR (100 MHz, CDCl$_3$) δ 137.47, 136.03, 134.63, 131.40, 130.03, 129.28, 129.15, 128.88, 124.39, 124.36, 123.63, 123.59, 120.62, 120.35, 106.39, 72.26, 59.03, 56.16, 44.55, 34.30, 21.04. HRMS (ESI-TOF) calcd for C26H27F3N3O [M+H]$^+$ 454.2106, found: 454.2122.

(R)-2-(2-imino-3-(4-methylbenzyl)-2,3-dihydro-1H-benzo[d]imidazol-1-yl)-3-phenyl propan-1-ol (ARN-350): (R)-2-(2-(4-methylbenzylamino)phenylamino)-3-phenylpropan-1-ol (0.10 g, 0.30 mmole) with cyanogen bromide yielded product as Viscous oil (85%); $^1$H NMR (400 MHz, CDCl$_3$) δ 7.47-7.04 (m, 8H), 6.91 (dt, J=8.9, 5.5 Hz, 2H), 6.76 (dd, J=14.2, 7.1 Hz, 2H), 4.88 (d, J=4.8 Hz, 2H), 4.44-4.19 (m, 1H), 4.12 (d, J=12.4 Hz, 1H), 4.00 (dd, J=12.4, 4.6 Hz, 1H), 3.44 (dd, J=13.5, 7.5 Hz, 1H), 3.30 (dd, J=13.4, 7.9 Hz, 1H), 2.36 (s, 3H). $^{13}$C NMR (100 MHz, CDCl$_3$) δ 154.87, 138.54, 137.71, 132.30, 131.66, 131.59, 129.70, 129.44, 128.38, 126.67, 126.41, 121.01, 120.52, 106.92, 106.73, 62.95, 59.43, 44.93, 33.82, 21.18. HRMS (ESI-TOF) calcd for C24H26N3O [M+H]$^+$ 372.2070, found: 372.2071.

(S)-1-(1-methoxy-3-p-tolylpropan-2-yl)-3-(1-phenylethyl)-1H-benzo[d]imidazol-2(3H)-imine (ARN-353) Mixture of Distereomers: (S)—N1-(3,4-difluorobenzyl)-N2-(1-methoxy-3-p-tolylpropan-2-yl)benzene-1,2-diamine (0.17 g, 0.45) with cyanogen bromide yielded product as Viscous oil (71%); [α]$_D^{20}$=−100.5 (c 4.9, CHCl$_3$); $^1$H NMR (400 MHz, CDCl$_3$) δ 7.41-7.25 (m, 4H), 7.25-7.12 (m, 1H), 7.01 (s, 4H), 6.95-6.84 (m, 1H), 6.75 (t, J=7.8 Hz, 1H), 6.45 (dt, J=7.9, 1.5 Hz, 1H), 5.68 (s, 1H), 4.76 (s, 1H), 3.96 (t, J=8.4 Hz, 1H), 3.84 (ddd, J=9.4, 5.2, 3.9 Hz, 2H), 3.40 (d, J=1.9 Hz, 4H), 3.22 (ddd, J=13.8, 6.4, 2.7 Hz, 1H), 2.29 (d, J=3.6 Hz, 3H), 1.78 (dd, J=16.3, 7.1 Hz, 3H). $^{13}$C NMR (100 MHz, CDCl$_3$) δ 139.55, 135.90, 134.71, 134.65, 130.09, 129.04, 128.96, 128.59, 128.52, 127.30, 127.27, 126.57, 119.84, 108.43, 108.27, 72.49, 59.06, 50.45, 50.32, 34.19, 21.08, 16.19. HRMS (ESI-TOF) calcd for C26H30N3O [M+H]$^+$ 400.2389, found: 400.2389.

(S)-1-(3-chloro-4-fluorobenzyl)-3-(1-methoxy-3-p-tolylpropan-2-yl)-1H-benzo[d]imidazol-2(3H)-imine (ARN-362): (S)—N1-(3-chloro-4-fluorobenzyl)-N2-(1-methoxy-3-p-tolyl propan-2-yl)benzene-1,2-diamine (0.15 g, 0.36 mmol) with cyanogen bromide yielded product as Viscous oil (75%); [α]$_D^{20}$=−100.3 (c 5.5, CHCl$_3$); $^1$H NMR (400 MHz, CDCl$_3$) δ 7.30-7.22 (m, 1H), 7.19-6.84 (m, 9H), 6.65 (d, J=7.5 Hz, 1H), 5.00-4.80 (m, 2H), 4.74 (s, 1H), 3.98 (t, J=8.8 Hz, 1H), 3.80 (dd, J=9.9, 4.8 Hz, 1H), 3.37 (s, 4H), 3.23 (dd, J=13.9, 6.3 Hz, 1H), 2.27 (s, 3H). $^{13}$C NMR (100 MHz, CDCl$_3$) δ 158.62, 156.15, 136.02, 134.61, 131.30, 129.18, 128.95, 128.86, 126.61, 126.54, 120.59, 120.34, 116.87, 116.66, 106.35, 72.27, 59.05, 56.12, 43.84, 34.27, 21.09. HRMS (ESI-TOF) calcd for C25H26ClFN3O [M+H]+ 438.1743, found: 438.1778.

(S)-1-(3,4-difluorobenzyl)-3-(1-methoxy-3-p-tolylpropan-2-yl)-1H-benzo[d]imidazol-2(3H)-imine (ARN-366): (S)—N1-(4-methylbenzyl)-N2-(1-(4-methylbenzyloxy)-3-p-tolyl propan-2-yl)benzene-1,2-diamine (0.24 g, 0.52 mmole) with cyanogen bromide yielded product as Viscous oil (74%); $[\alpha]_D^{20}$=−62.7 (c 2.65, CHCl3); 1H NMR (400 MHz, CDCl3) δ 7.24-6.87 (m, 15H), 6.72 (dd, J=6.9, 1.8 Hz, 1H), 5.05-4.89 (m, 4H), 4.64-4.42 (m, 3H), 4.05 (s, 1H), 3.92 (dd, J=10.0, 4.9 Hz, 1H), 3.39 (td, J=14.5, 13.1, 7.1 Hz, 2H), 3.27 (dd, J=13.9, 6.4 Hz, 1H), 2.37 (s, 3H), 2.34 (s, 3H), 2.31 (s, 3H). 13C NMR (100 MHz, CDCl3) δ 137.28, 137.06, 135.83, 134.93, 134.73, 132.90, 131.60, 129.41, 129.36, 129.09, 129.05, 128.98, 127.84, 126.69, 120.44, 120.31, 106.70, 73.14, 69.83, 44.82, 34.35, 29.76, 21.22, 21.15, 21.14. HRMS (ESI-TOF) calcd for C33H36N3O [M+H]+ 490.2852, found: 490.2857.

(R)-2-(2-imino-3-(4-methylbenzyl)-2,3-dihydro-1H-benzo[d]imidazol-1-yl)-3-p-tolyl propan-1-ol (ARN-374): (R)-2-(2-(4-methylbenzylamino)phenylamino)-3-p-tolylpropan-1-ol (0.24 g, 0.66 mmole) with cyanogen bromide yielded product as white solid (80%) yield; $[\alpha]_D^{20}$=+126.2 (c 5.86, CHCl3); 1H NMR (400 MHz, CDCl3) δ 7.25-7.07 (m, 6H), 7.03 (d, J=7.5 Hz, 2H), 7.00-6.85 (m, 2H), 6.85-6.68 (m, 2H), 4.94-4.85 (m, 2H), 4.26 (dt, J=12.2, 6.1 Hz, 1H), 4.07 (d, J=12.4 Hz, 1H), 3.94 (ddd, J=11.9, 4.5, 1.4 Hz, 1H), 3.43 (ddd, J=13.8, 8.3, 1.8 Hz, 1H), 3.15 (dd, J=13.4, 7.2 Hz, 1H), 2.35 (d, J=1.7 Hz, 3H), 2.28 (d, J=1.7 Hz, 3H). 13C NMR (100 MHz, CDCl3) δ 154.85, 137.75, 135.85, 135.35, 132.16, 131.64, 129.69, 129.29, 129.05, 126.60, 121.04, 120.49, 106.87, 106.70, 62.65, 59.54, 44.99, 33.33, 21.13, 21.04. HRMS (ESI-TOF) calcd for C25H28N3O+ [M+H]+ 386.2226, found: 386.2229.

(R)-1-(4-methylbenzyl)-3-(1-(4-(methylthio)benzyloxy)-3-p-tolylpropan-2-yl)-1H-benzo[d]imidazol-2(3H)-imine (ARN-375): (R)—N1-(4-methylbenzyl)-N2-(1-(4-(methylthio) benzyloxy)-3-p-tolylpropan-2-yl)benzene-1,2-diamine (0.24 g, 0.48 mmole) with cyanogen bromide yielded product as Viscous oil (70%); $[\alpha]_D^{20}$=+49.3 (c 2.745, CHCl3); 1H NMR (400 MHz, CDCl3) δ 7.24-6.99 (m, 12H), 6.98-6.86 (m, 2H), 6.72 (dd, J=7.0, 1.7 Hz, 1H), 4.94 (q, J=16.6 Hz, 3H), 4.63-4.45 (m, 3H), 4.07 (s, 1H), 3.94 (dd, J=10.0, 5.0 Hz, 1H), 3.41 (s, 1H), 3.29 (dd, J=13.8, 6.4 Hz, 1H), 2.38 (s, 3H), 2.36 (s, 3H), 2.33 (s, 3H). 13C NMR (100 MHz, CDCl3) δ 155.05, 137.28, 137.04, 135.82, 135.00, 134.87, 133.06, 131.72, 129.43, 129.11, 129.07, 129.01, 127.84, 126.70, 120.29, 120.14, 106.52, 73.14, 69.82, 55.95, 44.72, 34.39, 21.25, 21.18, 21.17. HRMS (ESI-TOF) calcd for C33H36N3OS+ [M+H]+ 522.2573, found: 522.2581.

(R)-1-(4-methylbenzyl)-3-(1-(4-methylbenzyloxy)-3-p-tolylpropan-2-yl)-1H-benzo[d]imidazol-2(3H)-imine (ARN-376): (R)—N1-(4-methylbenzyl)-N2-(1-(4-methylbenzyloxy)-3-p-tolylpropan-2-yl)benzene-1,2-diamine (0.25 g, 0.54 mmole) with cyanogen bromide yielded product as white solid (73%); $[\alpha]_D^{20}$=+56.0 (c 6.89, CHCl3); 1H NMR (400 MHz, CDCl3) δ 7.21-7.10 (m, 4H), 7.11-6.93 (m, 8H), 6.96-6.77 (m, 3H), 6.76-6.63 (m, 1H), 4.99-4.80 (m, 3H), 4.59-4.36 (m, 3H), 4.02 (s, 1H), 3.86 (dd, J=9.9, 4.9 Hz, 1H), 3.33 (s, 1H), 3.22 (dd, J=13.8, 6.6 Hz, 1H), 2.47 (s, 3H), 2.31 (s, 3H), 2.28 (s, 3H). 13C NMR (100 MHz, CDCl3) δ 137.65, 137.07, 135.85, 134.83, 134.72, 132.93, 131.66, 129.39, 129.07, 128.93, 128.27, 126.60, 126.52, 120.25, 120.11, 106.47, 72.73, 69.70, 44.67, 34.37, 29.71, 21.11, 21.10, 15.90. HRMS (ESI-TOF) calcd for C33H36N3O+ [M+H]+ 490.2852, found: 490.2846.

N-(1-(4-methylbenzyl)-3-(1-p-tolylpropan-2-yl)-1H-benzo[d]imidazol-2(3H)-ylidene) methanamine type (ARN-387): White solid (76%) yield; $[\alpha]_D^{20}$=+41.8 (c 8.5, CHCl3); 1H NMR (400 MHz, CDCl3) δ 7.33-7.23 (m, 2H), 7.21-7.03 (m, 5H), 6.90-6.74 (m, 2H), 6.73-6.61 (m, 1H), 6.44-6.30 (m, 1H), 5.07-4.79 (m, 2H), 4.57 (ddt, J=8.9, 7.7, 5.6 Hz, 1H), 4.32 (dd, J=12.5, 8.8 Hz, 1H), 4.06 (dd, J=12.6, 5.8 Hz, 1H), 3.20 (dd, J=13.7, 5.5 Hz, 1H), 2.96 (dd, J=13.7, 7.6 Hz, 1H), 2.38 (s, 3H), 2.33 (s, 3H). 13C NMR (100 MHz, CDCl3) δ 161.26, 137.27, 137.12, 136.36, 134.20, 133.20, 130.34, 129.46, 129.41, 129.34, 127.45, 120.79, 120.05, 107.83, 106.96, 63.78, 60.22, 46.11, 39.19, 21.19, 21.16. HRMS (ESI-TOF) calcd for C25H26N3+ [M+H]+ 368.2121, found: 368.2119.

(S)-2-(2-imino-3-(4-methylbenzyl)-2,3-dihydro-1H-benzo[d]imidazol-1-yl)-3-p-tolyl propan-1-ol (ARN-388, 525,557): (S)-2-(2-(4-methylbenzylamino)phenylamino)-3-p-tolyl propan-1-ol (0.20 g, 0.55) with cyanogen bromide yielded product as Viscous oil (90%); $[\alpha]_D^{20}$=−113.5 (c 3.45, CHCl3); 1H NMR (400 MHz, CDCl3) δ 7.24-7.08 (m, 6H), 7.03 (d, J=7.5 Hz, 2H), 6.98-6.87 (m, 2H), 6.87-6.69 (m, 2H), 4.90 (d, J=4.2 Hz, 2H), 4.26 (dt, J=11.9, 6.0 Hz, 1H), 4.07 (d, J=12.4 Hz, 1H), 3.94 (dd, J=12.4, 4.2 Hz, 1H), 3.43 (dd, J=13.2, 8.3 Hz, 1H), 3.15 (dd, J=13.4, 7.2 Hz, 1H), 2.35 (s, 3H), 2.28 (s, 3H). 13C NMR (100 MHz, CDCl3) δ 154.91, 137.70, 135.85, 135.38, 132.28, 131.65, 129.70, 129.32, 129.12, 129.09, 126.65, 121.04, 120.51, 106.96, 106.73, 62.67, 59.48, 44.94, 33.40, 21.17, 21.09. HRMS (ESI-TOF) calcd for $C_{25}H_{28}N_3O$ [M+H]+ 386.2227, found: 386.2230.

(S)-1-(1-(3-chloro-4-fluorobenzyloxy)-3-p-tolylpropan-2-yl)-3-(4-methylbenzyl)-1H-benzo[d]imidazol-2(3H)-imine (ARN-392): (S)—N1-(1-(3-chloro-4-fluorobenzyloxy)-3-p-tolylpropan-2-yl)-N2-(4-methylbenzyl)benzene-1,2-diamine (0.10 g, 0.20 mmole) with cyanogen bromide yielded product as Viscous oil (71%); $[\alpha]_D^{20}$=−40.0 (c 0.83, CHCl3); H NMR (400 MHz, CDCl3) δ 7.23 (dd, J=7.2, 2.0 Hz, 2H), 7.19-6.79 (m, 13H), 6.71 (dd, J=6.7, 2.0 Hz, 1H), 5.06-4.74 (m, 3H), 4.59-4.32 (m, 3H), 4.07 (s, 1H), 3.85 (dd, J=9.9, 4.6 Hz, 1H), 3.62 (s, 2H), 3.35 (s, 1H), 3.22 (dd, J=13.9, 6.8 Hz, 1H), 2.31 (s, 3H), 2.28 (s, 3H). 13C NMR (100 MHz, CDCl3) δ 158.65, 156.18, 137.17, 135.94, 132.79, 131.62, 129.71, 129.40, 129.11, 128.90, 127.24, 127.16, 126.60, 120.36, 120.23, 116.42, 116.21, 106.59, 71.76, 69.83, 44.72, 34.39, 30.94, 29.70, 21.09.

(S)-1-(1-ethoxy-3-p-tolylpropan-2-yl)-3-(4-methylbenzyl)-1H-benzo[d]imidazol-2 (3H)-imine (ARN-409): (S)—N1-(1-ethoxy-3-p-tolylpropan-2-yl)-N2-(4-methylbenzyl) benzene-1,2-diamine (0.17 g, 0.45) with cyanogen bromide yielded product as Viscous oil (80%) yield; $[\alpha]_D^{20}$=−81.0 (c 4.7, CHCl3); 1H NMR (400 MHz, CDCl3) δ 7.22-6.98 (m, 9H), 6.91 (dt, J=24.0, 7.6 Hz, 2H), 6.69 (d, J=7.6 Hz, 1H), 5.02-4.83 (m, 3H), 4.68 (s, 1H), 3.99 (s, 1H), 3.88 (dd, J=10.0, 5.0 Hz, 1H), 3.62-3.47 (m, 2H), 3.29 (dd, J=13.8, 6.5 Hz, 1H), 2.34 (s, 3H), 2.31 (s, 3H), 1.22 (t, J=7.0 Hz, 3H). 13C NMR (100 MHz, CDCl3) δ δ 137.02, 135.77, 134.96, 133.11, 131.73, 129.39, 129.08, 129.00, 126.70, 120.21, 120.10, 106.47, 70.33, 66.70, 55.86, 44.66, 34.33, 21.15, 21.14, 15.26. HRMS (ESI-TOF) calcd for C27H32N3O+ [M+H]+ 414.2540, found: 414.2540.

(S)-1-(4-methylbenzyl)-3-(1-propoxy-3-p-tolylpropan-2-yl)-1H-benzo[d]imidazol-2(3H)-imine (ARN-414): (S)—N1-(4-methylbenzyl)-N2-(1-propoxy-3-p-tolylpropan-2-yl) benzene-1,2-diamine (0.17 g, 0.42 mmole) with cyanogen bromide yielded product as Viscous oil (71%); $[\alpha]_D^{20}$=−79.1 (c 4.8, CHCl3); 1H NMR (400 MHz, CDCl3) δ 7.38-6.79 (m, 11H), 6.70 (d, J=7.5 Hz, 1H), 5.01-4.88 (m, 2H), 4.68 (s, 1H), 3.98 (s, 1H), 3.88 (dd, J=10.1, 5.0 Hz, 1H), 3.56-3.20 (m, 4H), 2.33 (d, J=12.7 Hz, 6H), 1.62 (h, J=7.1 Hz, 2H), 0.92 (t, J=7.4 Hz, 3H). $^{13}$C NMR (100 MHz, CDCl$_3$) δ 137.02, 135.77, 135.00, 133.12, 131.72, 129.39, 129.09, 129.01, 126.71, 120.20, 120.09, 106.45, 73.05, 70.55, 55.97, 44.68, 34.33, 22.97, 21.15, 21.14, 10.68. HRMS (ESI-TOF) calcd for C28H34N3O+ [M+H]$^+$ 428.2696, found: 428.2712.

(S)-1-(1-(2-methoxyethoxy)-3-p-tolylpropan-2-yl)-3-(4-methylbenzyl)-1H-benzo[d]imidazol-2(3H)-imine (ARN-422): (S)—N1-(1-(2-methoxyethoxy)-3-p-tolylpropan-2-yl)-N2-(4-methylbenzyl)benzene-1,2-diamine (0.17 g, 0.45) with cyanogen bromide yielded product as Viscous oil (68%) yield; [α]$_D^{20}$=−101.21 (c 6.3, CHCl$_3$); $^1$H NMR (400 MHz, CDCl$_3$) δ 7.11-6.85 (m, 11H), 6.77-6.63 (m, 1H), 4.96-4.84 (m, 3H), 3.95 (dd, J=10.1, 5.2 Hz, 1H), 3.74-3.56 (m, 2H), 3.52 (t, J=4.7 Hz, 2H), 3.35 (s, 4H), 3.26 (dd, J=13.9, 6.3 Hz, 1H), 2.33 (s, 3H), 2.31 (s, 3H). $^{13}$C NMR (100 MHz, CDCl$_3$) δ 137.03, 135.77, 134.83, 133.04, 131.68, 129.38, 129.06, 128.98, 126.67, 120.26, 120.13, 106.48, 71.94, 71.01, 70.58, 59.02, 55.88, 44.65, 34.27, 21.14, 21.12. HRMS (ESI-TOF) calcd for C28H34N3O2 [M+H]$^+$ 444.2646, found: 444.2650.

(S)-1-(1-(4-isopropylbenzyloxy)-3-p-tolylpropan-2-yl)-3-(4-methylbenzyl)-1H-benzo[d]imidazol-2(3H)-imine (ARN-424): (S)—N1-(1-(4-isopropylbenzyloxy)-3-p-tolylpropan-2-yl)-N2-(4-methylbenzyl)benzene-1,2-diamine (0.10 g, 0.20 mmole) with cyanogen bromide yielded product as Viscous oil (71%); $^1$H NMR (400 MHz, CDCl$_3$) δ 7.30-7.16 (m, 4H), 7.15-6.86 (m, 10H), 6.73 (dd, J=7.0, 1.8 Hz, 1H), 5.02-4.85 (m, 3H), 4.64-4.48 (m, 2H), 4.35 (s, 1H), 4.08 (s, 1H), 3.95 (dd, J=10.0, 5.1 Hz, 1H), 3.41 (s, 1H), 3.30 (dd, J=13.9, 6.4 Hz, 1H), 3.00-2.90 (m, 1H), 2.36 (s, 3H), 2.33 (s, 3H), 1.31 (d, J=7.0 Hz, 6H). $^{13}$C NMR (100 MHz, CDCl$_3$) δ 148.31, 137.05, 135.82, 135.40, 134.86, 133.05, 131.72, 129.43, 129.11, 129.01, 127.85, 126.70, 126.45, 120.30, 120.17, 106.54, 73.16, 69.88, 44.73, 34.41, 33.92, 24.11, 21.17.

1-(2-methoxypropyl)-3-(4-methylbenzyl)-1H-benzo[d]imidazol-2(3H)-imine type mol. (ARN-441): Viscous oil (51%); $^1$H NMR (400 MHz, CDCl$_3$) (7.28 (d, J=7.8 Hz, 2H), 7.25-7.11 (m, 4H), 7.03 (d, J=7.8 Hz, 2H), 5.72-5.48 (m, 2H), 4.27-3.89 (m, 4H), 3.71-3.57 (m, 1H), 3.38 (s, 3H), 2.20 (s, 3H). $^{13}$C NMR (100 MHz, CDCl$_3$) δ 137.03, 135.77, 134.83, 133.04, 131.68, 129.38, 129.06, 128.98, 126.67, 120.26, 120.13, 106.48, 71.94, 71.01, 70.58, 59.02, 55.88, 44.65, 34.27, 21.14, 21.12. HRMS (ESI-TOF) calcd for C$_{19}$H$_{22}$N$_3$O [M+H]$^+$ 308.1758, found: 308.1770.

(S)-2-(2-(2-imino-3-(4-methylbenzyl)-2,3-dihydro-1H-benzo[d]imidazol-1-yl)-3-p-tolylpropoxy)-N,N-dimethylethanamine (ARN-452): (S)—N1-(1-(2-(dimethylamino)ethoxy)-3-p-tolylpropan-2-yl)-N2-(4-methylbenzyl)benzene-1,2-diamine (0.40 g, 0.93 mmole) with cyanogen bromide yielded product as Viscous oil (68%); [α]$_D^{20}$=−80.6 (c 2.06, CHCl$_3$); $^1$H NMR (400 MHz, CDCl$_3$) δ 7.43 (s, 2H), 7.16-6.78 (m, 10H), 5.45-5.05 (m, 6H), 4.09 (dd, J=10.8, 6.9 Hz, 1H), 3.91 (dd, J=10.7, 4.0 Hz, 1H), 3.60 (m, J=16.1, 10.6, 5.5 Hz, 2H), 3.65-3.54 (m, 2H), 2.57-2.06 (m, 12H). $^{13}$C NMR (100 MHz, CDCl$_3$) δ 152.65, 137.30, 136.04, 133.63, 131.73, 130.78, 129.38, 129.13, 128.87, 126.81, 121.99, 121.88, 108.63, 70.77, 69.22, 58.51, 57.35, 45.75, 45.57, 34.17, 21.09, 21.07. HRMS (ESI-TOF) calcd for C29H37N4O [M+H]$^+$ 457.2962, found: 457.2965.

(S)-methyl 3-(2-(2-imino-3-(4-methylbenzyl)-2,3-dihydro-1H-benzo[d]imidazol-1-yl)-3-p-tolylpropoxy)propanoate (ARN-460): (S)-methyl 3-(2-(2-(4-methylbenzylamino)phenyl amino)-3-p-tolylpropoxy)propanoate (0.17 g, 0.38 mmole) with cyanogen bromide yielded product as Viscous oil (62%); [α]$_D^{20}$=−73.2 (c 4.5, CHCl$_3$); $^1$H NMR (400 MHz, CDCl$_3$) δ 7.17-6.86 (m, 11H), 6.69 (d, J=7.5 Hz, 1H), 5.03-4.47 (m, 5H), 4.02 (s, 1H), 3.89 (dd, J=10.0, 4.9 Hz, 1H), 3.83-3.69 (m, 2H), 3.63 (s, 2H), 3.46-3.29 (m, 1H), 3.30-3.15 (m, 1H), 2.31 (d, J=14.7 Hz, 6H). $^{13}$C NMR (100 MHz, CDCl$_3$) δ 171.93, 137.07, 135.81, 132.96, 131.63, 129.41, 129.09, 128.99, 128.91, 126.65, 120.35, 120.17, 106.51, 70.83, 66.67, 51.67, 44.69, 34.97, 34.91, 34.20, 21.15, 21.13. HRMS (ESI-TOF) calcd for C29H34N3O3+ [M+H]$^+$ 472.2595, found: 472.2605.

(S)-1-(1-(3,5-bis(trifluoromethyl)benzyloxy)-3-p-tolylpropan-2-yl)-3-(4-methylbenzyl)-1H-benzo[d]imidazol-2(3H)-imine (ARN-485): (S)—N1-(1-(3,5-bis(trifluoromethyl)benzyloxy)-3-p-tolylpropan-2-yl)-N2-(4-methylbenzyl)benzene-1,2-diamine (0.31 g, 0.56 mmole) with cyanogen bromide yielded product as Viscous oil (65%) yield; [α]$_D^{20}$=−34.8 (c 4.9, CHCl$_3$); H NMR (400 MHz, CDCl$_3$) δ 7.75 (d, J=36.2 Hz, 3H), 7.21-6.86 (m, 11H), 6.74 (dd, J=7.4, 1.5 Hz, 1H), 4.90 (d, J=5.9 Hz, 2H), 4.74-4.53 (m, 2H), 4.23 (s, 2H), 3.95 (dd, J=10.0, 4.6 Hz, 1H), 3.45 (s, 1H), 3.28 (dd, J=13.9, 6.9 Hz, 1H), 2.33 (s, 3H), 2.32 (s, 3H). $^{13}$C NMR (100 MHz, CDCl$_3$) δ 140.85, 137.22, 136.02, 134.58, 132.78, 131.70, 129.43, 129.17, 128.93, 127.37, 127.26, 127.22, 126.57, 124.66, 121.95, 121.41, 120.42, 120.26, 106.59, 71.61, 71.58, 71.56, 70.46, 44.63, 34.39, 21.07. HRMS (ESI-TOF) calcd for C29H36N3O2+ [M+H]$^+$ 458.2802, found: 458.2815.

(S)-1-(1-(3-methoxypropoxy)-3-p-tolylpropan-2-yl)-3-(4-methylbenzyl)-1H-benzo[d]imidazol-2(3H)-imine (ARN-496): (S)—N1-(1-(3-methoxypropoxy)-3-p-tolylpropan-2-yl)-N2-(4-methylbenzyl)benzene-1,2-diamine (0.20 g, 0.46 mmole) with cyanogen bromide yielded product as Viscous oil (83%) yield; [α]$_D^{20}$=−72.1 (c 3.17, CHCl$_3$); $^1$H NMR (400 MHz, CDCl$_3$) δ 7.15-6.85 (m, 11H), 6.69 (d, J=7.5 Hz, 1H), 5.00-4.83 (m, 2H), 4.42 (s, 1H), 3.98 (s, 1H), 3.86 (dd, J=10.0, 4.9 Hz, 1H), 3.64-3.46 (m, 2H), 3.39 (t, J=6.5 Hz, 3H), 3.27 (s, 4H), 2.32 (s, 3H), 2.32 (s, 3H), 1.83 (p, J=6.4 Hz, 2H). $^{13}$C NMR (100 MHz, CDCl$_3$) δ 137.04, 135.80, 134.89, 133.05, 131.67, 129.39, 129.09, 128.98, 126.68, 120.25, 120.13, 106.49, 70.60, 69.56, 68.15, 58.60, 58.57, 44.66, 34.31, 29.98, 21.13. HRMS (ESI-TOF) calcd for C29H36N3O2+ [M+H]$^+$ 458.2802, found: 458.2815.

(S)-2-(2-imino-7-methyl-3-(4-methylbenzyl)-2,3-dihydro-1H-benzo[d]imidazol-1-yl)-3-p-tolylpropan-1-ol (ARN-524): (S)-2-(2-methyl-6-(4-methylbenzylamino)phenylamino)-3-p-tolylpropan-1-ol (0.35 g, 0.94 mmole) with cyanogen bromide yielded product as Viscous oil (80%) yield; [α]$_D^{20}$=−106.51 (c 4.5, CHCl$_3$); $^1$H NMR (400 MHz, CDCl$_3$) δ 7.22-7.08 (m, 6H), 7.03 (d, J=7.7 Hz, 2H), 6.83 (t, J=7.7 Hz, 1H), 6.68 (d, J=7.8 Hz, 2H), 4.93-4.84 (m, 3H), 4.16 (dd, J=12.3, 1.1 Hz, 1H), 3.99 (dd, J=12.3, 4.8 Hz, 1H), 3.48 (dd, J=13.6, 7.8 Hz, 1H), 3.35 (dd, J=13.5, 7.5 Hz, 1H), 2.43 (s, 3H), 2.36 (s, 3H), 2.29 (s, 3H). $^{13}$C NMR (100 MHz, CDCl$_3$) δ 155.45, 137.71, 135.81, 135.57, 132.27, 132.13, 129.74, 129.71, 129.29, 129.04, 126.63, 125.43, 120.62, 118.39, 105.20, 63.96, 60.15, 44.93, 33.21, 21.17, 21.07, 20.25. HRMS (ESI-TOF) calcd for C26H30N3O [M+H]$^+$ 400.2383, found: 400.2382.

(S)-2-(2-imino-3-(4-methylbenzyl)-5-(trifluoromethyl)-2,3-dihydro-1H-benzo[d]imidazol-1-yl)-3-p-tolylpropan-1-ol (ARN-528): (S)-2-(2-(4-methylbenzylamino)-4-(trifluoromethyl)phenylamino)-3-p-tolylpropan-1-ol (0.30 g, 0.70 mmole) with cyanogen bromide yielded product as white solid (71%) yield; [α]$_D^{20}$=−136.0 (c 3.6, CHCl$_3$); $^1$H NMR (400 MHz, CDCl$_3$) δ 7.23-7.14 (m, 3H), 7.09 (d, J=7.9 Hz, 4H), 7.04-6.94 (m, 3H), 6.73 (d, J=8.3 Hz, 1H), 4.98-4.82

(m, 2H), 4.35 (q, J=7.1 Hz, 1H), 4.17-3.96 (m, 2H), 3.38-3.24 (m, 2H), 2.36 (s, 3H), 2.26 (s, 3H). $^{13}$C NMR (100 MHz, CDCl$_3$) δ 155.00, 138.01, 136.09, 134.93, 134.37, 131.63, 131.54, 129.82, 129.12, 126.54, 118.60, 118.55, 106.63, 103.35, 103.32, 62.90, 59.96, 45.02, 33.36, 21.12, 20.97. HRMS (ESI-TOF) calcd for C26H27F3N3O+ [M+H]$^+$ 454.2100, found: 454.2093.

(S)-1-(1-methoxy-3-p-tolylpropan-2-yl)-3-(4-methylbenzyl)-5-(trifluoromethyl)-1H-benzo[d]imidazol-2(3H)-imine (ARN-531): (S)—N1-(1-methoxy-3-p-tolylpropan-2-yl)-N2-(4-methylbenzyl)-4-(trifluoromethyl)benzene-1,2-diamine (0.25 g, 0.55 mmole) with cyanogen bromide yielded product as Viscous oil (74%) yield; [α]$_D^{20}$=–103.0 (c 4.35, CHCl$_3$); H NMR (400 MHz, CDCl$_3$) δ 7.15 (dd, J=41.0, 7.8 Hz, 3H), 7.06-6.92 (m, 6H), 6.89 (d, J=1.8 Hz, 1H), 4.93 (d, J=8.4 Hz, 2H), 3.98 (s, 1H), 3.77 (dd, J=10.0, 4.4 Hz, 1H), 3.37 (s, 4H), 3.20 (dd, J=14.0, 6.3 Hz, 2H), 2.32 (s, 3H), 2.27 (s, 3H). $^{13}$C NMR (100 MHz, CDCl$_3$) δ 137.50, 136.09, 134.20, 131.95, 131.63, 129.56, 129.15, 128.88, 128.84, 126.53, 118.21, 118.16, 103.25, 103.21, 72.28, 59.09, 44.93, 34.06, 21.11, 21.07. HRMS (ESI-TOF) calcd for C27H29F3N3O [M+H]$^+$ 468.2257, found: 468.2252.

(S)-2-(7-fluoro-2-imino-3-(4-methylbenzyl)-2,3-dihydro-1H-benzo[d]imidazol-1-yl)-3-p-tolylpropan-1-ol (ARN-535): (S)-2-(2-fluoro-6-(4-methylbenzylamino)phenylamino)-3-p-tolylpropan-1-ol (0.30 g, 0.79 mmole) with cyanogen bromide yielded product as Viscous oil (70%) yield; $^1$H NMR (400 MHz, CDCl$_3$) δ 7.33-6.91 (m, 8H), 6.83-6.78 (m, 1H), 6.77-6.61 (m, 1H), 6.54 (d, J=7.8 Hz, 1H), 4.89-4.85 (m, 3H), 4.19 (d, J=12.5 Hz, 1H), 3.99 (d, J=12.7 Hz, 1H), 3.37 (s, 2H), 2.37 (s, 3H), 2.29 (s, 3H). MS (ESI-TOF) calcd for C25H27FN3O [M+H]$^+$ 404.2138, found: 404.3000.

(S)-4-fluoro-3-(1-methoxy-3-p-tolylpropan-2-yl)-1-(4-methylbenzyl)-1H-benzo[d]imidazol-2(3H)-imine (ARN-541): (S)-3-fluoro-N2-(1-methoxy-3-p-tolylpropan-2-yl)-N1-(4-methylbenzyl)benzene-1,2-diamine (0.24 g, 0.59 mmole) with cyanogen bromide yielded product as Viscous oil (68%); $^1$H NMR (400 MHz, CDCl$_3$) δ 7.23-6.51 (m, 10H), 6.47 (d, J=7.6 Hz, 1H), 5.07-4.87 (m, 2H), 4.76 (d, J=17.2 Hz, 1H), 4.23 (s, 2H), 3.77 (s, 1H), 3.37 (s, 3H), 3.16 (dd, J=13.5, 6.3 Hz, 2H), 2.30 (d, J=13.4 Hz, 6H). $^{13}$C NMR (100 MHz, CDCl$_3$) δ 137.16, 135.80, 134.62, 132.55, 129.40, 129.31, 129.06, 128.96, 128.84, 126.58, 108.78, 108.57, 102.97, 102.94, 73.79, 58.99, 55.30, 45.06, 36.59, 21.12, 21.10.

(S)-2-(2-imino-5-methyl-3-(4-methylbenzyl)-2,3-dihydro-1H-benzo[d]imidazol-1-yl)-3-p-tolylpropan-1-ol (ARN-545): (S)-2-(4-methyl-2-(4-methylbenzylamino)phenylamino)-3-p-tolylpropan-1-ol (0.15 g, 0.42) with cyanogen bromide yielded product as Viscous oil (80%) yield; [α]$_D^{20}$=–155.0 (c 2.8, CHCl$_3$); $^1$H NMR (400 MHz, CDCl$_3$) δ 7.30-6.92 (m, 8H), 6.80 (q, J=8.1 Hz, 2H), 6.64 (s, 1H), 5.04-4.77 (m, 2H), 4.42 (s, 1H), 4.20-3.94 (m, 2H), 3.43 (dd, J=13.5, 7.5 Hz, 1H), 3.20 (dd, J=13.3, 7.8 Hz, 1H), 2.58-2.09 (m, 9H). $^{13}$C NMR (100 MHz, CDCl$_3$) δ 154.76, 137.55, 135.79, 135.27, 132.33, 131.69, 130.58, 129.67, 129.29, 129.24, 129.11, 126.56, 121.77, 107.79, 107.25, 62.55, 59.58, 44.88, 33.45, 21.41, 21.20, 21.19, 21.14. HRMS (ESI-TOF) calcd for C26H30N3O [M+H]$^+$ 400.2383, found: 400.2388.

(S)—N-(1-(1-methoxy-3-p-tolylpropan-2-yl)-5-methyl-3-(4-methylbenzyl)-1H-benzo [d]imidazol-2(3H)-ylidene)methanamine (ARN-547): white solid (68%); [α]$_D^{20}$=–230.60 (c 1.65, CHCl$_3$); $^1$H NMR (400 MHz, CDCl$_3$) δ 7.81 (d, J=8.5 Hz, 1H), 7.42-7.29 (m, 1H), 7.10 (d, J=7.9 Hz, 2H), 7.03-6.85 (m, 3H), 6.79 (d, J=7.8 Hz, 2H), 6.70 (d, J=7.7 Hz, 2H), 5.59 (d, J=17.5 Hz, 1H), 5.20 (d, J=17.6 Hz, 1H), 4.99 (qd, J=8.0, 4.3 Hz, 1H), 4.26 (dd, J=10.3, 8.3 Hz, 1H), 4.14 (dd, J=10.3, 4.4 Hz, 1H), 3.43 (s, 2H), 3.26 (d, J=7.9 Hz, 2H), 2.89 (s, 4H), 2.44 (s, 3H), 2.32 (s, 3H), 2.16 (d, J=9.1 Hz, 3H). $^{13}$C NMR (100 MHz, CDCl$_3$) δ 154.76, 137.55, 135.79, 135.27, 132.33, 131.69, 130.58, 129.67, 129.29, 129.24, 129.11, 126.56, 121.77, 107.79, 107.25, 62.55, 59.58, 44.88, 33.45, 21.41, 21.20, 21.19, 21.14. HRMS (ESI-TOF) calcd for C28H33N3O [M+H]$^+$ 428.2696, found: 428.2699.

(S)—N-(1-(1-methoxy-3-p-tolylpropan-2-yl)-3-(4-methylbenzyl)-1H-benzo[d]imidazol-2(3H)-ylidene)methanamine Structure not confirmed(ARN-567): Viscous oil (67%); [α]$_D^{20}$=–318.0 (c 13.0, CHCl$_3$); $^1$H NMR (400 MHz, CDCl$_3$) δ 7.83 (d, J=8.3 Hz, 1H), 7.43-7.28 (m, 1H), 7.17 (t, J=7.8 Hz, 1H), 6.94 (d, J=8.2 Hz, 1H), 6.83 (d, J=7.9 Hz, 2H), 6.67-6.42 (m, 6H), 5.42 (d, J=17.5 Hz, 1H), 5.09-4.92 (m, 1H), 4.87 (ddt, J=12.8, 8.8, 4.5 Hz, 1H), 4.12 (dd, J=10.5, 8.8 Hz, 1H), 3.96 (dd, J=10.5, 4.0 Hz, 1H), 3.18 (s, 3H), 3.07 (qd, J=14.1, 7.9 Hz, 2H), 2.70 (s, 5H), 2.05 (s, 3H), 1.90 (s, 3H). $^{13}$C NMR (100 MHz, CDCl$_3$) δ 154.25, 137.66, 136.36, 132.67, 130.95, 130.10, 129.49, 129.09, 128.42, 128.22, 125.91, 125.34, 114.85, 112.14, 71.68, 62.39, 59.26, 49.61, 42.60, 34.02, 20.96, 20.92.

(S)-2-(2-imino-3-(4-methylbenzyl)-6-(trifluoromethyl)-2,3-dihydro-1H-benzo[d]imidazol-1-yl)-3-p-tolylpropan-1-ol (ARN-572): (S)-2-(2-(4-methylbenzylamino)-5-(trifluoromethyl)phenylamino)-3-p-tolylpropan-1-ol (0.30 g, 0.70 mmole) with cyanogen bromide yielded product as white (80%); [α]$_D^{20}$=–156.50 (c 6.5, CHCl$_3$); $^1$H NMR (400 MHz, CDCl$_3$) δ 7.27-6.88 (m, 9H), 6.75 (d, J=7.5 Hz, 2H), 4.99-4.82 (m, 2H), 4.33 (s, 1H), 4.21-4.00 (m, 2H), 3.41-3.19 (m, 2H), 2.37 (s, 3H), 2.23 (s, 3H). $^{13}$C NMR (100 MHz, CDCl$_3$) δ 154.89, 138.02, 137.99, 136.17, 135.04, 133.88, 131.95, 131.69, 129.79, 129.09, 129.07, 126.62, 117.84, 106.03, 104.09, 63.26, 60.12, 44.99, 33.57, 21.13, 20.87. HRMS (ESI-TOF) calcd for C26H27F3N3O [M+H]$^+$ 454.2106, 454.2103.

(S)-3-(1-methoxy-3-p-tolylpropan-2-yl)-1-(4-methylbenzyl)-5-(trifluoromethyl)-1H-benzo[d]imidazol-2(3H)-imine (ARN-575): Viscous oil (68%); [α]$_D^{20}$=–101.21 (c 6.3, CHCl$_3$); $^1$H NMR (400 MHz, CDCl$_3$) δ 7.21-6.88 (m, 10H), 6.68 (d, J=8.1 Hz, 1H), 4.98-4.88 (m, 3H), 4.62 (s, 1H), 4.00 (s, 1H), 3.79 (dd, J=10.0, 4.4 Hz, 1H), 3.39 (s, 4H), 3.22 (dd, J=13.9, 6.3 Hz, 1H), 2.33 (s, 3H), 2.27 (s, 3H). $^{13}$C NMR (100 MHz, CDCl$_3$) δ 154.79, 137.44, 136.09, 134.29, 134.15, 132.25, 129.51, 129.12, 128.91, 126.61, 122.68, 117.83, 117.78, 105.79, 72.33, 59.04, 56.43, 44.83, 34.16, 21.11, 21.04. HRMS (ESI-TOF) calcd for C27H29F3N3O [M+H]$^+$ 468.2257, found: 468.2250.

(S)-3-(1-methoxy-3-p-tolylpropan-2-yl)-5-methyl-1-(4-methylbenzyl)-1H-benzo[d]imidazol-2(3H)-imine (ARN-586): (S)—N2-(1-methoxy-3-p-tolylpropan-2-yl)-4-methyl-N1-(4-methylbenzyl)benzene-1,2-diamine (0.20 g, 0.50 mmole) with cyanogen bromide yielded product as Viscous oil (83%); $^1$H NMR (400 MHz, CDCl$_3$) δ 7.24-6.80 (m, 9H), 6.70 (d, J=8.0 Hz, 1H), 6.58 (d, J=7.9 Hz, 1H), 4.94-4.83 (m, 3H), 4.02 (s, 1H), 3.82 (dd, J=9.9, 5.1 Hz, 1H), 3.40 (s, 4H), 3.26 (dd, J=13.9, 6.4 Hz, 1H), 2.43-2.29 (m, 9H). $^{13}$C NMR (100 MHz, CDCl$_3$) δ 155.06, 136.99, 135.80, 134.93, 133.15, 129.83, 129.64, 129.38, 129.14, 129.09, 129.04, 126.67, 126.63, 120.50, 106.17, 72.29, 59.03, 44.70, 34.36, 29.77, 21.64, 21.14.

(S)-2-(2-imino-3-(4-methylbenzyl)-5-(trifluoromethyl)-2,3-dihydro-1H-benzo[d]imidazol-1-yl)-3-p-tolylpropan-1-ol (ARN-589) (S)-2-(2-(4-methylbenzylamino)-4-(trifluoromethyl)phenylamino)-3-p-tolylpropan-1-ol (0.17 g, 0.40 mmole) with cyanogen bromide yielded product as white solid (80%); [α]$_D^{20}$=−121.04 (c 5.05, CHCl$_3$); $^1$H NMR (400 MHz, CDCl$_3$) δ 7.24-7.14 (m, 3H), 7.10 (dd, J=8.1, 2.7 Hz, 4H), 7.06-6.92 (m, 3H), 6.72 (d, J=8.3 Hz, 1H), 4.99-4.83 (m, 2H), 4.33 (td, J=8.1, 4.9 Hz, 1H), 4.15-3.97 (m, 2H), 3.30 (qd, J=13.6, 7.7 Hz, 2H), 2.37 (s, 3H), 2.26 (s, 3H). $^{13}$C NMR (100 MHz, CDCl$_3$) δ 155.01, 138.02, 136.09, 134.98, 134.42, 131.66, 131.55, 129.83, 129.14, 129.11, 126.55, 118.58, 118.54, 106.54, 103.31, 103.27, 62.94, 59.97, 45.03, 33.35, 21.13, 20.97. HRMS (ESI-TOF) calcd for C26H27F3N3O [M+H]$^+$ 454.2101, found: 454.2104.

(S)-1-(1-methoxy-3-p-tolylpropan-2-yl)-3-(4-methylbenzyl)-5-(trifluoromethyl)-1H-benzo[d]imidazol-2(3H)-imine (ARN-592): (S)—N1-(1-methoxy-3-p-tolylpropan-2-yl)-N2-(4-methylbenzyl)-4-(trifluoromethyl)benzene-1,2-diamine (0.15 g, 0.34 mmole) with cyanogen bromide yielded product as Viscous oil (78%) yield; [α]$_D^{20}$=−80.0 (c 5.32, CHCl$_3$); $^1$H NMR (400 MHz, CDCl$_3$) δ 7.30-6.84 (m, 11H), 5.02-4.81 (m, 3H), 4.75 (s, 1H), 4.02 (s, 1H), 3.80 (dd, J=10.0, 4.5 Hz, 1H), 3.39 (s, 4H), 3.23 (dd, J=13.9, 6.3 Hz, 1H), 2.35 (s, 3H), 2.31 (s, 3H). $^{13}$C NMR (100 MHz, CDCl$_3$) δ 155.01, 137.42, 136.04, 134.43, 132.24, 131.83, 129.57, 129.17, 128.91, 126.56, 126.10, 118.03, 117.99, 102.96, 102.92, 72.30, 59.05, 44.74, 34.11, 21.11, 21.09.

(S)-2-(2-imino-4-methyl-3-(4-methylbenzyl)-2,3-dihydro-1H-benzo[d]imidazol-1-yl)-3-p-tolylpropan-1-ol (ARN-603): (S)-2-(3-methyl-2-(4-methylbenzylamino)phenylamino)-3-p-tolylpropan-1-ol (0.20 g, 0.53 mmol) with cyanogen bromide yielded product as Viscous oil (68%); [α]$_D^{20}$=−146.8 (c 5.1, CHCl$_3$); $^1$H NMR (400 MHz, CDCl$_3$) δ 7.35-6.81 (m, 9H), 6.71 (t, J=6.5 Hz, 2H), 5.16 (q, J=17.9 Hz, 2H), 4.31 (s, 1H), 4.17-3.86 (m, 2H), 3.50 (dd, J=13.6, 8.4 Hz, 1H), 3.18 (dd, J=13.1, 7.0 Hz, 1H), 2.55-2.07 (m, 9H). $^{13}$C NMR (100 MHz, CDCl$_3$) δ 155.38, 137.42, 135.84, 135.45, 133.79, 131.93, 129.80, 129.75, 129.39, 129.12, 125.71, 124.22, 121.01, 118.14, 105.18, 62.56, 59.38, 46.35, 33.29, 21.16, 21.13, 18.22. HRMS (ESI-TOF) calcd for C26H30N3O [M+H]$^+$ 400.23890, found: 400.23890.

(S)-1-(1-methoxy-3-p-tolylpropan-2-yl)-4-methyl-3-(4-methylbenzyl)-1H-benzo[d]imidazol-2(3H)-imine (ARN-608): (S)—N1-(1-methoxy-3-p-tolylpropan-2-yl)-3-methyl-N2-(4-methylbenzyl)benzene-1,2-diamine (0.20 g, 0.50 mmole) with cyanogen bromide yielded product as Viscous oil (76%); [α]$_D^{20}$=−109.4 (c 1.84, CHCl$_3$); $^1$H NMR (400 MHz, CDCl$_3$) δ 7.19-6.99 (m, 7H), 6.90-6.84 (m, 3H), 6.65 (d, J=7.6 Hz, 1H), 5.17 (s, 2H), 4.39 (s, 1H), 4.02 (s, 1H), 3.82 (dd, J=9.9, 5.1 Hz, 1H), 3.38 (s, 4H), 3.23 (dd, J=13.9, 6.4 Hz, 1H), 2.41-2.25 (m, 9H). NMR (100 MHz, CDCl$_3$) δ 154.57, 136.70, 135.80, 134.89, 134.82, 134.80, 134.67, 129.67, 129.48, 129.09, 129.00, 125.61, 123.84, 120.28, 117.85, 72.25, 59.05, 55.71, 46.10, 34.21, 21.14, 21.10, 18.41. HRMS (ESI-TOF) calcd for C27H32N3O [M+H]$^+$ 414.2545, found: 414.2541.

(S)-2-(5-chloro-2-imino-3-(4-methylbenzyl)-2,3-dihydro-1H-benzo[d]imidazol-1-yl)-3-p-tolylpropan-1-ol (ARN-626): (S)-2-(4-chloro-2-(4-methylbenzylamino)phenylamino)-3-p-tolylpropan-1-ol (0.20 g, 0.50 mmole) with cyanogen bromide yielded product as Viscous oil (74%); $^1$H NMR (400 MHz, CDCl$_3$) δ 7.17-6.78 (m, 9H), 6.66 (dd, J=11.3, 5.1 Hz, 2H), 4.87-4.70 (m, 2H), 4.33 (s, 1H), 3.97 (qd, J=12.2, 4.2 Hz, 3H), 3.26-3.12 (m, 2H), 2.30 (s, 3H), 2.22 (s, 3H). $^{13}$C NMR (100 MHz, CDCl$_3$) δ 155.07, 137.74, 135.95, 134.68, 132.33, 131.65, 129.97, 129.65, 129.03, 128.96, 126.43, 125.92, 120.67, 108.08, 107.16, 62.59, 59.18, 44.85, 33.31, 21.03, 20.95.

(S)-5-chloro-1-(1-methoxy-3-p-tolylpropan-2-yl)-3-(4-methylbenzyl)-1H-benzo[d]imidazol-2(3H)-imine (ARN-629): (S)-4-chloro-N1-(1-methoxy-3-p-tolylpropan-2-yl)-N2-(4-methylbenzyl)benzene-1,2-diamine (0.20 g, 0.49 mmole) with cyanogen bromide yielded product as Viscous oil (75%); $^1$H NMR (400 MHz, CDCl$_3$) δ 7.17-6.83 (m, 10H), 6.66 (d, J=2.0 Hz, 1H), 4.91-4.78 (m, 2H), 4.64 (s, 2H), 3.98 (s, 1H), 3.78 (dd, J=9.9, 4.6 Hz, 1H), 3.38 (s, 4H), 3.19 (dd, J=13.9, 6.2 Hz, 1H), 2.34 (s, 3H), 2.30 (s, 3H). $^{13}$C NMR (100 MHz, CDCl$_3$) δ 154.79, 137.29, 135.94, 134.51, 132.71, 132.42, 129.51, 129.14, 128.93, 126.59, 125.57, 120.03, 106.81, 72.40, 59.07, 56.00, 44.72, 34.12, 21.15.

(S)-5-bromo-1-(1-methoxy-3-p-tolylpropan-2-yl)-3-(4-methylbenzyl)-1H-benzo[d]imidazol-2(3H)-imine (ARN-632): (S)-4-bromo-N1-(1-methoxy-3-p-tolylpropan-2-yl)-N2-(4-methylbenzyl)benzene-1,2-diamine (0.13 g, 0.30 mmole) with cyanogen bromide yielded product as Viscous oil (68%); [α]$_D^{20}$=−120.21 (c 0.85, CHCl$_3$); $^1$H NMR (400 MHz, CDCl$_3$) δ 7.16-6.84 (m, 11H), 6.78 (d, J=1.8 Hz, 1H), 4.86 (dd, J=17.1, 14.4 Hz, 2H), 4.60 (s, 1H), 3.96 (s, 1H), 3.77 (dd, J=9.9, 4.6 Hz, 1H), 3.37 (s, 4H), 3.18 (dd, J=13.9, 6.2 Hz, 1H), 2.34 (s, 3H), 2.30 (s, 3H). $^{13}$C NMR (100 MHz, CDCl$_3$) δ 154.74, 137.30, 135.94, 134.51, 133.03, 132.39, 129.51, 129.13, 128.91, 126.57, 126.55, 122.87, 119.98, 112.65, 109.39, 106.77, 72.37, 59.07, 44.72, 44.69, 34.10, 21.15, 21.14.

(S)-5,6-dichloro-1-(1-methoxy-3-p-tolylpropan-2-yl)-3-(4-methylbenzyl)-1H-benzo[d]imidazol-2(3H)-imine (ARN-642): (S)-4,5-dichloro-N1-(1-methoxy-3-p-tolylpropan-2-yl)-N2-(4-methylbenzyl)benzene-1,2-diamine (0.13 g, 0.30 mmole) with cyanogen bromide yielded product as Viscous oil (68%); [α]$_D^{20}$=−25.3 (c 1.1, CHCl$_3$); $^1$H NMR (400 MHz, CDCl$_3$) δ 7.10 (d, J=7.8 Hz, 2H), 7.04-6.93 (m, 6H), 6.67 (s, 1H), 4.84 (t, J=16.4 Hz, 2H), 3.93 (s, 1H), 3.73 (dd, J=10.0, 4.4 Hz, 1H), 3.37 (s, 3H), 3.16 (dd, J=13.9, 6.3 Hz, 1H), 2.33 (s, 3H), 2.29 (s, 3H). $^{13}$C NMR (100 MHz, CDCl$_3$) δ 137.48, 136.11, 134.20, 131.99, 131.37, 129.55, 129.17, 128.88, 126.50, 123.50, 123.41, 107.51, 72.24, 59.07, 53.45, 44.81, 34.01, 21.12, 21.10. HRMS (ESI-TOF) calcd for C26H28Cl2N3O [M+H]$^+$ 468.1604, found: 468.1611.

(S)-5-bromo-3-(1-methoxy-3-p-tolylpropan-2-yl)-1-(4-methylbenzyl)-1H-benzo[d]imidazol-2(3H)-imine (ARN-643): (S)-4-bromo-N2-(1-methoxy-3-p-tolylpropan-2-yl)-N1-(4-methylbenzyl)benzene-1,2-diamine (0.15 g, 0.36 mmole) with cyanogen bromide yielded product as Viscous oil (71%); [α]$_D^{20}$=−82.4 (c 4.7, CHCl$_3$); $^1$H NMR (400 MHz, CDCl$_3$) δ 7.24-6.87 (m, 11H), 6.49 (d, J=8.2 Hz, 1H), 4.93-4.78 (m, 2H), 4.61 (s, 1H), 3.97 (s, 1H), 3.76 (dd, J=10.0, 4.6 Hz, 1H), 3.38 (s, 4H), 3.20 (dd, J=13.9, 6.5 Hz, 1H), 2.33 (s, 3H), 2.30 (s, 3H). $^{13}$C NMR (100 MHz, CDCl$_3$) δ 154.76, 137.26, 135.99, 134.46, 132.52, 130.85, 129.47, 129.40, 129.15, 129.09, 128.98, 126.68, 126.60, 122.68, 112.79, 107.35, 72.23, 59.06, 55.98, 44.70, 34.16, 21.15. HRMS (ESI-TOF) calcd for C26H29BrN3O [M+H]$^+$ 478.1489, found: 478.1491.

(S)-1-(4-methylbenzyl)-3-(1-(methylthiomethoxy)-3-p-tolylpropan-2-yl)-1H-benzo[d]imidazol-2(3H)-imine (ARN-757): (S)—N1-(4-methylbenzyl)-N2-(1-(methylthiomethoxy)-3-p-tolylpropan-2-yl)benzene-1,2-diamine (0.17 g, 0.45) with cyanogen bromide yielded product as Viscous oil (68%) yield; [α]$_D^{20}$=−101.21 (c 6.3, CHCl$_3$); $^1$H NMR (400 MHz, CDCl$_3$) δ 7.20-6.79 (m, 11H), 6.76-6.60 (m, 1H), 4.95-4.83 (m, 2H), 4.63 (s, 2H), 4.18 (s, 2H), 3.92 (dd, J=10.0, 4.9 Hz, 1H), 3.38 (s, 2H), 3.22 (dd, J=13.9, 6.4 Hz, 1H), 2.32 (s, 3H), 2.29 (s, 3H), 1.96 (s, 3H). $^{13}$C NMR (100 MHz, CDCl$_3$) δ 137.10, 135.90, 134.59, 132.92, 131.66, 129.38, 129.11, 128.93, 126.63, 120.29, 120.13, 106.48, 75.45, 67.52, 55.51, 44.67, 34.49, 21.12, 13.74. HRMS (ESI-TOF) calcd for C27H31N3OS [M+H]$^+$ 446.2260, found: 446.2265.

(S,Z)-2-(2-(methoxymethylimino)-3-(4-methylbenzyl)-2,3-dihydro-1H-benzo[d]imidazol-1-yl)-3-p-tolylpropan-1-ol (Structure was not confirmed)(ARN-795): Viscous oil (80%); [α]$_D^{20}$=−82.4 (c 4.7, CHCl$_3$); $^1$H NMR (400 MHz, CDCl$_3$) δ 8.17 (d, J=8.6 Hz, 1H), 7.65 (t, J=7.7 Hz, 1H), 7.51 (t, J=7.8 Hz, 1H), 7.41 (d, J=8.4 Hz, 1H), 7.07 (d, J=7.9 Hz, 2H), 6.96 (d, J=7.7 Hz, 2H), 6.82 (d, J=7.7 Hz, 2H), 6.73 (d, J=7.8 Hz, 2H), 5.89 (d, J=16.4 Hz, 1H), 5.72 (tdd, J=9.5, 5.9, 3.9 Hz, 1H), 5.52 (d, J=16.4 Hz, 1H), 4.67 (d, J=6.5 Hz, 2H), 4.55 (d, J=6.5 Hz, 2H), 4.48-4.30 (m, 2H), 4.22 (dd, J=10.8, 4.1 Hz, 1H), 3.41 (s, 3H), 2.30 (s, 3H), 2.22 (s, 3H). $^{13}$C NMR (100 MHz, CDCl$_3$) δ 150.14, 138.11, 136.95, 133.04, 130.66, 130.02, 129.58, 129.50, 129.02, 128.24, 127.16, 127.12, 125.86, 115.41, 114.49, 96.58, 67.05, 61.92, 55.64, 50.37, 49.42, 34.74, 21.09, 21.02.

1-(cyclopropyl(p-tolyl)methyl)-3-((S)-1-(2-methoxyethoxy)-3-p-tolylpropan-2-yl)-1H-benzo[d]imidazol-2(3H)-imine (ARN-805): N1-(cyclopropyl(p-tolyl)methyl)-N2-((S)-1-(2-methoxyethoxy)-3-p-tolylpropan-2-yl)benzene-1,2-diamine (0.05 g, 0.11 mmole) with cyanogen bromide yielded product as Viscous oil (71%); $^1$H NMR (400 MHz, CDCl$_3$) δ 7.25-6.75 (m, 12H), 4.27-3.97 (m, 3H), 3.84-3.71 (m, 2H), 3.68-3.18 (m, 8H), 2.34-2.19 (m, 6H), 1.22-0.77 (m, 3H), 0.60-0.20 (m, 2H). $^{13}$C NMR (100 MHz, CDCl$_3$) δ 137.75, 133.88, 132.73, 132.65, 129.41, 129.29, 129.18, 128.96, 128.89, 127.96, 126.93, 123.21, 122.99, 71.70, 70.79, 62.68, 58.88, 21.10, 21.08, 21.05, 13.70, 6.35, 6.24, 3.53.

1-(cyclopropyl(p-tolyl)methyl)-3-((S)-1-(methoxymethoxy)-3-p-tolylpropan-2-yl)-1H-benzo[d]imidazol-2(3H)-imine Mixture of DM (ARN-826): N1-(cyclopropyl(p-tolyl)methyl)-N2-((S)-1-(methoxymethoxy)-3-p-tolylpropan-2-yl)benzene-1,2-diamine (0.05 g, 0.12 mmole) with cyanogen bromide yielded product as Viscous oil (70%); $^1$H NMR (400 MHz, CDCl$_3$) δ 7.79 (dd, J=30.3, 8.4 Hz, 1H), 7.57-7.39 (m, 1H), 7.25-6.78 (m, 10H), 4.81-4.62 (m, 2H), 4.35-4.07 (m, 2H), 3.54-3.44 (m, 2H), 3.36-3.11 (m, 3H), 2.43-2.16 (m, 6H), 1.69 (s, 1H), 1.11-0.77 (m, 2H), 0.73-0.39 (m, 2H). $^{13}$C NMR (100 MHz, CDCl$_3$) δ 154.76, 137.26, 135.99, 134.46, 132.52, 130.85, 129.47, 129.40, 129.15, 129.09, 128.98, 126.68, 126.60, 122.68, 112.79, 107.35, 72.23, 59.06, 55.98, 44.70, 34.16, 21.15.

2-((2S)-2-(2-imino-3-(1-p-tolylethyl)-2,3-dihydro-1H-benzo[d]imidazol-1-yl)-3-p-tolylpropoxy)ethanol (ARN-846): Viscous oil (90%); $^1$H NMR (400 MHz, CDCl$_3$) δ 9.37 (s, 1H), 7.97 (dd, J=5.1, 1.4 Hz, 1H), 7.09-6.94 (m, 6H), 6.89-6.73 (m, 3H), 6.67 (dt, J=7.8, 2.4 Hz, 2H), 5.62 (s, 1H), 4.26 (s, 1H), 3.84 (ddd, J=22.2, 10.6, 3.8 Hz, 2H), 3.63 (ddd, J=10.8, 5.4, 3.4 Hz, 1H), 3.52-3.25 (m, 3H), 3.20 (dd, J=14.0, 6.6 Hz, 1H), 2.18 (s, 3H), 2.07 (s, 3H), 1.65 (d, J=6.8 Hz, 3H). $^{13}$C NMR (100 MHz, CDCl$_3$) δ 150.77, 143.44, 142.73, 138.06, 136.30, 133.33, 132.43, 129.43, 128.99, 128.96, 126.80, 121.60, 119.57, 118.73, 71.42, 70.68, 70.23, 59.17, 54.67, 33.24, 21.03, 20.93, 17.02.

(2S)-2-(3-(cyclopropyl(p-tolyl)methyl)-2-imino-2,3-dihydro-1H-benzo[d]imidazol-1-yl)-3-p-tolylpropyl acetate (ARN-851): (2S)-2-(2-(cyclopropyl(p-tolyl)methylamino)phenyl amino)-3-p-tolylpropyl acetate (0.20 g, 0.45 mmole) with cyanogen bromide yielded product as Viscous oil (74%); $^1$H NMR (400 MHz, CDCl$_3$) δ 7.59 (d, J=9.1 Hz, 1H), 7.37-6.72 (m, 11H), 6.21 (s, 1H), 5.75 (dd, J=18.2, 10.0 Hz, 1H), 4.89-4.56 (m, 2H), 3.53-3.24 (m, 2H), 2.25 (d, J=21.4 Hz, 6H), 2.05 (d, J=14.2 Hz, 3H), 1.82-1.53 (m, 1H), 1.17-0.79 (m, 2H), 0.56-0.03 (m, 2H). $^{13}$C NMR (100 MHz, CDCl$_3$) δ 170.43, 150.95, 137.64, 137.41, 136.51, 136.47, 133.88, 131.81, 129.39, 129.24, 129.21, 129.10, 129.04, 128.92, 126.85, 126.65, 123.26, 123.24, 122.99, 122.94, 113.04, 112.59, 63.79, 63.65, 62.73, 62.59, 57.42, 34.26, 21.17, 21.10, 21.07, 20.95, 13.77, 13.59, 6.42, 6.25, 3.30, 2.80. HRMS (ESI-TOF) calcd for C30H34N3O2 [M+H]$^+$ 468.2651, found: 468.2633.

(2S)-2-(3-(cyclopropyl(p-tolyl)methyl)-2-imino-2,3-dihydro-1H-benzo[d]imidazol-1-yl)-3-p-tolylpropyl cyclopropanecarboxylate salt (ARN-855): (2S)-2-(2-(cyclopropyl(p-tolyl) methylamino)phenylamino)-3-p-tolylpropylcyclopropane carboxylate (0.13 g, 0.28 mmole) with cyanogen bromide yielded product as Viscous oil (65%); $^1$H NMR (400 MHz, CDCl$_3$) δ 9.11 (s, 2H), 7.63 (t, J=7.8 Hz, 1H), 7.25-6.77 (m, 11H), 6.23 (s, 1H), 5.75 (dd, J=25.0, 9.9 Hz, 1H), 4.83 (td, J=12.3, 7.6 Hz, 1H), 4.60 (dd, J=11.4, 4.6 Hz, 2H), 3.36 (dt, J=12.8, 6.0 Hz, 2H), 2.26 (d, J=4.8 Hz, 6H), 1.80-1.51 (m, 2H), 1.28-0.70 (m, 7H), 0.52--0.00 (m, 2H). $^{13}$C NMR (100 MHz, CDCl$_3$) δ 174.25, 150.87, 137.60, 137.39, 136.46, 136.41, 133.89, 131.83, 129.36, 129.22, 129.17, 129.14, 129.07, 128.98, 128.87, 126.86, 126.71, 126.63, 123.27, 123.04, 113.14, 113.03, 112.69, 63.51, 63.37, 62.73, 62.57, 57.48, 57.36, 34.18, 34.02, 21.18, 21.10, 21.07, 13.76, 13.61, 13.03, 12.93, 8.88, 6.43, 6.27, 3.30, 2.77. HRMS (ESI-TOF) calcd for C32H36N3O2 [M+H]$^+$ 494.2808, found: 494.2801.

(2S)-2-(3-(cyclopropyl(p-tolyl)methyl)-2-imino-2,3-dihydro-1H-benzo[d]imidazol-1-yl)-3-p-tolylpropyl 1-methylazetidine-3-carboxylate (ARN-857): (2S)-2-(2-(cyclopropyl(p-tolyl)methylamino)phenylamino)-3-p-tolylpropyl1-methylazetidine-3-carboxylate (0.15 g, 0.36 mmole) with cyanogen bromide yielded product as Viscous oil (80%); $^1$H NMR (400 MHz, CDCl$_3$) δ 7.55 (d, J=8.2 Hz, 1H), 7.46-6.71 (m, 12H), 5.94-5.73 (m, 1H), 5.08-4.84 (m, 1H), 4.82-4.71 (m, 1H), 3.90-3.19 (m, 8H), 2.94-2.72 (m, 3H), 2.39-2.12 (m, 6H), 1.76-1.63 (m, 1H), 1.03-0.76 (m, 3H), 0.61-0.21 (m, 2H). $^{13}$C NMR (100 MHz, CDCl$_3$) δ Mixture of DM: Due to mixture not good 13 C.

(2S)-2-(3-(cyclopropyl(p-tolyl)methyl)-2-imino-2,3-dihydro-1H-benzo[d]imidazol-1-yl)-3-p-tolylpropyl 1-acetylazetidine-3-carboxylate (ARN-861): (2S)-2-(2-(cyclopropyl(p-tolyl)methylamino)phenylamino)-3-p-tolylpropyl1-acetylazetidine-3-carboxylate (0.20 g, 0.38 mmole) with cyanogen bromide yielded product as Viscous oil (74%); $^1$H NMR (400 MHz, CDCl$_3$) δ 9.04 (t, J=9.6 Hz, 2H), 7.52 (d, J=8.3 Hz, 1H), 7.32-6.73 (m, 11H), 6.31-6.09 (m, 1H), 5.80-5.51 (m, 1H), 4.87-4.70 (m, 2H), 4.38-3.95 (m, 4H), 3.40 (dd, J=34.0, 7.8 Hz, 3H), 2.38-2.17 (m, 6H), 1.82-1.66 (m, 3H), 1.08-0.73 (m, 3H), 0.32-0.17 (m, 2H). $^{13}$C NMR (100 MHz, CDCl$_3$) δ 171.76, 171.69, 171.65, 170.73, 150.71, 137.95, 136.70, 136.67, 136.63, 133.67, 133.63, 133.51, 131.53, 129.51, 129.33, 129.29, 129.23, 129.04, 128.93, 128.56, 126.80, 126.73, 126.56, 126.47, 123.54, 123.26, 113.38, 113.22, 113.15, 112.16, 62.88, 62.83, 57.51, 52.69, 50.30, 50.25, 34.31, 31.51, 31.45, 21.17, 21.09, 21.07, 18.74, 18.64, 13.55, 13.41, 6.29, 6.18, 2.77.

(2-((S)-1-(2-imino-3-(4-methylbenzyl)-2,3-dihydro-1H-benzo[d]imidazol-1-yl)-2-p-tolylethyl)-4,5-dihydrooxazol-5-yl)methanol Mixture of Distereomers (ARN-909) Yield (90%); H NMR (400 MHz, CDCl$_3$) δ 7.22 (d, J=31.6 Hz, 3H), 7.03 (q, J=6.2, 4.7 Hz, 4H), 6.84 (d, J=16.1 Hz, 6H), 5.81-5.60 (m, 1H), 5.29-5.07 (m, 2H), 4.66 (dt, J=38.9, 5.1 Hz, 2H), 3.70-3.38 (m, 7H), 2.27 (s, 3H), 2.18 (s, 3H). $^{13}$C NMR (100 MHz, CDCl$_3$) δ 150.34, 138.27, 136.88, 136.78, 131.37, 129.84, 129.68, 129.30, 128.83, 128.73, 126.70, 124.22, 118.29, 115.37, 110.16, 80.07, 79.77, 60.46, 60.40, 60.22, 46.20, 39.52, 38.05, 34.41, 21.09, 21.06, 21.00, 14.18, 13.52.

3-((S)-1-(methoxymethoxy)-3-p-tolylpropan-2-yl)-1-(1-p-tolylethyl)-1H-imidazo[4,5-b]pyridin-2(3H)-imine DM-1 (ARN-931) Reaction of N2-((S)-1-(methoxymethoxy)-3-p-tolylpropan-2-yl)-N3-(1-p-tolylethyl)pyridine-2,3-diamine with cynogen bromide yielded a pale yellow solid (46%); $[\alpha]_D^{20}$+11.0 (c 1.9, CHCl$_3$). $^1$H NMR (400 MHz, CDCl$_3$) δ 8.66 (s, 2H), 8.18-8.02 (m, 1H), 7.13-7.03 (m, 5H), 6.95-6.87 (m, 3H), 6.82 (dd, J=8.1, 1.5 Hz, 1H), 6.27 (d, J=6.9 Hz, 1H), 5.51 (s, 1H), 4.85 (s, 2H), 4.38-4.15 (m, 1H), 4.05 (dd, J=10.9, 2.8 Hz, 1H), 3.57 (dd, J=14.2, 10.4 Hz, 1H), 3.47-3.27 (m, 4H), 2.31 (s, 3H), 2.18 (s, 3H), 1.87 (d, J=6.8 Hz, 3H). $^{13}$C NMR (100 MHz, CDCl$_3$) δ 150.21, 143.24, 143.05, 138.45, 136.53, 133.05, 132.27, 129.62, 129.19, 128.92, 126.92, 121.56, 119.88, 119.04, 96.82, 77.28, 67.32, 56.27, 54.85, 33.31, 21.13, 21.02, 17.51. HRMS (ESI-TOF) calcd for C27H33N4O2 [M+H]$^+$ 445.2604, found: 445.2606.

3-((S)-1-(methoxymethoxy)-3-p-tolylpropan-2-yl)-1-(1-p-tolylethyl)-1H-imidazo[4,5-b]pyridin-2(3H)-imine DM-2 (ARN-932) Reaction of N2-((S)-1-(methoxymethoxy)-3-p-tolylpropan-2-yl)-N3-(1-p-tolylethyl)pyridine-2,3-diamine with cynogen bromide yielded a viscous oil (47%); $[\alpha]_D^{20}$−157.6 (c 1.44, CHCl$_3$). H NMR (400 MHz, CDCl$_3$) δ 8.01 (m, 1H), 7.05 (m, 4H), 6.99-6.82 (m, 4H), 6.79 (dd, J=8.0, 5.1 Hz, 1H), 6.67 (dd, J=8.0, 1.4 Hz, 1H), 6.25 (d, J=6.8 Hz, 1H), 5.59-5.48 (m, 1H), 4.76 (d, J=6.6 Hz, 1H), 4.64 (d, J=6.6 Hz, 1H), 4.54-4.42 (m, 1H), 4.08 (dd, J=10.6, 4.5 Hz, 1H), 3.52 (dd, J=13.8, 10.7 Hz, 1H), 3.34-3.18 (m, 4H), 2.36-2.17 (m, 6H), 1.81 (d, J=6.9 Hz, 3H). $^{13}$C NMR (100 MHz, CDCl$_3$) δ 151.78, 144.31, 141.24, 137.72, 136.14, 134.30, 133.31, 129.36, 129.11, 129.08, 129.03, 126.57, 122.41, 117.46, 96.52, 66.71, 55.55, 53.46, 53.06, 33.77, 21.11, 21.09, 16.98. HRMS (ESI-TOF) calcd for C27H33N4O2 [M+H]$^+$ 445.2604, found: 445.2603.

3-((S)-1-(2-methoxyethoxy)-3-p-tolylpropan-2-yl)-1-(1-p-tolylethyl)-1H-imidazo[4,5-b]pyridin-2(3H)-imine DM-1 (ARN-946). Reaction of N2-((S)-1-(2-methoxyethoxy)-3-p-tolylpropan-2-yl)-N3-(1-p-tolylethyl)pyridine-2,3-diamine with cynogen bromide yielded pale yellow solid (64%); $[\alpha]_D^{20}$=+10.71 (c 4.5, CHCl$_3$). H NMR (400 MHz, CDCl$_3$) δ 7.98 (dd, J=5.1, 1.4 Hz, 1H), 7.05-6.91 (m, 5H), 6.85-6.74 (m, 3H), 6.68 (dd, J=8.1, 1.4 Hz, 2H), 5.64-5.60 (m, 1H), 4.36-4.14 (m, 1H), 3.84 (ddd, J=22.1, 10.6, 3.9 Hz, 2H), 3.64 (ddd, J=10.8, 5.5, 3.4 Hz, 1H), 3.55-3.32 (m, 3H), 3.29 (s, 3H), 2.18 (s, 3H), 2.07 (s, 3H), 1.66 (d, J=7.0 Hz, 3H). $^{13}$C NMR (100 MHz, CDCl$_3$) δ 150.77, 143.44, 142.73, 138.06, 136.30, 133.33, 132.43, 129.44, 128.99, 128.96, 126.80, 121.60, 119.58, 118.73, 77.63, 71.42, 70.69, 70.23, 59.17, 54.67, 33.24, 21.03, 20.93, 17.02. 19.8. HRMS (ESI-TOF) calcd for C28H35N4O2 [M+H]$^+$ 459.2760, found: 459.2790.

3-((S)-1-(2-methoxyethoxy)-3-p-tolylpropan-2-yl)-1-(1-p-tolylethyl)-1H-imidazo[4,5-b]pyridin-2(3H)-imine DM-2 (ARN-947). Reaction of N2-((S)-1-(2-methoxyethoxy)-3-p-tolylpropan-2-yl)-N3-(1-p-tolylethyl)pyridine-2,3-diamine with cynogen bromide yielded a pale yellow viscous compound (51%); $[\alpha]_D^{20}$=−124.97 (c 2.4, CHCl$_3$). H NMR (400 MHz, CDCl$_3$) δ 7.96 (dd, J=5.2, 1.4 Hz, 1H), 7.10-6.88 (m, 8H), 6.76 (dd, J=8.0, 5.1 Hz, 1H), 6.64 (dd, J=7.9, 1.4 Hz, 1H), 6.47-6.26 (m, 1H), 5.44-5.38 (m, 1H), 4.34 (s, 1H), 3.97 (dd, J=10.9, 3.7 Hz, 1H), 3.87 (dt, J=10.9, 4.2 Hz, 1H), 3.70 (ddd, J=10.8, 5.4, 3.7 Hz, 1H), 3.54 (t, J=4.8 Hz, 2H), 3.45 (dd, J=13.9, 10.1 Hz, 1H), 3.35 (s, 3H), 3.25 (dd, J=13.8, 6.4 Hz, 1H), 2.28 (s, 3H), 2.21 (s, 3H), 1.80 (d, J=6.9 Hz, 3H). $^{13}$C NMR (100 MHz, CDCl$_3$) δ 151.66, 144.20, 141.29, 137.77, 136.16, 134.22, 133.28, 129.38, 129.05, 129.03, 126.69, 122.40, 117.62, 77.36, 71.67, 70.73, 70.33, 59.19, 53.21, 33.54, 21.07, 21.05, 16.98. HRMS (ESI-TOF) calcd for C28H35N4O2 [M+H]$^+$ 459.2760, found: 459.2811.

1-(1-(6-chloropyridin-3-yl)ethyl)-3-(1-methoxy-3-p-tolylpropan-2-yl)-1H-imidazo[4,5-b] pyridin-2(3H)-imine (ARN-956): To a solution of N3-(1-(6-chloropyridin-3-yl)ethyl)-N2-(1-methoxy-3-p-tolylpropan-2-yl)pyridine-2,3-diamine (0.200 g, 0.49 mmol) in MeOH (5 mL) was added cyanogens bromide (3 M in CH$_2$Cl$_2$, 0.4 mL, 1.2 mmol). The resulting solution was stirred at room temperature for 48 h and after completion of the reaction, the solvents was concentrated under reduced pressure. The remaining solid was mixed with saturated NaHCO$_3$ solution (25 mL), extracted with CH$_2$Cl$_2$ (3×25 mL). The combined organic layers were dried over Na$_2$SO$_4$, filtered and concentrated under reduced pressure. The flash chromatography on silica gel (1:19 MeOH/CH2CL2) provided the desired 1-(1-(6-chloropyridin-3-yl)ethyl)-3-(1-methoxy-3-p-tolylpropan-2-yl)-1H-imidazo [4,5b]pyridin-2(3H)-imine as a brown gel (0.920 g, 80% brs). $^1$H NMR (400 MHz, CDCl$_3$) δ 8.28 (d, J=2.6 Hz, 1H), 8.02 (dd, J=5.1, 1.3 Hz, 1H), 7.52 (dd, J=8.4, 2.6 Hz, 1H), 7.30-7.22 (m, 1H), 7.01 (d, J=7.9 Hz, 2H), 6.92 (d, J=7.8 Hz, 2H), 6.85 (dd, J=7.9, 5.1 Hz, 1H), 6.76 (dd, J=7.9, 1.3 Hz, 1H), 5.39 (s, J=5.9 Hz, 1H), 4.17-4.06 (m, 1H), 3.88 (dd, J=10.4, 3.3 Hz, 1H), 3.46 (s, 3H), 3.43-3.37 (m, 1H), 3.24 (dd, J=14.0, 6.7 Hz, 1H), 2.21 (s, 3H), 1.81 (d, J=7.0 Hz, 3H). $^{13}$C NMR (100 MHz, CDCl$_3$) δ 151.66, 151.36, 147.64, 144.45, 141.74, 138.08, 136.58, 132.80, 132.55, 129.11, 128.88, 124.40, 121.93, 117.85, 116.96, 72.15, 59.39, 56.11, 51.17, 33.39, 21.01, 16.78. HRMS (ESI-TOF) calcd for C24H27ClN5O [M+H]$^+$ 436.1904, found: 436.1911.

N3-(1-(6-chloropyridin-3-yl)ethyl)-N2-((S)-1-methoxy-3-p-tolylpropan-2-yl)pyridine-2,3-diamine (ARN-952): N$^2$-(1-methoxy-3-p-tolylpropan-2-yl)pyridine-2,3-diamine (1.0 g, 3.69 mmol) was dissolved in DMF (20 mL). At room temperature 5-(1-bromoethyl)-2-chloropyridine (1.6 g, 8.6 mmol) and K$_2$CO$_3$ (0.77 g, 5.5 mmol) were added. The resulting reaction suspension was stirred vigorously at 60° C. till consumption of starting materials. The suspension was filtered through a pad of celite and the filter cake was washed by a small amount of ethyl acetate. The resulting solution was extracted with EtOAc (3×50 mL) and the combined organic layers were dried over Na$_2$SO$_4$, filtered and concentrated under reduced pressure. The flash chromatography on silica gel (1:3 EtOAc/Hexane) provided the desired product (distereomer 1, 2) as oil (0.920 g, 61%). $^1$H NMR Distereomers 1 (400 MHz, CDCl$_3$) δ 8.34 (d, J=2.5 Hz, 1H), 7.90-7.78 (m, 1H), 7.31-7.21 (m, 2H), 7.18-7.06 (m, 2H), 6.96 (d, J=7.7 Hz, 2H), 6.45-6.27 (m, 2H), 4.45 (dt, J=13.0, 7.8 Hz, 2H), 3.79-3.56 (m, 2H), 3.29 (s, 4H), 3.08 (dd, J=13.9, 6.8 Hz, 1H), 2.19 (s, 3H), 1.72 (d, J=6.7 Hz, 3H). $^{13}$C NMR (100 MHz, CDCl$_3$) δ 136.1, 132.7, 129.0, 127.6, 61.4, 60.4, 49.4, 46.1, 39.3, 32.5, 27.3. $^1$H NMR Distereomers 2 (400 MHz, CDCl$_3$) δ 8.27 (d, J=2.5 Hz, 1H), 7.60 (dd, J=8.2, 2.5 Hz, 1H), 7.30 (d, J=7.8 Hz, 2H), 7.15 (d, J=8.3 Hz, 1H), 7.07 (dd, J=6.2, 1.3 Hz, 1H), 6.93 (d, J=7.7 Hz, 2H), 6.39-6.23 (m, 2H), 4.75-4.40 (m, 2H), 3.85-3.57 (m, 2H), 3.29 (s, 4H), 3.07 (dd, J=13.8, 6.2 Hz, 1H), 2.18 (s, 3H), 1.72 (d, J=6.7 Hz, 3H). $^{13}$C NMR (101 MHz, CDCl$_3$) δ 150.28, 147.89, 144.91, 138.01, 136.66, 136.16, 133.95, 132.43, 129.46, 129.06, 124.58, 121.38, 116.26, 112.62, 75.04, 59.25, 56.55, 51.23, 36.25, 24.40, 21.01.

Other Examples 3-(3-hydroxy-2-(2-imino-3-(4-methylbenzyl)-2,3-dihydro-1H-benzo[d]imidazol-1-yl)propyl)pyridin-2(1H)-one (ARN-19)

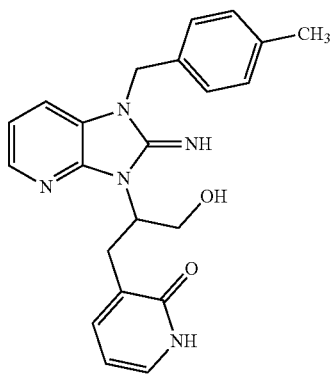 [SMILES: Cc1ccc(Cn2c(=N)n(C(CO)Cc3ccc[nH]c3=O)c3ncccc32)cc1]

To a flask equipped with a reflux condenser and stirring bar were added 2-(2-imino-3-(4-methylbenzyl)-2,3-dihydro-1H-benzo[d]imidazol-1-yl)-3-(2-methoxypyridin-3-yl)propan-1-ol (0.80 g, 0.20 mmol), anhydrous acetonitrile (5 mL), NaI (0.12 g, 0.80 mmol) and $Me_3SiCl$ (0.26 mL, 2.0 mmol). The resulting mixture was stirred at 75° C. for 3.5 h and then cooled to room temperature. 20% $NH_4Cl$ solution (6 mL) was added to the reaction mixture and after the evaporation of most acetonitrile under reduced pressure, the remaining slurry was diluted with water (10 mL) extracted with $CH_2Cl_2$ (3×25 mL). The combined organic layers were dried over $Na_2SO_4$, filtered and concentrated under reduced pressure to afford the entitled free amine product as brown foam (73 mg, 95%); $^1$H NMR (400 MHz, $CDCl_3$) δ 7.36-6.74 (m, 11H), 6.04 (t, J=6.6 Hz, 1H), 4.94 (dd, J=35.3, 18.4 Hz, 3H), 4.18-3.91 (m, 2H), 3.18 (ddd, J=40.3, 13.2, 7.5 Hz, 2H), 2.27 (s, 3H). $^{13}$C NMR (100 MHz, $CDCl_3$) δ 162.18, 154.69, 144.99, 139.95, 137.75, 132.17, 129.66, 126.63, 121.09, 120.56, 116.82, 106.93, 106.65, 62.89, 55.78, 53.31, 44.96, 28.72, 21.12. HRMS (ESI-TOF) calcd for C23H24N4O2 $[M+H]^+$ 389.1972, found: 389.1975.

5-(3-hydroxy-2-(2-imino-3-(4-methylbenzyl)-2,3-dihydro-1H-benzo[d]imidazol-1-yl)propyl)pyridin-2(1H)-one (ARN-29). To a flask equipped with a reflux condenser and stirring bar were added 2-(2-imino-3-(4-methylbenzyl)-2,3-dihydro-1H-benzo[d]imidazol-1-yl)-3-(6-methoxypyridin-3-yl)propan-1-ol (0.80 g, 0.20 mmol), anhydrous acetonitrile (5 mL), NaI (0.12 g, 0.80 mmol) and $Me_3SiCl$ (0.26 mL, 2.0 mmol). The resulting mixture was stirred at 75° C. for 4 h and then cooled to room temperature. 20% $NH_4Cl$ solution (5 mL) was added to the reaction mixture and after the evaporation of most acetonitrile under reduced pressure, the remaining slurry was diluted with water (10 mL) extracted with $CH_2Cl_2$ (3×25 mL). The combined organic layers were dried over $Na_2SO_4$, filtered and concentrated under reduced pressure to afford the entitled free amine product as brown foam (0.60 g, 78%); $^1$H NMR (400 MHz, $CDCl_3$+MeOH) δ 7.56-6.82 (m, 10H), 6.28 (dd, J=9.4, 2.8 Hz, 1H), 5.24 (d, J=3.0 Hz, 2H), 5.21-5.13 (m, 1H), 4.76 (d, J=8.6 Hz, 1H), 4.25-4.00 (m, 2H), 3.21-2.94 (m, 2H), 2.22 (s, 3H). $^{13}$C NMR (100 MHz, $CDCl_3$+MeOH) δ 163.29, 151.16, 143.73, 138.36, 134.02, 130.21, 129.98, 129.83, 126.54, 123.83, 123.71, 120.01, 115.55, 109.95, 61.76, 53.45, 46.36, 29.57, 20.98.

3-(2-imino-3-(4-methylbenzyl)-2,3-dihydro-1H-benzo[d]imidazol-1-yl)-2-phenylpropan-1-ol hydrobromide. To a solution of 3-((2-aminophenyl)amino)-2-phenylpropan-1-ol (0.0440 g, 0.18 mmol) in MeOH (3 mL) was added cyanogen bromide (3 M in DCM, 0.10 mL, 0.30 mmol). The resulting solution was stirred at room temperature overnight and after the evaporation of solvents, the residue was mixed with saturated $NaHCO_3$ solution (after which the aqueous layer's pH is about 8-9) and then extracted with DCM (3×30 mL). The combined organic layers were dried over $Na_2SO_4$, filtered and concentrated under reduced pressure to afford the 3-(2-imino-2,3-dihydro-1H-benzo[d]imidazol-1-yl)-2-phenylpropan-1-ol intermediate as a dark brown gel.

To a flask equipped with a reflux condenser and stirring bar were added the above 3-(2-imino-2,3-dihydro-1H-benzo[d]imidazol-1-yl)-2-phenylpropan-1-ol intermediate, 2-butanone (7 mL) and 1-(bromomethyl)-4-methylbenzene (0.0412 g, 0.22 mmol). The resulting mixture was stirred at 75° C. for 8 h and then cooled to room temperature. After the evaporation of most of the 2-butanone under reduced pressure, the residue was sonicated with $Et_2O$ (20 mL) and then the supernatant was removed using pipette. This procedure was repeated three times and the remaining solid was dried under vacuum to obtain the entitled amine HBr salt product as brown foam (0.0352 g, 43% two steps). $^1$H NMR (400 MHz, $CD_3OD$) δ 7.43-7.37 (m, 1H), 7.32-7.19 (m, 6H), 7.19-7.11 (m, 4H), 6.94 (d, J=8.2 Hz, 2H), 5.28 (s, 2H), 4.64 (dd, J=15.1, 5.8 Hz, 1H), 4.50 (dd, J=15.1, 9.3 Hz, 1H), 4.05-3.83 (m, 2H), 3.54-3.41 (m, 1H), 2.31 (s, 3H). $^{13}$C NMR (100 MHz, $CD_3OD$) δ 149.9, 138.2, 138.0, 130.7, 129.7, 129.5, 129.3, 128.4, 127.9, 127.4, 126.3, 123.8, 123.8, 110.6, 110.4, 62.7, 46.2, 45.8, 45.5, 19.7.

2-(3-(1-hydroxy-3-(p-tolyl)propan-2-yl)-2-imino-2,3-dihydro-1H-benzo[d]imidazol-1-yl)-1-(p-tolyl)ethan-1-one hydrobromide. To a flask equipped with a reflux condenser and stirring bar were added 2-(2-imino-2,3-dihydro-1H-benzo[d]imidazol-1-yl)-3-(p-tolyl)propan-1-ol (0.0470 g, 0.17 mmol), 2-butanone (7 mL) and 2-bromo-1-(p-tolyl)ethan-1-one (0.0500 g, 0.23 mmol). The resulting mixture was stirred at 75° C. for 15 h and then cooled down to room temperature. After the evaporation of most of the 2-butanone under reduced pressure, the residue was sonicated with $Et_2O$ (20 mL) and then the supernatant was removed using pipette. This procedure was repeated three times and the remaining solid was dried under vacuum to obtain the entitled amine HBr salt product as brown foam (0.0602 g, 73%). $^1$H NMR (400 MHz, $CD_3OD$) δ 8.04 (d, J=7.8 Hz, 2H), 7.41 (d, J=6.4 Hz, 2H), 7.36-7.14 (m, 3H), 7.12-6.77 (m, 5H), 5.80 (dd, J=31.8, 18.7 Hz, 2H), 4.31 (dd, J=12.1, 6.9 Hz, 1H), 4.09 (dd, J=12.1, 3.2 Hz, 1H), 3.46-3.34 (m, 1H), 3.23 (dd, J=14.5, 5.0 Hz, 1H), 2.45 (s, 3H), 2.35-2.03 (m, 1H), 2.18 (s, 3H). $^{13}$C NMR (100 MHz, $CD_3OD$) δ 193.8, 155.1, 149.5, 140.2, 137.2, 135.5, 133.3, 132.8, 132.7, 132.5, 132.3, 132.2, 127.6, 127.5, 113.7, 65.4, 65.1, 53.1, 36.9, 24.4, 23.6.

2-(2-imino-3-(4-methylphenethyl)-2,3-dihydro-1H-benzo[d]imidazol-1-yl)-4-(p-tolyl)butan-1-ol. To a solution of 2-((2-aminophenyl)amino)-4-(p-tolyl)butan-1-ol (0.2091 g, 0.77 mmol) in MeOH (12 mL) was added cyanogen bromide (3 M in DCM, 0.31 mL, 0.93 mmol). The resulting solution was stirred at room temperature for 19 h and after the evaporation of solvents, the residue was mixed with saturated $NaHCO_3$ solution (after which the aqueous layer's pH is about 8-9) and then extracted with DCM (3×30 mL). The combined organic layers were dried over Na$_2$SO$_4$, filtered and concentrated under reduced pressure to afford the 2-(2-imino-2,3-dihydro-1H-benzo[d]imidazol-1-yl)-4-(p-tolyl)butan-1-ol intermediate as a dark brown gel which was dissolved in DCM (8 mL). This intermediate solution (4 mL) was concentrated for next step without further purification. To a flask equipped with a reflux condenser and stirring bar were added the above 2-(2-imino-2,3-dihydro-1H-benzo[d]imidazol-1-yl)-4-(p-tolyl)butan-1-ol intermediate, 3-hexanone (6 mL) and 1-(2-bromoethyl)-4-methylbenzene (0.0895 g, 0.45 mmol). The resulting mixture was stirred at 120° C. for 24 h and then cooled to room temperature. After the evaporation of most of the 3-hexanone under reduced pressure, the residue was sonicated with Et$_2$O (20 mL) and then the supernatant was removed using pipette. This procedure was repeated three times and the remaining solid was mixed with saturated NaHCO$_3$ solution (30 mL), extracted with DCM (3×30 mL). The combined organic layers were dried over Na$_2$SO$_4$, filtered and concentrated under reduced pressure to afford the entitled free amine product as a brown gel (0.0664 g, 41% two steps). $^1$H NMR (400 MHz, CDCl$_3$) δ 7.13-7.02 (m, 8H), 7.00-6.89 (m, 3H), 6.80-6.74 (m, 1H), 6.73-6.67 (m, 1H), 4.15-4.05 (m, 1H), 4.01 (d, J=3.2 Hz, 2H), 3.91 (td, J=7.4, 2.2 Hz, 2H), 2.93 (t, J=7.5 Hz, 2H), 2.75-2.63 (m, 1H), 2.61-2.35 (m, 3H), 2.32 (s, 3H), 2.30 (s, 3H), 2.28 (s, 1H). $^{13}$C NMR (100 MHz, CDCl$_3$) δ 154.3, 138.0, 136.6, 135.4, 134.5, 131.4, 131.2, 129.5, 129.0, 128.6, 128.2, 121.0, 120.6, 107.1, 106.6, 63.3, 56.5, 43.5, 33.6, 31.8, 28.7, 21.0, 21.0.

2-(2-imino-3-(4-methylphenethyl)-2,3-dihydro-1H-benzo[d]imidazol-1-yl)-3-(p-tolyl)propan-1-ol. To a flask equipped with a reflux condenser and stirring bar were added 2-(2-imino-2,3-dihydro-1H-benzo[d]imidazol-1-yl)-3-(p-tolyl)propan-1-ol (0.0566 g, 0.20 mmol), 3-hexanone (4 mL) and 1-(2-bromoethyl)-4-methylbenzene (0.0641 g, 0.32 mmol). The resulting mixture was stirred at 120° C. for 27 h and then cooled down to room temperature. After the evaporation of most of the 3-hexanone under reduced pressure, the residue was sonicated with Et$_2$O (20 mL) and then the supernatant was removed using pipette. This procedure was repeated three times and the remaining solid was mixed with saturated NaHCO$_3$ solution (30 mL), extracted with DCM (3×30 mL). The combined organic layers were dried over Na$_2$SO$_4$, filtered and concentrated under reduced pressure to afford the entitled free amine product as a brown gel (0.0407 g, 51%). $^1$H NMR (400 MHz, CDCl$_3$) δ 7.19-6.99 (m, 9H), 6.96-6.88 (m, 2H), 6.77-6.67 (m, 2H), 4.22 (s, 1H), 4.01 (d, J=12.5 Hz, 1H), 3.95-3.84 (m, 3H), 3.41 (dd, J=13.4, 8.4 Hz, 1H), 3.05 (dd, J=13.4, 7.0 Hz, 1H), 2.94 (t, J=7.5 Hz, 2H), 2.32 (s, 3H), 2.27 (s, 3H), 2.24 (s, 1H). $^{13}$C NMR (100 MHz, CDCl$_3$) δ 154.4, 136.6, 135.9, 135.3, 134.6, 131.4, 131.2, 129.5, 129.2, 129.1, 128.6, 120.9, 120.5, 106.9, 106.5, 62.5, 59.5, 43.5, 33.6, 33.4, 21.1, 21.0.

2-(2-imino-3-(4-methylbenzyl)-2,3-dihydro-1H-benzo[d]imidazol-1-yl)-3-(p-tolyl)propan-1-amine. To a solution of tert-butyl (2-((2-aminophenyl)amino)-3-(p-tolyl)propyl)carbamate (0.0748 g, 0.21 mmol) in MeOH (5 mL) was added cyanogen bromide (3 M in DCM, 0.09 mL, 0.27 mmol). The resulting solution was stirred at room temperature for 3.5 h and after the evaporation of solvents, the residue was mixed with saturated NaHCO$_3$ solution (after which the aqueous layer's pH is about 8-9) and then extracted with DCM (3×30 mL). The combined organic layers were dried over Na$_2$SO$_4$, filtered and concentrated under reduced pressure to afford the tert-butyl (2-(2-imino-2,3-dihydro-1H-benzo[d]imidazol-1-yl)-3-(p-tolyl)propyl)carbamate intermediate as a dark brown gel which was used directly for next step without further purification. To a flask equipped with a reflux condenser and stirring bar were added the above tert-butyl (2-(2-imino-2,3-dihydro-1H-benzo[d]imidazol-1-yl)-3-(p-tolyl)propyl)carbamate intermediate, 2-butanone (7 mL) and 1-(bromomethyl)-4-methylbenzene (0.0533 g, 0.29 mmol). The resulting mixture was stirred at 75° C. overnight and then cooled down to room temperature. After the evaporation of most of the 2-butanone under reduced pressure, the residue was dissolved in 1,4-dioxane (3 mL) and conc. HCl (0.7 mL) was added. The resulting reaction mixture was stirred at room temperature for 1 h and after the evaporation of solvents and excess HCl, the residue was sonicated with Et$_2$O (25 mL) and then the supernatant was removed using pipette. This procedure was repeated three times and the remaining solid was mixed with saturated NaHCO$_3$ solution (30 mL), extracted with DCM (3×30 mL). The combined organic layers were dried over Na$_2$SO$_4$, filtered and concentrated under reduced pressure to afford the entitled free amine product as a brown gel (0.0810 g, >95% three steps). $^1$H NMR (400 MHz, CDCl$_3$) δ 7.18-6.81 (m, 11H), 6.72 (d, J=7.4 Hz, 1H), 5.14-4.79 (m, 2H), 4.65 (s, 1H), 3.47 (s, 1H), 3.37-3.18 (m, 1H), 3.17-3.05 (m, 2H), 2.74-2.33 (m, 2H), 2.31 (s, 3H), 2.28 (s, 3H). $^{13}$C NMR (100 MHz, CDCl$_3$) δ 155.3, 137.2, 135.9, 134.7, 132.8, 131.7, 129.5, 129.4, 129.1, 128.9, 128.6, 126.6, 120.5, 120.4, 106.8, 59.6, 44.8, 43.4, 35.6, 21.1, 21.1.

2-(2-imino-6-methyl-3-(4-methylbenzyl)-2,3-dihydro-1H-benzo[d]imidazol-1-yl)-3-(p-tolyl)propan-1-ol. Cyclization of 2-((2-amino-5-methylphenyl)amino)-3-(p-tolyl)propan-1-ol, followed by alkylation with 4-methylbenzyl bromide (Procedure E) yielded the title product (68% two steps). $^1$H NMR (400 MHz, CDCl$_3$) δ 7.20-7.12 (m, 4H), 7.08 (d, J=8.2 Hz, 2H), 7.02 (d, J=7.7 Hz, 2H), 6.71 (d, J=7.2 Hz, 1H), 6.65 (d, J=7.9 Hz, 1H), 6.54 (s, 1H), 4.88 (d, J=5.6 Hz, 2H), 4.33-4.18 (m, 1H), 4.04 (d, J=12.5 Hz, 1H), 3.92 (dd, J=12.4, 4.7 Hz, 1H), 3.42 (dd, J=13.4, 8.2 Hz, 1H), 3.10 (dd, J=13.4, 7.2 Hz, 1H), 2.33 (s, 3H), 2.30 (s, 3H), 2.27 (s, 3H). $^{13}$C NMR (100 MHz, CDCl$_3$) δ 154.9, 137.7, 135.8, 135.4, 132.2, 131.6, 130.9, 129.6, 129.5, 129.3, 129.0, 126.6, 121.0, 107.8, 106.5, 62.6, 59.6, 45.1, 33.4, 21.4, 21.1, 21.0.

2-(2-imino-6-methoxy-3-(4-methylbenzyl)-2,3-dihydro-1H-benzo[d]imidazol-1-yl)-3-(p-tolyl)propan-1-ol. To a flame-dried flask were added lithium aluminum hydride (0.0932 g, 2.45 mmol) and anhydrous THF (8 mL) at 0° C., followed by addition of ethyl 2-((5-methoxy-2-nitrophenyl)amino)-3-(p-tolyl)propanoate (0.4244 g, 1.19 mmol) in anhydrous THF (4 mL) under argon. The resulting reaction mixture was stirred at 0° C. for 80 min and 1 N KOH solution (12 mL) was added dropwise at 0° C. to quench the reaction while adding THF (12 mL) at the same time. Upon the addition of KOH solution, the mixture was stirred for 30 more min at rt and was condensed under reduced pressure to evaporate most of the THF. The residue was then mixed with water (60 mL) and extracted with EtOAc (3×60 mL). The combined organic layers were dried over Na$_2$SO$_4$, filtered and concentrated under reduced pressure to afford a mixture of 2-((5-methoxy-2-nitrophenyl)amino)-3-(p-tolyl)propan-1-ol (major one) and 2-((2-amino-5-methoxyphenyl)amino)-3-(p-tolyl)propan-1-ol (minor one). To a 50 mL flask were added the mixture above, methanol (10 mL) and Pd/C (3 spatula, 10% on active carbon). The reaction flask was sealed by a septum and after the removal of air using vacuum, a hydrogen balloon was fitted on the top of the septum. The reaction suspension was then stirred at room temperature for 4 h and was filtered through a pad of celite. The filtrate was concentrated under reduced pressure and the residue was purified through flash chromatography on silica gel (1:19 Methanol/DCM) to afford the 2-((2-amino-5-methoxyphenyl)amino)-3-(p-tolyl)propan-1-ol (0.0348 g) which was used for next step. To a solution of 2-((2-amino-5-methoxyphenyl)amino)-3-(p-tolyl)propan-1-ol (0.0348 g, 0.12 mmol) in MeOH (4 mL) was added cyanogen bromide (3 M in DCM, 0.05 mL, 0.15 mmol). The resulting solution was stirred at room temperature overnight and after the evaporation of solvents, the residue was mixed with saturated NaHCO$_3$ solution (after which the aqueous layer's pH is about 8-9) and then extracted with DCM (3×30 mL). The combined organic layers were dried over Na$_2$SO$_4$, filtered and concentrated under reduced pressure to afford the 2-(2-imino-6-methoxy-2,3-dihydro-1H-benzo[d]imidazol-1-yl)-3-(p-tolyl)propan-1-ol intermediate as a dark brown gel which was used directly for next step without further purification. To a flask equipped with a reflux condenser and stirring bar were added the above 2-(2-imino-6-methoxy-2,3-dihydro-1H-benzo[d]imidazol-1-yl)-3-(p-tolyl)propan-1-ol intermediate, 2-butanone (5 mL) and 1-(bromomethyl)-4-methylbenzene (0.0291 g, 0.16 mmol). The resulting mixture was stirred at 75° C. for 9 h and then cooled down to room temperature. After the evaporation of most of the 2-butanone under reduced pressure, the residue was sonicated with Et$_2$O (20 mL) and then the supernatant was removed using pipette. This procedure was repeated three times and the remaining solid was mixed with saturated NaHCO$_3$ solution (30 mL), extracted with DCM (3×30 mL). The combined organic layers were dried over Na$_2$SO$_4$, filtered and concentrated under reduced pressure to afford the entitled free amine product as a brown gel (0.0303 g, 6% four steps). $^1$H NMR (400 MHz, CDCl$_3$) δ 7.19-7.06 (m, 6H), 7.05-6.96 (m, 2H), 6.62 (d, J=8.4 Hz, 1H), 6.44 (dd, J=8.4, 2.3 Hz, 1H), 6.31 (s, 1H), 4.85 (d, J=4.0 Hz, 2H), 4.19 (q, J=7.0 Hz, 1H), 4.06 (d, J=11.8 Hz, 1H), 3.94 (dd, J=12.4, 4.7 Hz, 1H), 3.72 (s, 3H), 3.38 (dd, J=13.4, 7.7 Hz, 1H), 3.15 (dd, J=13.5, 7.5 Hz, 1H), 2.34 (s, 3H), 2.27 (s, 3H). $^{13}$C NMR (100 MHz, CDCl$_3$) δ 155.3, 155.2, 137.7, 135.9, 135.4, 132.5, 132.3, 129.7, 129.3, 129.1, 126.6, 125.8, 106.7, 105.3, 95.0, 62.7, 59.8, 56.0, 45.1, 33.4, 21.1, 21.0.

Other Synthesis Schemes

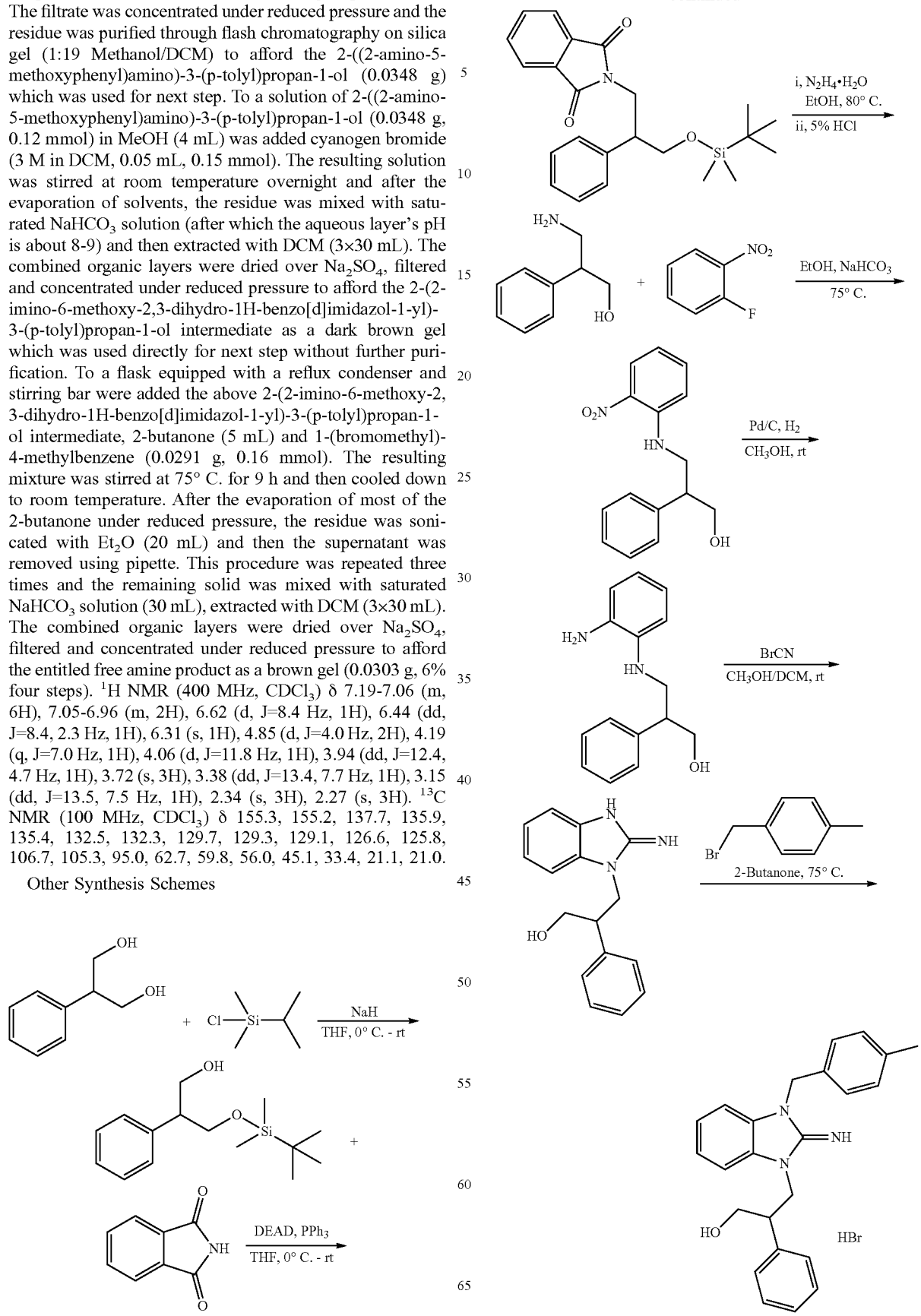

-continued

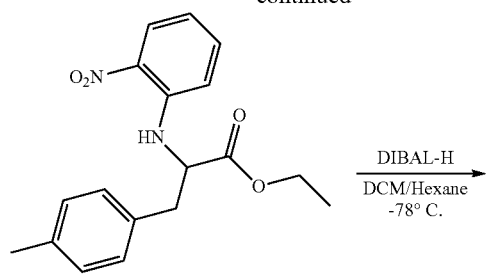

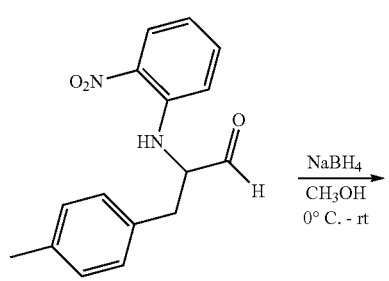

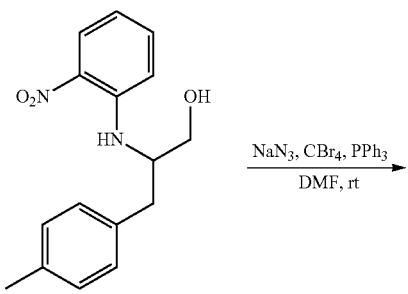

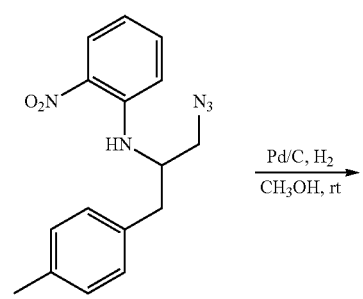

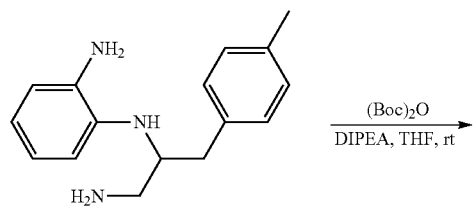

-continued

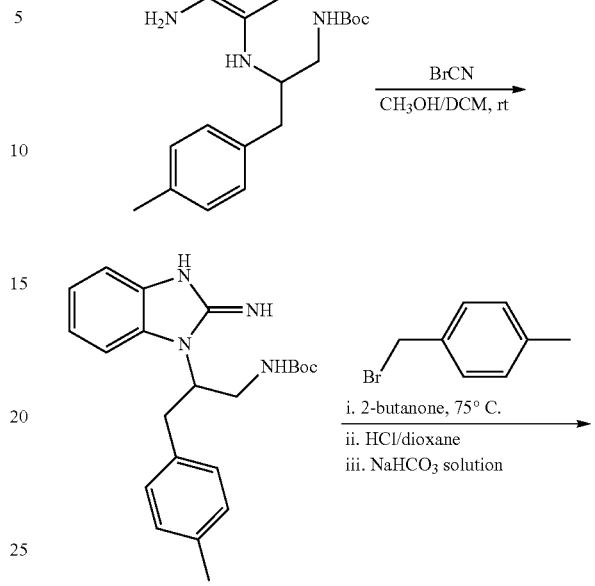

IP Accumulation Assay

HEK293 cells stably expressing OX2R are transfected with Gq alpha construct (6.4 ug per 10 cm dish) using Lipofectamine 3000 (ThermoFisher). 24 hours after transfection, cells are plated on poly-lysine-coated 96-well plates at 30,000 cells per well in Inositol-free DMEM+5% FCS with 5 uCi per ml Myo-[2-3H] Inositol (Perkin Elmer). Plates are incubated at 37° C. O/N in 8% C02 tissue culture incubator. Agonists are diluted serially in HBSS containing 10 mM Lithium Chloride. After removal of culture media, agonist solutions are added to the cells (100 ul/well) and incubated at 37° C. 45 min in 8% C02 incubator. Agonist solution is removed and cells are lysed on ice with 10 mM Formic Acid (40 ul/well) for 30 minutes. SPA Poly Lysine YSI beads (Perkin Elmer, cat #RPNQ0010) are added to the wells and mixed on a shaker for 30 minutes before reading on a Microbeta scintillation counter. Positive control curves run with all screens: orexin B and Yanagisawa (J. Med. Chem. 2015) agonist.

TABLE 1

SAR: Ranking (ignoring 100 uM data points for all assays due to toxicity)

| Structure | Title | ClogP | CLogD | TPSA (Å) | MW (g/mol) | H-BD | pKa (from imine) | CNS MPO | EC$_{50}$ | Page No. of EC$_{50}$ graphics | Microsomes stability T$_{1/2}$ (min) and Clint (ul/min/mg protein); PK; Compound Caco-2 cell permeability Papp value (Unit: 10e-6 cm/s); BBB (Brain AUC: Blood AUC) [From PK Data (5 or 10 mpk IV)] |
|---|---|---|---|---|---|---|---|---|---|---|---|
| 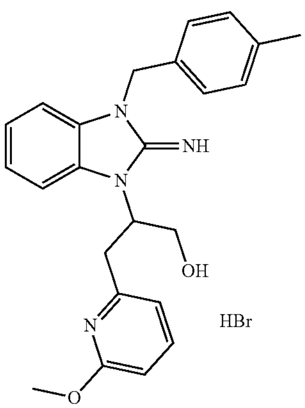 [SMILES: COc1cccc(CC(CO)n2c(=N)n(Cc3ccc(C)cc3)c3ccccc32)n1 ; Br] | ww3-309 | | | | 483.4 | | | | + | 1 | |
| 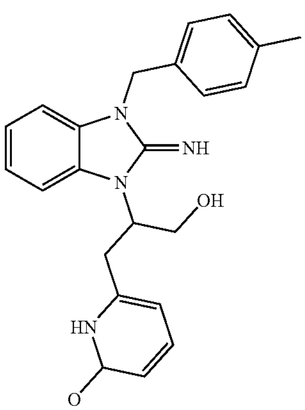 [SMILES: Cc1ccc(Cn2c(=N)n(C(CO)CC3=CC=CC(O)N3)c3ccccc32)cc1] | ww4-002 | 2.52521 | 0.86 | 79.66 | 388.5 | 3 | 9.18 | 4.4 | — | 1 | |

TABLE 1-continued
| | | | | | | | | | | |
|---|---|---|---|---|---|---|---|---|---|---|
| 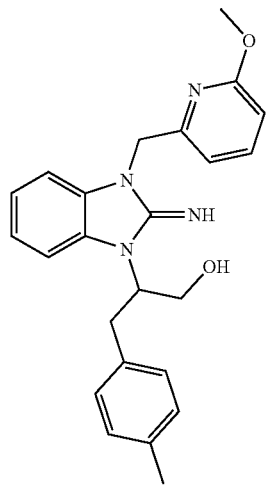 [SMILES: COc1cccc(Cn2c(=N)n(C(CO)Cc3ccc(C)cc3)c3ccccc32)n1] | ww4-23 | 4.56221 | 2.78 | 72.15 | 402.5 | 2 | 8.76 | 3.6 | — | 1 | |
| 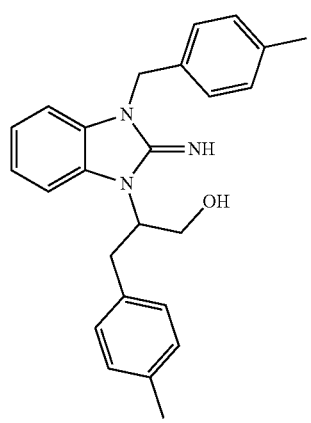 [SMILES: Cc1ccc(CC(CO)n2c(=N)n(Cc3ccc(C)cc3)c3ccccc32)cc1] | ww4-29 | 5.73821 | 3.61 | 50.56 | 385.51 | 2 | 9.22 | 2.9 | ++ | 1, 3, 5, 7, 19, 26, 42 | Papp A-->B: 2.36; Papp B-->A: 2.36; Eflux ratio: 1.0 |
| 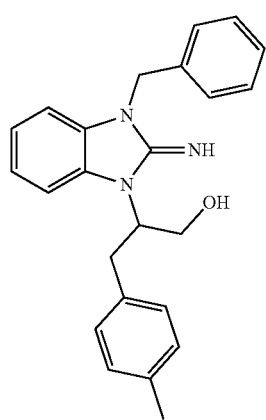 [SMILES: Cc1ccc(CC(CO)n2c(=N)n(Cc3ccccc3)c3ccccc32)cc1] | ww4-30 | 5.23921 | 3.07 | 50.56 | 371.48 | 2 | 9.25 | 3.3 | — | 1 | |

TABLE 1-continued

| Structure | ID | | | | | | | | | | Notes |
|---|---|---|---|---|---|---|---|---|---|---|---|
| 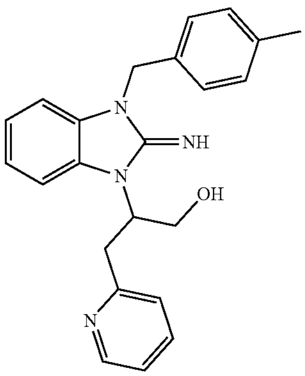 [SMILES: Cc1ccc(Cn2c(=N)n(C(CO)Cc3ccccn3)c3ccccc32)cc1] | ww4-67 | 3.74221 | 1.97 | 62.92 | 372.47 | 2 | 9.14 | 4.5 | — | 2 | |
| 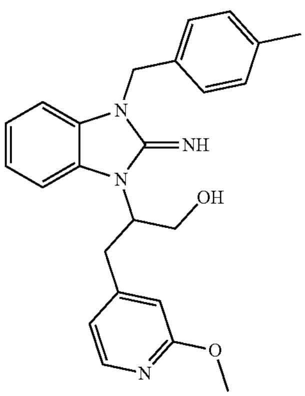 [SMILES: COc1cc(CC(CO)n2c(=N)n(Cc3ccc(C)cc3)c3ccccc32)ccn1] | ww4-86 | 4.56221 | 2.48 | 72.15 | 402.5 | 2 | 9.01 | 3.7 | — | 2 | |
| 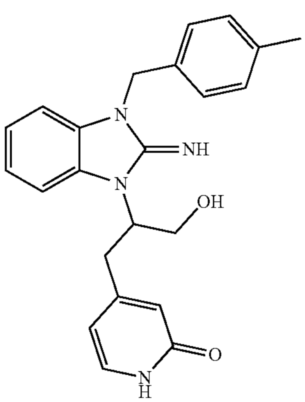 [SMILES: Cc1ccc(Cn2c(=N)n(C(CO)Cc3cc[nH]c(=O)c3)c3ccccc32)cc1] | ww4-89 | 2.5252 | 0.89 | 79.66 | 388.47 | 3 | 9.19 | 4.4 | — | 2 | solubility issue along with tautomerization, only proton NMR and LC-MS |
| 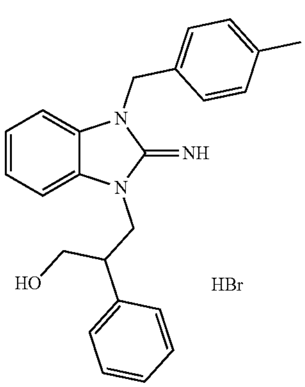 [SMILES: Cc1ccc(Cn2c(=N)n(CC(CO)c3ccccc3)c3ccccc32)cc1 ; Br] | ww4-103 | | | | 452.4 | | | | — | 2 | |

TABLE 1-continued
| | | | | | | | | | | |
|---|---|---|---|---|---|---|---|---|---|---|
| 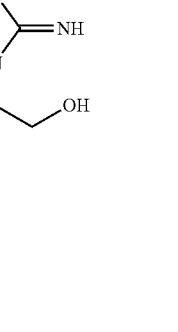 | ww4-105 (impure version of DM-68) | 4.5122 | 3.15 | 72.15 | 412.49 | 2 | 8.48 | 3.6 | + | 2 | 80% purity; DM-68 is the pure version of ww4-105 |
| 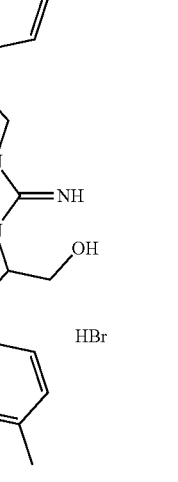 | ww4-106 | | | | 494.43 | | | | — | 2 | |
| 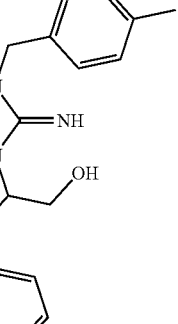 | ww4-143 | 5.23921 | 3.05 | 50.56 | 371.48 | 2 | 9.28 | 3.3 | ++ | 3 | named ww4-123 in test graphics and summary |

TABLE 1-continued

| Structure | ID | | | | | | | | |
|---|---|---|---|---|---|---|---|---|---|
| 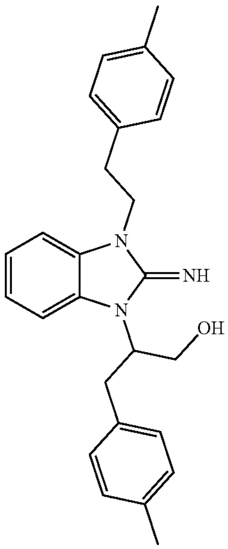 [SMILES: Cc1ccc(CCn2c(=N)n(C(CO)Cc3ccc(C)cc3)c3ccccc32)cc1] | ww4-163 | 6.11321 | 3.77 | 50.56 | 399.54 | 2 | 9.39 | 2.6 | — |
| 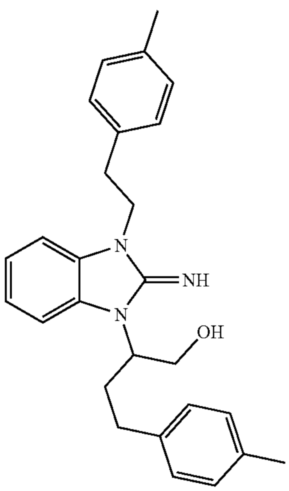 [SMILES: Cc1ccc(CCC(CO)n2c(=N)n(CCc3ccc(C)cc3)c3ccccc32)cc1] | ww4-169 | 6.49221 | 4.27 | 50.56 | 413.57 | 2 | 9.31 | 2.5 | — |
| 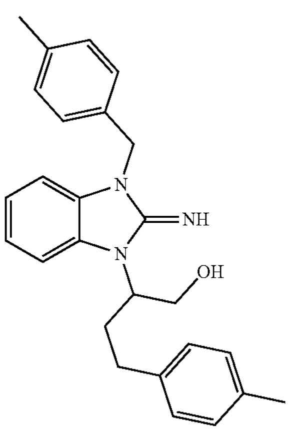 [SMILES: Cc1ccc(CCC(CO)n2c(=N)n(Cc3ccc(C)cc3)c3ccccc32)cc1] | ww4-170 | 6.11721 | 4.12 | 50.56 | 399.54 | 2 | 9.13 | 2.7 | — |

TABLE 1-continued
| | | | | | | | | | | |
|---|---|---|---|---|---|---|---|---|---|---|
| 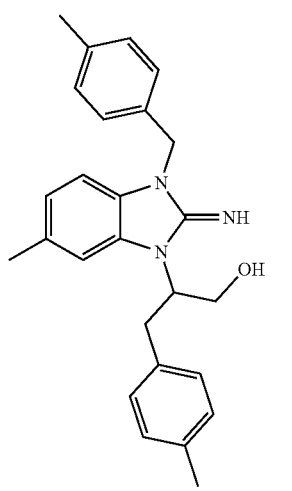 [SMILES: Cc1ccc(CC(CO)n2c(=N)n(Cc3ccc(C)cc3)c3ccc(C)cc32)cc1] | ww4-187 | 6.23721 | 4.1 | 50.56 | 399.54 | 2 | 9.25 | 2.6 | ++ | 5 |
|  | ww4-190 | 5.81521 | 1.4 | 56.35 | 384.53 | 3 | 9.1 | 3.4 | ++ | 5 |
| 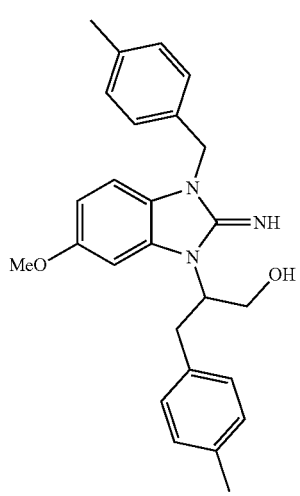 [SMILES: COc1ccc2c(c1)n(C(CO)Cc1ccc(C)cc1)c(=N)n2Cc1ccc(C)cc1] | ww4-198 | 5.65721 | 3.66 | 59.79 | 415.54 | 2 | 8.96 | 2.8 | NA | |

TABLE 1-continued
| | | | | | | | | | | |
|---|---|---|---|---|---|---|---|---|---|---|
| 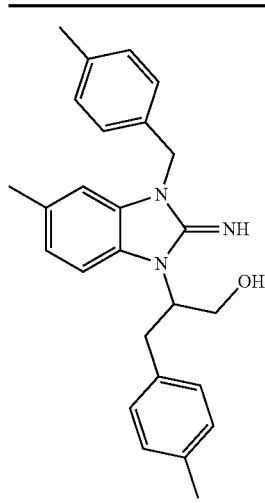 | ww4-204 | 6.23721 | 4.1 | 50.56 | 399.54 | 2 | 9.25 | 2.6 | NA | |
| 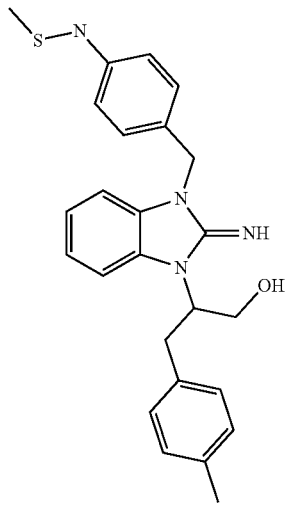 [SMILES: CSNc1ccc(Cn2c(=N)n(C(CO)Cc3ccc(C)cc3)c3ccccc32)cc1] | ww4-213 | 5.96821 | 4.41 | 50.56 | 449.63 | 2 | 8.83 | 2.4 | | |
|  | ww4-230 (impure version of ww4-234) | 6.04721 | 3.99 | 50.56 | 399.54 | 2 | 9.26 | 2.6 | + | 19 | Not pure; ww4-234 is the pure version |

TABLE 1-continued
| | | | | | | | | | | | |
|---|---|---|---|---|---|---|---|---|---|---|---|
| 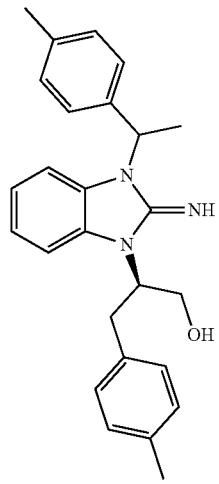 [SMILES: Cc1ccc(C[C@H](CO)n2c(=N)n(C(C)c3ccc(C)cc3)c3ccccc32)cc1] | ww4-234 (pure version of ww4-230) | 6.04721 | 3.99 | 50.56 | 399.54 | 2 | 9.26 | 2.6 | + | 19 | mixture of two diastereomer; R configuration at the lower chiral center |
| 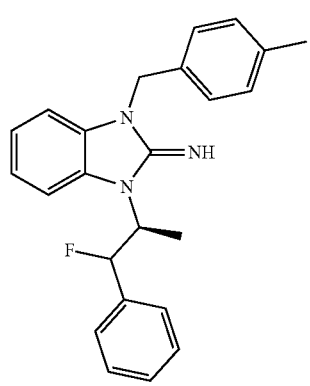 [SMILES: Cc1ccc(Cn2c(=N)n([C@@H](C)C(F)c3ccccc3)c3ccccc32)cc1] | ww4-273 | 6.419 | 4.2 | 30.33 | 373.48 | 1 | 9.11 | 2.7 | — | 6 | |
| 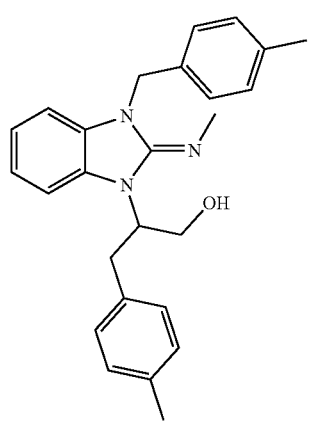 [SMILES: C/N=c1\n(Cc2ccc(C)cc2)c2ccccc2n1C(CO)Cc1ccc(C)cc1] | ww4-276 | 6.61421 | 4.29 | 39.07 | 399.54 | 1 | 8.67 | 3.2 | ++ | 6 | Papp A-->B: 2.19; Papp B-->A: 5.47; Eflux ratio: 2.50 |

TABLE 1-continued

| Structure | ID | | | | | | | | Refs |
|---|---|---|---|---|---|---|---|---|---|
| (benzimidazol-2-imine with N-(4-methylbenzyl) and N-CH(CH₃)CH₂-(4-methylphenyl) with NHAc) | ww4-281 | 5.67031 | 3.21 | 59.43 | 426.56 | 2 | 9.37 | 2.7 | ++ | 6, 7, 9, 10, 11, 12, 13, 15, 16, 18 |
| (benzimidazol-2-imine with N-(4-methylbenzyl) and N-CH₂CHF-CH₂-(4-methylphenyl)) | ww4-290 | 6.638 | 4.71 | 30.33 | 387.5 | 1 | 8.96 | 2.7 | + | 6 |
| (benzimidazol-2-imine with N-(4-methylbenzyl) and N-CH(CH(F)Ph)CH₂OH) | ww4-301 | 5.46221 | 3.4 | 50.56 | 389.47 | 2 | 8.82 | 3.2 | + | 7 |
| (benzimidazol-2-imine with N-(4-methylbenzyl) and N-CH(CH₂CH₃)CH₂-(4-methylcyclohexadienyl)) | ww5-17 | 6.568 | 4.6 | 30.33 | 387.5 | 1 | 9.09 | 2.6 | | |

TABLE 1-continued
| | | | | | | | | | | |
|---|---|---|---|---|---|---|---|---|---|---|
| 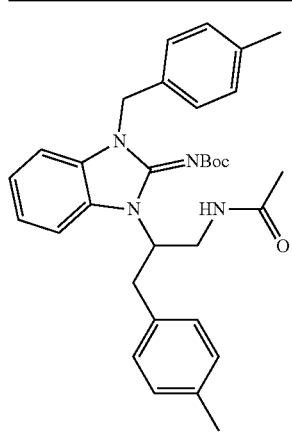 | ww5-29 | 7.78331 | 6.26 | 74.24 | 526.68 | 1 | 6.29 | 2.8 | + | 9 | aka ww5-81 |
| 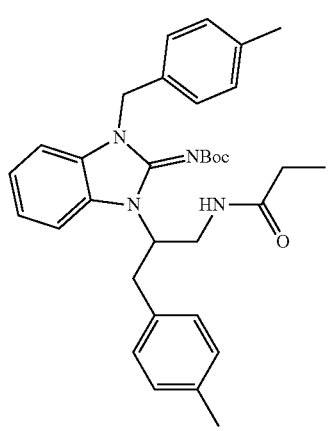 | ww5-34 | 8.31231 | 6.96 | 74.24 | 540.71 | 1 | 6.27 | 2.8 | + | 9 | |
| 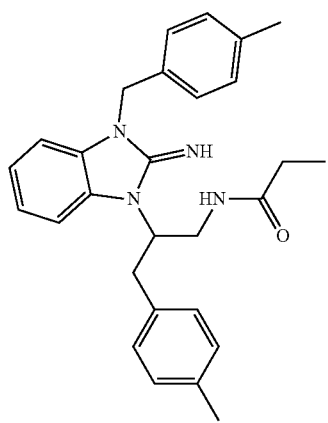 [SMILES: CCC(=O)NCC(Cc1ccc(C)cc1)n1c(=N)n(Cc2ccc(C)cc2)c2ccccc21] | ww5-40 | 6.19931 | 3.93 | 59.43 | 440.59 | 2 | 9.34 | 2.3 | ++ | 9, 10 | |

TABLE 1-continued
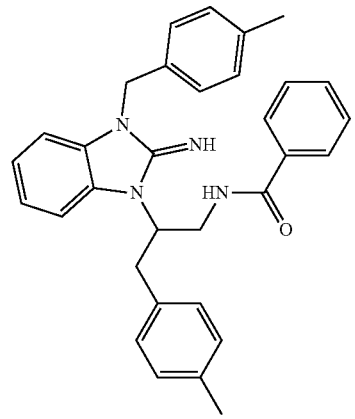 [SMILES: Cc1ccc(CC(CNC(=O)c2ccccc2)n2c(=N)n(Cc3ccc(C)cc3)c3ccccc32)cc1]
ww5-43   7.40231   5.2   59.43   488.64   2   9.18   2   +   10
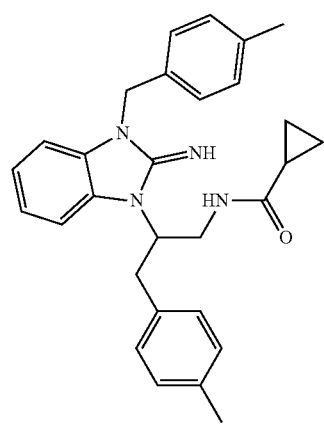 [SMILES: Cc1ccc(CC(CNC(=O)C2CC2)n2c(=N)n(Cc3ccc(C)cc3)c3ccccc32)cc1]
ww5-45   6.25431   4.03   59.43   452.6   2   9.31   2.2   ++   10
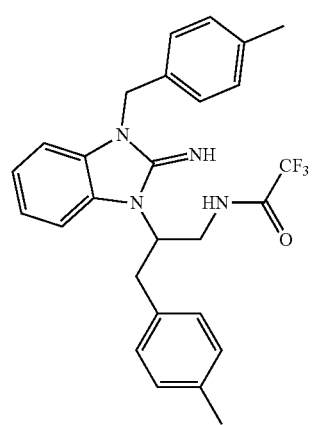 [SMILES: Cc1ccc(CC(CNC(=O)C(F)(F)F)n2c(=N)n(Cc3ccc(C)cc3)c3ccccc32)cc1]
ww5-52   6.77931   5.82   59.43   480.54   2   9.06   2.1   ++   11

TABLE 1-continued

| | | | | | | | | | |
|---|---|---|---|---|---|---|---|---|---|
| ww5-60 | 7.39231 | 5.22 | 59.43 | 502.66 | 2 | 9.13 | 1.9 | ++ | 12, 14 |
| ww5-66 | 5.57651 | 3.15 | 59.43 | 412.54 | 2 | 9.37 | 2.9 | ++ | 13 |
| ww5-74 | 7.31131 | 5.08 | 68.66 | 532.69 | 2 | 9.12 | 1.9 | + | 14 |
| ww5-79 | 6.40797 | 4.45 | 47.94 | 424.55 | 1 | 8.17 (amide) | 3.3 | ++ | 13 |

TABLE 1-continued

| Structure | Compound | | | | | | | | | Notes |
|---|---|---|---|---|---|---|---|---|---|---|
| (benzimidazole imine with N-benzyl p-tolyl, and CH2-N(CH3)2, CH2-p-tolyl substituents) | ww5-80 | 6.68811 | 3.13 | 33.57 | 412.58 | 1 | 9.58 | 2.8 | ++ | 13 |
| (benzimidazole imine with N-benzyl p-tolyl, and crotonamide, CH2-p-tolyl substituents) | ww5-90 | 6.59081 | 4.4 | 59.43 | 452.6 | 2 | 9.3 | 2.2 | + | 15 |
| (benzimidazole imine with N-benzyl p-tolyl, and acetamide (R), CH2-p-tolyl substituents) | ww5-73 | 5.67031 | 3.21 | 59.43 | 426.56 | 2 | 9.37 | 2.7 | + | 16 | R-enantiomer of ww4-281 |
| (benzimidazole imine with N-benzyl p-tolyl, and acetamide (S), CH2-p-tolyl substituents) | ww5-98 | 5.67031 | 3.21 | 59.43 | 426.56 | 2 | 9.37 | 2.7 | ++ | 16, 18 | Papp A-->B: 0.45; Papp B-->A: 9.05; Efflux ratio: 20.00; S-enantiomer of ww4-281 |

TABLE 1-continued

| Structure | Compound | | | | | | | | | |
|---|---|---|---|---|---|---|---|---|---|---|
| 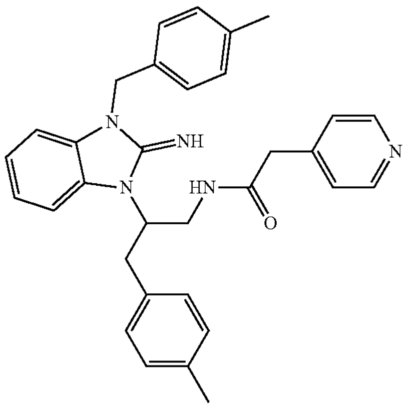 [SMILES: Cc1ccc(CC(CNC(=O)Cc2ccncc2)n2c(=N)n(Cc3ccc(C)cc3)c3ccccc32)cc1] | ww5-100 | 5.89531 | 4.04 | 71.79 | 503.65 | 2 | 9.09 | 2 | + | 14, 23 |
| 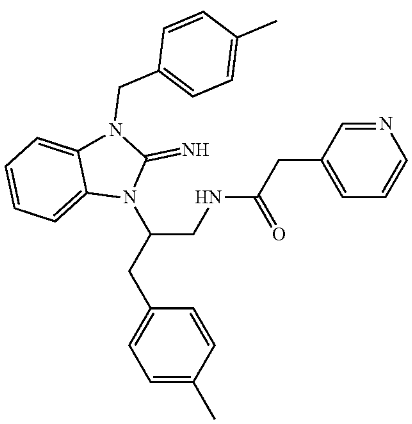 [SMILES: Cc1ccc(CC(CNC(=O)Cc2cccnc2)n2c(=N)n(Cc3ccc(C)cc3)c3ccccc32)cc1] | ww5-111 | 5.89531 | 4.04 | 71.79 | 503.65 | 2 | 9.09 | 2 | ++ | 17, 23 |
| 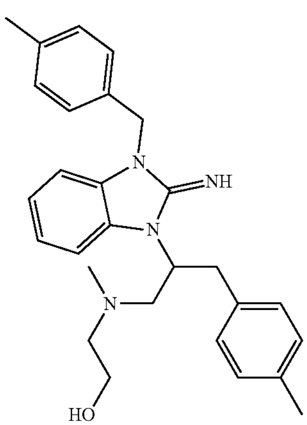 | ww5-123 | 6.27271 | 2.67 | 53.8 | 442.61 | 2 | 9.48 | 2.8 | — | 18 |

TABLE 1-continued
| | | | | | | | | | | |
|---|---|---|---|---|---|---|---|---|---|---|
| 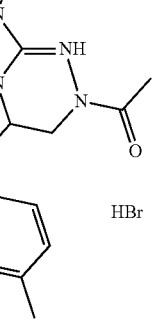 | ww5-126 | | | | 521.5 | | | ++ | 18 | Papp A-->B: 2.27; Papp B-->A: 13.63; Efflux ratio: 6.00 |
|  | ww5-150 | 6.04721 | 3.99 | 50.56 | 399.54 | 2 | 9.26 | 2.6 | +++ | 19 | mixture of two diastereo-mer; S config-uration at the lower chiral center |
| 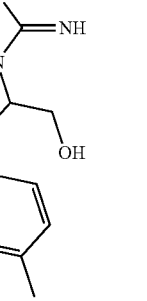 | ww5-163 | 5.81931 | 2.82 | 79.66 | 456.59 | 3 | 9.35 | 2.4 | ++++ | 20, 22, 24, 41 | mixture of two diastereo-mer; S config-uration at the lower chirla center |

TABLE 1-continued

| Structure | Name | | | | | | | | | Notes |
|---|---|---|---|---|---|---|---|---|---|---|
| (structure) | ww5-166 | 5.81931 | 2.82 | 79.66 | 456.59 | 3 | 9.35 | 2.4 | +++ | 20, 22 | diastereomer A |
| (structure) | ww5-167 (impure version of ww5-189) | 5.81931 | 2.82 | 79.66 | 456.59 | 3 | 9.35 | 2.4 | ++++ | 20, 21 | 85% diastereomer B mixed with about 15% diastereomer A |
| (structure) | ww5-189 (pure version of ww5-167) | 5.81931 | 2.82 | 79.66 | 456.59 | 3 | 9.35 | 2.4 | ++++ | 22, 24, 25, 26, 27, 29, 30, 31, 33, 34, 35, 42 | Plasma PK (5mg/kg IV, Female CD-1 Mice), Estimate Plasma: HL_Lambda_z 230.35342 min, Tmax 10 min, Cmax 600.33333 ng/mL, AUClast 41473.919 min*ng/ml, Vz_F_obs 904.08626 mL, Cl_F_obs 2.7204495 mL/min; Brain PK (5mg/kg IV, Female CD-1 Mice), Estimate Brain: HL_Lambda_z 728.55418 min, Tmax 30 min, Cmax 15.293333 ng/mL, |

TABLE 1-continued
AUClast 11291.545 min*ng/ml; Papp A-->B: 0.25; Papp B-->A: 6.37; Eflux ratio: 25.00; 0.3:1; diastereomer B (injected into mice by Noelle; ww5-167 is the mixture of 85% diastereomer B and 15% diastereomer A)
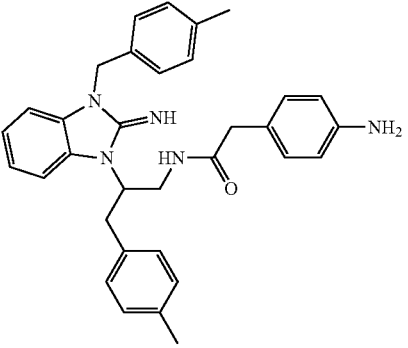 [SMILES: Cc1ccc(CC(CNC(=O)Cc2ccc(N)cc2)n2c(=N)n(Cc3ccc(C)cc3)c3ccccc32)cc1]
ww5-171   6.16531   4.39   85.45   517.68   4   9.14   1.4   ++   21
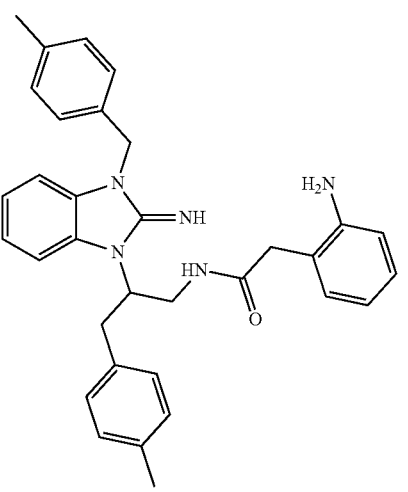 [SMILES: Cc1ccc(CC(CNC(=O)Cc2ccccc2N)n2c(=N)n(Cc3ccc(C)cc3)c3ccccc32)cc1]
ww5-177   6.11531   4.44   85.45   517.68   4   9.08   1.5   ++   22

TABLE 1-continued
| Structure | Compound | | | | | | | | | Notes |
|---|---|---|---|---|---|---|---|---|---|---|
| 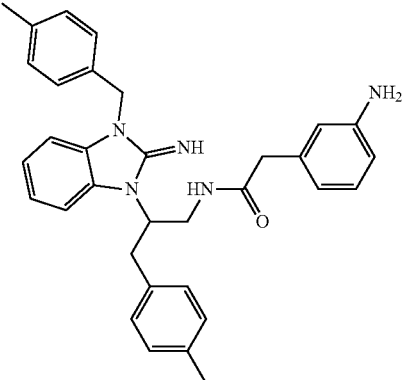 [SMILES: Cc1ccc(CC(CNC(=O)Cc2cccc(N)c2)n2c(=N)n(Cc3ccc(C)cc3)c3ccccc32)cc1] | ww5-179 | 6.16531 | 4.43 | 85.45 | 517.68 | 4 | 9.09 | 1.5 | ++ | 22 |
| 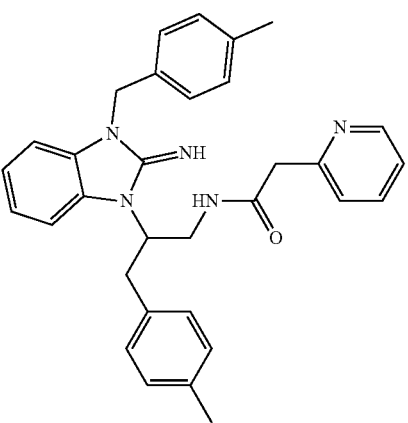 [SMILES: Cc1ccc(CC(CNC(=O)Cc2ccccn2)n2c(=N)n(Cc3ccc(C)cc3)c3ccccc32)cc1] | ww5-188 | 5.89531 | 4.43 | 71.79 | 503.65 | 2 | 9.09 | 2 | ++ | 23, 25 | Papp A-->B: 1.28; Papp B-->A: 8.51; Eflux ratio: 6.67 |
| 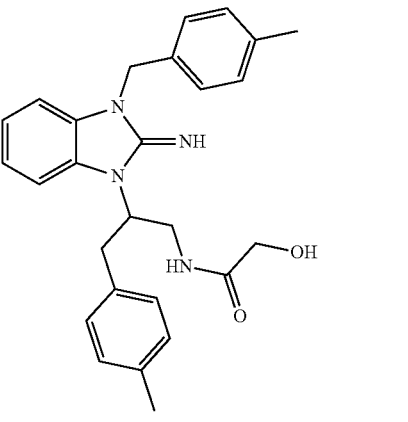 [SMILES: Cc1ccc(CC(CNC(=O)CO)n2c(=N)n(Cc3ccc(C)cc3)c3ccccc32)cc1] | ww5-190 (aka KM-4-214-1) | 5.5103 | 2.43 | 79.66 | 442.56 | 3 | 9.31 | 2.7 | +++ | aka KM-4-214-1 |
| | ww5-194 | 5.14331 | 1.56 | 85.45 | 441.58 | 4 | 9.36 | 2.7 | ++ | 23 |

TABLE 1-continued
| | | | | | | | | | | |
|---|---|---|---|---|---|---|---|---|---|---|
| 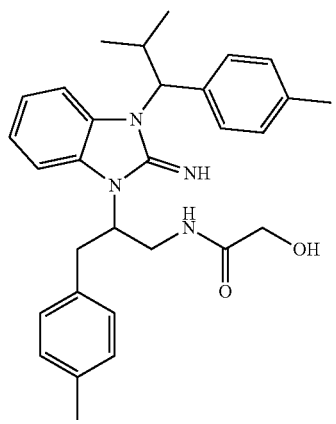 [SMILES: Cc1ccc(CC(CNC(=O)CO)n2c(=N)n(C(c3ccc(C)cc3)C(C)C)c3ccccc32)cc1] | ww5-205 | 6.74731 | 3.62 | 79.66 | 484.64 | 3 | 9.47 | 1.7 | ++ | 24 |
| 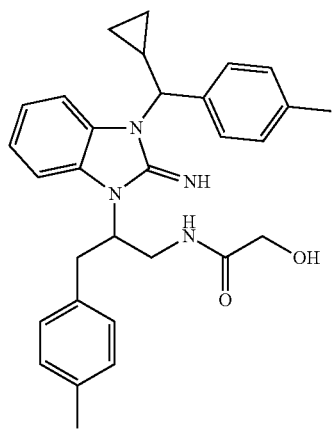 [SMILES: Cc1ccc(CC(CNC(=O)CO)n2c(=N)n(C(c3ccc(C)cc3)C3CC3)c3ccccc32)cc1] | ww5-209 | 6.26331 | 3.18 | 79.66 | 482.63 | 3 | 9.44 | 2 | ++++ | 24, 25, 41 | Papp A-->B: 0.37; Papp B-->A: 7.46; Efflux ratio: 20.00; mixture of two diastereomers |
| 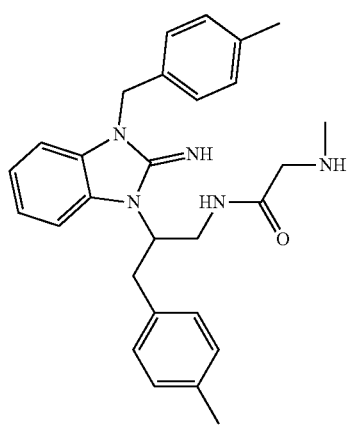 [SMILES: CNCC(=O)NCC(Cc1ccc(C)cc1)n1c(=N)n(Cc2ccc(C)cc2)c2ccccc21] | ww5-210 | 5.48451 | 1.43 | 71.46 | 455.61 | 3 | 9.41 | 2.8 | ++ | 24 |

TABLE 1-continued
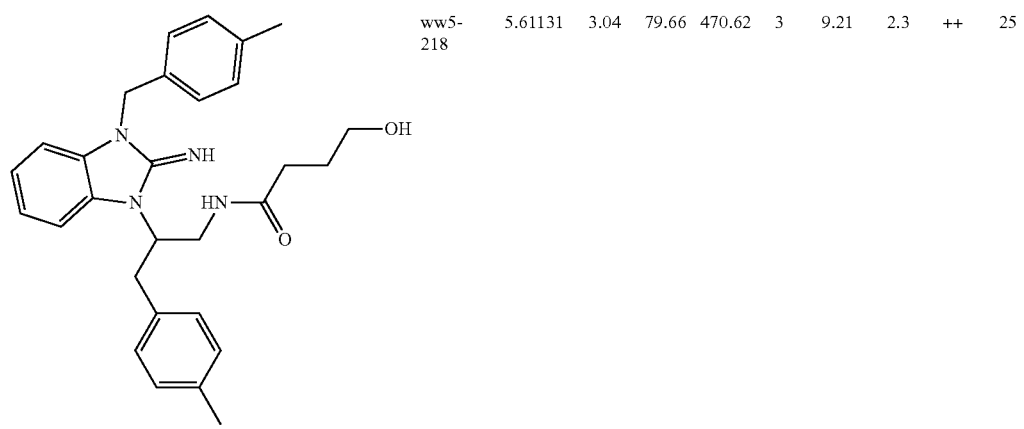
ww5-218  5.61131  3.04  79.66  470.62  3  9.21  2.3  ++  25
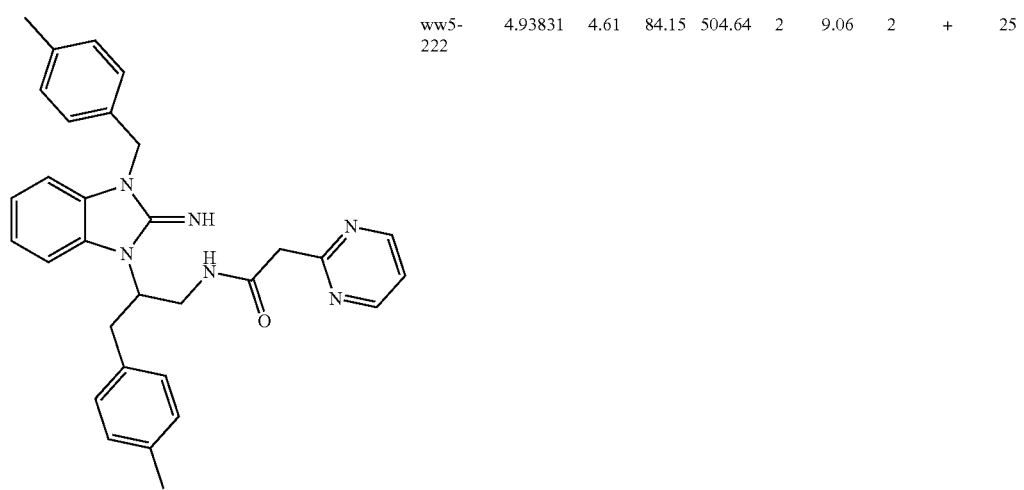
ww5-222  4.93831  4.61  84.15  504.64  2  9.06  2  +  25
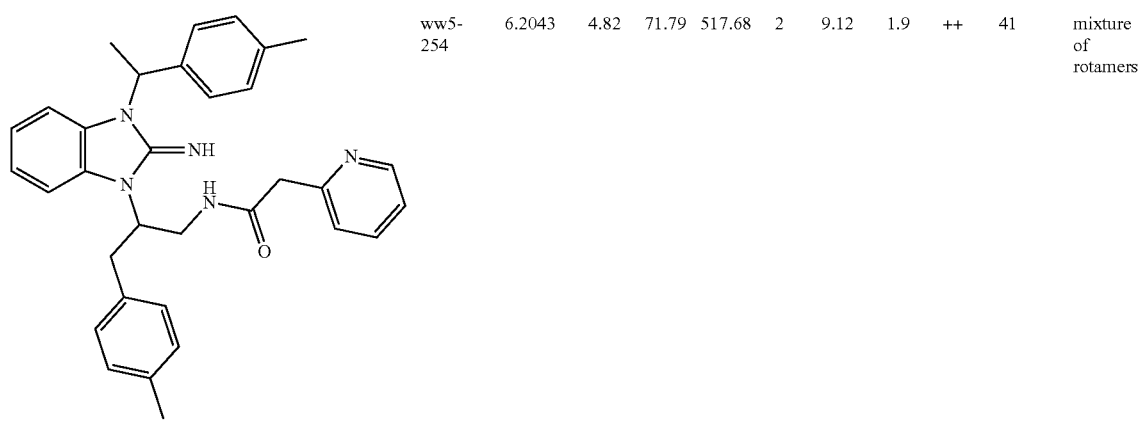
ww5-254  6.2043  4.82  71.79  517.68  2  9.12  1.9  ++  41  mixture of rotamers TABLE 1-continued
| | | | | | | | | | | |
|---|---|---|---|---|---|---|---|---|---|---|
| 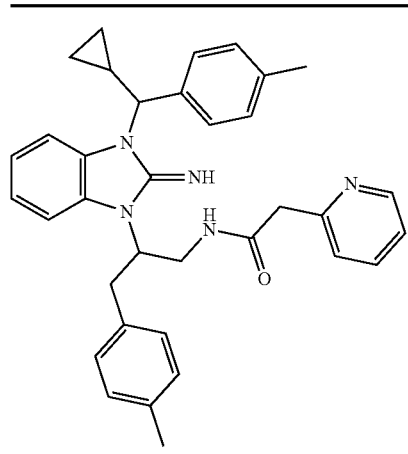 | ww5-255 | 6.6483 | 5.17 | 71.79 | 543.72 | 2 | 9.21 | 1.9 | ++ | 41 | mixture of rotamers |
| 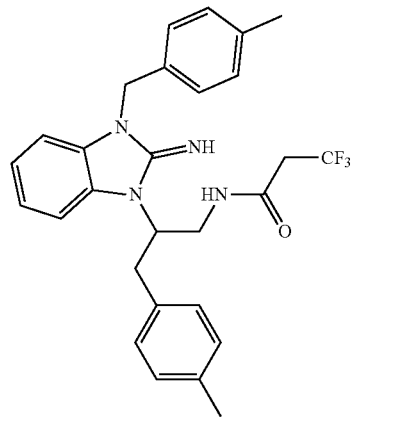 [SMILES: Cc1ccc(CC(CNC(=O)CC(F)(F)F)n2c(=N)n(Cc3ccc(C)cc3)c3ccccc32)cc1] | ww5-307 | 6.46331 | 4.51 | 59.43 | 494.56 | 2 | 9.06 | 2 | ++ | 26 | |
| | ww5-308 | 5.84331 | 3.34 | 59.43 | 444.55 | 2 | 9.28 | 2.6 | ++ | 26, 28 | Papp A-->B: 3.05; Papp B-->A: 8.72; Eflux ratio: 2.86 |

TABLE 1-continued
| | | | | | | | | | |
|---|---|---|---|---|---|---|---|---|---|
| 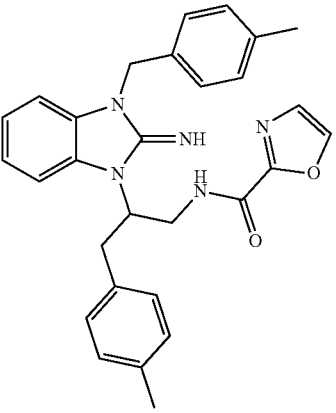 [SMILES: Cc1ccc(CC(CNC(=O)c2ncco2)n2c(=N)n(Cc3ccc(C)cc3)c3ccccc32)cc1] | ww6-002 | 6.17531 | 3.59 | 81.02 | 479.58 | 2 | 9.1 | 2.3 | ++ | 27 |
| 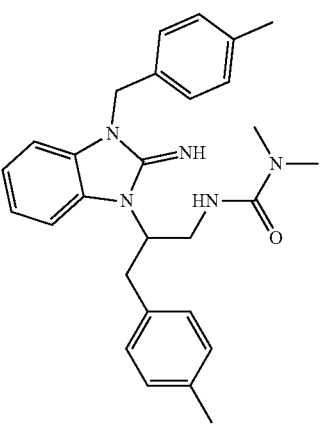 [SMILES: Cc1ccc(CC(CNC(=O)N(C)C)n2c(=N)n(Cc3ccc(C)cc3)c3ccccc32)cc1] | ww6-004 | 5.95701 | 3.37 | 62.67 | 455.61 | 2 | 9.3 | 2.5 | ++ | 27 |
| 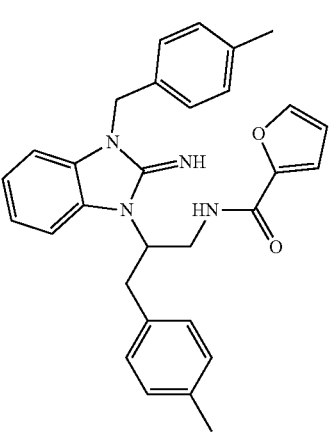 | ww6-10 | 6.57831 | 4.3 | 68.66 | 478.6 | 2 | 9.13 | 2.1 | ++ | 28 |

TABLE 1-continued
| | | | | | | | | | |
|---|---|---|---|---|---|---|---|---|---|
| 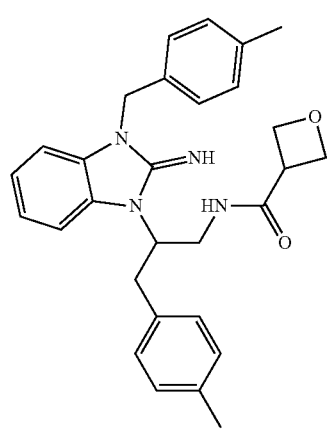 [SMILES: Cc1ccc(CC(CNC(=O)C2COC2)n2c(=N)n(Cc3ccc(C)cc3)c3ccccc32)cc1] | ww6-13 | 6.23591 | 3.14 | 68.66 | 468.6 | 2 | 9.25 | 2.5 | ++ | 29 |
| 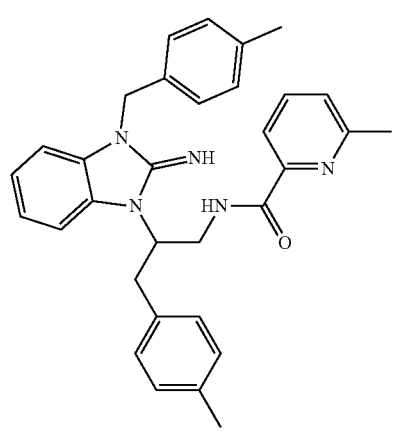 [SMILES: Cc1ccc(CC(CNC(=O)c2cccc(C)n2)n2c(=N)n(Cc3ccc(C)cc3)c3ccccc32)cc1] | ww6-15 | 7.49831 | 4.58 | 71.79 | 503.65 | 2 | 9.08 | 2 | + | 29 |
| 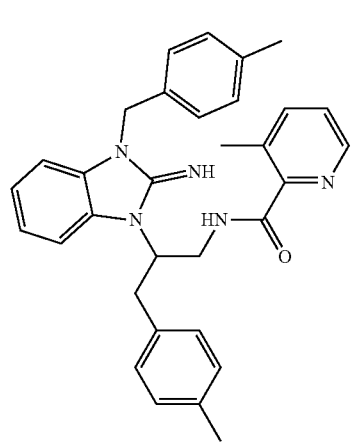 [SMILES: Cc1ccc(CC(CNC(=O)c2ncccc2C)n2c(=N)n(Cc3ccc(C)cc3)c3ccccc32)cc1] | ww6-16 | 7.15831 | 4.95 | 71.79 | 503.65 | 2 | 9.1 | 2 | + | 29 |

TABLE 1-continued

| Structure | ID | | | | | | | | |
|---|---|---|---|---|---|---|---|---|---|
| (structure) | ww6-23 | 5.82004 | 3.46 | 84.15 | 490.61 | 2 | 9.1 | 2.3 | ++ | 30 |
| (structure) | ww6-33 | 5.10504 | 3.18 | 79.66 | 442.56 | 3 | 8.6 | 2.7 | ++ | 31 |
| (structure) | ww6-34 | 6.18811 | 3.55 | 81.02 | 479.58 | 2 | 9.1 | 2.3 | ++ | 31 |

TABLE 1-continued
| | | | | | | | | | |
|---|---|---|---|---|---|---|---|---|---|
| 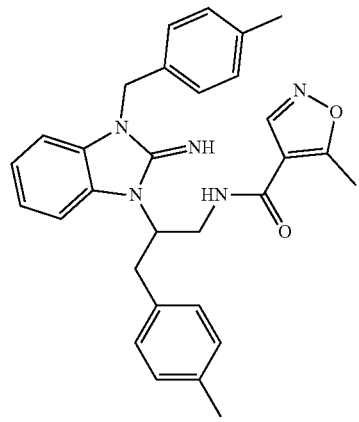 [SMILES: Cc1ccc(CC(CNC(=O)c2cnoc2C)n2c(=N)n(Cc3ccc(C)cc3)c3ccccc32)cc1] | ww6-35 | 6.11711 | 3.86 | 81.02 | 493.61 | 2 | 9.07 | 2.1 | ++ | 31 |
| 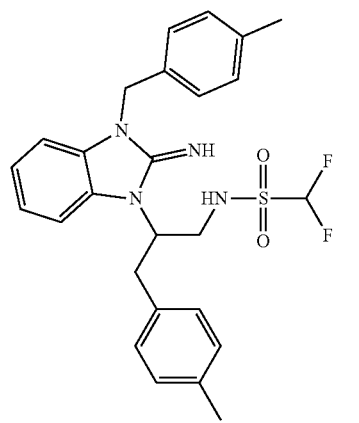 [SMILES: Cc1ccc(CC(CNS(=O)(=O)C(F)F)n2c(=N)n(Cc3ccc(C)cc3)c3ccccc32)cc1] | ww6-36 | 6.77801 | 5.4 | 76.5 | 498.59 | 2 | 9.02 | 2 | ++ | 31 |
| 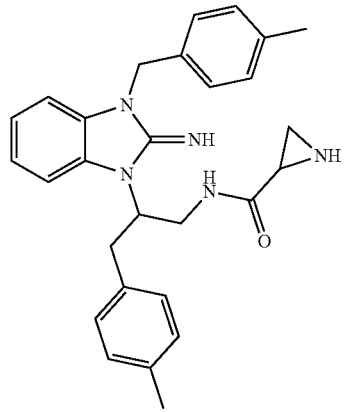 [SMILES: Cc1ccc(CC(CNC(=O)C2CN2)n2c(=N)n(Cc3ccc(C)cc3)c3ccccc32)cc1] | ww6-39 | 6.06931 | 2.79 | 81.37 | 453.59 | 3 | 9.31 | 2.4 | ++++ | 32 |

TABLE 1-continued

| Structure | Compound | | | | | | | | | Notes |
|---|---|---|---|---|---|---|---|---|---|---|
| (structure of ww6-40) | ww6-40 | 6.26208 | 3.41 | 75.03 | 506.65 | 2 | 9.12 | 2.2 | + | 32 |
| (structure of ww6-56, mixture of diastereomers) | ww6-56 | 7.24861 | 4.98 | 39.56 | 439.6 | 1 | 9.37 | 2.6 | ++++ | 33, 34, 38, 40 | mixture of two diastereomers |
| (structure of ww6-61, diastereomer A) | ww6-61 | 7.24861 | 4.98 | 39.56 | 439.6 | 1 | 9.37 | 2.6 | ++++ | 34, 36, 37, 39 | T1/2 (min) = 19 and Clint (ul/min/mg protein) = 17.01; Plasma PK (5 mpk IV, female CD1), Estimate Plasma: HL_Lambda_z 74.038003 min, Tmax 10 min, Cmax 841 ng/mL, AUClast 59182.833 min*ng/ml, Vz_F_obs 205.30839 mL, Cl_F_obs 1.9221065 mL/min; Brain PK (5 mpk IV, female CD1 mice) Estimate Brain: HL_ |

TABLE 1-continued
| | | | | | | | | | | |
|---|---|---|---|---|---|---|---|---|---|---|
| | | | | | | | | | | Lambda_z 134.09403 min, Tmax 30 min, Cmax 143.31 ng/mL, AUClast 38968.815 min*ng/ml; Papp A-->B: 0.66; Papp B-->A: 1.97; Eflux ratio: 3.00; 0.65:1; diastereomer A (x-ray crystallography for absolute configuration) |
| 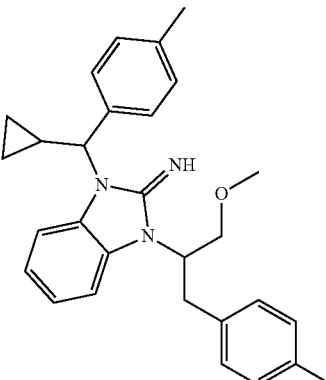 diastereomer B | ww6-60 | 7.24861 | 4.98 | 39.56 | 439.6 | 1 | 9.37 | 2.6 | +++ | 34 | diastereomer B |
| 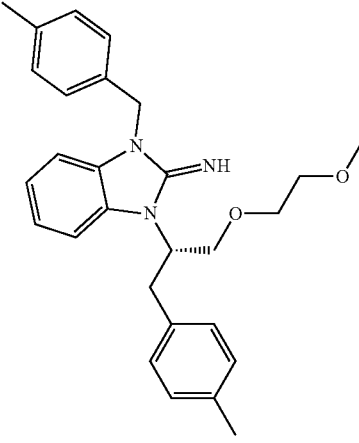 | ww6-67 | 6.32001 | 4.28 | 48.79 | 443.59 | 1 | 9.13 | 2.7 | ++ | 35 | Papp A-->B: 2.93; Papp B-->A: 4.88; Eflux ratio: 1.67; aka A RN-422 |

TABLE 1-continued
| | | | | | | | | | | |
|---|---|---|---|---|---|---|---|---|---|---|
| 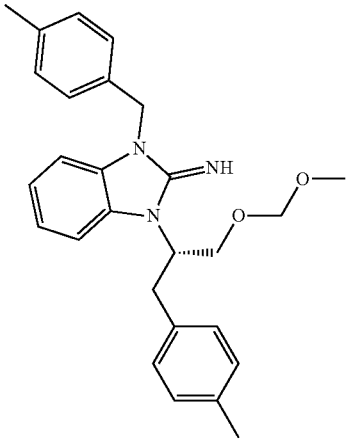 | ww6-71 | 6.24941 | 4.35 | 48.79 | 429.56 | 1 | 9.17 | 2.8 | ++ | 36 | Papp A-->B: 3.10; Papp B-->A: 3.10; Eflux ratio: 1.0 |
| 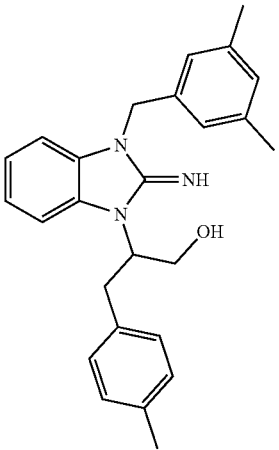 [SMILES: Cc1ccc(CC(CO)n2c(=N)n(Cc3cc(C)cc(C)c3)c3ccccc32)cc1] | DM-006 | 6.2372 | 4.1 | 50.56 | 399.54 | 2 | 9.25 | 2.6 | — | 2 | In summary, named DM-005 |
| 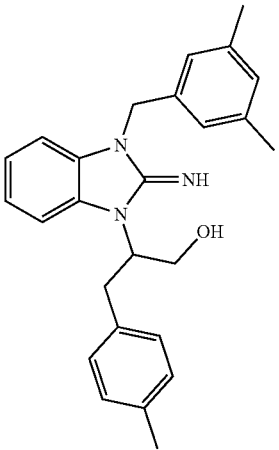 [SMILES: Cc1ccc(CC(CO)n2c(=N)n(Cc3cc(C)cc(C)c3)c3ccccc32)cc1] | DM-13 | 4.5622 | 2.51 | 72.15 | 402.5 | 2 | 8.98 | 3.7 | — | | |

TABLE 1-continued

| Structure | ID | | | | | | | | |
|---|---|---|---|---|---|---|---|---|---|
| 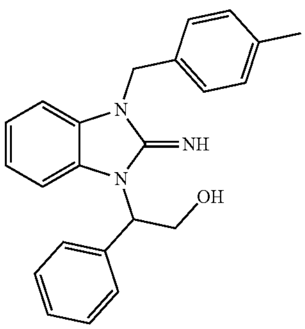 [SMILES: Cc1ccc(Cn2c(=N)n(C(CO)c3ccccc3)c3ccccc32)cc1] | DM-14 | 4.8642 | 2.9 | 50.56 | 357.46 | 2 | 9.1 | 3.6 | — |
| 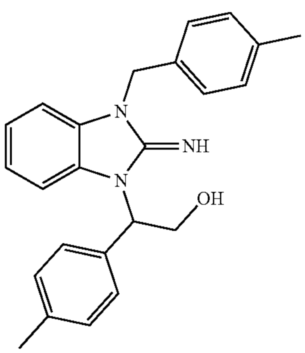 [SMILES: Cc1ccc(Cn2c(=N)n(C(CO)c3ccc(C)cc3)c3ccccc32)cc1] | DM-18 | 5.3632 | 3.45 | 50.56 | 371.48 | 2 | 9.06 | 3.2 | — |
| 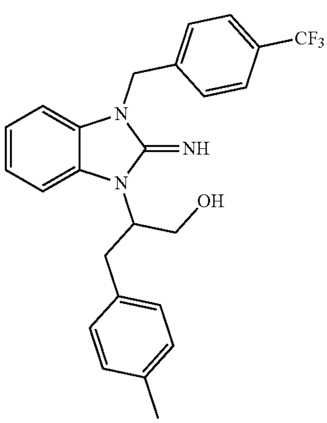 [SMILES: Cc1ccc(CC(CO)n2c(=N)n(Cc3ccc(C(F)(F)F)cc3)c3ccccc32)cc1] | DM-19 | 6.1222 | 4.29 | 50.56 | 439.48 | 2 | 8.83 | 2.5 | — |
| 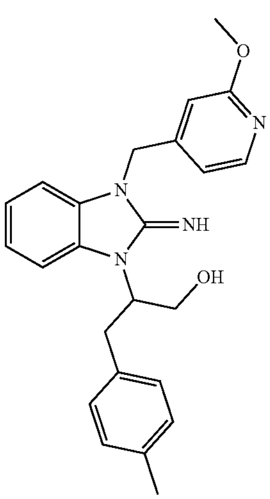 [SMILES: COc1cc(Cn2c(=N)n(C(CO)Cc3ccc(C)cc3)c3ccccc32)ccn1] | DM-20 | 4.5622 | 2.51 | 72.15 | 402.5 | 2 | 8.98 | 3.7 | — |

TABLE 1-continued
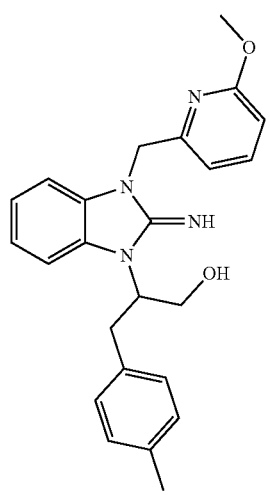 [SMILES: COc1cccc(Cn2c(=N)n(C(CO)Cc3ccc(C)cc3)c3ccccc32)n1]
DM-21  4.5622  2.78  72.15  402.5  2  8.76  3.6
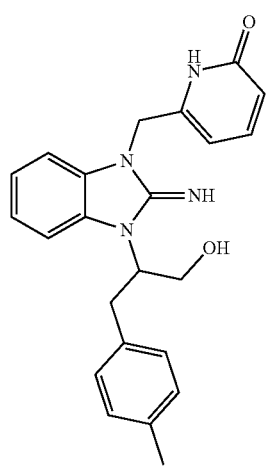 [SMILES: Cc1ccc(CC(CO)n2c(=N)n(Cc3cccc(=O)[nH]3)c3ccccc32)cc1]
DM-23  2.5252  1.18  79.66  388.47  3  9.07  4.4  —  3
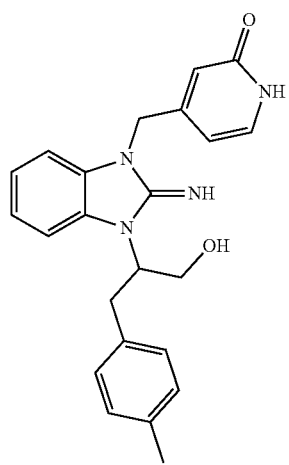 [SMILES: Cc1ccc(CC(CO)n2c(=N)n(Cc3cc[nH]c(=O)c3)c3ccccc32)cc1]
DM-24  2.5252  0.88  79.66  388.47  3  9.2  4.4  —  3

TABLE 1-continued

| Structure | ID | | | | | | | | | |
|---|---|---|---|---|---|---|---|---|---|---|
| 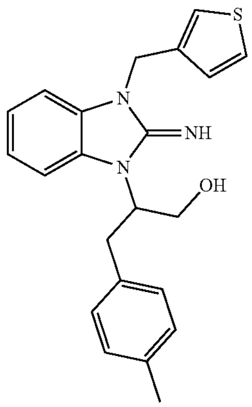 [SMILES: Cc1ccc(CC(CO)n2c(=N)n(Cc3ccsc3)c3ccccc32)cc1] | DM-27 | 4.8852 | 2.98 | 50.56 | 377.51 | 2 | 9.09 | 3.4 | + | 3 |
| 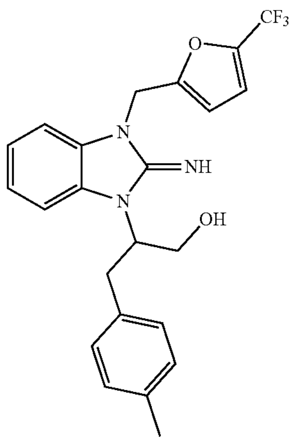 [SMILES: Cc1ccc(CC(CO)n2c(=N)n(Cc3ccc(C(F)(F)F)o3)c3ccccc32)cc1] | DM-28 | 5.2982 | 3.68 | 59.79 | 429.44 | 2 | 8.37 | 3 | — | 3 |
| 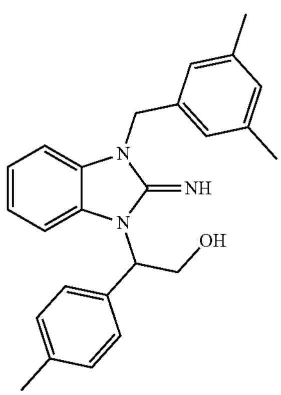 [SMILES: Cc1ccc(C(CO)n2c(=N)n(Cc3cc(C)cc(C)c3)c3ccccc32)cc1] | DM-29 | 5.8622 | 3.94 | 50.56 | 385.51 | 2 | 9.09 | 2.8 | + | 3 |
| 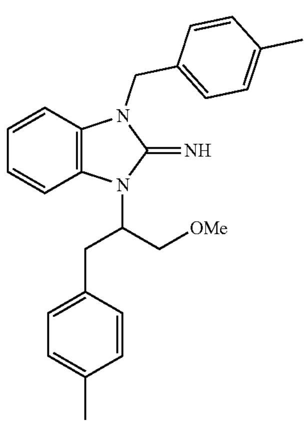 [SMILES: COCC(Cc1ccc(C)cc1)n1c(=N)n(Cc2ccc(C)cc2)c2ccccc21] | DM-65 | 6.4956 | 4.23 | 39.56 | 399.54 | 1 | 9.25 | 2.9 | ++ | |

TABLE 1-continued
| | | | | | | | | | | |
|---|---|---|---|---|---|---|---|---|---|---|
| 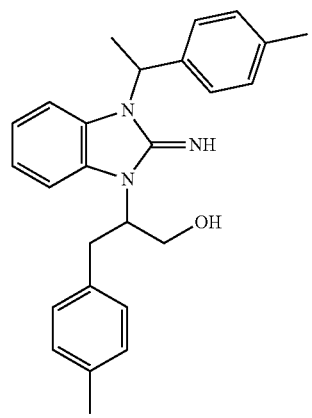 [SMILES: Cc1ccc(CC(CO)n2c(=N)n(C(C)c3ccc(C)cc3)c3ccccc32)cc1] | DM-66 | 6.0472 | 3.99 | 50.56 | 399.54 | 2 | 9.26 | 2.6 | ++ | 5, 19 | a mixture of two pairs of enantiomers |
| 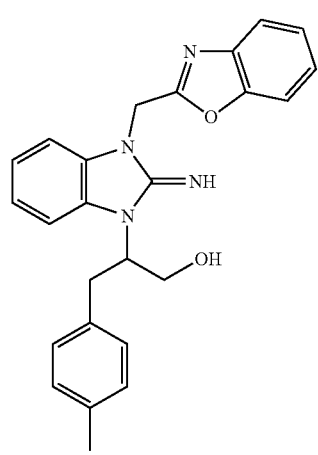 [SMILES: Cc1ccc(CC(CO)n2c(=N)n(Cc3nc4ccccc4o3)c3ccccc32)cc1] | DM-68 (pure version of ww4-105) | 4.5122 | 3.15 | 72.15 | 412.49 | 2 | 8.48 | 3.6 | ++ | 5 | pure version of ww4-105 |
| 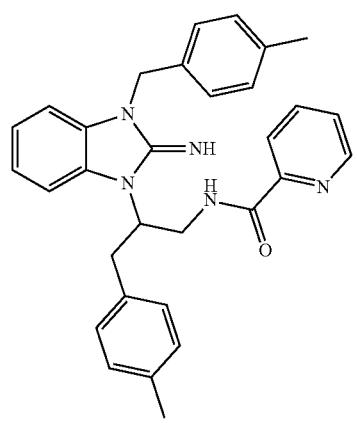 [SMILES: Cc1ccc(CC(CNC(=O)c2ccccn2)n2c(=N)n(Cc3ccc(C)cc3)c3ccccc32)cc1] | WM-120 | 6.9993 | 4.41 | 71.79 | 489.62 | 2 | 9.13 | 2 | ++ | 42 | |

TABLE 1-continued
| | | | | | | | | | | | |
|---|---|---|---|---|---|---|---|---|---|---|---|
| 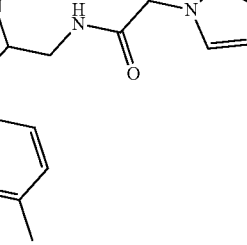 | WM-126 | 6.8773 | 4.33 | 62.67 | 491.64 | 2 | 9.17 | 2 | ++ | 42 | |
| 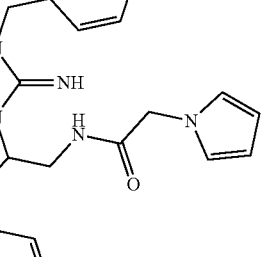 | WM-132 | 6.8773 | 4.33 | 62.67 | 491.64 | 2 | 9.17 | 2 | ++ | 26 | s-enantiomer of WM-126 |
| 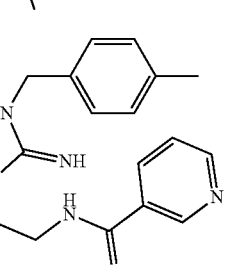 | WM-136 | 6.6493 | 4.03 | 71.79 | 489.62 | 2 | 9.13 | 2 | ++ | 27, 28 | |
| 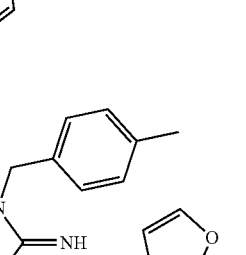 | WM-138 | 6.5783 | 4.38 | 68.66 | 478.6 | 2 | 9.13 | 2.1 | | | |

TABLE 1-continued
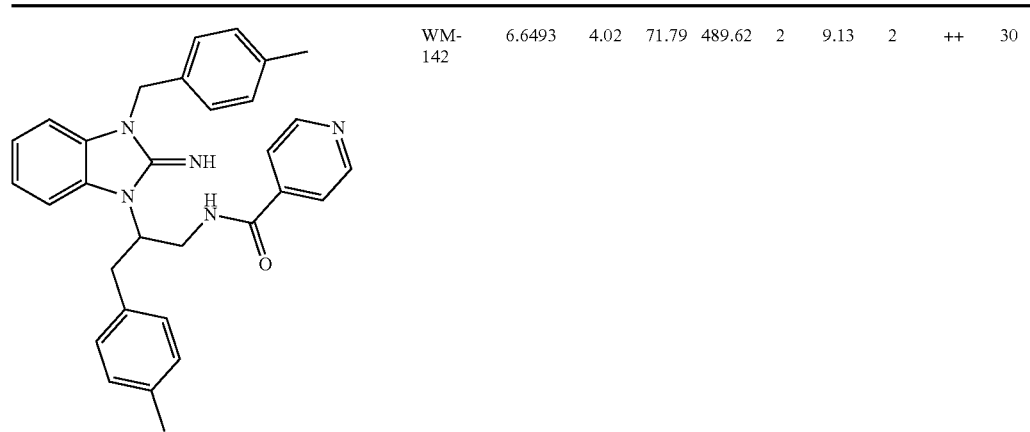
| | | | | | | | | | |
|---|---|---|---|---|---|---|---|---|---|
| WM-142 | 6.6493 | 4.02 | 71.79 | 489.62 | 2 | 9.13 | 2 | ++ | 30 |
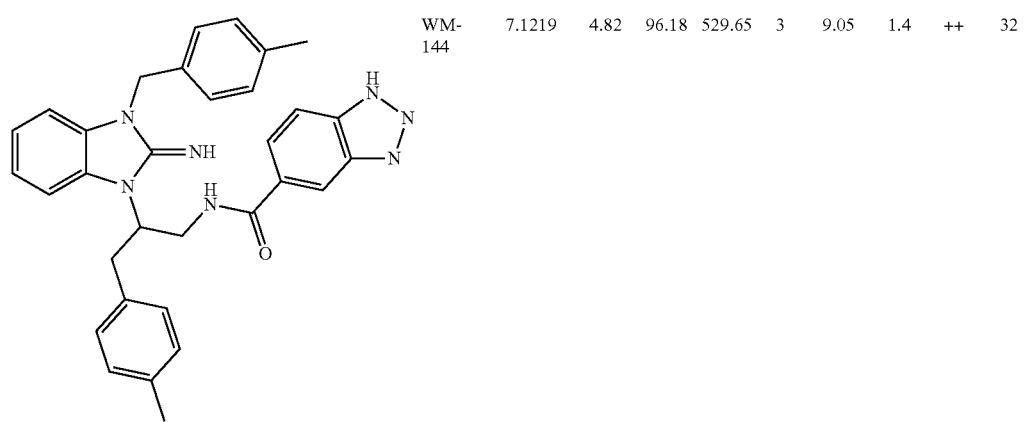
| | | | | | | | | | |
|---|---|---|---|---|---|---|---|---|---|
| WM-144 | 7.1219 | 4.82 | 96.18 | 529.65 | 3 | 9.05 | 1.4 | ++ | 32 |
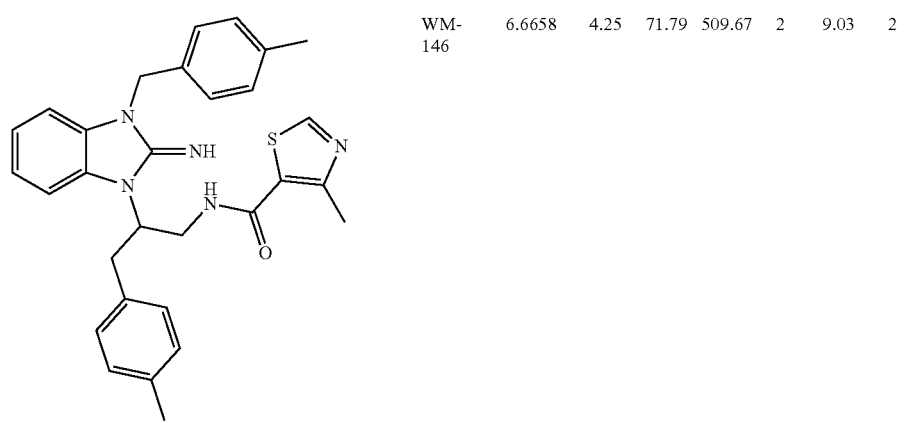
| | | | | | | | |
|---|---|---|---|---|---|---|---|
| WM-146 | 6.6658 | 4.25 | 71.79 | 509.67 | 2 | 9.03 | 2 |

TABLE 1-continued
| | | | | | | | | | | |
|---|---|---|---|---|---|---|---|---|---|---|
| 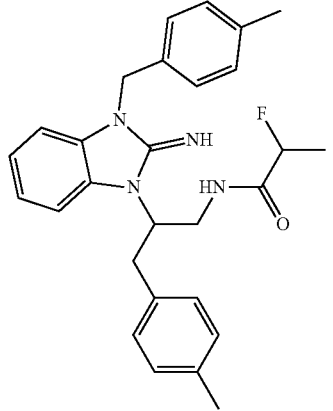 [SMILES: Cc1ccc(CC(CNC(=O)C(C)F)n2c(=N)n(Cc3ccc(C)cc3)c3ccccc32)cc1] | WM-148 | 6.3723 | 3.93 | 59.43 | 458.58 | 2 | 9.26 | 2.2 | | |
| 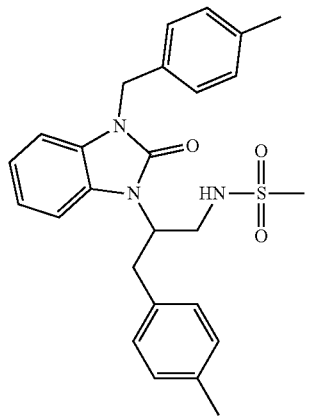 [SMILES: Cc1ccc(CC(CNS(C)(=O)=O)n2c(=O)n(Cc3ccc(C)cc3)c3ccccc32)cc1] | KM-4-173-3 | 5.668 | 4.58 | 69.72 | 463.6 | 1 | 10.62 (sulfon-a-mide) | 2.1 | + | 9 |
| 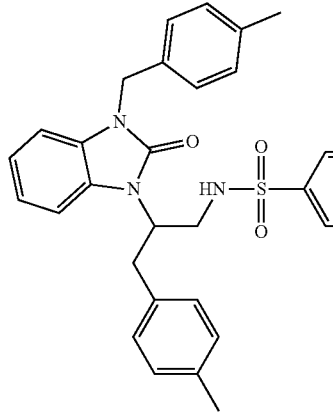 | KM-4-174-2 | 7.2845 | 6.69 | 69.72 | 525.67 | 1 | 10.18 (sulfon-a-mide) | 1.8 | — | 9 |

TABLE 1-continued
| | | | | | | | | | | |
|---|---|---|---|---|---|---|---|---|---|---|
| 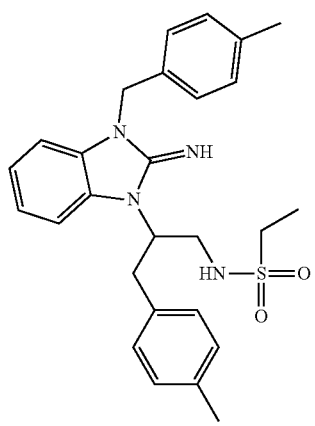 [SMILES: CCS(=O)(=O)NCC(Cc1ccc(C)cc1)n1c(=N)n(Cc2ccc(C)cc2)c2ccccc21] | KM-4-180-1 | 6.361 | 3.37 | 76.5 | 476.64 | 2 | 9.16 | 2.4 | ++ | 10 | |
| 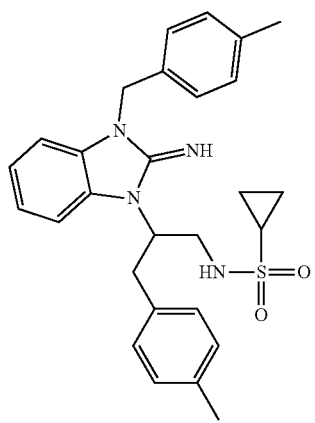 [SMILES: Cc1ccc(CC(CNS(=O)(=O)C2CC2)n2c(=N)n(Cc3ccc(C)cc3)c3ccccc32)cc1] | KM-4-181-1 | 6.416 | 3.65 | 76.5 | 488.65 | 2 | 9.13 | 2.2 | ++ | 10 | In summary named KM-1811 |
| 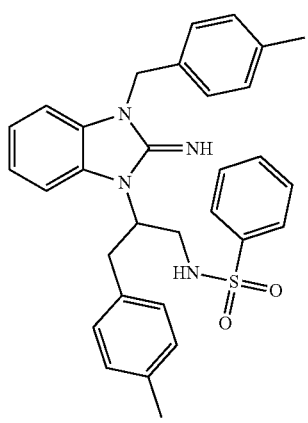 [SMILES: Cc1ccc(CC(CNS(=O)(=O)c2ccccc2)n2c(=N)n(Cc3ccc(C)cc3)c3ccccc32)cc1] | KM-4-182-2 | 7.4485 | 5.11 | 76.5 | 524.68 | 2 | 8.98 | 2 | + | 10 | In summary named KM-1822 |

TABLE 1-continued
| | | | | | | | | | | | |
|---|---|---|---|---|---|---|---|---|---|---|---|
| 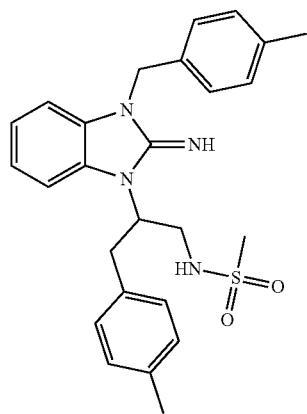 [SMILES: Cc1ccc(CC(CNS(C)(=O)=O)n2c(=N)n(Cc3ccc(C)cc3)c3ccccc32)cc1] | KM-4-189-org | 5.832 | 2.84 | 76.5 | 462.61 | 2 | 9.17 | 2.8 | ++ | 31 | Papp A-->B: 3.06; Papp B-->A: 9.19; Eflux ratio: 3.00 |
| 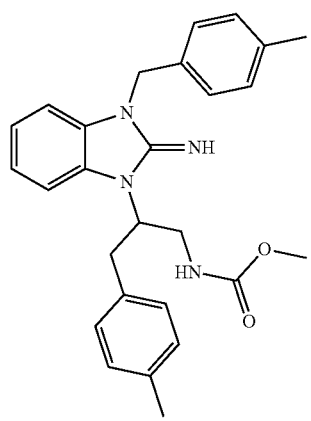 [SMILES: COC(=O)NCC(Cc1ccc(C)cc1)n1c(=N)n(Cc2ccc(C)cc2)c2ccccc21] | KM-4-190-org | 6.3787 | 3.87 | 68.66 | 442.56 | 2 | 9.3 | 2.3 | ++ | 11 | |
| 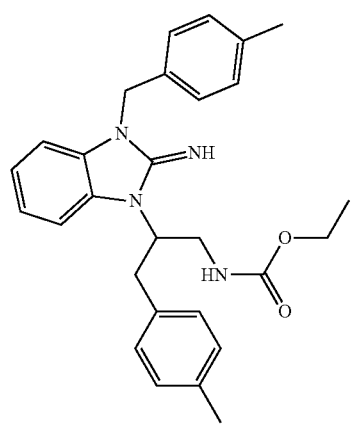 [SMILES: CCOC(=O)NCC(Cc1ccc(C)cc1)n1c(=N)n(Cc2ccc(C)cc2)c2ccccc21] | KM-4-191-org | 6.9077 | 4.27 | 68.66 | 456.59 | 2 | 9.25 | 2.2 | ++ | | |

TABLE 1-continued
| | | | | | | | | | | |
|---|---|---|---|---|---|---|---|---|---|---|
| 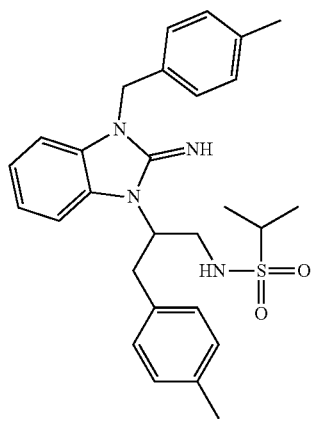 [SMILES: Cc1ccc(CC(CNS(=O)(=O)C(C)C)n2c(=N)n(Cc3ccc(C)cc3)c3ccccc32)cc1] | KM-4-196-1 | 6.67 | 3.95 | 76.5 | 490.67 | 2 | 9.14 | 2 | ++ | 12 |
| 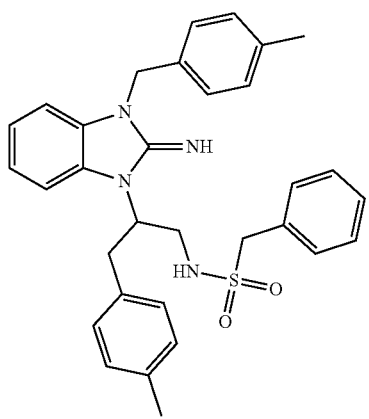 [SMILES: Cc1ccc(CC(CNS(=O)(=O)Cc2ccccc2)n2c(=N)n(Cc3ccc(C)cc3)c3ccccc32)cc1] | KM-4-197-1 | 7.4616 | 4.9 | 76.5 | 538.71 | 2 | 8.95 | 2 | ++ | 12 |
| 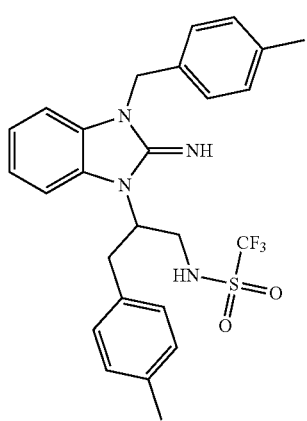 | KM-4-198-1 | 7.941 | 6.37 | 76.5 | 516.58 | 2 | 8.91 | 2 | — | 12 |

TABLE 1-continued

| Structure | ID | | | | | | | | | |
|---|---|---|---|---|---|---|---|---|---|---|
| (benzimidazol-2-imine with p-methylbenzyl, CH2-p-tolyl, and NHC(O)OH carbamate) | KM-4-207-1 | 5.2531 | 3.87 | 79.66 | 428.54 | 3 | 9.38 | 2.1 | + | |
| (benzimidazol-2-imine with p-methylbenzyl, CH2-p-tolyl, and NHC(O)NH2 urea) | KM-4-208-1 | 5.3224 | 2.88 | 85.45 | 427.55 | 4 | 9.36 | 2.4 | +++ | 14, 15, 16, 27 | Papp A-->B: 0.07; Papp B-->A: 4.58; Efflux ratio: 66.67 |
| (benzimidazol-2-imine with p-methylbenzyl, CH2-p-tolyl, and NHC(O)CH2-p-tolyl amide) | KM-4-209-1 | 7.8913 | 5.73 | 59.43 | 516.69 | 2 | 9.13 | 1.9 | + | 14 |
| (benzimidazol-2-imine with p-methylbenzyl, CH2-p-tolyl, and NHC(O)NHCH3 methylurea) | KM-4-213-1 | 6.0784 | 3.12 | 71.46 | 441.58 | 3 | 9.33 | 2.4 | ++ | |

TABLE 1-continued
| | Compound | | | | | | | | | |
|---|---|---|---|---|---|---|---|---|---|---|
| 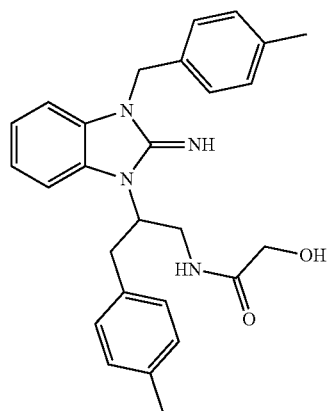 | KM-4-214-1 (different batch ww5-190) | 5.5103 | 2.43 | 79.66 | 442.56 | 3 | 9.31 | 2.7 | +++ | 15, 17, 18, 20, 21, 22, 23, 24, 25, | ww5-190 = different batch of, KM-4-214-1 |
| 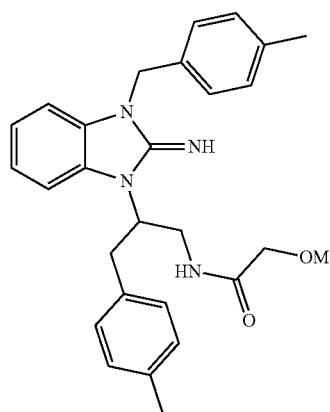 | KM-4-215-1 | 5.8489 | 3.11 | 68.66 | 456.59 | 2 | 9.26 | 2.6 | ++ | |
| 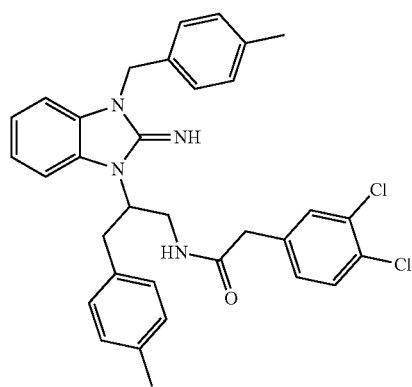 [SMILES: Cc1ccc(CC(CNC(=O)Cc2ccc(Cl)c(Cl)c2)n2c(=N)n(Cc3ccc(C)cc3)c3ccccc32)cc1] | KM-4-229-2 | 8.6983 | 6.6 | 59.43 | 571.55 | 2 | 8.93 | 2 | ++ | |
| 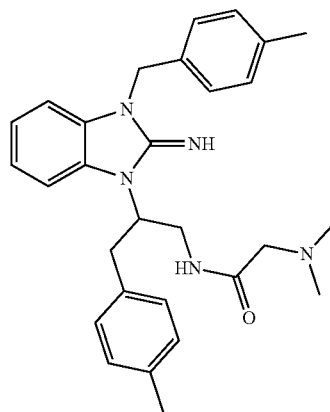 | KM-4-237-2 | 6.0909 | 2.88 | 62.67 | 469.63 | 2 | 9.24 | 2.7 | ++ | 17 |

TABLE 1-continued
| | Name | | | | | | | | | | Notes |
|---|---|---|---|---|---|---|---|---|---|---|---|
| 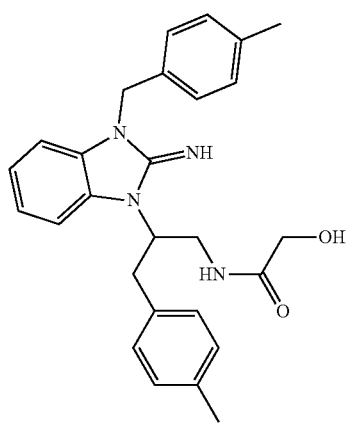 [SMILES: Cc1ccc(CC(CNC(=O)CO)n2c(=N)n(Cc3ccc(C)cc3)c3ccccc32)cc1] | KM-4-267-3 (impure version of KM-4-287) | 5.5103 | 2.43 | 79.66 | 442.56 | 3 | 9.31 | 2.7 | +++ | 19 | KM-4-287 is the pure version |
| 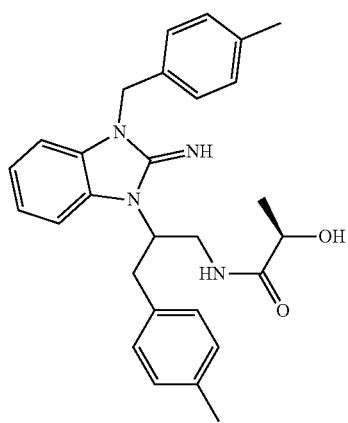 [SMILES: Cc1ccc(CC(CNC(=O)[C@@H](C)O)n2c(=N)n(Cc3ccc(C)cc3)c3ccccc32)cc1] | KM-4-273-1 | 5.8193 | 3.02 | 79.66 | 456.59 | 3 | 9.28 | 2.3 | ++ | | |
| 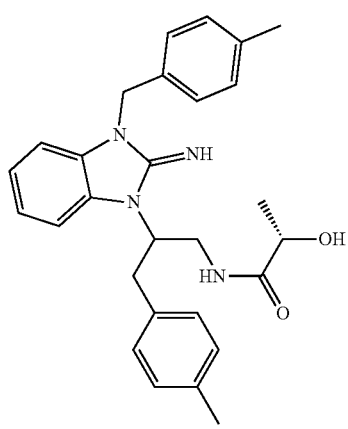 [SMILES: Cc1ccc(CC(CNC(=O)[C@H](C)O)n2c(=N)n(Cc3ccc(C)cc3)c3ccccc32)cc1] | KM-4-281-1 | 5.8193 | 3.02 | 79.66 | 456.59 | 3 | 9.28 | 2.3 | ++ | 21 | Papp A-->B: 0.21; Papp B-->A: 8.48; Eflux ratio: 40.00 |

TABLE 1-continued
| | Compound | | | | | | | | | | Notes |
|---|---|---|---|---|---|---|---|---|---|---|---|
| 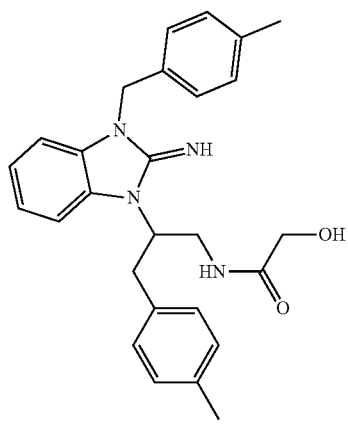 [SMILES: Cc1ccc(CC(CNC(=O)CO)n2c(=N)n(Cc3ccc(C)cc3)c3ccccc32)cc1] | KM-4-287 (pure version of KM-4-267-3) | 5.5103 | 2.43 | 79.66 | 442.56 | 3 | 9.31 | 2.7 | +++ | 21, 26, 28 | Papp A-->B: 0.39; Papp B-->A: 5.90; Eflux ratio: 15.00; KM-4-287 is the pure version of KM-4-267-3 |
| 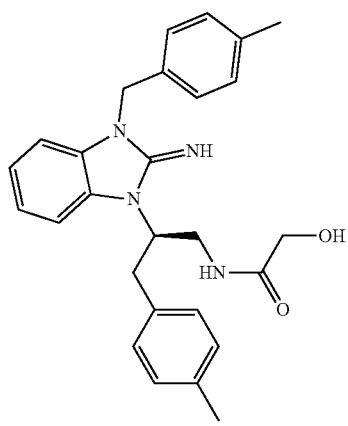 [SMILES: Cc1ccc(C[C@H](CNC(=O)CO)n2c(=N)n(Cc3ccc(C)cc3)c3ccccc32)cc1] | KM-4-289 | 5.5103 | 2.43 | 79.66 | 442.56 | 3 | 9.31 | 2.7 | + | 21 | |
| 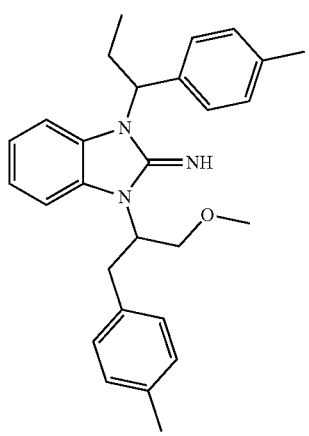 [SMILES: CCC(c1ccc(C)cc1)n1c(=N)n(C(COC)Cc2ccc(C)cc2)c2ccccc21] | ww6-90 | 7.3336 | 5.09 | 39.56 | 427.59 | 1 | 9.35 | 2.7 | ++++ | 38 | mixture of two diastereomers |

TABLE 1-continued
| | | | | | | | | | | |
|---|---|---|---|---|---|---|---|---|---|---|
| 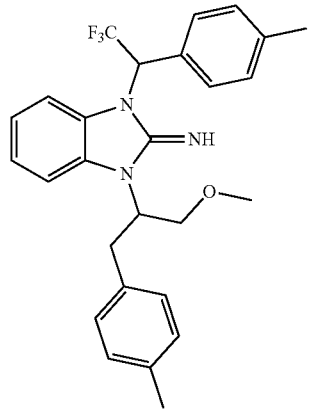 [SMILES: COCC(Cc1ccc(C)cc1)n1c(=N)n(C(c2ccc(C)cc2)C(F)(F)F)c2ccccc21] | ww6-106 | 6.7686 | 6.38 | 39.56 | 467.54 | 1 | 7.89 | 3 | ++ | 39 | ratio of two diastereo-mers is 2:3 |
| 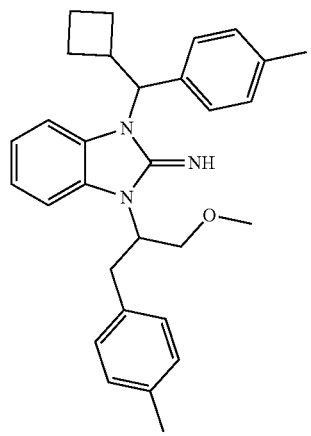 [SMILES: COCC(Cc1ccc(C)cc1)n1c(=N)n(C(c2ccc(C)cc2)C2CCC2)c2ccccc21] | ww6-112 | 7.8076 | 5.39 | 39.56 | 453.28 | 1 | 9.41 | 2.4 | +++ | 40 | mixture of two diastereo-mers |
| 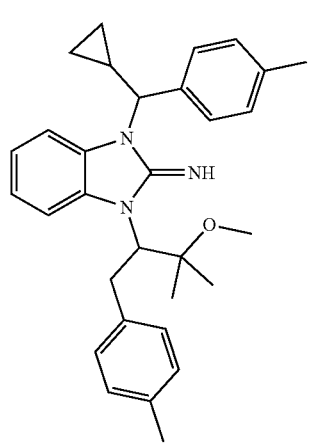 [SMILES: COC(C)(C)C(Cc1ccc(C)cc1)n1c(=N)n(C(c2ccc(C)cc2)C2CC2)c2ccccc21] | ww6-130 | 7.9566 | 5.59 | 39.56 | 467.66 | 1 | 9.49 | 2.3 | + | 43 | mixture of two diastereo-mers in the form of rotamers |

TABLE 1-continued

| Structure | Compound | | | | | | | | | Notes |
|---|---|---|---|---|---|---|---|---|---|---|
| (structure shown) | ww6-131 | 6.6276 | 4.8 | 39.56 | 431.56 | 1 | 8.87 | 2.9 | +++ 43 | mixture of two diastereomers |
| (structure shown) | ww6-157 | 6.35621 | 4.37 | 50.56 | 413.6 | 2 | 9.32 | | 0 44 | mixture of two diastereomers |
| (structure shown) | ww6-162 | | | | 551.5 | 2 | | | +++ 44 | mixture of two diastereomers |

| | | | | | | | | | |
|---|---|---|---|---|---|---|---|---|---|
| 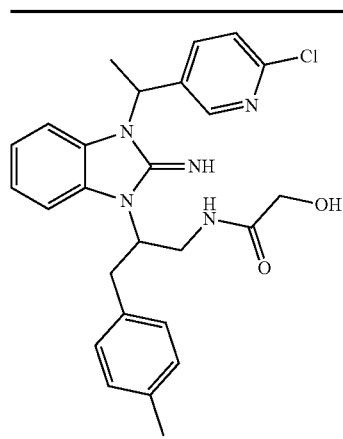 | ww6-185 | 4.62031 | 2.2 | 92.02 | 478 | 3 | 8.99 | +++ 45 | mixture of two diastereomers |
| 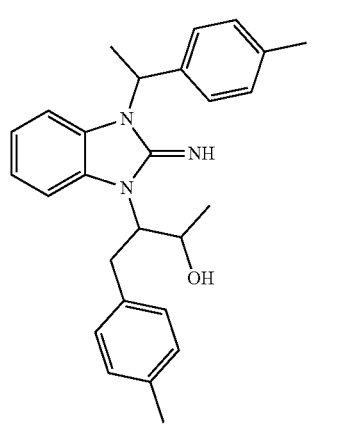 [SMILES: Cc1ccc(CC(C(C)O)n2c(=N)n(C(C)c3ccc(C)cc3)c3ccccc32)cc1] | ww6-187 | 6.35621 | 4.37 | 50.56 | 413.6 | 2 | 9.32 | +++ 45 | mixture of two diastereomers |
| 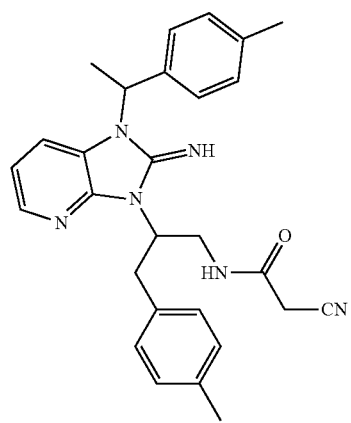 [SMILES: Cc1ccc(CC(CNC(=O)CC#N)n2c(=N)n(C(C)c3ccc(C)cc3)c3cccnc32)cc1] | ww6-230 | 4.17291 | 4.36 | 95.58 | 466.59 | 2 | 7.53 | — 46 | diastereomer B |

TABLE 1-continued

| Structure | ID | | | | | | | | Notes |
|---|---|---|---|---|---|---|---|---|---|
| | ww6-236 | 4.17291 | 4.36 | 95.58 | 466.59 | 2 | 7.53 | — | 46 diastereomer A |
| | ww6-248 | 5.74831 | 2.95 | 47.4 | 445.63 | 1 | 9.71 | +++ | 46 |
| | ww6-266 | 4.03581 | 4.6 | 86.71 | 439.6 | 2 | 7.51 | + | 47 diastereomer D; only H NMR |

TABLE 1-continued
| Structure | Name | | | | | | | | | Notes |
|---|---|---|---|---|---|---|---|---|---|---|
| 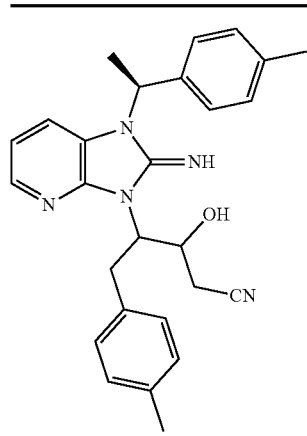 | ww6-268-first (mixture of 2 diastereomers) | 4.03581 | 4.6 | 86.71 | 439.6 | 2 | 7.51 | + | 47 | diastereomer A and C (3.4:1); only H NMR |
| 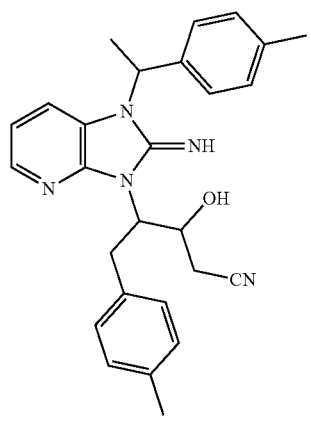 [SMILES: Cc1ccc(CC(C(O)CC#N)n2c(=N)n(C(C)c3ccc(C)cc3)c3cccnc32)cc1] | ww6-268-second | 4.03581 | 4.6 | 86.71 | 439.6 | 2 | 7.51 | + | 47 | diastereomer B; only H NMR |
| 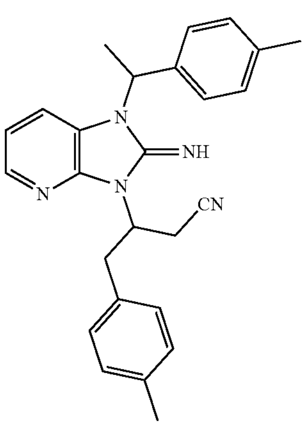 [SMILES: Cc1ccc(CC(CC#N)n2c(=N)n(C(C)c3ccc(C)cc3)c3cccnc32)cc1] | ww6-272 | 4.87361 | 4.69 | 66.48 | 409.54 | 1 | 8.25 | + | 48 | diastereomer A |

TABLE 1-continued
| | | | | | | | | | |
|---|---|---|---|---|---|---|---|---|---|
| 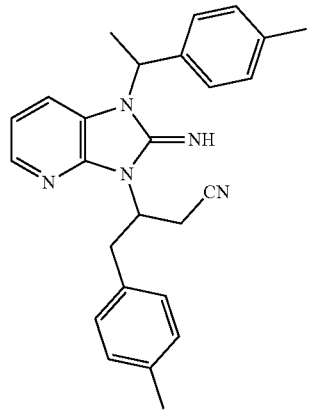 [SMILES: Cc1ccc(CC(CC#N)n2c(=N)n(C(C)c3ccc(C)cc3)c3cccnc32)cc1] | ww6-273 | 4.87361 | 4.69 | 66.48 | 409.54 | 1 | 8.25 | +++ | 48 | diastereomer B |
| 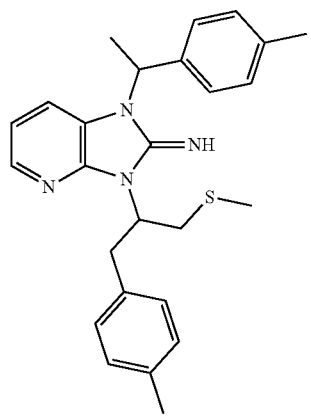 [SMILES: CSCC(Cc1ccc(C)cc1)n1c(=N)n(C(C)c2ccc(C)cc2)c2cccnc21] | ww6-288-second | 5.96071 | 6.1 | 42.69 | 430.61 | 1 | 7.76 | ++ | 49 | diastereomer A |
| 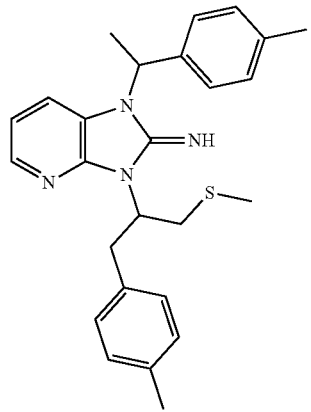 [SMILES: CSCC(Cc1ccc(C)cc1)n1c(=N)n(C(C)c2ccc(C)cc2)c2cccnc21] | ww6-289-second | 5.96071 | 6.1 | 42.69 | 430.61 | 1 | 7.76 | ++++ (page 49); +++ (page 51) | 49 | diastereomer B |

TABLE 1-continued
| | | | | | | | | | | |
|---|---|---|---|---|---|---|---|---|---|---|
| 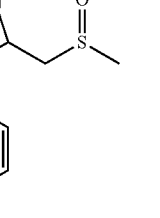 | ww6-306 | 4.25131 | 3.74 | 59.76 | 446.61 | 1 | 7.95 | + | 50 | Ratio 2.1:1; Mixture of two sulfoxide diastereomers; from diastereomer A precursor |
| 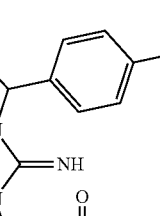 | ww6-308 | 4.15891 | 3.93 | 76.83 | 462.61 | 1 | 7.84 | + | 50 | diastereomer A |
| 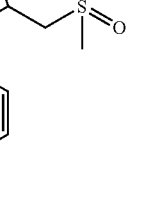 | ww7-002 | 4.15891 | 3.93 | 76.83 | 462.61 | 1 | 7.84 | +++ | 51 | diastereomer B |
| 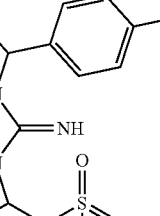 | ww7-003 | 4.25131 | 3.74 | 59.76 | 446.61 | 1 | 7.95 | +++ | 51 | Ratio 4.4:1; Mixture of two sulfoxide diastereomers; from diastereomer B precursor |

TABLE 1-continued
| | | | | | | | | | |
|---|---|---|---|---|---|---|---|---|---|
| 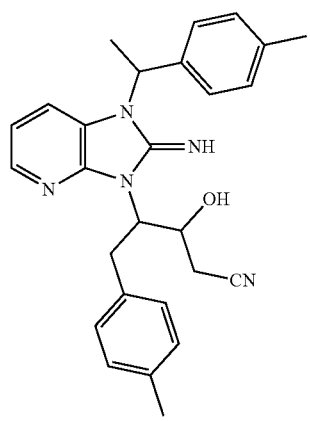 [SMILES: Cc1ccc(CC(C(O)CC#N)n2c(=N)n(C(C)c3ccc(C)cc3)c3cccnc32)cc1] | ww7-31 | 4.03581 | 4.6 | 86.71 | 439.6 | 2 | 7.51 | + | 52, 53 | Diastereomer C |
| 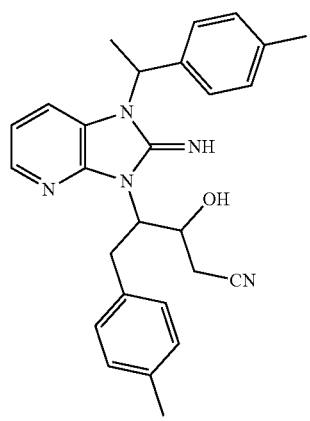 [SMILES: Cc1ccc(CC(C(O)CC#N)n2c(=N)n(C(C)c3ccc(C)cc3)c3cccnc32)cc1] | ww7-32 (aka ww6-266) | 4.03581 | 4.6 | 86.71 | 439.6 | 2 | 7.51 | + | 52, 53 | Diastereomer D |
| 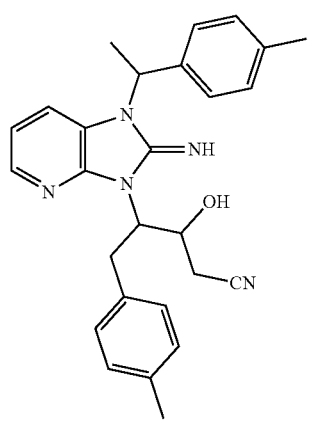 [SMILES: Cc1ccc(CC(C(O)CC#N)n2c(=N)n(C(C)c3ccc(C)cc3)c3cccnc32)cc1] | ww7-39 | 4.03581 | 4.6 | 86.71 | 439.6 | 2 | 7.51 | + | 53 | Diastereomer A |

TABLE 1-continued

| Structure | Compound | | | | | | | | Notes |
|---|---|---|---|---|---|---|---|---|---|
| (structure) | ww7-40 (aka ww6-268-second) | 4.03581 | 4.6 | 86.71 | 439.6 | 2 | 7.51 | + | 53 Diastereomer B |
| (structure) from ChemAxon (PH = 7.4) | ww7-51 | 6.85061 | 5.47 | 39.56 | 449.6 | 1 | 8.41 | ++ | 54 |
| (structure) HBr | WZ-I-30-3 | 6.19 | 4.5 | 62.92 | 467.41 | 2 | 7.19 | | Papp A-->B: 5.47; Papp B-->A: 3.28; Efflux ratio: 0.60 |

TABLE 1-continued

| Structure | ID | | | | | | | | |
|---|---|---|---|---|---|---|---|---|---|
| (imidazopyridine with p-tolyl benzyl, CH₂OH substituent; HBr) | WZ-I-81 | 5.36 | 4.99 | 51.92 | 481.44 | 1 | 7.53 | ++ | 1 |
| (imidazopyridine with p-tolyl benzyl, CH₂OMe substituent; HBr) | WZ-I-89 | 5.36 | 4.99 | 51.92 | 481.44 | 1 | 7.53 | ++ | 1 |
| (benzimidazole with N=C(OMe), methyl carbonate group) | WZ-I-190-2 | 6.55 | 6.55 | 80.67 | 501.58 | 0 | | + | 2 |
| (benzimidazole with C(O)NHMe amide; HBr) | WZ-I-236 | 5.07 | 3.81 | 59.43 | 493.45 | 2 | 8.66 | — | 2 |

TABLE 1-continued

| Structure | Name | | | | | | | | |
|---|---|---|---|---|---|---|---|---|---|
| (structure with benzimidazole-imine, N-benzyl-4-methylphenyl, azetidine amide, 4-methylbenzyl, HBr) | WZ-I-244 | 5.18 | 3.91 | 50.64 | 519.49 | 1 | 8.69 | ++ | 2, 3 |
| (structure with benzimidazole-imine, N-(4-methylbenzyl), pyrrolidine amide, 4-methylbenzyl, HBr) | WZ-I-243 | 5.7 | 4.42 | 50.64 | 533.51 | 1 | 8.69 | ++ | 2 |
| (structure with benzimidazole-imine, N-(4-methylbenzyl), piperidine amide, 4-methylbenzyl, HBr) | WZ-I-249 | 7.08 | 4.6 | 50.64 | 547.54 | 1 | 8.66 | ++ | 2 |
| (structure with benzimidazole-imine, N-(4-methylbenzyl), azetidine-3-carboxylic acid methyl ester amide, 4-methylbenzyl, HBr) | WZ-I-283 | 4.94 | 3.85 | 76.94 | 577.52 | 1 | 8.47 | + | 4 |

| | | | | | | | | | |
|---|---|---|---|---|---|---|---|---|---|
| 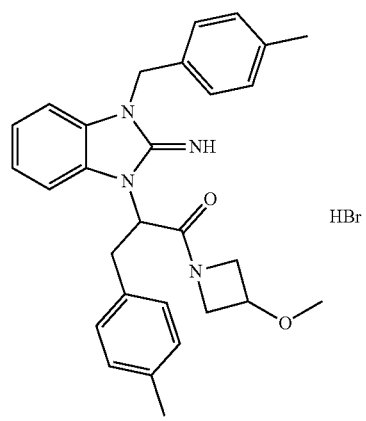 [SMILES: COC1CN(C(=O)C(Cc2ccc(C)cc2)n2c(=N)n(Cc3ccc(C)cc3)c3ccccc32)C1 ; Br] | WZ-I-298 | 5.14 | 3.96 | 59.87 | 549.51 | 1 | 8.58 | + | 4 |
| 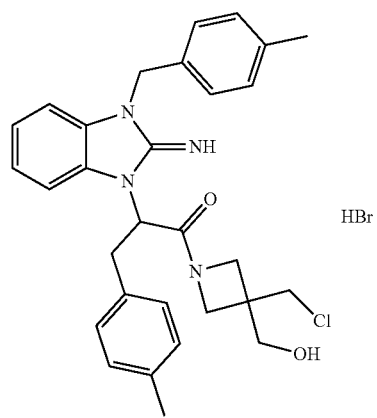 [SMILES: Cc1ccc(CC(C(=O)N2CC(CO)(CCl)C2)n2c(=N)n(Cc3ccc(C)cc3)c3ccccc32)cc1 ; Br] | WZ-I-300 | 5.66 | 3.93 | 70.87 | 597.98 | 2 | 8.39 | ++++ | 4, 9 |
| 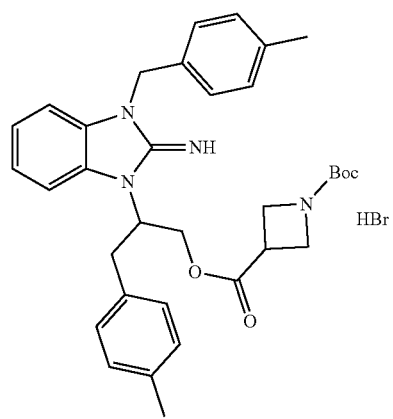 [SMILES: Cc1ccc(CC(COC(=O)C2CN(C(=O)OC(C)(C)C)C2)n2c(=N)n(Cc3ccc(C)cc3)c3ccccc32)cc1 ; Br] | WZ-I-310 | 8.63 | 4.85 | 86.17 | 649.63 | 1 | 9.23 | + | 7 |

TABLE 1-continued
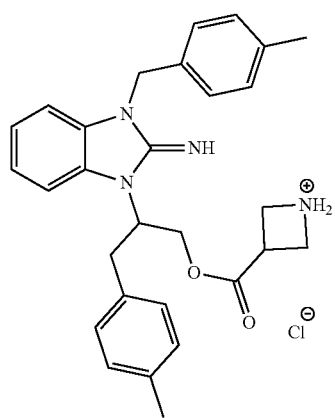 [SMILES: Cc1ccc(CC(COC(=O)C2C[NH2+]C2)n2c(=N)n(Cc3ccc(C)cc3)c3ccccc32)cc1 ; [Cl-]]
| Compound | | | | | | | | |
|---|---|---|---|---|---|---|---|---|
| WZ-II-2 | 6.86 | 1.88 | 73.24 | 469.61 | 2 | 8.81 | — | 7 |
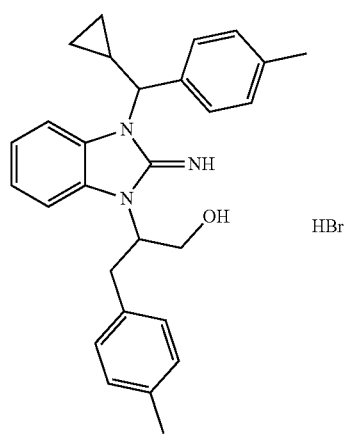 [SMILES: Cc1ccc(CC(CO)n2c(=N)n(C(c3ccc(C)cc3)C3CC3)c3ccccc32)cc1 ; Br]
| WZ-II-39-1 | 6.49 | 4.59 | 50.56 | 506.49 | 2 | 9.04 | +++ | 5 | diastereomer 1 |
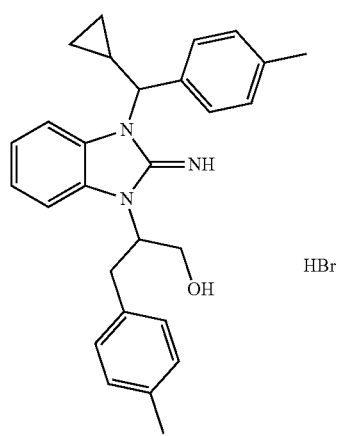 [SMILES: Cc1ccc(CC(CO)n2c(=N)n(C(c3ccc(C)cc3)C3CC3)c3ccccc32)cc1 ; Br]
| WZ-II-39-2 | 6.49 | 4.59 | 50.56 | 506.49 | 2 | 9.04 | ++ | 5 | diastereomer 2 |

TABLE 1-continued
| | | | | | | | | | | |
|---|---|---|---|---|---|---|---|---|---|---|
| 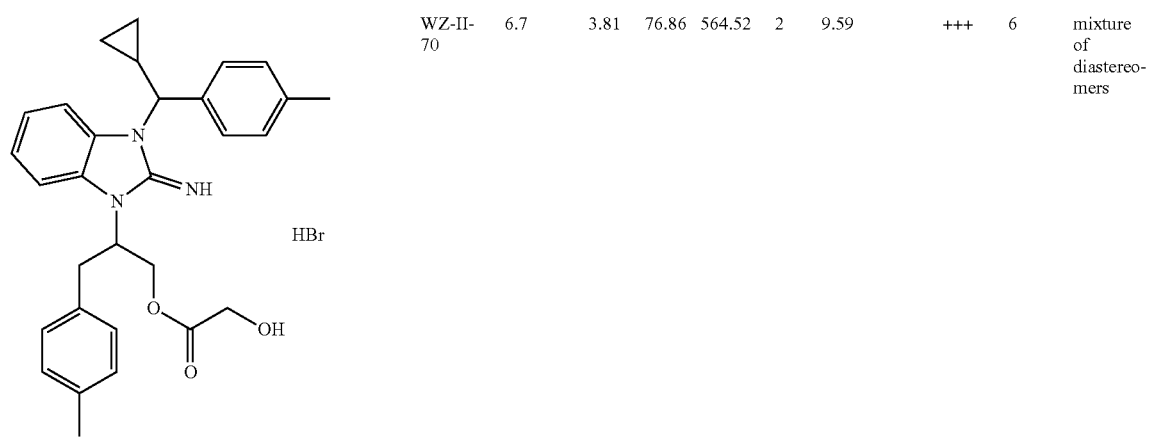 | WZ-II-70 | 6.7 | 3.81 | 76.86 | 564.52 | 2 | 9.59 | +++ | 6 | mixture of diastereomers |
| 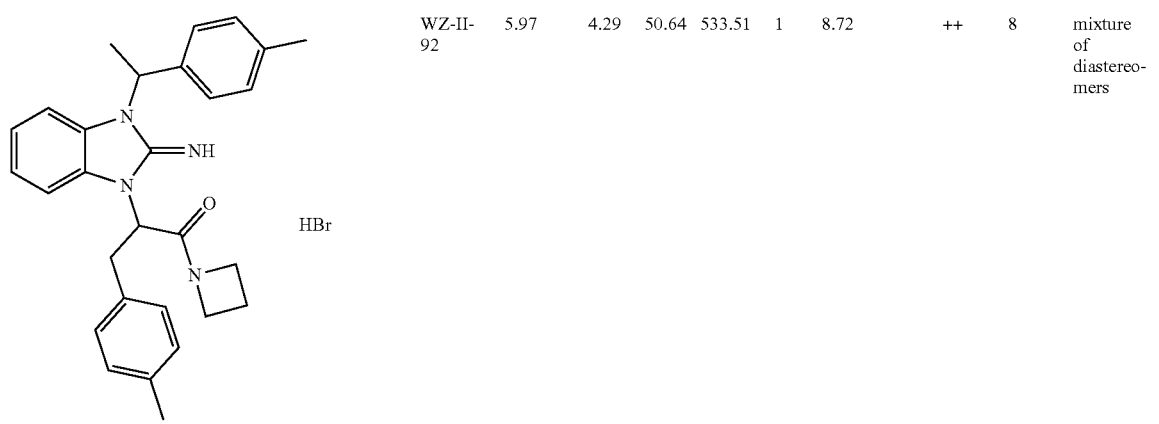 | WZ-II-92 | 5.97 | 4.29 | 50.64 | 533.51 | 1 | 8.72 | ++ | 8 | mixture of diastereomers |
| 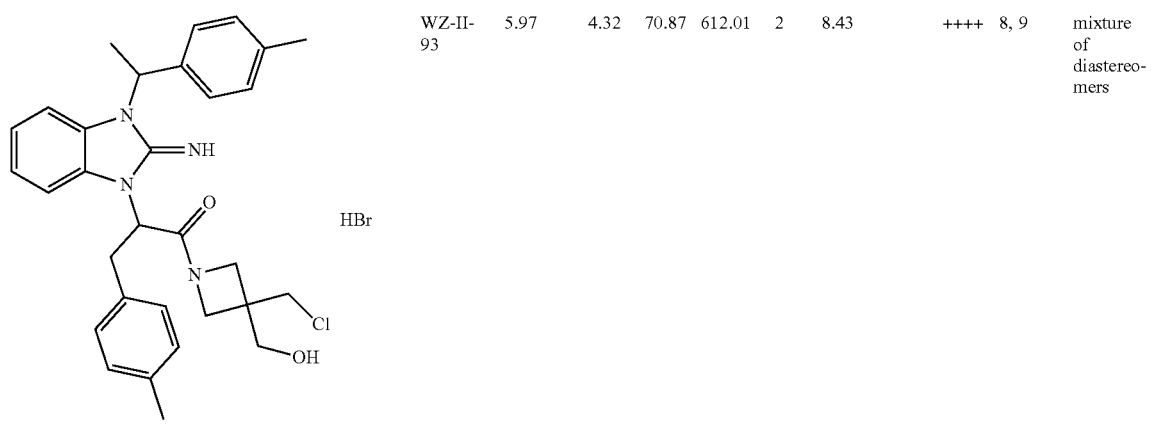 | WZ-II-93 | 5.97 | 4.32 | 70.87 | 612.01 | 2 | 8.43 | ++++ | 8, 9 | mixture of diastereomers |

TABLE 1-continued
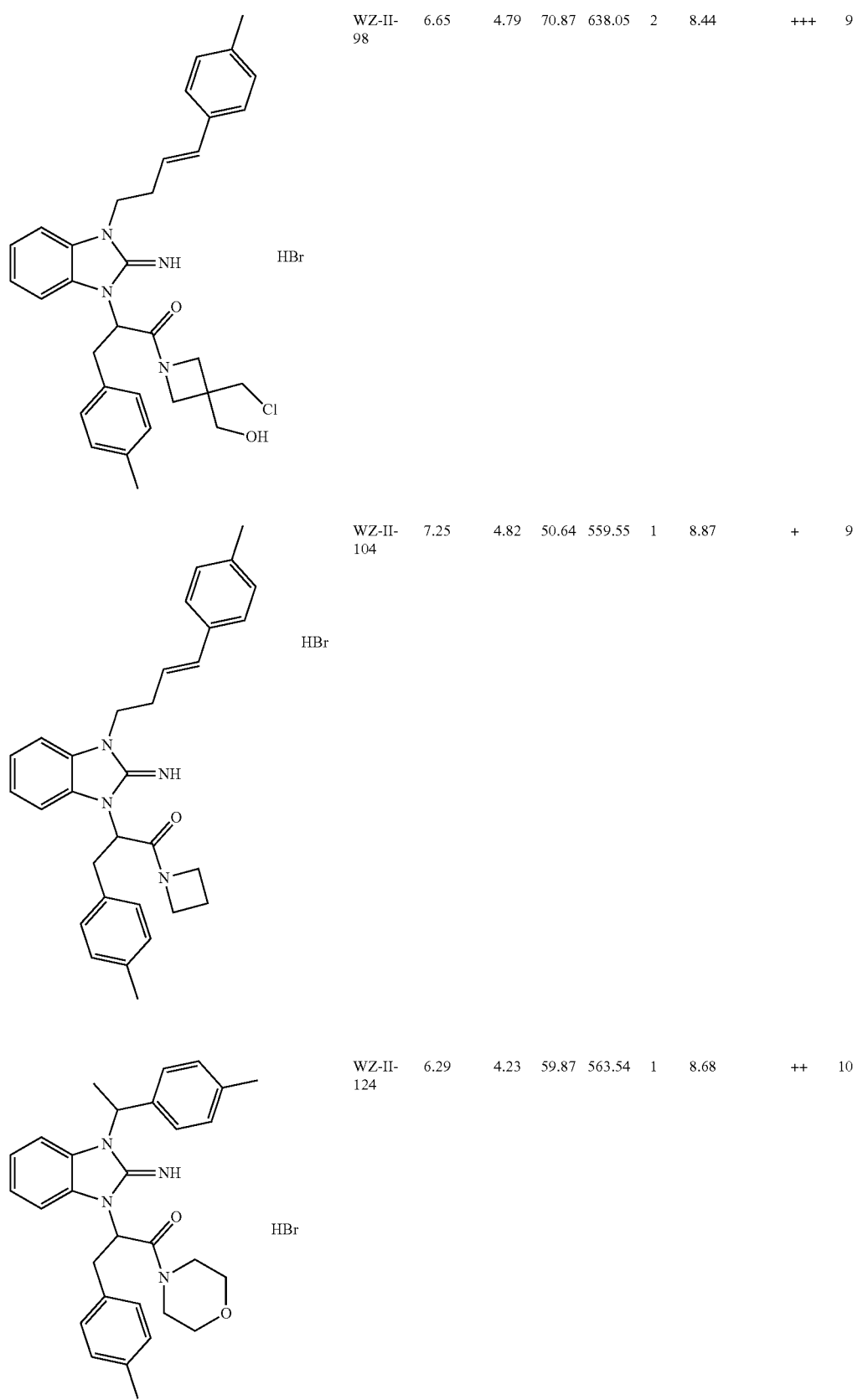
| | | | | | | | | |
|---|---|---|---|---|---|---|---|---|
| WZ-II-98 | 6.65 | 4.79 | 70.87 | 638.05 | 2 | 8.44 | +++ | 9 |
| WZ-II-104 | 7.25 | 4.82 | 50.64 | 559.55 | 1 | 8.87 | + | 9 |
| WZ-II-124 | 6.29 | 4.23 | 59.87 | 563.54 | 1 | 8.68 | ++ | 10 |

TABLE 1-continued

| Structure | Salt | Compound | c1 | c2 | c3 | c4 | c5 | c6 | c7 | # | Notes |
|---|---|---|---|---|---|---|---|---|---|---|---|
| (structure) | HBr | WZ-II-129 | 5.28 | 3.69 | 70.87 | 563.54 | 2 | 8.62 | +++ | 10 | |
| (structure) | HBr | WZ-II-149 | 5.31 | 5.38 | 51.92 | 495.46 | 1 | 7.56 | ++++ | 11 | Plasma PK (5mpk IV) HL_Lambda_z 41.667647 min, Tmax 10 min, Cmax 1046.6667 ng/mL, AUClast 67665.865 min*ng/ml, Vz_F_obs 101565.51 mL, Cl_F_obs 1689.5566 mL/min; Plasma PK (10 mpk IP) HL_Lambda_z 38.91983 min, Tmax 10 min, Cmax 638.0333 ng/mL, AUClast 60049.5 min*ng/ml, Vz_F_obs 208114 mL, Cl_F_obs 3706.43 mL/min; Brain PK (5mpk IV), HL_Lambda_z 133.1075 min, Tmax 10 min, Cmax 1297.933 ng/mL, AUClast 76594.69 min*ng/ml, Vz_F_obs 286490.1 mL, Cl_F_obs 1491.875 mL/min; Brain PK (10 mpk |

TABLE 1-continued
| | | | | | | | | | |
|---|---|---|---|---|---|---|---|---|---|
| | | | | | | | | | IP), HL_Lambda_z 64.37396 min, Tmax 10 min, Cmax 77.79233 ng/mL, AUClast 8061.515 min*ng/ml, Vz_F_obs 2306714 mL, Cl_F_obs 24837.56 mL/min; 1.13; diastereomer 1; diastereomer of WZ-II-231 |
| 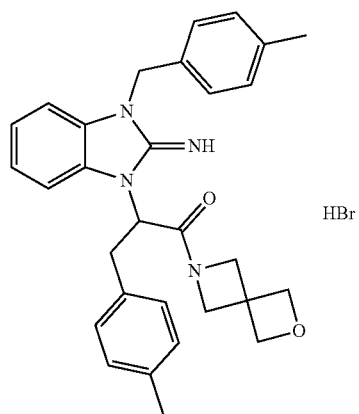 [SMILES: Cc1ccc(CC(C(=O)N2CC3(COC3)C2)n2c(=N)n(Cc3ccc(C)cc3)c3ccccc32)cc1 ; Br] HBr | WZ-II-150 | 5.87 | 3.59 | 59.87 | 561.52 | 1 | 8.57 | +++ | 11 | |
| 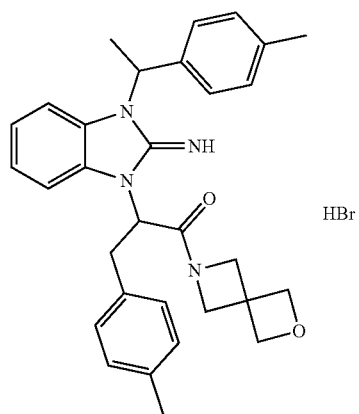 [SMILES: Cc1ccc(CC(C(=O)N2CC3(COC3)C2)n2c(=N)n(C(C)c3ccc(C)cc3)c3ccccc32)cc1 ; Br] HBr | WZ-II-151 | 6.18 | 3.97 | 59.87 | 575.55 | 1 | 8.6 | +++ | 11 | Plasma PK (5 mg/Kg IV) T1/2 131 min, Tmax 10 min, Cmax 869 ng/mL, AUClast 54500 min*ng/ml, Vz_F_obs 453 mL, Cl_F_obs 2.39 mL/min; Brain PK (5 mg/Kg IV), T1/2 269 min, Tmax 10 min, Cmax 22.7 ng/mL, AUClast 5585 min*ng/ml, Vz_F_obs 8876 mL, |

TABLE 1-continued

| Structure | Compound | | | | | | | | |
|---|---|---|---|---|---|---|---|---|---|
| | | | | | | | | | Cl_F_obs 22.9 mL/min; mixture of diastereomers |
| | WZ-II-174 | 5 | 3.8 | 70.87 | 577.57 | 2 | 8.63 | ++ | 12 | mixture of diastereomers |
| | WZ-II-184-1 | 6.19 | 2.55 | 76.66 | 655.48 | 2 | 8.25 | + | 12 | mixture of diastereomers |
| | WZ-II-184-2 | 6.17 | 1.18 | 62.67 | 574.57 | 2 | 8.6 | + | 12 | mixture of diastereomers |

TABLE 1-continued

| Structure | ID | | | | | | | | | Notes |
|---|---|---|---|---|---|---|---|---|---|---|
| (imidazopyridine with 1-(p-tolyl)ethyl, CH2-p-tolyl, CH2NH-C(O)-CH2OH; HBr) | WZ-II-186 | 4.32 | 3.75 | 92.02 | 538.49 | 3 | 7.34 | + | 12 | diastereomer 1 |
| (same core, diastereomer) | WZ-II-187 | 4.32 | 3.75 | 92.02 | 538.49 | 3 | 7.34 | ++++ | 12 | diastereomer 2 |
| (N-methyl amide variant; HBr) | WZ-II-205 | 4.91 | 3.96 | 83.23 | 552.52 | 2 | 7.38 | ++ | 13 | diastereomer 1 |
| (N-methyl amide variant; HBr) | WZ-II-206 | 4.91 | 3.96 | 83.23 | 552.52 | 2 | 7.38 | +++ | 13 | diastereomer 2 |

| | | | | | | | | | |
|---|---|---|---|---|---|---|---|---|---|
| 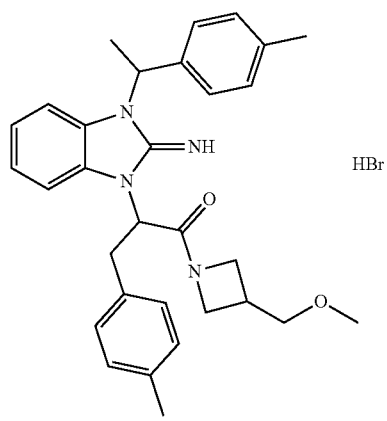 [SMILES: COCC1CN(C(=O)C(Cc2ccc(C)cc2)n2c(=N)n(C(C)c3ccc(C)cc3)c3ccccc32)C1 ; Br] | WZ-II-207 | 5.21 | 4.38 | 59.87 | 577.57 | 1 | 8.56 | +++ | 13 | mixture of diastereomers |
| 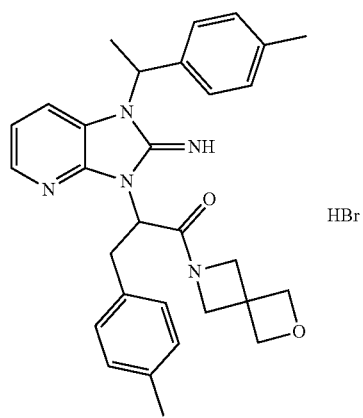 [SMILES: Cc1ccc(CC(C(=O)N2CC3(COC3)C2)n2c(=N)n(C(C)c3ccc(C)cc3)c3cccnc32)cc1 ; Br] | WZ-II-208-1 | 4.43 | 4.68 | 72.23 | 576.54 | 1 | 6.9 | + | 13 | diastereomer 1 |
| 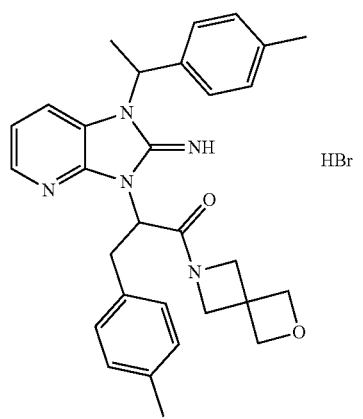 [SMILES: Cc1ccc(CC(C(=O)N2CC3(COC3)C2)n2c(=N)n(C(C)c3ccc(C)cc3)c3cccnc32)cc1 ; Br] | WZ-II-209-1 | 4.43 | 4.68 | 72.23 | 576.54 | 1 | 6.9 | +++ | 13 | diastereomer 2 |

TABLE 1-continued

| Structure | Name | | | | | | | | | |
|---|---|---|---|---|---|---|---|---|---|---|
| 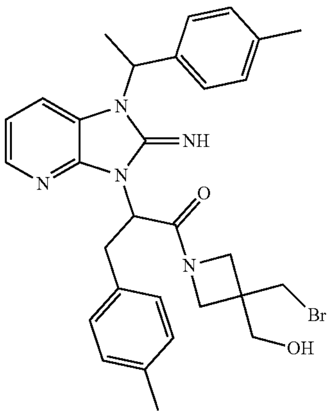 | WZ-II-208-2 | 4.61 | 4.87 | 83.23 | 657.45 | 2 | 6.59 | + | 13 | diastereomer 1 |
| 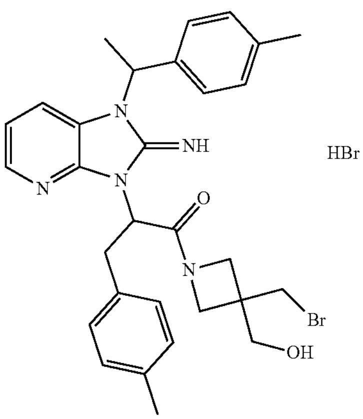 [SMILES: Cc1ccc(CC(C(=O)N2CC(CO)(CBr)C2)n2c(=N)n(C(C)c3ccc(C)cc3)c3cccnc32)cc1 ; Br] | WZ-II-209-2 | 4.61 | 4.87 | 83.23 | 657.45 | 2 | 6.59 | +++ | 13 | diastereomer 2 |
| 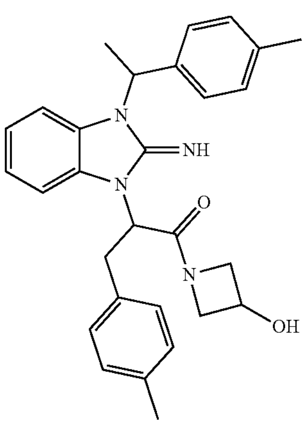 [SMILES: Cc1ccc(CC(C(=O)N2CC(C#N)C2)n2c(=N)n(C(C)c3ccc(C)cc3)c3ccccc32)cc1] | WZ-II-229 | 6.29 | 3.65 | 70.87 | 549.51 | 2 | 8.67 | +++ | 14 | mixture of diastereomers |
| 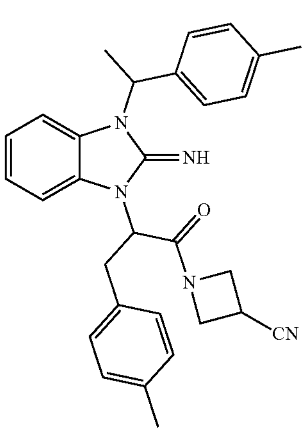 | WZ-II-230 | 6.52 | 4.06 | 74.43 | FALSE | 1 | 8.61 | ++++ | 14 | mixture of diastereomers |

TABLE 1-continued
| Structure | Compound | | | | | | | | Notes |
|---|---|---|---|---|---|---|---|---|---|
| 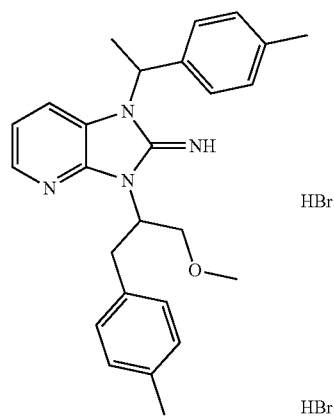 [SMILES: COCC(Cc1ccc(C)cc1)n1c(=N)n(C(C)c2ccc(C)cc2)c2cccnc21 ; Br ; Br] HBr | WZ-II-231 | 5.31 | 5.38 | 51.92 | 495.46 | 1 | 7.56 | +++ 14 | diastereomer 2; diastereomer of WZ-II-149; |
| 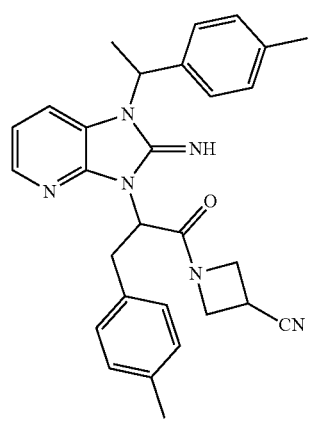 [SMILES: Cc1ccc(CC(C(=O)N2CC(C#N)C2)n2c(=N)n(C(C)c3ccc(C)cc3)c3cccnc32)cc1] | WZ-II-252 | 5.02 | 4.52 | 86.79 | 559.51 | 1 | 6.9 | +++ 15 | diastereomer 1 |
| 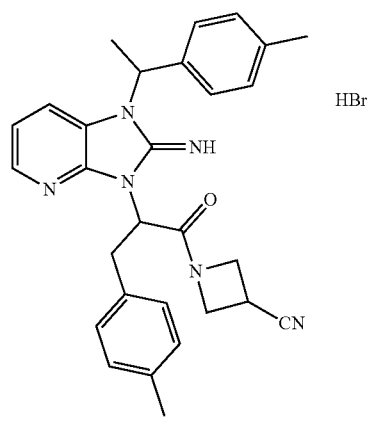 [SMILES: Cc1ccc(CC(C(=O)N2CC(C#N)C2)n2c(=N)n(C(C)c3ccc(C)cc3)c3cccnc32)cc1 ; Br] HBr | WZ-II-253 | 5.02 | 4.52 | 86.79 | 559.51 | 1 | 6.9 | ++++ 15 | Plasma PK (5 mg/Kg IV) T1/2: 40 min, Tmax 10 min, Cmax 651 ng/mL, AUClast 31089 min*ng/ml, Vz_F_obs 221 mL, Cl_F_obs 3.86 mL/min; Brain PK (5 mg/Kg IV), T1/2: 47 min, Tmax 10 min, Cmax 218 ng/mL, AUClast 12554 min*ng/ml, Vz_F_obs 642 mL, Cl_F_obs 9.5 mL/min; diastereomer 2 |

TABLE 1-continued
| | Compound | | | | | | | | | |
|---|---|---|---|---|---|---|---|---|---|---|
| 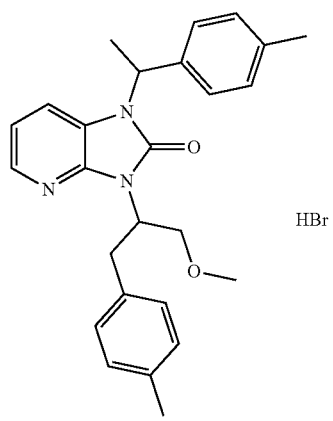 [SMILES: COCC(Cc1ccc(C)cc1)n1c(=O)n(C(C)c2ccc(C)cc2)c2cccnc21 ; Br] | WZ-II-264 | 5.55 | 5.81 | 45.14 | 496.45 | 0 | N/A | — | 16 | single diastereomer |
| 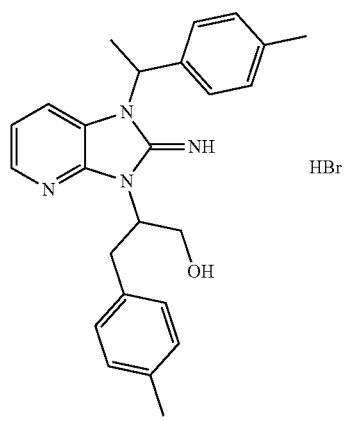 [SMILES: Cc1ccc(CC(CO)n2c(=N)n(C(C)c3ccc(C)cc3)c3cccnc32)cc1 ; Br] | WZ-II-269 | 4.55 | 4.9 | 62.92 | 481.44 | 2 | 7.23 | + | 17 | diastereomer 1 |
| 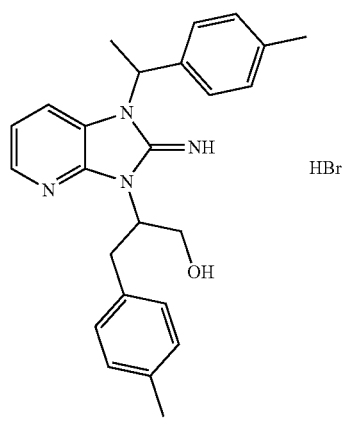 [SMILES: Cc1ccc(CC(CO)n2c(=N)n(C(C)c3ccc(C)cc3)c3cccnc32)cc1 ; Br] | WZ-II-270 | 4.55 | 4.9 | 62.92 | 481.44 | 2 | 7.23 | + | 17 | diastereomer 2 |

TABLE 1-continued

| Structure | Name | | | | | | | | | Notes |
|---|---|---|---|---|---|---|---|---|---|---|
| 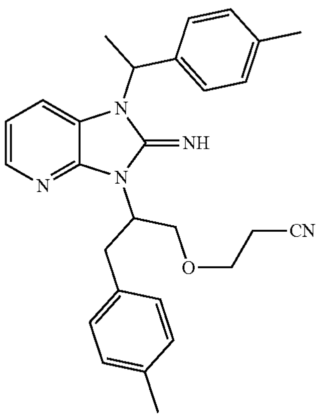 [SMILES: Cc1ccc(CC(COCCC#N)n2c(=N)n(C(C)c3ccc(C)cc3)c3cccnc32)cc1] | WZ-III-10 | 4.92 | 5.22 | 75.71 | 534.5 | 1 | 7.45 | + | 18 | diastereomer 1 |
| | WZ-III-11 · HBr | 4.92 | 5.22 | 75.71 | 534.5 | 1 | 7.45 | ++++ | 18 | diastereomer 2 |
| 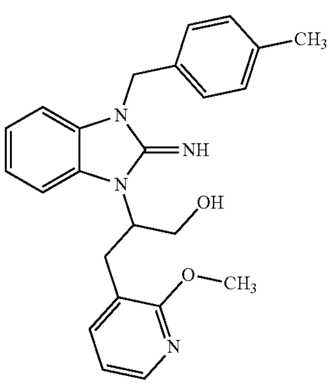 [SMILES: COc1ncccc1CC(CO)n1c(=N)n(Cc2ccc(C)cc2)c2ccccc21] | ARN-1-17 | 4.56221 | 2.46 | 72.15 | 402.49 | 2 | 9.04 | — | 1 | |
| 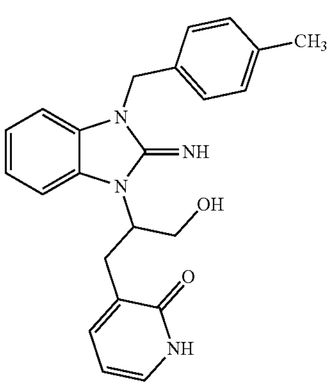 [SMILES: Cc1ccc(Cn2c(=N)n(C(CO)Cc3ccc[nH]c3=O)c3ccccc32)cc1] | ARN-1-19 | 2.52521 | 0.69 | 79.66 | 388.46 | 3 | 9.2 | — | 1 | |

TABLE 1-continued

| Structure | Name | | | | | | | | |
|---|---|---|---|---|---|---|---|---|---|
| (structure) | ARN-1-28 | 4.56221 | 2.51 | 72.15 | 402.49 | 2 | 8.98 | + | 1 |
| (structure) | ARN-1-29 | 2.52521 | 0.9 | 79.66 | 388.46 | 3 | 9.17 | — | 1 |
| (structure) | ARN-1-37 | 4.28221 | 2.7 | 72.15 | 412.4837 | 2 | 8.93 | — | |
| (structure) | ARN-1-85 | 4.73942 | 2.08 | 70.79 | 387.47 | 3 | 8.96 | + | Same as ARN-110 |

TABLE 1-continued
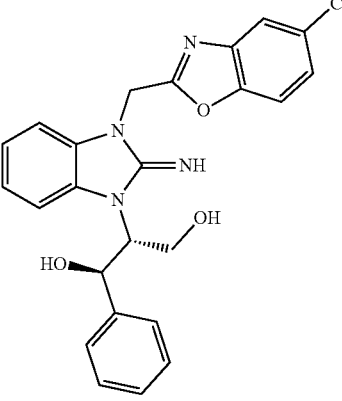
| Compound | | | | | | | |
|---|---|---|---|---|---|---|---|
| ARN-1-99 | 4.28942 | 2.73 | 92.38 | 448.1 | 3 | 7.99 | — | |
| ARN-1-110 | 4.73942 | 2.08 | 70.79 | 387.47 | 3 | 8.96 | + | Same as ARN-85 |
| ARN-1-163 | 5.99661 | 3.67 | 39.56 | 385.5 | 1 | 9.31 | + | |
| ARN-1-174 | 4.99861 | 2.7 | 51.92 | 400.51 | 1 | 9.11 | — | named as ARN-173 in active assignment summary; |

TABLE 1-continued

| Structure | ID | | | | | | | | |
|---|---|---|---|---|---|---|---|---|---|
| (benzimidazole imine with CH3-benzyl, OMe, HO, phenyl) | ARN-1-199 | 4.90082 | 3.01 | 59.79 | 401.5 | 2 | 8.99 | — | 4 |
| (benzimidazole imine with CH3-benzyl, OMe, HO, phenyl) | ARN-1-212 | 4.90082 | 3.01 | 59.79 | 401.5 | 2 | 8.99 | + | 4 |
| (benzimidazole imine with 6-methylpyridin-2-ylmethyl, OMe, 4-methylbenzyl) | ARN-1-223 | 4.99861 | 2.98 | 51.92 | 400.51 | 1 | 8.92 | + | 4 |
| (benzimidazole imine with 6-methylpyridin-3-ylmethyl, OMe, 4-methylbenzyl) | ARN-1-229 | 4.99861 | 2.75 | 51.92 | 400.51 | 1 | 9.09 | — | 4 |

TABLE 1-continued
| | | | | | | | |
|---|---|---|---|---|---|---|---|
| 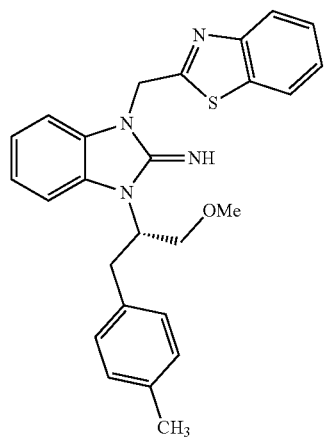 [SMILES: COC[C@H](Cc1ccc(C)cc1)n1c(=N)n(Cc2nc3ccccc3s2)c2ccccc21] | ARN-1-237 | 5.93461 | 4.4 | 51.92 | 442.57 | 1 | 8.69 | ++ |
| 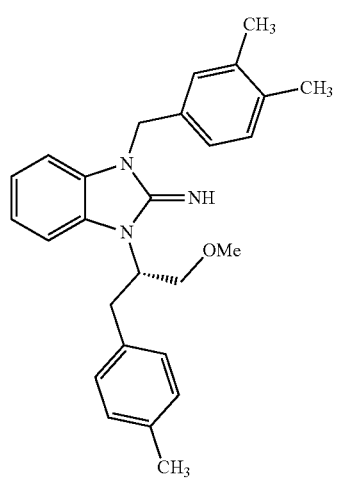 [SMILES: COC[C@H](Cc1ccc(C)cc1)n1c(=N)n(Cc2ccc(C)c(C)c2)c2ccccc21] | ARN-1-238 | 6.94461 | 4.74 | 39.56 | 413.57 | 1 | 9.25 | + |
| 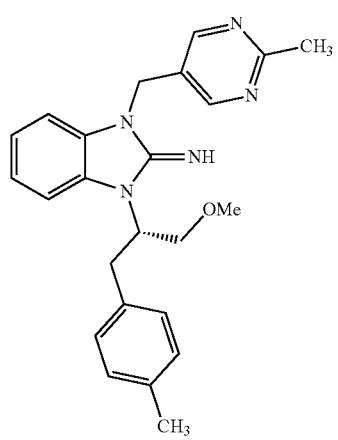 [SMILES: COC[C@H](Cc1ccc(C)cc1)n1c(=N)n(Cc2cnc(C)nc2)c2ccccc21] | ARN-1-243 | 4.04161 | 3 | 64.28 | 401.5 | 1 | 8.96 | + |

TABLE 1-continued
| | | | | | | | | | |
|---|---|---|---|---|---|---|---|---|---|
| 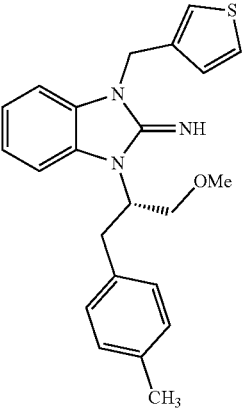 [SMILES: COC[C@H](Cc1ccc(C)cc1)n1c(=N)n(Cc2ccsc2)c2ccccc21] | ARN-1-255 | 5.64261 | 3.6 | 39.56 | 391.53 | 1 | 9.12 | + | 6 |
| 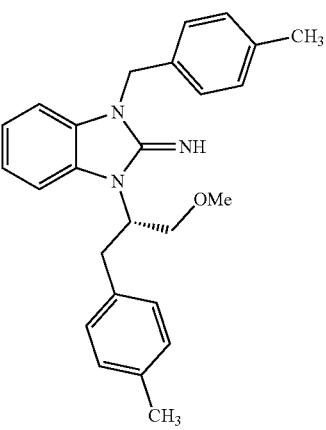 | ARN-1-256 (568, 574) | 6.49561 | 4.23 | 39.56 | 399.53 | 1 | 9.25 | ++ | 6 | Papp A-->B: 7.37; Papp B-->A: 4.91; Efflux ratio: 0.67; aka ARN-1-568 and ARN-1-574 |
| 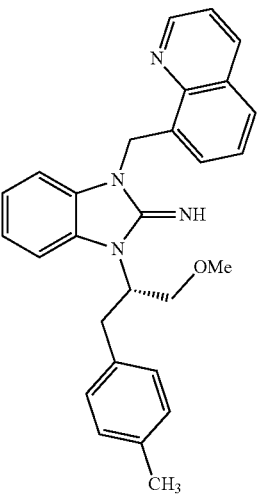 [SMILES: COC[C@H](Cc1ccc(C)cc1)n1c(=N)n(Cc2cccc3cccnc23)c2ccccc21] | ARN-1-260 | 5.88361 | 3.87 | 51.92 | 436.55 | 1 | 9.25 | — | 6 |

TABLE 1-continued
| | Compound | | | | | | | |
|---|---|---|---|---|---|---|---|---|
| 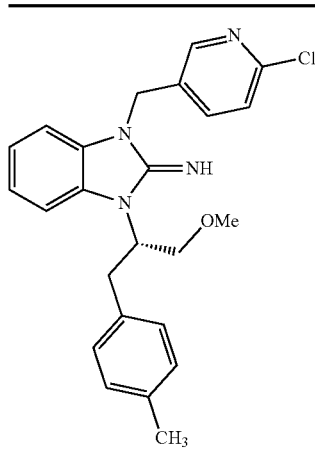 | ARN-1-265 | 5.29661 | 3.64 | 51.92 | 420.93 | 1 | 8.87 | ++ | |
| 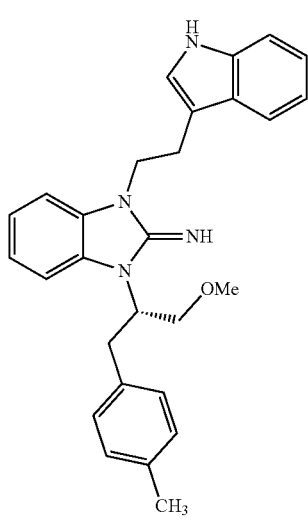 [SMILES: COC[C@H](Cc1ccc(C)cc1)n1c(=N)n(CCc2c[nH]c3ccccc23)c2ccccc21] | ARN-1-267 | 6.36161 | 3.96 | 51.59 | 438.56 | 1 | 9.44 | + | <90% pure, broad peak in nmr |
| 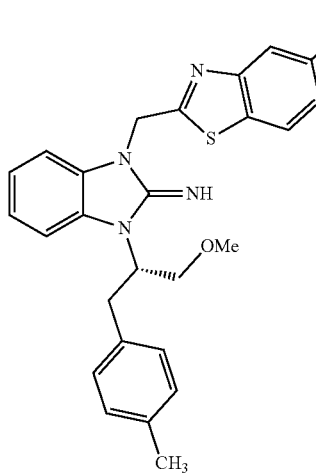 | ARN-1-269 | 6.67492 | 5.19 | 51.92 | 477.02 | 1 | 8.48 | + | |

TABLE 1-continued
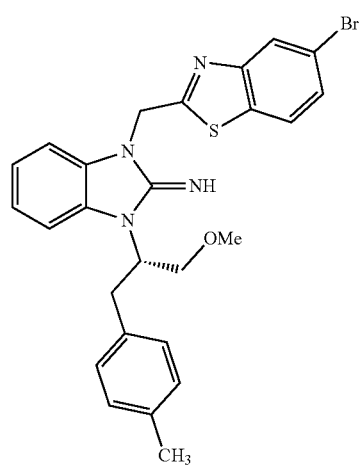 [SMILES: COC[C@H](Cc1ccc(C)cc1)n1c(=N)n(Cc2nc3cc(Br)ccc3s2)c2ccccc21]
ARN-1-279    6.82492    5.49    51.92    521.47    1    8.32    —
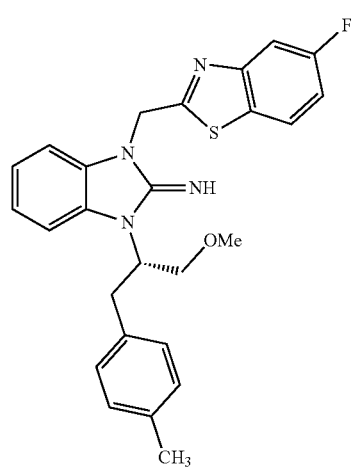 [SMILES: COC[C@H](Cc1ccc(C)cc1)n1c(=N)n(Cc2nc3cc(F)ccc3s2)c2ccccc21]
ARN-1-284    6.10492    4.67    51.92    460.56    1    8.55    +
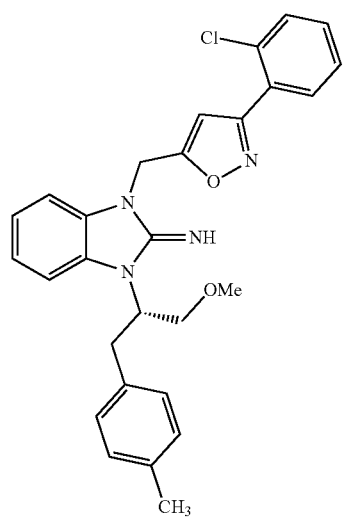 [SMILES: COC[C@H](Cc1ccc(C)cc1)n1c(=N)n(Cc2cc(-c3ccccc3Cl)no2)c2ccccc21]
ARN-1-288    6.56755    5.39    61.15    486.99    1    8.37    —

TABLE 1-continued
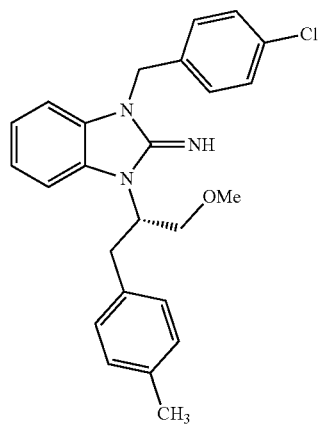 [SMILES: COC[C@H](Cc1ccc(C)cc1)n1c(=N)n(Cc2ccc(Cl)cc2)c2ccccc21]
| | | | | | | | |
|---|---|---|---|---|---|---|---|
| ARN-1-303 | 6.70961 | 4.51 | 39.56 | 419.94 | 1 | 9.01 | ++ |
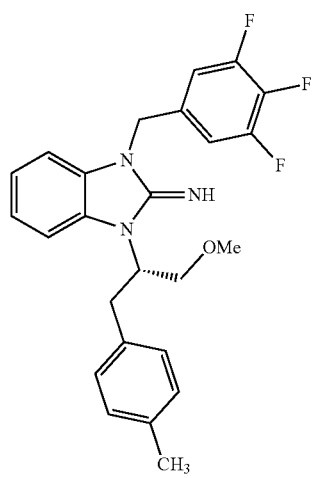 [SMILES: COC[C@H](Cc1ccc(C)cc1)n1c(=N)n(Cc2cc(F)c(F)c(F)c2)c2ccccc21]
| | | | | | | | |
|---|---|---|---|---|---|---|---|
| ARN-1-306 | 6.28561 | 4.83 | 39.56 | 439.47 | 1 | 8.72 | — |
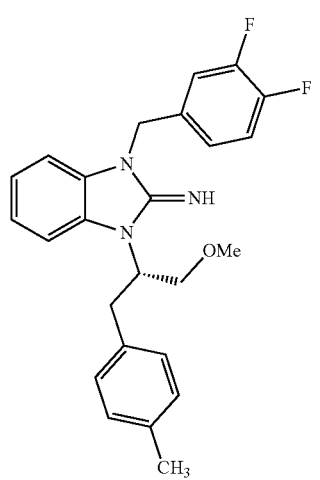 [SMILES: COC[C@H](Cc1ccc(C)cc1)n1c(=N)n(Cc2ccc(F)c(F)c2)c2ccccc21]
| | | | | | | | |
|---|---|---|---|---|---|---|---|
| ARN-1-307 | 6.21261 | 4.29 | 39.56 | 421.48 | 1 | 8.89 | + |

TABLE 1-continued
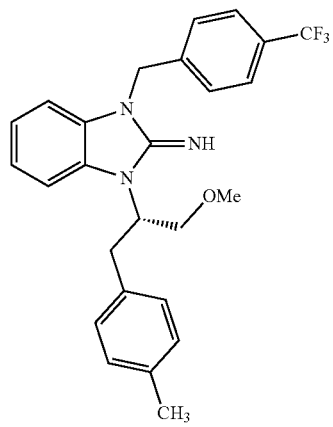 [SMILES: COC[C@H](Cc1ccc(C)cc1)n1c(=N)n(Cc2ccc(C(F)(F)F)cc2)c2ccccc21]
ARN-1-311  6.87961  4.9  39.56  453.5  1  8.87  ++  8  data only
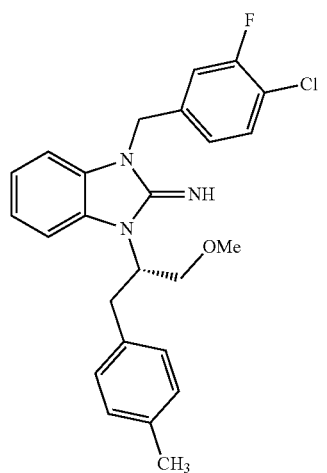
ARN-1-312  6.85261  4.81  39.56  437.67  1  8.83  ++  8  data only
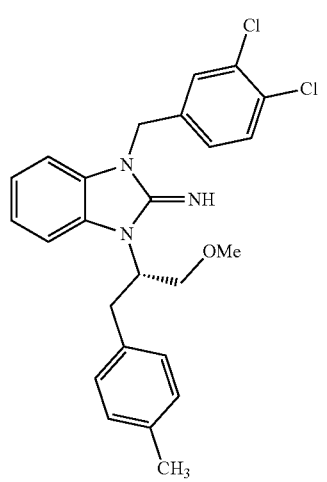 [SMILES: COC[C@H](Cc1ccc(C)cc1)n1c(=N)n(Cc2ccc(Cl)c(Cl)c2)c2ccccc21]
ARN-1-313  7.30261  5.31  39.56  454.39  1  8.79  ++  8  data only TABLE 1-continued
| | | | | | | | | | |
|---|---|---|---|---|---|---|---|---|---|
| 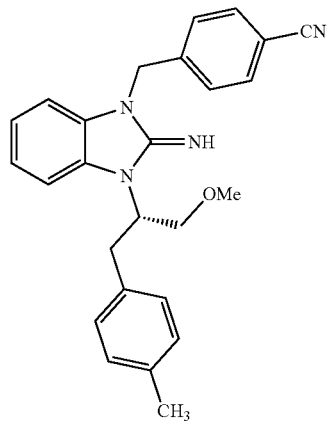 [SMILES: COC[C@H](Cc1ccc(C)cc1)n1c(=N)n(Cc2ccc(C#N)cc2)c2ccccc21] | ARN-1-316 | 5.42961 | 3.71 | 63.35 | 410.51 | 1 | 9.07 | + | 8 data only |
| 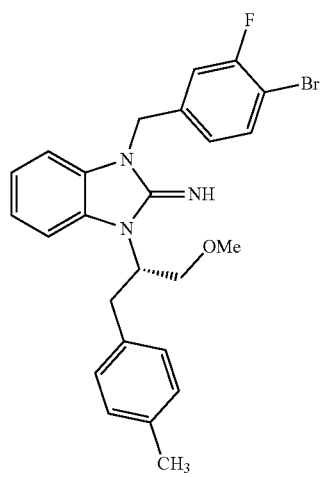 [SMILES: COC[C@H](Cc1ccc(C)cc1)n1c(=N)n(Cc2ccc(Br)c(F)c2)c2ccccc21] | ARN-1-317 | 7.00261 | 5.11 | 39.56 | 482.38 | 1 | 8.68 | ++ | 8 data only |
| 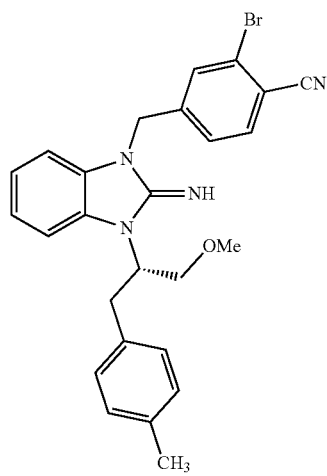 [SMILES: COC[C@H](Cc1ccc(C)cc1)n1c(=N)n(Cc2ccc(C#N)c(Br)c2)c2ccccc21] | ARN-1-320 | 6.29261 | 4.79 | 63.35 | 489.41 | 1 | 8.72 | — | 9 |

| | | | | | | | | |
|---|---|---|---|---|---|---|---|---|
| 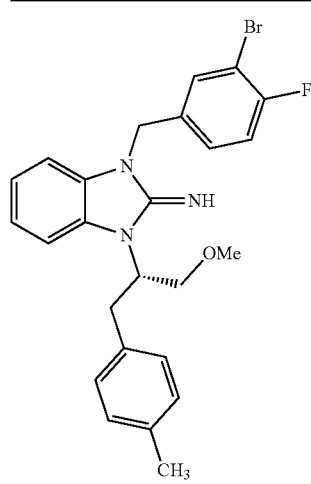 | ARN-1-321 | 7.00261 | 5.07 | 39.56 | 482.38 | 1 | 8.72 | + | 9 |
| 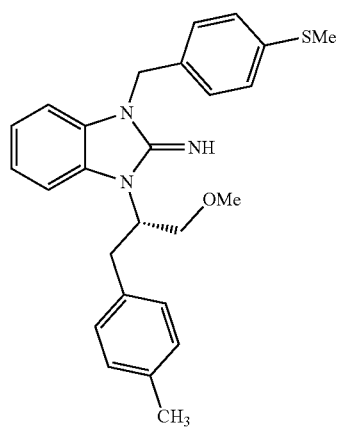 [SMILES: COC[C@H](Cc1ccc(C)cc1)n1c(=N)n(Cc2ccc(SC)cc2)c2ccccc21] | ARN-1-328 | 6.55561 | 4.51 | 39.56 | 431.59 | 1 | 9.05 | ++ | 10 |
| 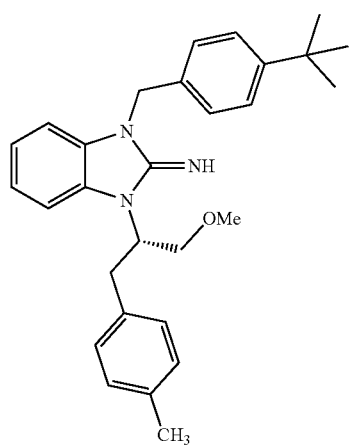 [SMILES: COC[C@H](Cc1ccc(C)cc1)n1c(=N)n(Cc2ccc(C(C)(C)C)cc2)c2ccccc21] | ARN-1-333 | 7.82261 | 5.4 | 39.56 | 441.61 | 1 | 9.07 | ++ | 10 |

TABLE 1-continued

| Structure | Compound | | | | | | | |
|---|---|---|---|---|---|---|---|---|
| (4-OCF₃ benzyl benzimidazol-2-imine with (S)-1-methoxy-3-(4-methylphenyl)propan-2-yl) | ARN-1-337 | 7.02461 | 5.53 | 48.79 | 469.5 | 1 | 8.78 | + | 10 |
| (3-CN benzyl benzimidazol-2-imine with (S)-1-methoxy-3-(4-methylphenyl)propan-2-yl) | ARN-1-338 | 5.42961 | 3.7 | 63.35 | 410.51 | 1 | 9.09 | ++ | 10 |
| (3-CH₃ benzyl benzimidazol-2-imine with (S)-1-methoxy-3-(4-methylphenyl)propan-2-yl) | ARN-1-344 | 6.87961 | 4.87 | 39.56 | 453.5 | 1 | 8.91 | + |

TABLE 1-continued
| | | | | | | | | |
|---|---|---|---|---|---|---|---|---|
| 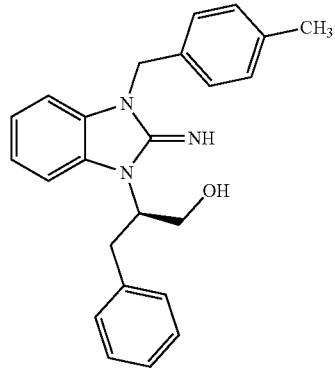 [SMILES: Cc1ccc(Cn2c(=N)n([C@@H](CO)Cc3ccccc3)c3ccccc32)cc1] | ARN-1-350 | 2.52521 | 3.05 | 79.66 | 371.47 | 2 | 9.28 | + |
| 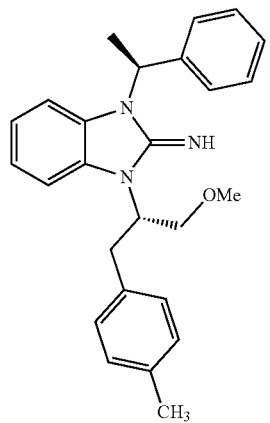 [SMILES: COC[C@H](Cc1ccc(C)cc1)n1c(=N)n([C@@H](C)c2ccccc2)c2ccccc21] | ARN-1-353 | 6.30561 | 4.08 | 39.56 | 399.2 | 1 | 9.32 | ++ | 12 |
| 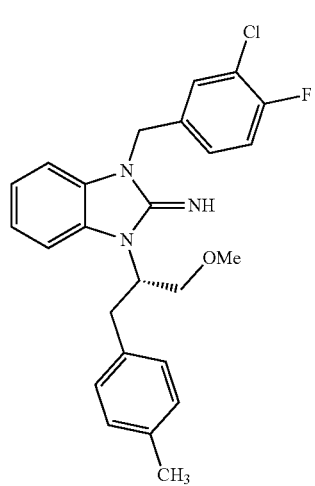 | ARN-1-362 | 6.85261 | 4.8 | 39.56 | 437.2 | 1 | 8.84 | + | 12 |

TABLE 1-continued
| | | | | | | | | |
|---|---|---|---|---|---|---|---|---|
| 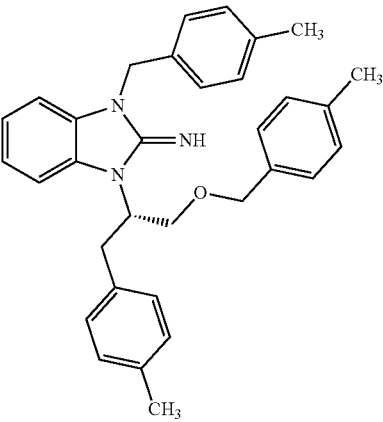 [SMILES: Cc1ccc(COC[C@H](Cc2ccc(C)cc2)n2c(=N)n(Cc3ccc(C)cc3)c3ccccc32)cc1] | ARN-1-366 | 8.74601 | 6.64 | 39.56 | 489.3 | 1 | 9.03 | + | 13 |
| 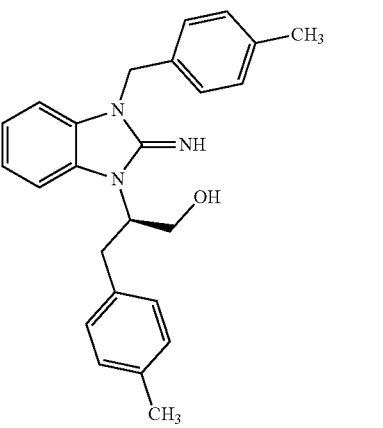 [SMILES: Cc1ccc(C[C@H](CO)n2c(=N)n(Cc3ccc(C)cc3)c3ccccc32)cc1] | ARN-1-374 | 5.73821 | 3.61 | 50.56 | 385.2 | 2 | 9.22 | + | 14 |
| 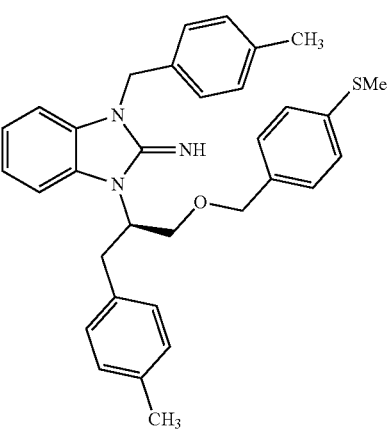 [SMILES: CSc1ccc(COC[C@@H](Cc2ccc(C)cc2)n2c(=N)n(Cc3ccc(C)cc3)c3ccccc32)cc1] | ARN-1-375 | 8.80601 | 6.86 | 39.56 | 521.3 | 1 | 8.91 | + | 14 |

TABLE 1-continued
| | Compound | | | | | | | | | |
|---|---|---|---|---|---|---|---|---|---|---|
| 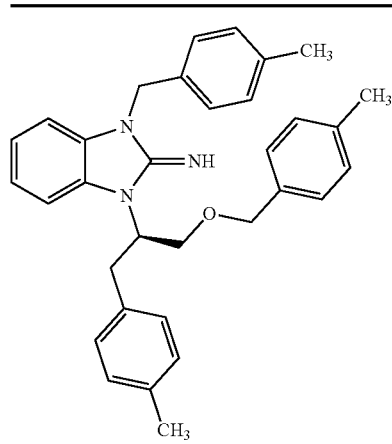 | ARN-1-376 | 8.74601 | 6.64 | 39.56 | 489.3 | 1 | 9.03 | | + | 14 | |
| 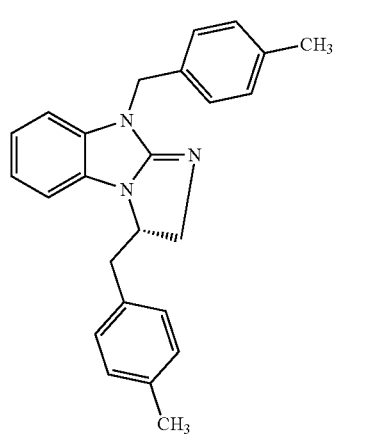 [SMILES: Cc1ccc(C[C@H]2CN=C3N(Cc4ccc(C)cc4)c4ccccc4N32)cc1] | ARN-1-387 | 6.454 | 5.37 | 18.84 | 367.2 | 0 | | | + | 15 | |
| 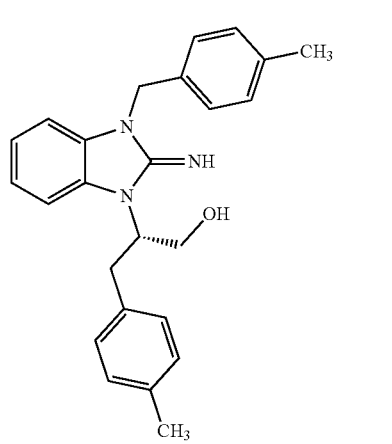 [SMILES: Cc1ccc(C[C@@H](CO)n2c(=N)n(Cc3ccc(C)cc3)c3ccccc32)cc1] | ARN-1-388 (525, 557) | 5.738 | 3.61 | 50.56 | 385.5 | 2 | 9.22 | ++ | 15 | aka ARN-1-525 and ARN-1-557 |

TABLE 1-continued
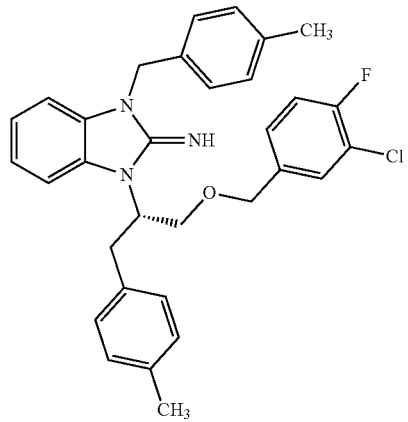 [SMILES: Cc1ccc(C[C@@H](COCc2ccc(F)c(Cl)c2)n2c(=N)n(Cc3ccc(C)cc3)c3ccccc32)cc1]
ARN-1-392   9.10301   7.11   39.56   527.2   1   8.76   +     15
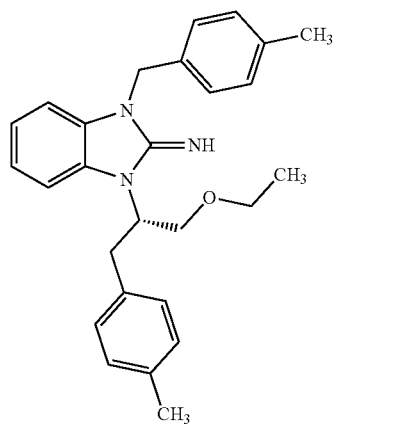 [SMILES: CCOC[C@H](Cc1ccc(C)cc1)n1c(=N)n(Cc2ccc(C)cc2)c2ccccc21]
ARN-1-409   6.88461   4.59   39.56   413.5   1   9.24   +++   16
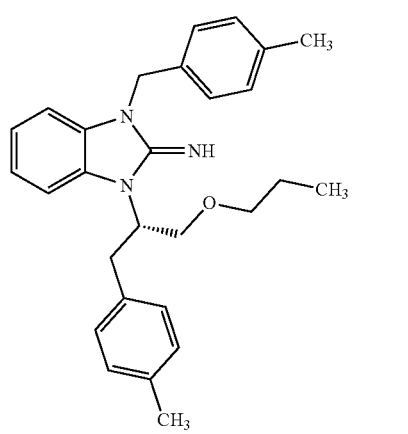 [SMILES: CCCOC[C@H](Cc1ccc(C)cc1)n1c(=N)n(Cc2ccc(C)cc2)c2ccccc21]
ARN-1-414   7.41361   5.14   39.56   427.3   1   9.21   ++    16

TABLE 1-continued
| | | | | | | | | |
|---|---|---|---|---|---|---|---|---|
| 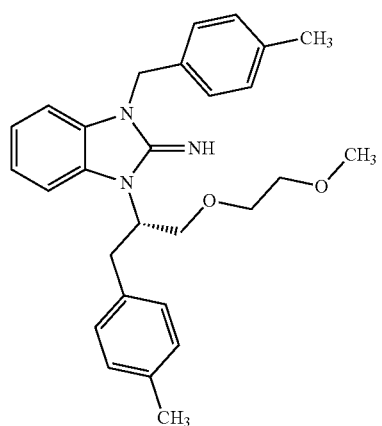 | ARN-1-422 | 6.36001 | 4.28 | 48.79 | 443.3 | 1 | 9.13 | +++ | 16 |
| 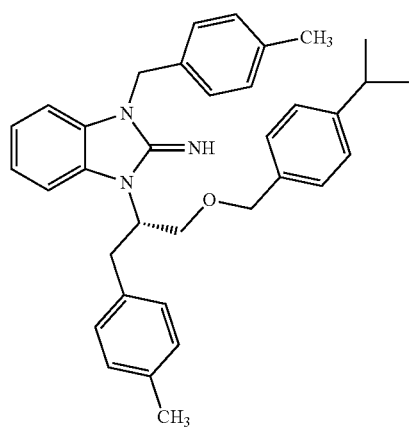 [SMILES: Cc1ccc(C[C@@H](COCc2ccc(C(C)C)cc2)n2c(=N)n(Cc3ccc(C)cc3)c3ccccc32)cc1] | ARN-1-424 | 9.67401 | 7.37 | 39.56 | 517.3 | 1 | 9.03 | + | |
| 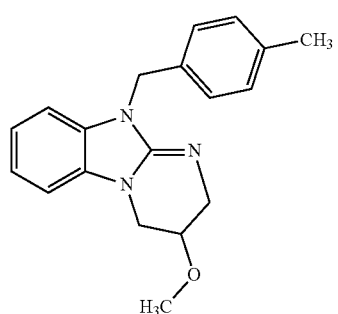 [SMILES: COC1CN=C2N(Cc3ccc(C)cc3)c3ccccc3N2C1] | ARN-1-441 | 4.71706 | 2.8 | 28.07 | 307.2 | 0 | | — | |
| 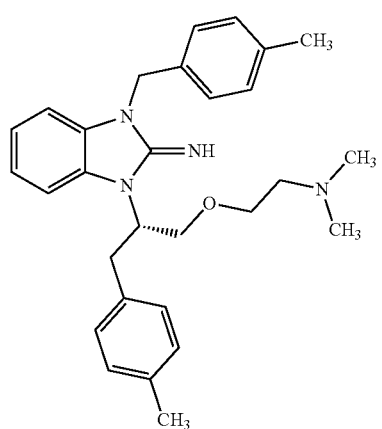 [SMILES: Cc1ccc(C[C@@H](COCCN(C)C)n2c(=N)n(Cc3ccc(C)cc3)c3ccccc32)cc1] | ARN-1-452 | 6.76901 | 2.95 | 42.8 | 456.6 | 1 | 9.3 | + | 18 |

TABLE 1-continued
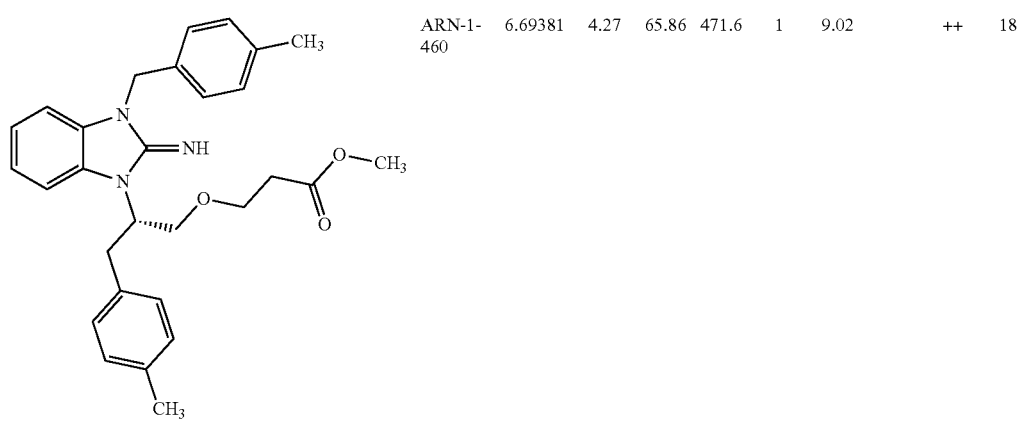
| | | | | | | | | |
|---|---|---|---|---|---|---|---|---|
| ARN-1-460 | 6.69381 | 4.27 | 65.86 | 471.6 | 1 | 9.02 | ++ | 18 |
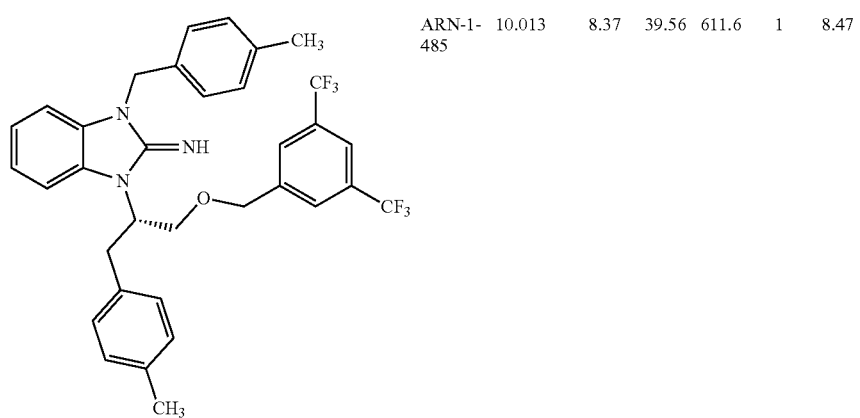
| | | | | | | | |
|---|---|---|---|---|---|---|---|
| ARN-1-485 | 10.013 | 8.37 | 39.56 | 611.6 | 1 | 8.47 | |
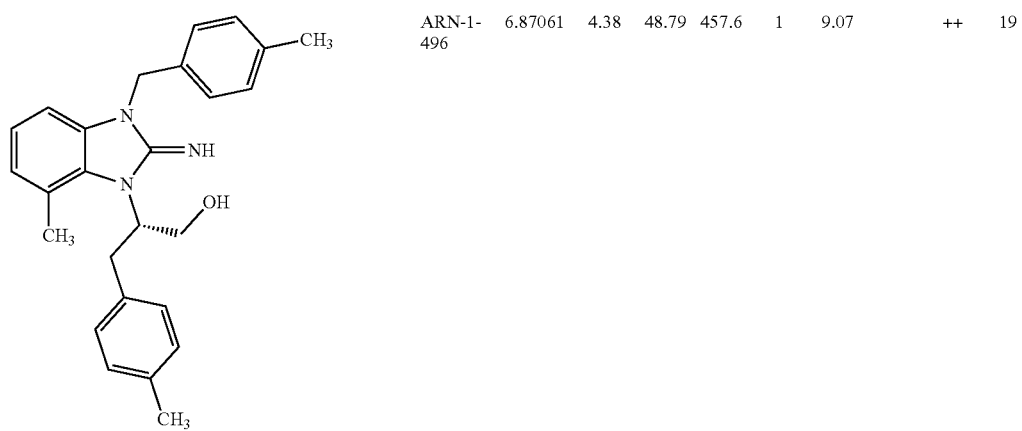
| | | | | | | | | |
|---|---|---|---|---|---|---|---|---|
| ARN-1-496 | 6.87061 | 4.38 | 48.79 | 457.6 | 1 | 9.07 | ++ | 19 |

TABLE 1-continued
| | | | | | | | | | |
|---|---|---|---|---|---|---|---|---|---|
| 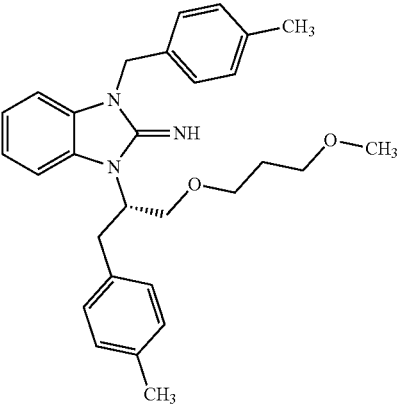 [SMILES: COCCCOC[C@H](Cc1ccc(C)cc1)n1c(=N)n(Cc2ccc(C)cc2)c2ccccc21] | ARN-1-524 | 6.23721 | 4.07 | 50.56 | 399.5 | 2 | 9.29 | + | 20 |
| 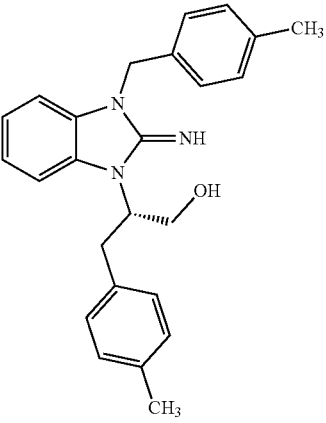 [SMILES: Cc1ccc(C[C@@H](CO)n2c(=N)n(Cc3ccc(C)cc3)c3ccccc32)cc1] | ARN-1-525 (388, 557) | 5.738 | 3.61 | 50.56 | 385.5 | 2 | 9.22 | ++ | 20 | AKA ARN-1-388 and ARN-1-557 |
| 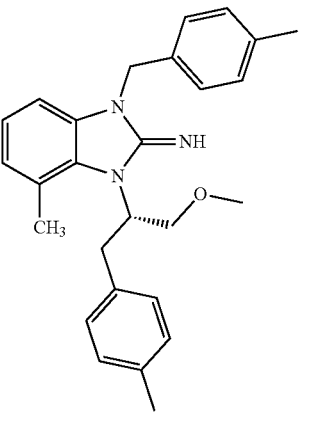 [SMILES: COC[C@H](Cc1ccc(C)cc1)n1c(=N)n(Cc2ccc(C)cc2)c2cccc(C)c21] | ARN-1-527 | 6.99461 | 4.69 | 39.56 | 413.5 | 1 | 9.32 | + | |

TABLE 1-continued
| Structure | Compound | | | | | | | | |
|---|---|---|---|---|---|---|---|---|---|
| 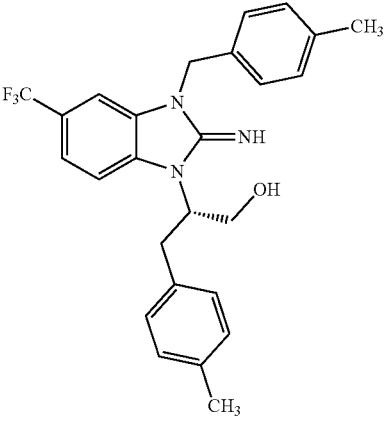 [SMILES: Cc1ccc(C[C@@H](CO)n2c(=N)n(Cc3ccc(C)cc3)c3cc(C(F)(F)F)ccc32)cc1] | ARN-1-528 | 6.62121 | 4.91 | 50.56 | 453.5 | 2 | 8.72 | + | 20 |
| 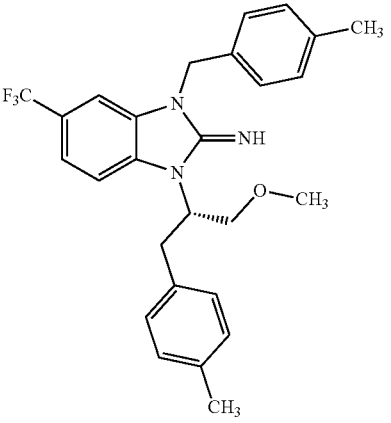 [SMILES: COC[C@H](Cc1ccc(C)cc1)n1c(=N)n(Cc2ccc(C)cc2)c2cc(C(F)(F)F)ccc21] | ARN-1-531 | 7.37861 | 4.8 | 39.56 | 467.5 | 1 | 8.76 | + | 20 |
| 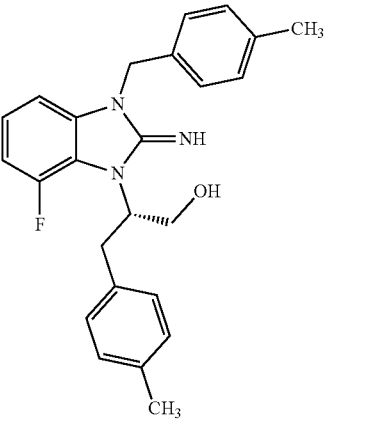 [SMILES: Cc1ccc(C[C@@H](CO)n2c(=N)n(Cc3ccc(C)cc3)c3cccc(F)c32)cc1] | ARN-1-535 | 5.88121 | 4.84 | 50.56 | 403.5 | 2 | 7.93 | ++ | 20 |

TABLE 1-continued

| Structure | Name | | | | | | | | Notes |
|---|---|---|---|---|---|---|---|---|---|
| (4-fluoro-benzimidazol-2-imine with methoxymethyl and p-tolyl substituents) | ARN-1-541 | 6.63861 | 5.46 | 39.56 | 417.5 | 1 | 7.97 | ++ | 21 |
| (5-methyl-benzimidazol-2-imine with hydroxymethyl and p-tolyl substituents) | ARN-1-545 | 6.23721 | 4.1 | 50.56 | 399.5 | 2 | 9.25 | + | 21 |
| (5-methyl-benzimidazol-2-(N-methyl)imine with methoxymethyl and p-tolyl substituents) | ARN-1-547 | 8.25461 | 5.97 | 28.07 | 481.5 | 0 | | + | 21 named as ARN-546 in graphic |

TABLE 1-continued
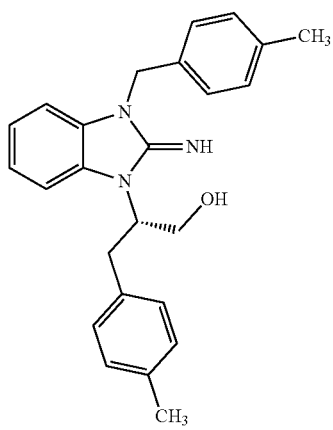 [SMILES: Cc1ccc(C[C@@H](CO)n2c(=N)n(Cc3ccc(C)cc3)c3ccccc32)cc1]
| | | | | | | | | | |
|---|---|---|---|---|---|---|---|---|---|
| ARN-1-557 (388, 525) | 5.738 | 3.61 | 50.56 | 385.5 | 2 | 9.22 | ++ | 22 | AKA ARN-1-388 and ARN-1-525 |
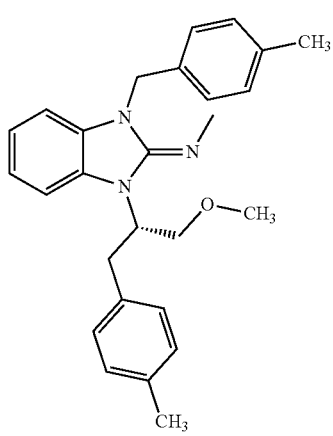 [SMILES: C/N=c1\n(Cc2ccc(C)cc2)c2ccccc2n1[C@H](COC)Cc1ccc(C)cc1]
| | | | | | | | | |
|---|---|---|---|---|---|---|---|---|
| ARN-1-567 | 7.37161 | 4.65 | 28.07 | 413.5 | 0 | | ++ | 22 |
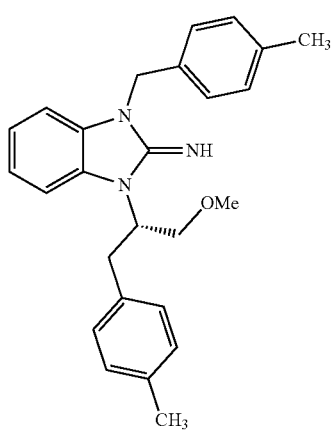 [SMILES: COC[C@H](Cc1ccc(C)cc1)n1c(=N)n(Cc2ccc(C)cc2)c2ccccc21]
| | | | | | | | | | |
|---|---|---|---|---|---|---|---|---|---|
| ARN-1-568 (574, 256) | 6.49561 | 4.23 | 39.56 | 399.53 | 1 | 9.25 | +++ | 22 | AKA ARN-1-256 and ARN-1-574 |

TABLE 1-continued
| Structure | Name | | | | | | | | Notes |
|---|---|---|---|---|---|---|---|---|---|
| 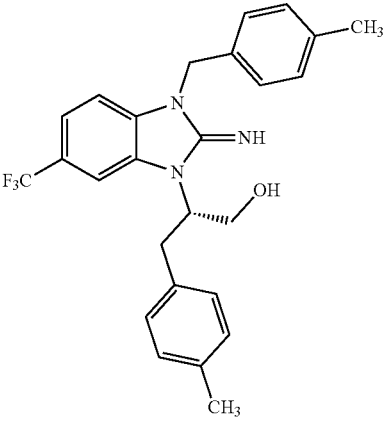 [SMILES: Cc1ccc(C[C@@H](CO)n2c(=N)n(Cc3ccc(C)cc3)c3ccc(C(F)(F)F)cc32)cc1] | ARN-1-572 | 6.62121 | 4.91 | 50.56 | 453.5 | 2 | 8.72 | + | 23 |
| 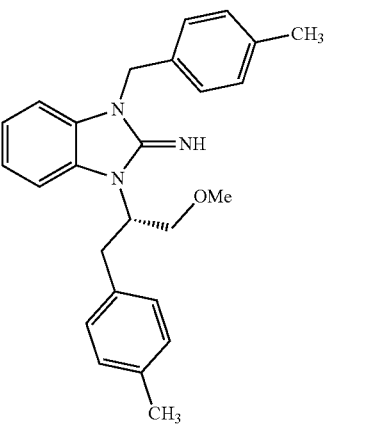 [SMILES: COC[C@H](Cc1ccc(C)cc1)n1c(=N)n(Cc2ccc(C)cc2)c2ccccc21] | ARN-1-574 (568, 256) | 6.49561 | 4.23 | 39.56 | 399.53 | 1 | 9.25 | +++ | 23 aka ARN-1-256 and ARN-1-568 |
| 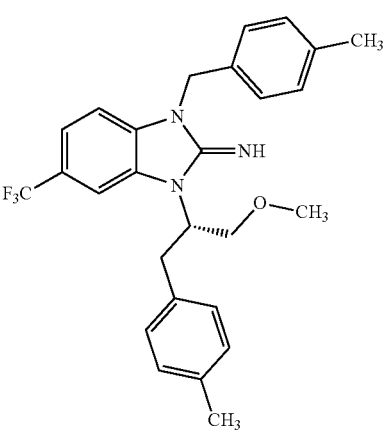 [SMILES: COC[C@H](Cc1ccc(C)cc1)n1c(=N)n(Cc2ccc(C)cc2)c2ccc(C(F)(F)F)cc21] | ARN-1-575 | 7.37861 | 5.51 | 39.56 | 467.5 | 1 | 8.76 | + | 23 |

TABLE 1-continued
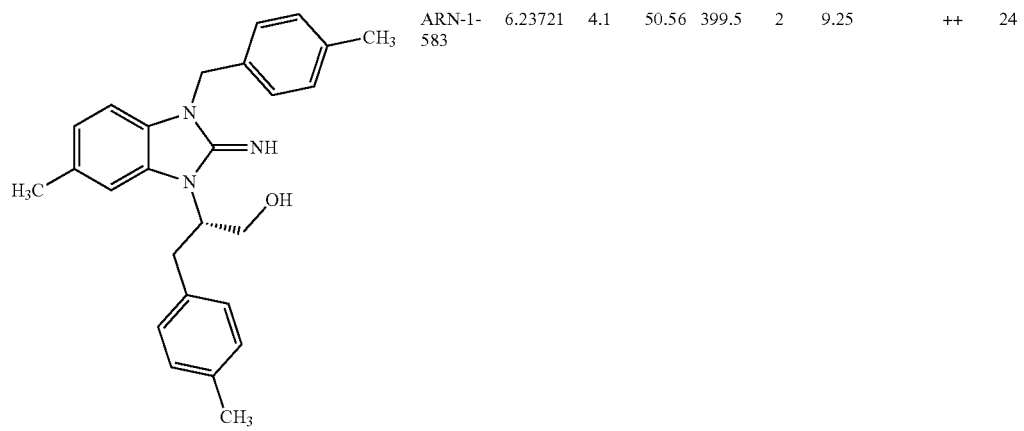
| | | | | | | | |
|---|---|---|---|---|---|---|---|
| ARN-1-583 | 6.23721 | 4.1 | 50.56 | 399.5 | 2 | 9.25 | ++ | 24 |
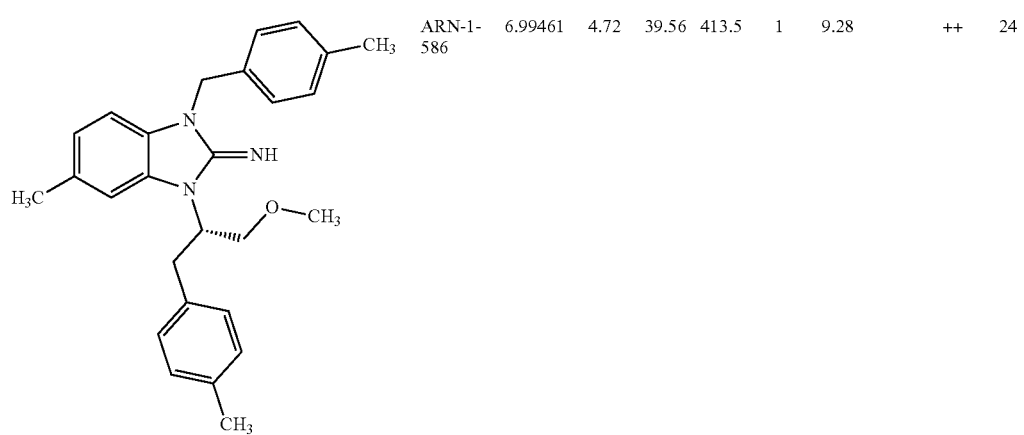
| | | | | | | | |
|---|---|---|---|---|---|---|---|
| ARN-1-586 | 6.99461 | 4.72 | 39.56 | 413.5 | 1 | 9.28 | ++ | 24 |
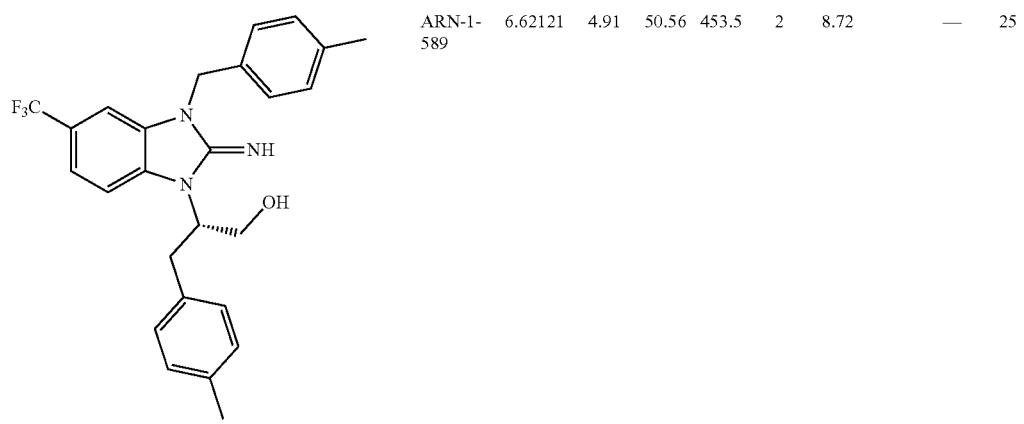
| | | | | | | | |
|---|---|---|---|---|---|---|---|
| ARN-1-589 | 6.62121 | 4.91 | 50.56 | 453.5 | 2 | 8.72 | — | 25 |

TABLE 1-continued
| Structure | Name | | | | | | | | |
|---|---|---|---|---|---|---|---|---|---|
| 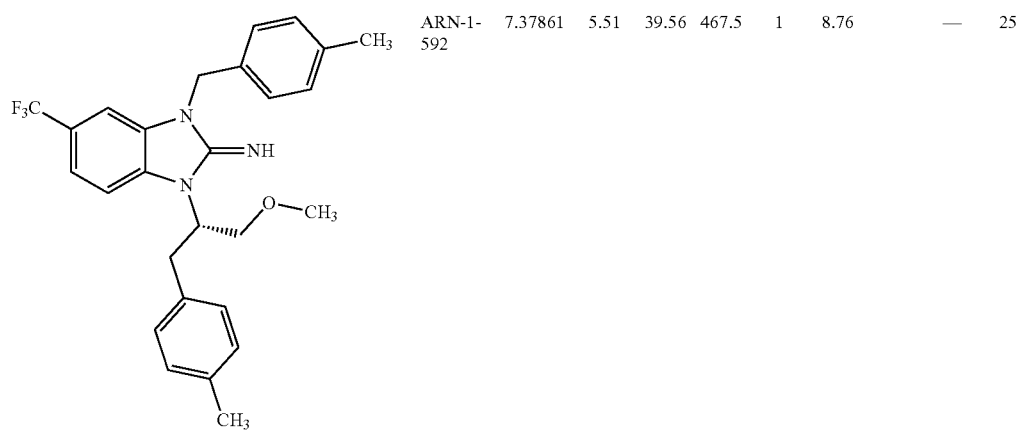 | ARN-1-592 | 7.37861 | 5.51 | 39.56 | 467.5 | 1 | 8.76 | — | 25 |
| 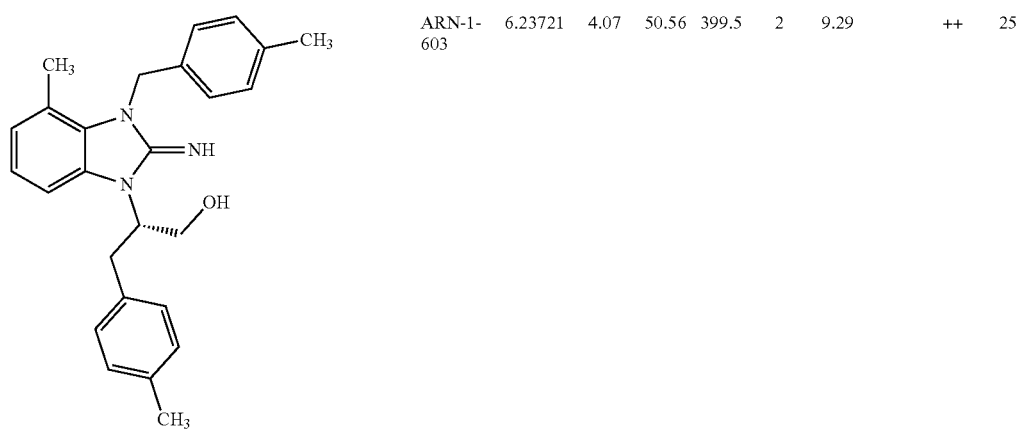 | ARN-1-603 | 6.23721 | 4.07 | 50.56 | 399.5 | 2 | 9.29 | ++ | 25 |
| 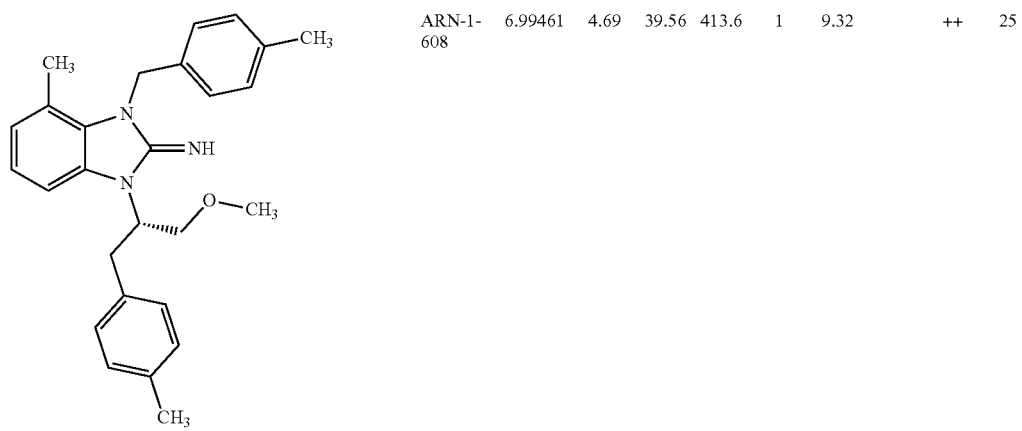 | ARN-1-608 | 6.99461 | 4.69 | 39.56 | 413.6 | 1 | 9.32 | ++ | 25 |

TABLE 1-continued
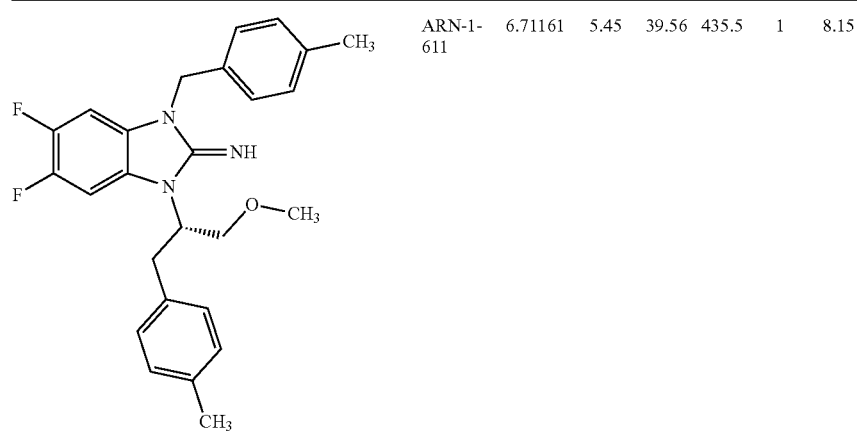
ARN-1-611  6.71161  5.45  39.56  435.5  1  8.15
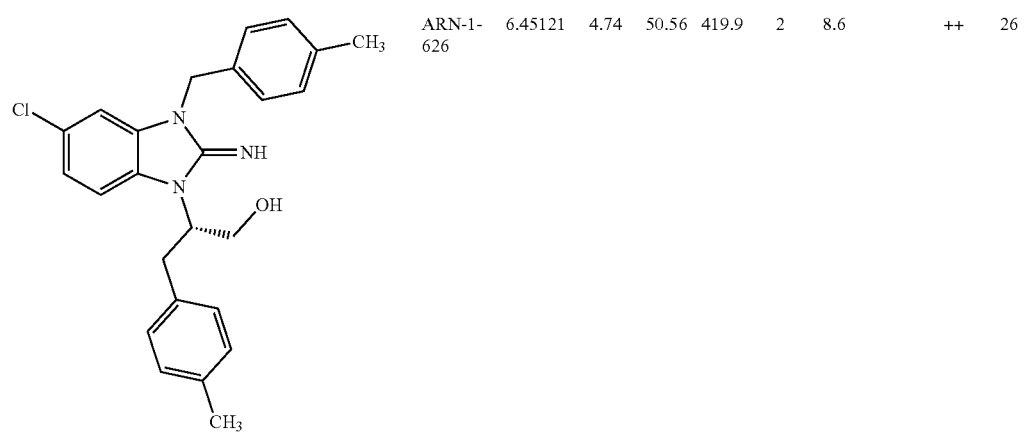
ARN-1-626  6.45121  4.74  50.56  419.9  2  8.6  ++  26
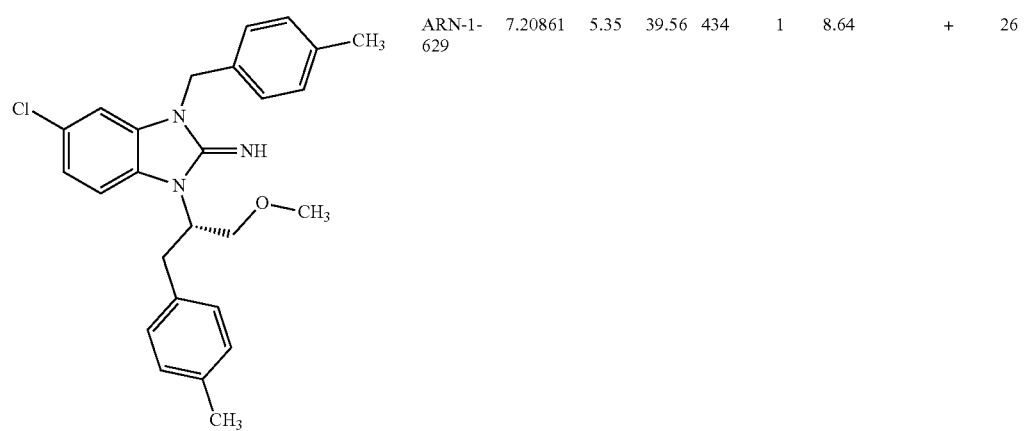
ARN-1-629  7.20861  5.35  39.56  434  1  8.64  +  26

TABLE 1-continued
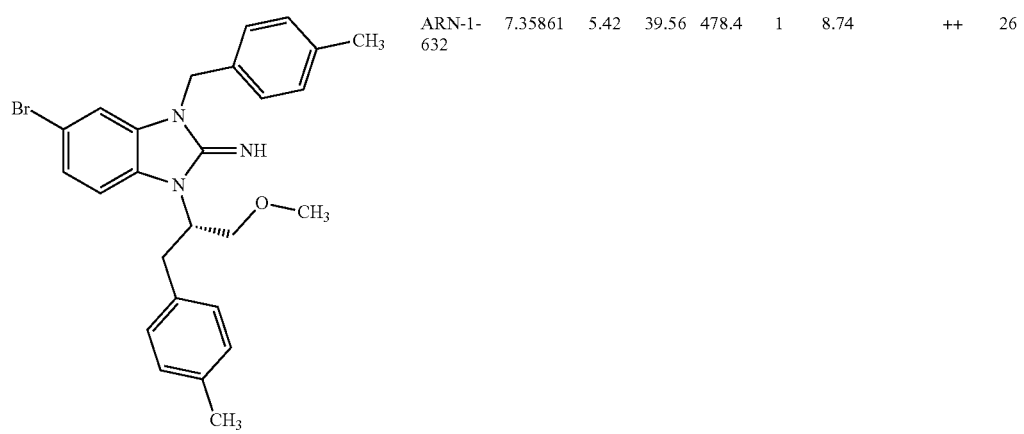
ARN-1-632  7.35861  5.42  39.56  478.4  1  8.74  ++  26
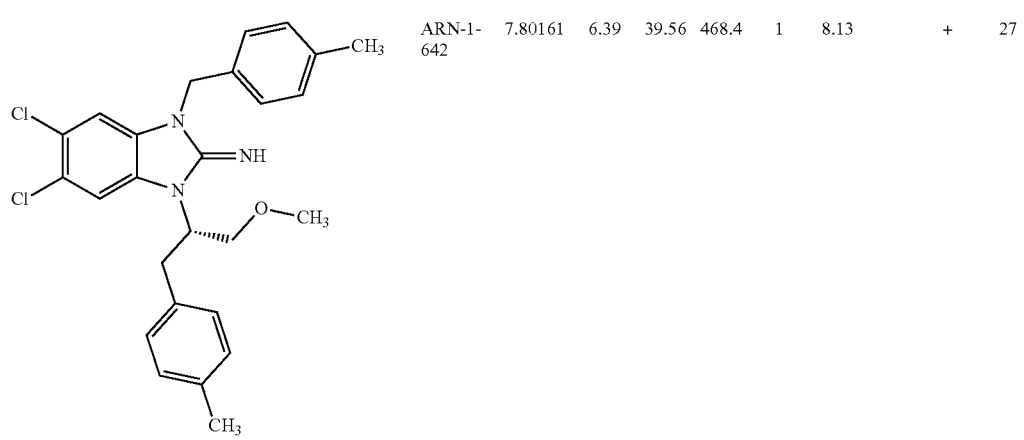
ARN-1-642  7.80161  6.39  39.56  468.4  1  8.13  +  27
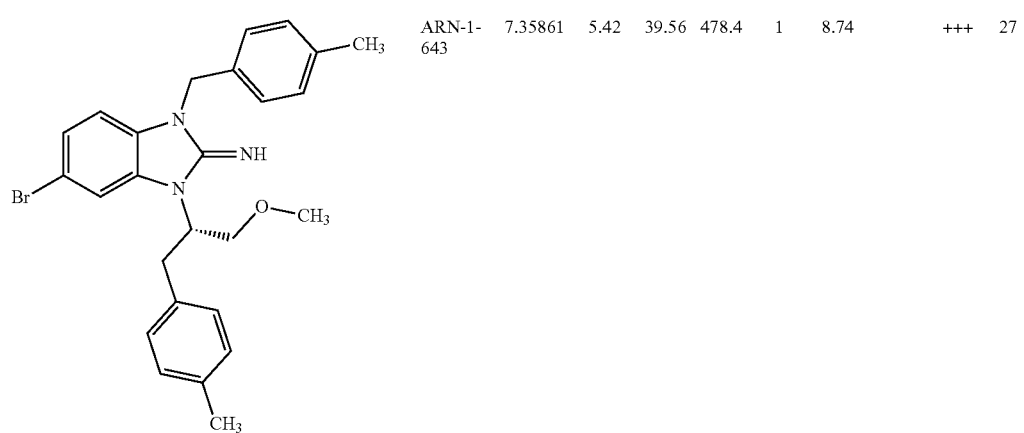
ARN-1-643  7.35861  5.42  39.56  478.4  1  8.74  +++  27

TABLE 1-continued
| | | | | | | | | | |
|---|---|---|---|---|---|---|---|---|---|
| 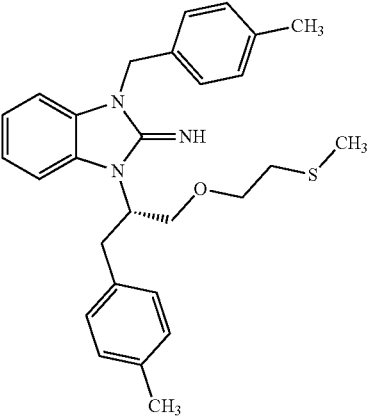 [SMILES: CSCCOC[C@H](Cc1ccc(C)cc1)n1c(=N)n(Cc2ccc(C)cc2)c2ccccc21] | ARN-1-757 | 7.18221 | 5.16 | 39.56 | 459.6 | 1 | 9.07 | + | 28 |
| 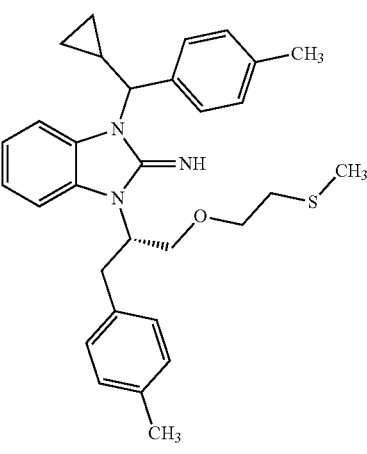 [SMILES: CSCCOC[C@H](Cc1ccc(C)cc1)n1c(=N)n(C(c2ccc(C)cc2)C2CC2)c2ccccc21] | ARN-1-761 | 7.93521 | 5.9 | 39.56 | 499.27 | 1 | 9.2 | + | 28 | Purity <80% Mixture DM |
| 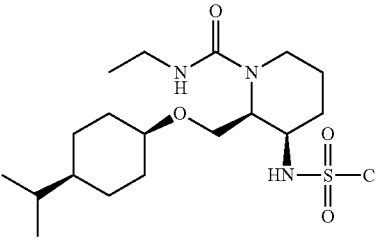 | ARN-1-770 | 3.9066 | 1.48 | 87.74 | 403.6 | 2 | | +++ | 29 |
| 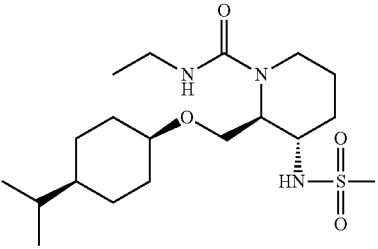 | ARN-1-771 | 3.9066 | 1.48 | 87.74 | 403.6 | 2 | | | |
| 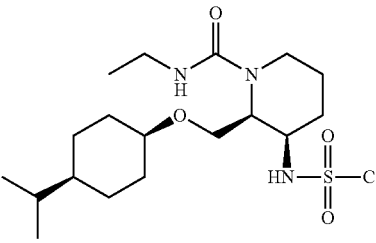 | ARN-1-776 | 3.9066 | 1.48 | 87.74 | 403.6 | 2 | | +++++ | 31 |

TABLE 1-continued
| | Name | | | | | | | | | |
|---|---|---|---|---|---|---|---|---|---|---|
| 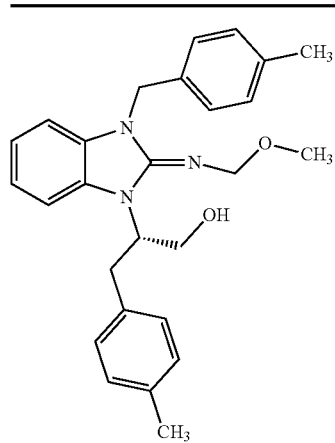 | ARN-1-795 | 6.62545 | 5.39 | 48.3 | 429.55 | 1 | | + | 29 | |
| 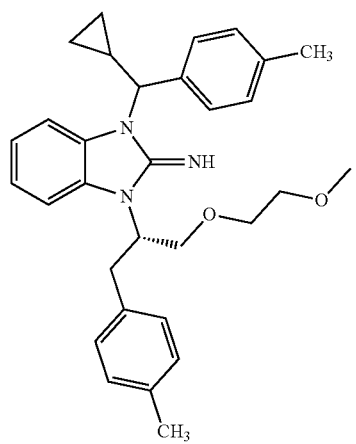 [SMILES: COCCOC[C@H](Cc1ccc(C)cc1)n1c(=N)n(C(c2ccc(C)cc2)C2CC2)c2ccccc21] | ARN-1-805 | 7.11301 | 5.02 | 48.79 | 483.6 | 1 | 9.25 | ++++ | 29 | Mixture of DM |
| 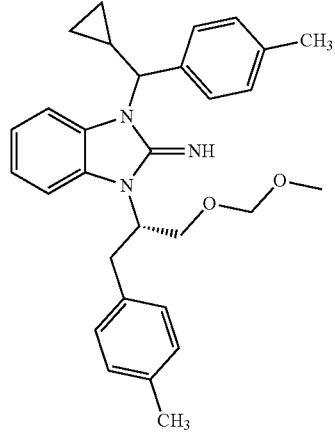 [SMILES: COCOC[C@H](Cc1ccc(C)cc1)n1c(=N)n(C(c2ccc(C)cc2)C2CC2)c2ccccc21] | ARN-1-826 | 7.00241 | 5.1 | 48.79 | 469.6 | 1 | 9.3 | +++ | 30 | Purity <80% Mixture of DM |

TABLE 1-continued
| Structure | Compound | | | | | | | | | Notes |
|---|---|---|---|---|---|---|---|---|---|---|
| 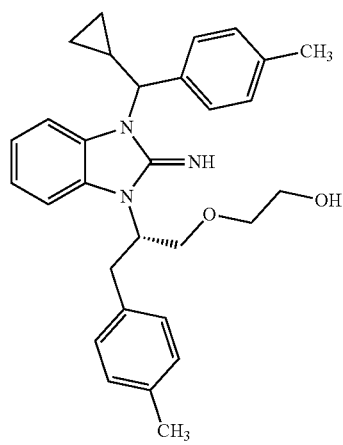 [SMILES: Cc1ccc(C[C@@H](COCCO)n2c(=N)n(C(c3ccc(C)cc3)C3CC3)c3ccccc32)cc1] | ARN-1-846 | 6.55 | 4.33 | 59.71 | 469.63 | 2 | 9.31 | +++ | 31 | named as ARN in graph |
| 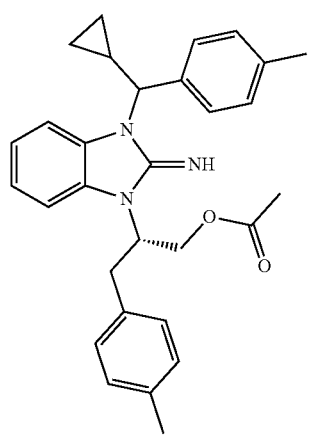 [SMILES: CC(=O)OC[C@H](Cc1ccc(C)cc1)n1c(=N)n(C(c2ccc(C)cc2)C2CC2)c2ccccc21] | ARN-1-851 | 7.39351 | 4.59 | 56.63 | 467.6 | 1 | 9.64 | +++ | 33 | Mixture of DM |
| 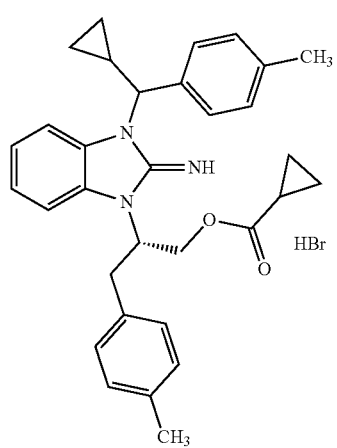 [SMILES: Cc1ccc(C[C@@H](COC(=O)C2CC2)n2c(=N)n(C(c3ccc(C)cc3)C3CC3)c3ccccc32)cc1 ; Br] | ARN-1-855 | 7.97751 | 5.41 | 56.63 | 574.56 | 1 | 9.59 | ++ | 34 | Mixture of DM |

TABLE 1-continued
| | | | | | | | | | |
|---|---|---|---|---|---|---|---|---|---|
| 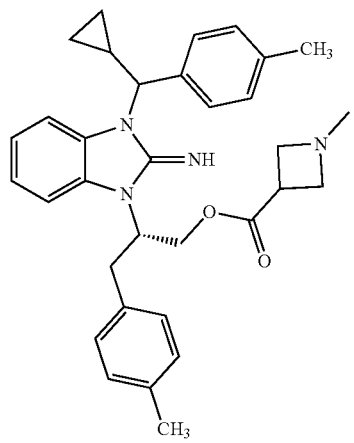 [SMILES: Cc1ccc(C[C@@H](COC(=O)C2CN(C)C2)n2c(=N)n(C(c3ccc(C)cc3)C3CC3)c3ccccc32)cc1] | ARN-1-857 | 8.01251 | 4.36 | 59.87 | 522.29 | 1 | 9.49 | ++ | 34 | Mixture of DM |
| 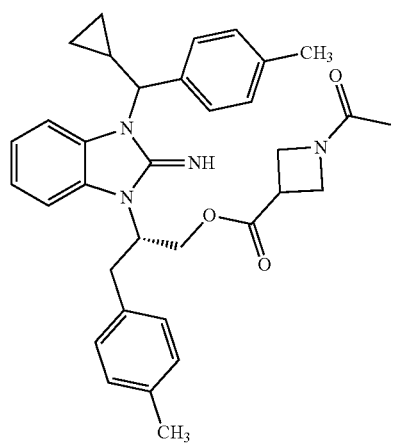 [SMILES: CC(=O)N1CC(C(=O)OC[C@H](Cc2ccc(C)cc2)n2c(=N)n(C(c3ccc(C)cc3)C3CC3)c3ccccc32)C1] | ARN-1-861 | 7.25651 | 3.15 | 76.94 | 550.69 | 1 | 9.26 | ++++ | 34 | Mixture of DM |
| 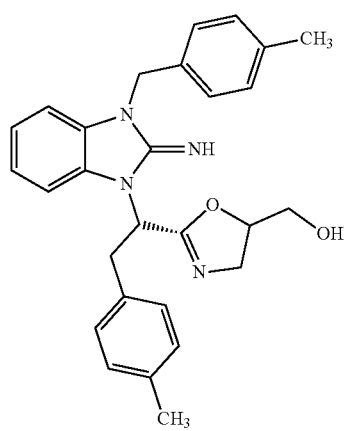 | ARN-1-909 | 6.22204 | 3.46 | 72.15 | 454.56 | 2 | 9.24 | ++ | 35 | Mixture of DM |

TABLE 1-continued
| | | | | | | | | | |
|---|---|---|---|---|---|---|---|---|---|
| 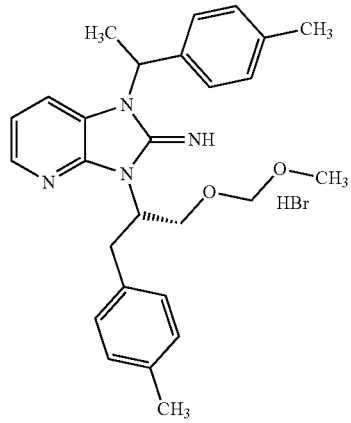 | ARN-1-931 | 5.06141 | 5.49 | 61.15 | 535.49 | 1 | 7.5 | + | 36 | Diastereomers-1 |
| 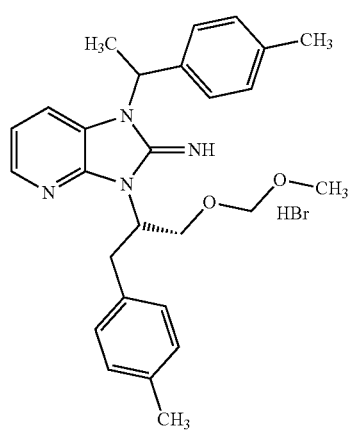 | ARN-1-932 | 5.06141 | 5.49 | 61.15 | 535.49 | 1 | 7.5 | +++ | 36 | Diastereomers-2 |
| 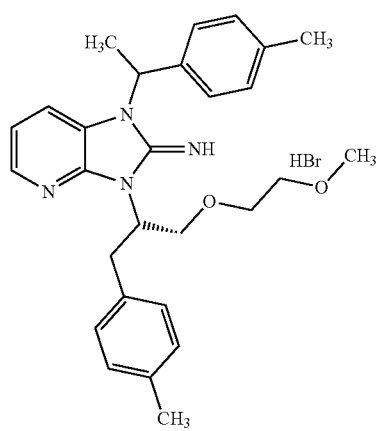 | ARN-1-946 | 5.17201 | 5.4 | 61.15 | 539.52 | 1 | 7.46 | ++ | 37 | Diastereomers-1 |

TABLE 1-continued
| | | | | | | | | | |
|---|---|---|---|---|---|---|---|---|---|
| 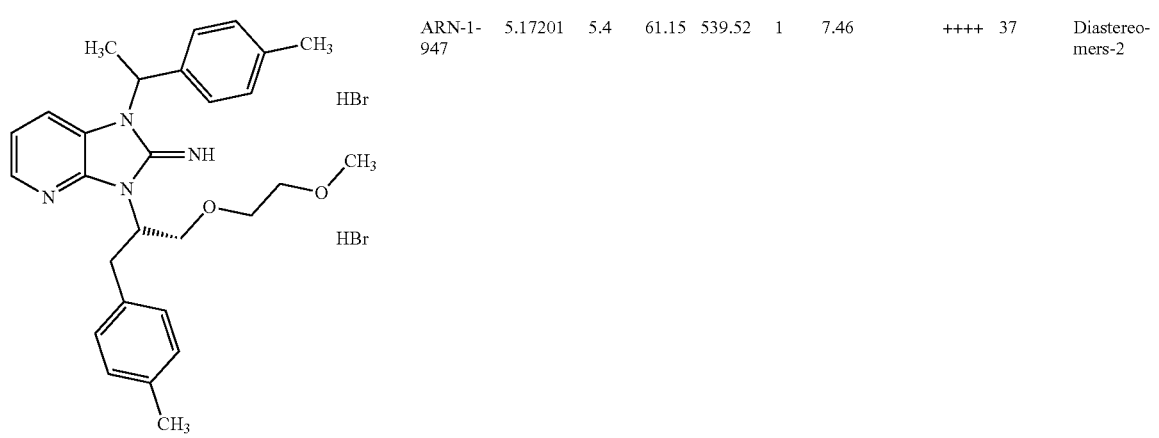 | ARN-1-947 | 5.17201 | 5.4 | 61.15 | 539.52 | 1 | 7.46 | ++++ | 37 Diastereomers-2 |
| 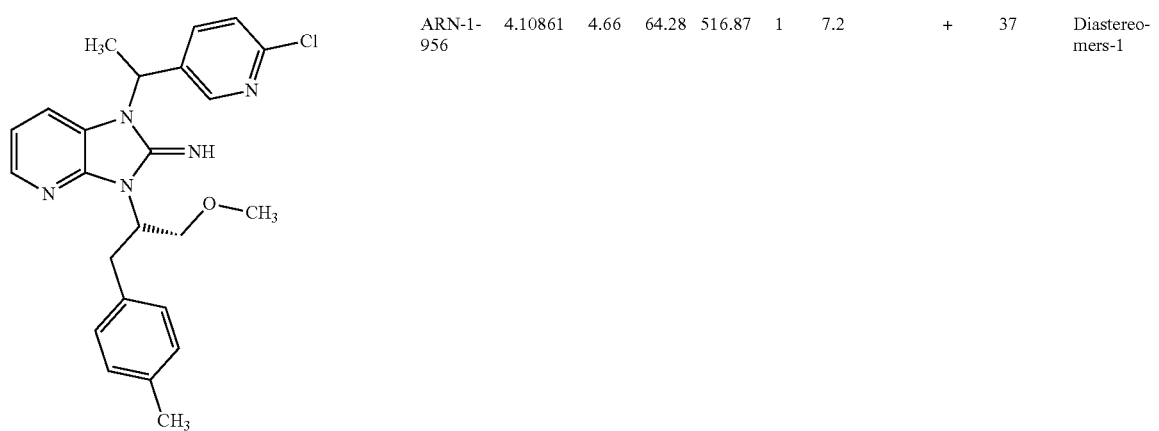 | ARN-1-956 | 4.10861 | 4.66 | 64.28 | 516.87 | 1 | 7.2 | + | 37 Diastereomers-1 |
| 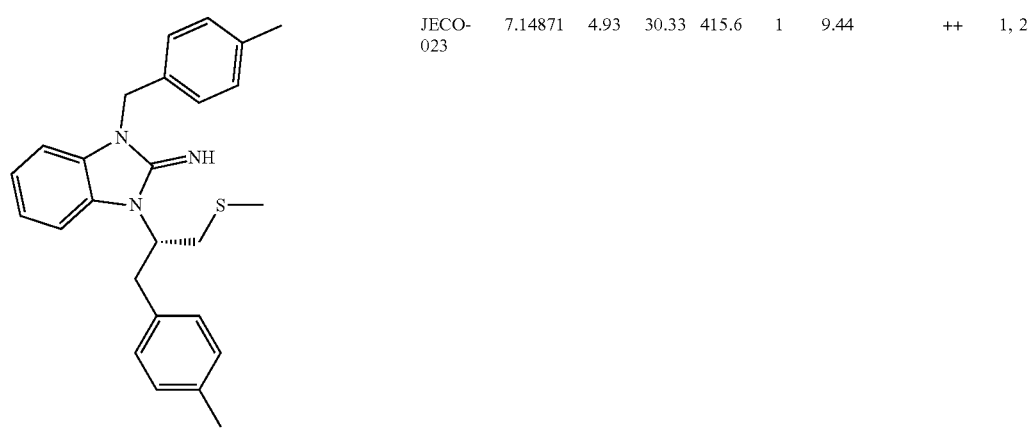 | JECO-023 | 7.14871 | 4.93 | 30.33 | 415.6 | 1 | 9.44 | ++ | 1, 2 |

TABLE 1-continued
| | | | | | | | | | |
|---|---|---|---|---|---|---|---|---|---|
| 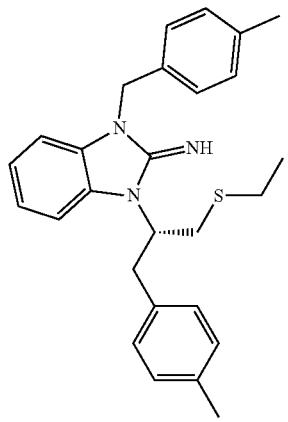 [SMILES: CCSC[C@H](Cc1ccc(C)cc1)n1c(=N)n(Cc2ccc(C)cc2)c2ccccc21] | JECO-036 | 7.67771 | 5.18 | 30.33 | 429.6 | 1 | 9.43 | ++ | 2 |
| 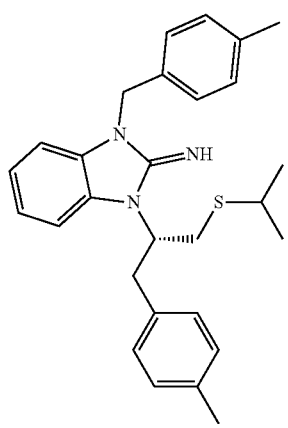 [SMILES: Cc1ccc(C[C@@H](CSC(C)C)n2c(=N)n(Cc3ccc(C)cc3)c3ccccc32)cc1] | JECO-037 | 7.98671 | 5.5 | 30.33 | 443.7 | 1 | 9.43 | ++ | 2 |
| 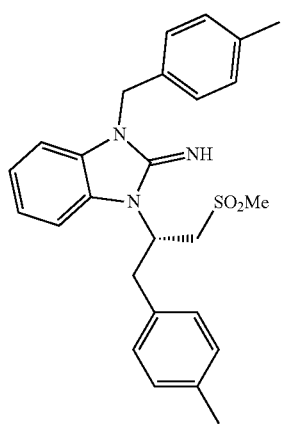 [SMILES: Cc1ccc(C[C@@H](CS(C)(=O)=O)n2c(=N)n(Cc3ccc(C)cc3)c3ccccc32)cc1] | JECO-038 | 5.34691 | 2.74 | 64.47 | 447.6 | 1 | 9.56 | ++ | 2, 3 sulfone |

TABLE 1-continued
| | | | | | | | | | |
|---|---|---|---|---|---|---|---|---|---|
| 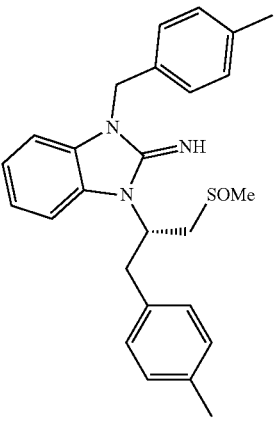 | JECO-044 | 5.43931 | 2.56 | 47.4 | 431.6 | 1 | 9.67 | ++ | 3 | sulfoxide |
| 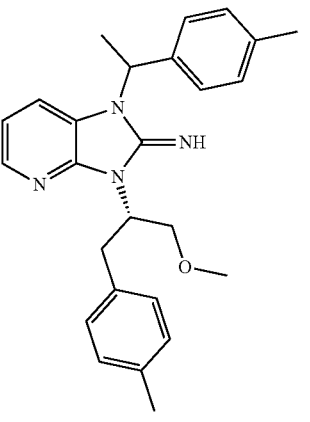 [SMILES: COC[C@H](Cc1ccc(C)cc1)n1c(=N)n(C(C)c2ccc(C)cc2)c2cccnc21] | MKG-25 | 5.31 | 5.38 | 51.92 | 414.55 | 1 | 7.56 | ++++ | 4 | diastereomer 2; the free base of WZ-II-149 |
| 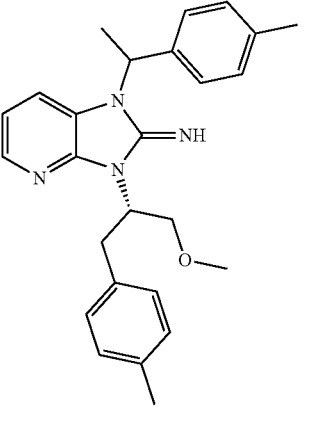 [SMILES: COC[C@H](Cc1ccc(C)cc1)n1c(=N)n(C(C)c2ccc(C)cc2)c2cccnc21] | MKG-26 | 5.31 | 5.38 | 51.92 | 414.55 | 1 | 7.56 | '+++ | 4 | diastereomer 1; the free base of WZ-II-231 |
+ Increases beyond 1 μM; does not saturate;
++ EC50 2 μM to 8 μM, saturation but Emax <OXB;
+++ EC50 1-2 μM, Emax near OXB;
++++ EC50 less than 1 μM, Emax near OXB;
In the test result graphics, ww4-126 is the compound 26 in J. Med. Chem. 2015, 58, 7931-7937.

TABLE 2
New Analogs
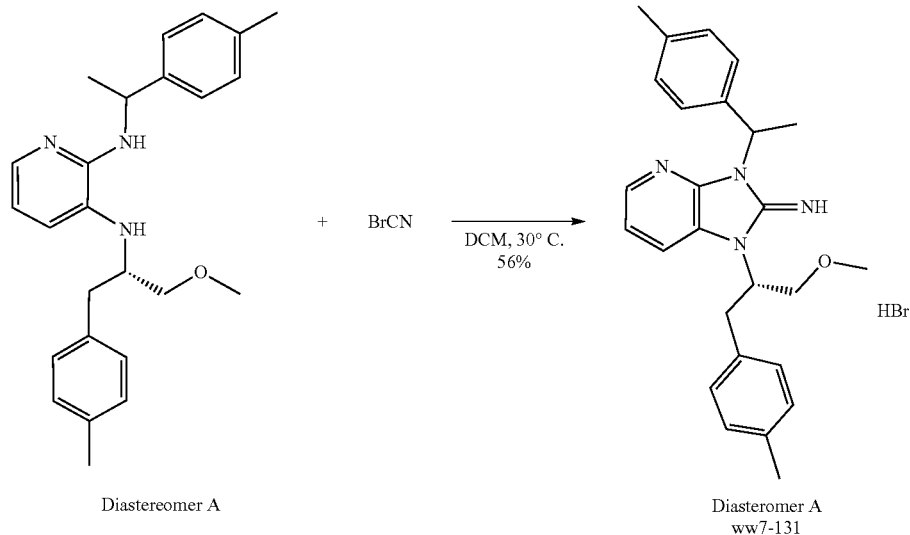 [SMILES: COC[C@H](Cc1ccc(C)cc1)Nc1cccnc1NC(C)c1ccc(C)cc1 ; "BrCN" ; COC[C@H](Cc1ccc(C)cc1)n1c(=N)n(C(C)c2ccc(C)cc2)c2ncccc21 ; Br]
Diastereomer A
Diasteromer A
ww7-131
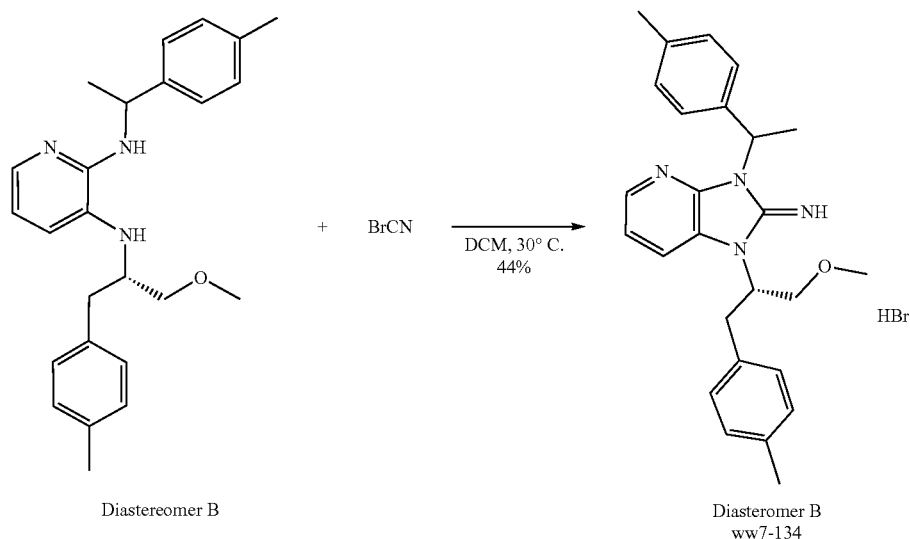 [SMILES: COC[C@H](Cc1ccc(C)cc1)Nc1cccnc1NC(C)c1ccc(C)cc1 ; "BrCN" ; COC[C@H](Cc1ccc(C)cc1)n1c(=N)n(C(C)c2ccc(C)cc2)c2ncccc21 ; Br]
Diastereomer B
Diasteromer B
ww7-134

TABLE 3
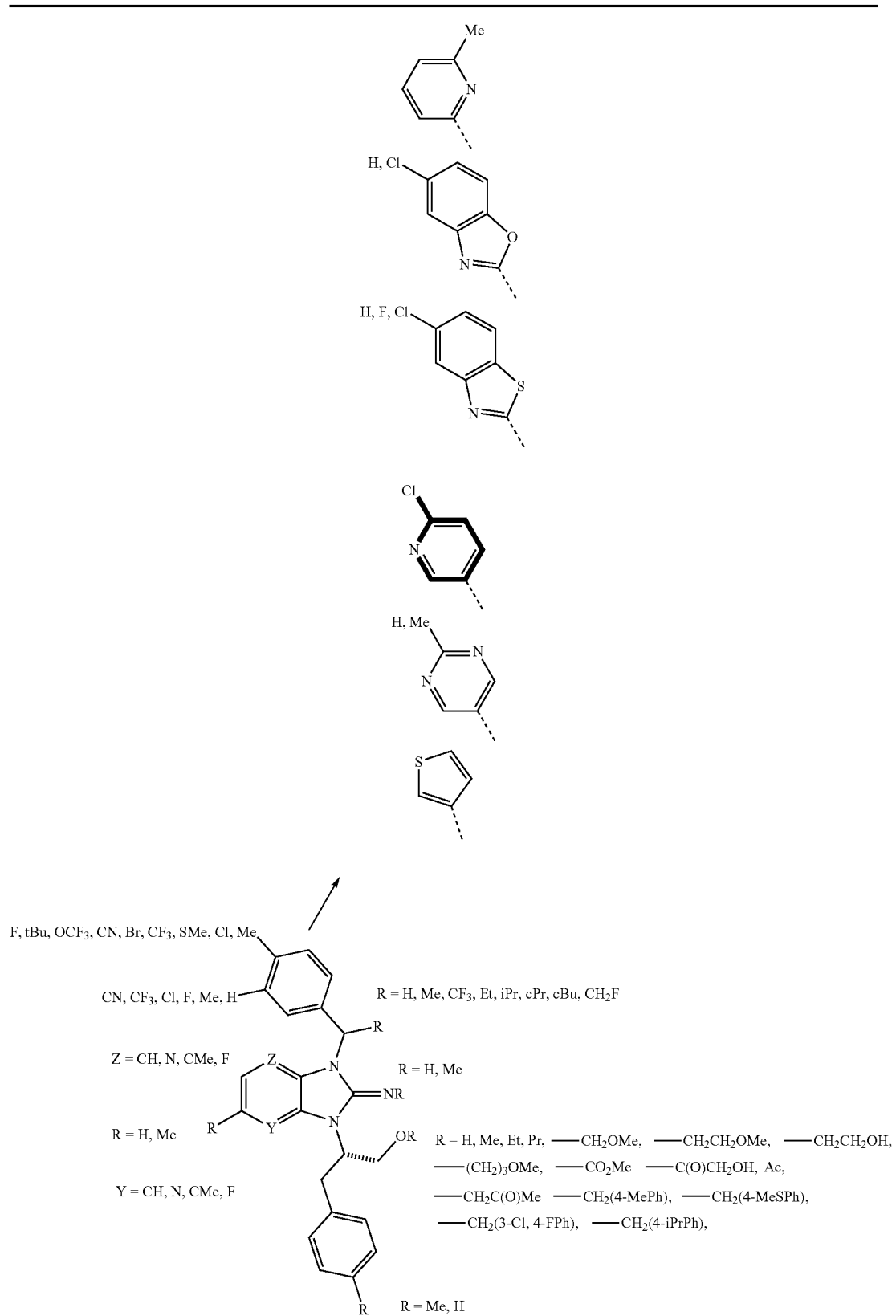
PREFERED 3

TABLE 3-continued

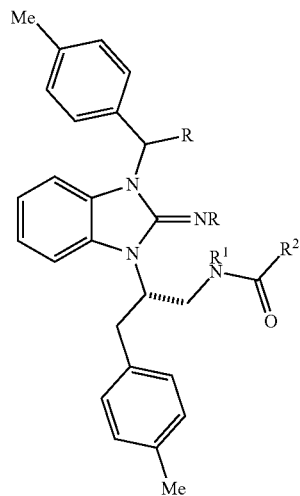

R₂ = —CH₂OH, aziridin-2-yl, NH₂, —CHMeOH (S), —CHMeOH (R), —CH₂NH₂, —CH₂NHMe, —CH₂NMe₂, —CH₂OMe, —(CH₂)OH, —(CH₂)₃OH, H, Me, CF₃, Et, CF₃, —CH₂F, cPr, OEt, NMe₂, OH, Ph, Bn, 4-MeBn, 4-MeOBn, 4-NH₂Bn, 3-NH₂Bn, 2-NH₂Bn, —CH=CHMe, —CH₂(pyridine-2-yl), —CH₂(pyridin-4yl), —CH₂(3-pyridinyl), —CH₂(pyrimidin-2-yl), oxazol-2-yl, furan-2-yl, oxetan-3-yl, pyridine-3-yl, 6-Me-pyridin-2-yl, 3-Me-pyridin-2-yl, pyridazin-3-yl, isoxazol-5-yl, 5-Me-isoxazol-4-yl, 1,4-Me₂-imidazol-5-yl, —CH₂(pyrrol-1-yl), 3,4-Cl₂Bn R¹ = H, Me

PREFERED 2

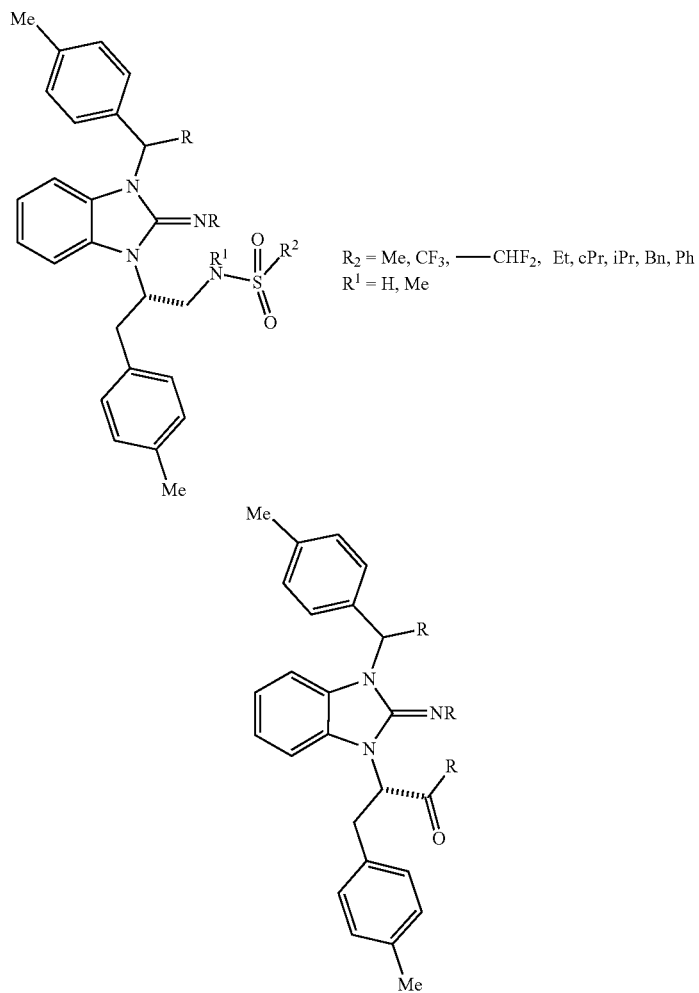

R₂ = Me, CF₃, —CHF₂, Et, cPr, iPr, Bn, Ph
R¹ = H, Me

TABLE 3-continued
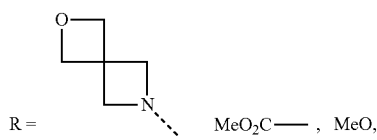
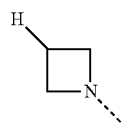
PREFERED 1
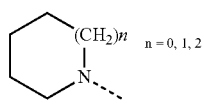  n = 0, 1, 2
| TABLE 4 |
|---|
| Series 3 |
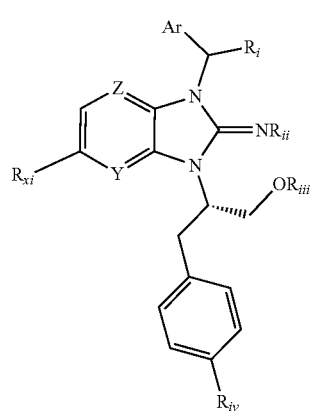
Ar =
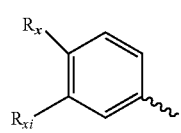
$R_x$ = F, tBu, CN, Br, CF$_3$, SMe, Cl, Me
$R_{xi}$ = CN, CF$_3$, Cl, F, Me, H
| TABLE 4-continued |
|---|
| Series 3 |
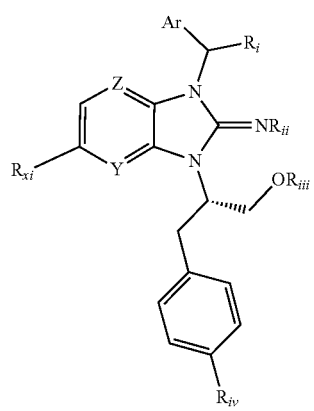
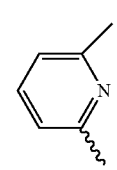
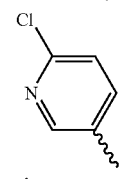

TABLE 4-continued
Series 3
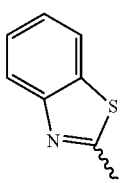
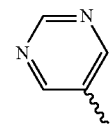
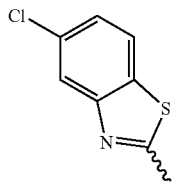
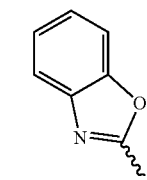
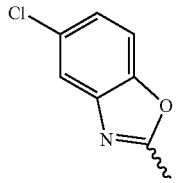
TABLE 4-continued
Series 3
| | |
|---|---|
| $R_i$ = | H, Me, CF3, Et, iPr, cPr, cBu, CH2F |
| $R_{ii}$ = | H, Me |
| $R_{iii}$ = | H, Me, Et, Pr, —CH$_2$OMe, —CH$_2$CH$_2$OMe, —CH$_2$CH$_2$OH, —(CH$_2$)$_3$OMe, —CO$_2$Me, —C(O)CH$_2$OH, Ac, —CH$_2$C(O)Me, —CH$_2$(4-MePh), —CH$_2$(4-MeSPh), —CH$_2$(3-Cl, 4-FPh), —CH$_2$(4-iPrPh) |
| $R_{iv}$ = | H, Me |
| $R_{xi}$ = | H, Me |
| Y | CH, N, CMe, CF |
| X | CH, N, CMe, CF |
TABLE 5
Series 3A Ar = 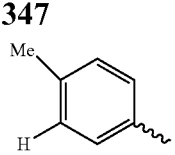

| | |
|---|---|
| $R_i$ = | Me, Et, cPr |
| $R_{ii}$ = | H, Me |
| $R_{iii}$ = | H, Me, Et, Pr, —CH$_2$OMe, —CH$_2$CH$_2$OMe, —CH$_2$CH$_2$OH, |
| $R_{iv}$ = | Me |
| $R_{xi}$ = | H |
| Y | CH, N, |
| X | CH, N, |

TABLE 6

Ether Series

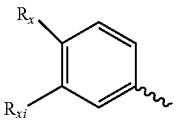

Ar = 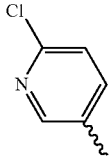

$R_x$ = Cl, Me
$R_{xi}$ = Cl, F, Me, H

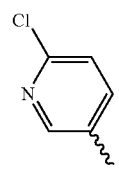

| | |
|---|---|
| $R_i$ = | Me, Et, cPr, |
| $R_{ii}$ = | H, Me |
| $R_{iii}$ = | H, Me, Et, Pr, —CH$_2$OMe, —CH$_2$CH$_2$OMe, —CH$_2$CH$_2$OH, |
| $R_{iv}$ = | Me |
| $R_{xi}$ = | H |
| Y | CH, N, CF |
| X | CH, N, CF |

TABLE 6-continued

Ether Series B

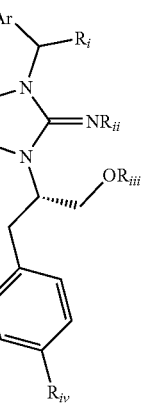

Ar = 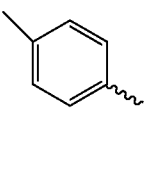

| | |
|---|---|
| $R_i$ = | Me, Et, cPr, |
| $R_{ii}$ = | H, Me |
| $R_{iii}$ = | Me, Et, —CH$_2$CH$_2$OMe, |
| $R_{iv}$ = | Me |
| $R_{xi}$ = | H |
| Y | CH, N |
| X | CH, N |

TABLE 7

Series 2

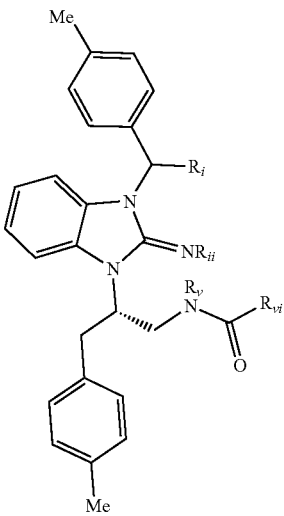

| | |
|---|---|
| $R_i$ = | H, Me, CF$_3$, Et, iPr, cPr, cBu, CH$_2$F |
| $R_{ii}$ = | H, Me |
| $R_{vi}$ = | —CH$_2$OH, aziridin-2-yl, NH$_2$, —CHMeOH (S), —CMeOH (R), NHMe, —CH$_2$NH$_2$, —CH$_2$NHMe, —CH$_2$NMe$_2$, —CH$_2$OMe, —(CH2)$_3$OH, H, Me, CF$_3$, Et, —CH$_2$F, cPt, OEt, NMe$_2$, OH, Ph, Bn, 4-MeBn, 4-MeOBn, 4-NH$_2$Bn, 3-NH$_2$Bn, 2-NH$_2$Bn, —CH═CHMe, —CH$_2$(pyridine-2-yl), —CH$_2$(pyridin-4yl), —CH$_2$(3-pyridinyl), —CH$_2$(pyrimidin-2-yl), oxazol-2-yl, furan-2-yl, oxetan-3-yl, pyrdiine-3-yl, 6-Me-pyridin-2-yl, 3-Me-pyridin-2-yl, pyridazin-3-yl, isoxazol-5-yl, 5-Me-isoxazol-4-yl, 1,4-Me$_2$-imidazol-5-yl, —CH$_2$(pyrrol-1-yl), 3,4-Cl$_2$Bn |
| $R_v$ | H, Me |

TABLE 8

Series 2B

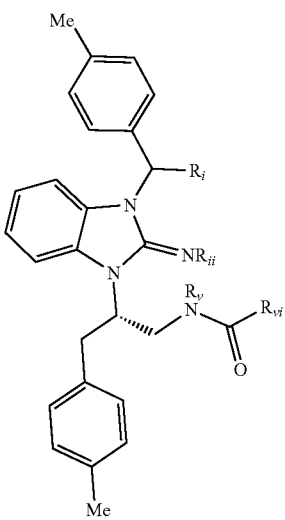

| | |
|---|---|
| $R_i$ = | H, Me, CF$_3$, Et, iPr, cPr, cBu, CHF |
| $R_{ii}$ = | H, Me |
| $R_{vi}$ = | —CH$_2$OH, aziridin-2-yl, NH$_2$, —CHMeOH (S), |
| $R_v$ | H, Me |

TABLE 9

Amide (glycoamide) series

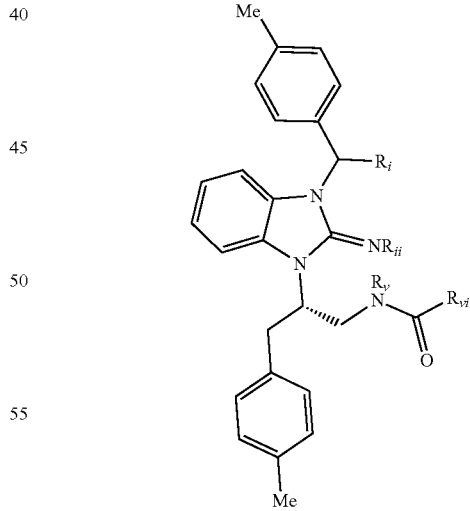

| | |
|---|---|
| $R_i$ = | Me, cPr, |
| $R_{ii}$ = | H, Me |
| $R_{vi}$ = | —CH$_2$OH, aziridin-2-yl, CHMeOH (S), CHMeOH (R), |
| $R_v$ | H, Me |

TABLE 10
Amide (glycoamide) series B
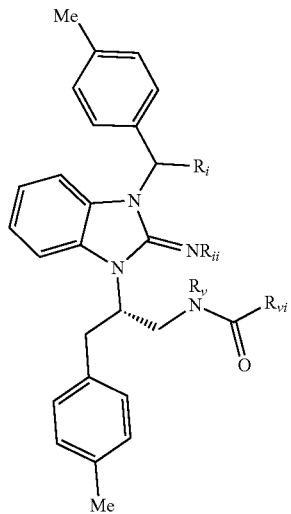
| | |
|---|---|
| $R_i$ = | Me, cPr, |
| $R_{ii}$ = | H, Me |
| $R_{vi}$ = | —CH$_2$OH, aziridin-2-yl, |
| $R_v$ | H, Me |
TABLE 11
Series 1
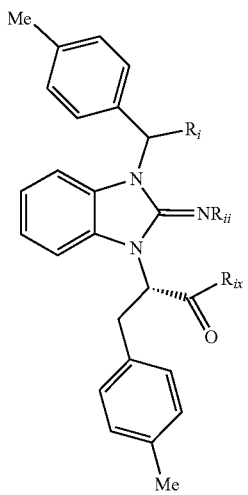
| | |
|---|---|
| $R_i$ = | H, Me, CF3, Et, iPr, cPr, cBu, CH2F |
| $R_{ii}$ = | H, Me |
TABLE 11-continued
Series 1
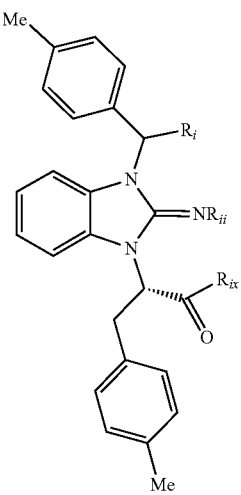
$R_{ix}$ =
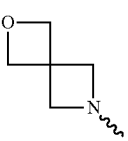
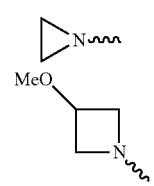
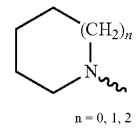
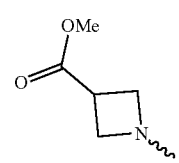

TABLE 12
Series 1B
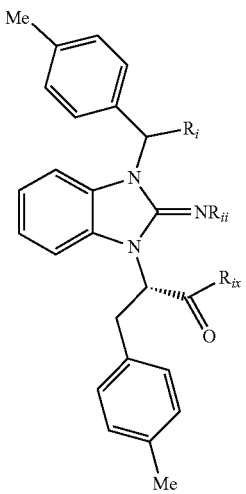
R$_i$ = H, Me, CF3, Et, iPr, cPr, cBu, CH2F
R$_{ii}$ = H, Me
R$_{ix}$ =
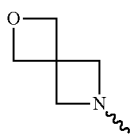
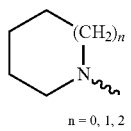
n = 0, 1, 2
TABLE 13
Reverse Amide Series
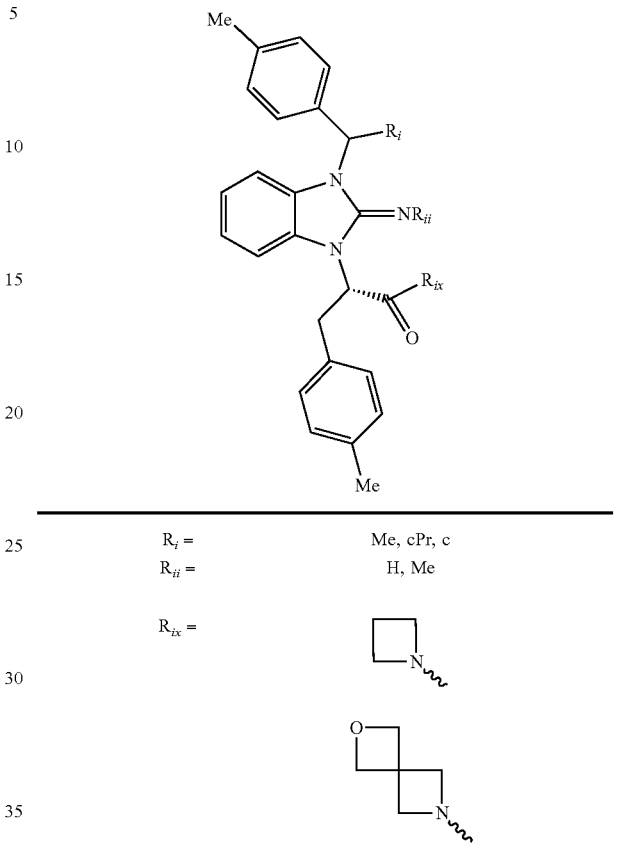
R$_i$ = Me, cPr, c
R$_{ii}$ = H, Me
R$_{ix}$ =
TABLE 14
Series S
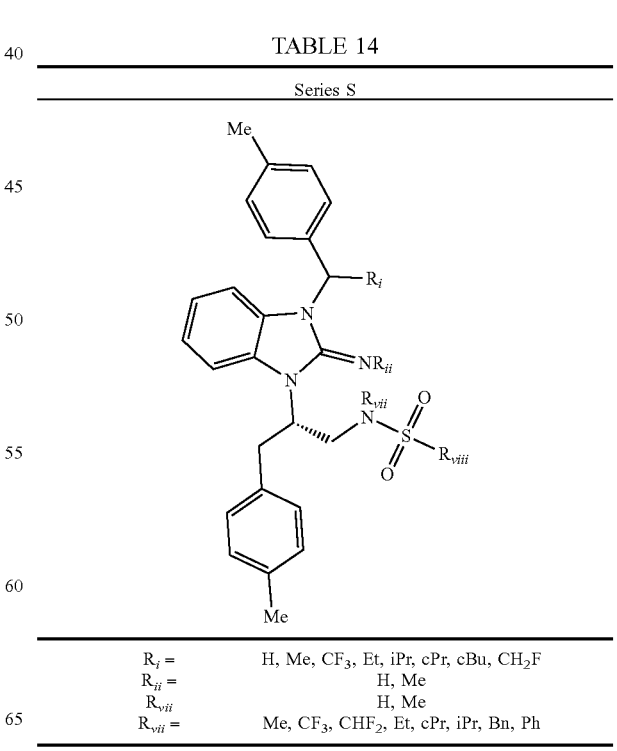
R$_i$ = H, Me, CF$_3$, Et, iPr, cPr, cBu, CH$_2$F
R$_{ii}$ = H, Me
R$_{vii}$ = H, Me
R$_{vii}$ = Me, CF$_3$, CHF$_2$, Et, cPr, iPr, Bn, Ph Chemotype 3

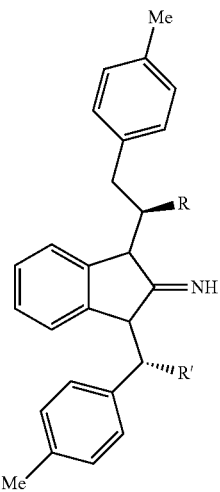

SAR on top and bottom aromatic rings exensively explored:

p-Me on both rings highest activity other substituents and various di-substituted aryl rings as well as various mono- and bicyclic fused R heterocycles

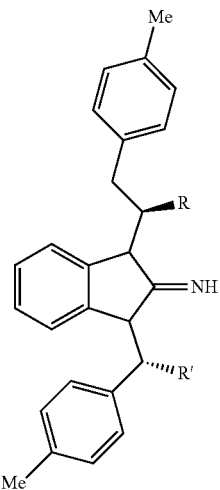

SAR results for Chemotype 3

We have identified a hotspot for modifications (R) Large amount of variations in R possible (sterics, electronics, amides, reverse amides, ethers . . . ) Potency can be gained here (R) Physiochemical properties can be adjusted here (R) Primary amides are not BBB penetrable R Ethers BBB penetrable R═OH BBB penetrable Inverse secondary amides promising, BBB expected to improve because of removal of one H-bond donor NH Introduction of stereogenic R' improves potency Screen for New OXR Agonists 220,000-compound library screened for OX2R activation at 5 uM in a CHO NFAT luciferase reporter assay. This assay uses a cell-based transcriptional reporter dependent on Gq stimulated $Ca^{2+}$ release due to activation of a stably trans- fected Gq-coupled GPCR.

384-well plates screened: 678

Average Z' across all plates: 0.758

960 compounds cherry-picked (CPHits) with z-score >2.3

Average z-score of all CPHits in primary screen: 8.119

CPHits were re-screened in duplicate for activation of the NFAT luciferase reporter: 72 compounds have z-score >2 (average of duplicates). 126 compounds have zscore >1 (average of duplicates).

CPHits were counter-screened in duplicate for activation of 'receptor-less'CHO reporter cell line: z-score=−0.291 (average of duplicates).

CPHits were counter-screened in duplicate for activation of a CRE (Gs/cAMP-dependent) luciferase reporter cell line: z-score=−0.152 (average of duplicates).

Compounds remaining after counter-screens were tested in a GRPR-transfected cell line (different neuropeptide- activated Gq-coupled GPCR).

OXR specific agonists curated: rank order in re-screening, drug-like physical properties, stability/reactivity, synthetic accessibility.

The examples herein are provided by way of illustration only and not by way of limitation. Those skilled in the art will readily recognize a variety of noncritical parameters that could be changed or modified to yield essentially similar results.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by refer- ence in their entirety for all purposes.

What is claimed is:

1. A method of treating a subject suffering from or diagnosed with a disease, disorder, or medical condition mediated by orexin receptor activity, wherein the disease, disorder, or medical condition is a disorder of the sleep-wake cycle, insomnia, restless legs syndrome, jet-lag, disturbed sleep, a sleep disorder secondary to neurological disorders, mania, depression, manic depression, schizophrenia, a pain syndromes, fibromyalgia, neuropathic pain, catatonia, Par- kinson's disease, Tourette's syndrome, anxiety, delirium, dementia, overweight, obesity or a condition related to overweight or obesity, insulin resistance, type II diabetes, hyperlipidemia, gallstones, angina, hypertension, breath- lessness, tachycardia, infertility, sleep apnea, back and joint pain, varicose veins, osteoarthritis, arrhythmias, angina pec- toris, acute heart failure, ulcers, irritable bowel syndrome, diarrhea, gastroesophageal reflux, post-traumatic stress dis- order, panic disorders, attention deficit disorders, cognitive deficiencies, or substance abuse, comprising administering to the subject in need thereof an effective amount of a compound of formula I:

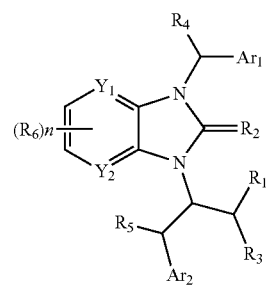

or a pharmaceutically acceptable salt thereof, wherein:
$Y^1$ and $Y^2$ are each independently N, CH or $CR^6$;
$Ar^1$ and $Ar^2$ are each independently C5-C10 aryl or 5- to 10-membered heteroaryl comprising one, two, or three heteroatoms selected from N, O, and S, and optionally substituted with one or more $R^{10}$;
$R^1$ is —OH, halogen, CN, $CH_2CN$, —$C_1$-$C_4$ alkoxy, —$C_1$-$C_4$ haloalkoxy, —$NR^aR^b$, —$NR^aCOR^9$, —$NR^aCO$(optionally substituted heterocyclyl), $SO_2R^{12}$, —O—($C_1$-$C_3$ alkylene)-O—($C_1$-$C_4$ alkyl) or —O—($C_1$-$C_3$ alkylene)-O—($C_1$-$C_4$ haloalkyl);
$R^2$ is NH or $NR^{11}$,
$R^3$ is H, —OH or methyl;
$R^4$ is H —$C_1$-$C_4$ alkyl, —$C_1$-$C_4$ haloalkyl, or —$C_3$-$C_4$ cycloalkyl;
$R^5$ is H, OH, or F;
$R^6$ is halogen, —CN, —$NO_2$, —$SCH_3$, —$COR^g$, —$C_1$-$C_4$ alkyl, —$C_1$-$C_4$ haloalkyl, —$C_3$-$C_4$ cycloalkyl, —$C_1$-$C_4$ alkoxy, or —$C_1$-$C_4$ haloalkoxy;
$R^a$ and $R^b$ are each independently H, —$C_1$-$C_4$ alkyl, —$C_1$-$C_4$ haloalkyl, —CHO, —CO($C_1$-$C_3$ alkyl), —CO($C_1$-$C_6$ alkylene)-OH, —$CONR^eR^f$, —CO($C_1$-$C_3$ alkylene)-$NR^eR^f$, —CO($C_1$-$C_3$ alkylene)-$NR^eSR^f$, —CO($C_1$-$C_3$ alkylene)-$NR^eSOR^g$, —CO($C_1$-$C_3$ alkylene)-$NR^eSO_2R^f$, —CO($C_2$-$C_3$ alkenyl), —CO($C_1$-$C_3$ haloalkyl), —CO($CH_2$)$_n$(cycloalkyl), —CO($CH_2$)$_n$(optionally substituted aryl), —CO($CH_2$)$_n$(optionally substituted heterocyclyl), —CO($CH_2$)$_n$(optionally substituted heteroaryl), or $SO_2R^{12}$;
$R^e$ and $R^f$ are each independently H, —$C_1$-$C_6$ alkyl, —$C_1$-$C_6$ haloalkyl, or —$C_1$-$C_6$ alkylene-OH;
$R^g$ is H, —$C_1$-$C_6$ alkyl, —$C_3$-$C_6$ cycloalkyl, —$C_1$-$C_6$ haloalkyl, phenyl, or benzyl,
$R^9$ is —$C_1$-$C_3$ alkylene-OH, —$C_1$-$C_3$ alkylene-CN, —$C_1$-$C_3$ alkylene-($C_1$-$C_3$ alkoxy), or —$C_1$-$C_3$ alkylene-$NR^aR^b$, —$C_1$-$C_4$ alkyl, —$C_1$-$C_4$ fluoroalkyl, or 2-aziridinyl;
$R^{10}$ is halogen, —CN, —$C_1$-$C_6$ alkyl, —$C_1$-$C_6$ haloalkyl, —$C_1$-$C_6$ alkoxy, —$C_1$-$C_6$ haloalkoxy, —S—S—($C_1$-$C_6$ alkyl), or optionally substituted phenyl;
$R^{11}$ is —$C_1$-$C_4$ alkyl, —$C_1$-$C_4$ fluoroalkyl, —$C_1$-$C_4$ alkoxy, or COO($C_1$-$C_4$ alkyl);
$R^{12}$ is —OH, —$C_1$-$C_6$ alkyl, —$C_3$-$C_6$ cycloalkyl, —$C_1$-$C_6$ haloalkyl, —$C_1$-$C_6$ alkoxy, phenyl, benzyl, —$NR^aR^b$, —$CONR^aR^b$, or —$NR^aCOR^g$;
n is 0, 1, or 2.

2. The method of claim 1, wherein each of $Ar^1$ and $Ar^2$ is phenyl optionally substituted with one or more $R^{10}$.

3. The method of claim 1, wherein $R^{10}$ is halogen, —CN, —$C_1$-$C_4$ alkyl, or —$C_1$-$C_4$ fluoroalkyl.

4. The method of claim 1, wherein each of $Ar^1$ and $Ar^2$ is 4-methylphenyl.

5. The method of claim 4, wherein:
$R^1$ is —OH, —F, $C_1$-$C_4$ alkoxy, —O—($C_1$-$C_3$ alkylene)-O—($C_1$-$C_4$ alkyl) or —O—($C_1$-$C_3$ alkylene)-O—($C_1$-$C_4$ haloalkyl), $C_1$-$C_4$ haloalkoxy, —$NR^aR^b$, —$NHCOR^9$, or —$NR^aCO$(optionally substituted heterocyclyl);
$R^a$ and $R^b$ are each independently H, —$C_1$-$C_4$ alkyl or —$C_1$-$C_4$ fluoroalkyl; and
$R^9$ is —$C_1$-$C_3$ alkylene-OH, —$C_1$-$C_3$ alkylene-CN, or —$C_1$-$C_3$ alkylene-$NR^aR^b$.

6. The method of claim 1, wherein:
$R^1$ is —OH, —$OCH_3$, —F, $C_1$-$C_4$ haloalkoxy, —$NR^aR^b$, —$NHCOR^9$, or —$OCH_2O$—($C_1$-$C_4$ alkyl), —$OCH_2O$—($C_1$-$C_4$ haloalkyl), or —$NR^aCO$(optionally substituted heterocyclyl);
$R^a$ and $R^b$ are each independently H, —$C_1$-$C_4$ alkyl or —$C_1$-$C_4$ fluoroalkyl; and
$R^9$ is —$C_1$-$C_3$ alkylene-OH, —$C_1$-$C_3$ alkylene-$NR^aR^b$, —$C_1$-$C_4$ alkyl or —$C_1$-$C_4$ fluoroalkyl.

7. The method of claim 1, wherein:
$R^1$ is —OH, —$OCH_3$, —F, —$NHCH_3$, —$N(CH_3)_2$, —$NHSO_2R^{12}$, or —$NHCOR^9$; and
$R^{12}$ is —$CH_3$, —$CH_2CH_3$, isopropyl, —$CF_3$, cyclopropyl, phenyl or benzyl; and
$R^9$ is —$CH_2OH$, —$CH_2NH_2$, —$CH_2NHMe$, —$CH_2NMe_2$ or 2-aziridinyl.

8. The method of claim 1, wherein $R^2$ is NH.

9. The method of claim 1, wherein $R^3$ is H.

10. The method of claim 1, wherein $R^4$ is H or methyl.

11. The method of claim 1, wherein $R^6$ is halogen, —$CH_3$, —$CF_3$, —CN, —$SCH_3$, t-butyl, —$OCH_3$, or —$OCF_3$, and n is 1 or 2.

12. The method of claim 1, wherein:
$Y^1$ is CH and $Y^2$ is N, CH or $CR^6$, wherein $R^6$ is halogen;
$Ar^1$ and $Ar^2$ are independently 4-MePh, 4-$CF_3$Ph, 4-Me-2,5-pyrazin-1-yl, 4-Cl-3-pyridin-1-yl, 4-ClPh, 3-F-4MePh, 3-F-4ClPh, 3-F-4BrPh, 3,4-$Cl_2$Ph, or 3,4-$Me_2$Ph;
$R^1$ is —OH, —$C_1$-$C_4$ alkoxy, —$C_1$-$C_4$ haloalkoxy, —$NR^aCOR^9$, or —$NR^aCO$(aziridin-2-yl);
$R^3$ is H;
$R^4$ is H, —$C_1$-$C_4$ alkyl, —$C_1$ haloalkyl, or —$C_3$ cycloalkyl;
$R^5$ is H;
$R^6$ is halogen;
$R^a$ and $R^b$ are each independently H or Me;
$R^9$ is $CH_2OH$, $CH_2NH_2$, $CH_2NHMe$, $CH_2NMe_2$, or 2-aziridinyl; and
$R^{11}$ is —$C_1$-$C_4$ alkyl, —$C_1$-$C_4$ fluoroalkyl, or —$C_1$-$C_4$ alkoxy.

13. The method of claim 1, wherein:
$R^1$ is —OH, —$C_1$-$C_4$ alkoxy, —$C_1$-$C_4$ haloalkoxy, —$NR^aR^b$, —$NR^aCOR^9$, —$NR^aCO$(optionally substituted heterocyclyl), $SO_2R^{12}$, —O—($C_1$-$C_3$ alkylene)-O—($C_1$-$C_4$ alkyl) or —O—($C_1$-$C_3$ alkylene)-O—($C_1$-$C_4$ haloalkyl);
$R^5$ is H, and
$R^a$ and $R^b$ are each independently H, —$C_1$-$C_4$ alkyl, —$C_1$-$C_4$ haloalkyl, —CHO, —CO($C_1$-$C_3$ alkyl), —CO($C_1$-$C_6$ alkylene)-OH, —$CONR^eR^f$, —CO($C_1$-$C_3$ alkylene)-$NR^eR^f$, —CO($C_1$-$C_3$ alkylene)-$NR^eSR^f$, —CO($C_1$-$C_3$ alkylene)-$NR^eSOR^g$, —CO($C_1$-$C_3$ alkylene)-$NR^eSO_2R^f$, —CO($C_2$-$C_3$ alkenyl), —CO($C_1$-$C_3$ haloalkyl), —CO($CH_2$)$_n$(cycloalkyl), —CO($CH_2$)$_n$(optionally substituted aryl), —CO($CH_2$)$_n$(optionally substituted heterocyclyl), or —CO($CH_2$)$_n$(optionally substituted heteroaryl).

14. A method of treating a subject suffering from or diagnosed with a disease, disorder, or medical condition mediated by orexin receptor activity, wherein the disease, disorder, or medical condition is a disorder of the sleep-wake cycle, insomnia, restless legs syndrome, jet-lag, disturbed sleep, a sleep disorder secondary to neurological disorders, mania, depression, manic depression, schizophrenia, a pain syndromes, fibromyalgia, neuropathic pain, catatonia, Parkinson's disease, Tourette's syndrome, anxiety, delirium, dementia, overweight, obesity or a condition related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, arrhythmias, angina pectoris, acute heart failure, ulcers, irritable bowel syndrome, diarrhea, gastroesophageal reflux, post-traumatic stress disorder, panic disorders, attention deficit disorders, cognitive deficiencies, or substance abuse, comprising administering to the subject in need thereof an effective amount of a compound of formula I:

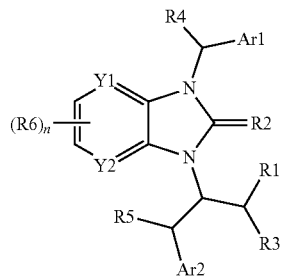

or a pharmaceutically acceptable salts thereof, wherein:
Y1 and Y2 are independently N, CH or CR6;
Ar1 and Ar2 are independently optionally substituted C5-C10 aryl or heteroaryl having from one to three heteroatoms selected from nitrogen, oxygen and sulfur;
R1 is optionally substituted, optionally cyclic C1-C10 hydrocarbyl or heterohydrocarbyl, or optionally substituted heteroatom;
R2 is NR, wherein R is H, Me, tert-butyloxycarbonyl (Boc), optionally fluorinated C1-C4 alkyl, C1-C4 alkyloxy, or C1-C4 alkyloxycarbonyl;
R3 is H or Me;
R4 is H or optionally fluorinated C1-C4 alkyl or —C$_3$-C$_4$ cycloalkyl, or cyano, nitro, carboxyl or acetyl;
R5 is H or Me;
each R6 is independently halide, optionally fluorinated C1-C4 alkyl or —C$_3$-C$_4$ cycloalkyl or cyano, nitro, carboxyl acetyl, SMe, OCF$_3$ or OMe;
n is an integer 0-2.

15. The method of claim 14, wherein each of Ar1 and Ar2 is optionally substituted phenyl.

16. The method of claim 14, wherein each of Ar1 and Ar2 is phenyl, optionally substituted with halo, cyano, or optionally fluorinated C1-C4 alkyl.

17. The method of claim 14, wherein each of Ar1 and Ar2 is 4-methyl phenyl.

18. The method of claim 14, wherein R1 is amide, amine, hydroxyl or hydrocarbyloxy.

19. The method of claim 14, wherein R1 is OR, NRR, NHCOR, or CONRR, wherein each R is independently H or optionally fluorinated C1-C4 alkyl.

20. The method of claim 14, wherein R1 is OH, OMe, OR, NRR, CONRR, NHC(O)R, wherein each R is independently H or optionally fluorinated C1-C4 alkyl.

21. The method of claim 14, wherein R1 is OH, OMe, NHMe, NMe$_2$, NHSO$_2$R16 or NHCOR16, where R16 is Me, CF$_3$, OH, OMe, OEt, ethyl, phenyl, cyclo propyl, isopropyl, benzyl, NH$_2$, NRR, CONR2 or NHC(O)R, wherein each R is independently H or optionally fluorinated C1-C4 alkyl.

22. The method of claim 14, wherein R2 is NH or NMe.
23. The method of claim 14, wherein R2 is NH.
24. The method of claim 14, wherein R3 is H.

25. The method of claim 14, wherein R4 is H, Me, Et, CF$_3$, isopropyl, cyclopropyl or cyclobutyl.
26. The method of claim 14, wherein R4 is H or Me.
27. The method of claim 14, wherein R5 is H.
28. The method of claim 14, wherein each R6 is independently Me, Et, CF$_3$, isopropyl, cyclopropyl, cyclobutyl, cyano, nitro, carboxyl, acetyl, halide, SMe, t-butyl, OCF$_3$ or OMe.

29. The method of claim 14, wherein the compound is of the structure:

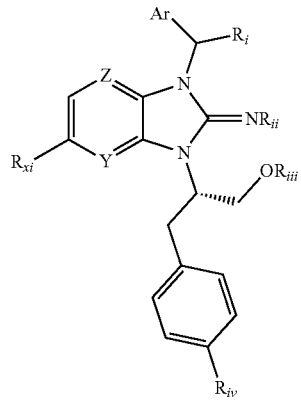

wherein,
Ar is selected from: 4-MePh, 4-CF$_3$Ph, 4-Me-2,5-pyrazin-1-yl, 4-Cl-3-pyridin-1-yl, 4-ClPh, 3-F-4MePh, 3-F-4ClPh, 3-F-4BrPh, 3,4-Cl$_2$Ph, or 3,4-Me$_2$Ph;
Rxi is Br, Cl, CF$_3$, F, Me or H;
R$_i$ is H, Me, CF$_3$, Et, iPr, cPr, cBu or CH$_2$F;
R$_{ii}$ is H or Me;
R$_{iii}$ is H, Me, Et, Pr, —CH$_2$OMe, —CH$_2$CH$_2$OMe, —CH$_2$CH$_2$OH, —(CH$_2$)$_3$OMe, —CO$_2$Me, —C(O)CH$_2$OH, Ac, —CH$_2$C(O)Me, —CH$_2$(4-MePh), —CH2 (4-MeSPh), —CH$_2$(3-Cl, 4-FPh), or —CH$_2$(4-iPrPh);
R$_{iv}$ is Cl or Me;
Y is CH, N, CMe or CF; and
Z=CH, N, CMe or CF.

30. The method of claim 14, wherein the compound is of the structure:

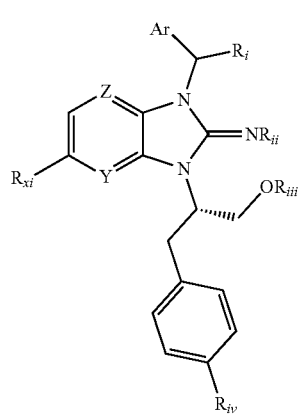

wherein,

Ar is

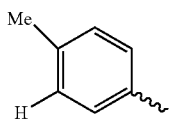

Ri is Me, Et or cPr;

Rii is H or Me;

Riii is H, Me, Et, Pr, —CH2OMe, —CH$_2$CH$_2$OMe, or —CH$_2$CH$_2$OH;

Riv is Me;

Rxi is H;

Y is CH, or N; and

Z is CH or N.

31. The method of claim 14, wherein the compound is of the structure:

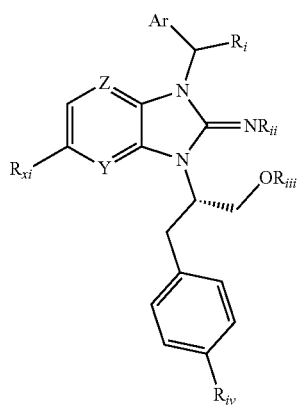

wherein,

Ar is

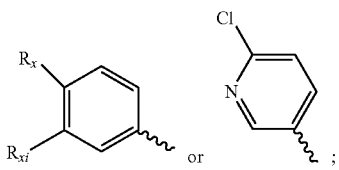

Rx is Cl or Me;

Rxi is Cl, F, Me or H;

Ri is Me, Et or cPr;

Rii is H or Me;

Riii is H, Me, Et, Pr, —CH2OMe, —CH2CH2OMe, or —CH2CH2OH;

Riv is Me;

Rxi is H;

Y is CH, N or CF; and

Z is CH, N or CF.

32. The method of claim 14, wherein the compound is of the structure:

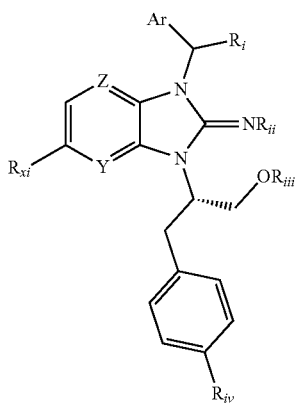

wherein,

Ar is

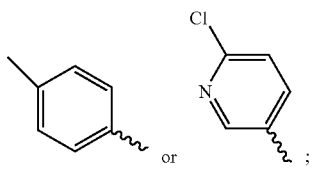

Ri is Me, Et or cPr;

Rii is H or Me;

Riii is Me, Et, or —CH$_2$CH$_2$OMe;

Riv is Me;

Rxi is H;

Y is CH or N; and

Z is CH or N.

33. The method of claim 14, wherein the compound is of the structure:

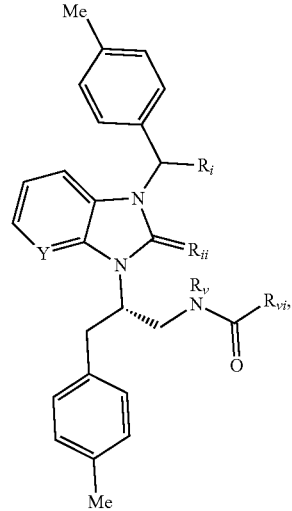

wherein,

Y=N, CH, or CF;

Ri is H, Me, CF₃, Et, iPr, cPr, cBu, or CH₂F;

Rii is H or Me;

Rv is H or Me;

$R_{vi}$ is —CH₂OH, aziridin-2-yl, NH₂, —CHMeOH (S), —CHMeOH (R), NHMe, —CH₂NH₂, —CH₂NHMe, —CH₂NMe₂, —CH₂OMe, —(CH₂)₂OH, —(CH₂)₃OH, H, Me, CF₃, Et, CHF₂, CH₂F, cPr, OEt, NMe₂, OH, Ph, Bn, 4-MeBn, 4-MeOBn, 4-NH2Bn, 3-NH₂Bn, 2-NH₂Bn, —CH=CHMe, —CH₂(pyridine-2-yl), CH₂(pyridin-4-yl), CH₂(3-pyridinyl), CH₂(pyrimidin-2-yl), oxazol-2-yl, furan-2-yl, oxetan-3-yl, pyridine-3-yl, 6-Me-pyridin-2-yl, 3-Me-pyridin-2-yl, pyridazin-3-yl, isoxazol-5-yl, 5-Me-isoxazol-4-yl, 1,4-Me₂-imidazol-5-yl, —CH₂(pyrrol-1-yl) or 3,4-Cl₂Bn.

34. The method of claim 14, wherein the compound is of the structure:

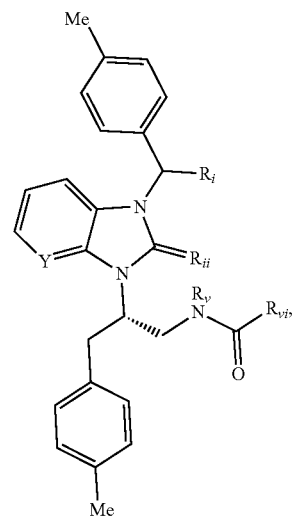

wherein,

Y=N, CH, or CF;

$R_i$ is H, Me, CF₃, Et, iPr, cPr, cBu or CH₂F;

$R_{ii}$ is H or Me;

$R_v$ is H or Me; and $R_{vi}$ is —CH₂OH, aziridin-2-yl, NH₂, or —CHMeOH (S).

35. The method of claim 14, wherein the compound is of the structure:

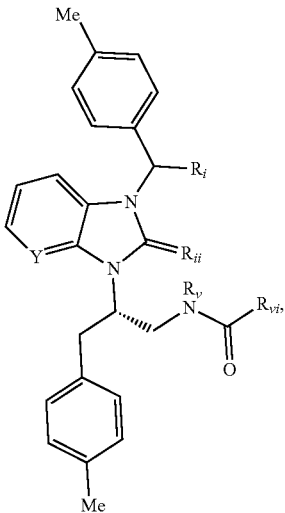

wherein,

Y=N, CH, or CF;

$R_i$ is Me or cPr;

$R_{ii}$ is H or Me;

$R_v$ is H or Me, and $R_{vi}$ is —CH₂OH, aziridin-2-yl, CHMeOH (S) or CHMeOH (R).

36. The method of claim 14, wherein the compound is of the structure:

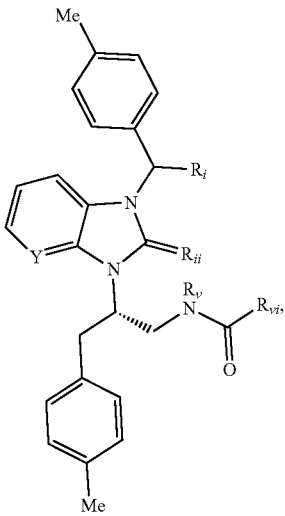

wherein,

Y=N, CH, or CF;

$R_i$ is Me or cPr;

$R_{ii}$ is H or Me;

$R_v$ is H or Me; and $R_{vi}$ is —CH₂OH or aziridin-2-yl.

37. The method of claim 14, wherein the compound is of the structure:

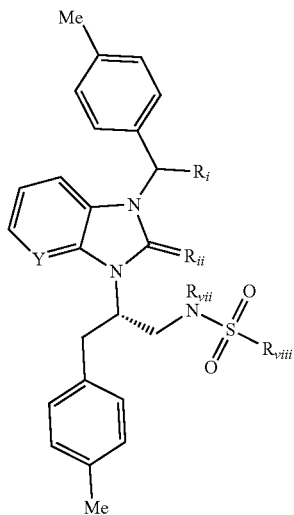

wherein,

Y=N, CH, or CF;

$R_i$ is H, Me, $CF_3$, Et, iPr, cPr, cBu, or $CH_2F$;

$R_{ii}$ is H or Me;

$R_{vii}$ is H or Me; and $R_{viii}$ is Me, $CF_3$, $CHF_2$, Et, cPr, iPr, Bn or Ph.

38. The method of claim 1, for increasing resistance to diet-induced accumulation of body fat, in a subject in need thereof.

39. The method of claim 1, for shortening recovery period from general anesthesia or jet lag, in a subject in need thereof.

40. The method of claim 1, for treating narcolepsy, in a subject in need thereof.

* * * * *

UNITED STATES PATENT AND TRADEMARK OFFICE
CERTIFICATE OF CORRECTION

| | |
|---|---|
| PATENT NO. | : 11,479,560 B2 |
| APPLICATION NO. | : 17/100810 |
| DATED | : October 25, 2022 |
| INVENTOR(S) | : Jef De Brabander et al. |

It is certified that error appears in the above-identified patent and that said Letters Patent is hereby corrected as shown below:

In the Specification

At Column 1, Lines 6-9, the cross-reference to related applications should read as follows:
This application is a continuation application of Ser. No. 17/033879, filed Sep 27, 2020, which is a continuation application of International Application No. PCT/US2019/024426, filed March 27, 2019, which claims priority to U.S. Provisional Application No. 62/648,933, filed March 27, 2018, the disclosures of which are hereby incorporated by reference in their entireties for all purposes.

And at Column 1, Lines 10-13, the government support clause should read as follows:
Government Support Clause
This invention was made with government support under Grant Numbers NS068963, NS097594, and NS103939 awarded by the National Institutes of Health (NIH). The government has certain rights in the invention.

Signed and Sealed this
Twelfth Day of November, 2024

Katherine Kelly Vidal
*Director of the United States Patent and Trademark Office*